US012599668B2

(12) United States Patent
Grosveld et al.

(10) Patent No.: US 12,599,668 B2
(45) Date of Patent: Apr. 14, 2026

(54) ANTIBODIES

(71) Applicants: HARBOUR ANTIBODIES BV, Rotterdam (NL); UNIVERSITEIT UTRECHT HOLDING B.V., Utrecht (NL); ERASMUS UNIVERSITY MEDICAL CENTER ROTTERDAM, Rotterdamn (NL)

(72) Inventors: Franklin Gerardus Grosveld, Rotterdam (NL); Marinus Johannes Van Haperen, Rotterdam (NL); Dubravka Drabek, Rotterdam (NL); Berend Jan Bosch, Utrecht (NL); Ivy Widjaja, Utrecht (NL); Chunyan Wang, Utrecht (NL); Brenda Van Dieren, Utrecht (NL); Wentao Li, Utrecht (NL); Frank J.M. Van Kuppeveld, Utrecht (NL); Bart L. Haagmans, Rotterdam (NL); Nisreen M.A. Okba, Rotterdam (NL)

(73) Assignees: HARBOUR ANTIBODIES BV, Rotterdam (NL); UNIVERSITEIT UTRECHT HOLDING B.V., Utrecht (NL); ERASMUS UNIVERSITY MEDICAL CENTER ROTTERDAM, Rotterdam (NL)

( * ) Notice: Subject to any disclaimer, the term of this patent is extended or adjusted under 35 U.S.C. 154(b) by 1273 days.

(21) Appl. No.: 17/432,745

(22) PCT Filed: Feb. 20, 2020

(86) PCT No.: PCT/EP2020/054521
§ 371 (c)(1),
(2) Date: Aug. 20, 2021

(87) PCT Pub. No.: WO2020/169755
PCT Pub. Date: Aug. 27, 2020

(65) Prior Publication Data
US 2022/0275059 A1 Sep. 1, 2022

(30) Foreign Application Priority Data

Feb. 20, 2019 (EP) ..................................... 19382123
Oct. 7, 2019 (EP) ..................................... 19382869

(51) Int. Cl.
| | |
|---|---|
| *A61P 31/14* | (2006.01) |
| *A61K 47/00* | (2006.01) |
| *C07K 16/08* | (2006.01) |
| *C07K 16/10* | (2006.01) |

(52) U.S. Cl.
CPC .............. *A61K 47/00* (2013.01); *A61P 31/14* (2018.01); *C07K 16/08* (2013.01); *C07K 16/1002* (2023.08); *C07K 2317/21* (2013.01); *C07K 2317/24* (2013.01); *C07K 2317/34* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2017/0158752 A1 6/2017 Marasco et al.

FOREIGN PATENT DOCUMENTS

| | | |
|---|---|---|
| EP | 2898067 A2 | 7/2015 |
| WO | WO 99/53049 A1 | 10/1999 |
| WO | WO 2006/008548 A2 | 1/2006 |
| WO | WO 2007/096779 A2 | 8/2007 |
| WO | WO 2010/070263 A1 | 6/2010 |
| WO | WO 2010/109165 A2 | 9/2010 |
| WO | WO 2014/141189 A1 | 9/2014 |
| WO | WO 2014/141192 A1 | 9/2014 |
| WO | WO 2015/164865 A1 | 10/2015 |
| WO | WO-2015179535 A1 * | 11/2015 ............. A61K 39/12 |
| WO | WO 2016/138160 A1 | 9/2016 |

OTHER PUBLICATIONS

Chen et al., A novel neutralizing monoclonal antibody targeting the N-terminal domain of the MERS-CoV spike protein. Emerg Microbes Infect. May 24, 2017;6(5):e37(1-8).
Jiang et al., Potent neutralization of MERS-CoV by human neutralizing monoclonal antibodies to the viral spike glycoprotein. Sci Transl Med. Apr. 30, 2014;6(234):234ra59(1-10).
Kirchdoerfer et al., Pre-fusion structure of a human coronavirus spike protein. Nature. Mar. 3, 2016;531(7592):118-21.
Li et al., Identification of sialic acid-binding function for the Middle East respiratory syndrome coronavirus spike glycoprotein. Proc Natl Acad Sci U S A. Oct. 3, 2017;114(40):E8508-E8517.
Li et al., Middle East Respiratory Syndrome Coronavirus Causes Multiple Organ Damage and Lethal Disease in Mice Transgenic for Human Dipeptidyl Peptidase 4. J Infect Dis. Mar. 1, 2016;213(5):712-22.
Lip et al., Monoclonal antibodies targeting the HR2 domain and the region immediately upstream of the HR2 of the S protein neutralize in vitro infection of severe acute respiratory syndrome coronavirus. J Virol. Jan. 2006;80(2):941-50.

(Continued)

*Primary Examiner* — Benjamin P Blumel
*Assistant Examiner* — Jeffrey Mark Sifford
(74) *Attorney, Agent, or Firm* — Mintz Levin Cohn Ferris Glovsky and Popeo, P.C.

(57) ABSTRACT

The invention relates to antibodies and antigen-binding fragments thereof that recognize coronavirus spike proteins (CoV-S), such as the spike protein of Middle East respiratory syndrome coronavirus spike protein(MERS-S). In some embodiments, the antibodiesbind to CoV-S with high affinity, inhibit CoV infection of human cells, inhibit CoV sialic acid-binding activity and/or bind to multiple types of CoV-S. In some embodiments, the antibodies provide a means of preventing, treating or ameliorating CoV infection.

11 Claims, 60 Drawing Sheets

Specification includes a Sequence Listing.

(56)                    References Cited

OTHER PUBLICATIONS

Mou et al., The receptor binding domain of the new Middle East respiratory syndrome coronavirus maps to a 231-residue region in the spike protein that efficiently elicits neutralizing antibodies. J Virol. Aug. 2013;87(16):9379-83.

Ng et al., Substitution at aspartic acid 1128 in the SARS coronavirus spike glycoprotein mediates escape from a S2 domain-targeting neutralizing monoclonal antibody. PLoS One. Jul. 14, 2014;9(7):e102415(1-11).

Pascal et al., Pre- and postexposure efficacy of fully human antibodies against Spike protein in a novel humanized mouse model of MERS-CoV infection. Proc Natl Acad Sci U S A. Jul. 14, 2015;112(28):8738-43.

Prabakaran et al., Structure of severe acute respiratory syndrome coronavirus receptor-binding domain complexed with neutralizing antibody. J Biol Chem. Jun. 9, 2006;281(23):15829-36.

Raj et al., Chimeric camel/human heavy-chain antibodies protect against MERS-CoV infection. Sci Adv. Aug. 8, 2018;4(8):eaas9667(1-11).

Raj et al., Dipeptidyl peptidase 4 is a functional receptor for the emerging human coronavirus-EMC. Nature. Mar. 14, 2013;495(7440):251-4.

Roess et al., Camels, MERS-CoV, and other emerging infections in east Africa. Lancet Infect Dis. Jan. 2016;16(1):14-15.

Tang et al., Identification of human neutralizing antibodies against MERS-CoV and their role in virus adaptive evolution. Proc Natl Acad Sci U S A. May 13, 2014;111(19):E2018-26.

Walls et al., Cryo-electron microscopy structure of a coronavirus spike glycoprotein trimer. Nature. Mar. 3, 2016;531(7592):114-117.

Walls et al., Tectonic conformational changes of a coronavirus spike glycoprotein promote membrane fusion. Proc Natl Acad Sci U S A. Oct. 17, 2017;114(42):11157-11162.

Wang et al., Importance of Neutralizing Monoclonal Antibodies Targeting Multiple Antigenic Sites on the Middle East Respiratory Syndrome Coronavirus Spike Glycoprotein To Avoid Neutralization Escape. J Virol. Apr. 27, 2018;92(10):e02002-17(1-21).

Ying et al., Junctional and allele-specific residues are critical for MERS-CoV neutralization by an exceptionally potent germline-like antibody. Nat Commun. Sep. 15, 2015;6:8223(1-10).

Yu et al., Structural basis for the neutralization of MERS-CoV by a human monoclonal antibody MERS-27. Sci Rep. Aug. 18, 2015;5:13133(1-11).

Zhou et al., Sequential immunization with consensus influenza hemagglutinins raises cross-reactive neutralizing antibodies against various heterologous HA strains. Vaccine. Jan. 5, 2017;35(2):305-312.

Zhu et al., Potent cross-reactive neutralization of SARS coronavirus isolates by human monoclonal antibodies. Proc Natl Acad Sci U S A. Jul. 17, 2007;104(29):12123-8.

* cited by examiner

Fig. 1(A)  Structure of MERS spike protein

Fig. 2(A)

```
3.33 VH  QVQLVESGGGVVQPGRSLRLSCAAS GFTFSSYG MHWVRQAPGKGLEWVAV IWYDGSNK YYADSVKGRFTISRDNSKNTLYLQMNSLRAEDTAVYYC AR                              WGQGTTITVSS...
7.7f3    QVQLVESGGGVVQPGRSLRLSCTAS GFTFSGYG MHWVRQAPGKGLEWVAI IWYDGSNT YYTDSAKGRFTISRDNSKDTLYLQMNSLRVEDTAVYYC ARDRGISVAALWKYYYHGLDV     WGQGTTVTVSS...
4.2c3    QVQLVESGGGVVQPGRSLRLSCTAS GFTFSGYG MHWVRQAPGKGLEWVAI IWYDGSNT YYADSAKGRFTISRDNSKNTLYLQMNSLRVEDTAVYYC ARDRGISVAALWKYYYHGLDV     WGQGTTVTVSS...
4.2f1    QVQLVESGGGVVQPGRSLRLSCTAS GFTFSGYG MHWVRQAPGKGLEWVAI IWYDGSNT YYADSAKGRFTISRDNSKNTLYLQMNSLRVEDTAVYYC ARDRGISVAALWKYYYHGLDV     WGQGTTVTVSS...
4.9f12   QVQLVESGGGVVQPGMSLRLSCTAS GFTFSGVA MHWVRQAPVKGLEWVAI IWYDGSNK YYADSVKGRFTISRDNSKNTLYLQMNSLRAEDTAVYYC ARDRGISEAAKWKYYYYGMDV      WGGGTTVTVSS...
4.9e5    QVQLVESGGGVVQPGMSLRLSCTAS GFTFSGVA MHWVRQAPVKGLEWVAI IWYDGSNK YYADSVKGRFTISRDNSKNTLYLQMNSLRAEDTAVYYC ARDRGISEAAKWKYYYYGMDV      WGGGTTVTVSS...
7.7a6    QVQLVESGGGVVQPGRSLRLSCTAS GFTFSGVA MHWVRQAPVKGLEWVAI IWYDGSNK YYADSVKGRFTISRDNSKNTLYLQMNSLRAEDTAVYYC ARDRGISEAAKWKYYYYGMDV      WGGGTTVTVSS...
7.7h8    QVQLVESGGGVVQPGRSLRLSCTAS GFTFSAXA MHWVRQAPGKGLEWVTF IGYEESNK YHADSVKGRFTISRDNSKNTLYLQMNSLRAEDTAVYYC ARDRGISVAATWDYYYYGMDV      WGGGTTVTVSS...
7.3a9    QVQLVESGGGVVQTGRSLRLSCAAS GFNFSSDG MHWVRQAPGKGLEWVAV IWYDGRNK YYADSVKGRFTISRDNTKNTLYLQMNSLRAEDTAVYYC ARDRGITMGRGPYYYYYGMDV       WGGGTTVTVSS...
7.6c11   QVQLVESGGGVVQPGRSLRLSCAAS GFTFSSDG MHWVRQAPGKGLEWVAV IWYDGSSE YYGDSVKGRFTISRDNSKNTMYLQMNSLRAEDTAVYYC ARDRGITMGRGVYYYYYGMDV       WGGGTTVTVSS...
5.2b7    QVQLVESGGGVVQPGRSLRLSCAAS GFTFSSDG MHWVRQAPGKGLEWVAV IWFDGSNK YYADSVKGRFTISRDNSKNTLYLQMNSLRAEDTAVYYC TRDRGITMGRGRYYYYGMDV        WGGGTTVTVSS...
7.9c10   QVQLVESGGDVVQPGRSLRLSCAAS GITFSNYG MHWVRQAPGKGLEWVAV IWYDGSNK YYADSVKGRFTISRDNSKNTLYLQMNSLRAEDTAVYYC ARDRGMTGTTWEYYYYGMDV        WGGGTTVTVSS...
7.9g1    QVQLVESGGGVVQPGRSLRLSCAAS GFTFSTYA MHWVRQAPGKGLEWVAV IWYDGSNK YYADSVKGRLTISRDNSKNTLFLQMNSLRAEDTAVYYC ARDRGITTTDTGYYYYYGLDI       WGGGTTVTVSS...
2.9d7    QRKLVESGGGVVQPGRSLRLSCAVS GLIFSNYG MHWVRQTPGKGLEWVAI IWYDGSNT YYTDSVKGRFTISRDNSKNTLYLQMNSLRAEDTAVYYC ARDRGMTAPGPGTYYYFYGMDV     WGQGTMVTVSS...
7.9c2    QVQLVESGGGVVQPGRSLRLSCVAS GFTFSNYG MHWVRQTPGKGLEWVAI IWFDGSNK YYADSVKGRFTISRDNSKNTLYLQMNSLRAEDTAVYYC ARERGVWNSGWSHAYDI          WGQGTMVTVSS...
7.2e7    QVQLVESGGGVVQPGRSLRLSCAAS GFTFSNYG MHWVRQTPGKGLQWVAF IWFDGSNK YYADAVKVRFTISRDNSKNTLYLQMNSLRAEDTAVYYC ARERGVWNSGWSHAYDI          WGGGTLVTVSS...
1.3h2    QVQLVESGGGVVQPGRSLRLSCAAS GFTFSSYG MHWVRQAPGKGLEWVAV IWFDGTNI YYADSVRGRFTISRDNSKNTLYLQMNSLRAEDSAVYYC ATEGDYYGSGSYSRAEYFQE       WGGGTLVTVSS...
7.5d3    QVQLVESGGGVVQPGRSLRLSCAAT GFTFSSYG MHWVRQAPGKGLEWVAV IWFDGTNI YYADSVQGRFTISRDNSKNTLYLQMNSLRAEDTAVYYC ARDRRSSDWYVVFDY            WGGGTLVTVSA...
4.6e10   QVQLVESGGGVVQPGRSLRLSCTAS GFTFTYG  LHWVRQAPGKGLEWVAV IWYDGSNQ YYADSVQGRFTISRDNSKNTLYLQMNSLRAEDTAVYYC AREGLGAVAGYFDY            WGQGTLVTVSA...
1.10f3   QVQLVESGGGVVQPGRSLRLSCTAS GFTFRGYG MHWVRQAPGKGLEWVTV WHDASNK  YYVDSVKGRFSISRDNSKNMLYLQMNSLRAEDTAVYFC ARDAGLSFDI                WGGGTMVTVSS...
1.17f10  QVQLVESGGGVVQPGRSLRLSCAAS GFTFSKYG MHWVRQAPGKGLEWVAN IGYDGSDK YYTDSVRGRFTISRDNSKNTLYLQMNSLRVEDTAMYFC ARGGWIDDYYGLDV            WGGGTTVTVSS...
1.12g2   QVQLVESGGGVVQPGRSLRLSCAAS GFTFSSYG MHWVRQAPGKGLEWVAV ICYDGSDK YYTDSVRGRFTISRDNSKNTLYLQMNSLRVEDTAMYFC ARGGWIDDYYGMDV            WGGGTLVTVSS...
1.5d6    QVQLVESGGGVVQPGRSLRLSCAAS GFTFSRYG MHWVRQAPGKGLEWVAV IGYDGSNK YYADSVKGRFTISRDNSKNTLSLQMNSLRAEDTAVYYC ARGGWNDDYYGLDV            WGGGTTVTVSS...

1.69 VH  QVQLVQSGAEVKKPGSSVKVSCKAS GGTFSSYA ISWVRQAPGQGLEWMGG IIPIFGTA NYAQKFQGRVTITADESTSTAYMELSSLRSEDTAVYYC AR                          WGGGTMVTVSS...
5.5e11   QVQLVQSGAEVKKPGSSVKISCKAS GGTFSTHA FTWVRQAPGQGLEWIGR IIPIFDTP KYAQKFQGRVITAADISTSTVFMELSSLRSEDTAVFYC AREGYYISGSYRDAFDI          WGRGTLVTVSS...
7.9g10   QVQLVQSGAEVKKPGSSVKVSCKAS GGTFSSYA ISWVRQAPGQGLEWMGG IIPIFGTA NYAQKFQGRVTITADKSTNTAYMELSSLRSEDTAVYYC AREDIMVRGVINYWYFDL         WGGGTLVTVSS...
1.3g2    QVQLVQSGAEVKKPGSSVKVSCKAS GGTFSTYA ISWVRQAPGQGLEWMGG IIPIFGTA NYAQKFQGRVTILADKSTNTAYMDLSSLRSEDTAVYYC AREGNLGYDVVTGYSYFVY        WGGGTLVTVSS...
7.2h5    QVQLVQSGAEVKKPGSSVKVSCKAS GGTFSSYA ISWVRQAPGQGLEWMGG IIPIFGTV KNAQKFQGRVTITADKSTGTAYMELSSLRSEDTAVYYC ARDHYYDSNDYWYFDL           WGGGTLVTVSS...
1.6e1    QVQLVQSGAEVKKPGSSVKVSCKAS GGAFSAYA ISWVRQAPGQGLEWMGG IIPIFGTA NYAQKFQGRVTITADTSTSTAYMELSSLRSEDTAVYYC AREGDIEVVLAARGFFDY         WGGGTLVTVSS...
1.6f2    QVQLVQSGTEVKKPGSSVKVSCKAS GGAFSAYA ISWVRQAPGQGLEWMGG IIPIFGTA HYAQKFQGRVTITADKSTSTAFMELSSLRSEDTAVYYC AREGDIEVVLAGRGYFDY         WGGGTLVTVSS...
1.6f9    QVQLVQSGAEVKKPGSSVKVSCKAS GGAFSAYA ITWVRQAPGQGLEWMGG IIPVFGTA HYAQKFQGRVTITADKSTSTAFMELSSLRSEDTAVYYC AREGDIEVVLAGRGYFDY         WGGGTLVTVSS...
5.11h8   QVQLVQSGAEVKKPGSSVKVSCKAS GGAFSAYA IDWVRQAPGQGLEWMGG IIPIFGTA HYAQLQGRVTITADKSTNTAYMELSRLRSEDTAVYYC AREGDSGLVLAARGFFDY         WGGGTLVTVSS...
7.7g6    QVQLVQTGAEVKKPGSSVKVSCKAS GGTFSTYA ISWVRQAPRQGLEWMGG IIPIFGTA NYAQKFQGRVTILADKSTNTAYMELSRLRSEDTAVYYC AREGDDVIVPTSRGFFDY         WGGGTLVTVSS...
1.2g5    QVQLVQSGAEVKKPGSSVKVSCKAS GGTFSYA  ISWVRQAPGQGLEWMGG IIPIFGTA NYAQKFQGRVTILADKSTNTAYMDLSSLRSEDTAVYYC AREGNLGYDVVTGYSYFVY        WGGGTLVTVSS...

6.1 VH   QVQLQQSGPGLVKPSQTLSLTCAIS GDSVSNSAA WNWIRQSPSRGLEWLGR TYYRSKWYN DYAVSVKSRITINPDTSKNQFSLQLNSVTPEDTAVYCC AR                          WGRGTLVTVSS...
1.10e9   QVQLQQSGPGLVKPSQTLSLTCAIS GDSVSNSAA WNWIRQSPSRGLEWLGR TYYRSKWYN DYAVSVKSRITINPNTSKNQFSLQLNPVTPEDTAVYFC AREWFGEGYFDL              WGGGTLVTVSS...
1.6a9    QVQLQQSGPGLVKPSQTLSLTCAIS GDSVSNSAA WNWIRQSPSRGLEWLGR TYYRSKWYN DYAVSVKSRITINPDTSKNQFSLQLNPVTPEDTAVYCC ARTITMIRGIIISFDY          WGGGTLVTVSS...

4.4 VH   QVQLQESGPGLVKPGGTLSLTCAVS GGSISSSNW WSWVRQPPGKGLEWIGE IYHSGST NYNPSLKSRVTISVDKSKNQFSLKLSSVTAADTAVYCC AR                          WGGGTMVTVSS...
1.8e5    QVQLQESGPGLVKPSGTLSLTCAVS GGSISSNRW WITWVRRSPGKGLEWIGE IYHSGST NYNPSLKSRVTISVDRSKNQFSLKLSSVTAADTAVYYC ASLTLIWFGEKAFDI            WGGGTMVTVSS...
1.8c5    QVQLQESGPGLVKPSGTLSLTCAVS GGSISSSKW WSWVRQSPGKGLEWIGE IYHSGST NYNPSLKSRVTISVDKSKNQFSLKLSSVTAADTAVYYC ASLTLIWFGEKAFDI            WGGGTMVTVSS...
```

Fig. 2(A) (continued)

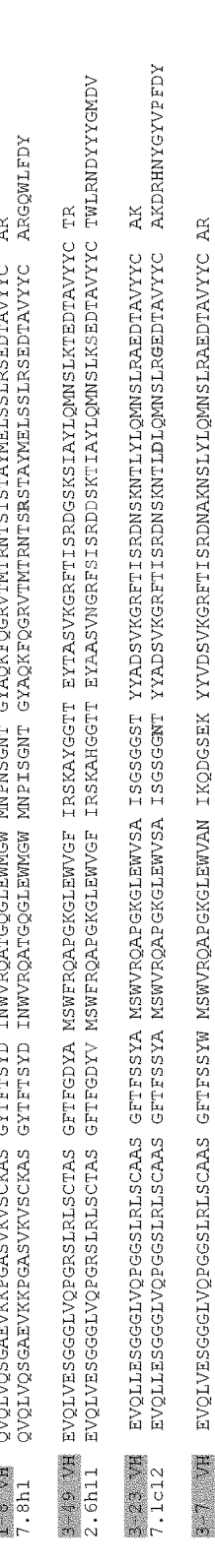

```
1.8 VH   QVQLVQSGAEVKKPGASVKVSCKAS GYTFTSYD INWVRQATGQGLEWMGW MNPNSGNT GYAQKFQGRVTMTRNTSISTAYMELSSLRSEDTAVYYC AR ARGQWLFDY   WGQGTLVTVSS..
7.8h1    QVQLVQSGAEVKKPGASVKVSCKAS GYTFTSYD INWVRQATGQGLEWMGW MNPISGNT GYAQKFQGRVTMTRNTSRSTAYMELSSLRSEDTAVYYC ARGQWLFDY 3.49 VH  EVQLVESGGGLVQPGRSLRLSCTAS GFTFGDYA MSWFRQAPGKGLEWVGF IRSKAYGGTT EYTASVKGRFTISRDGSKSIAYLQMNSLKTEDTAVYYC TR                WGLGTTVTVSS..
2.6h11   EVQLVESGGGLVQPGRSLRLSCTAS GFTFGDYV MSWFRQAPGKGLEWVGF IRSKAHGGTT EYAASVNGRFSISRDDSKTIAYLQMNSLKSEDTAVYYC TWLRNDYYYGMDV 3.23 VH  EVQLLESGGGLVQPGGSLRLSCAAS GFTFSSYA MSWVRQAPGKGLEWVSA ISGSGGST YYADSVKGRFTISRDNSKNTLYLQMNSLRAEDTAVYYC AK                  WGQGTLVTVSS..
7.1c12   EVQLLESGGGLVQPGGSLRLSCAAS GFTFSSYA MSWVRQAPGKGLEWVSA ISGSGGNT YYADSVKGRFTISRDNSKNTLDLQMNSLRGEDTAVYYC AKDRHNYGYVPFDY 3.7 VH   EVQLVESGGGLVQPGGSIRLSCAAS GFTFSSYW MSWVRQAPGKGLEWVAN IKQDGSEK YVVDSVKGRFTISRDNAKNSLYLQMNSLRAEDTAVYYC AR                  WGQGTMVTVSS..
1.13a9   EVQLVESGGGLVQPGGSIRLSCAAS GFTFSNYW MTWVRQAPGKGLEWVAN IKEDGSEK YVVDSVKGRFTLSRDNAKNSLYLQMNSLRAEDTAVYYC AKEGALLMFGVLRPRAFDI
```

Fig. 2(B)

```
1-27 Vk    DIQMTQSPSSLSASVGDRVTITCRAS QGISNY LAWYQQKPGKVPKLLIY AAS TLQSGVPSRFSGSGSGTDFTLTISSLQPEDVATYYC QKYNSAP   FPGRTMEEIKR..
7.9c2      DIQMTQSPSSLSASVGDRVTITCRAS QGITNY LAWYQQKPGKVPKLLIY AAS ILQSGVPSRFSGSGSGTDFTLTISSLQPEDVATFYC QKYNIAPCF FPGRTMEEIRG..
7.2e7      DIQMTQSPSSLSASVGDRVTITCRAS QGITNY LAWYQQKPGKVPKLLIY AAS ILQSGVPSRFSGSGSGTDFTLTISSLQPEDVATFYC QKYNIVPCF FPGRTMEEIRG..
7.9g10     DIQMTQSPSSLSASVGDRVTITCRAS QDISNY LAWYQQKPGKVPKLLIY AAS TLQSGVPSRFSGSGSGTDFTLTISSLQPEDVATYYC QKSNNAPLT FGGGTKVEIKR..
1.6e1      DIQMTQSPSSLSASVGDRVTITCRAS QGISNY LAWYQQKPGKVPKLLIY AAS TLQSGVPSRFSGSGSGTDFTLTISSLQPEDVATYYC QKYNSAPWT FGQGTKVEIKR..
5.11h8     DIQMTQSPSSLSASVGDRVTITCRAS QGISNY LAWYQQKPGKVPKLLIY AAS TLQSGVPSRFSGSGSGTDFTLTISSLQPEDVATYYC QKYNSAPWT FGQGTKVEIKR..

4-1 Vk     DIVMTQSPDSLAVSLGERATINCKSS QSVLYSSNNKNY LAWYQQKPGQPPKLLIY WAS TRESGVPDRFSGSGSGTDFTLTISSLQAEDVAVYYC QQYYSTP
5.5e11     DIVMTQSPDSLAVSLGERATINCKSS QSVLYGSNNKNY LAWYQQKPGQPPRLLIY WAS TRESGVPDRFSGSGSGTDFTLTISSLQAEDVAVYYC QQYYSTPYT FGQGTKLEIKR..

3-15 Vk    EIVMTQSPATLSVSPGERATLSCRAS QSVSSN LAWYQQKPGQAPRLLIY GAS TRATGIPARFSGSGSGTEFTLTISSLQSEDFAVYYC QQYNNW
7.7f3      EIVMTQSPATLSVSPGERATLSCRAS QSVSSN LTWYQQKPGQAPRLLIY GAS TRATGIPTRFSGSGSGTEFTLTISSLQSEDFAVYYC QQYNNWPIT FGQGTRLEIKR..
4.2c3      EIVMTQSPATLSVSPGERATLSCRAS QSVSSN LTWYQQKPGQAPRLLIY GAS TRATGIPTRFSGSGSGTEFTLTISSLQSEDFAVYYC QQYNNWPIT FGQGTRLEIKR..
4.2f1      EIVMTQSPATLSVSPGERATLSCRAS QSVSSN LTWYQQKPGQAPRLLIY GAS TRATGIPTRFSGSGSGTEFTLTISSLQSEDFAVYYC QQYNNWPIT FGQGTRLEIKR..
4.9f12     EIVMTQSPATLSVSPGERATLSCRAS QSVSSN LAWYQQKPGQAPRLLIY GAS TRATGIPARFSGSGSGTEFTLTISSLQSEDFAVYYC QQYNNWPIT FGQGTRLEIKR..
4.9e5      EIVMTQSPATLSVSPGERATLSCRAS QSVSSN LAWYQQKPGQAPRLLIY GAS TRATGIPARFSGSGSGTEFTLTISSLQSEDFAVYYC QQYNNWPIT FGQGTRLEIKR..
4.7a6      EIVMTQSPATLSVSPGERATLSCRAS QSVSSN LAWYQQKPGQAPRLLIY GAS TRATGIPARFSGSGSGTEFTLTISSLQSEDFAVYYC QQYNNWPIT FGQGTRLEIKR..
7.7h8      EIVMTQSPATLSVSPGERATLSCRAS QSVSSD LAWYQQKPGQAPRLLIY GAS TRATGIPARFSGSGSGTEFTLTISSLQSEDFAVYYC QQYNNWPIT FGQGTRLEIKR..
7.3a9      EIVMTQSPATLSVSPGERATLSCRAG QSVSSD LAWYQQKPGQAPRLLIY GAS TRATGIPARFSGSGSGTEFTLTISSLQSEDFAVYYC QQYNNWPIT FGGGTKVEIKR..
7.6c11     EIVMTQSPATLSVSPGERATLSCRAS QSVSSN LAWYQQKPGQAPRLLIY GAS TRATGIPARFSGSGSGTEFTLTISSLQSEDFAVYYC QQYNNWPLT FGGGTKVEIKR..
5.2b7      EIVMTQSPATLSVSPGERATLSCRAS QSVGSN LAWYQQKPGQAPRLLIY GAS TRATGIPARFSGSGSGTEFTLTISSLQSEDFAVYYC QQYNNWPLT FGGGTKVEMKR..
7.9c10     EIVMTQSPATLSVSPGERATLSCRAS QSVSSN LAWYQQKPGQAPRLLIY GAS TRATGIPARFSGSGSGTEFTLTISSLQSEDFAVYYC QQYNNWPYT FGGGTKVEIKR..
7.9g1      EIVMTQSPATLSVSPGERATLSCRAS QSVSSN LAWYQQKPGQTPRLLIY GAS TRATGVPARFSGSGSGTEFTLTISSLQSEDFAVYYC QQYNNWPLT FGGGTKVEIKR..
2.9d7      EIVMTQSPATLSVSPGERATLSCRAS QSVSSN LAWYQQKPGQAPRLLIY GAS TRATGIPARFSGSGSGTEFTLTISSLQSEDFAVYYC QQYNNWPLT FGGGTKVEIKR..
1.3h2      EIVMTQSPATLSVSPGERATLSCRAS QSVSIN LAWYQQKPGQAPRLLIY DTS ARATGIPARFSGSGSGTEFTLTISSLQSEDFAVYYC QQYNNWPFT FGPGTKVDIKR..
7.2h5      EIVMTQSPATLSVSPGERATLSCRAS QSVSSN LAWYQKKPGQAPRLLIY GAS TRVTGIPARFSGSGSGTEFTLTISSLQSEDFAVYYC QQYNNWPLT FGGGTKVEIKR..
1.10e9     EIVMTQSPATLSVSPGESATLSCRAS QTIYSN LAWYQRKPGQAPRLLIY RAS TRATGIPARFSGSGSGTEFTLTISSLQSEDFAVYCC QQFNNWPYT FGQGTKLEIKR..
1.8e5      EIVMTQSPATLSVSPGERATLSCGAS PSVSTN LAWYQQRPGQAPRLLIY GIS TRAAGIPARFSGTGSGGTEFTLTISSLQSEDFALYYC QQYNNWPYT FGQGTKLEIKR..
1.8c5      EIVMTQSPATLSVSPGERATLSCRAS PSVSSN LAWYQQRPGQAPRLLIY GTS TRATGIPARFSGSGSGTEFTLTISSLQSEDFAVYYC QQYNNWPYT FGQGTKLEIKR..
7.1c12     EIVMTQSPATLSVSPGERATLSCRAS QSVNSN LVWYQQKPGQAPRLLIY GAS TRATGIPARFSGSGSGTEFTLTISSLQSEDFAVYYC QQYNTWPPWT FGQGTKVEIKR..

1-9 Vk     DIQLTQSPSFLSASVGDRVTITCRAS QGISSY LAWYQQKPGKAPKLLIY AAS TLQSGVPSRFSGSGSGTDFTLTISSLQPEDFATYYC QQLNSYP
7.5d3      DIQLTQSPSFLSASVGDRVTITCRAS QGISSY LAWYQQKPGKAPKLLIY AAS TLQSGVPSRFSGSGSGTDFTLTISSLQPEDFATYYC QQLNSYPWT FGQGTKVEIKR..

2-28 Vk    DIVMTQSPLSLPVTPGEPASISCRSS QSLLHSNGYNY LDWYLQKPGQSPQLLIY LGS NRASGVPDRFSGSGSGTDFTLKISRVEAEDVGVYYC MQALQTP
2.6h11     DIMMTQSPLSLPVTPGEPASISCRSS QRLLHSNGYSY VDWYLQKPGQSPQLLIY LGS DRASGVPDRFSGSGSGTDFTLKISRVEAEDVGVYYC MQTLQTPWT FGGGTKVEIKR..
1.17f10    DIVMTQSPLSLPVTPGEPASISCRSS QSLLHSNGYNY LDWYLQKPGQSPQLLIY LGS NRASGVPDRFSGSGSGTDFSLKISRVEAEDVGVYYC MQVLQTPWT FGGGTKVEIKR..
1.12g2     DIVMTQSPLSLPVTPGEPASISCRSS QSLLHSNGYNY LDWYLQKPGQSPQLLIF LGS NRASGVPDRFSGSGSGTDFTLKISRVEAEDVGAYYC MQVLQTPWT FGGGTKVEIKR..
1.5d6      DIVMTQSPLSLPVTPGEPASISCRSS QSLLHSNGYNY LDWYLQKPGQSPQLLIY LGS NRASGVPDRFSGSGSGTDFTLKISIVEAEDAGVYYC MQVLQTPWT FGGGTKVEIKR..
1.13a9     DIVMTQSPLSLPVTPGEPASISCRSS QSLLHSNGYNY LDWYLQNPGQSPHLLIY LAS NRASGVPDRFSGSGSGTDFTLKISRVEAADVGVYYC MQALQTPYT FGGGTKLEIKR..
7.7g6      DIVMTQSPLSLPVTPGEPASISCRSS QSLLHSNGYNY LDWYLQKPGQSPQLLIY LGS NRASGVPDRFSGSGSGTDFTLKISRVEAEDVGIYYC MQALQTPLI FGGGTKVEIKR..
1.6c2      DIVMTQSPLSLPVTPGEPASISCRSS QSLLHSNGYNY LDWYLQKPGQSPQLLIY LGS NRASGVPDRFSGSGSGTDFTLKISRVEAEDVGIYYC MQALQTPYT FGQGTKLEIKR..
1.6f9      DIVMTQSPLSLPVTPGEPASISCRSS QSLLHSNGYNY LDWYLQKPGQSPQLLIY LGS NRASGVPDRFSGSGSGTDFTLKISRVEAEDVGIYYC MQALQTPYT FGQGTKLEIKR..
```

Fig. 2(B) (continued)

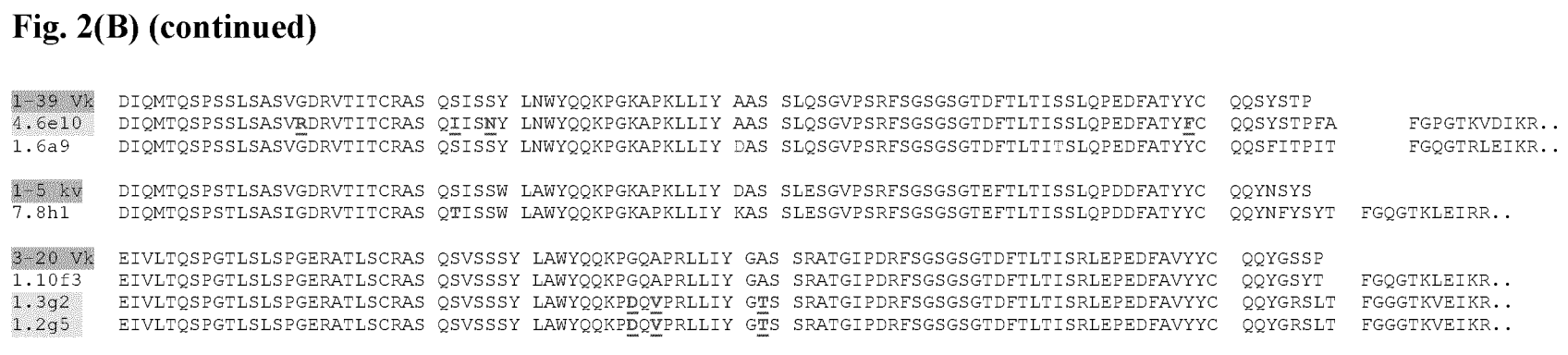

```
1-39 Vk  DIQMTQSPSSLSASVGDRVTITCRAS QSISSY LNWYQQKPGKAPKLLIY AAS SLQSGVPSRFSGSGSGTDFTLTISSLQPEDFATYYC QQSYSTP
4.6e10   DIQMTQSPSSLSASVRDRVTITCRAS QIISNY LNWYQQKPGKAPKLLIY AAS SLQSGVPSRFSGSGSGTDFTLTISSLQPEDFATYFC QQSYSTPFA  FGPGTKVDIKR...
1.6a9    DIQMTQSPSSLSASVGDRVTITCRAS QSISSY LNWYQQKPGKAPKLLIY DAS SLQSGVPSRFSGSGSGTDFTLTITSLQPEDFATYYC QQSFITPIT  FGQGTRLEIKR...

1-5 kV   DIQMTQSPSTLSASVGDRVTITCRAS QSISSW LAWYQQKPGKAPKLLIY DAS SLESGVPSRFSGSGSGTEFTLTISSLQPDDFATYYC QQYNSYS
7.8h1    DIQMTQSPSTLSASIGDRVTITCRAS QTISSW LAWYQQKPGKAPKLLIY KAS SLESGVPSRFSGSGSGTEFTLTISSLQPDDFATYYC QQYNFYSYT  FGQGTKLEIRR...

3-20 Vk  EIVLTQSPGTLSLSPGERATLSCRAS QSVSSSY LAWYQQKPGQAPRLLIY GAS SRATGIPDRFSGSGSGTDFTLTISRLEPEDFAVYYC QQYGSSP
1.10f3   EIVLTQSPGTLSLSPGERATLSCRAS QSVSSSY LAWYQQKPGQAPRLLIY GAS SRATGIPDRFSGSGSGTDFTLTISRLEPEDFAVYYC QQYGSYT   FGQGTKLEIKR...
1.3g2    EIVLTQSPGTLSLSPGERATLSCRAS QSVSSSY LAWYQQKPDQVPRLLIY GTS SRATGIPDRFSGSGSGTDFTLTISRLEPEDFAVYYC QQYGRSLT  FGGGTKVEIKR...
1.2g5    EIVLTQSPGTLSLSPGERATLSCRAS QSVSSSY LAWYQQKPDQVPRLLIY GTS SRATGIPDRFSGSGSGTDFTLTISRLEPEDFAVYYC QQYGRSLT  FGGGTKVEIKR...
```

Fig. 2(C)

Light variable chains

```
Vk3-15
60c12:  EIVMTQSPATLSVSPGERATLSCRAS QSVSSN LAWYQQKPGQAPRLLIY GAS TRATGIPARFSGSGSGTEFTLTISSLQSEDFAVYYC QHYNNWPLTF  GGGTKVEIKK
44c11:  EIVMTQSPATLSVSPGERATLSCRAS QSVSNN LAWYQQKPGQAPRLLIY GAS TRATGIPARFSGSGSGTEFTLTISSLQSEDFAVYYC QQYNNWPFTF  GPGTKVDIK
38f1:   EIVMTQSPATRSVSPGERATLSCRAS QTISSY LAWYQQKPGQAPGLLIY GAS NRATGIPARFSGSGSGTEFTLTISSLQSEDFVIYYR QQYNNWPLTF  GGGTKVEIK
24f5:   EVVMTQSPATLSVSPGERASLSCRAS QTVNSN LAWYQQKPGQTPRLLIY GAS TRATGIPARFSGSGSGTEFTLTISRLQSEDFTVYYC QQYNNWPLTF  GPGTKVDIK
47c4:   EIVMTQSPATLSVSPGERATLSCRAS QSVSSN LAWYQQKPGQAPRLLIY GAS TRATGIPARFSGSGSGTEFTLTISSLQSEDFAVYYC QQYNNWPITF  GGGTKVDIK
52d9:   EIVMTQSPATLSVSPGERATLSCRAS QSVSSN LAWYQQKPGQAPRLLIF RAS TRATGIPARFSGSGSGTEFTLTISSLQSEDFAVYYC QQYNSWPITF  GGGTRLEIK
58d7:   EIVMTQSPATLSVSPGERATLSCRAS QSVSSN FAWYQHKPGQAPRLLIY GAS TRVTGIPARFSGSGSGTEFTLTISSLQSEDCAIYYC QQYNNWPFTF  GPGTKVDIK
65h9:   ETVMTQSPATLSVSPGERATLSCRAS QSVSSN LAWYQQKPGQAPRLLIY GAS TRATGIPARFSGSGSGTEFTLTISSLQSEDFAVYYC QQYNSWPITF  GQGTRLEIK
48d5:   EIVMTQSPATLSVSPGERATLSCRAS QSISSN LAWYQQKPGQAPRLLIY GAS TRATGIPARFSGSGSGTEFTLTISSLQSEDFAIYYC QQFNNWITF   GQGTKLEIK
43f11:  EIVMTQSPATLSVSPGERATLSCRAS QSVISS LAWYQQTPGQAPRLLIY GAS TRATGIPARFSGSGSGTEFFTLISSLQSEDFAVYYC QQYNNWPPYTF GPGTKMDIK
50c12:  RIVMTQSPATLSVSPGERATLSCRAS QSVSSN LAWYQQKPGQVPRLLIY GAS TRATGIPARFSGSGSGTEFTLTISSLQSEDFAVYYC QQYHYWPFTF  GPGTKVDIK
45h1:   RIVLTQSPATLSVSPGERATLSCRAS QSIRSN LAWYQQKPGQAPRHLIY GAS TRATGIPARFSGSGSGTEFTLTISSLQSEDFAIYYC QQYNNWPLTF  GQGTRLEIK

Vk3-11
41b5:   EIVLTQSPATLSLSPGERATLSCRAS QSVSSY LAWYQQKPGQAPRLLIY DAS NRATGIPARFSGSGSGTDFTLTISSLEPEDFAVYYC QQRSNWP
        EIVLTQSPATLSLSPGERATLSCRAS QSVSSS LAWYQQKPGQAPRLLIY DTS NRATGIPARFSGSGSGTDFTLTISSLEPEDFAVYYC QQRSNTF    GQGTKLEIK

Vk1-5
52a7:   DIQMTQSPSTLSASVGDRVTITCRAS QSISSW LAWYQQKPGKAPKLLIY KAS SLESGVPSRFSGSGSGTEFTLTISSLQPDDFATYYC QQYNSYS
53c8:   DIQMTQSPSTLSASVGDRATITCRAS QSISTW LAWYQQKPGKAPKLLIY KAS SLESGVPSRFSGSGSGTEFTLTISRLQPDDFATYYC QQYKTYSPFSF GPGTNVDIE
        DIQMTQSPSTLSASVGDRVTITCRAS QSISSW LAWYQQKPGKAPKLLIY KAS SLESGVPSRFSGSGSGTEFTLTISSLQSDDFATYYC QQYKSYSPFSF GPGTKVDIK

Vk1-9
44g3:   DIQLTQSPSFLSASVGDRVTITCRAS QGISSY LAWYQQKPGKAPKLLIY AAS TLQSGVPSRFSGSGSGTEFTLTISSLQPEDFATYYC QQLNSYP
62f8:   DIQLTQSPSFLSASVGDRVTITCRAS QGISSY LAWYQQKPGKAPKLLIY AAS TLQSGVPSRFSGSGSGTEFTLTISSLQPEDFATYYC QQLNSYPLTF  GGGTKVEIK
1B2:    VIQLTQSPSFLSASVGDRVTITCRAS QDISSY LAWYQQKPGKAPKLLIY GAS TLQSGVPSRFSGSGESGTEFTLTISSLQPEDFATYYC QQLNSYPYTF GQGTKLEIK
63c12:  DIQLTQSPSFRSASVGDRVTITCRAS QDISSY LAWYQQKPGKAPKLLIY GAS TLQSGVPSRFSGSGSGTEFTLTISSLQPEDFATYYC QQLNSYPYTF  GQGTKVEIK
        DIQLTQSPSFLSASVGDRVTISCRAS QGISSY LAWYQQKPGKGPKLLIY AAS TLQSGVPSRFSGSGSGTEFTLTISSLQPEDFATYYC QQLNSYPLTF GGGTKVEIK

Vk1-27
57f5:   DIQMTQSPSSLSASVGDRVTITCRAS QGISNY LAWYQQKPGKVPKLLIY AAS TLQSGVPSRFSGSGSGTDFTLTISSLQPEDVATYYC QKYNSAP
        DIQMTQSPSSLSASVGDRVTITCRAS QGINNY LAWYQQKPGKVPKLLIY AAS TLQSGVPSRFSGSGSGTDFTLTISSLQPEDVATYYC QKYYSAPLTF GGGTKVEIK
```

Fig. 2(C) (Continued)

```
Vk1.39
62a11:  DIQMTQSPSSLSASVGDRVTITCRAS QSISSY     LNWYQQKPGKAPKLLIY AAS SLQSGVPSRFSGSGSGTDFTLTISSLQPEDFATYYC QQSYSTP
        DIQMTQSPSSLSASVGDRVTITCRAS QSLGSY     LNWFQQKPGKAPKLLIY GAF SLQSGVPSRFSGSGSGTDFTLTISSLQPEDFAIYYC QQSYTTPLTF GGGTKVEIK

Vk2.28
66b1:   DIVMTQSPLSLPVTPGEPASISCRSS QSLLHSNGYNY LDWYLQKPGQSPQLLIY LGS NRASGVPDRFSGSGSGTDFTLKISRVEAEDVGVYYC MQALQTP
35e2:   DIVMTQSPLSLPVTPGEPASISCRSS QSLLHSNGYNY LDWYLQKPGQSPQLLIY LGS YRASGVPDRFSGSGSGTDFTLKISRVEAEDVGVYYC MQALQTPWTF GQGTKVEIK
55h1:   DIVMTQSPLLPVTPEEPASISCRSS  QSLLHNNGYNY LDWYLQKPGQSPQLLIY LGS NRASGVPDRFSGSGSGTDFSLKISRVEAEDVGVYYC MQALQTPWTF GQGTKVEIK
        DIVMTQSPLSLPVTPGEPASISCRSS QSLLHGNGYNY LDWYLQKPGQSPQLLIY LGS NRASGVPDRFSGSGSGTDFTLKISRVEAEDVGVYYC MQALQTPFTF GPGTKVDIK

Vk4.1
28d9:   DIVMTQSPDSLAVSLGERATINCKSS QSVLYSSNNKNY LAWYQQKPGQPPKLLIY WAS TRESGVPDRFSGSGSGTDFTLTISSLQAEDVAVYYC QQYYSTP
        DIVMTQSPDSLAVSLGERATINCKSS QSVLASSNMNY  LAWYQQKPGQPPKLLIY WAS IRESGVPDRFSGSGSGPGTDFTLTISSLQTEDVAVYYC HQYYSIPNTF GGGTKLEIK
```

Heavy variable chains

```
Vh3.33
62a11:  QVQLVESGGGVVQPGRSLRLSCAAS GFTFSSYG MHWVRQAPGKGLEWVAV IWYDGSNK YYADSVKGRFTISRDNSKNTLYLQMNSLRAEDTAVYYCAR
62a11:  QVQLVESGGGVVQPGRSLRLSCAVS GFIFSNYG MHWVRQAPGKGLEWVAV IWYDGSKK FHTDSVKGRFTISRDNSKNTLYLYLQMNSLRAEDTAVYYC ARDQGITMVRGLIILDY       WGQGTLVTVSS
52d9:   QVHLVESGGGVVQPGRSLRLSCAAS GFTFSSYG MHWVRQGPGKGLEGVAG IWFDGSHE YYADAVKGRFTISRDNSKNTLYLEMSSLRAGDTGIYYC ARGGDILTP                WGQGSLVTVSS
45h1:   QVQLVESGGGVVQPGRSLRLSCAAS GFTFSSYG IHWVRQAPGKGLEWVAL IWYDENNK YYGDSVKGRFTISRDNSKNTLYLQMNSLRAEDTAVYYC AREGDGSYQGMDV            WGQGTTVTVSS
52a7:   QVQLLESGGGVVQPGRSLRLSCAAS GSSFSTDV MHWVRQAPGKGLEWVAV IWYDGSNK YYADSVKGRFTISRDNSKNTLYLQMNSLRAEDTAVYYC AREGVYQTFMYPDAFDI        WGQGTMVTVSS
43f11:  QVQLVESGGGVVQPGRSLRLSCAAS GFDFSNYG MHWVRQAPGKGLEWVAV IWYDAVNK YYADSVKGRFTISRDNSKNTLYLQMNSLRAEDTAVYYC ARDQTYYDSSGYFFDY         WGQGTLVTVSS
35e2:   LVQLVDSGGGVVQPGRSLRLSCAAS GFTFSSYA MHWVRQAPGKGLEWVAV IWFDGSNK FYADSVKGRFTISRDNSKNTMYLQMHSLGAEDTAEYYC ARGGAYGLFDY             WGQGTMVTVSS
53c8:   QVQLLESGGGVVQPGRSLRLACAAS GFTFSSYV MHWVRQAPGKGLEWVAV IWHDGSNK YYADSVKGRFTISRDNSKNTLYLQMNSLRAEDTAVYYC AREGMYQPLLYPDAFDI        WGQGTVTVSS
41b5:   QVHLVESGGGVVQPGRSLRLSCAAS GFTFSSYG MHWVRQAPGKGLEWVAV IWYDGFNK YYADSVKGRFTISRDNAKNTLYLQMNSLRAEDTAIYYC ARSRISNFDILTGYYHYYYGMDV  WGQGTVTVSS
62f8:   QVQLVESGGGVVQPGRSLRLSCAAS GFTFSSYG MHWVRQAPGKGLEWVAI IWYDENNK YYADSVKGRFTISRDNSKNTLYLQMNSLRAEDTAVYYC TRERAKYYGSGRDYYYYGMDV     WGQGTVTVSS
48d5:   QVQLVESGGGVVQPGKSLRLSCAAS GFTFSNYG MHWVRQAPGKGLEWVSF IWYDGSDK GYADSVKGRFTISRDNSKNTLYLQMNSLRAEDTAVYFC AKTFASSWYGDYFDY          WGQGTLVTVSS
63c12:  QVYLVESGGGVVQPGGSLRLSCAAS GFTFGYYG MHWVRQTPGKGLEWVAV IFYDGSNK YYADSAKGRFTISRDNSKNSLSLQMNSLRVEDTAVYYC ARGGSNRYYVYLDA           WGQGVSVTVSS
1b2:    QVQLVESGGGVVQPGRSLRLSCAAS GFTFSSYG MHWVRQAPGKGLEWVAI IWYDENNK YYADSVKGRFTISRDNSKNTLYLQMNSLRAEDTAVYYC TRERAKYYGSGRDYYYYGMDV     WGQGTTVTVSS
47c4:   QVHLVESGGGVVQPGRSLRLSCAAS GFDFNNYG MHWVRQAPGKGLEWVAV IWYDAVNK YYGDSVKGRFTISRDNSKNTLYLQMNSLRAEDTAVYYC ARDQTYYDSSGYFFDC         WGQGTLVTVSS
58d7:   QVQLVESGGGVVQPGRSLRLSCVAS GLTFSTYA MHWVRQAPGKGLEWVAV IWDDGINK NYADSVKGRFTISRDNSKKTLFLQMNSLRSEDTAVYFC ARDRLPVPGGLFDY           WGQGTLVTVSS
```

Fig. 2(C) (Continued)

```
Vh3-23: EVQLLESGGGLVQPGGSLRLSCAAS GFTFSSYA MSWVRQAPGKGLEWVSA ISGSGGST YYADSVKGRFTISRDNSKNTLYLQMNSLRAEDTAVYYC AK
57f5:   EVQLLESGGGLVQPGGSLRLSCAAS GFIFSRYA MSWVRQAPGKGLEWVSG ISGSGDNP YYADSMKGRFTISRDNSKNTLFLQMNSLRAEDTAVYYC AKGGLLWFGDLLDPFDY WGQGTLVTVSS
44c11:  EVKLLESGGGLVQPGGSLRLSCAAS GFIFSRYA MNWVRQAPGKGLEWVSV VSGSGDYT YYADFVKGRFTISRDNAKNTLYLQMKSLRAEDTAIYYC ARTIVWFGELFPSDY WGQGTLVTVSS
50c12:  EVQLLESGGGLVQPGGSLRLSCAAS GFTFSSYA MNWVRQAPGKGLEWVSV ISGSGDYT YYADFVKGRFTISRDNSKNTLYLQMNSLRAEDTAIYYC ARTIVWFGELFPSDY W
60c12:  EVQLLESGGGLVQPGGSLRLSCAAS GFTFRSYA MSWVRQAPGKGLEWVSG ISGSGGIT SYADSVKGRFTISRDNSKNTLYLQMNSLRAEDTAVYYC AREDYYGSGSYWYLDL WGRGTLVTVSS
65h9:   EVQLLESGGGLVQPGGSLRLSCAAS GFTFSIYA MNWVRQAPGKGLEWVSG ISGSGNHI HYADSVKGRFTISRENSKSTLYLHMNSLRAEDTAVYYC AKDGGLYWFDL WGRGTLVTVSS
44g3:   EVQLLESGGGLVQPGGSLRLSCAAS GFTFSIYA MNWVRQAPGKGLEWVSG ISGSGNHI HYADSVKGRFTISRENSKSTLYLHMNSLRAEDTAVYYC AKDGGLYWFDL WGRGTLVTVSS

Vh3-15: EVQLVESGGGLVKPGGSLRLSCAAS GFTFSNAW MSWVRQAPGKGLEWVGR IKSKTDGGTT DYAAPVKGRFTISRDDSKNTLYLQMNSLKTEDTAVYYC TT
55H11:  EVQLVESGGGLVKPGGSLRLSCSAS GFTFSNAW MSWVRQAPGKGLEWVGR IKTKTDGGTT DYAAPVKGRFTISRDDSKNTMYLQMNSLKTEDTALYYC STPGIAAAGTWYYWYWYGMDV WGQGTTVTVSS

Vh1-69: QVQLVQSGAEVKKPGSSVKVSCKAS GGTFSSYA ISWVRQAPGQGLEWMGG IIPIFGTA NYAQKFQGRVTITADKSTSTAYMELSSLRSEDTAVYYC AR
66b1:   QVQLVQSGAEVKKPGSSVKVSCKGS GGTFSSYA ISWVRQAPGQGLEWMGG IIPFFGAT NYAQKFQGRVTITADKSTSTAYMELSSLRSEDTAVYYC ARYNWNDNYYYGMDV WGQGTTVTVSS

Vh4-38: QVQLQESGPGLVKPSETLSLTCAVS GYSISSGYY WGWIRQPPGKGLEWIGS IYHSGST YYNPSLKSRVTISVDTSKNQFSLKLSSVTAADTAVYYC AR
24f5:   QVQLQESGPGLVKPSETLSLTCDVS GHSIRSGYY WGWIRQSPGKGLIWIGS FFYSGNT YYNPSLKSRVTISVDTSKNQFSLNLSSVTAADTAVYYC AGRGHDSGEYVAPDF WGQGTMITVSS

Vh4-34: QVQLQQWGAGLLKPSETLSLTCAVY GGSFSGYY WSWIRQPPGKGLEWIGE INHSGST NYNPSLKSRVTISVDTSKNQFSLKLSSVTAADTAVYYC AR
38f1:   QVQLRQWGAGLLQPSETLSLTCAVY GESFSGYF WTWIRQAPGKGLEWIGE VDHVGST NYKPSLESLITISVDTSKNQFSLKLTSVTAADTAVYFC ARTGTVFGTSFDY WGQGTLVTVSS 6-1 VH: QVQLQQSGPGLVKPSQTLSLTCAIS GDSVSSNSAA WNWIRQSPSRGLEWLGR TYYRSKWYN DYAVSVKSRITINPDTSKNQFSLQLNSVTPEDTAVYYC AR
28d9:   QVQLQQSGPGLVKPSQTLSLTCAIS GDNVFSNSAA WNWIRQSPSRGLEWLGR TYYRSKWNN DYAVSVKGRITINPDTYKNQFSLQLNPVTPEDTAVYFC ARVPMNRGGMDV WGQGTTVTVSS
```

| constant region | oc43 g1 | oc43 g2b | oc43 g2c | MERS g1 | MERS g2b | MERS g2c | SARS g1 | SARS g2b | SARS g2c | PBS g1 | PBS g2b | PBS g2c |
|---|---|---|---|---|---|---|---|---|---|---|---|---|
| 63c12 | 1 0.047 | 3.364 | 0.047 | 0.047 | 2.826 | 0.048 | 0.051 | 2.779 | 0.109 | 0.059 | 0.136 | 0.060 |
| 63c12 | 2 0.047 | 2.507 | 0.048 | 0.047 | 2.440 | 0.047 | 0.047 | 2.982 | 0.053 | 0.048 | 0.046 | 0.045 |
| 63c12 | 3 0.050 | 2.438 | 0.048 | 0.047 | 2.291 | 0.047 | 0.047 | 2.851 | 0.047 | 0.045 | 0.046 | 0.045 |

Antigen specifc Elisa

OC43     MERS     SARS     PBS control

63C12
In triplo

Fig. 3(A)

Affinities (preliminary) of anti MERS CoV S1

VH3.33 derived H2L2 antibodies

| | | | | |
|---|---|---|---|---|
| 7.7f3 | $1.2 \times 10^{-10}$ | | 7.9g1 | $2.1 \times 10^{-10}$ |
| 4.2c3 | $1.2 \times 10^{-10}$ | | 2.9d7 | $3.5 \times 10^{-10}$ |
| 4.9f12 | $1.3 \times 10^{-10}$ | | 7.9c2 | $1.2 \times 10^{-8}$ |
| 4.7a6 | $1.3 \times 10^{-10}$ | | 7.2e7 | $2.6 \times 10^{-9}$ |
| 7.7h8 | $5.4 \times 10^{-10}$ | | 1.3h2 | $1.9 \times 10^{-9}$ |
| 7.3a9 | $4.3 \times 10^{-10}$ | | 7.5d3 | $6.0 \times 10^{-9}$ |
| 7.6c11 | $4.0 \times 10^{-10}$ | | 4.6e10 | $6.2 \times 10^{-10}$ |
| 5.2b7 | $3.6 \times 10^{-10}$ | | | |
| 7.9c10 | $1.1 \times 10^{-10}$ | | | |

VH1.69 derived H2L2 antibodies

| | | | | |
|---|---|---|---|---|
| 5.5e11 | $3.0 \times 10^{-10}$ | | 1.6c2 | $8.6 \times 10^{-10}$ |
| 7.9g10 | $2.0 \times 10^{-10}$ | | 5.11h8 | $6.8 \times 10^{-11}$ |
| 1.3g2 | $1.1 \times 10^{-9}$ | | | |
| 7.2h5 | $3.6 \times 10^{-10}$ | | | |
| 1.6e1 | $1.1 \times 10^{-10}$ | | | |

VH3.23 derived H2L2 antibodies

| | |
|---|---|
| 7.7a9 | $2.7 \times 10^{-10}$ |

VH6-1 derived H2L2 antibodies

| | |
|---|---|
| 1.10e9 | $4.4 \times 10^{-10}$ |

Table 1. Binding kinetics of mAbs/MERS-S$^{ecto}$ or DPP4/MERS-S$^{ecto}$ from bio-layer interferometry measurements

| mAb | $K_D$ (M) | $k_{on}$ (M$^{-1}$ sec$^{-1}$) | $k_{off}$ (sec$^{-1}$) |
|---|---|---|---|
| 7.7g6 | $3.612 \times 10^{-10}$ | $3.196 \times 10^4$ | $1.154 \times 10^{-5}$ |
| 1.6f9 | $5.298 \times 10^{-10}$ | $1.175 \times 10^4$ | $6.227 \times 10^{-6}$ |
| 1.2g5 | $8.086 \times 10^{-11}$ | $7.587 \times 10^4$ | $6.134 \times 10^{-6}$ |
| 1.8e5 | $3.178 \times 10^{-10}$ | $2.442 \times 10^4$ | $4.232 \times 10^{-6}$ |
| 4.6e10 | $3.592 \times 10^{-10}$ | $3.569 \times 10^4$ | $1.134 \times 10^{-5}$ |
| 1.10f3 | $4.784 \times 10^{-9}$ | $9.550 \times 10^3$ | $4.569 \times 10^{-5}$ |
| 1.6c7 | $5.007 \times 10^{-10}$ | $5.927 \times 10^4$ | $2.968 \times 10^{-5}$ |
| 3.5g6 | $2.246 \times 10^{-9}$ | $2.107 \times 10^4$ | $4.733 \times 10^{-5}$ |
| α-MERS-CTRL | $1.289 \times 10^{-10}$ | $4.576 \times 10^4$ | $5.900 \times 10^{-6}$ |
| DPP4 | $3.416 \times 10^{-9}$ | $1.423 \times 10^4$ | $4.859 \times 10^{-5}$ |

Alexa Fluor 649 fluorescence (A)

Fig. 6
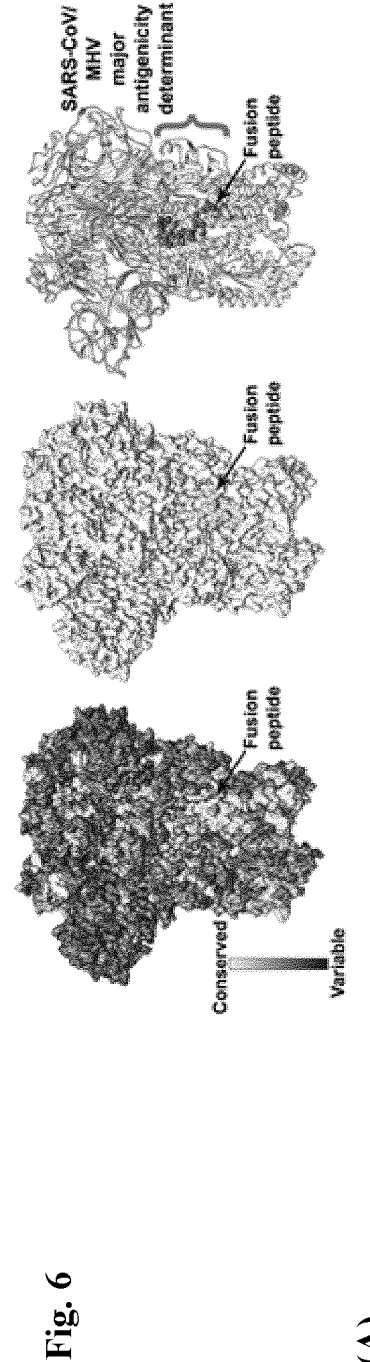
(A)
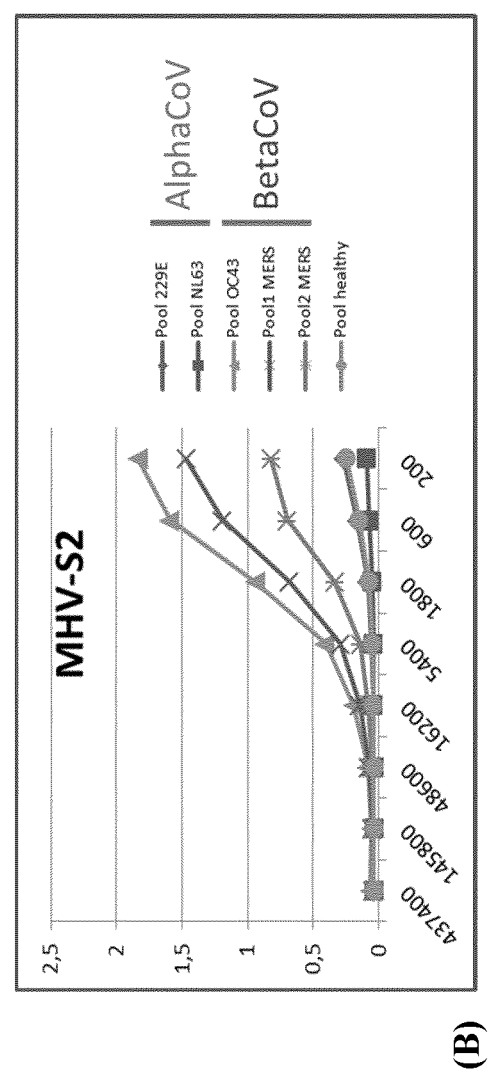
(B)

Fig. 6(C)
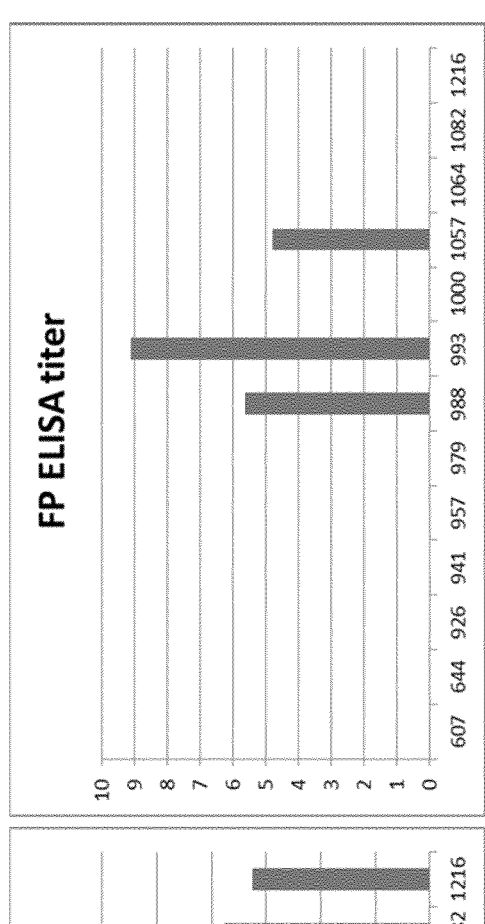
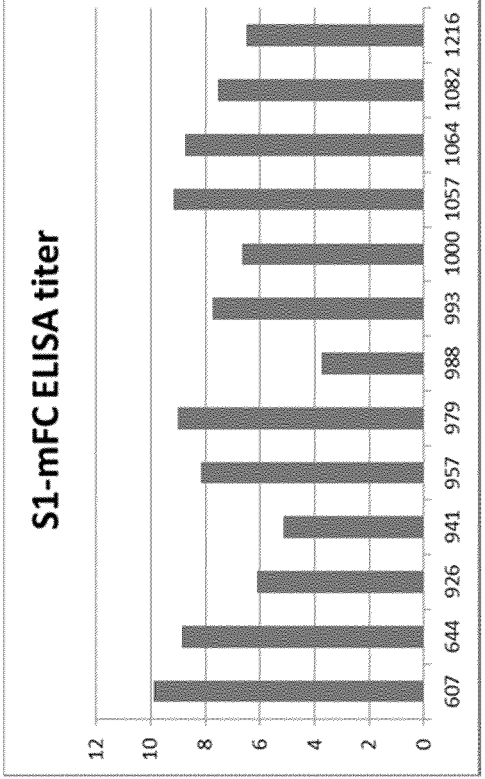

Fig. 8
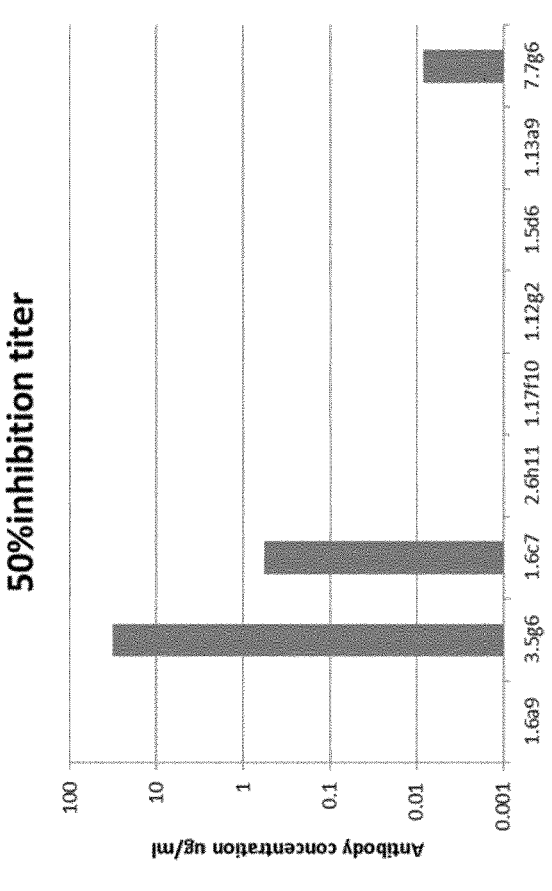
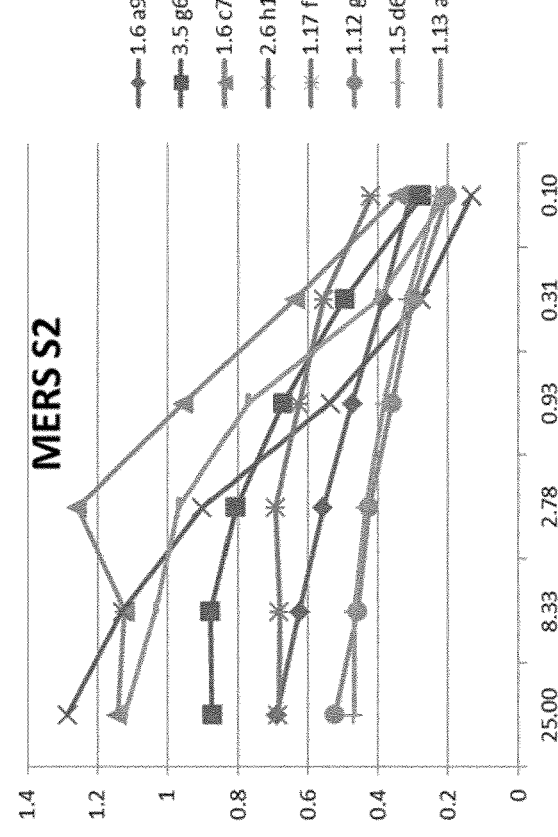

Fig. 9

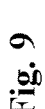 

```
6-1 VH  QVQLQQSGPGLVKPSQTLSLTCAIS GDSVSSNSAA WNWIRQSPSRGLEWLGR TYYRSKWYN DYAVSVKSRITINPDTSKNQFSLQLNSVTPEDTAVYYC AR              WGQGTLVTVSS...
3.5g6   QVQLQQSGPGLVKPSQTLSLTCAIS GHSVSSNSAD WNWIRQSPSRGLEWLGR TYCRSKCYN DYAVSVKSRITINPDTSKNQFSLQLNPVTPEDTAVYYC ARSLGSGTYPFDS   WGQGTLVTVSS...
1.6c7   QVQLQQSGPGLVKPSQTLSLTCAIS GDSVSSDSAA WNWIRQSPSRGLEWLGR TYFRSKWNN HYAVSVKSRITINPDTSKNQFSLLLNPVTPEDTAVYYC ARATLARGALDY

139 VK  DIQMTQSPSSLSASVGDRVTITCRAS QSISSY LNWYQQKPGKAPKLLIY AAS SLQSGVPSRFSGSGSGTDFTLTISSLQPEDFATYYC QQSYSTP
3.5g6   DIQMTQSPSSLSASVGDRVTITCRAS QRISRF LNWYQQTPGKAPKFLIY AAS SLQSGVPSRFSGSGSGTDFTLTISSLQPEDFATYYC QQSYSTPLT   FGGGTTVEIKR...

4-1 VK  DIVMTQSPDSLAVSLGERATINCKSS QSVLYSSNNKNY LAWYQQKPGQPPKLLIY WAS TRESGVPDRFSGSGSGTDFTLTISSLQAEDVAVYYC QQYYSTP
1.6c7   DIVMTQSPDSLAVSLGERATINCKSS QSVLYSSNNMNY LAWYQQKPGQPPKLLIY WAS TRESGVPDRFSGSGSPGTDFTLTISSLQAEDVAVYYC QQYYSTPWT   FGQGTKVEIKR...
```

Fig. 12
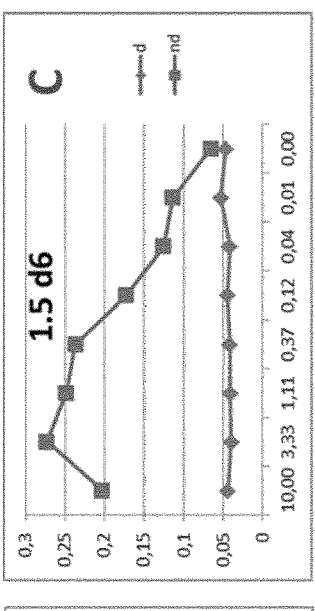
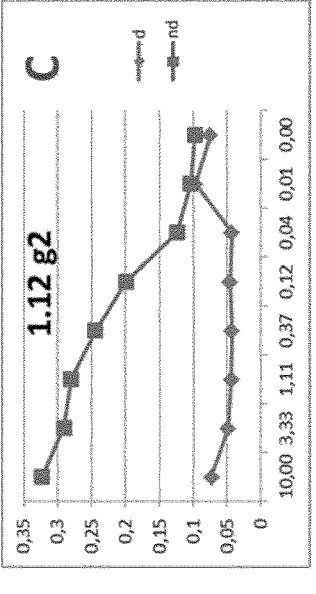
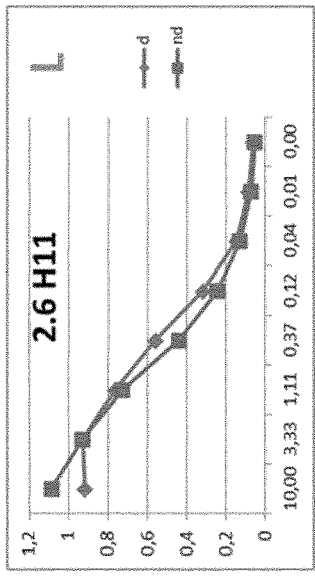
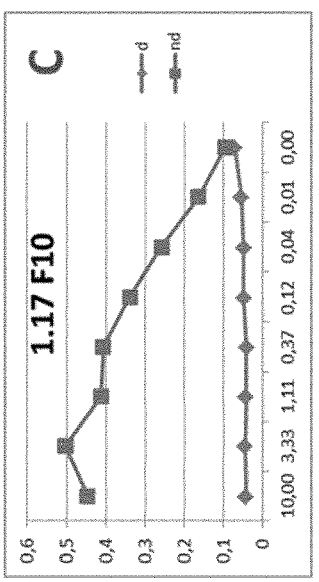
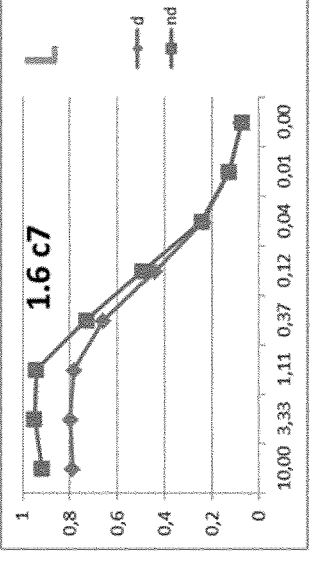
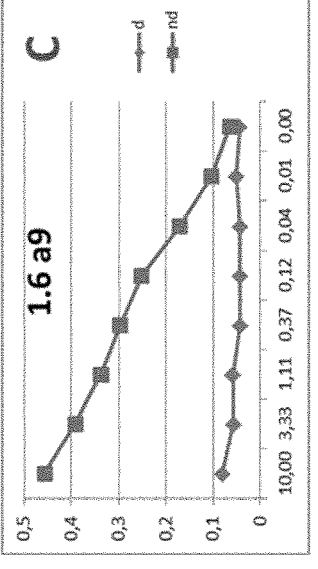
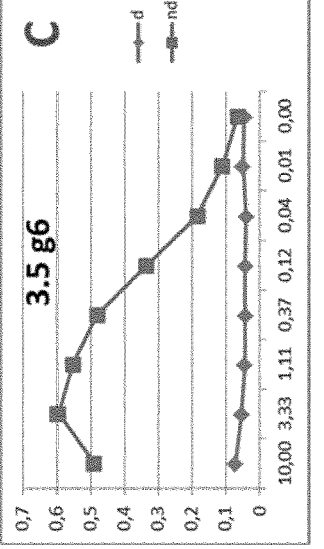

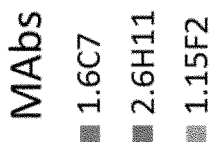
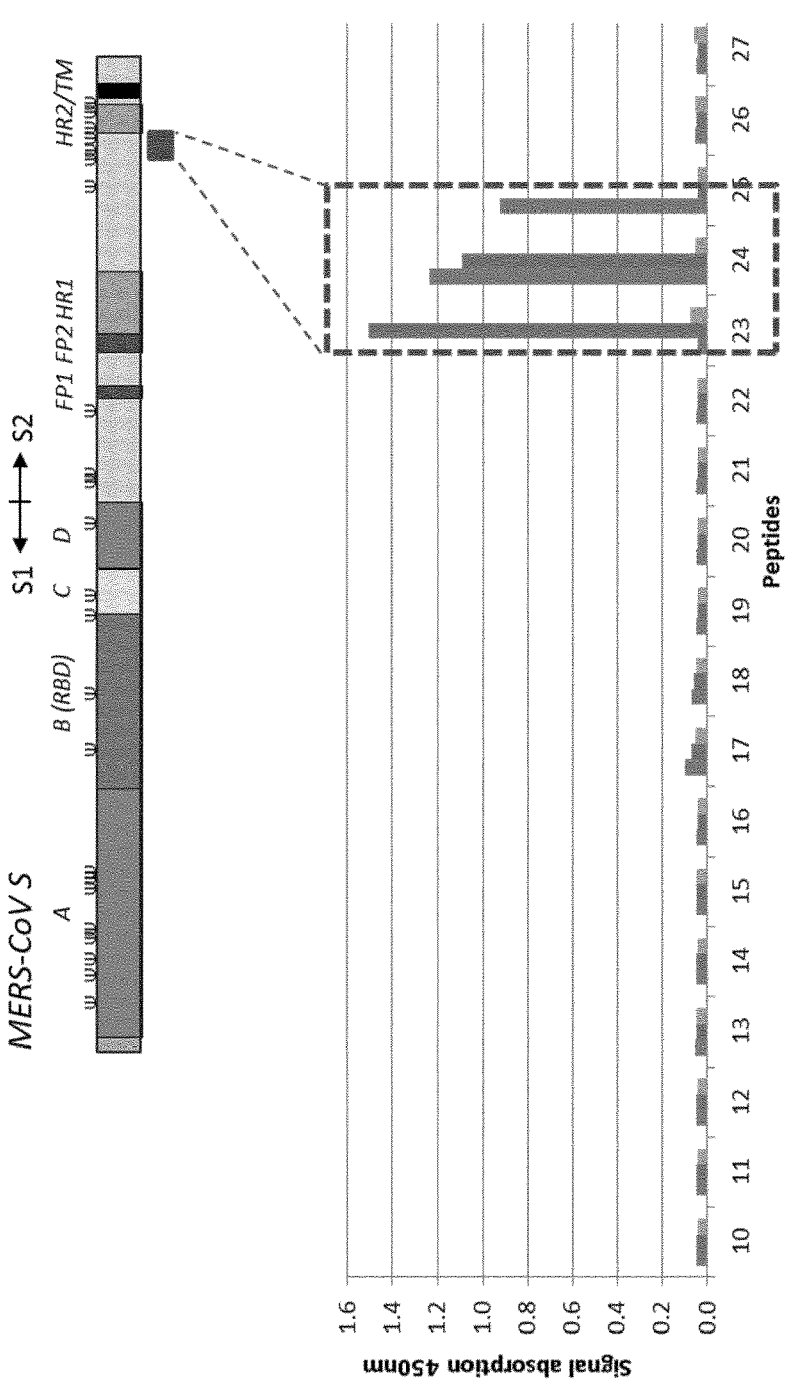
Fig. 13

Fig. 14(B)

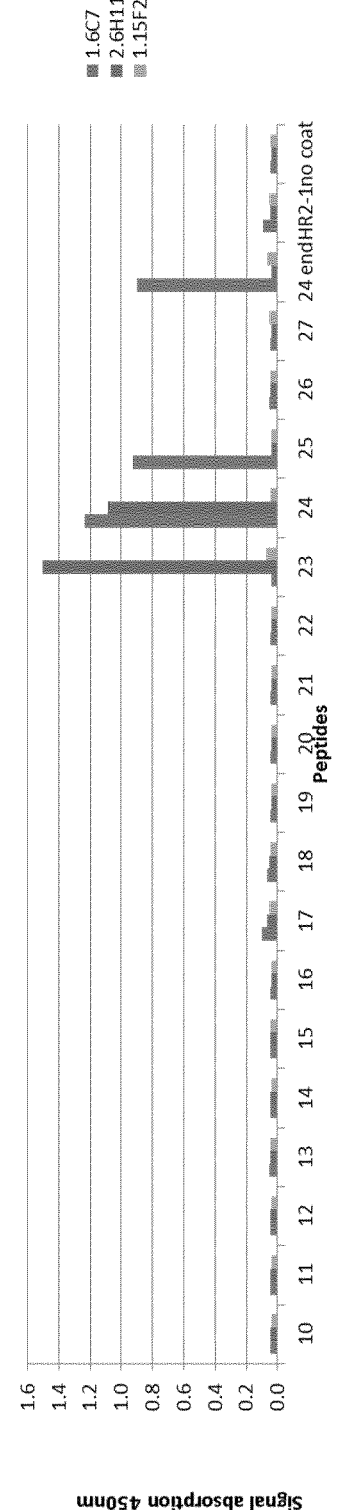

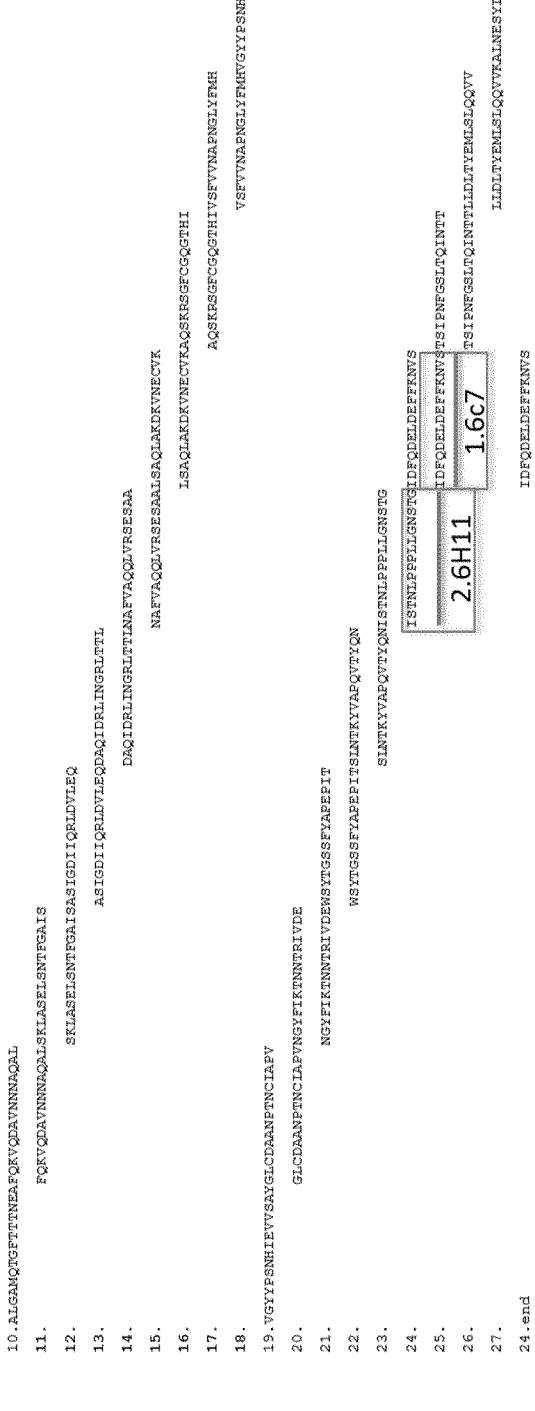

MERS-CoV S peptides (region covered: a.a. 1004-1288)

10. ALGAMQTGFTTNEAFQKVQDAVNNNAQAL
11.        FQKVQDAVNNNAQALSKLASELSNTFGAIS
12.               SKLASELSNTFGAISASIGDIIQRLDVLEQ
13.                      ASIGDIIQRLDVLEQDAQIDRLINGRLTTL
14.                             DAQIDRLINGRLTTLNAFVAQQLVRSESAA
15.                                    NAFVAQQLVRSESAALSAQLAKDKVNECVK
16.                                           LSAQLAKDKVNECVKAQSKRSGFCGQGTHI
17.                                                  AQSKRSGFCGQGTHIVSFVNAPNGLYFMH
18.                                                         VSFVNAPNGLYFMVGYYPSNHIEVVSAY
19. VGYYPSNHIEVVSAYGLCDAANPTNCIAPV
20.        GLCDAANPTNCIAPVNGYFIKTNNTRIVDE
21.               NGYFIKTNNTRIVDEWSYTGSSFYAPEPIT
22.                      WSYTGSSFYAPEPITSLNTKYVAPQVTYQN
23.                             SLNTKYVAPQVTYQNISTNLPPPLLGNSTG
24.                                    ISTNLPPPLLGNSTGIDFQDELDEFFKNVS
25.                                           IDFQDELDEFFKNVSTSIPNFGSLTQINTT
26.                                                  TSIPNFGSLTQINTTLLDLTYEMLSLQQVV
27.                                                         LLDLTYEMLSLQQVVKALNESYIDLKELGN
24.end                                  IDFQDELDEFFKNVS

Fig. 14(C)

```
>MERS-CoV S

MIHSVFLLMFLLTPTESYVDVGPDSVKSACIEVDIQQTFFDKTWPRPIDVSKADGIIYPQ
GRTYSNITITYQGLFPYQGDHGDMYVYSAGHATGTTPQKLFVANYSQDVKQFANGFVVRI
GAAANSTGTVIISPSTSATIRKIYPAFMLGSSVGNFSDGKMGRFFNHTLVLLPDGCGTLL
RAFYCILEPRSGNHCPAGNSYTSFATYHTPATDCSDGNYNRNASLNSFKEYFNLRNCTFM
YTYNITEDEILEWFGITQTAQGVHLFSSRYVDLYGGNMFQFATLPVVDTIKYYSIIPHSI
RSIQSDRKAWAAFYVVKLQPLTFLLDFSVDGYIRRAIDCGFNDLSQLHCSYESFDVESGV
YSVSSFEAKPSGSVVEQAEGVEDCDFSPLLSGTPPQVINFKRLVFTNCNYNLTKLLSLFSV
NDFTCSQISPAAIASNCYSSLILDYFSYPLSMKSDLSVSSAGPISQFNYKQSFSNPTCLI
LATVPHNLTTITKPLKYSYINKCSRLLSDDRTEVPQLVNANQYSPCVSIVPSTVWEDGDY
YRKQLSPLEGGGWLVASGSTVAMTEQLQMGFGITVQYGTDTNSVCPKLEFANDTKIASQL
GNCVEYSLYGVSGRGVFQNCTAVGVRQQRFVYDAYQNLVGYYSDDGNYYCLRACVSVPVS
VIYDKETKTHATLFGSVACEHISSTMSQYSRSTRSMLKRRDSTYGPLQTPVGCVLGLVNS
SLFVEDCKLPLGQSLCALPDTPSTLTPRSVRSVPGEMRLASIAFNHPIQVDQLNSSYFKL
SIPTNFSFGVTQEYIQTTIQKVTVDCKQYVCNGFQKCEQLLREYGQFCSKINQALHGANL
RQDDSVRNLFASVKSSQSSPIIPGFGGDFNLTLLEPVSISTGSRSARSAIEDLLFDKVTI
ADPGYMQGYDDCMQQGPASARDLICAQYVAGYKVLPPLMDVNMEAAYTSSLLGSIAGVGW
TAGLSSFAAIPFAQSIFYRLNGVGITQQVLSENQKLIANKFNQALGAMQTGFTTNEARQ
KVQDAVNNNAQALSKLASELSNTFGAISASIGDIIQRLDVLEQDAQIDRLINGRLTTLNA
FVAQQLVRSESAALSAQLAKDKVNECVKAQSKRSGFCGQGTHIVSFVVNAENGLYEMVVG
YIPSNHIEVVSAYGLCDAANPTNCIAPVNGYFIKTNNTRIVDEWSYTGSSFYAPEPITSL
NTKYVARQVYQNTISTNLPPLLGNSTGIDPQDELDEFEKNVSTSIPNFGSLTQINTTLL
DLTYEMLSLQQVVKALNESYIDLKELGNYTYYNKWPWYIWLGFIAGLVALALCVFFILCC
TGCGTNCMGKLKCNRCCDRYEYDLEPHKVHVH
```

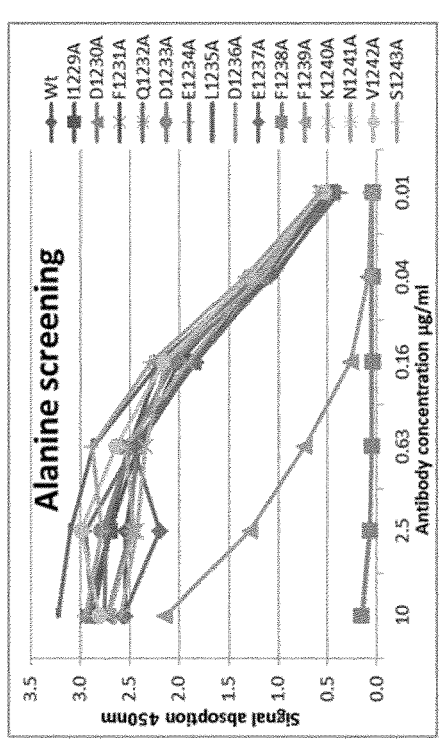
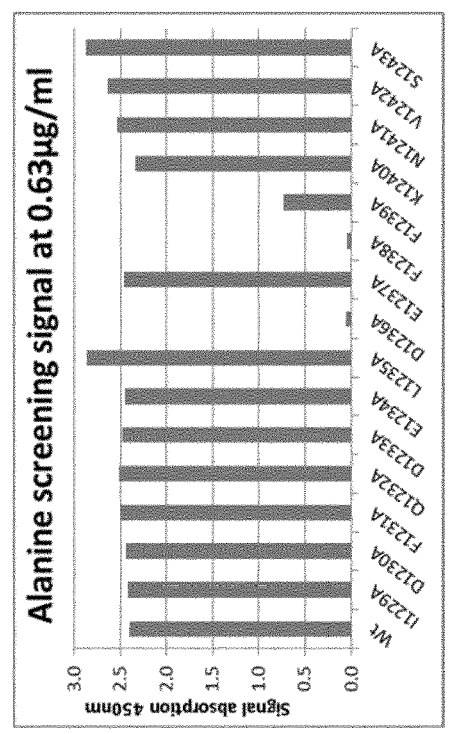
| IDFQDELDEFFKNVS | Res. 1229-1243 |
|---|---|
| ADFQDELDEFFKNVS | I1229A |
| ILAFQDELDEFFKNVS | D1230A |
| IDAQDELDEFFKNVS | F1231A |
| IDFADELDEFFKNVS | Q1232A |
| IDFQAELDEFFKNVS | D1233A |
| IDFQDALDEFFKNVS | E1234A |
| IDFQDEADEFFKNVS | L1235A |
| IDFQDELAEFFKNVS | D1236A |
| IDFQDELDAFFKNVS | E1237A |
| IDFQDELDEAFKNVS | F1238A |
| IDFQDELDEFAKNVS | F1239A |
| IDFQDELDEFFANVS | K1240A |
| IDFQDELDEFFKAVS | N1241A |
| IDFQDELDEFFKNAS | V1242A |
| IDFQDELDEFFKNVA | S1243A |
Fig. 14(D)

Fig. 16

| MAb name | S domain | Epitope group | MERS S residues involved in MAb binding | Epitope: Linear (L) Conformational (C | H2L2 MAb MERS-S VSV ps. 50% inh titer (µg/ml) | H2L2 MAb MERS-CoV 50% inh titer (µg/ml) | VH+VL cloned into Human IgG1 vector | Reactivity Human IgG1 MAb confirmed | Human IgG MAb MERS-S VSV ps. 50% inh titer (µg/ml) | Reactivity towards other betaCoV | Yield (mg/L) |
|---|---|---|---|---|---|---|---|---|---|---|---|
| 7.7 g6 | | | unknown | C | 0.00011 | 0.0003 | Y | Y | 0.002 | | 5,05 |
| 1.6 f9 | | | unknown | C | 0.00038 | 0.003 | Y | Y | 0.019 | | 2,28 |
| 1.2 g5 | S1ʙ | 1.3 g2 | unknown | C | 0.00062 | 0.001 | Y | Y | 0.007 | | 1,87 |
| 5.2 b7 | | | unknown | C | 0.00081 | 0.005 | N | | | | |
| 5.5 e11 | | | unknown | C | 0.00170 | 0.0006 | Y | Y | | | |
| 1.8 e5 | S1ʙ | 1.8 e5 | unknown | C | 0.09026 | 1.25 | Y | Y | 2.59 | | 2,28 |
| 4.6 e10 | S1ʙ | 4.6 e10 | 507/509 | C | 0.03131 | 0.32 | Y | Y | 0.07 | | 1,66 |
| 1.10 f3 | S1ᴀ | 1.10 f3 | unknown | n.d. | Non-neutr. | >20 | Y | Y | >20 | | 3,27 |
| 7.8 h1 | S1 | 7.8 h1 | unknown | n.d. | Non-neutr. | >20 | Y | Y | | | |
| 1.6 c7 | S2 | 1.6 c7 | 1230-1242 | L | 0.59 | n.d. | Y | Y | 2.5 | SARS-CoV, MHV | 2,04 |
| 3.5 g6 | S2 | 3.5 g6 | unknown | C | 20.15 | n.d. | Y | Y | >20 | | 3,68 |
| REGN3051* | S1ʙ | | unknown | C | 0.0098 | 0.069 | Y | Y | 0.007 | | 1,98 |
| IsotypeCtrl | | | | | >20 | >20 | Y | Y | | | 2,92 |

Fig. 17

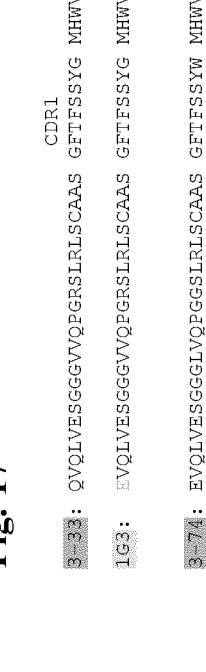

```
                                    CDR1                        CDR2                                              CDR3
3H3:  QVQLVESGGGVVQPGRSLRLSCAAS  GFTFSSYG  MHWVRQAPGKGLEWVAV  IWYDGSNK  YYADSVKGRFTISRDNSKNTLYLQMNSLRAEDTAVYYC  AR
1G3:  EVQLVESGGGVVQPGRSLRLSCAAS  GFTFSSYG  MHWVRQAPGKGLEWVAV  IWYDGSNK  YYADSVKGRFTISRDNSKNTLYLQMNSLRAEDTAVYYC  ARDERIFGVPDAFDI  RGQGTMVTVSS
3H74: EVQLVESGGGLVQPGGSLRLSCAAS  GFTFSSYW  MHWVRQAPGKGLVWVSR  INSDGSST  SYADSVKGRFTISRDNAKNTLYLQMNSLRAEDTAVYYC  AR
5F1:  EVQLVESGGGLVQPGGSLRLSCAAS  GFTFSSYW  MHWVRQAPGKGLVWVSR  INSDGSST  SYADSVKGRFTISRDNAKNTLYLQMNSLRAEDTAVYYC  GNPYFDY          WGQGTLVTVSS
1H5:  EVQLVESGGGLVQPGGSLRLSCAAS  GFTFSSYW  MLWVRQAPGEGLVWVSR  IDSDGSNT  TYADSVKGRFTVSRDNAKNTLYLQMNSLRAEDTAVYYC  ARSGYGYAFDI     WGQGTMVTVSS
3H23: EVQLLESGGGLVQPGGSLRLSCAAS  GFTFSSYA  MSWVRQAPGKGLEWVSA  ISGSGGST  YYADSVKGRFTISRDNSKNTLYLQMNSLRAEDTAVYYC  AK
1E10: EVQLLESGGWVQPGGSLRLSCAAS   GFTFSTNA  MSWVRQAPGKGLEWVSG  ISGSGGST  DYADSVKGRFTISRDNSKNTLYLQMNSLRAEDTAVYYC  APRIAVAPDALDI   WGQGTMVTVSS
```

| | MERS-S domain | MERS-S VSVpp $IC_{50}$ (µg/ml) | MERS-CoV $IC_{50}$ (µg/ml) |
|---|---|---|---|
| 7.7g6 | $S1^B$ | 0.001 | 0.008 |
| 1.6f9 | | 0.006 | 0.03 |
| 1.2g5 | | 0.002 | 0.03 |
| 1.8e5 | | 1.500 | >1 |
| 4.6e10 | | 0.048 | 1 |
| 1.10f3 | $S1^A$ | >10 | >1 |
| 1.6c7 | $S2$ | 0.367 | 1 |
| 3.5g6 | | 3.974 | >1 |
| Anti-MERS-CTRL | $S1^B$ | 0.005 | 0.03 |
| Iso-CTRL | - | >10 | >1 |

Fig. 19(B)

| | MERS-S domain | RBI50 (µg/ml) |
|---|---|---|
| 7.7g6 | S1B | 0.008 |
| 1.6f9 | | 0.014 |
| 1.2g5 | | 0.014 |
| 1.8e5 | | - |
| 4.6e10 | | 0.14 |
| 1.10f3 | S1A | - |
| 1.6c7 | S2 | - |
| 3.5g6 | | - |
| Anti-MERS-CTRL | S1B | 0.02 |

(B)

(A)

Fig. 26
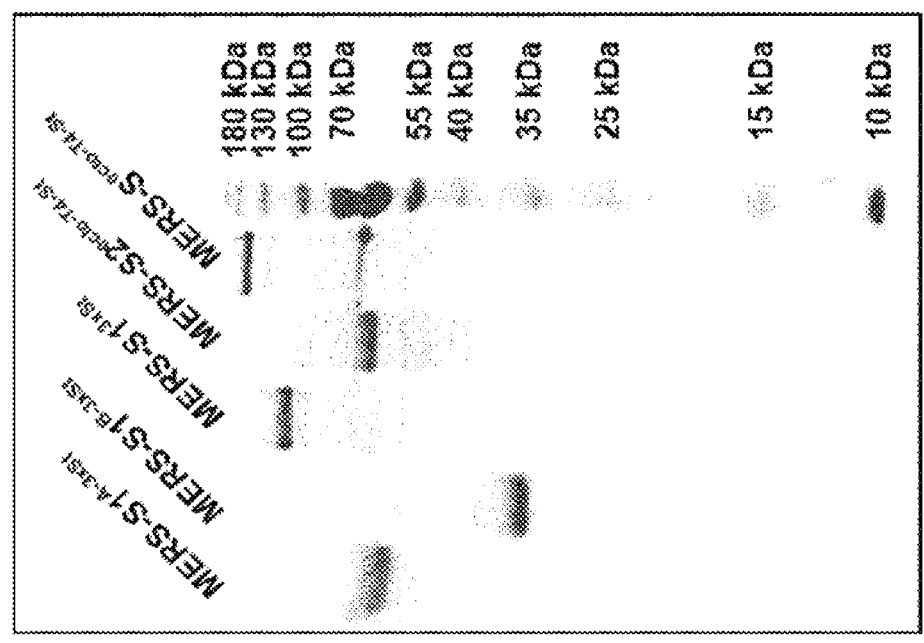
(B)
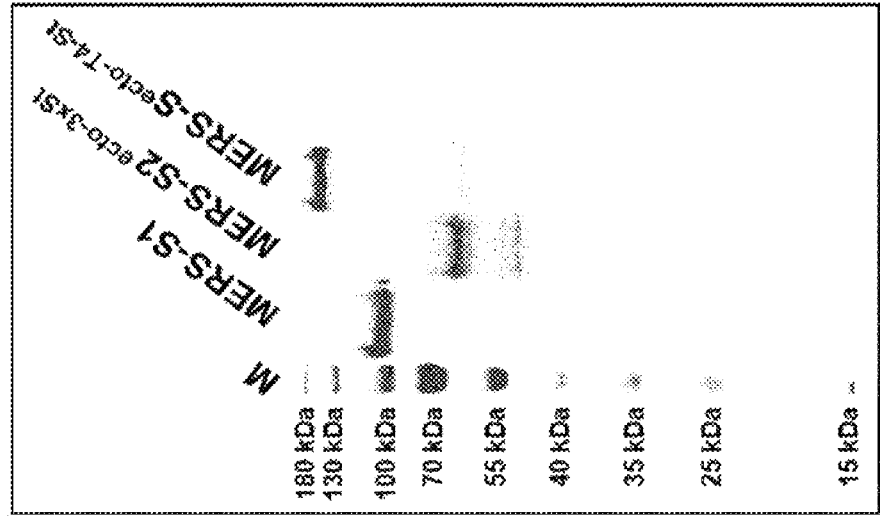
(A)

Fig. 27(Continued) Domain-based epitope mapping by ELISA

Fig. 28

| | 1.3 g2 | binding second ab | 1.8 e5 | binding second ab | 4.6 e10 | binding second ab | 3.5 g6 | binding second ab |
|---|---|---|---|---|---|---|---|---|
| 1.2g5 | 100% | 0% | | | | | | |
| 1.3g2 | 100% | 0% | 100% | 96% | | | | |
| 1.3h2 | 100% | 75% | 100% | 95% | 100% | 0% | | |
| 1.6c2 | 100% | 0% | | | | | | |
| 1.6e1 | 100% | 0% | 100% | | | | | |
| 1.6f9 | 100% | 0% | | | | | | |
| 1.8c5 | 100% | 79% | 100% | 0% | 100% | 100% | | |
| 1.8e5 | 100% | 90% | 100% | 0% | 100% | 100% | | |
| 1.10e9 | 100% | 100% | 100% | 0% | | | | |
| 1.10f3 | 100% | 97% | | | | | | |
| 2.9d7 | 100% | 0% | | | | | | |
| 4.2f1 | 100% | 0% | 100% | 71% | | | | |
| 4.6e10 | 100% | 71% | 100% | | 100% | | | |
| 4.7a6 | 100% | 0% | | | | | | |
| 4.9e5 | 100% | 0% | | | 100% | 95% | | |
| 4.10g3 | 100% | 96% | 100% | 85% | | | | |
| 5.2b7 | 100% | 0% | | | | | | |
| 5.5e11 | 100% | 0% | | | | | | |
| 5.11h8 | 100% | 0% | | | | | | |
| 7.1c12 | 100% | 96% | 100% | 0% | 100% | 97% | | |
| 7.1g9 | 100% | 94% | 100% | 53% | 100% | 100% | | |
| 7.2e7 | 100% | 61% | 100% | 0% | | | | |
| 7.2h5 | 100% | 0% | | | | | | |
| 7.3a9 | 100% | 0% | 100% | 0% | | | | |
| 7.5d3 | 100% | 74% | 100% | 95% | | | | |
| 7.6c11 | 100% | 0% | | | | | | |
| 7.7a9 | 100% | 70% | | | 100% | 0% | | |
| 7.7g6 | 100% | 0% | | | | | | |
| 7.7h8 | 100% | 0% | | | | | | |
| 7.8h1 | 100% | 54% | 100% | 0% | 100% | 78% | | |
| 7.9c2 | 100% | 55% | 100% | 0% | | | | |
| 7.9c10 | 100% | 0% | | | | | | |
| 7.9g1 | 100% | 0% | | | | | | |
| 7.9g10 | 100% | 0% | | | | | | |
| 3.5g6 | | | | | | | 100% | 0% |
| 4.6c7 | | | | | | | 100% | 50% |

| | MERS-S domain | VH | | | | | | Vκ | | | | |
|---|---|---|---|---|---|---|---|---|---|---|---|---|
| | | V | D | J | Identity (%) | CDR3 (aa) | Length (aa) | V | J | Identity (%) | CDR3 (aa) | Length (aa) |
| 7.7g6 | | IGHV1-69*06 F | IGHD2-2*01 F | IGHJ4*02 F | 97.92 | CAREGDDVLVPTSRGFFDYW | 20 | IGKV2-28*01 F | IGKJ4*01 F | 100.00 | CMQALQTPLTF | 11 |
| 1.6f9 | S1B | IGHV1-69*06 F | IGHD2-2*01 F | IGHJ4*02 F | 96.88 | CAREGDIEVVLAGRGYFDYW | 20 | IGKV2-28*01 F | IGKJ2*01 F | 98.98 | CMQALQTPYTF | 11 |
| 1.2g5 | | IGHV1-69*06 F | IGHD3-9*01 F | IGHJ4*02 F | 97.92 | CAREGNLGYDVVTGYSYFVYW | 21 | IGKV3-20*01 F | IGKJ4*01 F | 98.23 | CQQYGRSLTF | 10 |
| 1.8e5 | | IGHV4-4*02 F | IGHD3-10*01 F | IGHJ3*02 F | 97.57 | CASLTLIWFGEKAFDIW | 17 | IGKV3-15*01 F | IGKJ2*01 F | 96.06 | CQQYNNWPYTF | 11 |
| 4.6e10 | | IGHV3-33*01 F | IGHD6-19*01 F | IGHJ4*02 F | 97.22 | CAREGLGAVAGYYFDYW | 17 | IGKV1-39*01 F | IGKJ3*01 F | 96.77 | CQQSYSTPFAF | 11 |
| 1.10f3 | S1A | IGHV3-33*01 F | IGHD3-9*01 F | IGHJ3*02 F | 95.49 | CARDAGLSFDIW | 12 | IGKV3-20*01 F | IGKJ2*01 F | 99.65 | CQQYGSYTF | 9 |
| 1.6c7 | S2 | IGHV6-1*01 F | IGHD3-10*01 F | IGHJ4*02 F | 97.98 | CARATLARGALDYW | 14 | IGKV4-1*01 F | IGKJ1*01 F | 98.99 | CQQYYSTPWTF | 11 |
| 3.5g6 | S2 | IGHV6-1*01 F | IGHD3-10*01 F | IGHJ4*02 F (a) | 97.64 | CARSLGSGTYPFDSW | 15 | IGKV1-39*01 F | IGKJ4*01 F | 96.42 | CQQSYSTPLTF | 11 |

Fig. 29(B)

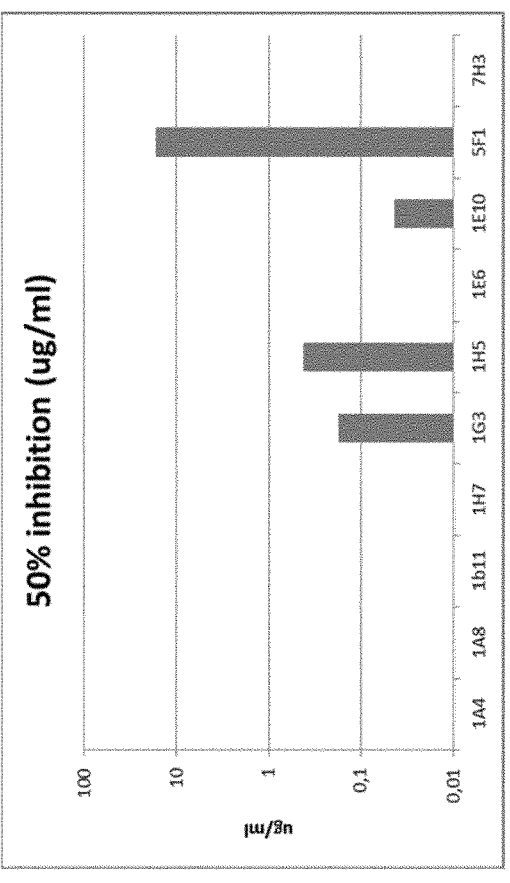
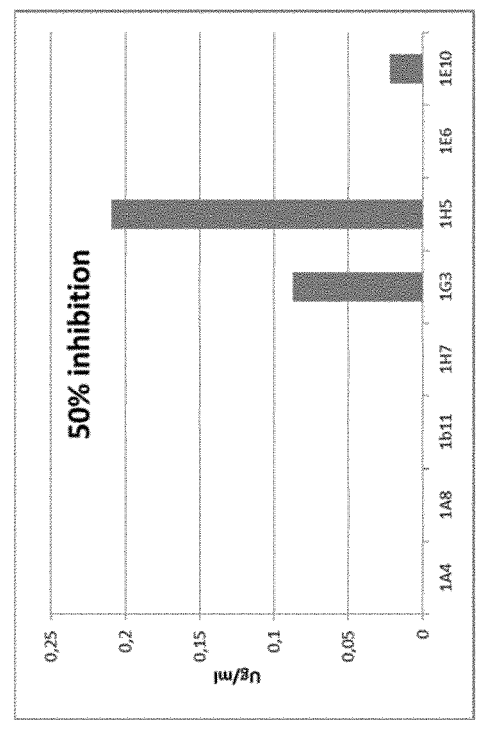
Fig. 31

Fig. 32 anti MERS-S1 HCABs 1.2g5H2L2 is from the group 1.3g2

-1H5 HCAB competes with 1.3g2H2L2 group for epitope binding
-1H5 HCAB binds different epitope than 1.8e5 H2L2 (7.5d3h2L2) group
-1H5 HCAB interferes also with the binding of 4.6e10H2L2

1.2g5H2L2 is from the group 1.3g2H2L2

~1G3 HCAB does not interfere with the binding of 1.2g5 H2L2(group 1.3g2)
~1G3 HCAB does not interfere with the binding of 4.6e10H2L2
~1G3 HCAB does interfere with the binding of 1.8e10 (7.5d3) i.e. looks like it binds
different epitope (right panels), but 1.8e10 H2L2(7.5d3) once bound interferes/abolishes
the binding of 1G3HCAb almost completely.

Table 2. Virus neutralization and receptor binding inhibition by anti-MERS-S mAbs.

| mAb | MERS-S target | IC50* MERS-S VSVpp | | PRNT50** MERS-CoV | | RBI50*** | |
|---|---|---|---|---|---|---|---|
| | | μg/ml | nM | μg/ml | nM | μg/ml | nM |
| 7.7g6 | S1B | 0.001 | 0.007 | 0.008 | 0.053 | 0.007 | 0.047 |
| 1.6f9 | S1B | 0.006 | 0.04 | 0.03 | 0.200 | 0.013 | 0.087 |
| 1.2g5 | S1B | 0.002 | 0.013 | 0.03 | 0.200 | 0.014 | 0.093 |
| 1.8e5 | S1B | 1.500 | 10 | >1 | >6.67 | >10 | >66.7 |
| 4.6e10 | S1B | 0.048 | 0.320 | 1 | 6.667 | 0.137 | 0.913 |
| 1.10f3 | S1A | >10 | >66.7 | >1 | >6.67 | >10 | >66.7 |
| 1.6c7 | S2 | 0.367 | 2.447 | 1 | 6.67 | >10 | >66.7 |
| 3.5g6 | S2 | 2.488 | 16.6 | >1 | >6.6 | >10 | >66.7 |
| α-MERS-CTRL | S1B | 0.005 | 0.033 | 0.03 | 0.200 | 0.022 | 0.147 |
| Iso-CTRL | - | >10 | >66.7 | >1 | >6.67 | - | - |

* IC50: mAb concentration resulting in half-maximal infection of MERS-S VSV pseudovirus (MERS-S VSVpp) on Vero cells.

** PRNT50: highest mAb dilution resulting in > 50% reduction in the number of MERS-CoV infected Vero cells.

*** RBI50: mAb concentration of that gives half-maximal receptor binding.

Fig. 34

SEQUENCE LISTING

```
<160> NUMBER OF SEQ ID NOS: 655

<210> SEQ ID NO 1
<211> LENGTH: 98
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 2
<211> LENGTH: 132
<212> TYPE: PRT
<213> ORGANISM: Homo sapiens

<400> SEQUENCE: 2

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45
```

```
Ala Ile Ile Trp Tyr Asp Gly Ser Asn Thr Tyr Tyr Thr Asp Ser Ala
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Val Glu Asp Thr Ala Val Tyr Tyr Cys
                85                  90                  95

Ala Arg Asp Arg Gly Ile Ser Val Ala Ala Leu Trp Lys Tyr Tyr Tyr
            100                 105                 110

Tyr His Gly Leu Asp Val Trp Gly Gln Gly Thr Thr Thr Thr Val Ser
        115                 120                 125

Ser Ala Gln Thr
    130
```

```
<210> SEQ ID NO 3
<211> LENGTH: 132
<212> TYPE: PRT
<213> ORGANISM: Homo sapiens

<400> SEQUENCE: 3
```

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Gly Tyr
                20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Arg Gly Ile Ser Val Ala Ala Leu Trp Lys Tyr Tyr Tyr
            100                 105                 110

Tyr His Gly Leu Asp Val Trp Gly Gln Gly Thr Thr Val Thr Val Ser
        115                 120                 125

Ser Ala Gln Thr
    130
```

```
<210> SEQ ID NO 4
<211> LENGTH: 132
<212> TYPE: PRT
<213> ORGANISM: Homo sapiens

<400> SEQUENCE: 4
```

```
Gln Val Gln Leu Val Glu Ser Gly Gly Gly Val Val Gln Pro Gly Met
1               5                   10                  15

Ser Leu Arg Leu Ser Cys Thr Ala Ser Gly Phe Thr Phe Ser Gly Tyr
                20                  25                  30

Ala Met His Trp Val Arg Gln Ala Pro Val Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Arg Gly Ile Ser Glu Ala Ala Lys Trp Lys Tyr Tyr Tyr
        100                 105                 110

Tyr Tyr Gly Met Asp Val Trp Gly Gln Gly Thr Thr Val Thr Val Ser
        115                 120                 125

Ser Ala Gln Thr
    130

<210> SEQ ID NO 5
<211> LENGTH: 132
<212> TYPE: PRT
<213> ORGANISM: Homo sapiens

<400> SEQUENCE: 5

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Gly Tyr
            20                  25                  30

Ala Met His Trp Val Arg Gln Ala Pro Val Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Glu Ala Ala Lys Trp Lys Tyr Tyr Tyr
        100                 105                 110

Tyr Tyr Gly Met Asp Val Trp Gly Gln Gly Thr Thr Val Thr Val Ser
        115                 120                 125

Ser Ala Gln Thr
    130

<210> SEQ ID NO 6
<211> LENGTH: 132
<212> TYPE: PRT
<213> ORGANISM: Homo sapiens

<400> SEQUENCE: 6

Gln Val Gln Leu Val Glu Ser Gly Gly Gly Val Val Gln Thr Gly Arg
1               5                   10                  15

Ser Leu Arg Leu Ser Cys Ala Ala Ser Gly Phe Thr Phe Ser Ala Tyr
            20                  25                  30

Ala Met His Trp Val Arg Gln Ala Pro Gly Lys Gly Leu Glu Trp Val
        35                  40                  45

Thr Phe Ile Gly Tyr Glu Glu Ser Asn Lys Tyr His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Val Ala Ala Thr Trp Asp Tyr Tyr Tyr
        100                 105                 110

Tyr Tyr Gly Met Asp Val Trp Gly Gln Gly Thr Thr Val Thr Val Ser
        115                 120                 125

Ser Ala Glu Thr
    130
```

```
<210> SEQ ID NO 7
<211> LENGTH: 131
<212> TYPE: PRT
<213> ORGANISM: Homo sapiens

<400> SEQUENCE: 7

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Asn Phe Ser Ser Asp
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Ala Asp Ser Val
    50                  55                  60

Lys Gly Arg Phe Thr Ile Ser Arg Asp Asn Thr Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Thr Met Gly Arg Gly Pro Tyr Tyr Tyr Tyr
            100                 105                 110

Tyr Gly Met Asp Val Trp Gly Gln Gly Thr Thr Val Thr Val Ser Ser
        115                 120                 125

Ala Gln Thr
    130

<210> SEQ ID NO 8
<211> LENGTH: 131
<212> TYPE: PRT
<213> ORGANISM: Homo sapiens

<400> SEQUENCE: 8

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Asp
            20                  25                  30

Gly Met His Trp Val Arg Gln Ala Pro Gly Lys Gly Leu Glu Trp Val
        35                  40                  45

Ala Val Ile Trp Tyr Asp Gly Ser Ser Glu Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Thr Met Gly Arg Gly Val Tyr Tyr Tyr Tyr
            100                 105                 110

Tyr Gly Met Asp Val Trp Gly Gln Gly Thr Thr Val Thr Val Ser Ser
        115                 120                 125

Ala Gln Thr
    130

<210> SEQ ID NO 9
<211> LENGTH: 131
<212> TYPE: PRT
<213> ORGANISM: Homo sapiens

<400> SEQUENCE: 9
```

-continued

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Asp
            20                  25                  30

Gly Met His Trp Val Arg Gln Ala Pro Gly Lys Gly Leu Glu Trp Val
            35                  40                  45

Ala Val Ile Trp Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr Tyr Cys
                85                  90                  95

Thr Arg Asp Arg Gly Ile Thr Met Gly Arg Gly Arg Tyr Tyr Tyr Tyr
            100                 105                 110

Tyr Gly Met Asp Val Trp Gly Gln Gly Thr Thr Val Thr Val Ser Ser
            115                 120                 125

Ala Gln Thr
    130

<210> SEQ ID NO 10
<211> LENGTH: 131
<212> TYPE: PRT
<213> ORGANISM: Homo sapiens

<400> SEQUENCE: 10

Gln Val Gln Leu Val Glu Ser Gly Gly Asp Val Val Gln Pro Gly Arg
1               5                   10                  15

Ser Leu Arg Leu Ser Cys Ala Ala Ser Gly Ile Thr Phe Ser Asn Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Met Thr Gly Thr Thr Trp Glu Tyr Tyr Tyr Tyr
            100                 105                 110

Tyr Gly Met Asp Val Trp Gly Gln Gly Thr Thr Val Thr Val Ser Ser
            115                 120                 125

Ala Gln Thr
    130

<210> SEQ ID NO 11
<211> LENGTH: 132
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
            35                  40                  45
```

-continued

```
Ala Val Ile Trp Tyr Asp Gly Ser Asn Lys Tyr Tyr Ala Asp Ser Val
    50                  55                  60

Lys Gly Arg Leu Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Arg Gly Ile Thr Thr Thr Asp Thr Gly Tyr Tyr Tyr Tyr
                100                 105                 110

Tyr Tyr Gly Leu Asp Ile Trp Gly Gln Gly Thr Thr Val Thr Val Ser
        115                 120                 125

Ser Ala Gln Thr
    130

<210> SEQ ID NO 12
<211> LENGTH: 132
<212> TYPE: PRT
<213> ORGANISM: Homo sapiens

<400> SEQUENCE: 12

Gln Arg Lys Leu Val Glu Ser Gly Gly Gly Val Val Gln Pro Gly Arg
1               5                   10                  15

Ser Leu Arg Leu Ser Cys Ala Val Ser Gly Leu Ile Phe Ser Asn Tyr
                20                  25                  30

Gly Met His Trp Val Arg Gln Ala Pro Gly Lys Gly Leu Glu Trp Val
        35                  40                  45

Ala Val Ile Trp Tyr Asp Gly Ser Asn Thr Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Met Thr Ala Pro Gly Pro Gly Thr Tyr Tyr Tyr
                100                 105                 110

Phe Tyr Gly Met Asp Val Trp Gly Gln Gly Thr Thr Val Thr Val Ser
        115                 120                 125

Ser Ala Gln Thr
    130

<210> SEQ ID NO 13
<211> LENGTH: 127
<212> TYPE: PRT
<213> ORGANISM: Homo sapiens

<400> SEQUENCE: 13

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asn Tyr
                20                  25                  30

Gly Met His Trp Val Arg Gln Thr Pro Gly Lys Gly Leu Glu Trp Val
        35                  40                  45

Ala Ile Ile Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg Glu Arg Gly Val Trp Asn Ser Gly Trp Ser His Ala Tyr Asp
            100                 105                 110

Ile Trp Gly Gln Gly Thr Met Val Thr Val Ser Ser Ala Gln Thr
        115                 120                 125

<210> SEQ ID NO 14
<211> LENGTH: 127
<212> TYPE: PRT
<213> ORGANISM: Homo sapiens

<400> SEQUENCE: 14

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asn Tyr
            20                  25                  30

Gly Met His Trp Val Arg Gln Thr Pro Gly Lys Gly Leu Glu Trp Val
        35                  40                  45

Ala Ile Ile Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Val Trp Asn Ser Gly Trp Ser His Ala Tyr Asp
            100                 105                 110

Ile Trp Gly Gln Gly Thr Met Val Thr Val Ser Ser Ala Gln Thr
        115                 120                 125

<210> SEQ ID NO 15
<211> LENGTH: 130
<212> TYPE: PRT
<213> ORGANISM: Homo sapiens

<400> SEQUENCE: 15

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Gln Trp Val
        35                  40                  45

Ala Phe Ile Trp Tyr Asp Gly Ser Asn Lys Tyr Tyr Ala Asp Ala Val
    50                  55                  60

Lys Val Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Glu Gly Asp Tyr Tyr Gly Ser Gly Ser Tyr Ser Arg Ala Glu
            100                 105                 110

Tyr Phe Gln Glu Trp Gly Gln Gly Thr Leu Val Thr Val Ser Ser Ala
        115                 120                 125

Glu Thr
    130

<210> SEQ ID NO 16
<211> LENGTH: 125
<212> TYPE: PRT
<213> ORGANISM: Homo sapiens
```

<400> SEQUENCE: 16

```
Gln Val Gln Leu Val Glu Ser Gly Gly Gly Val Val Gln Pro Gly Arg
1               5                   10                  15

Ser Leu Arg Leu Ser Cys Ala Ala Thr Gly Phe Thr Phe Ser Tyr Tyr
                20                  25                  30

Gly Met His Trp Val Arg Gln Ala Pro Gly Lys Gly Leu Glu Trp Val
            35                  40                  45

Ala Val Ile Trp Phe Asp Gly Thr Asn Ile Tyr Tyr Ala Asp Ser Val
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Asp Arg Arg Ser Ser Asp Trp Tyr Val Val Phe Asp Tyr Trp
                100                 105                 110

Gly Gln Gly Thr Leu Val Thr Val Ser Ser Ala Gln Thr
            115                 120                 125
```

<210> SEQ ID NO 17
<211> LENGTH: 125
<212> TYPE: PRT
<213> ORGANISM: Homo sapiens

<400> SEQUENCE: 17

```
Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Thr Tyr Tyr
                20                  25                  30

Gly Leu His Trp Val Arg Gln Ala Pro Gly Lys Gly Leu Glu Trp Val
            35                  40                  45

Ala Val Ile Trp Tyr Asp Gly Ser Asn Gln Tyr Tyr Ala Asp Ser Val
        50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Leu Gly Ala Val Ala Gly Tyr Tyr Phe Asp Tyr Trp
                100                 105                 110

Gly Gln Gly Thr Leu Val Thr Val Ser Ala Ala Glu Thr
            115                 120                 125
```

<210> SEQ ID NO 18
<211> LENGTH: 120
<212> TYPE: PRT
<213> ORGANISM: Homo sapiens

<400> SEQUENCE: 18

```
Gln Val Gln Leu Val Glu Ser Gly Gly Gly Val Val Gln Pro Gly Arg
1               5                   10                  15

Ser Leu Arg Leu Ser Cys Lys Ala Ser Gly Phe Thr Phe Arg Gly Tyr
                20                  25                  30

Gly Met His Trp Val Arg Gln Ala Pro Gly Lys Gly Leu Glu Trp Val
            35                  40                  45

Thr Val Ile Trp His Asp Ala Ser Asn Lys Tyr Tyr Val Asp Ser Val
        50                  55                  60

Lys Gly Arg Phe Ser Ile Ser Arg Asp Asn Ser Lys Asn Thr Leu Tyr
```

```
65                    70                    75                    80

Leu Gln Met Asn Ser Leu Arg Ala Glu Asp Thr Ala Val Tyr Tyr Cys
                85                    90                    95

Ala Arg Asp Ala Gly Leu Ser Phe Asp Ile Trp Gly Gln Gly Thr Met
            100                   105                   110

Val Thr Val Ser Ser Ala Gln Thr
            115                   120

<210> SEQ ID NO 19
<211> LENGTH: 98
<212> TYPE: PRT
<213> ORGANISM: Homo sapiens

<400> SEQUENCE: 19

Gln Val Gln Leu Val Gln Ser Gly Ala Glu Val Lys Lys Pro Gly Ser
1               5                     10                    15

Ser Val Lys Val Ser Cys Lys Ala Ser Gly Gly Thr Phe Ser Ser Tyr
                20                    25                    30

Ala Ile Ser Trp Val Arg Gln Ala Pro Gly Gln Gly Leu Glu Trp Met
            35                    40                    45

Gly Gly Ile Ile Pro Ile Phe Gly Thr Ala Asn Tyr Ala Gln Lys Phe
        50                    55                    60

Gln Gly Arg Val Thr Ile Thr Ala Asp Glu Ser Thr Ser Thr Ala Tyr
65                    70                    75                    80

Met Glu Leu Ser Ser Leu Arg Ser Glu Asp Thr Ala Val Tyr Tyr Cys
                85                    90                    95

Ala Arg

<210> SEQ ID NO 20
<211> LENGTH: 127
<212> TYPE: PRT
<213> ORGANISM: Homo sapiens

<400> SEQUENCE: 20

Gln Val Gln Leu Val Gln Ser Gly Ala Glu Val Lys Lys Pro Gly Ser
1               5                     10                    15

Ser Val Lys Ile Ser Cys Lys Ala Ser Gly Gly Thr Phe Ser Thr His
                20                    25                    30

Ala Phe Thr Trp Val Arg Gln Ala Pro Gly Gln Gly Leu Glu Trp Ile
            35                    40                    45

Gly Arg Ile Ile Pro Ile Phe Asp Thr Pro Lys Tyr Ala Gln Lys Phe
        50                    55                    60

Gln Gly Arg Val Thr Ile Ala Ala Asp Ile Ser Thr Ser Thr Val Phe
65                    70                    75                    80

Met Glu Leu Ser Ser Leu Arg Ser Glu Asp Thr Ala Val Phe Tyr Cys
                85                    90                    95

Ala Arg Glu Gly Tyr Tyr Ile Ser Gly Ser Tyr Arg Asp Ala Phe Asp
            100                   105                   110

Ile Trp Gly Gln Gly Thr Met Val Thr Val Ser Ser Ala Gln Thr
            115                   120                   125

<210> SEQ ID NO 21
<211> LENGTH: 130
<212> TYPE: PRT
<213> ORGANISM: Homo sapiens

<400> SEQUENCE: 21
```

-continued

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Asp Ile Thr Met Val Arg Gly Val Ile Thr Asn Tyr Trp
            100                 105                 110

Tyr Phe Asp Leu Trp Gly Arg Gly Thr Leu Val Thr Val Ser Ser Ala
            115                 120                 125

Gln Thr
    130

<210> SEQ ID NO 22
<211> LENGTH: 129
<212> TYPE: PRT
<213> ORGANISM: Homo sapiens

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Ile Ala Asp Lys Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Glu Gly Asn Leu Gly Tyr Asp Val Val Thr Gly Tyr Ser Tyr
            100                 105                 110

Phe Val Tyr Trp Gly Gln Gly Thr Leu Val Thr Val Ser Ser Ala Gln
            115                 120                 125

Thr

<210> SEQ ID NO 23
<211> LENGTH: 127
<212> TYPE: PRT
<213> ORGANISM: Homo sapiens

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Val Lys Asn Ala Gln Lys Phe

-continued

```
        50              55              60

Gln Gly Arg Val Thr Ile Thr Ala Asp Lys Ser Thr Gly Thr Ala Tyr
65              70              75              80

Met Glu Leu Ser Ser Leu Arg Ser Glu Asp Thr Ala Val Tyr Tyr Cys
            85              90              95

Ala Arg Asp His Tyr Tyr Asp Ser Asn Asp Tyr Tyr Trp Tyr Phe Asp
            100             105             110

Leu Trp Gly Arg Gly Thr Leu Val Thr Val Ser Ser Ala Gln Thr
        115             120             125

<210> SEQ ID NO 24
<211> LENGTH: 128
<212> TYPE: PRT
<213> ORGANISM: Homo sapiens

<400> SEQUENCE: 24

Gln Val Gln Leu Val Gln Ser Gly Ala Glu Val Lys Lys Pro Gly Ser
1               5               10              15

Ser Val Lys Val Ser Cys Lys Ala Ser Gly Gly Ala Phe Ser Ala Tyr
            20              25              30

Ala Ile Ser Trp Val Arg Gln Ala Pro Gly Gln Gly Leu Glu Trp Met
            35              40              45

Gly Gly Ile Ile Pro Ile Phe Gly Thr Ala Asn Tyr Ala Gln Lys Phe
        50              55              60

Gln Gly Arg Val Thr Ile Thr Ala Asp Thr Ser Thr Ser Thr Ala Tyr
65              70              75              80

Met Glu Leu Ser Ser Leu Arg Ser Glu Asp Thr Ala Val Tyr Tyr Cys
            85              90              95

Ala Arg Glu Gly Asp Ile Glu Val Val Leu Ala Ala Arg Gly Phe Phe
            100             105             110

Asp Tyr Trp Gly Gln Gly Thr Leu Val Thr Val Ser Ser Ala Gln Thr
        115             120             125

<210> SEQ ID NO 25
<211> LENGTH: 128
<212> TYPE: PRT
<213> ORGANISM: Homo sapiens

<400> SEQUENCE: 25

Gln Val Gln Leu Val Gln Ser Gly Thr Glu Val Lys Lys Pro Gly Ser
1               5               10              15

Ser Val Lys Val Ser Cys Lys Ala Ser Gly Gly Ala Phe Ser Ala Tyr
            20              25              30

Ala Ile Thr Trp Val Arg Gln Ala Pro Gly Gln Gly Leu Glu Trp Met
            35              40              45

Gly Gly Ile Ile Pro Ile Phe Gly Thr Ala His Tyr Ala Gln Lys Phe
        50              55              60

Gln Gly Arg Val Thr Ile Thr Ala Asp Lys Ser Thr Ser Thr Ala Phe
65              70              75              80

Met Glu Leu Ser Ser Leu Arg Ser Glu Asp Thr Ala Val Tyr Tyr Cys
            85              90              95

Ala Arg Glu Gly Asp Ile Glu Val Val Leu Ala Gly Arg Gly Tyr Phe
            100             105             110

Asp Tyr Trp Gly Gln Gly Thr Leu Val Thr Val Ser Ser Ala Gln Thr
        115             120             125
```

-continued

```
<210> SEQ ID NO 26
<211> LENGTH: 128
<212> TYPE: PRT
<213> ORGANISM: Homo sapiens

<400> SEQUENCE: 26

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Ala Tyr
            20                  25                  30

Val Ile Thr Trp Val Arg Gln Ala Pro Gly Gln Gly Leu Glu Trp Met
        35                  40                  45

Gly Gly Ile Ile Pro Val Phe Gly Thr Ala His Tyr Ala Gln Lys Phe
    50                  55                  60

Gln Gly Arg Val Thr Ile Thr Ala Asp Lys Ser Thr Ser Thr Ala Phe
65                  70                  75                  80

Met Glu Leu Ser Ser Leu Arg Ser Glu Asp Thr Ala Val Tyr Tyr Cys
                85                  90                  95

Ala Arg Glu Gly Asp Ile Glu Val Val Leu Ala Gly Arg Gly Tyr Phe
            100                 105                 110

Asp Tyr Trp Gly Gln Gly Thr Leu Val Thr Val Ser Ser Ala Gln Thr
        115                 120                 125

<210> SEQ ID NO 27
<211> LENGTH: 128
<212> TYPE: PRT
<213> ORGANISM: Homo sapiens

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Ala Tyr
            20                  25                  30

Ala Ile Asp Trp Val Arg Gln Ala Pro Gly Gln Gly Leu Glu Trp Met
        35                  40                  45

Gly Gly Ile Ile Pro Ile Phe Gly Thr Ala His Tyr Ala Gln Lys Leu
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Asp Ser Gly Leu Val Leu Ala Ala Arg Gly Phe Phe
            100                 105                 110

Asp Tyr Trp Gly Gln Gly Thr Leu Val Thr Val Ser Ser Ala Gln Thr
        115                 120                 125

<210> SEQ ID NO 28
<211> LENGTH: 128
<212> TYPE: PRT
<213> ORGANISM: Homo sapiens

<400> SEQUENCE: 28

Gln Val Gln Leu Val Gln Thr Gly Ala Glu Val Lys Lys Pro Gly Ser
1               5                   10                  15

Ser Val Lys Val Ser Cys Lys Ala Ser Gly Gly Thr Phe Ser Ile Tyr
            20                  25                  30

Ala Ile Ser Trp Val Arg Gln Ala Pro Arg Gln Gly Leu Glu Trp Met
        35                  40                  45
```

```
Gly Gly Ile Ile Pro Ile Phe Gly Thr Ala Asn Tyr Ala Gln Lys Phe
    50              55              60

Gln Gly Arg Val Thr Ile Thr Ala Asp Lys Ser Thr Asn Thr Ala Tyr
65              70              75              80

Met Glu Leu Ser Arg Leu Arg Ser Glu Asp Thr Ala Val Tyr Tyr Cys
                85              90              95

Ala Arg Glu Gly Asp Asp Val Leu Val Pro Thr Ser Arg Gly Phe Phe
            100             105             110

Asp Tyr Trp Gly Gln Gly Thr Leu Val Thr Val Ser Ser Ala Gln Thr
        115             120             125
```

```
<210> SEQ ID NO 29
<211> LENGTH: 101
<212> TYPE: PRT
<213> ORGANISM: Homo sapiens

<400> SEQUENCE: 29
```

```
Gln Val Gln Leu Gln Gln Ser Gly Pro Gly Leu Val Lys Pro Ser Gln
1               5               10              15

Thr Leu Ser Leu Thr Cys Ala Ile Ser Gly Asp Ser Val Ser Ser Asn
            20              25              30

Ser Ala Ala Trp Asn Trp Ile Arg Gln Ser Pro Ser Arg Gly Leu Glu
        35              40              45

Trp Leu Gly Arg Thr Tyr Tyr Arg Ser Lys Trp Tyr Asn Asp Tyr Ala
    50              55              60

Val Ser Val Lys Ser Arg Ile Thr Ile Asn Pro Asp Thr Ser Lys Asn
65              70              75              80

Gln Phe Ser Leu Gln Leu Asn Ser Val Thr Pro Glu Asp Thr Ala Val
                85              90              95

Tyr Tyr Cys Ala Arg
            100
```

```
<210> SEQ ID NO 30
<211> LENGTH: 125
<212> TYPE: PRT
<213> ORGANISM: Homo sapiens

<400> SEQUENCE: 30
```

```
Gln Val Gln Leu Gln Gln Ser Gly Pro Gly Leu Val Lys Pro Ser Gln
1               5               10              15

Thr Leu Ser Leu Thr Cys Ala Ile Ser Gly Asp Ser Val Ser Ser Asn
            20              25              30

Ser Ala Ala Trp Asn Trp Ile Arg Gln Ser Pro Ser Arg Gly Leu Glu
        35              40              45

Trp Leu Gly Arg Thr Tyr Tyr Arg Ser Lys Trp Tyr Asn Asp Tyr Ala
    50              55              60

Val Ser Val Lys Ser Arg Ile Thr Ile Asn Pro Asn Thr Ser Lys Asn
65              70              75              80

Gln Phe Ser Leu Gln Leu Asn Pro Val Thr Pro Glu Asp Thr Ala Val
            85              90              95

Tyr Phe Cys Ala Arg Glu Trp Phe Gly Glu Gly Tyr Phe Asp Leu Trp
            100             105             110

Gly Arg Gly Thr Leu Val Thr Val Ser Ser Ala Arg Thr
        115             120             125
```

```
<210> SEQ ID NO 31
```

-continued

```
<211> LENGTH: 98
<212> TYPE: PRT
<213> ORGANISM: Homo sapiens

<400> SEQUENCE: 31

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg

<210> SEQ ID NO 32
<211> LENGTH: 125
<212> TYPE: PRT
<213> ORGANISM: Homo sapiens

<400> SEQUENCE: 32

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Asn
            20                  25                  30

Arg Trp Trp Thr Trp Val Arg Arg Ser Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Arg Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Leu Thr Leu Ile Trp Phe Gly Glu Lys Ala Phe Asp Ile Trp
            100                 105                 110

Gly Gln Gly Thr Met Val Thr Val Ser Ser Ala Glu Thr
        115                 120                 125

<210> SEQ ID NO 33
<211> LENGTH: 95
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

-continued

```
65                  70                  75                  80

Glu Asp Val Ala Thr Tyr Tyr Cys Gln Lys Tyr Asn Ser Ala Pro
                85                  90                  95

<210> SEQ ID NO 34
<211> LENGTH: 113
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Thr Asn Tyr
                20                  25                  30

Leu Ala Trp Tyr Gln Gln Lys Pro Gly Lys Val Pro Lys Leu Leu Ile
            35                  40                  45

Tyr Ala Ala Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Phe Tyr Cys Gln Lys Tyr Asn Ile Ala Pro Cys
                85                  90                  95

Phe Phe Pro Gly Arg Thr Met Glu Glu Ile Lys Arg Asp Asp Ala Ala
            100                 105                 110

Pro

<210> SEQ ID NO 35
<211> LENGTH: 113
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Thr Asn Tyr
                20                  25                  30

Leu Ala Trp Tyr Gln Gln Lys Pro Gly Lys Val Pro Gln Leu Leu Ile
            35                  40                  45

Tyr Ala Ala Ser Ile Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Phe Tyr Cys Gln Lys Tyr Asn Ile Val Pro Cys
                85                  90                  95

Phe Phe Pro Gly Arg Thr Met Glu Glu Ile Arg Gly Asp Asp Ala Ala
            100                 105                 110

Pro

<210> SEQ ID NO 36
<211> LENGTH: 113
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
```

-continued

```
                20              25              30

Leu Ala Trp Tyr Gln Gln Lys Pro Gly Lys Val Pro Lys Leu Leu Ile
        35              40              45

Tyr Ala Ala Ser Thr Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Val Ala Thr Tyr Tyr Cys Gln Lys Ser Asn Asn Ala Pro Leu
                85              90              95

Thr Phe Gly Gly Gly Thr Lys Val Glu Ile Lys Arg Ala Asp Ala Ala
                100             105             110

Pro

<210> SEQ ID NO 37
<211> LENGTH: 113
<212> TYPE: PRT
<213> ORGANISM: Homo sapiens

<400> SEQUENCE: 37

Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Ser Asn Tyr
                20              25              30

Leu Ala Trp Tyr Gln Gln Lys Pro Gly Lys Val Pro Lys Leu Leu Ile
        35              40              45

Tyr Ala Ala Ser Thr Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Val Ala Thr Tyr Tyr Cys Gln Lys Tyr Asn Ser Ala Pro Trp
                85              90              95

Thr Phe Gly Gln Gly Thr Lys Val Glu Ile Lys Arg Ala Asp Ala Ala
                100             105             110

Pro

<210> SEQ ID NO 38
<211> LENGTH: 113
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Ser Asn Tyr
                20              25              30

Leu Ala Trp Tyr Gln Gln Lys Pro Gly Lys Val Pro Lys Leu Leu Ile
        35              40              45

Tyr Ala Ala Ser Thr Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Val Ala Thr Tyr Tyr Cys Gln Lys Tyr Asn Ser Ala Pro Trp
                85              90              95

Thr Phe Gly Gln Gly Thr Lys Val Glu Ile Lys Arg Ala Asp Ala Ala
                100             105             110
```

-continued

```
Pro

<210> SEQ ID NO 39
<211> LENGTH: 101
<212> TYPE: PRT
<213> ORGANISM: Homo sapiens

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 40
<211> LENGTH: 119
<212> TYPE: PRT
<213> ORGANISM: Homo sapiens

<400> SEQUENCE: 40

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Gly
            20                  25                  30

Ser Asn Asn Lys Asn Tyr Leu Ala Trp Tyr Gln Gln Arg Pro Gly Gln
        35                  40                  45

Pro Pro Arg Leu Leu Ile Tyr Trp Ala Ser Thr Arg Glu Ser Gly Val
    50                  55                  60

Pro Asp Arg Phe Ser Gly Ser Gly Pro Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Leu Glu Ile
            100                 105                 110

Lys Arg Ala Asp Ala Ala Pro
        115

<210> SEQ ID NO 41
<211> LENGTH: 94
<212> TYPE: PRT
<213> ORGANISM: Homo sapiens

<400> SEQUENCE: 41

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45
```

```
Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp
                85                  90

<210> SEQ ID NO 42
<211> LENGTH: 113
<212> TYPE: PRT
<213> ORGANISM: Homo sapiens

<400> SEQUENCE: 42

Glu Ile Val Met Thr Gln Ser Pro Ala Thr Leu Ser Val Ser Pro Gly
1               5                  10                  15

Glu Arg Ala Thr Leu Ser Cys Arg Ala Ser Gln Ser Val Ser Ser Asn
                20                  25                  30

Leu Thr Trp Tyr Gln Gln Lys Pro Gly Gln Ala Pro Arg Leu Leu Ile
        35                  40                  45

Tyr Gly Ala Ser Thr Arg Ala Thr Gly Ile Pro Thr Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys Arg Ala Asp Ala Ala
            100                 105                 110

Pro

<210> SEQ ID NO 43
<211> LENGTH: 113
<212> TYPE: PRT
<213> ORGANISM: Homo sapiens

<400> SEQUENCE: 43

Glu Ile Val Met Thr Gln Ser Pro Ala Thr Leu Ser Val Ser Pro Gly
1               5                  10                  15

Glu Arg Ala Thr Leu Ser Cys Arg Ala Ser Gln Ser Val Ser Ser Asn
                20                  25                  30

Leu Thr Trp Tyr Gln Gln Lys Pro Gly Gln Ala Pro Arg Leu Leu Ile
        35                  40                  45

Tyr Gly Ala Ser Thr Arg Ala Thr Gly Ile Pro Thr Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys Arg Ala Asp Ala Ala
            100                 105                 110

Pro

<210> SEQ ID NO 44
<211> LENGTH: 113
<212> TYPE: PRT
<213> ORGANISM: Homo sapiens

<400> SEQUENCE: 44
```

-continued

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys Arg Ala Asp Ala Ala
            100                 105                 110

Pro
```

<210> SEQ ID NO 45
<211> LENGTH: 113
<212> TYPE: PRT
<213> ORGANISM: Homo sapiens

<400> SEQUENCE: 45

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys Arg Ala Asp Ala Ala
            100                 105                 110

Pro
```

<210> SEQ ID NO 46
<211> LENGTH: 113
<212> TYPE: PRT
<213> ORGANISM: Homo sapiens

<400> SEQUENCE: 46

```
Glu Ile Val Met Thr Gln Ser Pro Ala Thr Leu Ser Val Ser Pro Gly
1               5                   10                  15

Glu Arg Ala Thr Leu Ser Cys Arg Ala Gly Gln Ser Val Ser Ser Asp
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
```

-continued

```
                    85                  90                  95

Thr Phe Gly Gln Gly Thr Arg Leu Glu Ile Lys Arg Ala Asp Ala Ala
                100                 105                 110

Pro

<210> SEQ ID NO 47
<211> LENGTH: 113
<212> TYPE: PRT
<213> ORGANISM: Homo sapiens

<400> SEQUENCE: 47

Glu Ile Val Met Thr Gln Ser Pro Ala Thr Leu Ser Val Ser Pro Gly
1                   5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Ala Asp Ala Ala
                100                 105                 110

Pro

<210> SEQ ID NO 48
<211> LENGTH: 113
<212> TYPE: PRT
<213> ORGANISM: Homo sapiens

<400> SEQUENCE: 48

Glu Ile Val Met Thr Gln Ser Pro Ala Thr Leu Ser Val Ser Pro Gly
1                   5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
            50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Ala Asp Ala Ala
                100                 105                 110

Pro

<210> SEQ ID NO 49
<211> LENGTH: 113
<212> TYPE: PRT
<213> ORGANISM: Homo sapiens

<400> SEQUENCE: 49

Glu Ile Val Met Thr Gln Ser Pro Ala Thr Leu Ser Val Ser Pro Gly
1                   5                   10                  15
```

```
Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Met Lys Arg Ala Asp Ala Ala
            100                 105                 110

Pro
```

```
<210> SEQ ID NO 50
<211> LENGTH: 113
<212> TYPE: PRT
<213> ORGANISM: Homo sapiens

<400> SEQUENCE: 50
```

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys Arg Ala Asp Ala Ala
            100                 105                 110

Pro
```

```
<210> SEQ ID NO 51
<211> LENGTH: 108
<212> TYPE: PRT
<213> ORGANISM: Homo sapiens

<400> SEQUENCE: 51
```

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Thr Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg
```

-continued

```
                100                 105

<210> SEQ ID NO 52
<211> LENGTH: 108
<212> TYPE: PRT
<213> ORGANISM: Homo sapiens

<400> SEQUENCE: 52

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg
            100                 105

<210> SEQ ID NO 53
<211> LENGTH: 108
<212> TYPE: PRT
<213> ORGANISM: Homo sapiens

<400> SEQUENCE: 53

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ile Asn
                20                  25                  30

Leu Ala Trp Tyr Gln Gln Lys Pro Gly Gln Ala Pro Arg Leu Leu Ile
            35                  40                  45

Tyr Asp Thr Ser Ala Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys Arg
            100                 105

<210> SEQ ID NO 54
<211> LENGTH: 108
<212> TYPE: PRT
<213> ORGANISM: Homo sapiens

<400> SEQUENCE: 54

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Lys Lys Pro Gly Gln Ala Pro Arg Leu Leu Ile
            35                  40                  45

Tyr Gly Ala Ser Thr Arg Val Thr Gly Ile Pro Ala Arg Phe Ser Gly
        50                  55                  60
```

```
Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg
            100                 105

<210> SEQ ID NO 55
<211> LENGTH: 108
<212> TYPE: PRT
<213> ORGANISM: Homo sapiens

<400> SEQUENCE: 55

Glu Ile Val Met Thr Gln Ser Pro Ala Thr Leu Ser Val Ser Pro Gly
1               5                   10                  15

Glu Ser Ala Thr Leu Ser Cys Arg Ala Ser Gln Thr Ile Tyr Ser Asn
                20                  25                  30

Leu Ala Trp Tyr Gln Arg Lys Pro Gly Gln Ala Pro Arg Leu Leu Ile
            35                  40                  45

Tyr Arg Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Cys Cys Gln Gln Phe Asn Asn Trp Pro Tyr
                85                  90                  95

Thr Phe Gly Gln Gly Thr Lys Leu Glu Ile Lys Arg
            100                 105

<210> SEQ ID NO 56
<211> LENGTH: 108
<212> TYPE: PRT
<213> ORGANISM: Homo sapiens

<400> SEQUENCE: 56

Glu Ile Val Met Thr Gln Ser Pro Ala Thr Leu Ser Val Ser Pro Gly
1               5                   10                  15

Glu Arg Ala Thr Leu Ser Cys Gly Ala Ser Pro Ser Val Ser Thr Asn
                20                  25                  30

Leu Ala Trp Tyr Gln Gln Arg Pro Gly Gln Ala Pro Arg Leu Leu Ile
            35                  40                  45

Tyr Gly Ile Ser Thr Arg Ala Ala Gly Ile Pro Ala Arg Phe Ser Gly
    50                  55                  60

Thr Gly Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Asn Trp Pro Tyr
                85                  90                  95

Thr Phe Gly Gln Gly Thr Lys Leu Glu Ile Lys Arg
            100                 105

<210> SEQ ID NO 57
<211> LENGTH: 96
<212> TYPE: PRT
<213> ORGANISM: Homo sapiens

<400> SEQUENCE: 57

Glu Ile Val Leu Thr Gln Ser Pro Gly Thr Leu Ser Leu Ser Pro Gly
1               5                   10                  15
```

```
Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95
```

```
<210> SEQ ID NO 58
<211> LENGTH: 107
<212> TYPE: PRT
<213> ORGANISM: Homo sapiens

<400> SEQUENCE: 58
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Tyr Thr
                85                  90                  95

Phe Gly Gln Gly Thr Lys Leu Glu Ile Lys Arg
                100                 105
```

```
<210> SEQ ID NO 59
<211> LENGTH: 108
<212> TYPE: PRT
<213> ORGANISM: Homo sapiens

<400> SEQUENCE: 59
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Asp Gln Val Pro Arg Leu Leu
            35                  40                  45

Ile Tyr Gly Thr Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg
                100                 105
```

```
<210> SEQ ID NO 60
<211> LENGTH: 95
<212> TYPE: PRT
<213> ORGANISM: Homo sapiens
```

```
<400> SEQUENCE: 60

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

<210> SEQ ID NO 61
<211> LENGTH: 108
<212> TYPE: PRT
<213> ORGANISM: Homo sapiens

<400> SEQUENCE: 61

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Trp
                85                  90                  95

Thr Phe Gly Gln Gly Thr Lys Val Glu Ile Lys Arg
            100                 105

<210> SEQ ID NO 62
<211> LENGTH: 100
<212> TYPE: PRT
<213> ORGANISM: Homo sapiens

<400> SEQUENCE: 62

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100
```

<210> SEQ ID NO 63
<211> LENGTH: 113
<212> TYPE: PRT
<213> ORGANISM: Homo sapiens

<400> SEQUENCE: 63

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

Arg

<210> SEQ ID NO 64
<211> LENGTH: 113
<212> TYPE: PRT
<213> ORGANISM: Homo sapiens

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg

<210> SEQ ID NO 65
<211> LENGTH: 113
<212> TYPE: PRT
<213> ORGANISM: Homo sapiens

<400> SEQUENCE: 65

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro

-continued

```
        50              55              60

Asp Arg Phe Ser Gly Ser Gly Ser Gly Thr Asp Phe Thr Leu Lys Ile
65              70              75                          80

Ser Arg Val Glu Ala Glu Asp Val Gly Ile Tyr Tyr Cys Met Gln Ala
                85              90              95

Leu Gln Thr Pro Tyr Thr Phe Gly Gln Gly Thr Lys Leu Glu Ile Lys
            100             105             110

Arg

<210> SEQ ID NO 66
<211> LENGTH: 95
<212> TYPE: PRT
<213> ORGANISM: Homo sapiens

<400> SEQUENCE: 66

Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Ser Ser Tyr
                20              25              30

Leu Asn Trp Tyr Gln Gln Lys Pro Gly Lys Ala Pro Lys Leu Leu Ile
            35              40              45

Tyr Ala Ala Ser Ser Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70              75                          80

Glu Asp Phe Ala Thr Tyr Tyr Cys Gln Gln Ser Tyr Ser Thr Pro
                85              90              95

<210> SEQ ID NO 67
<211> LENGTH: 108
<212> TYPE: PRT
<213> ORGANISM: Homo sapiens

<400> SEQUENCE: 67

Asp Ile Gln Met Thr Gln Ser Pro Ser Ser Leu Ser Ala Ser Val Arg
1               5               10              15

Asp Arg Val Thr Ile Thr Cys Arg Ala Ser Gln Ile Ile Ser Asn Tyr
                20              25              30

Leu Asn Trp Tyr Gln Gln Lys Pro Gly Lys Ala Pro Lys Leu Leu Ile
            35              40              45

Tyr Ala Ala Ser Ser Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70              75                          80

Glu Asp Phe Ala Thr Tyr Phe Cys Gln Gln Ser Tyr Ser Thr Pro Phe
                85              90              95

Ala Phe Gly Pro Gly Thr Lys Val Asp Ile Lys Arg
            100             105

<210> SEQ ID NO 68
<211> LENGTH: 101
<212> TYPE: PRT
<213> ORGANISM: Homo sapiens

<400> SEQUENCE: 68

Gln Val Gln Leu Gln Gln Ser Gly Pro Gly Leu Val Lys Pro Ser Gln
1               5               10              15
```

```
Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg
            100

<210> SEQ ID NO 69
<211> LENGTH: 123
<212> TYPE: PRT
<213> ORGANISM: Homo sapiens

<400> SEQUENCE: 69

Gln Val Gln Leu Gln Gln Ser Gly Pro Gly Leu Val Lys Pro Ser Gln
1               5                   10                  15

Thr Leu Ser Leu Thr Cys Ala Ile Ser Gly His Ser Val Ser Ser Asn
            20                  25                  30

Ser Ala Asp Trp Asn Trp Ile Arg Gln Ser Pro Ser Arg Gly Leu Glu
        35                  40                  45

Trp Leu Gly Arg Thr Tyr Cys Arg Ser Lys Cys Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Pro Val Thr Pro Glu Asp Thr Ala Val
                85                  90                  95

Tyr Tyr Cys Ala Arg Ser Leu Gly Ser Gly Thr Tyr Pro Phe Asp Ser
            100                 105                 110

Trp Gly Gln Gly Thr Leu Val Thr Val Ser Ser
        115                 120

<210> SEQ ID NO 70
<211> LENGTH: 122
<212> TYPE: PRT
<213> ORGANISM: Homo sapiens

<400> SEQUENCE: 70

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Asn Trp Ile Arg Gln Ser Pro Ser Arg Gly Leu Glu
        35                  40                  45

Trp Leu Gly Arg Thr Tyr Phe Arg Ser Lys Trp Asn Asn His Tyr Ala
    50                  55                  60

Val Ser Val Lys Ser Arg Ile Thr Ile Asn Pro Asp Thr Ser Lys Asn
65                  70                  75                  80

Gln Phe Ser Leu Leu Leu Asn Pro Val Thr Pro Glu Asp Thr Ala Val
                85                  90                  95

Tyr Tyr Cys Ala Arg Ala Thr Leu Ala Arg Gly Ala Leu Asp Tyr Trp
            100                 105                 110
```

```
Gly Gln Gly Thr Leu Val Thr Val Ser Ser
        115                 120

<210> SEQ ID NO 71
<211> LENGTH: 95
<212> TYPE: PRT
<213> ORGANISM: Homo sapiens

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 72
<211> LENGTH: 108
<212> TYPE: PRT
<213> ORGANISM: Homo sapiens

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Arg Ile Ser Arg Phe
            20                  25                  30

Leu Asn Trp Tyr Gln Gln Thr Pro Gly Lys Ala Pro Lys Phe Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Thr Val Glu Ile Lys Arg
            100                 105

<210> SEQ ID NO 73
<211> LENGTH: 101
<212> TYPE: PRT
<213> ORGANISM: Homo sapiens

<400> SEQUENCE: 73

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
```

-continued

```
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100
```

<210> SEQ ID NO 74
<211> LENGTH: 114
<212> TYPE: PRT
<213> ORGANISM: Homo sapiens

<400> SEQUENCE: 74

```
Asp Ile Val Met Thr Gln Ser Pro Asp Ser Leu Ala Val Ser Leu Gly
1                   5                   10                  15

Glu Arg Ala Thr Ile Asn Cys Lys Ser Ser Gln Ser Val Leu Tyr Ser
                20                  25                  30

Ser Asn Asn Met Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Pro Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys Arg
```

<210> SEQ ID NO 75
<211> LENGTH: 122
<212> TYPE: PRT
<213> ORGANISM: Homo sapiens

<400> SEQUENCE: 75

```
Glu Val Gln Leu Val Glu Ser Gly Gly Gly Val Val Gln Pro Gly Arg
1                   5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Ile Phe Gly Val Pro Asp Ala Phe Asp Ile Arg
            100                 105                 110

Gly Gln Gly Thr Met Val Thr Val Ser Ser
        115                 120
```

<210> SEQ ID NO 76
<211> LENGTH: 98
<212> TYPE: PRT
<213> ORGANISM: Homo sapiens

<400> SEQUENCE: 76

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 77
<211> LENGTH: 114
<212> TYPE: PRT
<213> ORGANISM: Homo sapiens

<400> SEQUENCE: 77

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Asn Pro Tyr Phe Asp Tyr Trp Gly Gln Gly Thr Leu Val Thr Val
                100                 105                 110

Ser Ser
```

<210> SEQ ID NO 78
<211> LENGTH: 118
<212> TYPE: PRT
<213> ORGANISM: Homo sapiens

<400> SEQUENCE: 78

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Leu Trp Val Arg Gln Ala Pro Gly Glu Gly Leu Val Trp Val
        35                  40                  45

Ser Arg Ile Asp Ser Asp Gly Ser Asn Thr Thr Tyr Ala Asp Ser Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Gly Tyr Ala Phe Asp Ile Trp Gly Gln Gly Thr
                100                 105                 110
```

Met Val Thr Val Ser Ser
        115

<210> SEQ ID NO 79
<211> LENGTH: 98
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 80
<211> LENGTH: 120
<212> TYPE: PRT
<213> ORGANISM: Homo sapiens

<400> SEQUENCE: 80

Glu Val Gln Leu Leu Glu Ser Gly Gly Gly Trp Val Gln Pro Gly Gly
1               5                   10                  15

Ser Leu Arg Leu Ser Cys Ala Ala Ser Gly Phe Thr Phe Ser Thr Asn
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Asp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Pro Arg Ile Ala Val Ala Pro Asp Ala Leu Asp Ile Trp Gly Gln
            100                 105                 110

Gly Thr Met Val Thr Val Ser Ser
        115                 120

<210> SEQ ID NO 81
<211> LENGTH: 1353
<212> TYPE: PRT
<213> ORGANISM: Unknown
<220> FEATURE:
<223> OTHER INFORMATION: betacoronavirus 2c EMC/2012

<400> SEQUENCE: 81

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

```
Val Asp Ile Gln Gln Thr Phe Phe Asp Lys Thr Trp Pro Arg Pro Ile
        35                  40                  45

Asp Val Ser Lys Ala Asp Gly Ile Ile Tyr Pro Gln Gly Arg Thr Tyr
        50                  55                  60

Ser Asn Ile Thr Ile Thr Tyr Gln Gly Leu Phe Pro Tyr Gln Gly Asp
65                  70                  75                  80

His Gly Asp Met Tyr Val Tyr Ser Ala Gly His Ala Thr Gly Thr Thr
                85                  90                  95

Pro Gln Lys Leu Phe Val Ala Asn Tyr Ser Gln Asp Val Lys Gln Phe
                100                 105                 110

Ala Asn Gly Phe Val Val Arg Ile Gly Ala Ala Ala Asn Ser Thr Gly
                115                 120                 125

Thr Val Ile Ile Ser Pro Ser Thr Ser Ala Thr Ile Arg Lys Ile Tyr
        130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                165                 170                 175

Gly Thr Leu Leu Arg Ala Phe Tyr Cys Ile Leu Glu Pro Arg Ser Gly
                180                 185                 190

Asn His Cys Pro Ala Gly Asn Ser Tyr Thr Ser Phe Ala Thr Tyr His
        195                 200                 205

Thr Pro Ala Thr Asp Cys Ser Asp Gly Asn Tyr Asn Arg Asn Ala Ser
        210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                245                 250                 255

Thr Gln Thr Ala Gln Gly Val His Leu Phe Ser Ser Arg Tyr Val Asp
                260                 265                 270

Leu Tyr Gly Gly Asn Met Phe Gln Phe Ala Thr Leu Pro Val Tyr Asp
                275                 280                 285

Thr Ile Lys Tyr Tyr Ser Ile Ile Pro His Ser Ile Arg Ser Ile Gln
        290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
                340                 345                 350

Ser Phe Asp Val Glu Ser Gly Val Tyr Ser Val Ser Ser Phe Glu Ala
                355                 360                 365

Lys Pro Ser Gly Ser Val Val Glu Gln Ala Glu Gly Val Glu Cys Asp
        370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                405                 410                 415

Leu Phe Ser Val Asn Asp Phe Thr Cys Ser Gln Ile Ser Pro Ala Ala
                420                 425                 430

Ile Ala Ser Asn Cys Tyr Ser Ser Leu Ile Leu Asp Tyr Phe Ser Tyr
        435                 440                 445
```

-continued

```
Pro Leu Ser Met Lys Ser Asp Leu Ser Val Ser Ser Ala Gly Pro Ile
    450                 455                 460

Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
                500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Tyr Arg Lys Gln
    530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
                580                 585                 590

Asp Thr Lys Ile Ala Ser Gln Leu Gly Asn Cys Val Glu Tyr Ser Leu
            595                 600                 605

Tyr Gly Val Ser Gly Arg Gly Val Phe Gln Asn Cys Thr Ala Val Gly
    610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
                645                 650                 655

Val Pro Val Ser Val Ile Tyr Asp Lys Glu Thr Lys Thr His Ala Thr
                660                 665                 670

Leu Phe Gly Ser Val Ala Cys Glu His Ile Ser Ser Thr Met Ser Gln
            675                 680                 685

Tyr Ser Arg Ser Thr Arg Ser Met Leu Lys Arg Arg Asp Ser Thr Tyr
    690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
                740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
    770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
            835                 840                 845

Leu Phe Ala Ser Val Lys Ser Ser Gln Ser Ser Pro Ile Ile Pro Gly
    850                 855                 860

Phe Gly Gly Asp Phe Asn Leu Thr Leu Leu Glu Pro Val Ser Ile Ser
```

-continued

```
865                 870                 875                 880
Thr Gly Ser Arg Ser Ala Arg Ser Ala Ile Glu Asp Leu Leu Phe Asp
                885                 890                 895
Lys Val Thr Ile Ala Asp Pro Gly Tyr Met Gln Gly Tyr Asp Asp Cys
                900                 905                 910
Met Gln Gln Gly Pro Ala Ser Ala Arg Asp Leu Ile Cys Ala Gln Tyr
                915                 920                 925
Val Ala Gly Tyr Lys Val Leu Pro Pro Leu Met Asp Val Asn Met Glu
    930                 935                 940
Ala Ala Tyr Thr Ser Ser Leu Leu Gly Ser Ile Ala Gly Val Gly Trp
945                 950                 955                 960
Thr Ala Gly Leu Ser Ser Phe Ala Ala Ile Pro Phe Ala Gln Ser Ile
                965                 970                 975
Phe Tyr Arg Leu Asn Gly Val Gly Ile Thr Gln Gln Val Leu Ser Glu
                980                 985                 990
Asn Gln Lys Leu Ile Ala Asn Lys  Phe Asn Gln Ala Leu  Gly Ala Met
        995                 1000                1005
Gln Thr  Gly Phe Thr Thr Thr  Asn Glu Ala Phe Gln  Lys Val Gln
    1010                1015                1020
Asp Ala  Val Asn Asn Asn Ala  Gln Ala Leu Ser Lys  Leu Ala Ser
    1025                1030                1035
Glu Leu  Ser Asn Thr Phe Gly  Ala Ile Ser Ala Ser  Ile Gly Asp
    1040                1045                1050
Ile Ile  Gln Arg Leu Asp Val  Leu Glu Gln Asp Ala  Gln Ile Asp
    1055                1060                1065
Arg Leu  Ile Asn Gly Arg Leu  Thr Thr Leu Asn Ala  Phe Val Ala
    1070                1075                1080
Gln Gln  Leu Val Arg Ser Glu  Ser Ala Ala Leu Ser  Ala Gln Leu
    1085                1090                1095
Ala Lys  Asp Lys Val Asn Glu  Cys Val Lys Ala Gln  Ser Lys Arg
    1100                1105                1110
Ser Gly  Phe Cys Gly Gln Gly  Thr His Ile Val Ser  Phe Val Val
    1115                1120                1125
Asn Ala  Pro Asn Gly Leu Tyr  Phe Met His Val Gly  Tyr Tyr Pro
    1130                1135                1140
Ser Asn  His Ile Glu Val Val  Ser Ala Tyr Gly Leu  Cys Asp Ala
    1145                1150                1155
Ala Asn  Pro Thr Asn Cys Ile  Ala Pro Val Asn Gly  Tyr Phe Ile
    1160                1165                1170
Lys Thr  Asn Asn Thr Arg Ile  Val Asp Glu Trp Ser  Tyr Thr Gly
    1175                1180                1185
Ser Ser  Phe Tyr Ala Pro Glu  Pro Ile Thr Ser Leu  Asn Thr Lys
    1190                1195                1200
Tyr Val  Ala Pro Gln Val Thr  Tyr Gln Asn Ile Ser  Thr Asn Leu
    1205                1210                1215
Pro Pro  Pro Leu Leu Gly Asn  Ser Thr Gly Ile Asp  Phe Gln Asp
    1220                1225                1230
Glu Leu  Asp Glu Phe Phe Lys  Asn Val Ser Thr Ser  Ile Pro Asn
    1235                1240                1245
Phe Gly  Ser Leu Thr Gln Ile  Asn Thr Thr Leu Leu  Asp Leu Thr
    1250                1255                1260
Tyr Glu  Met Leu Ser Leu Gln  Gln Val Val Lys Ala  Leu Asn Glu
    1265                1270                1275
```

```
Ser Tyr  Ile Asp Leu Lys Glu  Leu Gly Asn Tyr Thr  Tyr Tyr Asn
    1280              1285              1290

Lys Trp  Pro Trp Tyr Ile Trp  Leu Gly Phe Ile Ala  Gly Leu Val
    1295              1300              1305

Ala Leu  Ala Leu Cys Val Phe  Phe Ile Leu Cys Cys  Thr Gly Cys
    1310              1315              1320

Gly Thr  Asn Cys Met Gly Lys  Leu Lys Cys Asn Arg  Cys Cys Asp
    1325              1330              1335

Arg Tyr  Glu Glu Tyr Asp Leu  Glu Pro His Lys Val  His Val His
    1340              1345              1350

<210> SEQ ID NO 82
<211> LENGTH: 13
<212> TYPE: PRT
<213> ORGANISM: Unknown
<220> FEATURE:
<223> OTHER INFORMATION: betacoronavirus 2c EMC/2012

<400> SEQUENCE: 82

Asp Phe Gln Asp Glu Leu Asp Glu Phe Phe Lys Asn Val
1               5               10

<210> SEQ ID NO 83
<211> LENGTH: 10
<212> TYPE: PRT
<213> ORGANISM: Homo sapiens

<400> SEQUENCE: 83

Gly Asp Ser Val Ser Ser Asp Ser Ala Ala
1               5               10

<210> SEQ ID NO 84
<211> LENGTH: 9
<212> TYPE: PRT
<213> ORGANISM: Homo sapiens

<400> SEQUENCE: 84

Thr Tyr Phe Arg Ser Lys Trp Asn Asn
1               5

<210> SEQ ID NO 85
<211> LENGTH: 12
<212> TYPE: PRT
<213> ORGANISM: Homo sapiens

<400> SEQUENCE: 85

Ala Arg Ala Thr Leu Ala Arg Gly Ala Leu Asp Tyr
1               5               10

<210> SEQ ID NO 86
<211> LENGTH: 12
<212> TYPE: PRT
<213> ORGANISM: Homo sapiens

<400> SEQUENCE: 86

Gln Ser Val Leu Tyr Ser Ser Asn Asn Met Asn Tyr
1               5               10

<210> SEQ ID NO 87
<211> LENGTH: 3
<212> TYPE: PRT
<213> ORGANISM: Homo sapiens
```

-continued

```
<400> SEQUENCE: 87

Trp Ala Ser
1

<210> SEQ ID NO 88
<211> LENGTH: 9
<212> TYPE: PRT
<213> ORGANISM: Homo sapiens

<400> SEQUENCE: 88

Gln Gln Tyr Tyr Ser Thr Pro Trp Thr
1               5

<210> SEQ ID NO 89
<211> LENGTH: 10
<212> TYPE: PRT
<213> ORGANISM: Homo sapiens

<400> SEQUENCE: 89

Gly His Ser Val Ser Ser Asn Ser Ala Asp
1               5                   10

<210> SEQ ID NO 90
<211> LENGTH: 9
<212> TYPE: PRT
<213> ORGANISM: Homo sapiens

<400> SEQUENCE: 90

Thr Tyr Cys Arg Ser Lys Cys Tyr Asn
1               5

<210> SEQ ID NO 91
<211> LENGTH: 13
<212> TYPE: PRT
<213> ORGANISM: Homo sapiens

<400> SEQUENCE: 91

Ala Arg Ser Leu Gly Ser Gly Thr Tyr Pro Phe Asp Ser
1               5                   10

<210> SEQ ID NO 92
<211> LENGTH: 6
<212> TYPE: PRT
<213> ORGANISM: Homo sapiens

<400> SEQUENCE: 92

Gln Arg Ile Ser Arg Phe
1               5

<210> SEQ ID NO 93
<211> LENGTH: 3
<212> TYPE: PRT
<213> ORGANISM: Homo sapiens

<400> SEQUENCE: 93

Ala Ala Ser
1

<210> SEQ ID NO 94
<211> LENGTH: 9
<212> TYPE: PRT
<213> ORGANISM: Homo sapiens

<400> SEQUENCE: 94
```

-continued

```
Gln Gln Ser Tyr Ser Thr Pro Leu Thr
1               5

<210> SEQ ID NO 95
<211> LENGTH: 8
<212> TYPE: PRT
<213> ORGANISM: Homo sapiens

<400> SEQUENCE: 95

Gly Gly Thr Phe Ser Ile Tyr Ala
1               5

<210> SEQ ID NO 96
<211> LENGTH: 8
<212> TYPE: PRT
<213> ORGANISM: Homo sapiens

<400> SEQUENCE: 96

Ile Ile Pro Ile Phe Gly Thr Ala
1               5

<210> SEQ ID NO 97
<211> LENGTH: 18
<212> TYPE: PRT
<213> ORGANISM: Homo sapiens

<400> SEQUENCE: 97

Ala Arg Glu Gly Asp Asp Val Leu Val Pro Thr Ser Arg Gly Phe Phe
1               5                   10                  15

Asp Tyr

<210> SEQ ID NO 98
<211> LENGTH: 11
<212> TYPE: PRT
<213> ORGANISM: Homo sapiens

<400> SEQUENCE: 98

Gln Ser Leu Leu His Ser Asn Gly Tyr Asn Tyr
1               5                   10

<210> SEQ ID NO 99
<211> LENGTH: 3
<212> TYPE: PRT
<213> ORGANISM: Homo sapiens

<400> SEQUENCE: 99

Leu Gly Ser
1

<210> SEQ ID NO 100
<211> LENGTH: 9
<212> TYPE: PRT
<213> ORGANISM: Homo sapiens

<400> SEQUENCE: 100

Met Gln Ala Leu Gln Thr Pro Leu Thr
1               5

<210> SEQ ID NO 101
<211> LENGTH: 8
<212> TYPE: PRT
<213> ORGANISM: Homo sapiens

<400> SEQUENCE: 101
```

-continued

```
Gly Gly Ala Phe Ser Ala Tyr Val
1               5

<210> SEQ ID NO 102
<211> LENGTH: 8
<212> TYPE: PRT
<213> ORGANISM: Homo sapiens

<400> SEQUENCE: 102

Ile Ile Pro Val Phe Gly Thr Ala
1               5

<210> SEQ ID NO 103
<211> LENGTH: 18
<212> TYPE: PRT
<213> ORGANISM: Homo sapiens

<400> SEQUENCE: 103

Ala Arg Glu Gly Asp Ile Glu Val Val Leu Ala Gly Arg Gly Tyr Phe
1               5                   10                  15

Asp Tyr

<210> SEQ ID NO 104
<211> LENGTH: 11
<212> TYPE: PRT
<213> ORGANISM: Homo sapiens

<400> SEQUENCE: 104

Gln Ser Leu Leu His Ser Asn Gly Tyr Asn Tyr
1               5                   10

<210> SEQ ID NO 105
<211> LENGTH: 3
<212> TYPE: PRT
<213> ORGANISM: Homo sapiens

<400> SEQUENCE: 105

Leu Gly Ser
1

<210> SEQ ID NO 106
<211> LENGTH: 9
<212> TYPE: PRT
<213> ORGANISM: Homo sapiens

<400> SEQUENCE: 106

Met Gln Ala Leu Gln Thr Pro Tyr Thr
1               5

<210> SEQ ID NO 107
<211> LENGTH: 126
<212> TYPE: PRT
<213> ORGANISM: Homo sapiens

<400> SEQUENCE: 107

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Ile Ala Asp Lys Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Glu Gly Asn Leu Gly Tyr Asp Val Val Thr Gly Tyr Ser Tyr
            100                 105                 110

Phe Val Tyr Trp Gly Gln Gly Thr Leu Val Thr Val Ser Ser
        115                 120                 125

<210> SEQ ID NO 108
<211> LENGTH: 108
<212> TYPE: PRT
<213> ORGANISM: Homo sapiens

<400> SEQUENCE: 108

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Asp Gln Val Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Leu
                85                  90                  95

Thr Phe Gly Gly Gly Thr Lys Val Glu Ile Lys Arg
            100                 105

<210> SEQ ID NO 109
<211> LENGTH: 8
<212> TYPE: PRT
<213> ORGANISM: Homo sapiens

<400> SEQUENCE: 109

Gly Gly Thr Phe Ser Thr Tyr Ala
1               5

<210> SEQ ID NO 110
<211> LENGTH: 8
<212> TYPE: PRT
<213> ORGANISM: Homo sapiens

<400> SEQUENCE: 110

Ile Ile Pro Ile Phe Gly Thr Ala
1               5

<210> SEQ ID NO 111
<211> LENGTH: 19
<212> TYPE: PRT
<213> ORGANISM: Homo sapiens

<400> SEQUENCE: 111

Ala Arg Glu Gly Asn Leu Gly Tyr Asp Val Val Thr Gly Tyr Ser Tyr
1               5                   10                  15

Phe Val Tyr

<210> SEQ ID NO 112
```

```
<211> LENGTH: 7
<212> TYPE: PRT
<213> ORGANISM: Homo sapiens

<400> SEQUENCE: 112

Gln Ser Val Ser Ser Ser Tyr
1               5

<210> SEQ ID NO 113
<211> LENGTH: 3
<212> TYPE: PRT
<213> ORGANISM: Homo sapiens

<400> SEQUENCE: 113

Gly Thr Ser
1

<210> SEQ ID NO 114
<211> LENGTH: 8
<212> TYPE: PRT
<213> ORGANISM: Homo sapiens

<400> SEQUENCE: 114

Gln Gln Tyr Gly Arg Ser Leu Thr
1               5

<210> SEQ ID NO 115
<211> LENGTH: 8
<212> TYPE: PRT
<213> ORGANISM: Homo sapiens

<400> SEQUENCE: 115

Gly Phe Thr Phe Ser Ser Asp Gly
1               5

<210> SEQ ID NO 116
<211> LENGTH: 8
<212> TYPE: PRT
<213> ORGANISM: Homo sapiens

<400> SEQUENCE: 116

Ile Trp Phe Asp Gly Ser Asn Lys
1               5

<210> SEQ ID NO 117
<211> LENGTH: 21
<212> TYPE: PRT
<213> ORGANISM: Homo sapiens

<400> SEQUENCE: 117

Thr Arg Asp Arg Gly Ile Thr Met Gly Arg Gly Arg Tyr Tyr Tyr Tyr
1               5                   10                  15

Tyr Gly Met Asp Val
            20

<210> SEQ ID NO 118
<211> LENGTH: 6
<212> TYPE: PRT
<213> ORGANISM: Homo sapiens

<400> SEQUENCE: 118

Gln Ser Val Gly Ser Asn
1               5
```

-continued

```
<210> SEQ ID NO 119
<211> LENGTH: 3
<212> TYPE: PRT
<213> ORGANISM: Homo sapiens

<400> SEQUENCE: 119

Gly Ala Ser
1

<210> SEQ ID NO 120
<211> LENGTH: 9
<212> TYPE: PRT
<213> ORGANISM: Homo sapiens

<400> SEQUENCE: 120

Gln Gln Tyr Asn Asn Trp Pro Leu Thr
1               5

<210> SEQ ID NO 121
<211> LENGTH: 8
<212> TYPE: PRT
<213> ORGANISM: Homo sapiens

<400> SEQUENCE: 121

Gly Gly Thr Phe Ser Thr His Ala
1               5

<210> SEQ ID NO 122
<211> LENGTH: 8
<212> TYPE: PRT
<213> ORGANISM: Homo sapiens

<400> SEQUENCE: 122

Ile Ile Pro Ile Phe Asp Thr Pro
1               5

<210> SEQ ID NO 123
<211> LENGTH: 17
<212> TYPE: PRT
<213> ORGANISM: Homo sapiens

<400> SEQUENCE: 123

Ala Arg Glu Gly Tyr Tyr Ile Ser Gly Ser Tyr Arg Asp Ala Phe Asp
1               5                   10                  15

Ile

<210> SEQ ID NO 124
<211> LENGTH: 12
<212> TYPE: PRT
<213> ORGANISM: Homo sapiens

<400> SEQUENCE: 124

Gln Ser Val Leu Tyr Gly Ser Asn Asn Lys Asn Tyr
1               5                   10

<210> SEQ ID NO 125
<211> LENGTH: 3
<212> TYPE: PRT
<213> ORGANISM: Homo sapiens

<400> SEQUENCE: 125

Trp Ala Ser
1
```

```
<210> SEQ ID NO 126
<211> LENGTH: 9
<212> TYPE: PRT
<213> ORGANISM: Homo sapiens

<400> SEQUENCE: 126

Gln Gln Tyr Tyr Ser Thr Pro Tyr Thr
1               5

<210> SEQ ID NO 127
<211> LENGTH: 8
<212> TYPE: PRT
<213> ORGANISM: Homo sapiens

<400> SEQUENCE: 127

Gly Gly Thr Phe Ser Thr Tyr Ala
1               5

<210> SEQ ID NO 128
<211> LENGTH: 8
<212> TYPE: PRT
<213> ORGANISM: Homo sapiens

<400> SEQUENCE: 128

Ile Ile Pro Ile Phe Gly Thr Ala
1               5

<210> SEQ ID NO 129
<211> LENGTH: 19
<212> TYPE: PRT
<213> ORGANISM: Homo sapiens

<400> SEQUENCE: 129

Ala Arg Glu Gly Asn Leu Gly Tyr Asp Val Val Thr Gly Tyr Ser Tyr
1               5                   10                  15

Phe Val Tyr

<210> SEQ ID NO 130
<211> LENGTH: 7
<212> TYPE: PRT
<213> ORGANISM: Homo sapiens

<400> SEQUENCE: 130

Gln Ser Val Ser Ser Ser Tyr
1               5

<210> SEQ ID NO 131
<211> LENGTH: 3
<212> TYPE: PRT
<213> ORGANISM: Homo sapiens

<400> SEQUENCE: 131

Gly Thr Ser
1

<210> SEQ ID NO 132
<211> LENGTH: 8
<212> TYPE: PRT
<213> ORGANISM: Homo sapiens

<400> SEQUENCE: 132

Gln Gln Tyr Gly Arg Ser Leu Thr
1               5
```

```
<210> SEQ ID NO 133
<211> LENGTH: 9
<212> TYPE: PRT
<213> ORGANISM: Homo sapiens

<400> SEQUENCE: 133

Gly Gly Ser Ile Ser Ser Asn Arg Trp
1               5

<210> SEQ ID NO 134
<211> LENGTH: 7
<212> TYPE: PRT
<213> ORGANISM: Homo sapiens

<400> SEQUENCE: 134

Ile Tyr His Ser Gly Ser Thr
1               5

<210> SEQ ID NO 135
<211> LENGTH: 15
<212> TYPE: PRT
<213> ORGANISM: Homo sapiens

<400> SEQUENCE: 135

Ala Ser Leu Thr Leu Ile Trp Phe Gly Glu Lys Ala Phe Asp Ile
1               5                   10                  15

<210> SEQ ID NO 136
<211> LENGTH: 6
<212> TYPE: PRT
<213> ORGANISM: Homo sapiens

<400> SEQUENCE: 136

Pro Ser Val Ser Thr Asn
1               5

<210> SEQ ID NO 137
<211> LENGTH: 3
<212> TYPE: PRT
<213> ORGANISM: Homo sapiens

<400> SEQUENCE: 137

Gly Ile Ser
1

<210> SEQ ID NO 138
<211> LENGTH: 9
<212> TYPE: PRT
<213> ORGANISM: Homo sapiens

<400> SEQUENCE: 138

Gln Gln Tyr Asn Asn Trp Pro Tyr Thr
1               5

<210> SEQ ID NO 139
<211> LENGTH: 8
<212> TYPE: PRT
<213> ORGANISM: Homo sapiens

<400> SEQUENCE: 139

Gly Phe Thr Phe Thr Tyr Tyr Gly
1               5

<210> SEQ ID NO 140
<211> LENGTH: 8
```

```
<212> TYPE: PRT
<213> ORGANISM: Homo sapiens

<400> SEQUENCE: 140

Ile Trp Tyr Asp Gly Ser Asn Gln
1               5

<210> SEQ ID NO 141
<211> LENGTH: 15
<212> TYPE: PRT
<213> ORGANISM: Homo sapiens

<400> SEQUENCE: 141

Ala Arg Glu Gly Leu Gly Ala Val Ala Gly Tyr Tyr Phe Asp Tyr
1               5                   10                  15

<210> SEQ ID NO 142
<211> LENGTH: 6
<212> TYPE: PRT
<213> ORGANISM: Homo sapiens

<400> SEQUENCE: 142

Gln Ile Ile Ser Asn Tyr
1               5

<210> SEQ ID NO 143
<211> LENGTH: 3
<212> TYPE: PRT
<213> ORGANISM: Homo sapiens

<400> SEQUENCE: 143

Ala Ala Ser
1

<210> SEQ ID NO 144
<211> LENGTH: 9
<212> TYPE: PRT
<213> ORGANISM: Homo sapiens

<400> SEQUENCE: 144

Gln Gln Ser Tyr Ser Thr Pro Phe Ala
1               5

<210> SEQ ID NO 145
<211> LENGTH: 8
<212> TYPE: PRT
<213> ORGANISM: Homo sapiens

<400> SEQUENCE: 145

Gly Phe Thr Phe Arg Gly Tyr Gly
1               5

<210> SEQ ID NO 146
<211> LENGTH: 8
<212> TYPE: PRT
<213> ORGANISM: Homo sapiens

<400> SEQUENCE: 146

Ile Trp His Asp Ala Ser Asn Lys
1               5

<210> SEQ ID NO 147
<211> LENGTH: 10
<212> TYPE: PRT
<213> ORGANISM: Homo sapiens
```

```
<400> SEQUENCE: 147

Ala Arg Asp Ala Gly Leu Ser Phe Asp Ile
1               5                   10

<210> SEQ ID NO 148
<211> LENGTH: 7
<212> TYPE: PRT
<213> ORGANISM: Homo sapiens

<400> SEQUENCE: 148

Gln Ser Val Ser Ser Ser Tyr
1               5

<210> SEQ ID NO 149
<211> LENGTH: 3
<212> TYPE: PRT
<213> ORGANISM: Homo sapiens

<400> SEQUENCE: 149

Gly Ala Ser
1

<210> SEQ ID NO 150
<211> LENGTH: 7
<212> TYPE: PRT
<213> ORGANISM: Homo sapiens

<400> SEQUENCE: 150

Gln Gln Tyr Gly Ser Tyr Thr
1               5

<210> SEQ ID NO 151
<211> LENGTH: 8
<212> TYPE: PRT
<213> ORGANISM: Homo sapiens

<400> SEQUENCE: 151

Gly Phe Thr Phe Ser Gly Tyr Gly
1               5

<210> SEQ ID NO 152
<211> LENGTH: 8
<212> TYPE: PRT
<213> ORGANISM: Homo sapiens

<400> SEQUENCE: 152

Ile Trp Tyr Asp Gly Ser Asn Thr
1               5

<210> SEQ ID NO 153
<211> LENGTH: 22
<212> TYPE: PRT
<213> ORGANISM: Homo sapiens

<400> SEQUENCE: 153

Ala Arg Asp Arg Gly Ile Ser Val Ala Ala Leu Trp Lys Tyr Tyr Tyr
1               5                   10                  15

Tyr His Gly Leu Asp Val
            20

<210> SEQ ID NO 154
<211> LENGTH: 6
<212> TYPE: PRT
```

<213> ORGANISM: Homo sapiens

<400> SEQUENCE: 154

Gln Ser Val Ser Ser Asn
1               5

<210> SEQ ID NO 155
<211> LENGTH: 3
<212> TYPE: PRT
<213> ORGANISM: Homo sapiens

<400> SEQUENCE: 155

Gly Ala Ser
1

<210> SEQ ID NO 156
<211> LENGTH: 9
<212> TYPE: PRT
<213> ORGANISM: Homo sapiens

<400> SEQUENCE: 156

Gln Gln Tyr Asn Asn Trp Pro Ile Thr
1               5

<210> SEQ ID NO 157
<211> LENGTH: 8
<212> TYPE: PRT
<213> ORGANISM: Homo sapiens

<400> SEQUENCE: 157

Gly Phe Thr Phe Ser Gly Tyr Gly
1               5

<210> SEQ ID NO 158
<211> LENGTH: 8
<212> TYPE: PRT
<213> ORGANISM: Homo sapiens

<400> SEQUENCE: 158

Ile Trp Tyr Asp Gly Ser Asn Thr
1               5

<210> SEQ ID NO 159
<211> LENGTH: 22
<212> TYPE: PRT
<213> ORGANISM: Homo sapiens

<400> SEQUENCE: 159

Ala Arg Asp Arg Gly Ile Ser Val Ala Ala Leu Trp Lys Tyr Tyr Tyr
1               5                   10                  15

Tyr His Gly Leu Asp Val
            20

<210> SEQ ID NO 160
<211> LENGTH: 6
<212> TYPE: PRT
<213> ORGANISM: Homo sapiens

<400> SEQUENCE: 160

Gln Ser Val Ser Ser Asn
1               5

<210> SEQ ID NO 161
<211> LENGTH: 3

<212> TYPE: PRT
<213> ORGANISM: Homo sapiens

<400> SEQUENCE: 161

Gly Ala Ser
1

<210> SEQ ID NO 162
<211> LENGTH: 9
<212> TYPE: PRT
<213> ORGANISM: Homo sapiens

<400> SEQUENCE: 162

Gln Gln Tyr Asn Asn Trp Pro Ile Thr
1               5

<210> SEQ ID NO 163
<211> LENGTH: 8
<212> TYPE: PRT
<213> ORGANISM: Homo sapiens

<400> SEQUENCE: 163

Gly Phe Thr Phe Ser Gly Tyr Ala
1               5

<210> SEQ ID NO 164
<211> LENGTH: 8
<212> TYPE: PRT
<213> ORGANISM: Homo sapiens

<400> SEQUENCE: 164

Ile Trp Tyr Asp Gly Ser Asn Lys
1               5

<210> SEQ ID NO 165
<211> LENGTH: 22
<212> TYPE: PRT
<213> ORGANISM: Homo sapiens

<400> SEQUENCE: 165

Ala Arg Asp Arg Gly Ile Ser Glu Ala Ala Lys Trp Lys Tyr Tyr Tyr
1               5                   10                  15

Tyr Tyr Gly Met Asp Val
            20

<210> SEQ ID NO 166
<211> LENGTH: 6
<212> TYPE: PRT
<213> ORGANISM: Homo sapiens

<400> SEQUENCE: 166

Gln Ser Val Ser Ser Asn
1               5

<210> SEQ ID NO 167
<211> LENGTH: 3
<212> TYPE: PRT
<213> ORGANISM: Homo sapiens

<400> SEQUENCE: 167

Gly Ala Ser
1

<210> SEQ ID NO 168

```
<211> LENGTH: 9
<212> TYPE: PRT
<213> ORGANISM: Homo sapiens

<400> SEQUENCE: 168

Gln Gln Tyr Asn Asn Trp Pro Ile Thr
1               5

<210> SEQ ID NO 169
<211> LENGTH: 8
<212> TYPE: PRT
<213> ORGANISM: Homo sapiens

<400> SEQUENCE: 169

Gly Phe Thr Phe Ser Gly Tyr Ala
1               5

<210> SEQ ID NO 170
<211> LENGTH: 8
<212> TYPE: PRT
<213> ORGANISM: Homo sapiens

<400> SEQUENCE: 170

Ile Trp Tyr Asp Gly Ser Asn Lys
1               5

<210> SEQ ID NO 171
<211> LENGTH: 22
<212> TYPE: PRT
<213> ORGANISM: Homo sapiens

<400> SEQUENCE: 171

Ala Arg Asp Arg Gly Ile Ser Glu Ala Ala Lys Trp Lys Tyr Tyr Tyr
1               5                   10                  15

Tyr Tyr Gly Met Asp Val
            20

<210> SEQ ID NO 172
<211> LENGTH: 6
<212> TYPE: PRT
<213> ORGANISM: Homo sapiens

<400> SEQUENCE: 172

Gln Ser Val Ser Ser Asn
1               5

<210> SEQ ID NO 173
<211> LENGTH: 3
<212> TYPE: PRT
<213> ORGANISM: Homo sapiens

<400> SEQUENCE: 173

Gly Ala Ser
1

<210> SEQ ID NO 174
<211> LENGTH: 9
<212> TYPE: PRT
<213> ORGANISM: Homo sapiens

<400> SEQUENCE: 174

Gln Gln Tyr Asn Asn Trp Pro Ile Thr
1               5
```

-continued

```
<210> SEQ ID NO 175
<211> LENGTH: 8
<212> TYPE: PRT
<213> ORGANISM: Homo sapiens

<400> SEQUENCE: 175

Gly Phe Thr Phe Ser Ala Tyr Ala
1               5

<210> SEQ ID NO 176
<211> LENGTH: 8
<212> TYPE: PRT
<213> ORGANISM: Homo sapiens

<400> SEQUENCE: 176

Ile Gly Tyr Glu Glu Ser Asn Lys
1               5

<210> SEQ ID NO 177
<211> LENGTH: 22
<212> TYPE: PRT
<213> ORGANISM: Homo sapiens

<400> SEQUENCE: 177

Ala Arg Asp Arg Gly Ile Ser Val Ala Ala Thr Trp Asp Tyr Tyr Tyr
1               5                   10                  15

Tyr Tyr Gly Met Asp Val
            20

<210> SEQ ID NO 178
<211> LENGTH: 6
<212> TYPE: PRT
<213> ORGANISM: Homo sapiens

<400> SEQUENCE: 178

Gln Ser Val Ser Ser Asp
1               5

<210> SEQ ID NO 179
<211> LENGTH: 3
<212> TYPE: PRT
<213> ORGANISM: Homo sapiens

<400> SEQUENCE: 179

Gly Ala Ser
1

<210> SEQ ID NO 180
<211> LENGTH: 9
<212> TYPE: PRT
<213> ORGANISM: Homo sapiens

<400> SEQUENCE: 180

Gln Gln Tyr Asn Asn Trp Pro Ile Thr
1               5

<210> SEQ ID NO 181
<211> LENGTH: 8
<212> TYPE: PRT
<213> ORGANISM: Homo sapiens

<400> SEQUENCE: 181

Gly Phe Asn Phe Ser Ser Asp Gly
1               5
```

```
<210> SEQ ID NO 182
<211> LENGTH: 8
<212> TYPE: PRT
<213> ORGANISM: Homo sapiens

<400> SEQUENCE: 182

Ile Trp Tyr Asp Gly Arg Asn Lys
1               5

<210> SEQ ID NO 183
<211> LENGTH: 21
<212> TYPE: PRT
<213> ORGANISM: Homo sapiens

<400> SEQUENCE: 183

Ala Arg Asp Arg Gly Ile Thr Met Gly Arg Gly Pro Tyr Tyr Tyr Tyr
1               5                   10                  15

Tyr Gly Met Asp Val
            20

<210> SEQ ID NO 184
<211> LENGTH: 6
<212> TYPE: PRT
<213> ORGANISM: Homo sapiens

<400> SEQUENCE: 184

Gln Ser Val Ser Ser Asn
1               5

<210> SEQ ID NO 185
<211> LENGTH: 3
<212> TYPE: PRT
<213> ORGANISM: Homo sapiens

<400> SEQUENCE: 185

Gly Ala Ser
1

<210> SEQ ID NO 186
<211> LENGTH: 9
<212> TYPE: PRT
<213> ORGANISM: Homo sapiens

<400> SEQUENCE: 186

Gln Gln Tyr Asn Asn Trp Pro Leu Thr
1               5

<210> SEQ ID NO 187
<211> LENGTH: 8
<212> TYPE: PRT
<213> ORGANISM: Homo sapiens

<400> SEQUENCE: 187

Gly Phe Thr Phe Ser Ser Asp Gly
1               5

<210> SEQ ID NO 188
<211> LENGTH: 8
<212> TYPE: PRT
<213> ORGANISM: Homo sapiens

<400> SEQUENCE: 188

Ile Trp Tyr Asp Gly Ser Ser Glu
1               5
```

-continued

```
<210> SEQ ID NO 189
<211> LENGTH: 21
<212> TYPE: PRT
<213> ORGANISM: Homo sapiens

<400> SEQUENCE: 189

Ala Arg Asp Arg Gly Ile Thr Met Gly Arg Gly Val Tyr Tyr Tyr Tyr
1               5                   10                  15

Tyr Gly Met Asp Val
            20

<210> SEQ ID NO 190
<211> LENGTH: 6
<212> TYPE: PRT
<213> ORGANISM: Homo sapiens

<400> SEQUENCE: 190

Gln Ser Val Ser Ser Asn
1               5

<210> SEQ ID NO 191
<211> LENGTH: 3
<212> TYPE: PRT
<213> ORGANISM: Homo sapiens

<400> SEQUENCE: 191

Gly Ala Ser
1

<210> SEQ ID NO 192
<211> LENGTH: 9
<212> TYPE: PRT
<213> ORGANISM: Homo sapiens

<400> SEQUENCE: 192

Gln Gln Tyr Asn Asn Trp Pro Leu Thr
1               5

<210> SEQ ID NO 193
<211> LENGTH: 8
<212> TYPE: PRT
<213> ORGANISM: Homo sapiens

<400> SEQUENCE: 193

Gly Ile Thr Phe Ser Asn Tyr Gly
1               5

<210> SEQ ID NO 194
<211> LENGTH: 8
<212> TYPE: PRT
<213> ORGANISM: Homo sapiens

<400> SEQUENCE: 194

Ile Trp Tyr Asp Gly Ser Asn Lys
1               5

<210> SEQ ID NO 195
<211> LENGTH: 21
<212> TYPE: PRT
<213> ORGANISM: Homo sapiens

<400> SEQUENCE: 195

Ala Arg Asp Arg Gly Met Thr Gly Thr Thr Trp Glu Tyr Tyr Tyr Tyr
```

-continued

```
1               5              10             15

Tyr Gly Met Asp Val
              20

<210> SEQ ID NO 196
<211> LENGTH: 6
<212> TYPE: PRT
<213> ORGANISM: Homo sapiens

<400> SEQUENCE: 196

Gln Ser Val Ser Ser Asn
1               5

<210> SEQ ID NO 197
<211> LENGTH: 3
<212> TYPE: PRT
<213> ORGANISM: Homo sapiens

<400> SEQUENCE: 197

Gly Ala Ser
1

<210> SEQ ID NO 198
<211> LENGTH: 9
<212> TYPE: PRT
<213> ORGANISM: Homo sapiens

<400> SEQUENCE: 198

Gln Gln Tyr Asn Asn Trp Pro Tyr Thr
1               5

<210> SEQ ID NO 199
<211> LENGTH: 8
<212> TYPE: PRT
<213> ORGANISM: Homo sapiens

<400> SEQUENCE: 199

Gly Phe Thr Phe Ser Thr Tyr Ala
1               5

<210> SEQ ID NO 200
<211> LENGTH: 8
<212> TYPE: PRT
<213> ORGANISM: Homo sapiens

<400> SEQUENCE: 200

Ile Trp Tyr Asp Gly Ser Asn Lys
1               5

<210> SEQ ID NO 201
<211> LENGTH: 22
<212> TYPE: PRT
<213> ORGANISM: Homo sapiens

<400> SEQUENCE: 201

Ala Arg Asp Arg Gly Ile Thr Thr Thr Asp Thr Gly Tyr Tyr Tyr Tyr
1               5              10             15

Tyr Tyr Gly Leu Asp Ile
              20

<210> SEQ ID NO 202
<211> LENGTH: 6
<212> TYPE: PRT
<213> ORGANISM: Homo sapiens
```

<400> SEQUENCE: 202

Gln Ser Val Ser Ser Asn
1               5

<210> SEQ ID NO 203
<211> LENGTH: 3
<212> TYPE: PRT
<213> ORGANISM: Homo sapiens

<400> SEQUENCE: 203

Gly Ala Ser
1

<210> SEQ ID NO 204
<211> LENGTH: 9
<212> TYPE: PRT
<213> ORGANISM: Homo sapiens

<400> SEQUENCE: 204

Gln Gln Tyr Asn Asn Trp Pro Leu Thr
1               5

<210> SEQ ID NO 205
<211> LENGTH: 8
<212> TYPE: PRT
<213> ORGANISM: Homo sapiens

<400> SEQUENCE: 205

Gly Leu Ile Phe Ser Asn Tyr Gly
1               5

<210> SEQ ID NO 206
<211> LENGTH: 8
<212> TYPE: PRT
<213> ORGANISM: Homo sapiens

<400> SEQUENCE: 206

Ile Trp Tyr Asp Gly Ser Asn Thr
1               5

<210> SEQ ID NO 207
<211> LENGTH: 22
<212> TYPE: PRT
<213> ORGANISM: Homo sapiens

<400> SEQUENCE: 207

Ala Arg Asp Arg Gly Met Thr Ala Pro Gly Pro Gly Thr Tyr Tyr Tyr
1               5                   10                  15

Phe Tyr Gly Met Asp Val
            20

<210> SEQ ID NO 208
<211> LENGTH: 6
<212> TYPE: PRT
<213> ORGANISM: Homo sapiens

<400> SEQUENCE: 208

Gln Ser Val Ser Ser Asn
1               5

<210> SEQ ID NO 209
<211> LENGTH: 3
<212> TYPE: PRT

```
<213> ORGANISM: Homo sapiens

<400> SEQUENCE: 209

Gly Ala Ser
1

<210> SEQ ID NO 210
<211> LENGTH: 9
<212> TYPE: PRT
<213> ORGANISM: Homo sapiens

<400> SEQUENCE: 210

Gln Gln Tyr Asn Asn Trp Pro Leu Thr
1               5

<210> SEQ ID NO 211
<211> LENGTH: 8
<212> TYPE: PRT
<213> ORGANISM: Homo sapiens

<400> SEQUENCE: 211

Gly Phe Thr Phe Ser Asn Tyr Gly
1               5

<210> SEQ ID NO 212
<211> LENGTH: 8
<212> TYPE: PRT
<213> ORGANISM: Homo sapiens

<400> SEQUENCE: 212

Ile Trp Phe Asp Gly Ser Asn Lys
1               5

<210> SEQ ID NO 213
<211> LENGTH: 17
<212> TYPE: PRT
<213> ORGANISM: Homo sapiens

<400> SEQUENCE: 213

Ala Arg Glu Arg Gly Val Trp Asn Ser Gly Trp Ser His Ala Tyr Asp
1               5                   10                  15

Ile

<210> SEQ ID NO 214
<211> LENGTH: 6
<212> TYPE: PRT
<213> ORGANISM: Homo sapiens

<400> SEQUENCE: 214

Gln Gly Ile Thr Asn Tyr
1               5

<210> SEQ ID NO 215
<211> LENGTH: 3
<212> TYPE: PRT
<213> ORGANISM: Homo sapiens

<400> SEQUENCE: 215

Ala Ala Ser
1

<210> SEQ ID NO 216
<211> LENGTH: 9
<212> TYPE: PRT
```

<213> ORGANISM: Homo sapiens

<400> SEQUENCE: 216

Gln Lys Tyr Asn Ile Ala Pro Cys Phe
1               5

<210> SEQ ID NO 217
<211> LENGTH: 8
<212> TYPE: PRT
<213> ORGANISM: Homo sapiens

<400> SEQUENCE: 217

Gly Phe Thr Phe Ser Asn Tyr Gly
1               5

<210> SEQ ID NO 218
<211> LENGTH: 8
<212> TYPE: PRT
<213> ORGANISM: Homo sapiens

<400> SEQUENCE: 218

Ile Trp Phe Asp Gly Ser Asn Lys
1               5

<210> SEQ ID NO 219
<211> LENGTH: 17
<212> TYPE: PRT
<213> ORGANISM: Homo sapiens

<400> SEQUENCE: 219

Ala Arg Glu Arg Gly Val Trp Asn Ser Gly Trp Ser His Ala Tyr Asp
1               5                   10                  15

Ile

<210> SEQ ID NO 220
<211> LENGTH: 6
<212> TYPE: PRT
<213> ORGANISM: Homo sapiens

<400> SEQUENCE: 220

Gln Gly Ile Thr Asn Tyr
1               5

<210> SEQ ID NO 221
<211> LENGTH: 3
<212> TYPE: PRT
<213> ORGANISM: Homo sapiens

<400> SEQUENCE: 221

Ala Ala Ser
1

<210> SEQ ID NO 222
<211> LENGTH: 9
<212> TYPE: PRT
<213> ORGANISM: Homo sapiens

<400> SEQUENCE: 222

Gln Lys Tyr Asn Ile Val Pro Cys Phe
1               5

<210> SEQ ID NO 223
<211> LENGTH: 8
<212> TYPE: PRT

<213> ORGANISM: Homo sapiens

<400> SEQUENCE: 223

Gly Phe Thr Phe Ser Arg Tyr Gly
1               5

<210> SEQ ID NO 224
<211> LENGTH: 8
<212> TYPE: PRT
<213> ORGANISM: Homo sapiens

<400> SEQUENCE: 224

Ile Trp Tyr Asp Gly Ser Asn Lys
1               5

<210> SEQ ID NO 225
<211> LENGTH: 20
<212> TYPE: PRT
<213> ORGANISM: Homo sapiens

<400> SEQUENCE: 225

Ala Thr Glu Gly Asp Tyr Tyr Gly Ser Gly Ser Tyr Ser Arg Ala Glu
1               5                   10                  15

Tyr Phe Gln Glu
            20

<210> SEQ ID NO 226
<211> LENGTH: 6
<212> TYPE: PRT
<213> ORGANISM: Homo sapiens

<400> SEQUENCE: 226

Gln Ser Val Ser Ile Asn
1               5

<210> SEQ ID NO 227
<211> LENGTH: 3
<212> TYPE: PRT
<213> ORGANISM: Homo sapiens

<400> SEQUENCE: 227

Asp Thr Ser
1

<210> SEQ ID NO 228
<211> LENGTH: 9
<212> TYPE: PRT
<213> ORGANISM: Homo sapiens

<400> SEQUENCE: 228

Gln Gln Tyr Asn Asn Trp Pro Phe Thr
1               5

<210> SEQ ID NO 229
<211> LENGTH: 8
<212> TYPE: PRT
<213> ORGANISM: Homo sapiens

<400> SEQUENCE: 229

Gly Phe Thr Phe Ser Tyr Tyr Gly
1               5

<210> SEQ ID NO 230
<211> LENGTH: 8

-continued

```
<212> TYPE: PRT
<213> ORGANISM: Homo sapiens

<400> SEQUENCE: 230

Ile Trp Phe Asp Gly Thr Asn Ile
1               5

<210> SEQ ID NO 231
<211> LENGTH: 15
<212> TYPE: PRT
<213> ORGANISM: Homo sapiens

<400> SEQUENCE: 231

Ala Arg Asp Arg Arg Ser Ser Asp Trp Tyr Val Val Phe Asp Tyr
1               5                   10                  15

<210> SEQ ID NO 232
<211> LENGTH: 6
<212> TYPE: PRT
<213> ORGANISM: Homo sapiens

<400> SEQUENCE: 232

Gln Gly Ile Ser Ser Tyr
1               5

<210> SEQ ID NO 233
<211> LENGTH: 3
<212> TYPE: PRT
<213> ORGANISM: Homo sapiens

<400> SEQUENCE: 233

Ala Ala Ser
1

<210> SEQ ID NO 234
<211> LENGTH: 9
<212> TYPE: PRT
<213> ORGANISM: Homo sapiens

<400> SEQUENCE: 234

Gln Gln Leu Asn Ser Tyr Pro Trp Thr
1               5

<210> SEQ ID NO 235
<211> LENGTH: 8
<212> TYPE: PRT
<213> ORGANISM: Homo sapiens

<400> SEQUENCE: 235

Gly Gly Thr Phe Ser Ser Tyr Ala
1               5

<210> SEQ ID NO 236
<211> LENGTH: 8
<212> TYPE: PRT
<213> ORGANISM: Homo sapiens

<400> SEQUENCE: 236

Ile Ile Pro Ile Phe Gly Thr Ala
1               5

<210> SEQ ID NO 237
<211> LENGTH: 20
<212> TYPE: PRT
<213> ORGANISM: Homo sapiens
```

<400> SEQUENCE: 237

Ala Arg Glu Asp Ile Thr Met Val Arg Gly Val Ile Thr Asn Tyr Trp
1               5                   10                  15

Tyr Phe Asp Leu
            20

<210> SEQ ID NO 238
<211> LENGTH: 6
<212> TYPE: PRT
<213> ORGANISM: Homo sapiens

<400> SEQUENCE: 238

Gln Asp Ile Ser Asn Tyr
1               5

<210> SEQ ID NO 239
<211> LENGTH: 3
<212> TYPE: PRT
<213> ORGANISM: Homo sapiens

<400> SEQUENCE: 239

Ala Ala Ser
1

<210> SEQ ID NO 240
<211> LENGTH: 9
<212> TYPE: PRT
<213> ORGANISM: Homo sapiens

<400> SEQUENCE: 240

Gln Lys Ser Asn Asn Ala Pro Leu Thr
1               5

<210> SEQ ID NO 241
<211> LENGTH: 8
<212> TYPE: PRT
<213> ORGANISM: Homo sapiens

<400> SEQUENCE: 241

Gly Gly Thr Phe Ser Ser Tyr Ala
1               5

<210> SEQ ID NO 242
<211> LENGTH: 8
<212> TYPE: PRT
<213> ORGANISM: Homo sapiens

<400> SEQUENCE: 242

Ile Ile Pro Ile Phe Gly Thr Val
1               5

<210> SEQ ID NO 243
<211> LENGTH: 17
<212> TYPE: PRT
<213> ORGANISM: Homo sapiens

<400> SEQUENCE: 243

Ala Arg Asp His Tyr Tyr Asp Ser Asn Asp Tyr Tyr Trp Tyr Phe Asp
1               5                   10                  15

Leu

<210> SEQ ID NO 244

-continued

```
<211> LENGTH: 6
<212> TYPE: PRT
<213> ORGANISM: Homo sapiens

<400> SEQUENCE: 244

Gln Ser Val Ser Ser Asn
1               5

<210> SEQ ID NO 245
<211> LENGTH: 3
<212> TYPE: PRT
<213> ORGANISM: Homo sapiens

<400> SEQUENCE: 245

Gly Ala Ser
1

<210> SEQ ID NO 246
<211> LENGTH: 9
<212> TYPE: PRT
<213> ORGANISM: Homo sapiens

<400> SEQUENCE: 246

Gln Gln Tyr Asn Asn Trp Pro Leu Thr
1               5

<210> SEQ ID NO 247
<211> LENGTH: 8
<212> TYPE: PRT
<213> ORGANISM: Homo sapiens

<400> SEQUENCE: 247

Gly Gly Ala Phe Ser Ala Tyr Ala
1               5

<210> SEQ ID NO 248
<211> LENGTH: 8
<212> TYPE: PRT
<213> ORGANISM: Homo sapiens

<400> SEQUENCE: 248

Ile Ile Pro Ile Phe Gly Thr Ala
1               5

<210> SEQ ID NO 249
<211> LENGTH: 18
<212> TYPE: PRT
<213> ORGANISM: Homo sapiens

<400> SEQUENCE: 249

Ala Arg Glu Gly Asp Ile Glu Val Val Leu Ala Ala Arg Gly Phe Phe
1               5                   10                  15

Asp Tyr

<210> SEQ ID NO 250
<211> LENGTH: 6
<212> TYPE: PRT
<213> ORGANISM: Homo sapiens

<400> SEQUENCE: 250

Gln Gly Ile Ser Asn Tyr
1               5

<210> SEQ ID NO 251
```

```
<211> LENGTH: 3
<212> TYPE: PRT
<213> ORGANISM: Homo sapiens

<400> SEQUENCE: 251

Ala Ala Ser
1

<210> SEQ ID NO 252
<211> LENGTH: 9
<212> TYPE: PRT
<213> ORGANISM: Homo sapiens

<400> SEQUENCE: 252

Gln Lys Tyr Asn Ser Ala Pro Trp Thr
1               5

<210> SEQ ID NO 253
<211> LENGTH: 8
<212> TYPE: PRT
<213> ORGANISM: Homo sapiens

<400> SEQUENCE: 253

Gly Gly Ala Phe Ser Ala Tyr Ala
1               5

<210> SEQ ID NO 254
<211> LENGTH: 8
<212> TYPE: PRT
<213> ORGANISM: Homo sapiens

<400> SEQUENCE: 254

Ile Ile Pro Ile Phe Gly Thr Ala
1               5

<210> SEQ ID NO 255
<211> LENGTH: 18
<212> TYPE: PRT
<213> ORGANISM: Homo sapiens

<400> SEQUENCE: 255

Ala Arg Glu Gly Asp Ile Glu Val Val Leu Ala Gly Arg Gly Tyr Phe
1               5                   10                  15

Asp Tyr

<210> SEQ ID NO 256
<211> LENGTH: 11
<212> TYPE: PRT
<213> ORGANISM: Homo sapiens

<400> SEQUENCE: 256

Gln Ser Leu Leu His Ser Asn Gly Tyr Asn Tyr
1               5                   10

<210> SEQ ID NO 257
<211> LENGTH: 3
<212> TYPE: PRT
<213> ORGANISM: Homo sapiens

<400> SEQUENCE: 257

Leu Gly Ser
1

<210> SEQ ID NO 258
```

```
<211> LENGTH: 9
<212> TYPE: PRT
<213> ORGANISM: Homo sapiens

<400> SEQUENCE: 258

Met Gln Ala Leu Gln Thr Pro Tyr Thr
1               5

<210> SEQ ID NO 259
<211> LENGTH: 8
<212> TYPE: PRT
<213> ORGANISM: Homo sapiens

<400> SEQUENCE: 259

Gly Gly Ala Phe Ser Ala Tyr Ala
1               5

<210> SEQ ID NO 260
<211> LENGTH: 8
<212> TYPE: PRT
<213> ORGANISM: Homo sapiens

<400> SEQUENCE: 260

Ile Ile Pro Ile Phe Gly Thr Ala
1               5

<210> SEQ ID NO 261
<211> LENGTH: 18
<212> TYPE: PRT
<213> ORGANISM: Homo sapiens

<400> SEQUENCE: 261

Ala Arg Glu Gly Asp Ser Gly Leu Val Leu Ala Ala Arg Gly Phe Phe
1               5                   10                  15

Asp Tyr

<210> SEQ ID NO 262
<211> LENGTH: 6
<212> TYPE: PRT
<213> ORGANISM: Homo sapiens

<400> SEQUENCE: 262

Gln Gly Ile Ser Asn Tyr
1               5

<210> SEQ ID NO 263
<211> LENGTH: 3
<212> TYPE: PRT
<213> ORGANISM: Homo sapiens

<400> SEQUENCE: 263

Ala Ala Ser
1

<210> SEQ ID NO 264
<211> LENGTH: 9
<212> TYPE: PRT
<213> ORGANISM: Homo sapiens

<400> SEQUENCE: 264

Gln Lys Tyr Asn Ser Ala Pro Trp Thr
1               5

<210> SEQ ID NO 265
```

```
<211> LENGTH: 10
<212> TYPE: PRT
<213> ORGANISM: Homo sapiens

<400> SEQUENCE: 265

Gly Asp Ser Val Ser Ser Asn Ser Ala Ala
1               5                   10

<210> SEQ ID NO 266
<211> LENGTH: 9
<212> TYPE: PRT
<213> ORGANISM: Homo sapiens

<400> SEQUENCE: 266

Thr Tyr Tyr Arg Ser Lys Trp Tyr Asn
1               5

<210> SEQ ID NO 267
<211> LENGTH: 12
<212> TYPE: PRT
<213> ORGANISM: Homo sapiens

<400> SEQUENCE: 267

Ala Arg Glu Trp Phe Gly Glu Gly Tyr Phe Asp Leu
1               5                   10

<210> SEQ ID NO 268
<211> LENGTH: 6
<212> TYPE: PRT
<213> ORGANISM: Homo sapiens

<400> SEQUENCE: 268

Gln Thr Ile Tyr Ser Asn
1               5

<210> SEQ ID NO 269
<211> LENGTH: 3
<212> TYPE: PRT
<213> ORGANISM: Homo sapiens

<400> SEQUENCE: 269

Arg Ala Ser
1

<210> SEQ ID NO 270
<211> LENGTH: 9
<212> TYPE: PRT
<213> ORGANISM: Homo sapiens

<400> SEQUENCE: 270

Gln Gln Phe Asn Asn Trp Pro Tyr Thr
1               5

<210> SEQ ID NO 271
<211> LENGTH: 8
<212> TYPE: PRT
<213> ORGANISM: Homo sapiens

<400> SEQUENCE: 271

Gly Phe Thr Phe Ser Ser Tyr Gly
1               5

<210> SEQ ID NO 272
<211> LENGTH: 8
<212> TYPE: PRT
```

-continued

<213> ORGANISM: Homo sapiens

<400> SEQUENCE: 272

Ile Trp Tyr Asp Gly Ser Asn Lys
1               5

<210> SEQ ID NO 273
<211> LENGTH: 15
<212> TYPE: PRT
<213> ORGANISM: Homo sapiens

<400> SEQUENCE: 273

Ala Arg Asp Glu Arg Ile Phe Gly Val Pro Asp Ala Phe Asp Ile
1               5                   10                  15

<210> SEQ ID NO 274
<211> LENGTH: 8
<212> TYPE: PRT
<213> ORGANISM: Homo sapiens

<400> SEQUENCE: 274

Gly Phe Thr Phe Ser Ser Tyr Trp
1               5

<210> SEQ ID NO 275
<211> LENGTH: 8
<212> TYPE: PRT
<213> ORGANISM: Homo sapiens

<400> SEQUENCE: 275

Ile Asp Ser Asp Gly Ser Asn Thr
1               5

<210> SEQ ID NO 276
<211> LENGTH: 11
<212> TYPE: PRT
<213> ORGANISM: Homo sapiens

<400> SEQUENCE: 276

Ala Arg Ser Gly Tyr Gly Tyr Ala Phe Asp Ile
1               5                   10

<210> SEQ ID NO 277
<211> LENGTH: 8
<212> TYPE: PRT
<213> ORGANISM: Homo sapiens

<400> SEQUENCE: 277

Gly Phe Thr Phe Ser Thr Asn Ala
1               5

<210> SEQ ID NO 278
<211> LENGTH: 8
<212> TYPE: PRT
<213> ORGANISM: Homo sapiens

<400> SEQUENCE: 278

Ile Ser Gly Ser Gly Gly Ser Thr
1               5

<210> SEQ ID NO 279
<211> LENGTH: 13
<212> TYPE: PRT
<213> ORGANISM: Homo sapiens

```
<400> SEQUENCE: 279

Ala Pro Arg Ile Ala Val Ala Pro Asp Ala Leu Asp Ile
1               5                   10

<210> SEQ ID NO 280
<211> LENGTH: 8
<212> TYPE: PRT
<213> ORGANISM: Homo sapiens

<400> SEQUENCE: 280

Gly Phe Thr Phe Ser Ser Tyr Trp
1               5

<210> SEQ ID NO 281
<211> LENGTH: 8
<212> TYPE: PRT
<213> ORGANISM: Homo sapiens

<400> SEQUENCE: 281

Ile Asn Ser Asp Gly Ser Ser Thr
1               5

<210> SEQ ID NO 282
<211> LENGTH: 7
<212> TYPE: PRT
<213> ORGANISM: Homo sapiens

<400> SEQUENCE: 282

Gly Asn Pro Tyr Phe Asp Tyr
1               5

<210> SEQ ID NO 283
<211> LENGTH: 129
<212> TYPE: PRT
<213> ORGANISM: Homo sapiens

<400> SEQUENCE: 283

Gln Val Gln Leu Val Glu Ser Gly Gly Gly Val Val Gln Pro Gly Arg
1               5                   10                  15

Ser Leu Arg Leu Ser Cys Thr Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Arg Gly Ile Ser Val Ala Ala Leu Trp Lys Tyr Tyr Tyr
            100                 105                 110

Tyr His Gly Leu Asp Val Trp Gly Gln Gly Thr Thr Val Thr Val Ser
        115                 120                 125

Ser

<210> SEQ ID NO 284
<211> LENGTH: 108
<212> TYPE: PRT
<213> ORGANISM: Homo sapiens

<400> SEQUENCE: 284
```

-continued

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Thr Trp Tyr Gln Gln Lys Pro Gly Gln Ala Pro Arg Leu Leu Ile
        35                  40                  45

Tyr Gly Ala Ser Thr Arg Ala Thr Gly Ile Pro Thr Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys Arg
            100                 105
```

```
<210> SEQ ID NO 285
<211> LENGTH: 8
<212> TYPE: PRT
<213> ORGANISM: Homo sapiens

<400> SEQUENCE: 285

Gly Phe Thr Phe Ser Gly Tyr Gly
1               5
```

```
<210> SEQ ID NO 286
<211> LENGTH: 8
<212> TYPE: PRT
<213> ORGANISM: Homo sapiens

<400> SEQUENCE: 286

Ile Trp Tyr Asp Gly Ser Asn Thr
1               5
```

```
<210> SEQ ID NO 287
<211> LENGTH: 22
<212> TYPE: PRT
<213> ORGANISM: Homo sapiens

<400> SEQUENCE: 287

Ala Arg Asp Arg Gly Ile Ser Val Ala Ala Leu Trp Lys Tyr Tyr Tyr
1               5                   10                  15

Tyr His Gly Leu Asp Val
            20
```

```
<210> SEQ ID NO 288
<211> LENGTH: 6
<212> TYPE: PRT
<213> ORGANISM: Homo sapiens

<400> SEQUENCE: 288

Gln Ser Val Ser Ser Asn
1               5
```

```
<210> SEQ ID NO 289
<211> LENGTH: 3
<212> TYPE: PRT
<213> ORGANISM: Homo sapiens

<400> SEQUENCE: 289

Gly Ala Ser
1
```

<210> SEQ ID NO 290
<211> LENGTH: 9
<212> TYPE: PRT
<213> ORGANISM: Homo sapiens

<400> SEQUENCE: 290

Gln Gln Tyr Asn Asn Trp Pro Ile Thr
1               5

<210> SEQ ID NO 291
<211> LENGTH: 129
<212> TYPE: PRT
<213> ORGANISM: Homo sapiens

<400> SEQUENCE: 291

Gln Val Gln Leu Val Glu Ser Gly Gly Gly Val Val Gln Pro Gly Met
1               5                   10                  15

Ser Leu Arg Leu Ser Cys Thr Ala Ser Gly Phe Thr Phe Ser Gly Tyr
            20                  25                  30

Ala Met His Trp Val Arg Gln Ala Pro Val Lys Gly Leu Glu Trp Val
            35                  40                  45

Ala Ile Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Glu Ala Ala Lys Trp Lys Tyr Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 292
<211> LENGTH: 108
<212> TYPE: PRT
<213> ORGANISM: Homo sapiens

<400> SEQUENCE: 292

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys Arg
            100                 105

<210> SEQ ID NO 293
<211> LENGTH: 8
<212> TYPE: PRT

<213> ORGANISM: Homo sapiens

<400> SEQUENCE: 293

Gly Phe Thr Phe Ser Gly Tyr Ala
1               5

<210> SEQ ID NO 294
<211> LENGTH: 8
<212> TYPE: PRT
<213> ORGANISM: Homo sapiens

<400> SEQUENCE: 294

Ile Trp Tyr Asp Gly Ser Asn Lys
1               5

<210> SEQ ID NO 295
<211> LENGTH: 22
<212> TYPE: PRT
<213> ORGANISM: Homo sapiens

<400> SEQUENCE: 295

Ala Arg Asp Arg Gly Ile Ser Glu Ala Ala Lys Trp Lys Tyr Tyr Tyr
1               5                   10                  15

Tyr Tyr Gly Met Asp Val
            20

<210> SEQ ID NO 296
<211> LENGTH: 6
<212> TYPE: PRT
<213> ORGANISM: Homo sapiens

<400> SEQUENCE: 296

Gln Ser Val Ser Ser Asn
1               5

<210> SEQ ID NO 297
<211> LENGTH: 3
<212> TYPE: PRT
<213> ORGANISM: Homo sapiens

<400> SEQUENCE: 297

Gly Ala Ser
1

<210> SEQ ID NO 298
<211> LENGTH: 9
<212> TYPE: PRT
<213> ORGANISM: Homo sapiens

<400> SEQUENCE: 298

Gln Gln Tyr Asn Asn Trp Pro Ile Thr
1               5

<210> SEQ ID NO 299
<211> LENGTH: 122
<212> TYPE: PRT
<213> ORGANISM: Homo sapiens

<400> SEQUENCE: 299

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

-continued

```
Lys Trp Trp Ser Trp Val Arg Gln Ser Pro Gly Lys Gly Leu Glu Trp
        35              40              45

Ile Gly Glu Ile Tyr His Ser Gly Ser Thr Asn Tyr Asn Pro Ser Leu
    50              55              60

Lys Ser Arg Val Thr Ile Ser Val Asp Lys Ser Lys Asn Gln Phe Ser
65              70              75              80

Leu Lys Leu Ser Ser Val Thr Ala Ala Asp Thr Ala Val Tyr Tyr Cys
                85              90              95

Ala Ser Leu Thr Leu Ile Trp Phe Gly Glu Lys Ala Phe Asp Ile Trp
            100             105             110

Gly Gln Gly Thr Met Val Thr Val Ser Ser
        115             120
```

<210> SEQ ID NO 300
<211> LENGTH: 108
<212> TYPE: PRT
<213> ORGANISM: Homo sapiens

<400> SEQUENCE: 300

```
Glu Ile Val Met Thr Gln Ser Pro Ala Thr Leu Ser Val Ser Pro Gly
1               5               10              15

Glu Arg Ala Thr Leu Ser Cys Arg Ala Ser Pro Ser Val Ser Ser Asn
            20              25              30

Leu Ala Trp Tyr Gln Gln Arg Pro Gly Gln Ala Pro Arg Leu Leu Ile
        35              40              45

Tyr Gly Thr Ser Thr Arg Ala Thr Gly Ile Pro Ala Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Val Tyr Tyr Cys Gln Gln Tyr Asn Asn Trp Pro Tyr
                85              90              95

Thr Phe Gly Gln Gly Thr Lys Leu Glu Ile Lys Arg
            100             105
```

<210> SEQ ID NO 301
<211> LENGTH: 9
<212> TYPE: PRT
<213> ORGANISM: Homo sapiens

<400> SEQUENCE: 301

```
Gly Gly Ser Ile Ser Ser Ser Lys Trp
1               5
```

<210> SEQ ID NO 302
<211> LENGTH: 7
<212> TYPE: PRT
<213> ORGANISM: Homo sapiens

<400> SEQUENCE: 302

```
Ile Tyr His Ser Gly Ser Thr
1               5
```

<210> SEQ ID NO 303
<211> LENGTH: 15
<212> TYPE: PRT
<213> ORGANISM: Homo sapiens

<400> SEQUENCE: 303

```
Ala Ser Leu Thr Leu Ile Trp Phe Gly Glu Lys Ala Phe Asp Ile
1               5               10              15
```

-continued

```
<210> SEQ ID NO 304
<211> LENGTH: 6
<212> TYPE: PRT
<213> ORGANISM: Homo sapiens

<400> SEQUENCE: 304

Pro Ser Val Ser Ser Asn
1               5

<210> SEQ ID NO 305
<211> LENGTH: 3
<212> TYPE: PRT
<213> ORGANISM: Homo sapiens

<400> SEQUENCE: 305

Gly Thr Ser
1

<210> SEQ ID NO 306
<211> LENGTH: 9
<212> TYPE: PRT
<213> ORGANISM: Homo sapiens

<400> SEQUENCE: 306

Gln Gln Tyr Asn Asn Trp Pro Tyr Thr
1               5

<210> SEQ ID NO 307
<211> LENGTH: 121
<212> TYPE: PRT
<213> ORGANISM: Homo sapiens

<400> SEQUENCE: 307

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Gly Glu Asp Thr Ala Val Tyr Tyr Cys
                85                  90                  95

Ala Lys Asp Arg His Asn Tyr Gly Tyr Val Pro Phe Asp Tyr Trp Gly
            100                 105                 110

Gln Gly Thr Leu Val Thr Val Ser Ser
        115                 120

<210> SEQ ID NO 308
<211> LENGTH: 109
<212> TYPE: PRT
<213> ORGANISM: Homo sapiens

<400> SEQUENCE: 308

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30
```

-continued

```
Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Trp Pro Pro
                    85                  90                  95

Trp Thr Phe Gly Gln Gly Thr Lys Val Glu Ile Lys Arg
                100                 105

<210> SEQ ID NO 309
<211> LENGTH: 8
<212> TYPE: PRT
<213> ORGANISM: Homo sapiens

<400> SEQUENCE: 309

Gly Phe Thr Phe Ser Ser Tyr Ala
1               5

<210> SEQ ID NO 310
<211> LENGTH: 8
<212> TYPE: PRT
<213> ORGANISM: Homo sapiens

<400> SEQUENCE: 310

Ile Ser Gly Ser Gly Gly Asn Thr
1               5

<210> SEQ ID NO 311
<211> LENGTH: 14
<212> TYPE: PRT
<213> ORGANISM: Homo sapiens

<400> SEQUENCE: 311

Ala Lys Asp Arg His Asn Tyr Gly Tyr Val Pro Phe Asp Tyr
1               5                   10

<210> SEQ ID NO 312
<211> LENGTH: 6
<212> TYPE: PRT
<213> ORGANISM: Homo sapiens

<400> SEQUENCE: 312

Gln Ser Val Asn Ser Asn
1               5

<210> SEQ ID NO 313
<211> LENGTH: 3
<212> TYPE: PRT
<213> ORGANISM: Homo sapiens

<400> SEQUENCE: 313

Gly Ala Ser
1

<210> SEQ ID NO 314
<211> LENGTH: 10
<212> TYPE: PRT
<213> ORGANISM: Homo sapiens

<400> SEQUENCE: 314
```

Gln Gln Tyr Asn Thr Trp Pro Pro Trp Thr
1               5                   10

<210> SEQ ID NO 315
<211> LENGTH: 116
<212> TYPE: PRT
<213> ORGANISM: Homo sapiens

<400> SEQUENCE: 315

Glu Val Gln Leu Leu Glu Ser Gly Gly Gly Ser Val Gln Pro Gly Gly
1               5                   10                  15

Ser Leu Arg Leu Ser Cys Glu Ala Ser Gly Phe Thr Phe Asn Thr Tyr
            20                  25                  30

Pro Met Ser Trp Val Arg Gln Ala Pro Gly Lys Gly Leu Glu Trp Val
        35                  40                  45

Ser Gly Ile Ser Gly Ser Gly Asp Arg Thr Phe Tyr Glu Asp Ser Val
    50                  55                  60

Lys Gly Arg Phe Thr Ile Ser Arg Asp Asn Ser Lys Asn Thr Leu Tyr
65                  70                  75                  80

Leu Gln Met His Ser Leu Arg Gly Glu Asp Thr Ala Val Tyr Tyr Cys
                85                  90                  95

Ala Lys Asp Leu Gly Gly Glu Gly Tyr Trp Gly Gln Gly Thr Leu Val
            100                 105                 110

Thr Val Ser Ser
        115

<210> SEQ ID NO 316
<211> LENGTH: 113
<212> TYPE: PRT
<213> ORGANISM: Homo sapiens

<400> SEQUENCE: 316

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Lys Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Ser Val Phe Gly Gly Gly Thr Lys Leu Thr Val Leu Gly Gln Pro
            100                 105                 110

Lys

<210> SEQ ID NO 317
<211> LENGTH: 8
<212> TYPE: PRT
<213> ORGANISM: Homo sapiens

<400> SEQUENCE: 317

Gly Phe Thr Phe Asn Thr Tyr Pro
1               5

<210> SEQ ID NO 318

```
<211> LENGTH: 8
<212> TYPE: PRT
<213> ORGANISM: Homo sapiens

<400> SEQUENCE: 318

Ile Ser Gly Ser Gly Asp Arg Thr
1               5

<210> SEQ ID NO 319
<211> LENGTH: 9
<212> TYPE: PRT
<213> ORGANISM: Homo sapiens

<400> SEQUENCE: 319

Ala Lys Asp Leu Gly Gly Glu Gly Tyr
1               5

<210> SEQ ID NO 320
<211> LENGTH: 9
<212> TYPE: PRT
<213> ORGANISM: Homo sapiens

<400> SEQUENCE: 320

Thr Gly Ala Val Thr Thr Ser Asn Tyr
1               5

<210> SEQ ID NO 321
<211> LENGTH: 3
<212> TYPE: PRT
<213> ORGANISM: Homo sapiens

<400> SEQUENCE: 321

Gly Thr Asn
1

<210> SEQ ID NO 322
<211> LENGTH: 9
<212> TYPE: PRT
<213> ORGANISM: Homo sapiens

<400> SEQUENCE: 322

Ala Leu Trp Tyr Ser Asn His Ser Val
1               5

<210> SEQ ID NO 323
<211> LENGTH: 116
<212> TYPE: PRT
<213> ORGANISM: Homo sapiens

<400> SEQUENCE: 323

Glu Val Gln Leu Leu Glu Ser Gly Gly Gly Leu Val Gln Pro Gly Gly
1               5                   10                  15

Ser Leu Arg Leu Ser Cys Glu Asp Ser Gly Val Thr Phe Ser Ser Asn
            20                  25                  30

Pro Met Ser Trp Val Arg Gln Gly Pro Gly Lys Gly Leu Glu Trp Val
            35                  40                  45

Ser Gly Ile Ser Gly Ser Gly Asp Arg Thr Phe Tyr Glu Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Asp Leu Gly Gly Glu Gly Asn Trp Gly Gln Gly Thr Leu Val
            100                 105                 110

Thr Val Ser Ser
        115

<210> SEQ ID NO 324
<211> LENGTH: 113
<212> TYPE: PRT
<213> ORGANISM: Homo sapiens

<400> SEQUENCE: 324

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Ile Ser
            20                  25                  30

Asn Tyr Ala Asn Trp Val Gln Glu Lys Pro Asp His Ser Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Asn Asn
                85                  90                  95

Gln Ser Val Phe Gly Gly Gly Thr Lys Leu Thr Val Leu Gly Gln Pro
            100                 105                 110

Lys

<210> SEQ ID NO 325
<211> LENGTH: 8
<212> TYPE: PRT
<213> ORGANISM: Homo sapiens

<400> SEQUENCE: 325

Gly Val Thr Phe Ser Ser Asn Pro
1               5

<210> SEQ ID NO 326
<211> LENGTH: 8
<212> TYPE: PRT
<213> ORGANISM: Homo sapiens

<400> SEQUENCE: 326

Ile Ser Gly Ser Gly Asp Arg Thr
1               5

<210> SEQ ID NO 327
<211> LENGTH: 9
<212> TYPE: PRT
<213> ORGANISM: Homo sapiens

<400> SEQUENCE: 327

Ala Lys Asp Leu Gly Gly Glu Gly Asn
1               5

<210> SEQ ID NO 328
<211> LENGTH: 9
<212> TYPE: PRT
<213> ORGANISM: Homo sapiens

<400> SEQUENCE: 328

Thr Gly Ala Val Thr Ile Ser Asn Tyr
```

-continued

```
1               5

<210> SEQ ID NO 329
<211> LENGTH: 3
<212> TYPE: PRT
<213> ORGANISM: Homo sapiens

<400> SEQUENCE: 329

Gly Thr Asn
1

<210> SEQ ID NO 330
<211> LENGTH: 9
<212> TYPE: PRT
<213> ORGANISM: Homo sapiens

<400> SEQUENCE: 330

Ala Leu Trp Tyr Asn Asn Gln Ser Val
1               5

<210> SEQ ID NO 331
<211> LENGTH: 116
<212> TYPE: PRT
<213> ORGANISM: Homo sapiens

<400> SEQUENCE: 331

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Ile Ser Gly Asn Thr Gly Tyr Ala Gln Lys Phe
    50                  55                  60

Gln Gly Arg Val Thr Met Thr Arg Asn Thr Ser Arg Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gln Trp Leu Phe Asp Tyr Trp Gly Gln Gly Thr Leu Val
            100                 105                 110

Thr Val Ser Ser
        115

<210> SEQ ID NO 332
<211> LENGTH: 108
<212> TYPE: PRT
<213> ORGANISM: Homo sapiens

<400> SEQUENCE: 332

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Thr Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Asp Asp Phe Ala Thr Tyr Tyr Cys Gln Gln Tyr Asn Phe Tyr Ser Tyr
                85                  90                  95

Thr Phe Gly Gln Gly Thr Lys Leu Glu Ile Arg Arg
            100                 105

<210> SEQ ID NO 333
<211> LENGTH: 8
<212> TYPE: PRT
<213> ORGANISM: Homo sapiens

<400> SEQUENCE: 333

Gly Tyr Thr Phe Thr Ser Tyr Asp
1               5

<210> SEQ ID NO 334
<211> LENGTH: 7
<212> TYPE: PRT
<213> ORGANISM: Homo sapiens

<400> SEQUENCE: 334

Met Asn Pro Ile Ser Gly Asn
1               5

<210> SEQ ID NO 335
<211> LENGTH: 9
<212> TYPE: PRT
<213> ORGANISM: Homo sapiens

<400> SEQUENCE: 335

Ala Arg Gly Gln Trp Leu Phe Asp Tyr
1               5

<210> SEQ ID NO 336
<211> LENGTH: 6
<212> TYPE: PRT
<213> ORGANISM: Homo sapiens

<400> SEQUENCE: 336

Gln Thr Ile Ser Ser Trp
1               5

<210> SEQ ID NO 337
<211> LENGTH: 3
<212> TYPE: PRT
<213> ORGANISM: Homo sapiens

<400> SEQUENCE: 337

Lys Ala Ser
1

<210> SEQ ID NO 338
<211> LENGTH: 9
<212> TYPE: PRT
<213> ORGANISM: Homo sapiens

<400> SEQUENCE: 338

Gln Gln Tyr Asn Phe Tyr Ser Tyr Thr
1               5

<210> SEQ ID NO 339
<211> LENGTH: 126
<212> TYPE: PRT
<213> ORGANISM: Homo sapiens

<400> SEQUENCE: 339
```

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
            35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Asn Pro Asp Thr Ser Lys Asn
65                  70                  75                  80

Gln Phe Ser Leu Gln Leu Asn Pro Val Thr Pro Glu Asp Thr Ala Val
                85                  90                  95

Tyr Tyr Cys Ala Arg Thr Ile Thr Met Ile Arg Gly Ile Ile Ile Ser
            100                 105                 110

Phe Asp Tyr Trp Gly Gln Gly Thr Leu Val Thr Val Ser Ser
        115                 120                 125

<210> SEQ ID NO 340
<211> LENGTH: 108
<212> TYPE: PRT
<213> ORGANISM: Homo sapiens

<400> SEQUENCE: 340

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Asp Ala Ser Ser Leu Gln Ser Gly Val Pro Ser Arg Phe Ser Gly
        50                  55                  60

Ser Gly Ser Gly Thr Asp Phe Thr Leu Thr Ile Thr Ser Leu Gln Pro
65                  70                  75                  80

Glu Asp Phe Ala Thr Tyr Tyr Cys Gln Gln Ser Phe Ile Thr Pro Ile
                85                  90                  95

Thr Phe Gly Gln Gly Thr Arg Leu Glu Ile Lys Arg
            100                 105

<210> SEQ ID NO 341
<211> LENGTH: 10
<212> TYPE: PRT
<213> ORGANISM: Homo sapiens

<400> SEQUENCE: 341

Gly Asp Ser Val Ser Ser Asn Ser Ala Ala
1               5                   10

<210> SEQ ID NO 342
<211> LENGTH: 9
<212> TYPE: PRT
<213> ORGANISM: Homo sapiens

<400> SEQUENCE: 342

Thr Tyr Tyr Arg Ser Lys Trp Tyr Asn
1               5

<210> SEQ ID NO 343
<211> LENGTH: 16
```

<212> TYPE: PRT
<213> ORGANISM: Homo sapiens

<400> SEQUENCE: 343

Ala Arg Thr Ile Thr Met Ile Arg Gly Ile Ile Ile Ser Phe Asp Tyr
1               5                   10                  15

<210> SEQ ID NO 344
<211> LENGTH: 6
<212> TYPE: PRT
<213> ORGANISM: Homo sapiens

<400> SEQUENCE: 344

Gln Ser Ile Ser Ser Tyr
1               5

<210> SEQ ID NO 345
<211> LENGTH: 3
<212> TYPE: PRT
<213> ORGANISM: Homo sapiens

<400> SEQUENCE: 345

Asp Ala Ser
1

<210> SEQ ID NO 346
<211> LENGTH: 9
<212> TYPE: PRT
<213> ORGANISM: Homo sapiens

<400> SEQUENCE: 346

Gln Gln Ser Phe Ile Thr Pro Ile Thr
1               5

<210> SEQ ID NO 347
<211> LENGTH: 122
<212> TYPE: PRT
<213> ORGANISM: Homo sapiens

<400> SEQUENCE: 347

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Val Met Ser Trp Phe Arg Gln Ala Pro Gly Lys Gly Leu Glu Trp Val
            35                  40                  45

Gly Phe Ile Arg Ser Lys Ala His Gly Gly Thr Thr Glu Tyr Ala Ala
    50                  55                  60

Ser Val Asn Gly Arg Phe Ser Ile Ser Arg Asp Asp Ser Lys Thr Ile
65                  70                  75                  80

Ala Tyr Leu Gln Met Asn Ser Leu Lys Ser Glu Asp Thr Ala Val Tyr
                85                  90                  95

Tyr Cys Thr Trp Leu Arg Asn Asp Tyr Tyr Tyr Gly Met Asp Val Trp
                100                 105                 110

Gly Leu Gly Thr Thr Val Thr Val Ser Ser
            115                 120

<210> SEQ ID NO 348
<211> LENGTH: 113
<212> TYPE: PRT
<213> ORGANISM: Homo sapiens -continued

```
<400> SEQUENCE: 348

Asp Ile Met Met Thr Gln Ser Pro Leu Ser Leu Pro Val Thr Pro Gly
1               5                   10                  15

Glu Pro Ala Ser Ile Ser Cys Arg Ser Ser Gln Arg Leu Leu His Ser
            20                  25                  30

Asn Gly Tyr Ser Tyr Val Asp Trp Tyr Leu Gln Lys Pro Gly Gln Ser
        35                  40                  45

Pro Gln Leu Leu Ile Tyr Leu Gly Ser Asp Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Trp Thr Phe Gly Gln Gly Thr Lys Val Glu Ile Lys
            100                 105                 110

Arg

<210> SEQ ID NO 349
<211> LENGTH: 8
<212> TYPE: PRT
<213> ORGANISM: Homo sapiens

<400> SEQUENCE: 349

Gly Phe Thr Phe Gly Asp Tyr Val
1               5

<210> SEQ ID NO 350
<211> LENGTH: 10
<212> TYPE: PRT
<213> ORGANISM: Homo sapiens

<400> SEQUENCE: 350

Ile Arg Ser Lys Ala His Gly Gly Thr Thr
1               5                   10

<210> SEQ ID NO 351
<211> LENGTH: 13
<212> TYPE: PRT
<213> ORGANISM: Homo sapiens

<400> SEQUENCE: 351

Thr Trp Leu Arg Asn Asp Tyr Tyr Tyr Gly Met Asp Val
1               5                   10

<210> SEQ ID NO 352
<211> LENGTH: 11
<212> TYPE: PRT
<213> ORGANISM: Homo sapiens

<400> SEQUENCE: 352

Gln Arg Leu Leu His Ser Asn Gly Tyr Ser Tyr
1               5                   10

<210> SEQ ID NO 353
<211> LENGTH: 3
<212> TYPE: PRT
<213> ORGANISM: Homo sapiens

<400> SEQUENCE: 353

Leu Gly Ser
1
```

```
<210> SEQ ID NO 354
<211> LENGTH: 9
<212> TYPE: PRT
<213> ORGANISM: Homo sapiens

<400> SEQUENCE: 354

Met Gln Thr Leu Gln Thr Pro Trp Thr
1               5

<210> SEQ ID NO 355
<211> LENGTH: 122
<212> TYPE: PRT
<213> ORGANISM: Homo sapiens

<400> SEQUENCE: 355

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Lys Tyr
                20                  25                  30

Gly Met His Trp Val Arg Gln Ala Pro Gly Lys Gly Leu Glu Trp Val
            35                  40                  45

Ala Asn Ile Gly Tyr Asp Gly Ser Asp Lys Tyr Tyr Ala Asp Ser Val
        50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Phe Cys
                85                  90                  95

Ala Arg Gly Gly Trp Ile Asp Asp Tyr Tyr Tyr Gly Leu Asp Val Trp
                100                 105                 110

Gly Gln Gly Thr Thr Val Thr Val Ser Ser
            115                 120

<210> SEQ ID NO 356
<211> LENGTH: 113
<212> TYPE: PRT
<213> ORGANISM: Homo sapiens

<400> SEQUENCE: 356

Asp Ile Val Met Thr Gln Ser Pro Leu Ser Leu Pro Val Ile Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Ser Leu Lys Ile
65                  70                  75                  80

Ser Arg Val Glu Ala Glu Asp Val Gly Val Tyr Tyr Cys Met Gln Val
                85                  90                  95

Leu Gln Thr Pro Trp Thr Phe Gly Gln Gly Thr Lys Val Glu Ile Lys
                100                 105                 110

Arg

<210> SEQ ID NO 357
<211> LENGTH: 8
<212> TYPE: PRT
```

-continued

<213> ORGANISM: Homo sapiens

<400> SEQUENCE: 357

Gly Phe Thr Phe Ser Lys Tyr Gly
1               5

<210> SEQ ID NO 358
<211> LENGTH: 8
<212> TYPE: PRT
<213> ORGANISM: Homo sapiens

<400> SEQUENCE: 358

Ile Gly Tyr Asp Gly Ser Asp Lys
1               5

<210> SEQ ID NO 359
<211> LENGTH: 15
<212> TYPE: PRT
<213> ORGANISM: Homo sapiens

<400> SEQUENCE: 359

Ala Arg Gly Gly Trp Ile Asp Asp Tyr Tyr Tyr Gly Leu Asp Val
1               5                   10                  15

<210> SEQ ID NO 360
<211> LENGTH: 11
<212> TYPE: PRT
<213> ORGANISM: Homo sapiens

<400> SEQUENCE: 360

Gln Ser Leu Leu His Ser Asn Gly Tyr Asn Tyr
1               5                   10

<210> SEQ ID NO 361
<211> LENGTH: 3
<212> TYPE: PRT
<213> ORGANISM: Homo sapiens

<400> SEQUENCE: 361

Leu Gly Ser
1

<210> SEQ ID NO 362
<211> LENGTH: 9
<212> TYPE: PRT
<213> ORGANISM: Homo sapiens

<400> SEQUENCE: 362

Met Gln Val Leu Gln Thr Pro Trp Thr
1               5

<210> SEQ ID NO 363
<211> LENGTH: 122
<212> TYPE: PRT
<213> ORGANISM: Homo sapiens

<400> SEQUENCE: 363

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
        35                  40                  45

-continued

```
Ala Val Ile Cys Tyr Asp Gly Ser Asp Lys Tyr Tyr Thr Asp Ser Val
    50              55              60

Arg Gly Arg Phe Thr Ile Ser Arg Asp Asn Ser Lys Asn Thr Leu Tyr
65              70              75              80

Leu Gln Met Asn Ser Leu Arg Val Glu Asp Thr Ala Met Tyr Phe Cys
                85              90              95

Ala Arg Gly Gly Trp Ile Asp Asp Tyr Tyr Tyr Gly Met Asp Val Trp
        100             105             110

Gly Gln Gly Thr Thr Val Thr Val Ser Ser
        115             120
```

```
<210> SEQ ID NO 364
<211> LENGTH: 113
<212> TYPE: PRT
<213> ORGANISM: Homo sapiens

<400> SEQUENCE: 364
```

```
Asp Ile Val Met Thr Gln Ser Pro Leu Ser Leu Pro Val Thr Pro Gly
1               5               10              15

Glu Pro Ala Ser Ile Ser Cys Arg Ser Ser Gln Ser Leu Leu His Ser
                20              25              30

Asn Gly Tyr Asn Tyr Leu Asp Trp Tyr Leu Gln Lys Pro Gly Gln Ser
        35              40              45

Pro Gln Leu Leu Ile Phe Leu Gly Ser Asn Arg Ala Ser Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Ala Tyr Tyr Cys Met Gln Val
                85              90              95

Leu Gln Thr Pro Trp Thr Phe Gly Gln Gly Thr Lys Val Glu Ile Lys
        100             105             110

Arg
```

```
<210> SEQ ID NO 365
<211> LENGTH: 8
<212> TYPE: PRT
<213> ORGANISM: Homo sapiens

<400> SEQUENCE: 365
```

```
Gly Phe Thr Phe Ser Ser Tyr Gly
1               5
```

```
<210> SEQ ID NO 366
<211> LENGTH: 8
<212> TYPE: PRT
<213> ORGANISM: Homo sapiens

<400> SEQUENCE: 366
```

```
Ile Cys Tyr Asp Gly Ser Asp Lys
1               5
```

```
<210> SEQ ID NO 367
<211> LENGTH: 15
<212> TYPE: PRT
<213> ORGANISM: Homo sapiens

<400> SEQUENCE: 367
```

```
Ala Arg Gly Gly Trp Ile Asp Asp Tyr Tyr Tyr Gly Met Asp Val
1               5               10              15
```

<210> SEQ ID NO 368
<211> LENGTH: 11
<212> TYPE: PRT
<213> ORGANISM: Homo sapiens

<400> SEQUENCE: 368

Gln Ser Leu Leu His Ser Asn Gly Tyr Asn Tyr
1               5                   10

<210> SEQ ID NO 369
<211> LENGTH: 3
<212> TYPE: PRT
<213> ORGANISM: Homo sapiens

<400> SEQUENCE: 369

Leu Gly Ser
1

<210> SEQ ID NO 370
<211> LENGTH: 9
<212> TYPE: PRT
<213> ORGANISM: Homo sapiens

<400> SEQUENCE: 370

Met Gln Val Leu Gln Thr Pro Trp Thr
1               5

<210> SEQ ID NO 371
<211> LENGTH: 122
<212> TYPE: PRT
<213> ORGANISM: Homo sapiens

<400> SEQUENCE: 371

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Gly Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Arg Gly Gly Trp Asn Asp Asp Tyr Tyr Tyr Gly Leu Asp Val Trp
            100                 105                 110

Gly Gln Gly Thr Thr Val Thr Val Ser Ser
        115                 120

<210> SEQ ID NO 372
<211> LENGTH: 113
<212> TYPE: PRT
<213> ORGANISM: Homo sapiens

<400> SEQUENCE: 372

Asp Ile Val Met Thr Gln Ser Pro Leu Ser Leu Pro Val Ile Pro Gly
1               5                   10                  15

Glu Pro Ala Ser Ile Ser Cys Arg Ser Ser Gln Ser Leu Leu His Ser
            20                  25                  30

```
Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Ile Val Glu Ala Glu Asp Ala Gly Val Tyr Tyr Cys Met Gln Val
                85                  90                  95

Leu Gln Thr Pro Trp Thr Phe Gly Gln Gly Thr Lys Val Glu Ile Lys
            100                 105                 110

Arg

<210> SEQ ID NO 373
<211> LENGTH: 8
<212> TYPE: PRT
<213> ORGANISM: Homo sapiens

<400> SEQUENCE: 373

Gly Phe Thr Phe Ser Arg Tyr Gly
1               5

<210> SEQ ID NO 374
<211> LENGTH: 8
<212> TYPE: PRT
<213> ORGANISM: Homo sapiens

<400> SEQUENCE: 374

Ile Gly Tyr Asp Gly Ser Asn Lys
1               5

<210> SEQ ID NO 375
<211> LENGTH: 15
<212> TYPE: PRT
<213> ORGANISM: Homo sapiens

<400> SEQUENCE: 375

Ala Arg Gly Gly Trp Asn Asp Asp Tyr Tyr Tyr Gly Leu Asp Val
1               5                   10                  15

<210> SEQ ID NO 376
<211> LENGTH: 11
<212> TYPE: PRT
<213> ORGANISM: Homo sapiens

<400> SEQUENCE: 376

Gln Ser Leu Leu His Ser Asn Gly Tyr Asn Tyr
1               5                   10

<210> SEQ ID NO 377
<211> LENGTH: 3
<212> TYPE: PRT
<213> ORGANISM: Homo sapiens

<400> SEQUENCE: 377

Leu Gly Ser
1

<210> SEQ ID NO 378
<211> LENGTH: 9
<212> TYPE: PRT
<213> ORGANISM: Homo sapiens

<400> SEQUENCE: 378
```

-continued

```
Met Gln Val Leu Gln Thr Pro Trp Thr
1               5

<210> SEQ ID NO 379
<211> LENGTH: 126
<212> TYPE: PRT
<213> ORGANISM: Homo sapiens

<400> SEQUENCE: 379

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Glu Asp Gly Ser Glu Lys Tyr Tyr Val Asp Ser Val
    50                  55                  60

Lys Gly Arg Phe Thr Leu Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Ala Leu Leu Trp Phe Gly Val Leu Arg Pro Arg Ala
            100                 105                 110

Phe Asp Ile Trp Gly Gln Gly Thr Met Val Thr Val Ser Ser
            115                 120                 125

<210> SEQ ID NO 380
<211> LENGTH: 113
<212> TYPE: PRT
<213> ORGANISM: Homo sapiens

<400> SEQUENCE: 380

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Asn Pro Gly Gln Ser
        35                  40                  45

Pro His Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Ala Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg

<210> SEQ ID NO 381
<211> LENGTH: 8
<212> TYPE: PRT
<213> ORGANISM: Homo sapiens

<400> SEQUENCE: 381

Gly Phe Thr Phe Ser Asn Tyr Trp
1               5
```

-continued

```
<210> SEQ ID NO 382
<211> LENGTH: 8
<212> TYPE: PRT
<213> ORGANISM: Homo sapiens

<400> SEQUENCE: 382

Ile Lys Glu Asp Gly Ser Glu Lys
1               5

<210> SEQ ID NO 383
<211> LENGTH: 19
<212> TYPE: PRT
<213> ORGANISM: Homo sapiens

<400> SEQUENCE: 383

Ala Lys Glu Gly Ala Leu Leu Trp Phe Gly Val Leu Arg Pro Arg Ala
1               5                   10                  15

Phe Asp Ile

<210> SEQ ID NO 384
<211> LENGTH: 11
<212> TYPE: PRT
<213> ORGANISM: Homo sapiens

<400> SEQUENCE: 384

Gln Ser Leu Leu His Ser Asn Gly Tyr Asn Tyr
1               5                   10

<210> SEQ ID NO 385
<211> LENGTH: 3
<212> TYPE: PRT
<213> ORGANISM: Homo sapiens

<400> SEQUENCE: 385

Leu Ala Ser
1

<210> SEQ ID NO 386
<211> LENGTH: 9
<212> TYPE: PRT
<213> ORGANISM: Homo sapiens

<400> SEQUENCE: 386

Met Gln Ala Leu Gln Thr Pro Tyr Thr
1               5

<210> SEQ ID NO 387
<211> LENGTH: 98
<212> TYPE: PRT
<213> ORGANISM: Homo sapiens

<400> SEQUENCE: 387

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80
```

Met Glu Leu Ser Ser Leu Arg Ser Glu Asp Thr Ala Val Tyr Tyr Cys
                    85                  90                  95

Ala Arg

<210> SEQ ID NO 388
<211> LENGTH: 95
<212> TYPE: PRT
<213> ORGANISM: Homo sapiens

<400> SEQUENCE: 388

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 389
<211> LENGTH: 100
<212> TYPE: PRT
<213> ORGANISM: Homo sapiens

<400> SEQUENCE: 389

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
                20                  25                  30

Ala Met Ser Trp Phe Arg Gln Ala Pro Gly Lys Gly Leu Glu Trp Val
            35                  40                  45

Gly Phe Ile Arg Ser Lys Ala Tyr Gly Gly Thr Thr Glu Tyr Thr Ala
        50                  55                  60

Ser Val Lys Gly Arg Phe Thr Ile Ser Arg Asp Gly Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg
            100

<210> SEQ ID NO 390
<211> LENGTH: 98
<212> TYPE: PRT
<213> ORGANISM: Homo sapiens

<400> SEQUENCE: 390

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

-continued

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 391

<400> SEQUENCE: 391

000

<210> SEQ ID NO 392

<400> SEQUENCE: 392

000

<210> SEQ ID NO 393
<211> LENGTH: 20
<212> TYPE: PRT
<213> ORGANISM: Homo sapiens

<400> SEQUENCE: 393

Cys Ala Arg Glu Gly Asp Asp Val Leu Val Pro Thr Ser Arg Gly Phe
1               5                   10                  15

Phe Asp Tyr Trp
            20

<210> SEQ ID NO 394
<211> LENGTH: 11
<212> TYPE: PRT
<213> ORGANISM: Homo sapiens

<400> SEQUENCE: 394

Cys Met Gln Ala Leu Gln Thr Pro Leu Thr Phe
1               5                   10

<210> SEQ ID NO 395
<211> LENGTH: 20
<212> TYPE: PRT
<213> ORGANISM: Homo sapiens

<400> SEQUENCE: 395

Cys Ala Arg Glu Gly Asp Ile Glu Val Val Leu Ala Gly Arg Gly Tyr
1               5                   10                  15

Phe Asp Tyr Trp
            20

<210> SEQ ID NO 396
<211> LENGTH: 11
<212> TYPE: PRT
<213> ORGANISM: Homo sapiens

<400> SEQUENCE: 396

Cys Met Gln Ala Leu Gln Thr Pro Tyr Thr Phe
1               5                   10

<210> SEQ ID NO 397
<211> LENGTH: 21
<212> TYPE: PRT
<213> ORGANISM: Homo sapiens
```

-continued

```
<400> SEQUENCE: 397

Cys Ala Arg Glu Gly Asn Leu Gly Tyr Asp Val Val Thr Gly Tyr Ser
1               5                   10                  15

Tyr Phe Val Tyr Trp
            20

<210> SEQ ID NO 398
<211> LENGTH: 10
<212> TYPE: PRT
<213> ORGANISM: Homo sapiens

<400> SEQUENCE: 398

Cys Gln Gln Tyr Gly Arg Ser Leu Thr Phe
1               5                   10

<210> SEQ ID NO 399
<211> LENGTH: 17
<212> TYPE: PRT
<213> ORGANISM: Homo sapiens

<400> SEQUENCE: 399

Cys Ala Ser Leu Thr Leu Ile Trp Phe Gly Glu Lys Ala Phe Asp Ile
1               5                   10                  15

Trp

<210> SEQ ID NO 400
<211> LENGTH: 11
<212> TYPE: PRT
<213> ORGANISM: Homo sapiens

<400> SEQUENCE: 400

Cys Gln Gln Tyr Asn Asn Trp Pro Tyr Thr Phe
1               5                   10

<210> SEQ ID NO 401
<211> LENGTH: 17
<212> TYPE: PRT
<213> ORGANISM: Homo sapiens

<400> SEQUENCE: 401

Cys Ala Arg Glu Gly Leu Gly Ala Val Ala Gly Tyr Tyr Phe Asp Tyr
1               5                   10                  15

Trp

<210> SEQ ID NO 402
<211> LENGTH: 11
<212> TYPE: PRT
<213> ORGANISM: Homo sapiens

<400> SEQUENCE: 402

Cys Gln Gln Ser Tyr Ser Thr Pro Phe Ala Phe
1               5                   10

<210> SEQ ID NO 403
<211> LENGTH: 12
<212> TYPE: PRT
<213> ORGANISM: Homo sapiens

<400> SEQUENCE: 403

Cys Ala Arg Asp Ala Gly Leu Ser Phe Asp Ile Trp
1               5                   10
```

<210> SEQ ID NO 404
<211> LENGTH: 9
<212> TYPE: PRT
<213> ORGANISM: Homo sapiens

<400> SEQUENCE: 404

Cys Gln Gln Tyr Gly Ser Tyr Thr Phe
1               5

<210> SEQ ID NO 405
<211> LENGTH: 14
<212> TYPE: PRT
<213> ORGANISM: Homo sapiens

<400> SEQUENCE: 405

Cys Ala Arg Ala Thr Leu Ala Arg Gly Ala Leu Asp Tyr Trp
1               5                   10

<210> SEQ ID NO 406
<211> LENGTH: 11
<212> TYPE: PRT
<213> ORGANISM: Homo sapiens

<400> SEQUENCE: 406

Cys Gln Gln Tyr Tyr Ser Thr Pro Trp Thr Phe
1               5                   10

<210> SEQ ID NO 407
<211> LENGTH: 15
<212> TYPE: PRT
<213> ORGANISM: Homo sapiens

<400> SEQUENCE: 407

Cys Ala Arg Ser Leu Gly Ser Gly Thr Tyr Pro Phe Asp Ser Trp
1               5                   10                  15

<210> SEQ ID NO 408
<211> LENGTH: 11
<212> TYPE: PRT
<213> ORGANISM: Homo sapiens

<400> SEQUENCE: 408

Cys Gln Gln Ser Tyr Ser Thr Pro Leu Thr Phe
1               5                   10

<210> SEQ ID NO 409
<211> LENGTH: 98
<212> TYPE: PRT
<213> ORGANISM: Homo sapiens

<400> SEQUENCE: 409

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

-continued

Ala Arg

<210> SEQ ID NO 410
<211> LENGTH: 127
<212> TYPE: PRT
<213> ORGANISM: Homo sapiens

<400> SEQUENCE: 410

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Ser Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Ile Phe Gly Val Pro Asp Ala Phe Asp Ile Trp
            100                 105                 110

Gly Gln Gly Thr Met Val Thr Val Ser Ser Val Pro Arg Asp Cys
        115                 120                 125

<210> SEQ ID NO 411
<211> LENGTH: 127
<212> TYPE: PRT
<213> ORGANISM: Homo sapiens

<400> SEQUENCE: 411

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Ile Phe Gly Val Pro Asp Ala Phe Asp Ile Trp
            100                 105                 110

Gly Gln Gly Thr Met Val Thr Val Ser Ser Val Pro Arg Asp Cys
        115                 120                 125

<210> SEQ ID NO 412
<211> LENGTH: 127
<212> TYPE: PRT
<213> ORGANISM: Homo sapiens

<400> SEQUENCE: 412

Glu Val Gln Leu Val Glu Ser Gly Gly Ser Val Val Gln Pro Gly Arg
1               5                   10                  15

Ser Leu Arg Leu Ser Cys Ala Ala Ser Gly Phe Thr Phe Ser Ser Tyr

-continued

```
                 20                    25                    30

Gly Met His Trp Val Arg Gln Ala Pro Gly Lys Gly Leu Glu Trp Val
             35                    40                    45

Ala Val Ile Trp Ser Asp Gly Ser Asn Lys Tyr Tyr Ala Asp Ser Val
         50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
                 85                    90                    95

Ala Arg Asp Glu Arg Ile Phe Gly Val Pro Asp Ala Phe Asp Ile Trp
             100                   105                   110

Gly Gln Gly Thr Met Val Thr Val Ser Ser Val Pro Arg Asp Cys
         115                   120                   125
```

<210> SEQ ID NO 413
<211> LENGTH: 127
<212> TYPE: PRT
<213> ORGANISM: Homo sapiens

<400> SEQUENCE: 413

```
Glu Val Gln Leu Val Glu Ser Gly Gly Gly Leu Val Gln Pro Gly Gly
1                 5                    10                    15

Ser Leu Arg Leu Ser Cys Ala Ala Ser Gly Phe Thr Phe Ser Ser Tyr
             20                    25                    30

Gly Met His Trp Val Arg Gln Ala Pro Gly Lys Gly Leu Glu Trp Val
             35                    40                    45

Ala Val Ile Trp Ser Asp Gly Ser Asn Lys Tyr Tyr Ala Asp Ser Val
         50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
                 85                    90                    95

Ala Arg Asp Glu Arg Ile Phe Gly Val Pro Asp Ala Phe Asp Ile Trp
             100                   105                   110

Gly Gln Gly Thr Met Val Thr Val Ser Ser Val Pro Arg Asp Cys
         115                   120                   125
```

<210> SEQ ID NO 414
<211> LENGTH: 127
<212> TYPE: PRT
<213> ORGANISM: Homo sapiens

<400> SEQUENCE: 414

```
Glu Val Gln Leu Val Glu Ser Gly Gly Gly Val Val Gln Pro Gly Arg
1                 5                    10                    15

Ser Leu Arg Leu Ser Cys Ala Ala Ser Gly Phe Thr Phe Ser Thr Ser
             20                    25                    30

Gly Met His Trp Val Arg Gln Ala Pro Gly Lys Gly Leu Glu Trp Val
             35                    40                    45

Ala Val Ile Trp Tyr Asp Gly Ser Asn Lys Tyr Tyr Ala Asp Ser Val
         50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Tyr Cys
                 85                    90                    95

Ala Arg Asp Glu Arg Ile Phe Gly Val Pro Asp Ala Phe Asp Ile Trp
```

-continued

```
                    100                 105                 110
Gly His Gly Thr Met Val Thr Val Ser Ser Val Pro Arg Asp Cys
        115                 120                 125

<210> SEQ ID NO 415
<211> LENGTH: 127
<212> TYPE: PRT
<213> ORGANISM: Homo sapiens

<400> SEQUENCE: 415

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Ser Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Arg Asp Glu Arg Ile Phe Gly Val Pro Asp Ala Phe Asp Ile Trp
            100                 105                 110

Gly Gln Gly Thr Met Val Thr Val Ser Ser Val Pro Arg Asp Cys
        115                 120                 125

<210> SEQ ID NO 416
<211> LENGTH: 127
<212> TYPE: PRT
<213> ORGANISM: Homo sapiens

<400> SEQUENCE: 416

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Ser Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Glu Arg Ile Phe Gly Val Pro Asp Thr Phe Asp Ile Trp
            100                 105                 110

Gly Gln Gly Thr Met Val Thr Val Ser Ser Val Pro Arg Asp Cys
        115                 120                 125

<210> SEQ ID NO 417
<211> LENGTH: 127
<212> TYPE: PRT
<213> ORGANISM: Homo sapiens

<400> SEQUENCE: 417

Glu Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Ile Phe Gly Val Pro Asp Thr Phe Asp Ile Arg
            100                 105                 110

Gly Gln Gly Thr Met Val Thr Val Ser Ser Val Pro Arg Asp Cys
        115                 120                 125
```

<210> SEQ ID NO 418
<211> LENGTH: 127
<212> TYPE: PRT
<213> ORGANISM: Homo sapiens

<400> SEQUENCE: 418

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Arg Ile Phe Gly Val Pro Asp Val Phe Asp Ile Arg
            100                 105                 110

Gly Gln Gly Thr Met Val Thr Val Ser Ser Val Pro Arg Asp Cys
        115                 120                 125
```

<210> SEQ ID NO 419
<211> LENGTH: 127
<212> TYPE: PRT
<213> ORGANISM: Homo sapiens

<400> SEQUENCE: 419

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
        20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Glu Arg Ile Phe Gly Val Pro Asp Ala Phe Asp Ile Arg
            100                 105                 110

Gly Gln Gly Thr Met Val Thr Val Ser Ser Val Pro Arg Asp Cys
        115                 120                 125

<210> SEQ ID NO 420
<211> LENGTH: 123
<212> TYPE: PRT
<213> ORGANISM: Homo sapiens

<400> SEQUENCE: 420

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Ala Gly Thr Thr Phe Asp Tyr Trp Gly Gln Gly Thr
            100                 105                 110

Leu Val Thr Val Ser Ser Val Pro Arg Asp Cys
        115                 120

<210> SEQ ID NO 421
<211> LENGTH: 98
<212> TYPE: PRT
<213> ORGANISM: Homo sapiens

<400> SEQUENCE: 421

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 422
<211> LENGTH: 125
<212> TYPE: PRT
<213> ORGANISM: Homo sapiens

<400> SEQUENCE: 422

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Ile Phe Ser His Tyr
```

-continued

```
                 20                  25                  30

Trp Met His Trp Val Arg Gln Ala Pro Gly Lys Gly Leu Val Trp Val
             35                  40                  45

Ser Arg Ile Asn Ser Asp Gly Ser Asn Thr Ser Tyr Ala Asp Ser Val
         50                  55                  60

Lys Gly Arg Phe Thr Ile Ser Arg Asp Asn Ala Arg Asn Thr Leu Tyr
65                  70                  75                  80

Leu Gln Met Asn Ser Leu Gly Ala Glu Asp Thr Ala Met Tyr Tyr Cys
                 85                  90                  95

Ala Arg Gly Glu Val Gly Thr Ser Tyr Trp Leu Asn Pro Trp Gly Gln
                 100                 105                 110

Gly Thr Leu Val Thr Val Ser Ser Val Pro Arg Asp Cys
             115                 120                 125

<210> SEQ ID NO 423
<211> LENGTH: 119
<212> TYPE: PRT
<213> ORGANISM: Homo sapiens

<400> SEQUENCE: 423

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
             20                  25                  30

Trp Met His Trp Val Arg Gln Ala Pro Gly Lys Gly Leu Val Trp Val
             35                  40                  45

Ser Arg Ile Asn Ser Asp Gly Ser Ser Thr Ser Tyr Ala Asp Ser Val
         50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                 85                  90                  95

Gly Asn Pro Tyr Phe Asp Tyr Trp Gly Gln Gly Thr Leu Val Thr Val
             100                 105                 110

Ser Ser Val Pro Arg Asp Cys
         115

<210> SEQ ID NO 424
<211> LENGTH: 123
<212> TYPE: PRT
<213> ORGANISM: Homo sapiens

<400> SEQUENCE: 424

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
             20                  25                  30

Trp Met Leu Trp Val Arg Gln Ala Pro Gly Glu Gly Leu Val Trp Val
             35                  40                  45

Ser Arg Ile Asp Ser Asp Gly Ser Asn Thr Thr Tyr Ala Asp Ser Val
         50                  55                  60

Lys Gly Arg Phe Thr Val Ser Arg Asp Asn Ala Gln Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Ser Gly Tyr Gly Tyr Ala Phe Asp Ile Trp Gly Gln Gly Thr
```

-continued

```
              100              105              110

Met Val Thr Val Ser Ser Val Pro Arg Asp Cys
        115              120

<210> SEQ ID NO 425
<211> LENGTH: 123
<212> TYPE: PRT
<213> ORGANISM: Homo sapiens

<400> SEQUENCE: 425

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
        20                  25                  30

Trp Met Leu Trp Val Arg Gln Ala Pro Gly Glu Gly Leu Val Trp Val
        35                  40                  45

Ser Arg Ile Asp Ser Asp Gly Ser Asn Thr Thr Tyr Ala Asp Ser Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Gly Tyr Ala Phe Asp Ile Trp Gly Gln Gly Thr
            100                 105                 110

Met Val Thr Val Ser Ser Val Pro Arg Asp Cys
        115              120

<210> SEQ ID NO 426
<211> LENGTH: 132
<212> TYPE: PRT
<213> ORGANISM: Homo sapiens

<400> SEQUENCE: 426

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
        20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Leu Met Asn Ser Leu Arg Ala Glu Asp Thr Ala Val Tyr Tyr Cys
                85                  90                  95

Ala Arg Gly Arg Asp Glu Arg Lys Gly Asn Tyr Tyr Gly Ser Glu Ile
            100                 105                 110

Tyr Pro Asp Tyr Trp Gly Gln Gly Thr Leu Val Thr Val Ser Ser Val
        115              120                  125

Pro Arg Asp Cys
    130

<210> SEQ ID NO 427
<211> LENGTH: 120
<212> TYPE: PRT
<213> ORGANISM: Homo sapiens

<400> SEQUENCE: 427
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Val Trp Val
        35                  40                  45

Ser Arg Ile Asn Thr Asp Gly Ser Thr Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Leu Met Asn Ser Leu Arg Ala Glu Asp Thr Ala Val Tyr Tyr Cys
                85                  90                  95

Ala Arg Asp Gln Tyr Tyr Tyr Val Ser Gly Gln Gly Thr Met Val Thr
            100                 105                 110

Val Ser Ser Val Pro Arg Asp Cys
        115                 120
```

```
<210> SEQ ID NO 428
<211> LENGTH: 120
<212> TYPE: PRT
<213> ORGANISM: Homo sapiens

<400> SEQUENCE: 428
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Leu Met Asn Ser Leu Arg Ala Glu Asp Thr Ala Val Tyr Tyr Cys
                85                  90                  95

Ala Arg Asp Gln Tyr Tyr Tyr Val Ser Gly Gln Gly Thr Met Val Thr
            100                 105                 110

Val Ser Ser Val Pro Arg Asp Cys
        115                 120
```

```
<210> SEQ ID NO 429
<211> LENGTH: 120
<212> TYPE: PRT
<213> ORGANISM: Homo sapiens

<400> SEQUENCE: 429
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80
```

Leu Leu Met Asn Ser Leu Arg Ala Glu Asp Thr Ala Val Tyr Tyr Cys
                85                      90                      95

Ala Arg Asp Gln Tyr Tyr Tyr Ile Ser Gly Gln Gly Thr Met Val Thr
            100                     105                     110

Val Ser Ser Val Pro Arg Asp Cys
        115                 120

<210> SEQ ID NO 430
<211> LENGTH: 98
<212> TYPE: PRT
<213> ORGANISM: Homo sapiens

<400> SEQUENCE: 430

Glu Val Gln Leu Leu Glu Ser Gly Gly Gly Leu Val Gln Pro Gly Gly
1               5                       10                      15

Ser Leu Arg Leu Ser Cys Ala Ala Ser Gly Phe Thr Phe Ser Ser Tyr
            20                      25                      30

Ala Met Ser Trp Val Arg Gln Ala Pro Gly Lys Gly Leu Glu Trp Val
        35                      40                      45

Ser Ala Ile Ser Gly Ser Gly Gly Ser Thr Tyr Tyr Ala Asp Ser Val
    50                      55                      60

Lys Gly Arg Phe Thr Ile Ser Arg Asp Asn Ser Lys Asn Thr Leu Tyr
65                      70                      75                      80

Leu Gln Met Asn Ser Leu Arg Ala Glu Asp Thr Ala Val Tyr Tyr Cys
                85                      90                      95

Ala Lys

<210> SEQ ID NO 431
<211> LENGTH: 125
<212> TYPE: PRT
<213> ORGANISM: Homo sapiens

<400> SEQUENCE: 431

Glu Val Gln Leu Leu Glu Ser Gly Gly Gly Trp Val Gln Pro Gly Gly
1               5                       10                      15

Ser Leu Arg Leu Ser Cys Ala Ala Ser Gly Phe Thr Phe Ser Thr Asn
            20                      25                      30

Ala Met Ser Trp Val Arg Gln Ala Pro Gly Lys Gly Leu Glu Trp Val
        35                      40                      45

Ser Gly Ile Ser Gly Ser Gly Gly Ser Thr Asp Tyr Ala Asp Ser Val
    50                      55                      60

Lys Gly Arg Phe Thr Ile Ser Arg Asp Asn Ser Lys Asn Thr Leu Tyr
65                      70                      75                      80

Leu Gln Met Asn Ser Leu Arg Ala Glu Asp Thr Ala Val Tyr Tyr Cys
                85                      90                      95

Ala Pro Arg Ile Ala Val Ala Pro Asp Ala Leu Asp Ile Trp Gly Gln
            100                     105                     110

Gly Thr Met Val Thr Val Ser Ser Val Pro Arg Asp Cys
        115                     120                     125

<210> SEQ ID NO 432
<211> LENGTH: 120
<212> TYPE: PRT
<213> ORGANISM: Homo sapiens

<400> SEQUENCE: 432

Glu Val Gln Leu Leu Glu Ser Gly Gly Gly Leu Val Gln Pro Gly Gly

-continued

```
1              5               10              15

Ser Leu Arg Leu Ser Cys Ala Ala Ser Gly Phe Thr Phe Ser Ser Tyr
        20              25              30

Ala Met Ser Trp Val Arg Gln Ala Pro Gly Lys Gly Leu Glu Trp Val
        35              40              45

Ser Ala Ile Ser Gly Ser Gly Gly Asn Thr Tyr Tyr Thr Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Asp Leu Val Gly Ala Tyr Arg Gly Gln Gly Thr Leu Val Thr
            100             105             110

Val Ser Ser Val Pro Arg Asp Cys
        115             120
```

<210> SEQ ID NO 433
<211> LENGTH: 125
<212> TYPE: PRT
<213> ORGANISM: Homo sapiens

<400> SEQUENCE: 433

```
Glu Val Gln Leu Leu Glu Ser Gly Gly Gly Leu Val Gln Pro Gly Gly
1              5               10              15

Ser Leu Arg Leu Ser Cys Ala Ala Ser Gly Phe Thr Phe Ser Ser Phe
        20              25              30

Ala Met Ser Trp Val Arg Gln Ala Pro Gly Lys Gly Leu Glu Trp Val
        35              40              45

Ser Ala Ile Ser Gly Ser Val Asn Ser Thr Tyr Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Lys Asp Trp Ala Ser Gly Asn Tyr Tyr Lys Asp Tyr Trp Gly Gln
            100             105             110

Gly Thr Leu Val Thr Val Ser Ser Val Pro Arg Asp Cys
        115             120             125
```

<210> SEQ ID NO 434
<211> LENGTH: 125
<212> TYPE: PRT
<213> ORGANISM: Homo sapiens

<400> SEQUENCE: 434

```
Glu Val Gln Leu Leu Glu Ser Gly Gly Gly Leu Val Gln Pro Gly Gly
1              5               10              15

Ser Leu Arg Leu Ser Cys Ala Ala Ser Gly Phe Thr Phe Ser Ser Tyr
        20              25              30

Ala Met Ser Trp Val Arg Gln Ala Pro Gly Lys Gly Leu Glu Trp Val
        35              40              45

Ser Ala Ile Ser Gly Asn Gly Gly Ser Thr Tyr Tyr Ala Asp Ser Val
        50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
```

-continued

```
                        85               90              95

Ala Lys Gly Glu Gln Gln Leu Ala Tyr Tyr Phe Asp Tyr Trp Gly Gln
            100             105             110

Gly Thr Leu Val Thr Val Ser Ser Val Pro Arg Asp Cys
        115             120             125

<210> SEQ ID NO 435
<211> LENGTH: 95
<212> TYPE: PRT
<213> ORGANISM: Homo sapiens

<400> SEQUENCE: 435

Glu Ile Val Met Thr Gln Ser Pro Ala Thr Leu Ser Val Ser Pro Gly
1               5               10              15

Glu Arg Ala Thr Leu Ser Cys Arg Ala Ser Gln Ser Val Ser Ser Asn
            20              25              30

Leu Ala Trp Tyr Gln Gln Lys Pro Gly Gln Ala Pro Arg Leu Leu Ile
        35              40              45

Tyr Gly Ala Ser Thr Arg Ala Thr Gly Ile Pro Ala Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Val Tyr Tyr Cys Gln Gln Tyr Asn Asn Trp Pro
            85              90              95

<210> SEQ ID NO 436
<211> LENGTH: 108
<212> TYPE: PRT
<213> ORGANISM: Homo sapiens

<400> SEQUENCE: 436

Glu Ile Val Met Thr Gln Ser Pro Ala Thr Leu Ser Val Ser Pro Gly
1               5               10              15

Glu Arg Ala Thr Leu Ser Cys Arg Ala Ser Gln Ser Val Ser Ser Asn
            20              25              30

Leu Ala Trp Tyr Gln Gln Lys Pro Gly Gln Ala Pro Arg Leu Leu Ile
        35              40              45

Tyr Gly Ala Ser Thr Arg Ala Thr Gly Ile Pro Ala Arg Phe Gly Gly
    50              55              60

Ser Gly Ser Gly Thr Glu Phe Thr Leu Ser Ile Ser Ser Leu Gln Ser
65              70              75              80

Glu Asp Phe Ala Val Tyr Tyr Cys Gln His Tyr Asn Asn Trp Pro Leu
            85              90              95

Thr Phe Gly Gly Gly Thr Lys Val Glu Ile Lys Lys
            100             105

<210> SEQ ID NO 437
<211> LENGTH: 107
<212> TYPE: PRT
<213> ORGANISM: Homo sapiens

<400> SEQUENCE: 437

Glu Ile Val Met Thr Gln Ser Pro Ala Thr Leu Ser Val Ser Pro Gly
1               5               10              15

Glu Arg Ala Thr Leu Ser Cys Arg Ala Ser Gln Ser Val Ser Asn Asn
            20              25              30

Leu Ala Trp Tyr Gln Gln Lys Pro Gly Gln Ala Pro Arg Leu Leu Ile
        35              40              45
```

-continued

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105

<210> SEQ ID NO 438
<211> LENGTH: 107
<212> TYPE: PRT
<213> ORGANISM: Homo sapiens

<400> SEQUENCE: 438

Glu Ile Val Met Thr Gln Ser Pro Ala Thr Arg Ser Val Ser Pro Gly
1               5                   10                  15

Glu Arg Ala Thr Leu Ser Cys Arg Ala Ser Gln Thr Ile Ser Ser Tyr
                20                  25                  30

Leu Ala Trp Tyr Gln Gln Lys Pro Gly Gln Ala Pro Gly Leu Leu Ile
            35                  40                  45

Tyr Gly Ala Ser Asn Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Val Ile Tyr Tyr Arg Gln Gln Tyr Asn Asn Trp Pro Leu
                85                  90                  95

Thr Phe Gly Gly Gly Thr Lys Val Glu Ile Lys
            100                 105

<210> SEQ ID NO 439
<211> LENGTH: 107
<212> TYPE: PRT
<213> ORGANISM: Homo sapiens

<400> SEQUENCE: 439

Glu Val Val Met Thr Gln Ser Pro Ala Thr Leu Ser Val Ser Pro Gly
1               5                   10                  15

Glu Arg Ala Ser Leu Ser Cys Arg Ala Ser Gln Thr Val Asn Ser Asn
                20                  25                  30

Leu Ala Trp Tyr Gln Gln Lys Pro Gly Gln Thr Pro Arg Leu Leu Ile
            35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Arg Leu Gln Ser
65                  70                  75                  80

Glu Asp Phe Thr Val Tyr Tyr Cys Gln Gln Tyr Asn Asn Trp Pro Leu
                85                  90                  95

Thr Phe Gly Pro Gly Thr Lys Val Asp Ile Lys
            100                 105

<210> SEQ ID NO 440
<211> LENGTH: 107
<212> TYPE: PRT
<213> ORGANISM: Homo sapiens

<400> SEQUENCE: 440

-continued

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ile
                85                  90                  95

Thr Phe Gly Gln Gly Thr Arg Leu Glu Ile Lys
            100                 105
```

<210> SEQ ID NO 441
<211> LENGTH: 107
<212> TYPE: PRT
<213> ORGANISM: Homo sapiens

<400> SEQUENCE: 441

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Phe Arg Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr His Cys Gln Gln Tyr Asn Ser Trp Pro Ile
                85                  90                  95

Thr Phe Gly Gln Gly Thr Arg Leu Glu Ile Lys
            100                 105
```

<210> SEQ ID NO 442
<211> LENGTH: 107
<212> TYPE: PRT
<213> ORGANISM: Homo sapiens

<400> SEQUENCE: 442

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Phe Ala Trp Tyr Gln His Lys Pro Gly Gln Ala Pro Arg Leu Leu Ile
        35                  40                  45

Tyr Gly Ala Ser Thr Arg Val Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Cys Ala Ile Tyr Tyr Cys Gln Gln Tyr Asn Asn Trp Pro Phe
                85                  90                  95

Thr Phe Gly Pro Gly Thr Lys Val Asp Ile Lys
            100                 105
```

```
<210> SEQ ID NO 443
<211> LENGTH: 106
<212> TYPE: PRT
<213> ORGANISM: Homo sapiens

<400> SEQUENCE: 443

Glu Thr Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asn Trp Ile Thr
                85                  90                  95

Phe Gly Gln Gly Thr Arg Leu Glu Ile Lys
            100                 105

<210> SEQ ID NO 444
<211> LENGTH: 108
<212> TYPE: PRT
<213> ORGANISM: Homo sapiens

<400> SEQUENCE: 444

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asn Asn Trp Pro Pro
                85                  90                  95

Tyr Thr Phe Gly Gln Gly Thr Lys Leu Glu Ile Lys
            100                 105

<210> SEQ ID NO 445
<211> LENGTH: 107
<212> TYPE: PRT
<213> ORGANISM: Homo sapiens

<400> SEQUENCE: 445

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ile Ser Ser
            20                  25                  30

Leu Ala Trp Tyr Gln Gln Thr Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Phe Thr Ile Ser Ser Leu Gln Ser
```

-continued

```
65                  70                  75                  80

Glu Asp Phe Ala Val Tyr Tyr Cys Gln Gln Tyr His Tyr Trp Pro Phe
                85                  90                  95

Thr Phe Gly Pro Gly Thr Lys Met Asp Ile Lys
            100                 105

<210> SEQ ID NO 446
<211> LENGTH: 107
<212> TYPE: PRT
<213> ORGANISM: Homo sapiens

<400> SEQUENCE: 446

Arg Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Val Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Pro Gly Thr Lys Val Asp Ile Lys
            100                 105

<210> SEQ ID NO 447
<211> LENGTH: 107
<212> TYPE: PRT
<213> ORGANISM: Homo sapiens

<400> SEQUENCE: 447

Arg Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Ile Arg Ser Asn
                20                  25                  30

Leu Ala Trp Tyr Gln Gln Lys Pro Gly Gln Ala Pro Arg His Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Ile Tyr Tyr Cys Gln Gln Tyr Asn Asn Trp Pro Leu
                85                  90                  95

Thr Phe Gly Gln Gly Thr Arg Leu Glu Ile Lys
            100                 105

<210> SEQ ID NO 448
<211> LENGTH: 95
<212> TYPE: PRT
<213> ORGANISM: Homo sapiens

<400> SEQUENCE: 448

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30
```

-continued

```
Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 449
<211> LENGTH: 104
<212> TYPE: PRT
<213> ORGANISM: Homo sapiens

<400> SEQUENCE: 449

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
        20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Thr Phe Gly
                85                  90                  95

Gln Gly Thr Lys Leu Glu Ile Lys
            100

<210> SEQ ID NO 450
<211> LENGTH: 95
<212> TYPE: PRT
<213> ORGANISM: Homo sapiens

<400> SEQUENCE: 450

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
        20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 451
<211> LENGTH: 108
<212> TYPE: PRT
<213> ORGANISM: Homo sapiens

<400> SEQUENCE: 451

Asp Ile Gln Met Thr Gln Ser Pro Ser Thr Leu Ser Ala Ser Val Gly
1               5                   10                  15
```

Asp Arg Ala Thr Ile Thr Cys Arg Ala Ser Gln Ser Ile Ser Thr Trp
                20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Arg Leu Gln Pro
65                  70                  75                  80

Asp Asp Phe Ala Thr Tyr Tyr Cys Gln Gln Tyr Lys Thr Tyr Ser Pro
                85                  90                  95

Phe Ser Phe Gly Pro Gly Thr Asn Val Asp Ile Glu
            100                 105

<210> SEQ ID NO 452

<400> SEQUENCE: 452

000

<210> SEQ ID NO 453
<211> LENGTH: 108
<212> TYPE: PRT
<213> ORGANISM: Homo sapiens

<400> SEQUENCE: 453

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Asp Asp Phe Ala Thr Tyr Tyr Cys Gln Gln Tyr Lys Ser Tyr Ser Pro
                85                  90                  95

Phe Ser Phe Gly Pro Gly Thr Lys Val Asp Ile Lys
            100                 105

<210> SEQ ID NO 454
<211> LENGTH: 95
<212> TYPE: PRT
<213> ORGANISM: Homo sapiens

<400> SEQUENCE: 454

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro
                85                  90                  95

```
<210> SEQ ID NO 455
<211> LENGTH: 107
<212> TYPE: PRT
<213> ORGANISM: Homo sapiens

<400> SEQUENCE: 455

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 456
<211> LENGTH: 107
<212> TYPE: PRT
<213> ORGANISM: Homo sapiens

<400> SEQUENCE: 456

Val Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Tyr
                85                  90                  95

Thr Phe Gly Gln Gly Thr Lys Leu Glu Ile Lys
            100                 105

<210> SEQ ID NO 457
<211> LENGTH: 107
<212> TYPE: PRT
<213> ORGANISM: Homo sapiens

<400> SEQUENCE: 457

Asp Ile Gln Leu Thr Gln Ser Pro Ser Phe Arg Ser Ala Ser Val Gly
1               5                   10                  15

Asp Arg Val Thr Ile Thr Cys Arg Ala Ser Gln Asp Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Thr Leu Gln Ser Gly Val Pro Ser Arg Phe Ser Gly
    50                  55                  60
```

```
Ser Glu Ser Gly Thr Glu Phe Thr Leu Thr Ile Ser Ser Leu Gln Pro
65              70                  75                  80

Glu Asp Phe Ala Thr Tyr Tyr Cys Gln Gln Leu Asn Ser Tyr Pro Tyr
                85                  90                  95

Thr Phe Gly Gln Gly Thr Lys Val Glu Ile Lys
            100                 105
```

```
<210> SEQ ID NO 458
<211> LENGTH: 107
<212> TYPE: PRT
<213> ORGANISM: Homo sapiens

<400> SEQUENCE: 458
```

```
Asp Ile Gln Leu Thr Gln Ser Pro Ser Phe Leu Ser Ala Ser Val Gly
1               5                   10                  15

Asp Arg Val Thr Ile Ser Cys Arg Ala Ser Gln Gly Ile Ser Ser Tyr
                20                  25                  30

Leu Ala Trp Tyr Gln Gln Lys Pro Gly Lys Gly Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65              70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105
```

```
<210> SEQ ID NO 459
<211> LENGTH: 95
<212> TYPE: PRT
<213> ORGANISM: Homo sapiens

<400> SEQUENCE: 459
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Gln Lys Tyr Asn Ser Ala Pro
                85                  90                  95
```

```
<210> SEQ ID NO 460
<211> LENGTH: 107
<212> TYPE: PRT
<213> ORGANISM: Homo sapiens

<400> SEQUENCE: 460
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
                20                  25                  30

Leu Ala Trp Tyr Gln Gln Lys Pro Gly Lys Val Pro Lys Leu Leu Ile
```

-continued

```
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Tyr Ser Ala Pro Leu
                85                  90                  95

Thr Phe Gly Gly Gly Thr Lys Val Glu Ile Lys
            100                 105
```

```
<210> SEQ ID NO 461
<211> LENGTH: 95
<212> TYPE: PRT
<213> ORGANISM: Homo sapiens

<400> SEQUENCE: 461

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95
```

```
<210> SEQ ID NO 462
<211> LENGTH: 107
<212> TYPE: PRT
<213> ORGANISM: Homo sapiens

<400> SEQUENCE: 462

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Ser Leu Gly Ser Tyr
                20                  25                  30

Leu Asn Trp Phe Gln Gln Lys Pro Gly Lys Ala Pro Lys Leu Leu Ile
            35                  40                  45

Tyr Gly Ala Phe Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Ser Tyr Thr Thr Pro Leu
                85                  90                  95

Thr Phe Gly Gly Gly Thr Lys Val Glu Ile Lys
            100                 105
```

```
<210> SEQ ID NO 463
<211> LENGTH: 100
<212> TYPE: PRT
<213> ORGANISM: Homo sapiens

<400> SEQUENCE: 463

Asp Ile Val Met Thr Gln Ser Pro Leu Ser Leu Pro Val Thr Pro Gly
1                   5                   10                  15
```

```
Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100
```

```
<210> SEQ ID NO 464
<211> LENGTH: 112
<212> TYPE: PRT
<213> ORGANISM: Homo sapiens

<400> SEQUENCE: 464

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Tyr Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

```
<210> SEQ ID NO 465
<211> LENGTH: 112
<212> TYPE: PRT
<213> ORGANISM: Homo sapiens

<400> SEQUENCE: 465

Asp Ile Val Met Thr Gln Ser Pro Leu Ser Leu Pro Val Thr Pro Glu
1               5                   10                  15

Glu Pro Ala Ser Ile Ser Cys Arg Ser Ser Gln Ser Leu Leu His Asn
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Ser Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

```
<210> SEQ ID NO 466
```

```
<211> LENGTH: 112
<212> TYPE: PRT
<213> ORGANISM: Homo sapiens

<400> SEQUENCE: 466

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Phe Thr Phe Gly Pro Gly Thr Lys Val Asp Ile Lys
            100                 105                 110

<210> SEQ ID NO 467
<211> LENGTH: 101
<212> TYPE: PRT
<213> ORGANISM: Homo sapiens

<400> SEQUENCE: 467

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro
            100

<210> SEQ ID NO 468
<211> LENGTH: 113
<212> TYPE: PRT
<213> ORGANISM: Homo sapiens

<400> SEQUENCE: 468

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ala Ser
            20                  25                  30

Ser Asn Asn Met Asn Tyr Leu Ala Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Pro Gly Thr Asp Phe Thr Leu Thr
65                  70                  75                  80
```

```
Ile Ser Ser Leu Gln Thr Glu Asp Val Ala Val Tyr Tyr Cys His Gln
                85              90              95

Tyr Tyr Ser Ile Pro Asn Thr Phe Gly Gln Gly Thr Lys Leu Glu Ile
            100             105             110

Lys

<210> SEQ ID NO 469
<211> LENGTH: 98
<212> TYPE: PRT
<213> ORGANISM: Homo sapiens

<400> SEQUENCE: 469

Gln Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Ser Ser Tyr
            20              25              30

Gly Met His Trp Val Arg Gln Ala Pro Gly Lys Gly Leu Glu Trp Val
        35              40              45

Ala Val Ile Trp Tyr Asp Gly Ser Asn Lys Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg

<210> SEQ ID NO 470
<211> LENGTH: 124
<212> TYPE: PRT
<213> ORGANISM: Homo sapiens

<400> SEQUENCE: 470

Gln Val Gln Leu Val Glu Ser Gly Gly Gly Val Val Gln Pro Gly Arg
1               5               10              15

Ser Leu Arg Leu Ser Cys Ala Val Ser Gly Phe Ile Phe Ser Asn Tyr
            20              25              30

Gly Met His Trp Val Arg Gln Ala Pro Gly Lys Gly Leu Glu Trp Val
        35              40              45

Ala Val Ile Trp Tyr Asp Gly Ser Lys Lys Phe His Thr Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Arg Asp Gln Gly Ile Thr Met Val Arg Gly Leu Ile Ile Leu Asp
            100             105             110

Tyr Trp Gly Gln Gly Thr Leu Val Thr Val Ser Ser
        115             120

<210> SEQ ID NO 471
<211> LENGTH: 116
<212> TYPE: PRT
<213> ORGANISM: Homo sapiens

<400> SEQUENCE: 471

Gln Val His Leu Val Glu Ser Gly Gly Gly Val Val Gln Pro Gly Arg
1               5               10              15
```

```
Ser Leu Arg Leu Ser Cys Ala Ala Ser Gly Phe Thr Phe Ser Ser Tyr
        20                  25                  30

Gly Met His Trp Val Arg Gln Gly Pro Gly Lys Gly Leu Glu Gly Val
        35                  40                  45

Ala Gly Ile Trp Phe Asp Gly Ser His Glu Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Glu Met Ser Ser Leu Arg Ala Gly Asp Thr Gly Ile Tyr Tyr Cys
                85                  90                  95

Ala Arg Gly Gly Asp Ile Leu Thr Pro Trp Gly Gln Gly Ser Leu Val
            100                 105                 110

Ile Val Ser Ser
        115

<210> SEQ ID NO 472
<211> LENGTH: 120
<212> TYPE: PRT
<213> ORGANISM: Homo sapiens

<400> SEQUENCE: 472

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
        20                  25                  30

Gly Ile His Trp Val Arg Gln Ala Pro Gly Lys Gly Leu Glu Trp Val
        35                  40                  45

Ala Leu Ile Trp Tyr Asp Glu Asn Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Asp Gly Ser Tyr Gln Gly Met Asp Val Trp Gly Gln
            100                 105                 110

Gly Thr Thr Val Thr Val Ser Ser
        115                 120

<210> SEQ ID NO 473
<211> LENGTH: 124
<212> TYPE: PRT
<213> ORGANISM: Homo sapiens

<400> SEQUENCE: 473

Gln Val Gln Leu Leu Glu Ser Gly Gly Gly Val Val Gln Pro Gly Arg
1               5                   10                  15

Ser Leu Arg Leu Ser Cys Ala Ala Ser Gly Ser Ser Phe Ser Thr Asp
        20                  25                  30

Val Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg Glu Gly Val Tyr Gln Thr Phe Met Tyr Pro Asp Ala Phe Asp
            100                 105                 110

Ile Trp Gly Gln Gly Thr Met Val Thr Val Ser Ser
        115                 120

<210> SEQ ID NO 474
<211> LENGTH: 124
<212> TYPE: PRT
<213> ORGANISM: Homo sapiens

<400> SEQUENCE: 474

Gln Val Gln Leu Val Glu Ser Gly Gly Val Val Gln Pro Gly Arg
1               5                   10                  15

Ser Leu Arg Leu Ser Cys Ala Ala Ser Gly Phe Asp Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Ala Val Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Thr Tyr Tyr Tyr Asp Ser Ser Gly Tyr Phe Phe Asp
            100                 105                 110

Tyr Trp Gly Gln Gly Thr Leu Val Thr Val Ser Ser
        115                 120

<210> SEQ ID NO 475
<211> LENGTH: 118
<212> TYPE: PRT
<213> ORGANISM: Homo sapiens

<400> SEQUENCE: 475

Leu Val Gln Leu Val Asp Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Trp Phe Asp Gly Ser Asn Lys Phe Tyr Ala Asp Ser Val
        50                  55                  60

Lys Gly Arg Phe Thr Ile Ser Arg Asp Asn Ser Lys Asn Thr Met Tyr
65                  70                  75                  80

Leu Gln Met His Ser Leu Gly Ala Glu Asp Thr Ala Glu Tyr Tyr Cys
                85                  90                  95

Ala Arg Gly Gly Ala Tyr Gly Leu Phe Asp Tyr Trp Gly Gln Gly Thr
            100                 105                 110

Leu Val Thr Val Ser Ser
        115

<210> SEQ ID NO 476
<211> LENGTH: 124
<212> TYPE: PRT
<213> ORGANISM: Homo sapiens

<400> SEQUENCE: 476

Gln Val Gln Leu Leu Glu Ser Gly Gly Gly Val Val Gln Pro Gly Arg
```

-continued

```
1               5                   10                  15

Ser Leu Arg Leu Ala Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ala Val Ile Trp His Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Met Tyr Gln Pro Leu Leu Tyr Pro Asp Ala Phe Asp
            100                 105                 110

Ile Trp Gly Gln Gly Thr Met Val Thr Val Ser Ser
            115                 120
```

<210> SEQ ID NO 477
<211> LENGTH: 131
<212> TYPE: PRT
<213> ORGANISM: Homo sapiens

<400> SEQUENCE: 477

```
Gln Val His Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Phe Asn Lys Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Ser Arg Ile Ser Asn Phe Asp Ile Leu Thr Gly Tyr Tyr His
            100                 105                 110

Tyr Tyr Tyr Tyr Gly Met Asp Val Trp Gly Gln Gly Thr Thr Val Thr
            115                 120                 125

Val Ser Ser
    130
```

<210> SEQ ID NO 478
<211> LENGTH: 130
<212> TYPE: PRT
<213> ORGANISM: Homo sapiens

<400> SEQUENCE: 478

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Glu Asn Asn Lys Tyr Tyr Ala Asp Ser Val
    50                  55                  60

Lys Gly Arg Phe Thr Ile Ser Arg Asp Asn Ser Lys Asn Thr Leu Tyr
```

```
65                    70                    75                    80

Leu Gln Met Asn Ser Leu Arg Ala Glu Asp Thr Ala Val Tyr Tyr Cys
                85                    90                    95

Thr Arg Glu Arg Ala Lys Tyr Tyr Gly Ser Gly Arg Arg Asp Tyr Tyr
                100                   105                   110

Tyr Tyr Tyr Gly Met Asp Val Trp Gly Gln Gly Thr Thr Val Thr Val
                115                   120                   125

Ser Ser
    130

<210> SEQ ID NO 479
<211> LENGTH: 123
<212> TYPE: PRT
<213> ORGANISM: Homo sapiens

<400> SEQUENCE: 479

Gln Val Gln Leu Val Glu Ser Gly Gly Gly Val Val Gln Pro Gly Lys
1                   5                     10                    15

Ser Leu Arg Leu Ser Cys Ala Ala Ser Gly Phe Thr Phe Ser Asn Tyr
                20                    25                    30

Gly Met His Trp Val Arg Gln Ala Pro Gly Lys Gly Leu Glu Trp Val
            35                    40                    45

Ser Phe Ile Trp Tyr Asp Gly Ser Asp Lys Gly Tyr Ala Asp Ser Val
        50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Val Tyr Phe Cys
                85                    90                    95

Ala Lys Thr Pro Phe Ala Ser Ser Trp Tyr Gly Asp Tyr Phe Asp Tyr
                100                   105                   110

Trp Gly Gln Gly Thr Leu Val Thr Val Ser Ser
            115                   120

<210> SEQ ID NO 480
<211> LENGTH: 121
<212> TYPE: PRT
<213> ORGANISM: Homo sapiens

<400> SEQUENCE: 480

Gln Val Tyr Leu Val Glu Ser Gly Gly Gly Val Val Gln Pro Gly Gly
1                   5                     10                    15

Ser Leu Arg Leu Ser Cys Ala Ala Ser Gly Phe Thr Phe Gly Tyr Tyr
                20                    25                    30

Gly Met His Trp Val Arg Gln Thr Pro Gly Lys Gly Leu Glu Trp Val
            35                    40                    45

Ala Val Ile Phe Tyr Asp Gly Ser Asn Lys Tyr Tyr Ala Asp Ser Ala
        50                    55                    60

Lys Gly Arg Phe Thr Ile Ser Arg Asp Asn Ser Lys Asn Ser Leu Ser
65                    70                    75                    80

Leu Gln Met Asn Ser Leu Arg Val Glu Asp Thr Ala Val Tyr Tyr Cys
                85                    90                    95

Ala Arg Gly Gly Ser Asn Arg Tyr Tyr Tyr Val Leu Asp Ala Trp Gly
                100                   105                   110

Gln Gly Val Ser Val Thr Val Ser Ser
            115                   120
```

```
<210> SEQ ID NO 481
<211> LENGTH: 130
<212> TYPE: PRT
<213> ORGANISM: Homo sapiens

<400> SEQUENCE: 481

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Glu Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Arg Ala Lys Tyr Tyr Gly Ser Gly Arg Arg Asp Tyr Tyr
                100                 105                 110

Tyr Tyr Tyr Gly Met Asp Val Trp Gly Gln Gly Thr Thr Val Thr Val
        115                 120                 125

Ser Ser
    130

<210> SEQ ID NO 482
<211> LENGTH: 124
<212> TYPE: PRT
<213> ORGANISM: Homo sapiens

<400> SEQUENCE: 482

Gln Val His Leu Val Glu Ser Gly Gly Gly Val Val Gln Pro Gly Arg
1               5                   10                  15

Ser Leu Arg Leu Ser Cys Ala Ala Ser Gly Phe Asp Phe Asn Asn Tyr
            20                  25                  30

Gly Met His Trp Val Arg Gln Ala Pro Gly Lys Gly Leu Glu Trp Val
        35                  40                  45

Ala Val Ile Trp Tyr Asp Ala Val Asn Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Thr Tyr Tyr Tyr Asp Ser Ser Gly Tyr Phe Phe Asp
                100                 105                 110

Cys Trp Gly Gln Gly Thr Leu Val Thr Val Ser Ser
        115                 120

<210> SEQ ID NO 483
<211> LENGTH: 121
<212> TYPE: PRT
<213> ORGANISM: Homo sapiens

<400> SEQUENCE: 483

Gln Val Gln Leu Val Glu Ser Gly Gly Gly Val Val Gln Pro Gly Arg
1               5                   10                  15

Ser Leu Arg Leu Ser Cys Val Ala Ser Gly Leu Thr Phe Ser Thr Tyr
            20                  25                  30
```

-continued

```
Ala Met His Trp Val Arg Gln Ala Pro Gly Lys Gly Leu Glu Trp Val
        35                  40                  45

Ala Val Ile Trp Asp Asp Gly Ile Asn Lys Asn Tyr Ala Asp Ser Val
    50                  55                  60

Lys Gly Arg Phe Thr Ile Ser Arg Asp Asn Ser Lys Lys Thr Leu Phe
65                  70                  75                  80

Leu Gln Met Asn Ser Leu Arg Ser Glu Asp Thr Ala Val Tyr Phe Cys
                85                  90                  95

Ala Arg Asp Arg Ile Pro Val Pro Gly Gly Leu Phe Asp Tyr Trp Gly
            100                 105                 110

Gln Gly Thr Leu Val Thr Val Ser Ser
        115                 120
```

<210> SEQ ID NO 484
<211> LENGTH: 98
<212> TYPE: PRT
<213> ORGANISM: Homo sapiens

<400> SEQUENCE: 484

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 485
<211> LENGTH: 124
<212> TYPE: PRT
<213> ORGANISM: Homo sapiens

<400> SEQUENCE: 485

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Arg Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Asp Asn Pro Tyr Tyr Ala Asp Ser Met
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Gly Gly Leu Leu Trp Phe Gly Asp Leu Leu Asp Pro Phe Asp
            100                 105                 110

Tyr Trp Gly Gln Gly Thr Leu Val Thr Val Ser Ser
        115                 120
```

<210> SEQ ID NO 486
<211> LENGTH: 122
<212> TYPE: PRT
<213> ORGANISM: Homo sapiens

<400> SEQUENCE: 486

Glu Val Lys Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Val Val Ser Gly Ser Gly Asp Tyr Thr Tyr Tyr Ala Asp Phe Val
    50                  55                  60

Lys Gly Arg Phe Thr Ile Ser Arg Asp Asn Ala Lys Asn Thr Leu Tyr
65                  70                  75                  80

Leu Gln Met Lys Ser Leu Arg Ala Glu Asp Thr Ala Ile Tyr Tyr Cys
                85                  90                  95

Ala Arg Thr Ile Val Trp Phe Gly Glu Leu Phe Pro Ser Asp Tyr Trp
            100                 105                 110

Gly Gln Gly Thr Leu Val Thr Val Ser Ser
            115                 120

<210> SEQ ID NO 487
<211> LENGTH: 112
<212> TYPE: PRT
<213> ORGANISM: Homo sapiens

<400> SEQUENCE: 487

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Val Ile Ser Gly Ser Gly Asp Tyr Thr Tyr Tyr Ala Asp Phe Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Ile Val Trp Phe Gly Glu Leu Phe Pro Ser Asp Tyr Trp
            100                 105                 110

<210> SEQ ID NO 488
<211> LENGTH: 123
<212> TYPE: PRT
<213> ORGANISM: Homo sapiens

<400> SEQUENCE: 488

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ile Thr Ser Tyr Ala Asp Ser Val

-continued

```
         50                55                60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Tyr Tyr Gly Ser Gly Ser Tyr Trp Tyr Leu Asp Leu
            100                 105                 110

Trp Gly Arg Gly Thr Leu Val Thr Val Ser Ser
        115                 120

<210> SEQ ID NO 489
<211> LENGTH: 119
<212> TYPE: PRT
<213> ORGANISM: Homo sapiens

<400> SEQUENCE: 489

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly Asn His Ile His Tyr Ala Asp Ser Val
    50                  55                  60

Lys Gly Arg Phe Thr Ile Ser Arg Glu Asn Ser Lys Ser Thr Leu Tyr
65                  70                  75                  80

Leu His Met Asn Ser Leu Arg Ala Glu Asp Thr Ala Val Tyr Tyr Cys
                85                  90                  95

Ala Lys Asp Gly Gly Leu Tyr Trp Tyr Phe Asp Leu Trp Gly Arg Gly
            100                 105                 110

Thr Leu Val Thr Val Ser Ser
        115

<210> SEQ ID NO 490
<211> LENGTH: 119
<212> TYPE: PRT
<213> ORGANISM: Homo sapiens

<400> SEQUENCE: 490

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Asn Trp Val Arg Gln Ala Pro Gly Lys Gly Leu Glu Trp Val
        35                  40                  45

Ser Gly Ile Ser Gly Ser Gly Asn His Ile His Tyr Ala Asp Ser Val
    50                  55                  60

Lys Gly Arg Phe Thr Ile Ser Arg Glu Asn Ser Lys Ser Thr Leu Tyr
65                  70                  75                  80

Leu His Met Asn Ser Leu Arg Ala Glu Asp Thr Ala Val Tyr Tyr Cys
                85                  90                  95

Ala Lys Asp Gly Gly Leu Tyr Trp Tyr Phe Asp Leu Trp Gly Arg Gly
            100                 105                 110

Thr Leu Val Thr Val Ser Ser
        115
```

-continued

<210> SEQ ID NO 491
<211> LENGTH: 122
<212> TYPE: PRT
<213> ORGANISM: Homo sapiens

<400> SEQUENCE: 491

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Asn Val Phe Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Asn Asn Asp Tyr Ala
    50                  55                  60

Val Ser Val Lys Gly Arg Ile Thr Ile Asn Pro Asp Thr Tyr Lys Asn
65                  70                  75                  80

Gln Phe Ser Leu Gln Leu Asn Pro Val Thr Pro Glu Asp Thr Ala Val
                85                  90                  95

Tyr Phe Cys Ala Arg Val Pro Met Asn Arg Gly Gly Met Asp Val Trp
            100                 105                 110

Gly Gln Gly Thr Thr Val Thr Val Ser Ser
        115                 120

<210> SEQ ID NO 492
<211> LENGTH: 100
<212> TYPE: PRT
<213> ORGANISM: Homo sapiens

<400> SEQUENCE: 492

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 493
<211> LENGTH: 129
<212> TYPE: PRT
<213> ORGANISM: Homo sapiens

<400> SEQUENCE: 493

Glu Val Gln Leu Val Glu Ser Gly Gly Gly Leu Val Lys Pro Gly Gly
1               5                   10                  15

Ser Leu Arg Leu Ser Cys Ser Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Thr Lys Thr Asp Gly Gly Thr Thr Asp Tyr Ala Ala
    50                  55                  60

```
Pro Val Lys Gly Arg Phe Thr Ile Ser Arg Asp Asp Ser Lys Asn Thr
65              70              75              80

Met Tyr Leu Gln Met Asn Ser Leu Lys Thr Glu Asp Thr Ala Leu Tyr
                85              90              95

Tyr Cys Ser Thr Pro Gly Ile Ala Ala Ala Gly Thr Trp Tyr Tyr Tyr
            100             105             110

Trp Tyr Gly Met Asp Val Trp Gly Gln Gly Thr Thr Val Thr Val Ser
        115             120             125

Ser

<210> SEQ ID NO 494
<211> LENGTH: 98
<212> TYPE: PRT
<213> ORGANISM: Homo sapiens

<400> SEQUENCE: 494

Gln Val Gln Leu Val Gln Ser Gly Ala Glu Val Lys Lys Pro Gly Ser
1               5               10              15

Ser Val Lys Val Ser Cys Lys Ala Ser Gly Gly Thr Phe Ser Ser Tyr
            20              25              30

Ala Ile Ser Trp Val Arg Gln Ala Pro Gly Gln Gly Leu Glu Trp Met
        35              40              45

Gly Gly Ile Ile Pro Ile Phe Gly Thr Ala Asn Tyr Ala Gln Lys Phe
    50              55              60

Gln Gly Arg Val Thr Ile Thr Ala Asp Lys Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg

<210> SEQ ID NO 495
<211> LENGTH: 122
<212> TYPE: PRT
<213> ORGANISM: Homo sapiens

<400> SEQUENCE: 495

Gln Val Gln Leu Val Gln Ser Gly Ala Glu Val Lys Lys Pro Gly Ser
1               5               10              15

Ser Val Lys Val Ser Cys Lys Gly Ser Gly Gly Thr Phe Ser Ser Tyr
            20              25              30

Ala Ile Ser Trp Val Arg Gln Ala Pro Gly Gln Gly Leu Glu Trp Met
        35              40              45

Gly Gly Ile Ile Pro Phe Phe Gly Ala Thr Asn Tyr Ala Gln Lys Phe
    50              55              60

Gln Gly Arg Val Thr Ile Thr Ala Asp Lys Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Tyr Asn Trp Asn Asp Asn Tyr Tyr Tyr Gly Met Asp Val Trp
            100             105             110

Gly Gln Gly Thr Thr Val Thr Val Ser Ser
        115             120

<210> SEQ ID NO 496
<211> LENGTH: 98
<212> TYPE: PRT
```

<213> ORGANISM: Homo sapiens

<400> SEQUENCE: 496

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg
```

<210> SEQ ID NO 497
<211> LENGTH: 122
<212> TYPE: PRT
<213> ORGANISM: Homo sapiens

<400> SEQUENCE: 497

```
Gln Val Gln Leu Gln Glu Ser Gly Pro Gly Leu Val Lys Pro Ser Glu
1               5                   10                  15

Thr Leu Ser Leu Thr Cys Asp Val Ser Gly His Ser Ile Arg Ser Gly
            20                  25                  30

Tyr Tyr Trp Gly Trp Ile Arg Gln Ser Pro Gly Lys Gly Leu Ile Trp
        35                  40                  45

Ile Gly Ser Phe Phe Tyr Ser Gly Asn Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Asn Leu Ser Ser Val Thr Ala Ala Asp Thr Ala Val Tyr Tyr Cys
                85                  90                  95

Ala Gly Arg Gly His Asp Ser Gly Glu Tyr Val Ala Phe Asp Phe Trp
                100                 105                 110

Gly Gln Gly Thr Met Ile Thr Val Ser Ser
        115                 120
```

<210> SEQ ID NO 498
<211> LENGTH: 97
<212> TYPE: PRT
<213> ORGANISM: Homo sapiens

<400> SEQUENCE: 498

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

Lys Leu Ser Ser Val Thr Ala Ala Asp Thr Ala Val Tyr Tyr Cys Ala
                85                  90                  95

Arg

<210> SEQ ID NO 499
<211> LENGTH: 119
<212> TYPE: PRT
<213> ORGANISM: Homo sapiens

<400> SEQUENCE: 499

Gln Val Gln Leu Arg Gln Trp Gly Ala Gly Leu Leu Gln Pro Ser Glu
1               5                   10                  15

Thr Leu Ser Leu Thr Cys Ala Val Tyr Gly Glu Ser Phe Ser Gly Tyr
                20                  25                  30

Phe Trp Thr Trp Ile Arg Gln Ala Pro Gly Lys Gly Leu Glu Trp Ile
            35                  40                  45

Gly Glu Val Asp His Val Gly Ser Thr Asn Tyr Lys Pro Ser Leu Glu
        50                  55                  60

Ser Leu Ile Thr Ile Ser Val Asp Thr Ser Lys Asn Gln Phe Ser Leu
65                  70                  75                  80

Lys Leu Thr Ser Val Thr Ala Ala Asp Thr Ala Val Tyr Phe Cys Ala
                85                  90                  95

Arg Thr Gly Thr Val Phe Gly Thr Ser Phe Asp Tyr Trp Gly Gln Gly
                100                 105                 110

Thr Leu Val Thr Val Ser Ser
            115

<210> SEQ ID NO 500
<211> LENGTH: 6
<212> TYPE: PRT
<213> ORGANISM: Homo sapiens

<400> SEQUENCE: 500

Gln Ser Val Ser Ser Asn
1               5

<210> SEQ ID NO 501
<211> LENGTH: 3
<212> TYPE: PRT
<213> ORGANISM: Homo sapiens

<400> SEQUENCE: 501

Gly Ala Ser
1

<210> SEQ ID NO 502
<211> LENGTH: 10
<212> TYPE: PRT
<213> ORGANISM: Homo sapiens

<400> SEQUENCE: 502

Gln His Tyr Asn Asn Trp Pro Leu Thr Phe
1               5                   10

<210> SEQ ID NO 503
<211> LENGTH: 8
<212> TYPE: PRT
<213> ORGANISM: Homo sapiens

<400> SEQUENCE: 503

Gly Phe Thr Phe Arg Ser Tyr Ala

-continued 1                    5

<210> SEQ ID NO 504
<211> LENGTH: 8
<212> TYPE: PRT
<213> ORGANISM: Homo sapiens

<400> SEQUENCE: 504

Ile Ser Gly Ser Gly Gly Ile Thr
1                    5

<210> SEQ ID NO 505
<211> LENGTH: 16
<212> TYPE: PRT
<213> ORGANISM: Homo sapiens

<400> SEQUENCE: 505

Ala Arg Glu Asp Tyr Tyr Gly Ser Gly Ser Tyr Trp Tyr Leu Asp Leu
1                    5                        10                        15

<210> SEQ ID NO 506
<211> LENGTH: 6
<212> TYPE: PRT
<213> ORGANISM: Homo sapiens

<400> SEQUENCE: 506

Gln Ser Val Ser Asn Asn
1                    5

<210> SEQ ID NO 507
<211> LENGTH: 3
<212> TYPE: PRT
<213> ORGANISM: Homo sapiens

<400> SEQUENCE: 507

Gly Ala Ser
1

<210> SEQ ID NO 508
<211> LENGTH: 10
<212> TYPE: PRT
<213> ORGANISM: Homo sapiens

<400> SEQUENCE: 508

Gln Gln Tyr Asn Asn Trp Pro Phe Thr Phe
1                    5                        10

<210> SEQ ID NO 509
<211> LENGTH: 8
<212> TYPE: PRT
<213> ORGANISM: Homo sapiens

<400> SEQUENCE: 509

Gly Phe Thr Phe Ser Ser Tyr Ala
1                    5

<210> SEQ ID NO 510
<211> LENGTH: 8
<212> TYPE: PRT
<213> ORGANISM: Homo sapiens

<400> SEQUENCE: 510

Val Ser Gly Ser Gly Asp Tyr Thr
1                    5

<210> SEQ ID NO 511
<211> LENGTH: 15
<212> TYPE: PRT
<213> ORGANISM: Homo sapiens

<400> SEQUENCE: 511

Ala Arg Thr Ile Val Trp Phe Gly Glu Leu Phe Pro Ser Asp Tyr
1               5                   10                  15

<210> SEQ ID NO 512
<211> LENGTH: 6
<212> TYPE: PRT
<213> ORGANISM: Homo sapiens

<400> SEQUENCE: 512

Gln Thr Ile Ser Ser Tyr
1               5

<210> SEQ ID NO 513
<211> LENGTH: 3
<212> TYPE: PRT
<213> ORGANISM: Homo sapiens

<400> SEQUENCE: 513

Gly Ala Ser
1

<210> SEQ ID NO 514
<211> LENGTH: 10
<212> TYPE: PRT
<213> ORGANISM: Homo sapiens

<400> SEQUENCE: 514

Gln Gln Tyr Asn Asn Trp Pro Leu Thr Phe
1               5                   10

<210> SEQ ID NO 515
<211> LENGTH: 8
<212> TYPE: PRT
<213> ORGANISM: Homo sapiens

<400> SEQUENCE: 515

Gly Glu Ser Phe Ser Gly Tyr Phe
1               5

<210> SEQ ID NO 516
<211> LENGTH: 7
<212> TYPE: PRT
<213> ORGANISM: Homo sapiens

<400> SEQUENCE: 516

Val Asp His Val Gly Ser Thr
1               5

<210> SEQ ID NO 517
<211> LENGTH: 13
<212> TYPE: PRT
<213> ORGANISM: Homo sapiens

<400> SEQUENCE: 517

Ala Arg Thr Gly Thr Val Phe Gly Thr Ser Phe Asp Tyr
1               5                   10

<210> SEQ ID NO 518

-continued

```
<211> LENGTH: 6
<212> TYPE: PRT
<213> ORGANISM: Homo sapiens

<400> SEQUENCE: 518

Gln Thr Val Asn Ser Asn
1               5

<210> SEQ ID NO 519
<211> LENGTH: 3
<212> TYPE: PRT
<213> ORGANISM: Homo sapiens

<400> SEQUENCE: 519

Gly Ala Ser
1

<210> SEQ ID NO 520
<211> LENGTH: 10
<212> TYPE: PRT
<213> ORGANISM: Homo sapiens

<400> SEQUENCE: 520

Gln Gln Tyr Asn Asn Trp Pro Leu Thr Phe
1               5                   10

<210> SEQ ID NO 521
<211> LENGTH: 9
<212> TYPE: PRT
<213> ORGANISM: Homo sapiens

<400> SEQUENCE: 521

Gly His Ser Ile Arg Ser Gly Tyr Tyr
1               5

<210> SEQ ID NO 522
<211> LENGTH: 7
<212> TYPE: PRT
<213> ORGANISM: Homo sapiens

<400> SEQUENCE: 522

Phe Phe Tyr Ser Gly Asn Thr
1               5

<210> SEQ ID NO 523
<211> LENGTH: 15
<212> TYPE: PRT
<213> ORGANISM: Homo sapiens

<400> SEQUENCE: 523

Ala Gly Arg Gly His Asp Ser Gly Glu Tyr Val Ala Phe Asp Phe
1               5                   10                  15

<210> SEQ ID NO 524
<211> LENGTH: 6
<212> TYPE: PRT
<213> ORGANISM: Homo sapiens

<400> SEQUENCE: 524

Gln Ser Val Ser Ser Asn
1               5

<210> SEQ ID NO 525
<211> LENGTH: 3
<212> TYPE: PRT
```

<213> ORGANISM: Homo sapiens

<400> SEQUENCE: 525

Gly Ala Ser
1

<210> SEQ ID NO 526
<211> LENGTH: 10
<212> TYPE: PRT
<213> ORGANISM: Homo sapiens

<400> SEQUENCE: 526

Gln Gln Tyr Asn Asn Trp Pro Ile Thr Phe
1               5                   10

<210> SEQ ID NO 527
<211> LENGTH: 8
<212> TYPE: PRT
<213> ORGANISM: Homo sapiens

<400> SEQUENCE: 527

Gly Phe Asp Phe Asn Asn Tyr Gly
1               5

<210> SEQ ID NO 528
<211> LENGTH: 8
<212> TYPE: PRT
<213> ORGANISM: Homo sapiens

<400> SEQUENCE: 528

Ile Trp Tyr Asp Ala Val Asn Lys
1               5

<210> SEQ ID NO 529
<211> LENGTH: 17
<212> TYPE: PRT
<213> ORGANISM: Homo sapiens

<400> SEQUENCE: 529

Ala Arg Asp Gln Thr Tyr Tyr Tyr Asp Ser Ser Gly Tyr Phe Phe Asp
1               5                   10                  15

Cys

<210> SEQ ID NO 530
<211> LENGTH: 6
<212> TYPE: PRT
<213> ORGANISM: Homo sapiens

<400> SEQUENCE: 530

Gln Ser Val Ser Ser Asn
1               5

<210> SEQ ID NO 531
<211> LENGTH: 3
<212> TYPE: PRT
<213> ORGANISM: Homo sapiens

<400> SEQUENCE: 531

Arg Ala Ser
1

<210> SEQ ID NO 532
<211> LENGTH: 10
<212> TYPE: PRT

<213> ORGANISM: Homo sapiens

<400> SEQUENCE: 532

Gln Gln Tyr Asn Ser Trp Pro Ile Thr Phe
1               5                   10

<210> SEQ ID NO 533
<211> LENGTH: 8
<212> TYPE: PRT
<213> ORGANISM: Homo sapiens

<400> SEQUENCE: 533

Gly Phe Thr Phe Ser Ser Tyr Gly
1               5

<210> SEQ ID NO 534
<211> LENGTH: 8
<212> TYPE: PRT
<213> ORGANISM: Homo sapiens

<400> SEQUENCE: 534

Ile Trp Phe Asp Gly Ser His Glu
1               5

<210> SEQ ID NO 535
<211> LENGTH: 9
<212> TYPE: PRT
<213> ORGANISM: Homo sapiens

<400> SEQUENCE: 535

Ala Arg Gly Gly Asp Ile Leu Thr Pro
1               5

<210> SEQ ID NO 536
<211> LENGTH: 6
<212> TYPE: PRT
<213> ORGANISM: Homo sapiens

<400> SEQUENCE: 536

Gln Ser Val Ser Ser Asn
1               5

<210> SEQ ID NO 537
<211> LENGTH: 3
<212> TYPE: PRT
<213> ORGANISM: Homo sapiens

<400> SEQUENCE: 537

Gly Ala Ser
1

<210> SEQ ID NO 538
<211> LENGTH: 10
<212> TYPE: PRT
<213> ORGANISM: Homo sapiens

<400> SEQUENCE: 538

Gln Gln Tyr Asn Asn Trp Pro Phe Thr Phe
1               5                   10

<210> SEQ ID NO 539
<211> LENGTH: 8
<212> TYPE: PRT
<213> ORGANISM: Homo sapiens -continued

```
<400> SEQUENCE: 539

Gly Leu Thr Phe Ser Thr Tyr Ala
1               5

<210> SEQ ID NO 540
<211> LENGTH: 8
<212> TYPE: PRT
<213> ORGANISM: Homo sapiens

<400> SEQUENCE: 540

Ile Trp Asp Asp Gly Ile Asn Lys
1               5

<210> SEQ ID NO 541
<211> LENGTH: 14
<212> TYPE: PRT
<213> ORGANISM: Homo sapiens

<400> SEQUENCE: 541

Ala Arg Asp Arg Ile Pro Val Pro Gly Gly Leu Phe Asp Tyr
1               5                   10

<210> SEQ ID NO 542
<211> LENGTH: 6
<212> TYPE: PRT
<213> ORGANISM: Homo sapiens

<400> SEQUENCE: 542

Gln Ser Val Ser Ser Asn
1               5

<210> SEQ ID NO 543
<211> LENGTH: 3
<212> TYPE: PRT
<213> ORGANISM: Homo sapiens

<400> SEQUENCE: 543

Gly Ala Ser
1

<210> SEQ ID NO 544
<211> LENGTH: 9
<212> TYPE: PRT
<213> ORGANISM: Homo sapiens

<400> SEQUENCE: 544

Gln Gln Phe Asn Asn Trp Ile Thr Phe
1               5

<210> SEQ ID NO 545
<211> LENGTH: 8
<212> TYPE: PRT
<213> ORGANISM: Homo sapiens

<400> SEQUENCE: 545

Gly Phe Thr Phe Ser Ile Tyr Ala
1               5

<210> SEQ ID NO 546
<211> LENGTH: 8
<212> TYPE: PRT
<213> ORGANISM: Homo sapiens

<400> SEQUENCE: 546
```

-continued

```
Ile Ser Gly Ser Gly Asn His Ile
1               5

<210> SEQ ID NO 547
<211> LENGTH: 12
<212> TYPE: PRT
<213> ORGANISM: Homo sapiens

<400> SEQUENCE: 547

Ala Lys Asp Gly Gly Leu Tyr Trp Tyr Phe Asp Leu
1               5                   10

<210> SEQ ID NO 548
<211> LENGTH: 6
<212> TYPE: PRT
<213> ORGANISM: Homo sapiens

<400> SEQUENCE: 548

Gln Ser Ile Ser Ser Asn
1               5

<210> SEQ ID NO 549
<211> LENGTH: 3
<212> TYPE: PRT
<213> ORGANISM: Homo sapiens

<400> SEQUENCE: 549

Gly Ala Ser
1

<210> SEQ ID NO 550
<211> LENGTH: 11
<212> TYPE: PRT
<213> ORGANISM: Homo sapiens

<400> SEQUENCE: 550

Gln Gln Tyr Asn Asn Trp Pro Pro Tyr Thr Phe
1               5                   10

<210> SEQ ID NO 551
<211> LENGTH: 8
<212> TYPE: PRT
<213> ORGANISM: Homo sapiens

<400> SEQUENCE: 551

Gly Phe Thr Phe Ser Asn Tyr Gly
1               5

<210> SEQ ID NO 552
<211> LENGTH: 8
<212> TYPE: PRT
<213> ORGANISM: Homo sapiens

<400> SEQUENCE: 552

Ile Trp Tyr Asp Gly Ser Asp Lys
1               5

<210> SEQ ID NO 553
<211> LENGTH: 16
<212> TYPE: PRT
<213> ORGANISM: Homo sapiens

<400> SEQUENCE: 553

Ala Lys Thr Pro Phe Ala Ser Ser Trp Tyr Gly Asp Tyr Phe Asp Tyr
1               5                   10                  15
```

```
<210> SEQ ID NO 554
<211> LENGTH: 6
<212> TYPE: PRT
<213> ORGANISM: Homo sapiens

<400> SEQUENCE: 554

Gln Ser Val Ile Ser Ser
1               5

<210> SEQ ID NO 555
<211> LENGTH: 3
<212> TYPE: PRT
<213> ORGANISM: Homo sapiens

<400> SEQUENCE: 555

Gly Ala Ser
1

<210> SEQ ID NO 556
<211> LENGTH: 10
<212> TYPE: PRT
<213> ORGANISM: Homo sapiens

<400> SEQUENCE: 556

Gln Gln Tyr His Tyr Trp Pro Phe Thr Phe
1               5                   10

<210> SEQ ID NO 557
<211> LENGTH: 8
<212> TYPE: PRT
<213> ORGANISM: Homo sapiens

<400> SEQUENCE: 557

Gly Phe Asp Phe Ser Asn Tyr Gly
1               5

<210> SEQ ID NO 558
<211> LENGTH: 8
<212> TYPE: PRT
<213> ORGANISM: Homo sapiens

<400> SEQUENCE: 558

Ile Trp Tyr Asp Ala Val Asn Lys
1               5

<210> SEQ ID NO 559
<211> LENGTH: 17
<212> TYPE: PRT
<213> ORGANISM: Homo sapiens

<400> SEQUENCE: 559

Ala Arg Asp Gln Thr Tyr Tyr Tyr Asp Ser Ser Gly Tyr Phe Phe Asp
1               5                   10                  15

Tyr

<210> SEQ ID NO 560
<211> LENGTH: 6
<212> TYPE: PRT
<213> ORGANISM: Homo sapiens

<400> SEQUENCE: 560

Gln Ser Val Ser Ser Asn
1               5
```

```
<210> SEQ ID NO 561
<211> LENGTH: 3
<212> TYPE: PRT
<213> ORGANISM: Homo sapiens

<400> SEQUENCE: 561

Gly Ala Ser
1

<210> SEQ ID NO 562
<211> LENGTH: 10
<212> TYPE: PRT
<213> ORGANISM: Homo sapiens

<400> SEQUENCE: 562

Gln Gln Tyr Asn Asn Trp Pro Phe Thr Phe
1               5                   10

<210> SEQ ID NO 563
<211> LENGTH: 8
<212> TYPE: PRT
<213> ORGANISM: Homo sapiens

<400> SEQUENCE: 563

Gly Phe Thr Phe Ser Ser Tyr Ala
1               5

<210> SEQ ID NO 564
<211> LENGTH: 8
<212> TYPE: PRT
<213> ORGANISM: Homo sapiens

<400> SEQUENCE: 564

Ile Ser Gly Ser Gly Asp Tyr Thr
1               5

<210> SEQ ID NO 565
<211> LENGTH: 15
<212> TYPE: PRT
<213> ORGANISM: Homo sapiens

<400> SEQUENCE: 565

Ala Arg Thr Ile Val Trp Phe Gly Glu Leu Phe Pro Ser Asp Tyr
1               5                   10                  15

<210> SEQ ID NO 566
<211> LENGTH: 6
<212> TYPE: PRT
<213> ORGANISM: Homo sapiens

<400> SEQUENCE: 566

Gln Ser Ile Arg Ser Asn
1               5

<210> SEQ ID NO 567
<211> LENGTH: 3
<212> TYPE: PRT
<213> ORGANISM: Homo sapiens

<400> SEQUENCE: 567

Gly Ala Ser
1
```

```
<210> SEQ ID NO 568
<211> LENGTH: 10
<212> TYPE: PRT
<213> ORGANISM: Homo sapiens

<400> SEQUENCE: 568

Gln Gln Tyr Asn Asn Trp Pro Leu Thr Phe
1               5                   10

<210> SEQ ID NO 569
<211> LENGTH: 8
<212> TYPE: PRT
<213> ORGANISM: Homo sapiens

<400> SEQUENCE: 569

Gly Phe Thr Phe Ser Ser Tyr Gly
1               5

<210> SEQ ID NO 570
<211> LENGTH: 8
<212> TYPE: PRT
<213> ORGANISM: Homo sapiens

<400> SEQUENCE: 570

Ile Trp Tyr Asp Glu Asn Asn Lys
1               5

<210> SEQ ID NO 571
<211> LENGTH: 13
<212> TYPE: PRT
<213> ORGANISM: Homo sapiens

<400> SEQUENCE: 571

Ala Arg Glu Gly Asp Gly Ser Tyr Gln Gly Met Asp Val
1               5                   10

<210> SEQ ID NO 572
<211> LENGTH: 6
<212> TYPE: PRT
<213> ORGANISM: Homo sapiens

<400> SEQUENCE: 572

Gln Ser Val Ser Ser Ser
1               5

<210> SEQ ID NO 573
<211> LENGTH: 3
<212> TYPE: PRT
<213> ORGANISM: Homo sapiens

<400> SEQUENCE: 573

Asp Thr Ser
1

<210> SEQ ID NO 574
<211> LENGTH: 7
<212> TYPE: PRT
<213> ORGANISM: Homo sapiens

<400> SEQUENCE: 574

Gln Gln Arg Ser Asn Thr Phe
1               5

<210> SEQ ID NO 575
<211> LENGTH: 8
```

<212> TYPE: PRT
<213> ORGANISM: Homo sapiens

<400> SEQUENCE: 575

Gly Phe Thr Phe Ser Ser Tyr Gly
1               5

<210> SEQ ID NO 576
<211> LENGTH: 8
<212> TYPE: PRT
<213> ORGANISM: Homo sapiens

<400> SEQUENCE: 576

Ile Trp Tyr Asp Gly Phe Asn Lys
1               5

<210> SEQ ID NO 577
<211> LENGTH: 24
<212> TYPE: PRT
<213> ORGANISM: Homo sapiens

<400> SEQUENCE: 577

Ala Arg Ser Arg Ile Ser Asn Phe Asp Ile Leu Thr Gly Tyr Tyr His
1               5                   10                  15

Tyr Tyr Tyr Tyr Gly Met Asp Val
            20

<210> SEQ ID NO 578
<211> LENGTH: 6
<212> TYPE: PRT
<213> ORGANISM: Homo sapiens

<400> SEQUENCE: 578

Gln Ser Ile Ser Thr Trp
1               5

<210> SEQ ID NO 579
<211> LENGTH: 3
<212> TYPE: PRT
<213> ORGANISM: Homo sapiens

<400> SEQUENCE: 579

Lys Ala Ser
1

<210> SEQ ID NO 580
<211> LENGTH: 11
<212> TYPE: PRT
<213> ORGANISM: Homo sapiens

<400> SEQUENCE: 580

Gln Gln Tyr Lys Thr Tyr Ser Pro Phe Ser Phe
1               5                   10

<210> SEQ ID NO 581
<211> LENGTH: 8
<212> TYPE: PRT
<213> ORGANISM: Homo sapiens

<400> SEQUENCE: 581

Gly Ser Ser Phe Ser Thr Asp Val
1               5

<210> SEQ ID NO 582

```
<211> LENGTH: 8
<212> TYPE: PRT
<213> ORGANISM: Homo sapiens

<400> SEQUENCE: 582

Ile Trp Tyr Asp Gly Ser Asn Lys
1               5

<210> SEQ ID NO 583
<211> LENGTH: 17
<212> TYPE: PRT
<213> ORGANISM: Homo sapiens

<400> SEQUENCE: 583

Ala Arg Glu Gly Val Tyr Gln Thr Phe Met Tyr Pro Asp Ala Phe Asp
1               5                   10                  15

Ile

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587
<211> LENGTH: 8
<212> TYPE: PRT
<213> ORGANISM: Homo sapiens

<400> SEQUENCE: 587

Gly Phe Thr Phe Ser Ile Tyr Ala
1               5

<210> SEQ ID NO 588
<211> LENGTH: 8
<212> TYPE: PRT
<213> ORGANISM: Homo sapiens

<400> SEQUENCE: 588

Ile Ser Gly Ser Gly Asn His Ile
1               5

<210> SEQ ID NO 589
<211> LENGTH: 12
<212> TYPE: PRT
<213> ORGANISM: Homo sapiens

<400> SEQUENCE: 589

Ala Lys Asp Gly Gly Leu Tyr Trp Tyr Phe Asp Leu
1               5                   10

<210> SEQ ID NO 590
<211> LENGTH: 6
```

```
<212> TYPE: PRT
<213> ORGANISM: Homo sapiens

<400> SEQUENCE: 590

Gln Ser Ile Ser Ser Trp
1               5

<210> SEQ ID NO 591
<211> LENGTH: 3
<212> TYPE: PRT
<213> ORGANISM: Homo sapiens

<400> SEQUENCE: 591

Lys Ala Ser
1

<210> SEQ ID NO 592
<211> LENGTH: 11
<212> TYPE: PRT
<213> ORGANISM: Homo sapiens

<400> SEQUENCE: 592

Gln Gln Tyr Lys Ser Tyr Ser Pro Phe Ser Phe
1               5                   10

<210> SEQ ID NO 593
<211> LENGTH: 8
<212> TYPE: PRT
<213> ORGANISM: Homo sapiens

<400> SEQUENCE: 593

Gly Phe Thr Phe Ser Ser Tyr Val
1               5

<210> SEQ ID NO 594
<211> LENGTH: 8
<212> TYPE: PRT
<213> ORGANISM: Homo sapiens

<400> SEQUENCE: 594

Ile Trp His Asp Gly Ser Asn Lys
1               5

<210> SEQ ID NO 595
<211> LENGTH: 17
<212> TYPE: PRT
<213> ORGANISM: Homo sapiens

<400> SEQUENCE: 595

Ala Arg Glu Gly Met Tyr Gln Pro Leu Leu Tyr Pro Asp Ala Phe Asp
1               5                   10                  15

Ile

<210> SEQ ID NO 596
<211> LENGTH: 6
<212> TYPE: PRT
<213> ORGANISM: Homo sapiens

<400> SEQUENCE: 596

Gln Gly Ile Ser Ser Tyr
1               5

<210> SEQ ID NO 597
<211> LENGTH: 3
```

-continued

```
<212> TYPE: PRT
<213> ORGANISM: Homo sapiens

<400> SEQUENCE: 597

Ala Ala Ser
1

<210> SEQ ID NO 598
<211> LENGTH: 10
<212> TYPE: PRT
<213> ORGANISM: Homo sapiens

<400> SEQUENCE: 598

Gln Gln Leu Asn Ser Tyr Pro Leu Thr Phe
1               5               10

<210> SEQ ID NO 599
<211> LENGTH: 8
<212> TYPE: PRT
<213> ORGANISM: Homo sapiens

<400> SEQUENCE: 599

Gly Phe Thr Phe Ser Ile Tyr Ala
1               5

<210> SEQ ID NO 600
<211> LENGTH: 8
<212> TYPE: PRT
<213> ORGANISM: Homo sapiens

<400> SEQUENCE: 600

Ile Ser Gly Ser Gly Asn His Ile
1               5

<210> SEQ ID NO 601
<211> LENGTH: 12
<212> TYPE: PRT
<213> ORGANISM: Homo sapiens

<400> SEQUENCE: 601

Ala Lys Asp Gly Gly Leu Tyr Trp Tyr Phe Asp Leu
1               5               10

<210> SEQ ID NO 602
<211> LENGTH: 6
<212> TYPE: PRT
<213> ORGANISM: Homo sapiens

<400> SEQUENCE: 602

Gln Asp Ile Ser Ser Tyr
1               5

<210> SEQ ID NO 603
<211> LENGTH: 3
<212> TYPE: PRT
<213> ORGANISM: Homo sapiens

<400> SEQUENCE: 603

Gly Ala Ser
1

<210> SEQ ID NO 604
<211> LENGTH: 10
<212> TYPE: PRT
<213> ORGANISM: Homo sapiens
```

-continued

<400> SEQUENCE: 604

Gln Gln Leu Asn Ser Tyr Pro Tyr Thr Phe
1               5                   10

<210> SEQ ID NO 605
<211> LENGTH: 8
<212> TYPE: PRT
<213> ORGANISM: Homo sapiens

<400> SEQUENCE: 605

Gly Phe Thr Phe Ser Ser Tyr Gly
1               5

<210> SEQ ID NO 606
<211> LENGTH: 8
<212> TYPE: PRT
<213> ORGANISM: Homo sapiens

<400> SEQUENCE: 606

Ile Trp Tyr Asp Glu Asn Asn Lys
1               5

<210> SEQ ID NO 607
<211> LENGTH: 23
<212> TYPE: PRT
<213> ORGANISM: Homo sapiens

<400> SEQUENCE: 607

Thr Arg Glu Arg Ala Lys Tyr Tyr Gly Ser Gly Arg Arg Asp Tyr Tyr
1               5                   10                  15

Tyr Tyr Tyr Gly Met Asp Val
            20

<210> SEQ ID NO 608
<211> LENGTH: 6
<212> TYPE: PRT
<213> ORGANISM: Homo sapiens

<400> SEQUENCE: 608

Gln Asp Ile Ser Ser Tyr
1               5

<210> SEQ ID NO 609
<211> LENGTH: 3
<212> TYPE: PRT
<213> ORGANISM: Homo sapiens

<400> SEQUENCE: 609

Gly Ala Ser
1

<210> SEQ ID NO 610
<211> LENGTH: 10
<212> TYPE: PRT
<213> ORGANISM: Homo sapiens

<400> SEQUENCE: 610

Gln Gln Leu Asn Ser Tyr Pro Tyr Thr Phe
1               5                   10

<210> SEQ ID NO 611
<211> LENGTH: 8
<212> TYPE: PRT

```
<213> ORGANISM: Homo sapiens

<400> SEQUENCE: 611

Gly Phe Thr Phe Ser Ser Tyr Gly
1               5

<210> SEQ ID NO 612
<211> LENGTH: 8
<212> TYPE: PRT
<213> ORGANISM: Homo sapiens

<400> SEQUENCE: 612

Ile Trp Tyr Asp Glu Asn Asn Lys
1               5

<210> SEQ ID NO 613
<211> LENGTH: 23
<212> TYPE: PRT
<213> ORGANISM: Homo sapiens

<400> SEQUENCE: 613

Thr Arg Glu Arg Ala Lys Tyr Tyr Gly Ser Gly Arg Arg Asp Tyr Tyr
1               5                   10                  15

Tyr Tyr Tyr Gly Met Asp Val
            20

<210> SEQ ID NO 614
<211> LENGTH: 6
<212> TYPE: PRT
<213> ORGANISM: Homo sapiens

<400> SEQUENCE: 614

Gln Gly Ile Ser Ser Tyr
1               5

<210> SEQ ID NO 615
<211> LENGTH: 3
<212> TYPE: PRT
<213> ORGANISM: Homo sapiens

<400> SEQUENCE: 615

Ala Ala Ser
1

<210> SEQ ID NO 616
<211> LENGTH: 10
<212> TYPE: PRT
<213> ORGANISM: Homo sapiens

<400> SEQUENCE: 616

Gln Gln Leu Asn Ser Tyr Pro Leu Thr Phe
1               5                   10

<210> SEQ ID NO 617
<211> LENGTH: 8
<212> TYPE: PRT
<213> ORGANISM: Homo sapiens

<400> SEQUENCE: 617

Gly Phe Thr Phe Gly Tyr Tyr Gly
1               5

<210> SEQ ID NO 618
<211> LENGTH: 8
```

```
<212> TYPE: PRT
<213> ORGANISM: Homo sapiens

<400> SEQUENCE: 618

Ile Phe Tyr Asp Gly Ser Asn Lys
1               5

<210> SEQ ID NO 619
<211> LENGTH: 14
<212> TYPE: PRT
<213> ORGANISM: Homo sapiens

<400> SEQUENCE: 619

Ala Arg Gly Gly Ser Asn Arg Tyr Tyr Tyr Val Leu Asp Ala
1               5               10

<210> SEQ ID NO 620
<211> LENGTH: 6
<212> TYPE: PRT
<213> ORGANISM: Homo sapiens

<400> SEQUENCE: 620

Gln Gly Ile Asn Asn Tyr
1               5

<210> SEQ ID NO 621
<211> LENGTH: 3
<212> TYPE: PRT
<213> ORGANISM: Homo sapiens

<400> SEQUENCE: 621

Ala Ala Ser
1

<210> SEQ ID NO 622
<211> LENGTH: 10
<212> TYPE: PRT
<213> ORGANISM: Homo sapiens

<400> SEQUENCE: 622

Gln Lys Tyr Tyr Ser Ala Pro Leu Thr Phe
1               5               10

<210> SEQ ID NO 623
<211> LENGTH: 8
<212> TYPE: PRT
<213> ORGANISM: Homo sapiens

<400> SEQUENCE: 623

Gly Phe Ile Phe Ser Arg Tyr Ala
1               5

<210> SEQ ID NO 624
<211> LENGTH: 8
<212> TYPE: PRT
<213> ORGANISM: Homo sapiens

<400> SEQUENCE: 624

Ile Ser Gly Ser Gly Asp Asn Pro
1               5

<210> SEQ ID NO 625
<211> LENGTH: 17
<212> TYPE: PRT
<213> ORGANISM: Homo sapiens
```

<400> SEQUENCE: 625

Ala Lys Gly Gly Leu Leu Trp Phe Gly Asp Leu Leu Asp Pro Phe Asp
1               5                   10                  15

Tyr

<210> SEQ ID NO 626
<211> LENGTH: 6
<212> TYPE: PRT
<213> ORGANISM: Homo sapiens

<400> SEQUENCE: 626

Gln Ser Leu Gly Ser Tyr
1               5

<210> SEQ ID NO 627
<211> LENGTH: 3
<212> TYPE: PRT
<213> ORGANISM: Homo sapiens

<400> SEQUENCE: 627

Gly Ala Phe
1

<210> SEQ ID NO 628
<211> LENGTH: 10
<212> TYPE: PRT
<213> ORGANISM: Homo sapiens

<400> SEQUENCE: 628

Gln Gln Ser Tyr Thr Thr Pro Leu Thr Phe
1               5                   10

<210> SEQ ID NO 629
<211> LENGTH: 8
<212> TYPE: PRT
<213> ORGANISM: Homo sapiens

<400> SEQUENCE: 629

Gly Phe Ile Phe Ser Asn Tyr Gly
1               5

<210> SEQ ID NO 630
<211> LENGTH: 8
<212> TYPE: PRT
<213> ORGANISM: Homo sapiens

<400> SEQUENCE: 630

Ile Trp Tyr Asp Gly Ser Lys Lys
1               5

<210> SEQ ID NO 631
<211> LENGTH: 17
<212> TYPE: PRT
<213> ORGANISM: Homo sapiens

<400> SEQUENCE: 631

Ala Arg Asp Gln Gly Ile Thr Met Val Arg Gly Leu Ile Ile Leu Asp
1               5                   10                  15

Tyr

<210> SEQ ID NO 632
<211> LENGTH: 11

<212> TYPE: PRT
<213> ORGANISM: Homo sapiens

<400> SEQUENCE: 632

Gln Ser Leu Leu His Ser Asn Gly Tyr Asn Tyr
1               5                   10

<210> SEQ ID NO 633
<211> LENGTH: 3
<212> TYPE: PRT
<213> ORGANISM: Homo sapiens

<400> SEQUENCE: 633

Leu Gly Ser
1

<210> SEQ ID NO 634
<211> LENGTH: 10
<212> TYPE: PRT
<213> ORGANISM: Homo sapiens

<400> SEQUENCE: 634

Met Gln Ala Leu Gln Thr Pro Trp Thr Phe
1               5                   10

<210> SEQ ID NO 635
<211> LENGTH: 8
<212> TYPE: PRT
<213> ORGANISM: Homo sapiens

<400> SEQUENCE: 635

Gly Gly Thr Phe Ser Ser Tyr Ala
1               5

<210> SEQ ID NO 636
<211> LENGTH: 8
<212> TYPE: PRT
<213> ORGANISM: Homo sapiens

<400> SEQUENCE: 636

Ile Ile Pro Phe Phe Gly Ala Thr
1               5

<210> SEQ ID NO 637
<211> LENGTH: 15
<212> TYPE: PRT
<213> ORGANISM: Homo sapiens

<400> SEQUENCE: 637

Ala Arg Tyr Asn Trp Asn Asp Asn Tyr Tyr Tyr Gly Met Asp Val
1               5                   10                  15

<210> SEQ ID NO 638
<211> LENGTH: 11
<212> TYPE: PRT
<213> ORGANISM: Homo sapiens

<400> SEQUENCE: 638

Gln Ser Leu Leu His Asn Asn Gly Tyr Asn Tyr
1               5                   10

<210> SEQ ID NO 639
<211> LENGTH: 3
<212> TYPE: PRT
<213> ORGANISM: Homo sapiens

<400> SEQUENCE: 639

Leu Gly Ser
1

<210> SEQ ID NO 640
<211> LENGTH: 10
<212> TYPE: PRT
<213> ORGANISM: Homo sapiens

<400> SEQUENCE: 640

Met Gln Ala Leu Gln Thr Pro Trp Thr Phe
1               5                   10

<210> SEQ ID NO 641
<211> LENGTH: 8
<212> TYPE: PRT
<213> ORGANISM: Homo sapiens

<400> SEQUENCE: 641

Gly Phe Thr Phe Ser Ser Tyr Ala
1               5

<210> SEQ ID NO 642
<211> LENGTH: 8
<212> TYPE: PRT
<213> ORGANISM: Homo sapiens

<400> SEQUENCE: 642

Ile Trp Phe Asp Gly Ser Asn Lys
1               5

<210> SEQ ID NO 643
<211> LENGTH: 11
<212> TYPE: PRT
<213> ORGANISM: Homo sapiens

<400> SEQUENCE: 643

Ala Arg Gly Gly Ala Tyr Gly Leu Phe Asp Tyr
1               5                   10

<210> SEQ ID NO 644
<211> LENGTH: 11
<212> TYPE: PRT
<213> ORGANISM: Homo sapiens

<400> SEQUENCE: 644

Gln Ser Leu Leu His Gly Asn Gly Tyr Asn Tyr
1               5                   10

<210> SEQ ID NO 645
<211> LENGTH: 3
<212> TYPE: PRT
<213> ORGANISM: Homo sapiens

<400> SEQUENCE: 645

Leu Gly Ser
1

<210> SEQ ID NO 646
<211> LENGTH: 10
<212> TYPE: PRT
<213> ORGANISM: Homo sapiens

<400> SEQUENCE: 646

```
Met Gln Ala Leu Gln Thr Pro Phe Thr Phe
1               5               10

<210> SEQ ID NO 647
<211> LENGTH: 8
<212> TYPE: PRT
<213> ORGANISM: Homo sapiens

<400> SEQUENCE: 647

Gly Phe Thr Phe Ser Asn Ala Trp
1               5

<210> SEQ ID NO 648
<211> LENGTH: 10
<212> TYPE: PRT
<213> ORGANISM: Homo sapiens

<400> SEQUENCE: 648

Ile Lys Thr Lys Thr Asp Gly Gly Thr Thr
1               5               10

<210> SEQ ID NO 649
<211> LENGTH: 20
<212> TYPE: PRT
<213> ORGANISM: Homo sapiens

<400> SEQUENCE: 649

Ser Thr Pro Gly Ile Ala Ala Ala Gly Thr Trp Tyr Tyr Tyr Trp Tyr
1               5               10              15

Gly Met Asp Val
            20

<210> SEQ ID NO 650
<211> LENGTH: 12
<212> TYPE: PRT
<213> ORGANISM: Homo sapiens

<400> SEQUENCE: 650

Gln Ser Val Leu Ala Ser Ser Asn Asn Met Asn Tyr
1               5               10

<210> SEQ ID NO 651
<211> LENGTH: 3
<212> TYPE: PRT
<213> ORGANISM: Homo sapiens

<400> SEQUENCE: 651

Trp Ala Ser
1

<210> SEQ ID NO 652
<211> LENGTH: 10
<212> TYPE: PRT
<213> ORGANISM: Homo sapiens

<400> SEQUENCE: 652

His Gln Tyr Tyr Ser Ile Pro Asn Thr Phe
1               5               10

<210> SEQ ID NO 653
<211> LENGTH: 10
<212> TYPE: PRT
<213> ORGANISM: Homo sapiens
```

-continued

```
<400> SEQUENCE: 653

Gly Asp Asn Val Phe Ser Asn Ser Ala Ala
1               5                   10

<210> SEQ ID NO 654
<211> LENGTH: 9
<212> TYPE: PRT
<213> ORGANISM: Homo sapiens

<400> SEQUENCE: 654

Thr Tyr Tyr Arg Ser Lys Trp Asn Asn
1               5

<210> SEQ ID NO 655
<211> LENGTH: 12
<212> TYPE: PRT
<213> ORGANISM: Homo sapiens

<400> SEQUENCE: 655

Ala Arg Val Pro Met Asn Arg Gly Gly Met Asp Val
1               5                   10
```

ANTIBODIES

CROSS REFERENCE TO RELATED APPLICATIONS

This application is a U.S. National Stage Application under 35 U.S.C. 371 of International Patent Application No. PCT/EP2020/054521, filed on Feb. 20, 2020, which claims priority to European Application No. 19382123.8, filed Feb. 20, 2019 and European Application No. 19382869.6, filed on Oct. 7, 2019, the entire contents of which are incorporated by reference herein.

SEQUENCE LISTING

The instant application contains a Sequence Listing which has been filed electronically in ASCII format and is hereby incorporated by reference in its entirety. Said ASCII copy, created on Mar. 18, 2022, is named 112171-0040-70016US00_SUBSEQ.txt and is 292,161 bytes in size.

TECHNICAL FIELD

The invention relates to antibodies and antigen-binding fragments thereof that recognize the spike (S) protein of Middle East respiratory syndrome coronavirus (MERS-CoV).

BACKGROUND

Middle East respiratory syndrome (MERS) is caused by the zoonotic Middle East respiratory syndrome coronavirus (MERS-CoV). The virus infects camels and dromedaries and can be transferred to humans. Human-to-human transmission is inefficient, but can occur at close contact such as in households or hospital settings among patients and from patients to health-care workers. It is an airway infection with fever, coughing and shortness of breath as the primary symptoms. MERS can lead to serious pneumonia and kidney failure leading to death. MERS is associated with high mortality rates (according to the WHO, in 2015 approximately 36% of reported patients with MERS died; see WHO MERS-CoV Global Summary and Assessment of Risk, August 2018 (WHO/MERS/RA/August18)). The first case was documented in Saudi Arabia in 2012 and has since spread to other parts of Asia, Africa and Europe (Roess et al. (2016) The Lancet Infectious Diseases 16(1):14-15). Despite its continuous threat to public health, antiviral therapies or vaccines to treat or prevent MERS-CoV infection are currently lacking.

Neutralizing epitopes for MERS-CoV have been described in several studies (see Chen et al. (2017) Emerging Microbes & Infections 6:e37 and Yu et al. (2015) Scientific Reports 5:13133). The neutralizing epitopes that have been identified are almost all located in the receptor binding domain (RBD) within the S1 subunit of the MERS spike protein (MERS-S1). It has also been reported that immunization with the MERS-CoV S1 N-terminal domain (residues 1-357) also elicits neutralizing antibodies to a lesser extent.

There remains a need for neutralizing antibodies that recognize the spike proteins of MERS (MERS-S) and of other Coronaviruses, such SARS, OC43, HKU1, or NL63. There also remains a need for antibodies that recognize the spike proteins of multiple Coronaviruses.

SUMMARY OF THE INVENTION

The invention provides an antibody that binds to Middle East Respiratory Syndrome coronavirus (MERS-CoV) spike protein (MERS-S).

In some embodiments, the antibody is capable of inhibiting the infection of human cells by MERS-CoV.

In some embodiments, the antibody binds to the S2 domain of MERS-S. In some embodiments, the antibody binds to the S2 domain of MERS-S and is cross-reactive for one or more other human coronaviruses, such as Severe Acute Respiratory Syndrome coronavirus (SARS-CoV), HKU1, OC43 and/or murine hepatitis virus (MHV).

In some embodiments, the antibody binds to the S1 domain of MERS-S. In some embodiments, the antibody binds to the S1 domain of MERS-S and inhibits the sialic acid-binding activity of MERS-S.

The invention further provides a combination of antibodies comprising: (i) a antibody that binds to the S2 domain of MERS-S and (ii) an antibody that binds to the S1 domain of MERS-S. In some embodiments, the antibody that binds to the S2 domain of MERS-S and the antibody that binds to the S1 domain of MERS-S are human antibodies.

The invention further provides a combination of antibodies comprising: (i) an antibody that binds to the S2 domain of MERS-S and (ii) an antibody that binds to the S1 domain of MERS-S and inhibits the sialic acid-binding activity of MERS-S. In some embodiments, the antibody that binds to the S2 domain of MERS-S and the antibody that binds to the S1 domain of MERS-S are human antibodies.

The invention further provides an antibody that binds to MERS-S and cross-reacts with other Coronaviruses.

The invention further provides an isolated nucleic acid encoding the antibody of the invention.

The invention further provides a vector comprising the nucleic acid of the invention.

The invention further provides a host cell comprising the vector of the invention.

The invention further provides a pharmaceutical composition comprising the antibody of the invention, or the combination of antibodies of the invention, and a pharmaceutically acceptable carrier.

The invention further provides an antibody of the invention, or a combination of antibodies of the invention, for use in therapy. In some embodiments, the therapy is preventing, treating or ameliorating betacoronavirus infection, such as MERS-CoV infection.

The invention further provides an antibody of the invention, or a combination of antibodies of the invention, for use in therapy of Coronaviruses other than MERS-CoV.

Figure 1B:
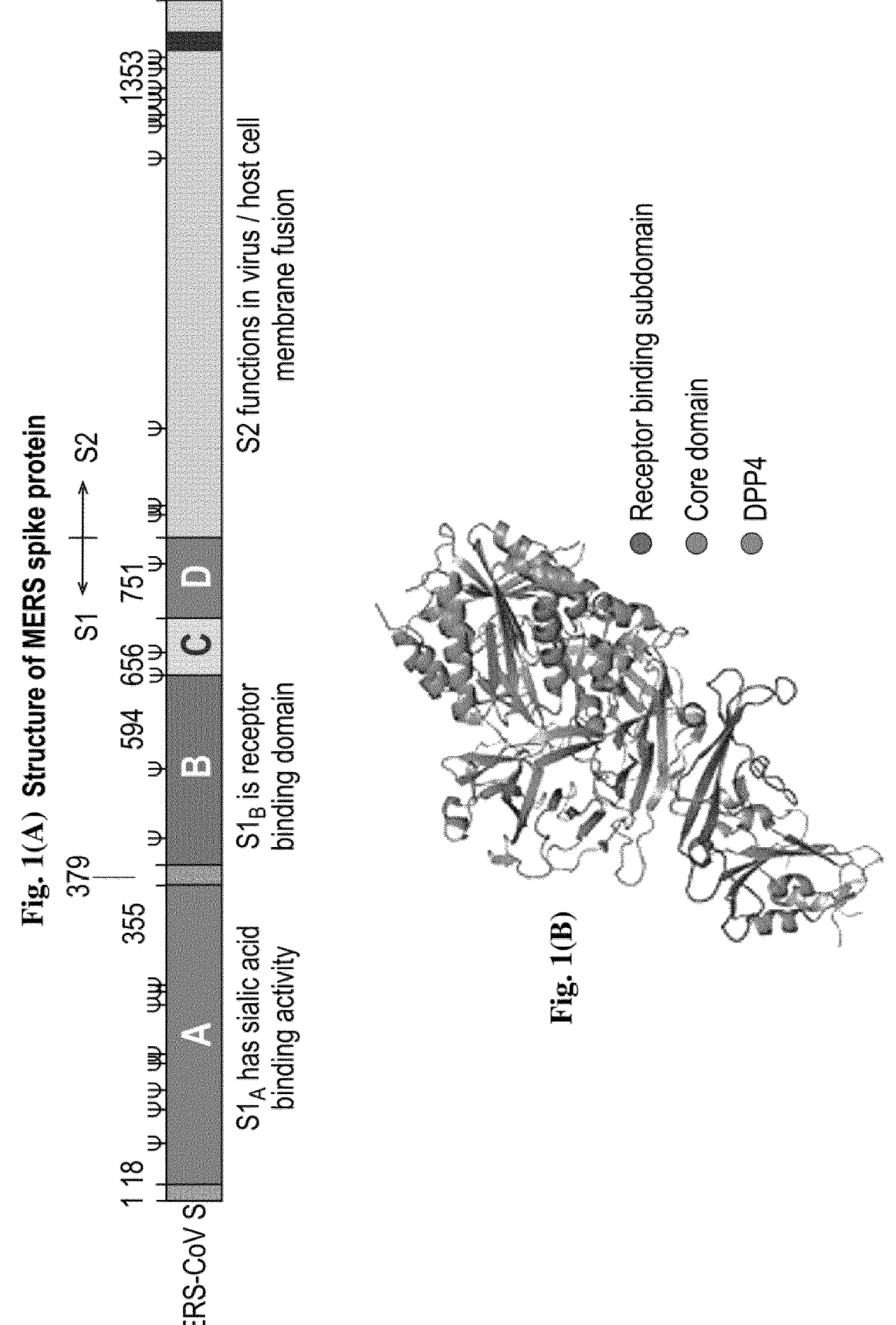
FIG. 1. Generation and characterization of monoclonal H2L2 antibodies targeting the MERS-CoV spike protein.
(A) Structure of MERS spike protein. The S1 subunit (residues 1-751) is mainly responsible for mediating viral particle attachment to the cell surface and is dependent on the dipeptidyl peptidase 4 (DPP4) receptor (also known as CD26). The S1 subunit folds into four distinct domains designated $S1_A$ to $S1_D$. $S1_A$ has sialic acid binding activity, which may aid in virion attachment to host cells. S1B is the receptor binding domain (RBD), and it is via this domain that MERS-CoV binds to the cell surface entry receptor DPP4. The S2 subunit functions in virus-host cell membrane fusion. Binding of the S1 subunit to the DPP4 receptor is thought to trigger conformational changes in the S2 subunit, which then inserts its fusion peptide into the target cell membrane to form a six-helix bundle fusion core that prepares the viral and cell membranes for fusion.

(B) Ribbon diagram showing the interaction between DPP4 and the receptor binding subdomain of MERS-S1.

(C) The MERS-CoV spike (S) protein and recombinant soluble MERS-CoV S antigens used for immunization of H2L2 transgenic mice to generate human monoclonal antibodies (mAbs).

Upper panel: Schematic representation of the MERS-CoV S protein, indicated are S subunits (S1 and S2), S1 domains (A through D), and known biological functions. Middle panel: Schematic representation of recombinant soluble MERS-CoV S antigens, including the MERS-CoV S S1 subunit (MERS-S1), the ectodomain of its S2 subunit (MERS-S2$^{ecto}$) or the entire MERS-S ectodomain (MERS-S$^{ecto}$), the latter containing a mutation at the furin cleavage site at the S1/S2 junction and a C-terminally fused T4 foldon trimerization tag to increase trimer stability (T4). Positions of signal peptides (SP) and StrepTag-affinity tags (ST) are indicated.

Lower panel: Immunization schedule for H2L2 mice. To generate monoclonal antibodies (mAbs) targeting the MERS-CoV S protein, groups of H2L2 mice (six mice/group) were immunized with either MERS-S1 (6×), or sequentially immunized with MERS-S$^{ecto}$ (3×), MERS-S2$^{ecto}$(2×) and MERS-Sc$^{ecto}$ (1×). Booster immunizations were done with two-week intervals and B-cells were harvested from spleen and lymph nodes four days after the last immunization.

(D) Identified MERS-S1-reactive mAbs of hybridomas derived from B-cells of S1-immunized H2L2 mice were characterized for epitope location and virus neutralization using MERS-S pseudotyped vesicular stomatitis virus (VSV). Pie charts show mAb frequencies relative to the total (indicated in the center circle). Domain-level epitope mapping was performed for MERS-S1-reactive mAbs and relative frequencies of mAbs binding to given S1 domains (S1$^A$, I$^B$ or S1$^{CD}$) are indicated. The percentage of mAbs that was reactive to S1 but not to the S1$^A$, S1$^B$ or S1$^{CD}$ domains (S1$^{other}$) is also shown. Virus neutralization by S1-reactive mAbs was analysed using the luciferase-encoding MERS-CoV S pseudotyped VSV particles.

(E) Identified MERS-S$^{ecto}$-reactive mAbs of hybridomas generated from S$^{ecto}$/S$^{ecto}$-immunized H2L2 mice were characterized for epitope location and virus neutralization as in (D).

(F) Immunization schedule for H2L2 mice. To generate monoclonal antibodies (mAbs) targeting several Corona CoV S proteins, groups of H2L2 mice (10 mice) were immunized sequentially with either OC43-S, MERS-S and SARS-S proteins with 2 week intervals. The entire procedure was repeated and the final booster immunization with all three proteins was done 2 weeks later. B-cells were harvested from spleen and lymph nodes four days after the last immunization.

FIG. 2. Variable region sequences of anti-MERS-S1 H2L2 antibodies and distribution of epitope groups over multiple domains of the MERS-CoV spike protein.

(A) Heavy variable region sequences of anti-MERS-S1 H2L2 antibodies. Germline V$_H$ sequences are at the top of each group of sequences (labelled as 3-33 VH, 1-69 VH, 3-23 VH, 6-1 VH and 4-4 VH).

(B) Light chain variable region sequences of anti-MERS-S1 H2L2 antibodies. Germline V$_κ$ sequences are at the top of each group of sequences (labelled as 1-27 Vk, 4-1 Vk, 3-15 Vk, 3-20 Vk, 1-9 Vk, 2-28 Vk and 1-39 Vk). In (A) and (B), the CDR1, 2 and 3 regions are indicated on top. Below each of the germline VH and VK sequences is a group of neutralizing antibodies (neutralization was determined by DPP4-S1 blocking and MERS-S VSV pseudo-virus neutralization assays). Underlined amino acids are somatic hypermutations. Also listed is mAb 1.10 f3, which targets the sialic acid binding MERS S1$^A$ domain and inhibits Sia-binding activity.

(C) Light and heavy variable region sequences of human antibodies that recognize more than one Corona virus S protein. Germline V$_H$ sequences are at the top of each group of sequences.

(D) ELISA reactivity of the human anti-MERS-S mAbs to the indicated MERS-CoV spike glycoprotein domains.

(E) Binding competition of anti-MERS-S mAbs analyzed by bio-layer interferometry (BLI). Immobilized MERS-S$_{ecto}$ antigen was saturated in binding with a given anti-MERS-S mAb (step 1) and then exposed to binding by a second mAb (step 2). Additional binding of the second antibody indicates the presence of an unoccupied epitope, whereas lack of binding indicates epitope blocking by the first antibody. As a control, the first mAb was also included in the second step to check for self-competition.

(F) Schematic distribution of epitope groups of anti-MERS-S mAbs over the different MERS-S domains.

(G) MERS-S specific mAbs bind MERS-S$^{ecto}$ with high affinity. The binding kinetics and affinity of anti-MERS-S mAbs and DPP4 receptor to recombinant soluble MERS-S$^{ecto}$ was measured by bio-layer interferometry (BLI). Antibodies and receptor were immobilized on the sensor surface, followed by injection of the MERS-S$^{ecto}$ at 200, 67, 22 and 7.4 nM concentrations. The kinetics constants were calculated using 1:1 Langmuir binding model on Fortebio Data Analysis 7.0 software. The binding rate constant $k_{on}$($M^{-1}$ $s^{-1}$), the dissociation constant $k_{off}$ ($s^{-1}$) and the equilibrium dissociation constant $K_D$ (M; $K_D$=$k_{off}$/$k_{on}$) are shown.

Figure 3B:
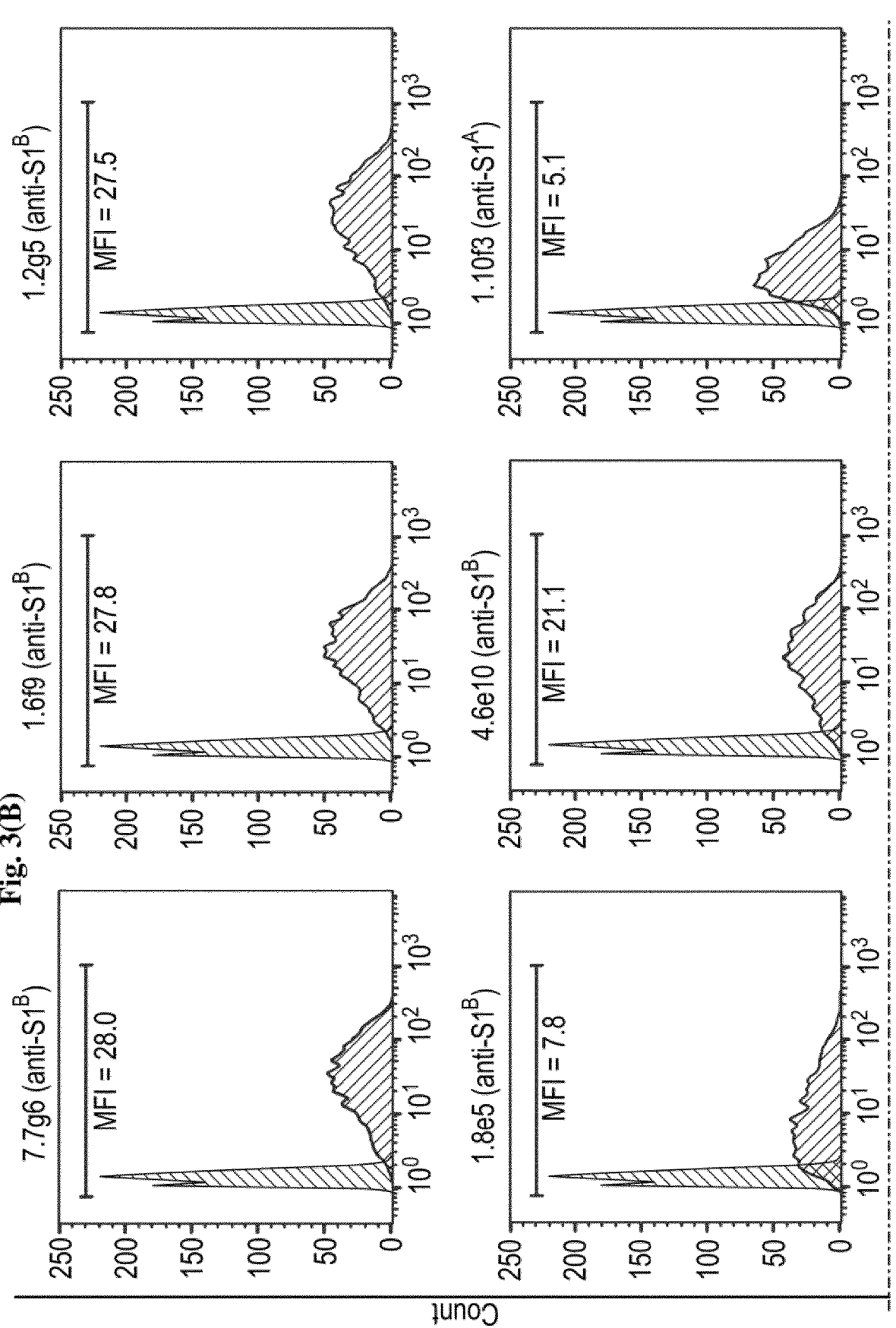
Figure 3B:
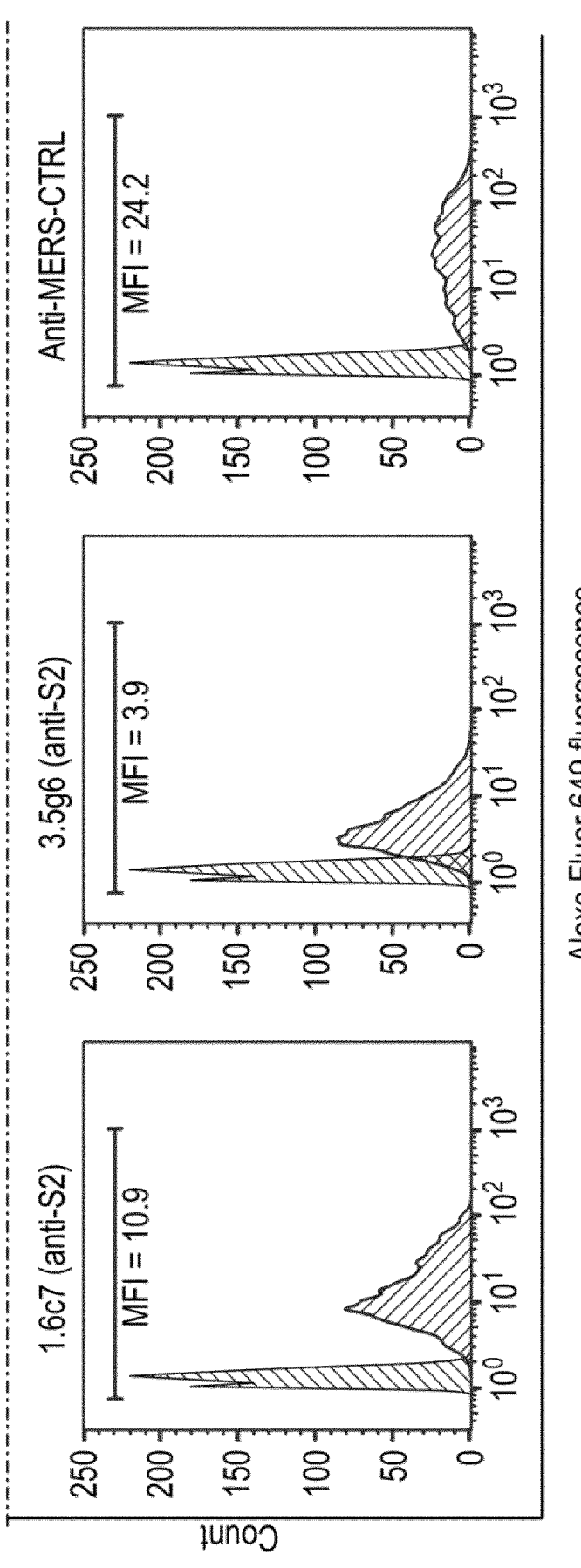

(H) Example of a human antibody cross-binding to MERS, SARS and OC43 spike proteins FIG. 3. Binding and Cross-binding (A) Binding affinities of anti-MERS-S1 H2L2 antibodies. These affinities were determined via kinetic measurements obtained using a ForteBio Octet instrument.

(B) Binding of anti-MERS-S mAbs to cells expressing MERS-CoV spike protein. Overlay histograms showing the binding of anti-MERS-S mAbs to MERS-CoV S expressing Huh-7 cells by flow cytometric analysis. Huh-7 cells were transfected with a plasmid encoding MERS-CoV S protein that was C-terminally extended with the green fluorescent protein, which was used for gating MERS-CoV S expressing cells. Cells were stained with eight anti-MERS-S mAbs and an anti-MERS-S control antibody with 5 µg/ml of each antibody. Antibody binding to cells was detected by flow cytometry using Alexa Fluor 649 conjugated goat anti-human IgG antibodies and mean fluorescence intensities (MFIs) were calculated.

Figure 4:
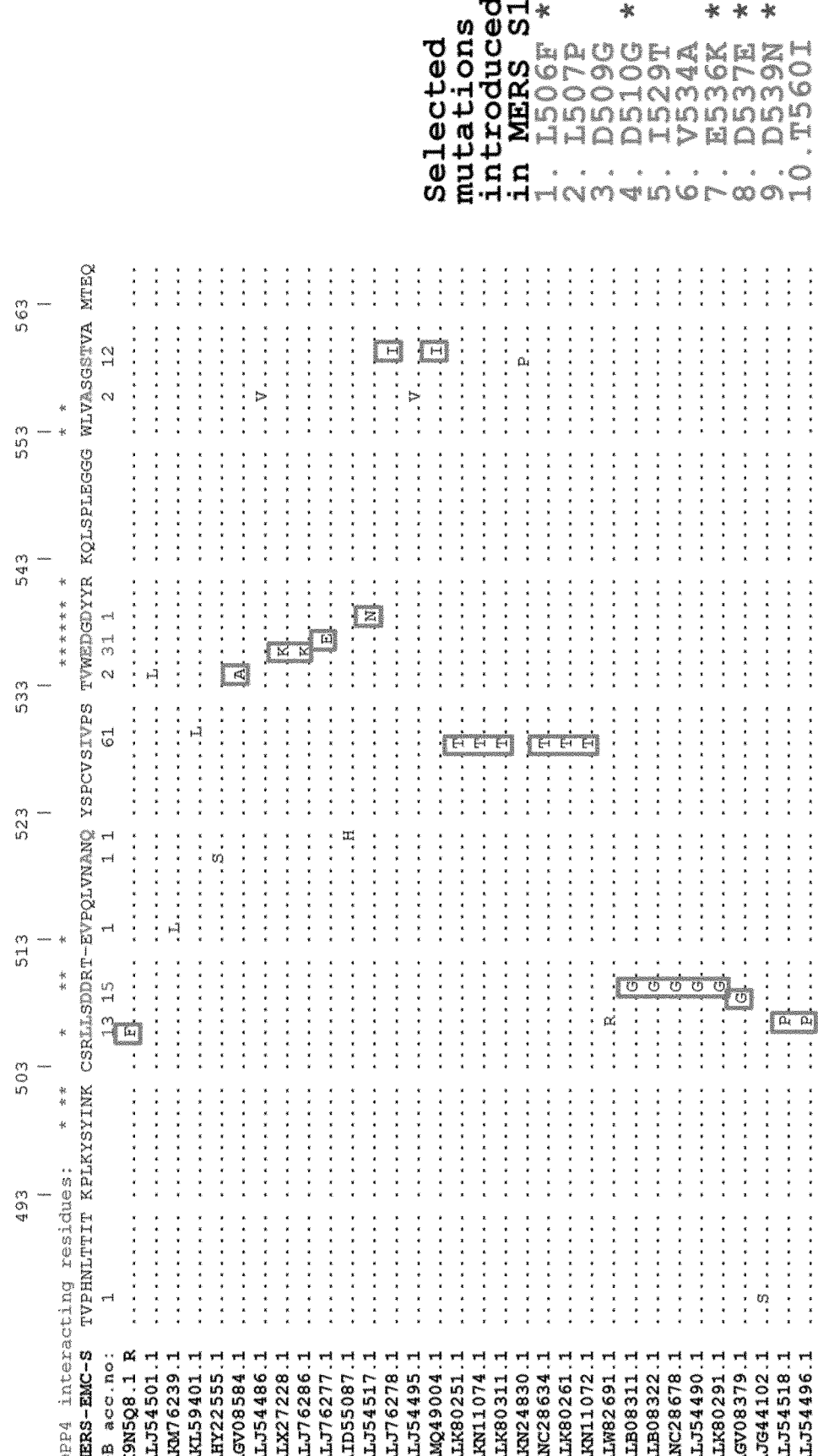

FIG. 4. Naturally occurring amino acid substitutions in receptor binding subdomain of MERS-S(amino acids 483-566 of MERS-S). GB acc. no refers to the Genbank accession no. DPP4-interacting residues are indicated with an asterisk. The boxed mutations are those that were selected to test for anti-MERS-S1 antibody reactivity to MERS-S1 variants.

Figure 5:
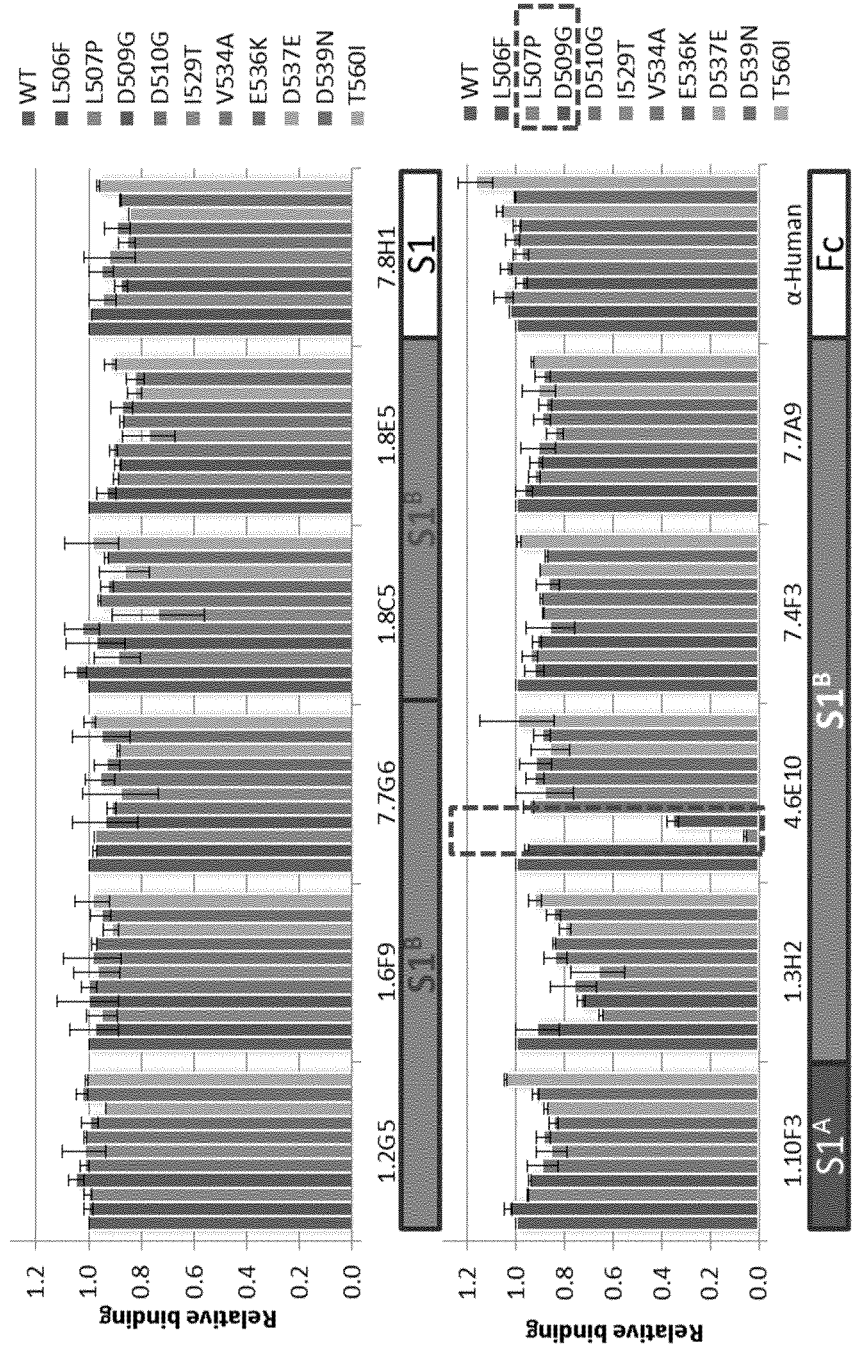
Figure 5B:
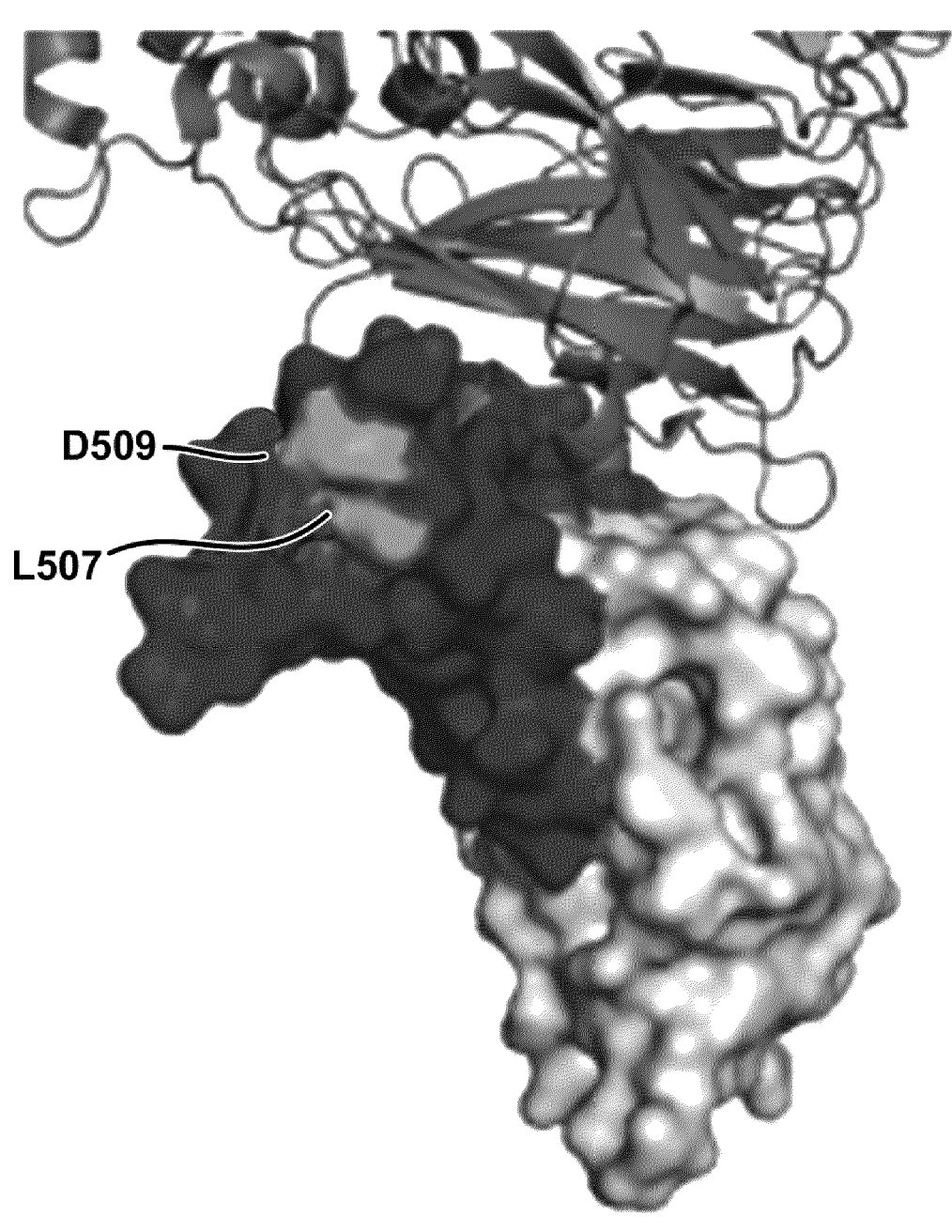

FIG. 5. (A) The anti-MERS-S1 antibodies display broad reactivity to Fc-tagged MERS-S1 variants containing naturally occurring amino acid substitutions in the receptor binding subdomain. Residues L507 and D509 were found to be critical epitope residues for antibody 4.6e10 binding to MERS-S1. (B) Position of residues L507 and D509 on the surface of the receptor binding subdomain of MERS-S. The DPP4 receptor is shown as a ribbon diagram.

FIG. 6. (A) Surface representation of the MHV S trimer according to sequence conservation (left hand image). Surface representation of the MHV S trimer highlighting the peripheral position of the fusion peptide (middle image). Ribbon diagrams of the MHV S trimer showing the overlapping positions of the fusion peptide (residues 870-887) and of a major antigenic determinant identified for MHV and SARS-CoV (residues 875-905, spheres) (right hand image). Exposed conserved epitopes form an attractive target for the development of neutralizing antibodies with broad reactivity. This figure originated from Walls et al. (2016) Nature 531(7592):114-117. (B) MHV-S2 graph. (C) S1-mFC and fusion peptide (FP) ELISA titer graphs. Conserved fusion peptide represents a linear epitope recognized during natural infection, and so this peptide is a candidate for development of broadly reactive epitope-based vaccines.

Figure 7:
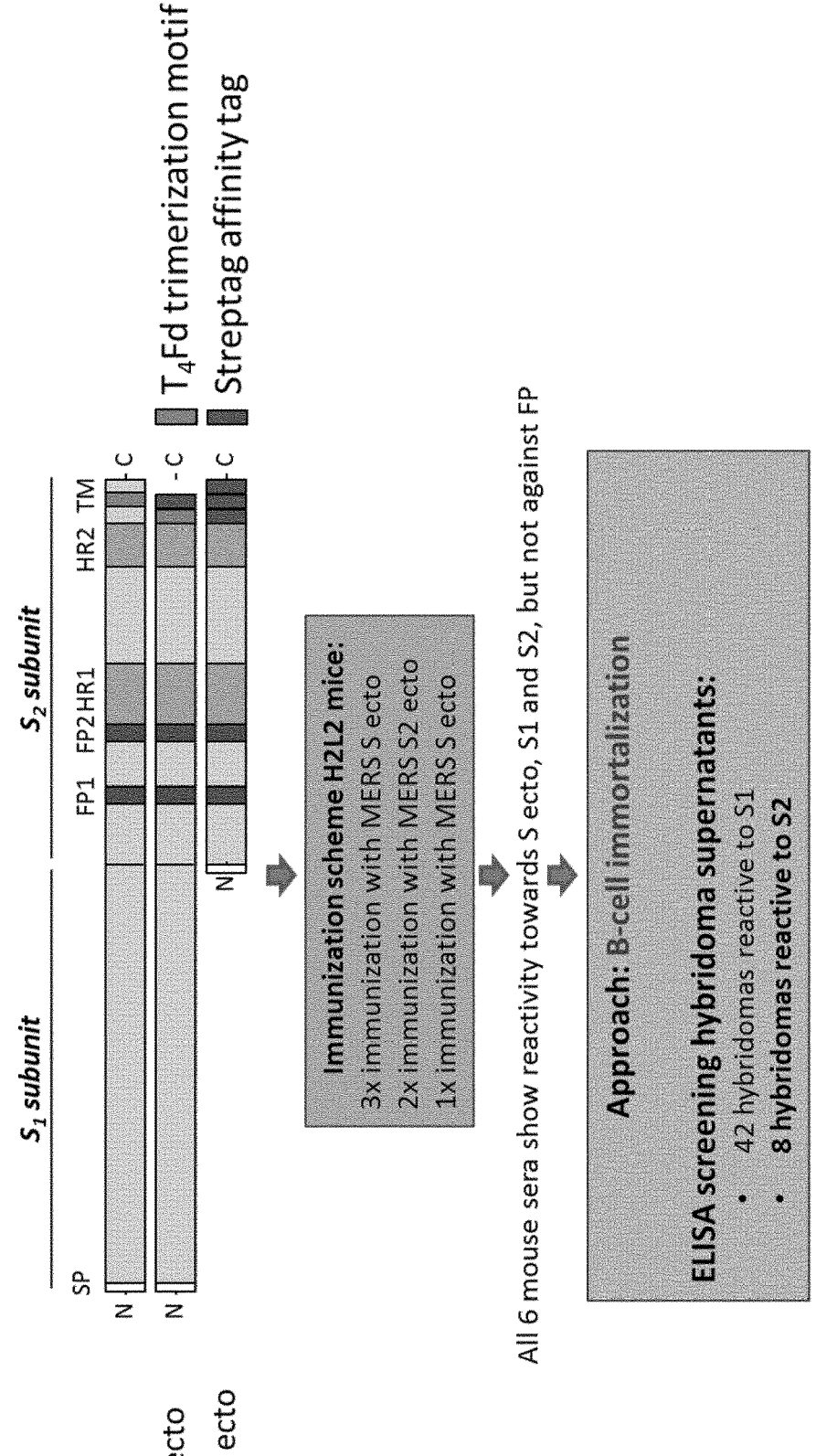

FIG. 7. Immunization schedule. Six H2L2 mice were immunized with prefusion trimeric MERS-S and S2 ectodomain. FP=fusion peptide.

FIG. 8. MERS-S2 reactivity. Antibodies 3.5 g6 and 1.6c7 can neutralize MERS-S. pseudotyped vesicular stomatitis virus (VSV).

FIG. 9. Heavy and light chain variable region sequences of anti-MERS-S2 H2L2 antibodies. The CDR1, 2 and 3 regions are indicated on top. Below each of the germline VH and VK sequences is a group of neutralizing antibodies (neutralization was determined by DPP4-S1 blocking and MERS-S VSV pseudo-virus neutralization assays). Underlined amino acids are somatic hypermutations. 1.6c7 recognizes a linear epitope (conserved residues) in the MERS-CoV-S2 subunit and cross-reacts with other beta corona viruses.

Figure 10:
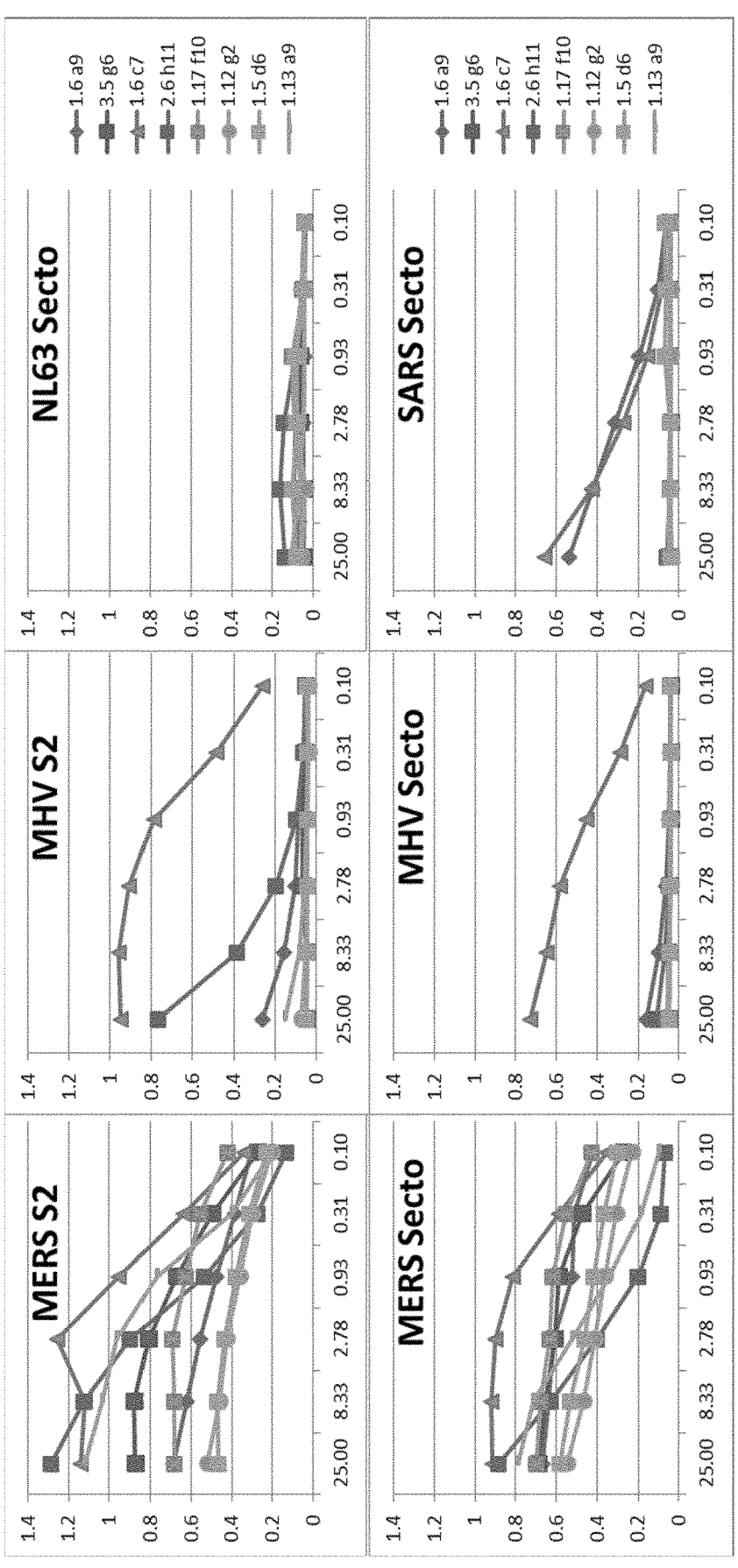

FIG. 10. Cross-reactivity of anti-MERS-S2 antibodies with other CoV S or S2 proteins by ELISA. Antibody 1.607 is reactive against MERS, MHV and SARS. $S^{ecto}$=S ectodomain.

Figure 11:
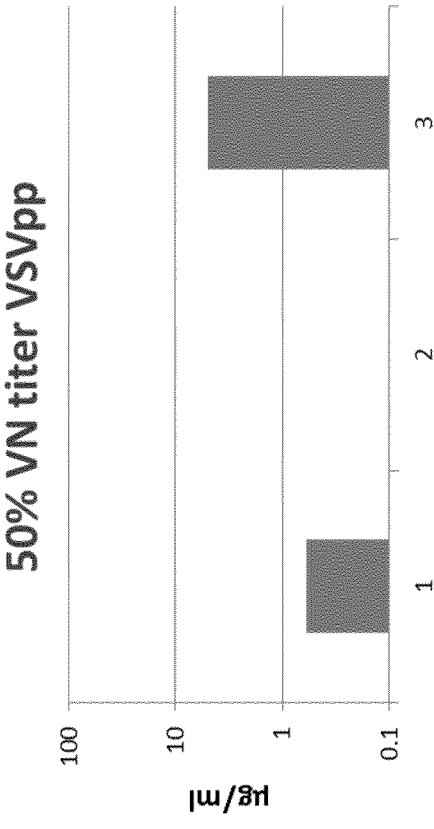

FIG. 11. Antibody 1.6c7 neutralizes MERS-S and MHV-S VSV pseudoparticles. The neutralization capacity for antibody 1.607 against beta-coronaviruses is shown.

FIG. 12. Anti-MERS-S2 antibodies recognize linear (L) and conformational (C) epitopes. ELISA of anti-MERS-S2 antibodies with MERS-$S^{ecto}$ domain antigen at denaturing (d) and non-denaturing (d) conditions identifying C or L epitopes.

FIG. 13. Epitope mapping of anti-MERS-S2 antibodies recognizing linear epitopes by ELISA using overlapping MERS-S2 peptides.

Figure 14A:
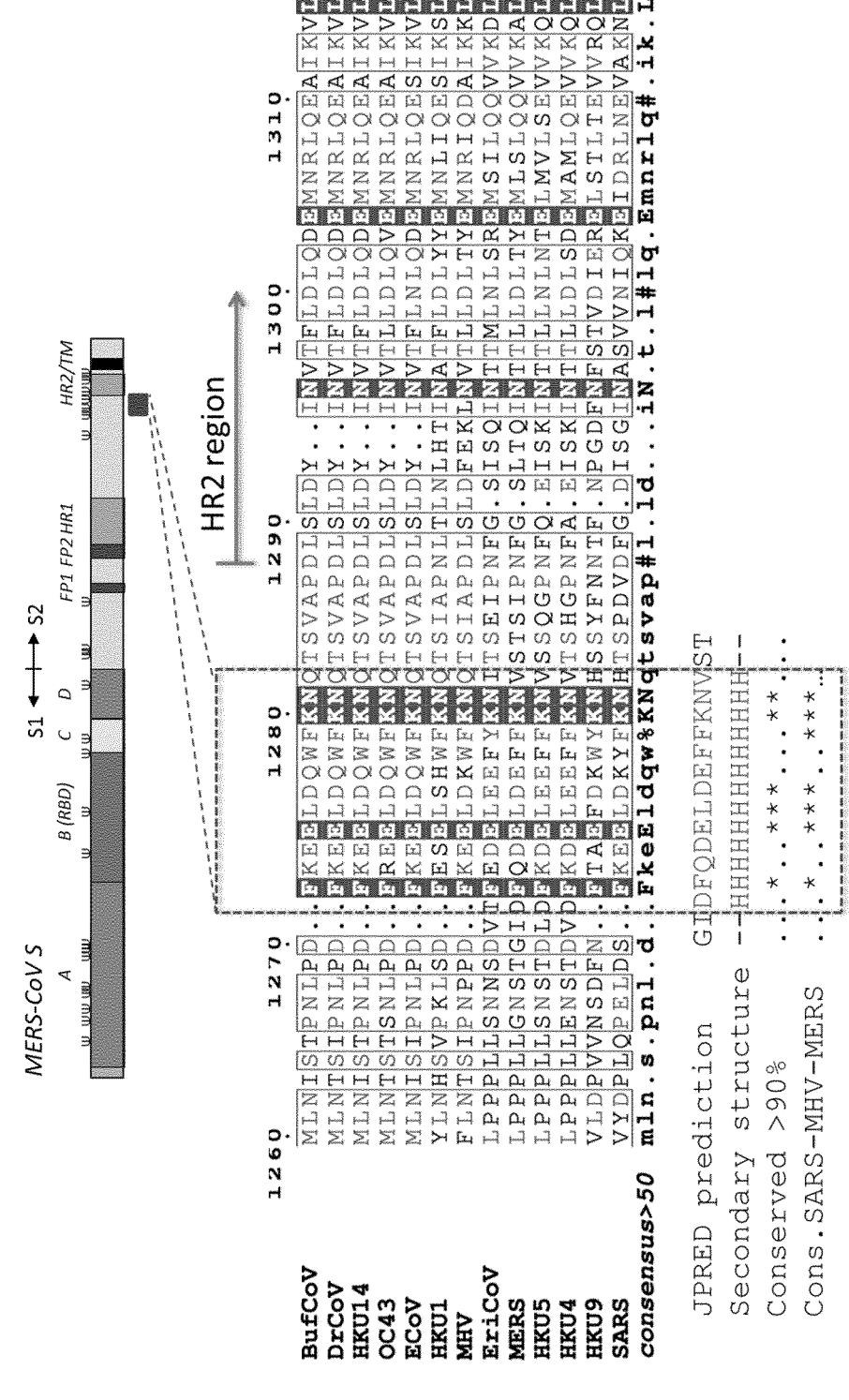

FIG. 14. (A) The epitope of 1.6c7 was determined to be a linear epitope (residues 1230-1242 of the S protein, namely DFQDELDEFFKNV (SEQ ID NO: 82)). Epitope mapping was performed by ELISA-based Pepscan analysis using overlapping peptides corresponding to a conserved region of the MERS-S2 ectodomain. In addition alanine scanning of the 15 amino acid linear epitope of 1.6c7 was performed. This epitope mapped to a conserved CoV domain (see dashed box). The mAb showed broader reactivity to MHV and SARS-CoV S in ELISA.

(B) Epitope peptide mapping for 1.6c7 and 2.6hl 1. (C) Overlapping peptides for mapping linear epitopes (a.a. 1004-1288; underlined in MERS-S sequence shown). Transmembrane region in italics. (D) Alanine scanning of the 15 amino acid linear epitope of 1.6c7.

Figure 15:
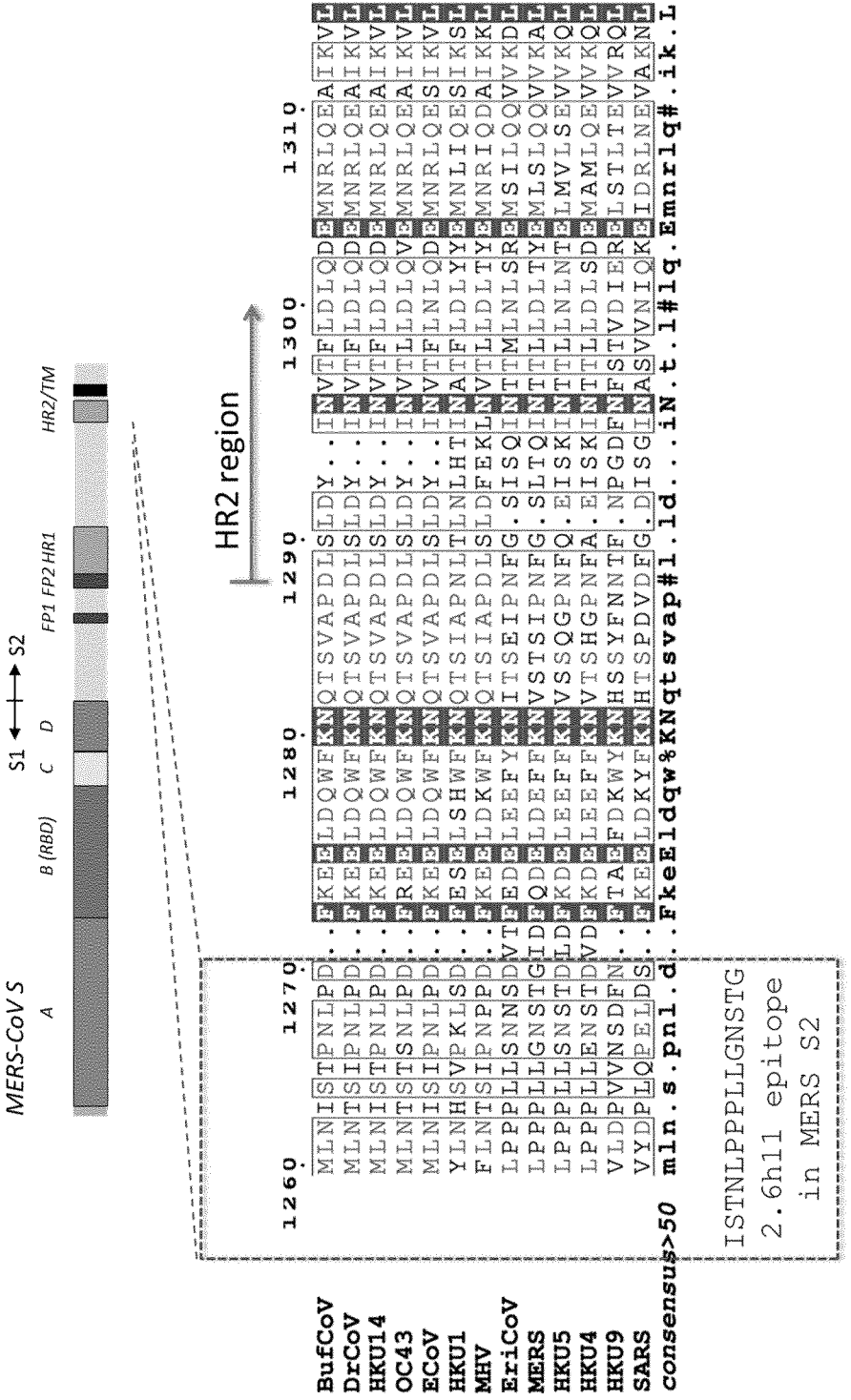

FIG. 15. The epitope of 2.6 h11 in MERS-S2 is not conserved among betacoronavirus S proteins.

FIG. 16. Functional properties of anti-MERS S protein H2L2 antibodies. Anti-MERS-CTRL (H1H15211P) is an IgG1 described in WO2015179535.

FIG. 17. Heavy variable region sequences of anti-MERS-S1 HCAb antibodies. Germline VH sequences are at the top of each group of sequences (labelled as 3-33, 3-74 and 3-23). The CDR1, 2 and 3 regions are indicated using labels at the top of the figure. Below each of the germline VH sequences is a group of neutralizing antibodies (neutralization was determined by MERS-S VSV pseudo-virus neutralization assays). Underlined amino acids are somatic hypermutations.

Figure 18:
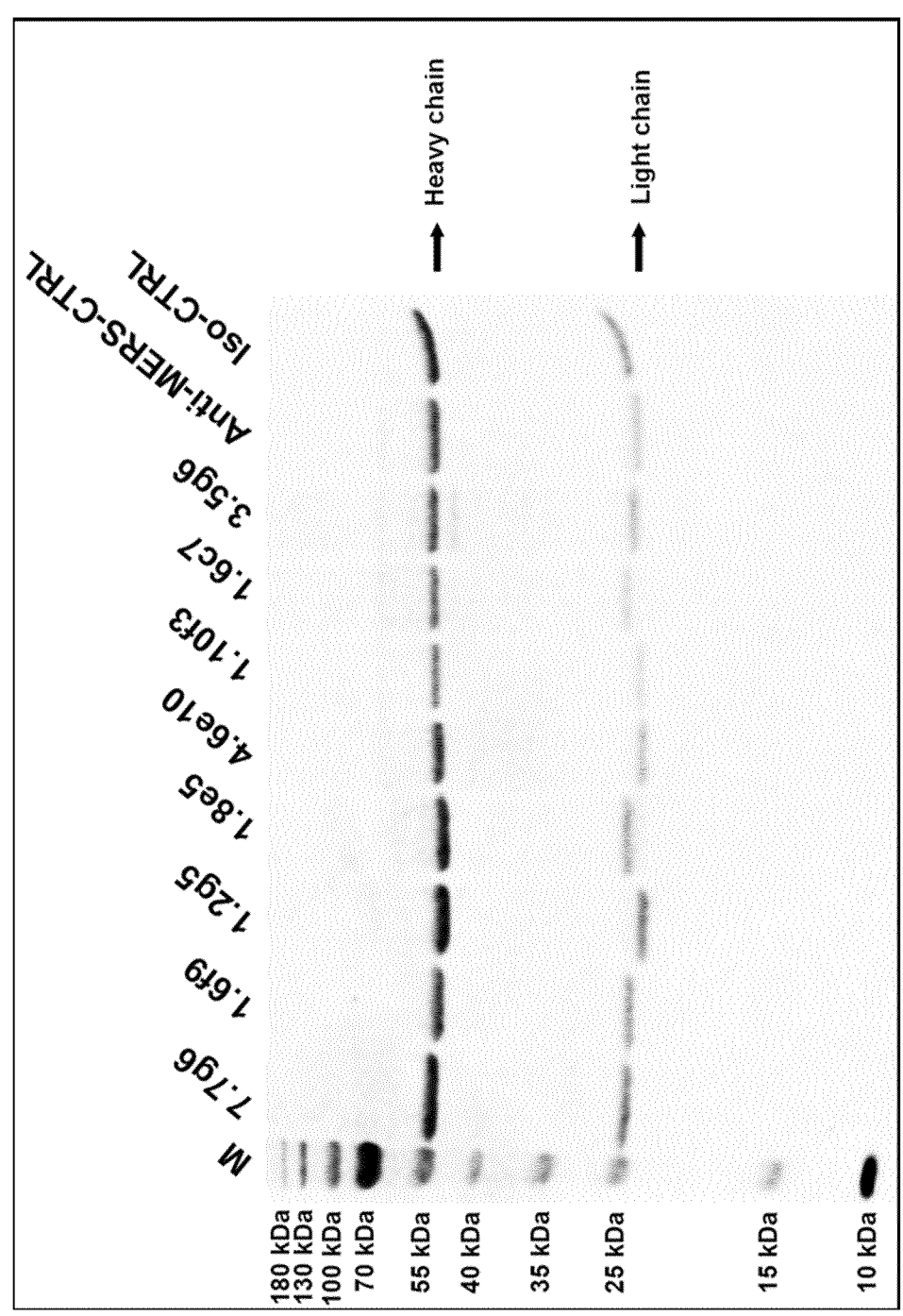

FIG. 18. SDS-PAGE analysis of purified monoclonal antibodies. Two microgram of the eight lead anti-MERS-S mAbs, an anti-MERS control antibody and an isotype control antibody were analysed by SDS-PAGE. All antibodies were expressed in human HEK-293T cells as human IgG1 isotype and purified using Protein A affinity purification.

FIG. 19. Virus neutralization and receptor binding inhibition by anti-MERS-S mAbs. (A) Analysis of MERS-CoV neutralizing activity by anti-MERS-S mAbs using MERS-S pseudotyped, luciferase-encoding VSV. A previously described RBD-specific, MERS-CoV-neutralizing human monoclonal antibody (anti-MERS-CTRL) and irrelevant isotype monoclonal antibody (Iso-CTRL) were included as positive and negative control, respectively. Luciferase-expressing VSV particles pseudotyped with the MERS-CoV S protein were incubated with antibodies at the indicated concentrations and the mix was used to transduce Vero cells. At 24 h postinfection luciferase expression was measured and neutralization (%) was calculated as the ratio of luciferase signal relative to non-antibody-treated controls. Data represent the mean standard deviation, SD) of three independent experiments. (B) The 50% inhibition titers of MERS-S pseudovirus and live virus by anti-MERS-CoV mAbs.

Figure 20:
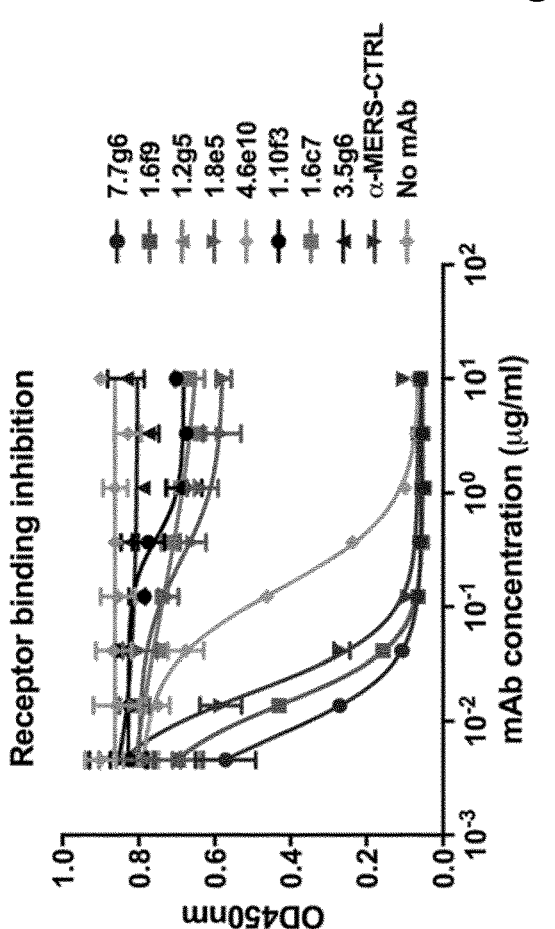

FIG. 20. Neutralization of anti-MERS $S1^B$ mAbs correlates with receptor binding inhibition. (A) Receptor binding inhibition by anti-MERS-S mAbs, determined by an ELISA-based assay. Recombinant soluble MERS-$S^{ecto}$ was preincubated with serially diluted anti-MERS-CoV mAbs and added to ELISA plates coated with soluble DPP4. Binding of MERS-$S^{ecto}$ to DPP4 was measured using HRP-conjugated antibody recognizing the Streptag affinity tag on MERS-$S^{ecto}$. Data represent the mean (±standard deviation, SD) of three independent experiments. (B) Table showing the concentration of mAb that gives half maximal receptor binding inhibition ($RBI_{50}$).

Figure 21:
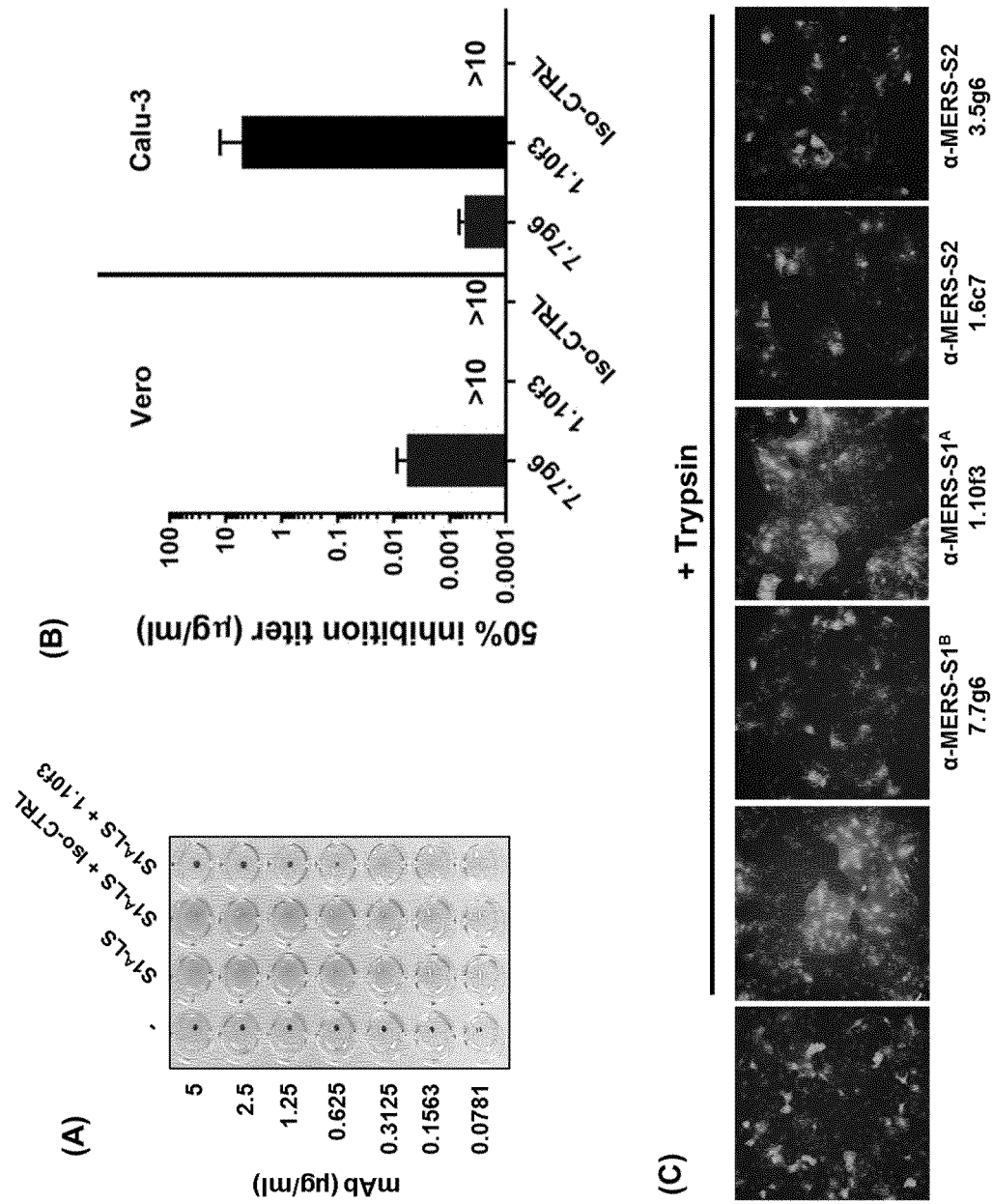

FIG. 21. Anti-MERS $S1^A$ and S2 mAbs block with MERS-CoV domain specific functions.

(A) The anti-MERS-$S1^A$ mAb 1.10f3 interferes with MERS-$S1^A$-mediated sialic acid binding, determined by a hemagglutination inhibition assay (Li, Hulswit et al. 2017). The sialic-acid binding domain $S1^A$ of MERS-S was fused to lumazine synthase (LS) protein that can self-assemble to form 60-meric nanoparticle ($S1^A$-LS), which enables multivalent, high affinity binding of the MERS-$S1^A$ domain to sialic acid on erythrocytes. Human red blood cells were mixed with S1$^A$-LS in the absence or presence of 2-fold dilutions of the MERS-S1$^A$-specific mAb 1.10f3. Isotype control antibody was included as a negative control. Hemagglutination was scored after 2 h of incubation at 4° C. The hemagglutination inhibition assay was performed three times, a representative experiment is shown.

(B) Neutralization of MERS-S pseudotyped VSV by anti-MERS-S mAb 1.10f3 on Vero and Calu-3 cells. Data represent the mean (I standard deviation, SD) of three independent experiments.

(C) The anti-MERS-S2 mAbs 1.607 and 3.5 g6 block MERS-S-mediated cell-cell fusion. Huh-7 cells were transfected with plasmid expressing MERS-CoV S, C-terminally fused to GFP. Two days after transfection, cells were treated with trypsin to activate membrane fusion function of the MERS-CoV S protein and incubated in the presence or absence of anti-MERS-S2 mAbs 1.6c7 and 3.5 g6, or the anti-MERS-S1$^B$ mAb 7.7 g6 and anti-MERS-S1$^A$ 1.103, all at 10 g/ml. Formation of MERS-S mediated cell-cell fusion was visualized by fluorescence microscopy. Merged images of MERS-S-GFP expressing cells and DAPI-stained cell nuclei are shown. Experiment was repeated two times and representative images are shown.

Figure 22:
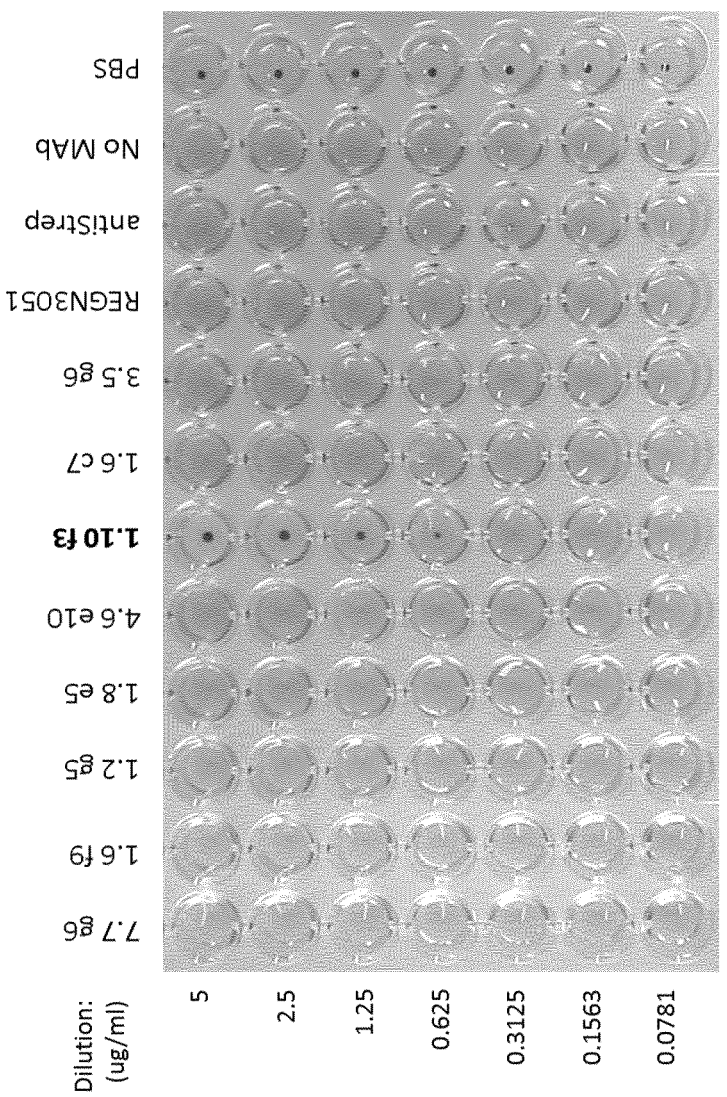

FIG. 22. The 1.10f3 antibody, which targets S1$_A$ domain blocks binding of MERS-S1$_A$ to sialic acid as shown by MERS-S1$_A$ haemagglutination inhibition assay.

Figure 23:
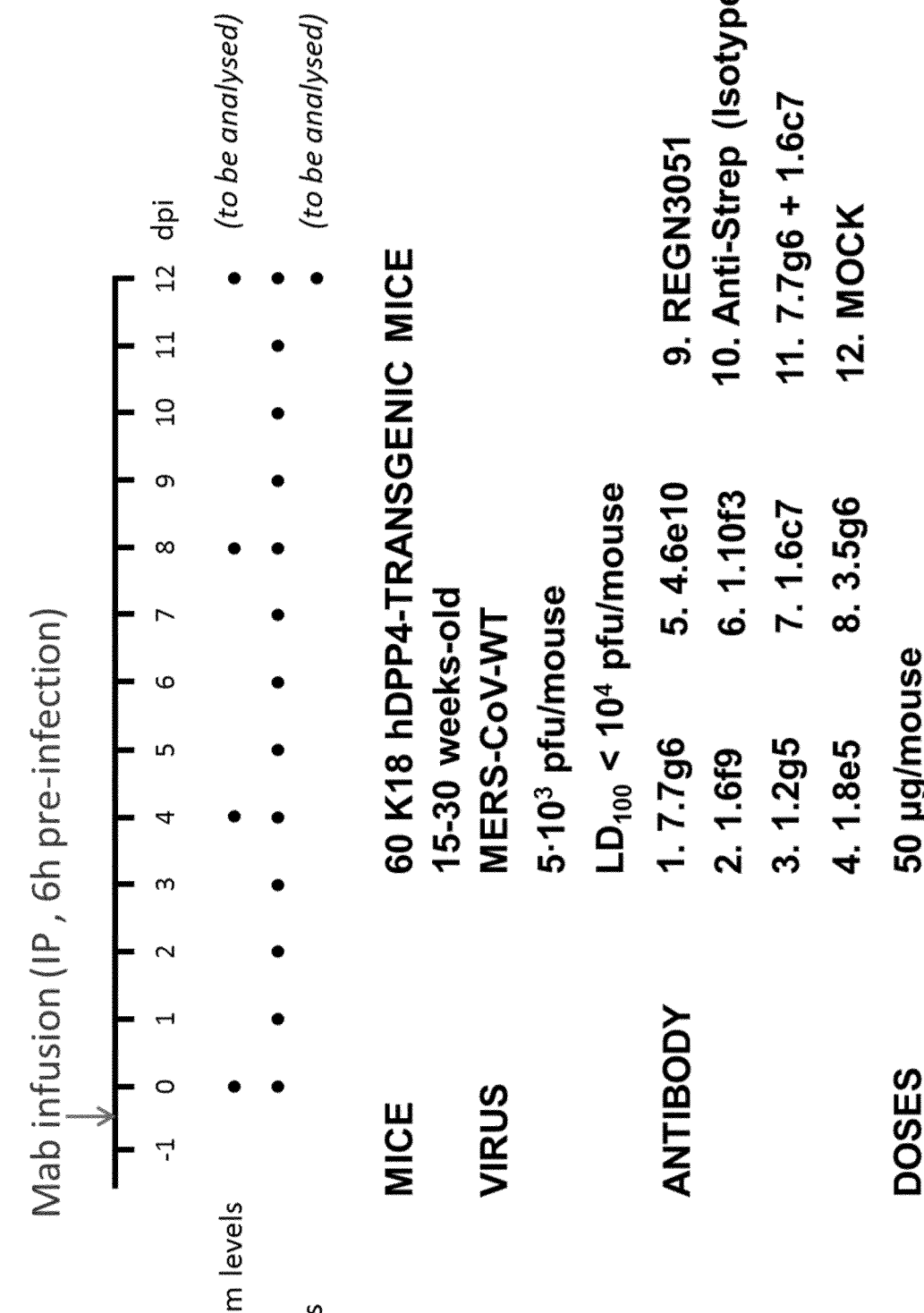

FIG. 23. Animal experiment protocol. The experiment was performed in hDPP4-transgenic mice to test prophylactic activity of eight human anti-MERS-S monoclonal antibodies.

Figure 24:
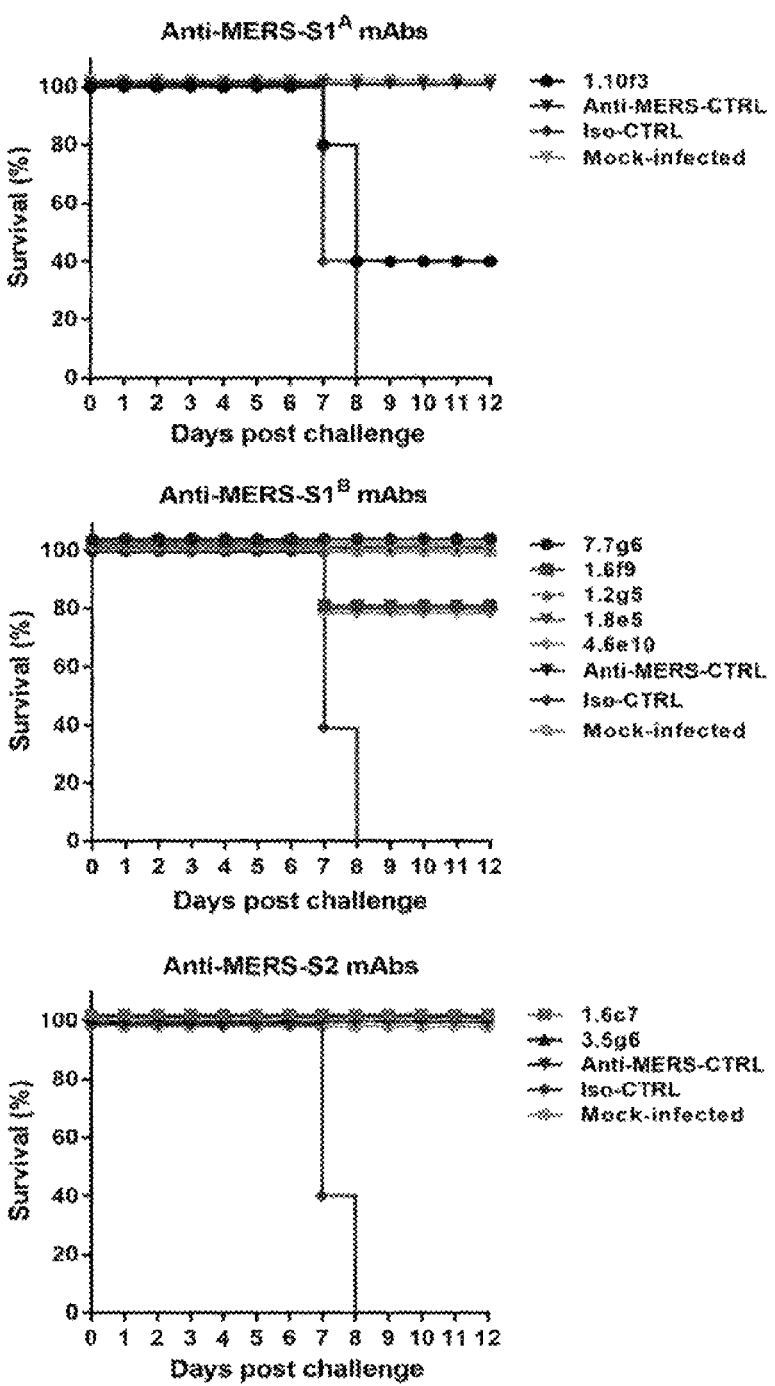

FIG. 24. Human anti-MERS-S mAbs protect mice against lethal MERS-CoV challenge: survival rates. Fifty microgram of antibody (equivalent to 1.8 mg mAb/kg body weight) was infused intraperitoneally in KI8-hDPP4-transgenic mice 6 hours before challenge with TCID50 of MERS-CoV. Five mice per group were used in the experiment. Survival rates were monitored daily until 12 days post-inoculation.

Figure 25:
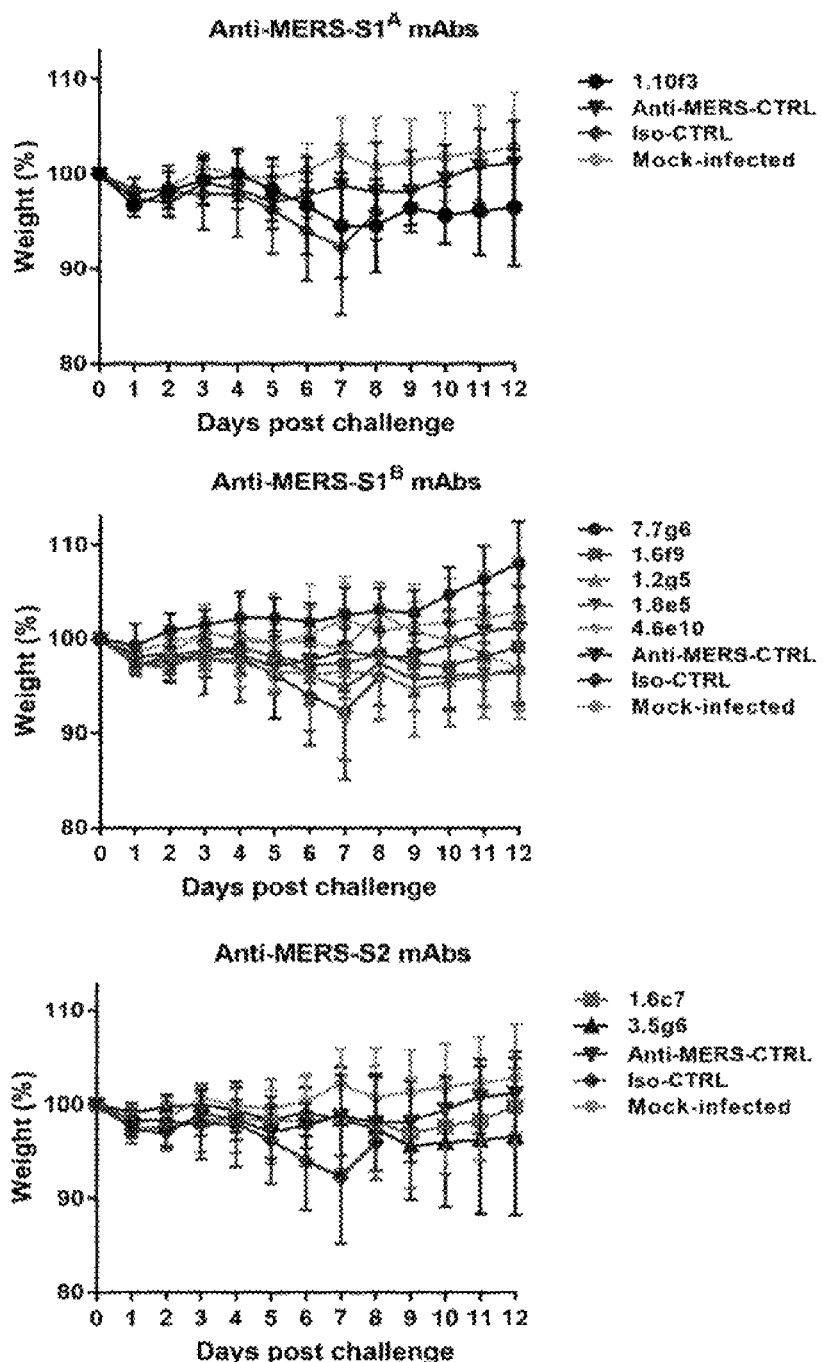

FIG. 25. Human anti-MERS-S mAbs protect mice against lethal MERS-CoV challenge: weight loss. Weight loss was monitored (expressed as a percentage of the initial weight) was monitored daily until 12 days post-inoculation in the experiment described in the legend for FIG. 24 above.

FIG. 26. SDS-PAGE analysis of purified, recombinant MERS-CoV S antigens.

SDS-PAGE analysis of purified MERS-CoV S antigens (2 microgram each) used for immunization of H2L2 transgenic mice (A) or for ELISA-based screening of antibodies (B).

Figure 27:
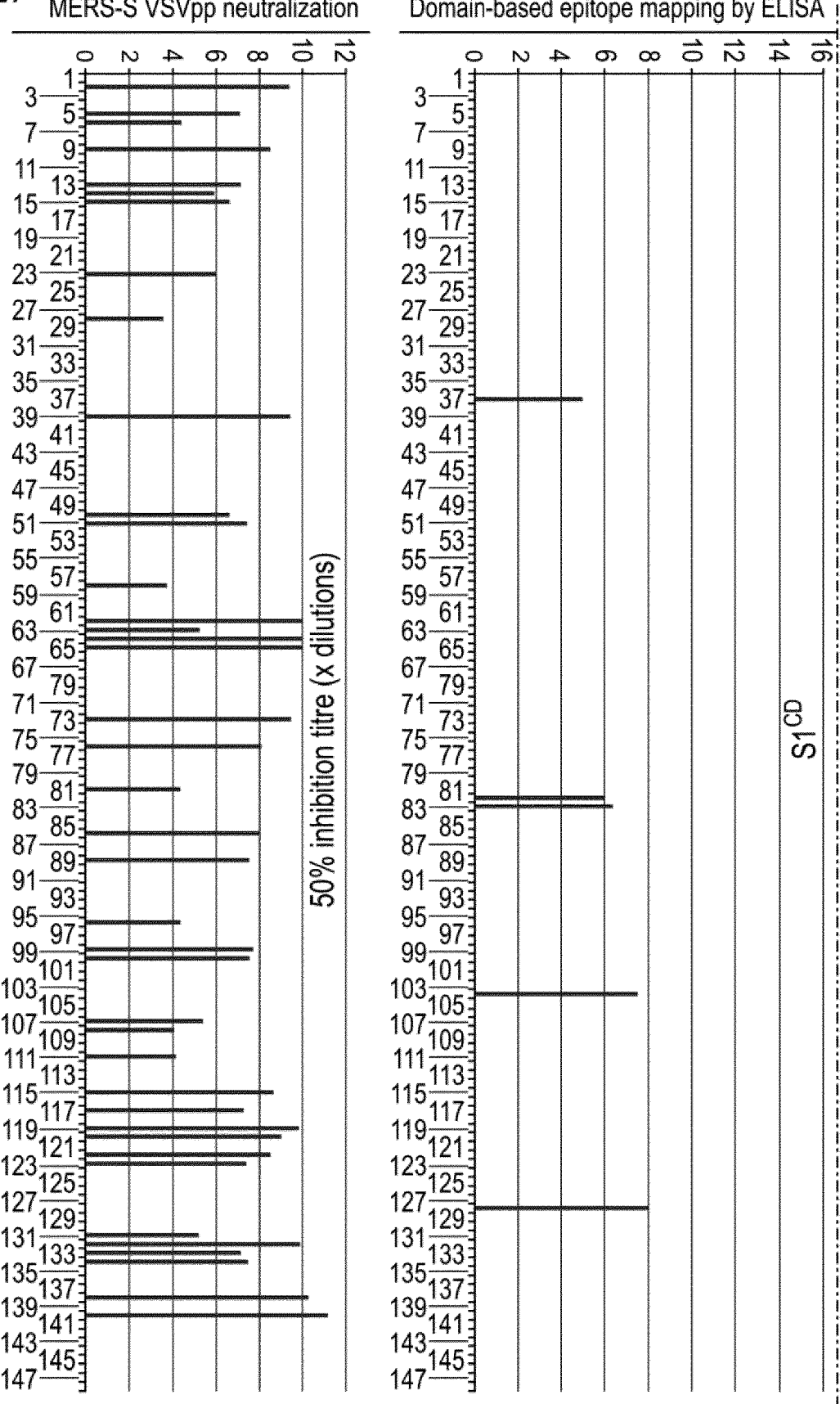
Figure 27:
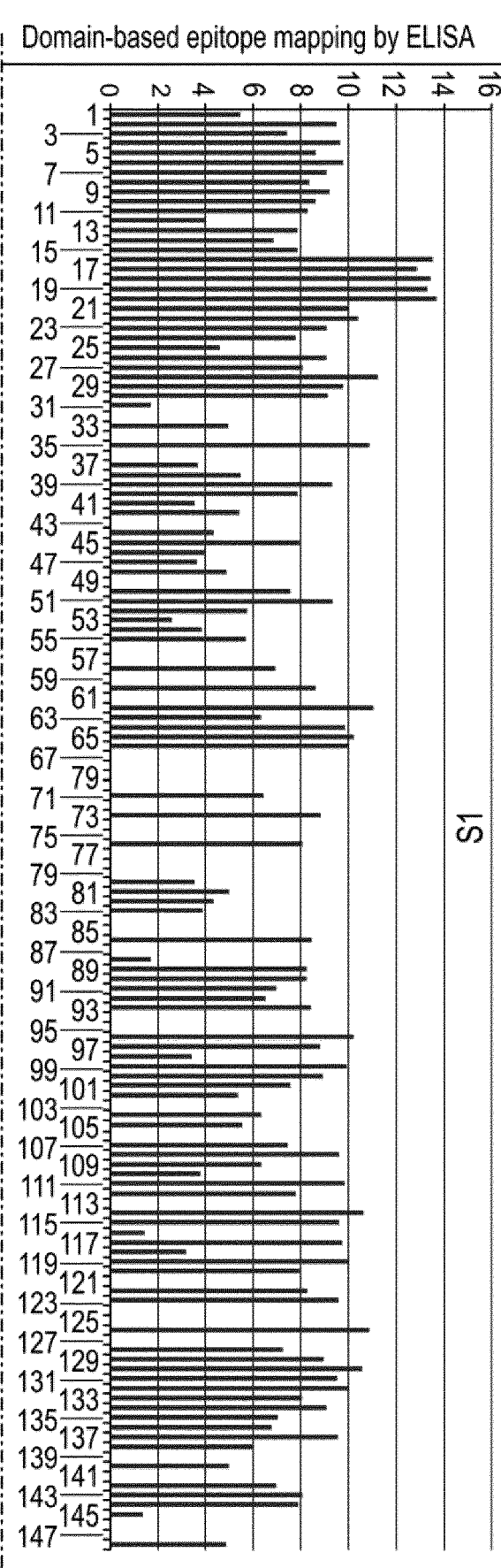

FIG. 27. Characterization of anti-MERS-S1 H2L2 antibodies from antibody-containing hybridoma supernatants. First, antibody-containing hybridoma supernatants (selected based on an initial MERS-S1 ELISA screen) were screened for ELISA-reactivity to S1 or individual domains of S1 (S1$^A$ S1$^B$ or S1$^{CD}$) (upper four panels). Second, virus neutralization by S1-reactive hybridoma supernatants was analysed using the luciferase expressing MERS-S pseudotyped VSV particles (bottom panel).

FIG. 28. Binding competition of anti-MERS-S mAbs using bio-layer interferometry. Immobilized MERS-S$^{ecto}$ antigen was saturated in binding with a given anti-MERS-S H2L2 mAb (step 1) and then exposed to binding by a second H2L2 mAb (step 2). Additional binding of the second antibody indicates the presence of an unoccupied epitope, whereas lack of binding indicates epitope blocking by the first antibody. As a control, the first mAb was also included in the second step to check for self-competition.

FIG. 29. H2L2 antibodies were purified from hybridoma supernatants that exhibited neutralizing activity. Neutralizing activity of purified H2L2 antibodies was assessed using MERS-S pseudotyped VSV and half-maximal inhibitory concentrations (IC$_{50}$; μg/ml) are shown. H2L2 antibodies were purified from hybridoma supernatants with neutralizing activity that were reactive to MERS-S1$^B$. In addition, H2L2 antibodies were purified from hybridoma supernatants showing MERS-S2 and MERS-S1$^A$ domain reactivity. Selection of lead mAbs was based on their potency to neutralize MERS-CoV relative to other mAbs within an epitope group (epitope groups are marked by shaded blocks), and on their unique VH and VL region sequences. Eight monoclonal antibodies (shown by arrows) with epitopes distributed throughout different domains of the MERS-CoV spike protein were selected as lead antibodies for further detailed biophysical and functional characterization.

Figure 30:
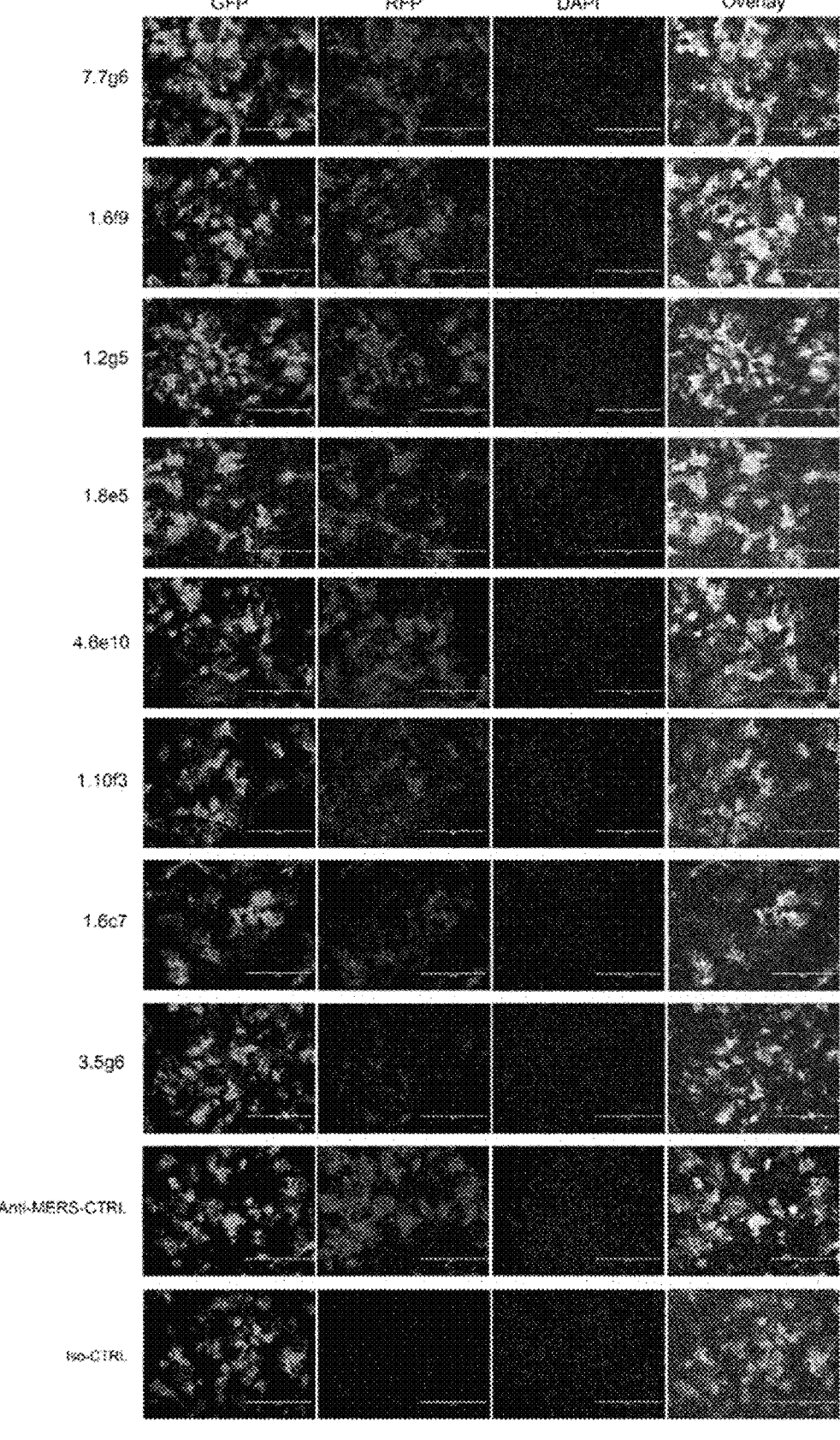

FIG. 30. Binding of anti-MERS-S mAbs to cell surface expressed MERS-CoV spike protein. Huh-7 cells were transfected with plasmid expressing a full-length MERS-CoV S construct. The encoding MERS-CoV S protein was C-terminally extended with the green fluorescent protein (GFP) and contained a mutated furin cleavage site to prevent cell-cell fusion. Fixed, nonpermeabilized MERS-CoV S transfected cells were stained with the eight lead anti-MERS-S mAbs, an anti-MERS control antibody and an isotype control antibody with 1.25 g/ml of each antibody. Antibody binding to cells was detected by fluorescence microscopy using Alexa Fluor 568 conjugated goat anti-human IgG antibodies (Alexa Fluor 568 channel). MERS-S-GFP transfected cells were detected by GFP fluorescence (GFP channel). DAPI was used for nuclear staining (DAPI channel). Panels on the right represent overlay profiles of the Alexa Fluor 568, GFP and DAPI channels.

FIG. 31. Neutralization activity of anti-MERS-S HCAbs. Analysis of MERS-CoV neutralizing activity by anti-MERS-S HCAbs using MERS-S pseudotyped, luciferase-encoding VSV. At 24 h post-infection luciferase expression was measured and neutralization (%) was calculated as the ratio of luciferase signal relative to luciferase readout in the absence of mAb. The experiment was performed twice and 50% inhibition titers (g/ml) for each experiment are shown.

Figure 32:
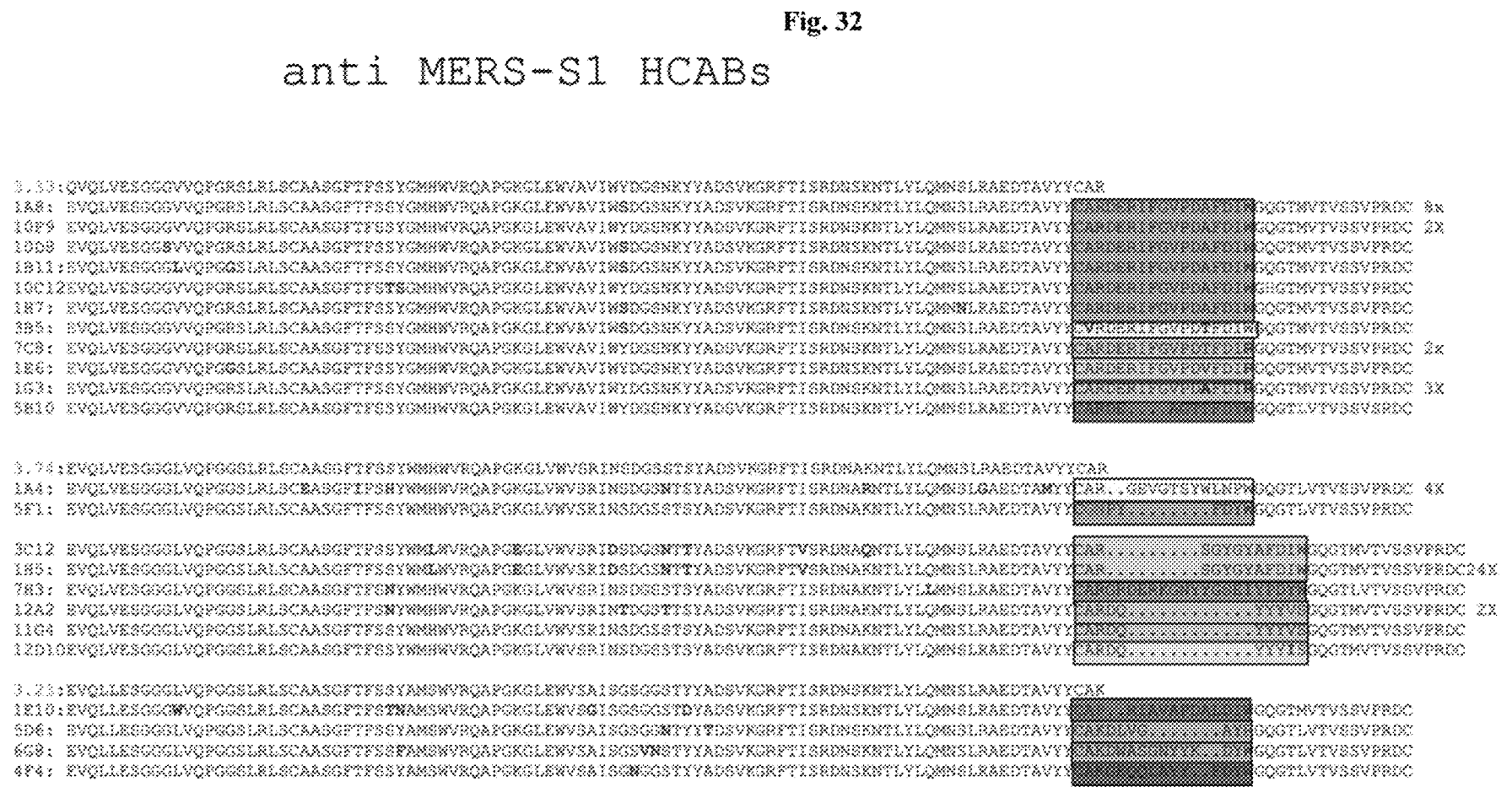

FIG. 32. Anti-MERS-S1 HCAb variable domain sequences. Boxed residues contribute to CDR3 in each antibody sequence.

Figure 33A:
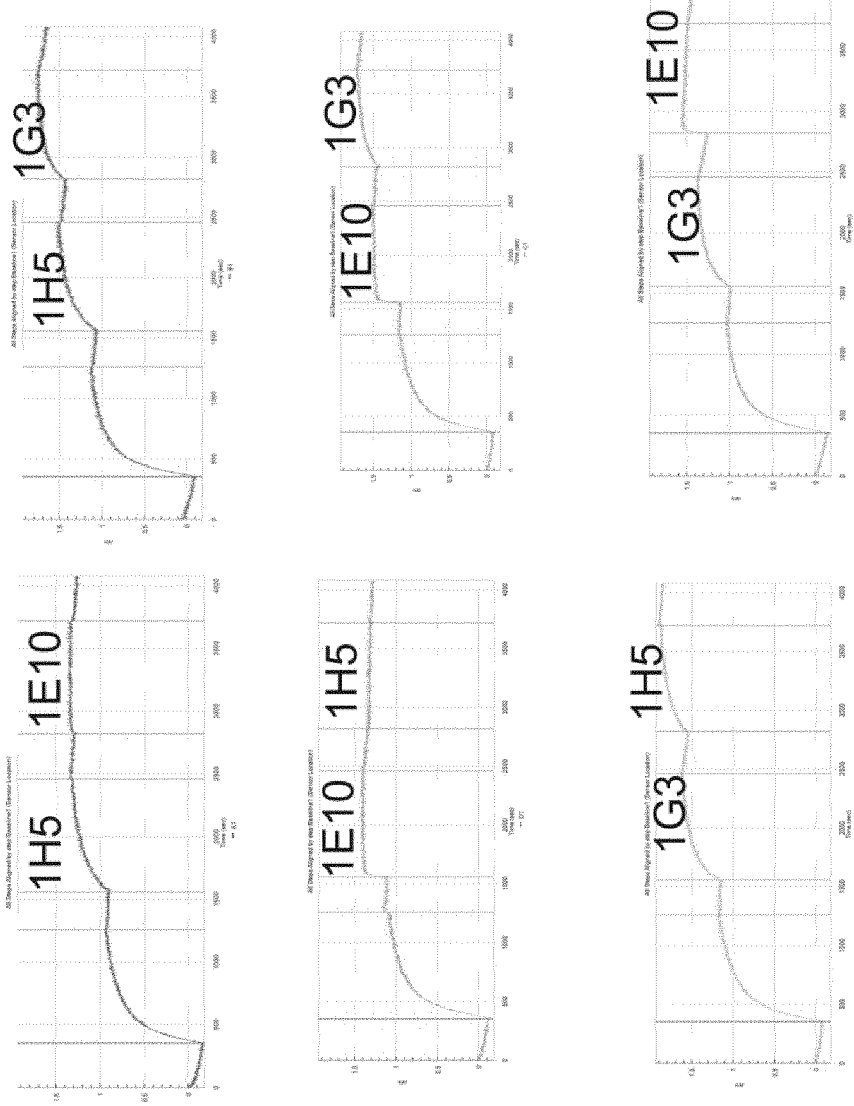
Figure 33B:
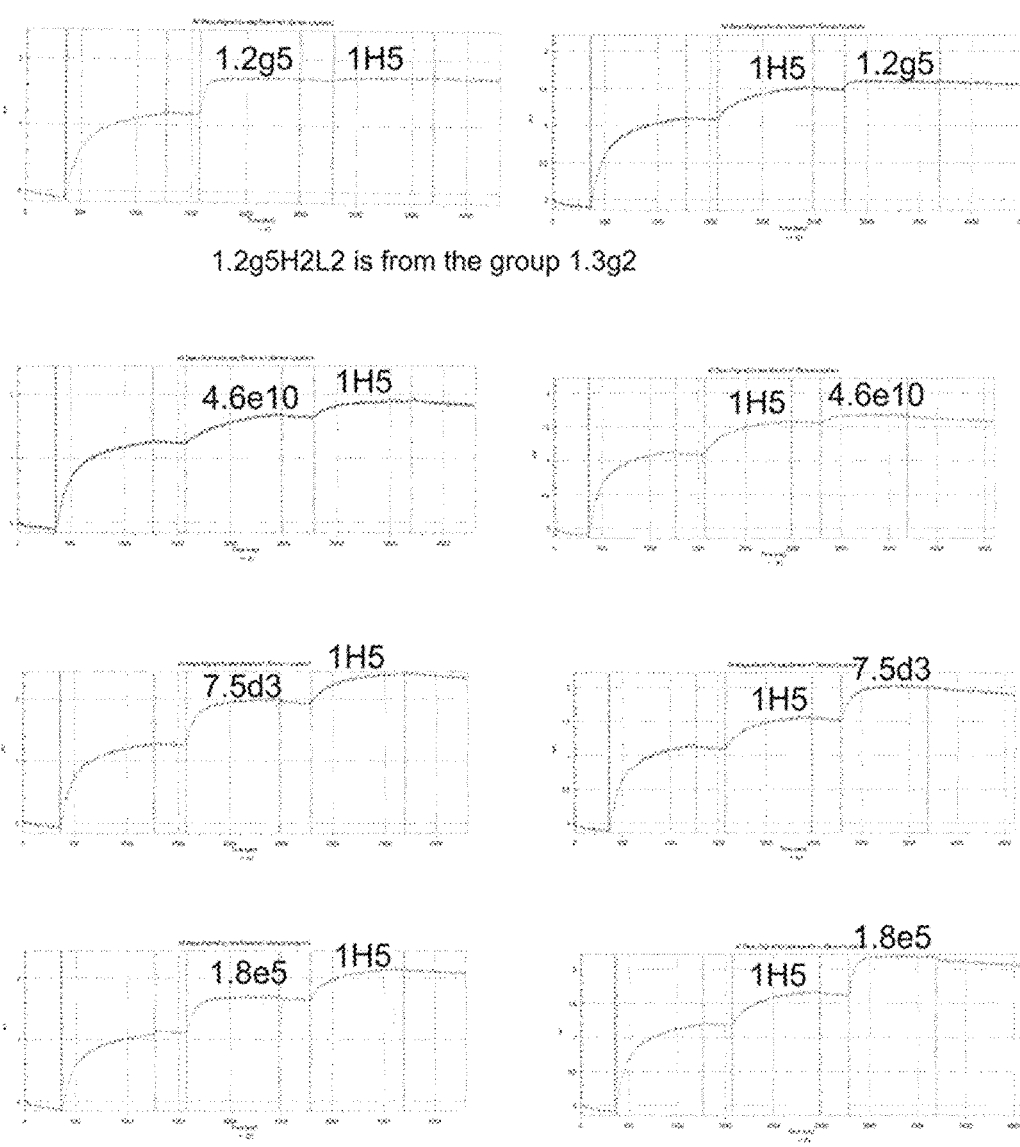
Figure 33C:
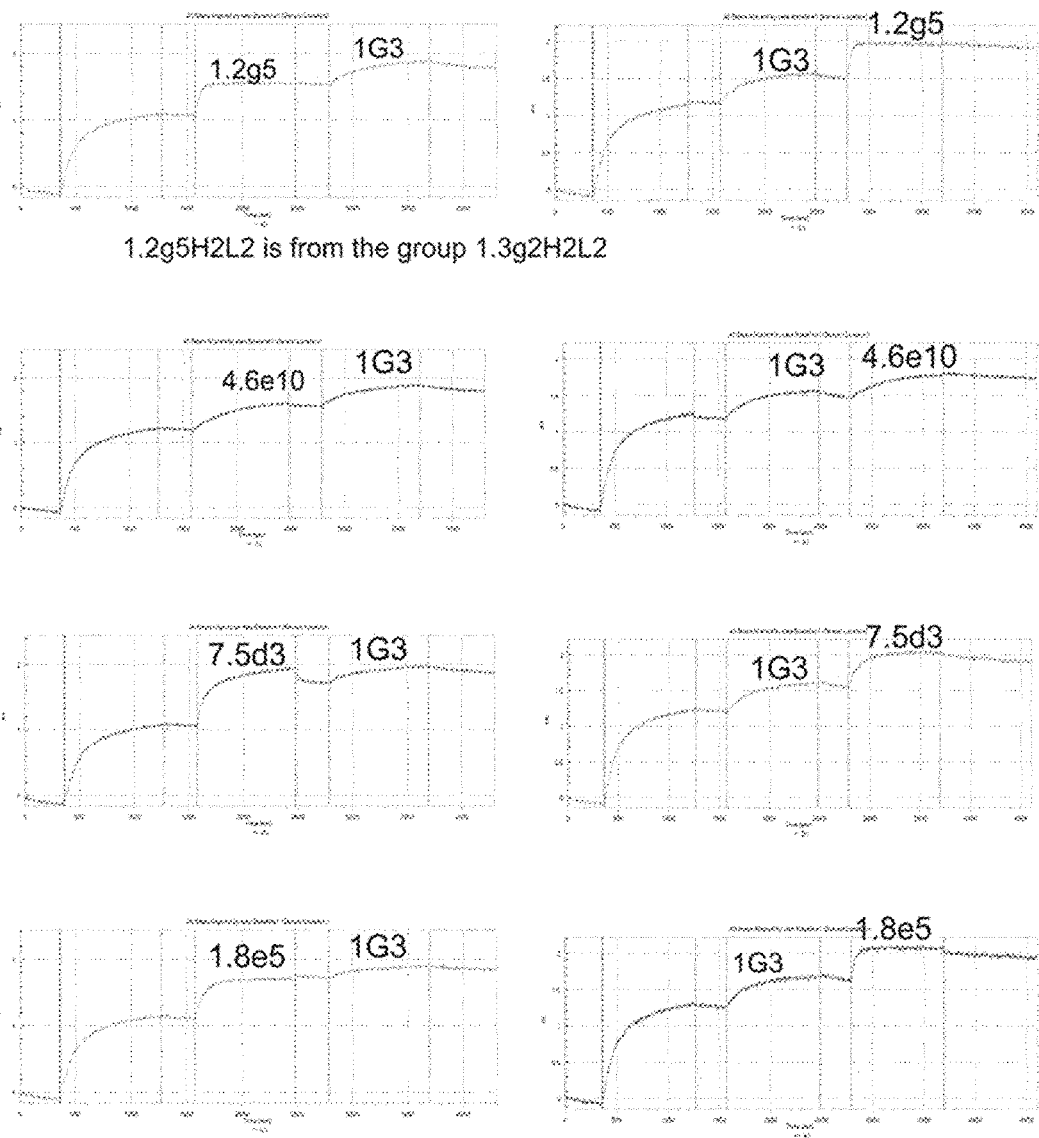

FIG. 33. Epitope binning anti-MERS HCAb. MERS-S1-Fc was loaded on huFc capture tips H2L2 antibodies were used at 10 micrograms/ml and HCAbs at 20 micrograms/ml.

(A) 1H5 HCAb and 1E10 HCAb compete for epitope binding, while 1G3 HCAb recognizes different epitope.

(B) 1H5 HCAb competes with 1.3 g2 H2L2 for epitope binding. 1H5 HCAb binds to a different epitope from that bound by the 1.8e5 H2L2 (7.5d3 H2L2) group. 1H5 HCAb interferes with the binding of 4.6e10 H2L2.

(C) 1G3 HCAb does not interfere with the binding of 1.2 g5 H2L2 (group 1.3 g2 H2L2) or 4.6e10 H2L2. 1G3 HCAb does not interfere with the binding of 1.8e10 H2L2 (7.5d3). However, once 1.8e10 H2L2 (7.5d3) is bound, it abolishes the binding of 1G3 HCAb almost completely.

FIG. 34. Table showing virus neutralization and receptor binding inhibition by anti-MERS-S mAbs.

DETAILED DESCRIPTION

Anti-MERS-S Antibodies

The examples show that the 1.6c7 antibody binds to the S2 domain (see FIGS. 8 and 10). The examples also show that the 1.6c7 antibody binds to MERS-S with a strong binding affinity (FIG. 3A shows an affinity value of approximately $5.0 \times 10^{-10}$ M). This antibody is also shown to be capable of neutralizing MERS-S VSV pseudoparticles infection (see FIGS. 8, 16, 19 and 20). The 1.6c7 antibody is advantageously capable of neutralizing MERS-S pseudovirus infectivity with an IC50 of approximately 0.59 pg/ml (see FIG. 16). The examples also show that a human IgG1 comprising the heavy and light chain variable sequences of the 1.6c7 antibody is advantageously capable of neutralizing MERS-S pseudovirus infectivity with an $IC_{50}$ of approximately 2.5 pg/ml (see FIG. 16). Without wishing to be bound by any theory, the inventors believe that the 1.6c7 antibody may neutralize MERS-CoV infection by inhibiting membrane fusion (see FIG. 21). The examples also show that the 1.6c7 antibody is protective in vivo in that 100% of treated mice survived after 12 days post-infection with MERS-CoV (see FIG. 24). The 1.607 antibody is also cross-reactive for SARS, MHV and NL63 coronaviruses (see FIG. 10). This is advantageous because it means that the antibody is useful for preventing, treating and diagnosing several types of betacoronavirus. Without wishing to be bound by any theory, the reason for this cross-reactivity is thought to be that the linear epitope recognized by the 1.6c7 antibody, residues 1230-1242 of the MERS-S protein (DFQDELD-EFFKNV), that is highly conserved across coronavirus species (see FIGS. 12, 13, 14 and 16).

Similar functional properties can be expected to be associated with the antibodies defined below which share structural and binding characteristics with the 1.6c7 antibody.

The invention provides an anti-MERS-S antibody that binds to the same epitope as an antibody comprising a heavy chain variable region of the amino acid sequence of SEQ ID NO: 70 and a light chain variable region of the amino acid sequence of SEQ ID NO: 74. Accordingly, in some embodiments, the anti-MERS-S antibody binds to an epitope that comprises residues 1230-1242 of the MERS-S protein (SEQ ID NO: 81).

The invention further provides an anti-MERS-S antibody that binds to the same epitope as a heavy chain-only antibody comprising a heavy chain variable region of the amino acid sequence of SEQ ID NO: 70.

The invention further provides an anti-MERS-S antibody that competes for binding to MERS-S with an antibody comprising a heavy chain variable region of the amino acid sequence of SEQ ID NO: 70 and a light chain variable region of the amino acid sequence of SEQ ID NO: 74.

The invention further provides an anti-MERS-S antibody that competes for binding to MERS-S with a heavy chain-only antibody comprising a heavy chain variable region of the amino acid sequence of SEQ ID NO: 70.

The invention further provides an anti-MERS-S antibody comprising complementarity determining regions (CDRs) with the sequences of:
   i. SEQ ID NO: 83 for CDR1 of the heavy chain;
   ii. SEQ ID NO: 84 for CDR2 of the heavy chain;
   iii. SEQ ID NO: 85 for CDR3 of the heavy chain;
   iv. SEQ ID NO: 86 for CDR2 of the light chain;
   v. SEQ TD NO: 87 for CDR2 of the light chain; and
   vi. SEQ ID NO: 88 for CDR3 of the light chain.

In some embodiments, the antibody comprises a heavy chain variable region of the amino acid sequence of SEQ ID NO: 70.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 70.

In some embodiments, the antibody comprises a light chain variable region of the amino acid sequence of SEQ ID NO: 74.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 74.

In some embodiments, the antibody comprises a heavy chain variable region of the amino acid sequence of SEQ ID NO: 70 and a light chain variable region of the amino acid sequence of SEQ ID NO: 74.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 70 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 74.

The invention further provides an anti-MERS-S antibody comprising complementarity determining regions (CDRs) with:
   i. a sequence that is at least 90% identical to SEQ ID NO: 83 for CDR1 of the heavy chain;
   ii. a sequence that is at least 90% identical to SEQ ID NO: 84 for CDR2 of the heavy chain;
   iii. a sequence that is at least 90% identical to SEQ ID NO: 85 for CDR3 of the heavy chain;
   iv. a sequence that is at least 90% identical to SEQ ID NO: 86 for CDR1 of the light chain;
   v. a sequence that is at least 90% identical to SEQ ID NO: 87 for CDR2 of the light chain; and
   vi. a sequence that is at least 90% identical to SEQ ID NO: 88 for CDR3 of the light chain,
wherein the antibody competes for binding to MERS-S with an antibody comprising a heavy chain variable region of the amino acid sequence of SEQ ID NO: 70 and a light chain variable region of the amino acid sequence of SEQ ID NO: 74.

The invention further provides an anti-MERS-S antibody comprising complementarity determining regions (CDRs) with:
   i. a sequence that is at least 95% identical to SEQ ID NO: 83 for CDR1 of the heavy
   ii. a sequence that is at least 95% identical to SEQ ID NO: 84 for CDR2 of the heavy chain;
   iii. a sequence that is at least 95% identical to SEQ ID NO: 85 for CDR3 of the heavy chain;
   iv. a sequence that is at least 95% identical to SEQ ID NO: 86 for CDR1 of the light chain;
   v. a sequence that is at least 95% identical to SEQ ID NO: 87 for CDR2 of the light chain; and
   vi. a sequence that is at least 95% identical to SEQ ID NO: 88 for CDR3 of the light chain, wherein the antibody competes for binding to MERS-S with an antibody comprising a heavy chain variable region of the amino acid sequence of SEQ ID NO: 70 and a light chain variable region of the amino acid sequence of SEQ ID NO: 74.

The examples show that the 3.5 g6 antibody binds to a conformational epitope in the S2 domain (see FIGS. 8, 10 and 12). The examples also show that the 3.5 g6 antibody binds to MERS-S with a strong binding affinity (FIG. 3A shows an affinity value of approximately $2.2 \times 10^{-9}$ M). This antibody is also shown to be capable of neutralizing MERS-S VSV pseudoparticles infection (see FIGS. 8, 16 and 19). Without wishing to be bound by any theory, the inventors believe that the 3.5 g6 antibody may neutralize MERS-CoV infection by inhibiting membrane fusion (see FIG. 21). The examples also show that the 3.5 g6 antibody is protective in vivo in that 100% of treated mice survived after 12 days post-infection with MERS-CoV (see FIG. 24).

Similar functional properties can be expected to be associated with the antibodies defined below which share structural and binding characteristics with the 3.5 g6 antibody.

The invention provides an anti-MERS-S antibody that binds to the same epitope as an antibody comprising a heavy chain variable region of the amino acid sequence of SEQ ID NO: 69 and a light chain variable region of the amino acid sequence of SEQ ID NO: 72.

The invention further provides an anti-MERS-S antibody that binds to the same epitope as a heavy chain-only antibody comprising a heavy chain variable region of the amino acid sequence of SEQ ID NO: 69.

The invention further provides an anti-MERS-S antibody that competes for binding to MERS-S with an antibody comprising a heavy chain variable region of the amino acid sequence of SEQ ID NO: 69 and a light chain variable region of the amino acid sequence of SEQ ID NO: 72.

The invention further provides an anti-MERS-S antibody that competes for binding to MERS-S with a heavy chain-only antibody comprising a heavy chain variable region of the amino acid sequence of SEQ ID NO: 69.

The invention further provides an anti-MERS-S antibody comprising complementarity determining regions (CDRs) with the sequences of:
  i. SEQ ID NO: 89 for CDR1 of the heavy chain;
  ii. SEQ ID NO: 90 for CDR2 of the heavy chain;
  iii. SEQ ID NO: 91 for CDR3 of the heavy chain;
  iv. SEQ ID NO: 92 for CDR1 of the light chain;
  v. SEQ ID NO: 93 for CDR2 of the light chain; and
  vi. SEQ ID NO: 94 for CDR3 of the light chain.

In some embodiments, the antibody comprises a heavy chain variable region of the amino acid sequence of SEQ ID NO: 69.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 69.

In some embodiments, the antibody comprises a light chain variable region of the amino acid sequence of SEQ ID NO: 72.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 72.

In some embodiments, the antibody comprises a heavy chain variable region of the amino acid sequence of SEQ ID NO: 69 and a light chain variable region of the amino acid sequence of SEQ ID NO: 72.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 69 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 72.

The invention further provides an anti-MERS-S antibody comprising complementarity determining regions (CDRs) with:
  i. a sequence that is at least 90% identical to SEQ ID NO: 89 for CDR1 of the heavy chain;
  ii. a sequence that is at least 90% identical to SEQ ID NO: 90 for CDR2 of the heavy chain;
  iii. a sequence that is at least 90% identical to SEQ ID NO: 91 for CDR3 of the heavy chain;
  iv. a sequence that is at least 90% identical to SEQ ID NO: 92 for CDR1 of the light chain;
  v. a sequence that is at least 90% identical to SEQ ID NO: 93 for CDR2 of the light chain; and
  vi. a sequence that is at least 90% identical to SEQ ID NO: 94 for CDR3 of the light chain,
wherein the antibody competes for binding to MERS-S with an antibody comprising a heavy chain variable region of the amino acid sequence of SEQ ID NO: 69 and a light chain variable region of the amino acid sequence of SEQ ID NO: 72.

The invention further provides an anti-MERS-S antibody comprising complementarity determining regions (CDRs) with:
  i. a sequence that is at least 95% identical to SEQ ID NO: 89 for CDR1 of the heavy chain;
  ii. a sequence that is at least 95% identical to SEQ ID NO: 90 for CDR2 of the heavy chain;
  iii. a sequence that is at least 95% identical to SEQ ID NO: 91 for CDR3 of the heavy chain;
  iv. a sequence that is at least 95% identical to SEQ ID NO: 92 for CDR1 of the light chain;
  v. a sequence that is at least 95% identical to SEQ ID NO: 93 for CDR2 of the light chain; and
  vi. a sequence that is at least 95% identical to SEQ ID NO: 94 for CDR3 of the light chain,
wherein the antibody competes for binding to MERS-S with an antibody comprising a heavy chain variable region of the amino acid sequence of SEQ ID NO: 69 and a light chain variable region of the amino acid sequence of SEQ ID NO: 72.

The 7.7 g6, 1.6f9, 1.2 g5, 5.2b7, 5.5e11 and 1.3 g2 antibodies bind to the same epitope group in the S1B domain (see FIGS. 5A, 16 and 19). The examples show that each of the 7.7 g6, 1.6f9, 1.2 g5, 5.2b7, 5.5e11 and 1.3 g2 bind to MERS-S1 with a strong binding affinity (FIG. 3A shows affinity values of approximately $3.6 \times 10^{-10}$, $5.3 \times 10^{-10}$, $8.1 \times 10^{-11}$, $3.6 \times 10^{-10}$, $3.0 \times 10^{-10}$ and $1.1 \times 10^{-9}$, respectively). Each of the 7.7 g6, 1.6f9, 1.2 g5, 5.2b7 and 5.5e11 antibodies is also shown to be capable of neutralizing MERS-S VSV pseudoparticles infection (see FIGS. 16 and 19). The 7.7 g6, 1.6f9, 1.2 g5, 5.2b7 and 5.5e11 antibodies are advantageously capable of neutralizing MERS-S pseudovirus infectivity with an IC50 of approximately 0.00011, 0.00038, 0.00062, 0.00081 and 0.0017 g/ml, respectively (see FIG. 16). In addition, the 7.7 g6, 1.6f9, 1.2 g5, 5.2b7 and 5.5e11 antibodies are advantageously capable of neutralizing MERS-CoV infectivity with an IC50 of approximately 0.0003, 0.003, 0.001, 0.005 and 0.0006 µg/ml, respectively (see FIG. 16). The examples also show that a human IgG1 comprising the heavy and light chain variable sequences of one of the 7.7 g6, 1.6f9 and 1.2 g5 antibodies is advantageously capable of neutralizing MERS-S pseudovirus infectivity with an $IC_{50}$ of approximately 0.02, 0.019 and 0.007 µg/ml, respectively (see FIG. 16). The 7.7 g6, 1.6f9 and 1.2 g5 antibodies are also shown to be capable of inhibiting MERS-S-DPP4 receptor binding (see FIG. 20). The examples also show that each of the 7.7 g6, 1.6f9 and 1.2 g5 antibodies is protective in vivo in that 80% (1.6f9) or 100% (7.7 g6, 1.2 g5) of treated mice survived after 12 days post-infection with MERS-CoV (see FIG. 24).

Similar functional properties can be expected to be associated with the antibodies defined below which share structural and binding characteristics with one or more of the 7.7 g6, 1.6f9, 1.2 g5, 5.2b7, 5.5e11 and 1.3 g2 antibodies.

The invention provides an anti-MERS-S antibody that binds to the same epitope as an antibody comprising a heavy chain variable region of the amino acid sequence of SEQ ID NO: 28 and a light chain variable region of the amino acid sequence of SEQ ID NO: 63.

The invention further provides an anti-MERS-S antibody that binds to the same epitope as a heavy chain-only antibody comprising a heavy chain variable region of the amino acid sequence of SEQ ID NO: 28.

The invention further provides an anti-MERS-S antibody that competes for binding to MERS-S with an antibody comprising a heavy chain variable region of the amino acid sequence of SEQ ID NO: 28 and a light chain variable region of the amino acid sequence of SEQ ID NO: 63.

The invention further provides an anti-MERS-S antibody that competes for binding to MERS-S with a heavy chain-only antibody comprising a heavy chain variable region of the amino acid sequence of SEQ ID NO: 28.

The invention further provides an anti-MERS-S antibody comprising complementarity determining regions (CDRs) with the sequences of:

i. SEQ ID NO: 95 for CDR1 of the heavy chain;
    ii. SEQ ID NO: 96 for CDR2 of the heavy chain;
    iii. SEQ ID NO: 97 for CDR3 of the heavy chain;
    iv. SEQ ID NO: 98 for CDR1 of the light chain;
    v. SEQ ID NO: 99 for CDR2 of the light chain; and
    vi. SEQ ID NO: 100 for CDR3 of the light chain.

In some embodiments, the antibody comprises a heavy chain variable region of the amino acid sequence of SEQ ID NO: 28.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 28.

In some embodiments, the antibody comprises a light chain variable region of the amino acid sequence of SEQ ID NO: 63.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 63.

In some embodiments, the antibody comprises a heavy chain variable region of the amino acid sequence of SEQ ID NO: 28 and a light chain variable region of the amino acid sequence of SEQ ID NO: 63.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 28 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 63.

The invention further provides an anti-MERS-S antibody comprising complementarity determining regions (CDRs) with:

i. a sequence that is at least 90% identical to SEQ ID NO: 95 for CDR1 of the heavy chain;
    ii. a sequence that is at least 90% identical to SEQ ID NO: 96 for CDR2 of the heavy chain;
    iii. a sequence that is at least 90% identical to SEQ ID NO: 97 for CDR3 of the heavy chain;
    iv. a sequence that is at least 90% identical to SEQ ID NO: 98 for CDR1 of the light chain;
    v. a sequence that is at least 90% identical to SEQ ID NO: 99 for CDR2 of the light chain; and
    vi. a sequence that is at least 90% identical to SEQ ID NO: 100 for CDR3 of the light chain, wherein the antibody competes for binding to MERS-S with an antibody comprising a heavy chain variable region of the amino acid sequence of SEQ ID NO: 28 and a light chain variable region of the amino acid sequence of SEQ ID NO: 63.

The invention further provides an anti-MERS-S antibody comprising complementarity determining regions (CDRs) with:

i. a sequence that is at least 95% identical to SEQ ID NO: 95 for CDR1 of the heavy chain;
    ii. a sequence that is at least 95% identical to SEQ ID NO: 96 for CDR2 of the heavy chain;
    iii. a sequence that is at least 95% identical to SEQ ID NO: 97 for CDR3 of the heavy chain;
    iv. a sequence that is at least 95% identical to SEQ ID NO: 98 for CDR1 of the light chain;
    v. a sequence that is at least 95% identical to SEQ ID NO: 99 for CDR2 of the light
    vi. a sequence that is at least 95% identical to SEQ ID NO: 100 for CDR3 of the light chain, wherein the antibody competes for binding to MERS-S with an antibody comprising a heavy chain variable region of the amino acid sequence of SEQ ID NO: 28 and a light chain variable region of the amino acid sequence of SEQ ID NO: 63.

The invention provides an anti-MERS-S antibody that binds to the same epitope as an antibody comprising a heavy chain variable region of the amino acid sequence of SEQ ID NO: 26 and a light chain variable region of the amino acid sequence of SEQ ID NO: 65.

The invention further provides an anti-MERS-S antibody that binds to the same epitope as a heavy chain-only antibody comprising a heavy chain variable region of the amino acid sequence of SEQ ID NO: 26.

The invention further provides an anti-MERS-S antibody that competes for binding to MERS-S with an antibody comprising a heavy chain variable region of the amino acid sequence of SEQ ID NO: 26 and a light chain variable region of the amino acid sequence of SEQ ID NO: 65.

The invention further provides an anti-MERS-S antibody that competes for binding to MERS-S with a heavy chain-only antibody comprising a heavy chain variable region of the amino acid sequence of SEQ ID NO: 26.

The invention further provides an anti-MERS-S antibody comprising complementarity determining regions (CDRs) with the sequences of:

i. SEQ ID NO: 101 for CDR1 of the heavy chain;
    ii. SEQ ID NO: 102 for CDR2 of the heavy chain;
    iii. SEQ ID NO: 103 for CDR3 of the heavy chain;
    iv. SEQ ID NO: 104 for CDR1 of the light chain;
    v. SEQ ID NO: 105 for CDR2 of the light chain; and
    vi. SEQ ID NO: 106 for CDR3 of the light chain.

In some embodiments, the antibody comprises a heavy chain variable region of the amino acid sequence of SEQ ID NO: 26.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 26.

In some embodiments, the antibody comprises a light chain variable region of the amino acid sequence of SEQ ID NO: 65.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 65.

In some embodiments, the antibody comprises a heavy chain variable region of the amino acid sequence of SEQ ID NO: 26 and a light chain variable region of the amino acid sequence of SEQ ID NO: 65.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 26 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 65.

The invention further provides an anti-MERS-S antibody comprising complementarity determining regions (CDRs) with:

i. a sequence that is at least 90% identical to SEQ ID NO: 101 for CDR1 of the heavy chain;
    ii. a sequence that is at least 90% identical to SEQ ID NO: 102 for CDR2 of the
    iii. a sequence that is at least 90% identical to SEQ ID NO: 103 for CDR3 of the heavy chain;
    iv. a sequence that is at least 90% identical to SEQ ID NO: 104 for CDR1 of the light chain;
    v. a sequence that is at least 90% identical to SEQ ID NO: 105 for CDR2 of the light chain; and
    vi. a sequence that is at least 90% identical to SEQ ID NO: 106 for CDR3 of the light chain, wherein the antibody competes for binding to MERS-S with an antibody comprising a heavy chain variable region of the amino acid sequence of SEQ ID NO: 26 and a light chain variable region of the amino acid sequence of SEQ ID NO: 65.

The invention further provides an anti-MERS-S antibody comprising complementarity determining regions (CDRs) with:

i. a sequence that is at least 95% identical to SEQ ID NO: 101 for CDR1 of the heavy chain;
    ii. a sequence that is at least 95% identical to SEQ ID NO: 102 for CDR2 of the heavy chain;
    iii. a sequence that is at least 95% identical to SEQ ID NO: 103 for CDR3 of the heavy chain;
    iv. a sequence that is at least 95% identical to SEQ ID NO: 104 for CDR1 of the light chain;
    v. a sequence that is at least 95% identical to SEQ ID NO: 105 for CDR2 of the light chain; and
    vi. a sequence that is at least 95% identical to SEQ ID NO: 106 for CDR3 of the light chain, wherein the antibody competes for binding to MERS-S with an antibody comprising a heavy chain variable region of the amino acid sequence of SEQ ID NO: 26 and a light chain variable region of the amino acid sequence of SEQ ID NO: 65.

The invention provides an anti-MERS-S antibody that binds to the same epitope as an antibody comprising a heavy chain variable region of the amino acid sequence of SEQ ID NO: 107 and a light chain variable region of the amino acid sequence of SEQ ID NO: 108.

The invention further provides an anti-MERS-S antibody that binds to the same epitope as a heavy chain-only antibody comprising a heavy chain variable region of the amino acid sequence of SEQ ID NO: 107.

The invention further provides an anti-MERS-S antibody that competes for binding to MERS-S with an antibody comprising a heavy chain variable region of the amino acid sequence of SEQ ID NO: 107 and a light chain variable region of the amino acid sequence of SEQ ID NO: 108.

The invention further provides an anti-MERS-S antibody that competes for binding to MERS-S with a heavy chain-only antibody comprising a heavy chain variable region of the amino acid sequence of SEQ ID NO: 107.

The invention further provides an anti-MERS-S antibody comprising complementarity determining regions (CDRs) with the sequences of:

i. SEQ ID NO: 109 for CDR1 of the heavy chain;
    ii. SEQ ID NO: 110 for CDR2 of the heavy chain;
    iii. SEQ ID NO: 111 for CDR3 of the heavy chain;
    iv. SEQ ID NO: 112 for CDR1 of the light chain;
    v. SEQ ID NO: 113 for CDR2 of the light chain; and
    vi. SEQ ID NO: 114 for CDR3 of the light chain.

In some embodiments, the antibody comprises a heavy chain variable region of the amino acid sequence of SEQ ID NO: 107.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 107.

In some embodiments, the antibody comprises a light chain variable region of the amino acid sequence of SEQ ID NO: 108.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 108.

In some embodiments, the antibody comprises a heavy chain variable region of the amino acid sequence of SEQ ID NO: 107 and a light chain variable region of the amino acid sequence of SEQ ID NO: 108.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 107 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 108.

The invention further provides an anti-MERS-S antibody comprising complementarity determining regions (CDRs) with:

i. a sequence that is at least 90% identical to SEQ ID NO: 109 for CDR1 of the heavy chain;

ii. a sequence that is at least 90% identical to SEQ ID NO: 110 for CDR2 of the heavy chain;

iii. a sequence that is at least 90% identical to SEQ ID NO: 111 for CDR3 of the heavy chain;

iv. a sequence that is at least 90% identical to SEQ ID NO: 112 for CDR1 of the light v. a sequence that is at least 90% identical to SEQ ID NO: 113 for CDR2 of the light chain; and vi. a sequence that is at least 90% identical to SEQ ID NO: 114 for CDR3 of the light chain, wherein the antibody competes for binding to MERS-S with an antibody comprising a heavy chain variable region of the amino acid sequence of SEQ ID NO: 107 and a light chain variable region of the amino acid sequence of SEQ ID NO: 108.

The invention further provides an anti-MERS-S antibody comprising complementarity determining regions (CDRs) with:

i. a sequence that is at least 95% identical to SEQ ID NO: 109 for CDR1 of the heavy chain;

ii. a sequence that is at least 95% identical to SEQ ID NO: 110 for CDR2 of the heavy chain;

iii. a sequence that is at least 95% identical to SEQ ID NO: 111 for CDR3 of the heavy chain;

iv. a sequence that is at least 95% identical to SEQ ID NO: 112 for CDR1 of the light chain;

v. a sequence that is at least 95% identical to SEQ ID NO: 113 for CDR2 of the light chain; and vi. a sequence that is at least 95% identical to SEQ ID NO: 114 for CDR3 of the light chain, wherein the antibody competes for binding to MERS-S with an antibody comprising a heavy chain variable region of the amino acid sequence of SEQ ID NO: 107 and a light chain variable region of the amino acid sequence of SEQ ID NO: 108.

The invention provides an anti-MERS-S antibody that binds to the same epitope as an antibody comprising a heavy chain variable region of the amino acid sequence of SEQ ID NO: 9 and a light chain variable region of the amino acid sequence of SEQ ID NO: 49.

The invention further provides an anti-MERS-S antibody that binds to the same epitope as a heavy chain-only antibody comprising a heavy chain variable region of the amino acid sequence of SEQ ID NO: 9.

The invention further provides an anti-MERS-S antibody that competes for binding to MERS-S with an antibody comprising a heavy chain variable region of the amino acid sequence of SEQ ID NO: 9 and a light chain variable region of the amino acid sequence of SEQ ID NO: 49.

The invention further provides an anti-MERS-S antibody that competes for binding to MERS-S with a heavy chain-only antibody comprising a heavy chain variable region of the amino acid sequence of SEQ ID NO: 9.

The invention further provides an anti-MERS-S antibody comprising complementarity determining regions (CDRs) with the sequences of:

i. SEQ ID NO: 115 for CDR1 of the heavy chain;

ii. SEQ ID NO: 116 for CDR2 of the heavy chain;

iii. SEQ ID NO: 117 for CDR3 of the heavy chain;

iv. SEQ ID NO: 118 for CDR1 of the light chain;

v. SEQ ID NO: 119 for CDR2 of the light chain; and vi. SEQ ID NO: 120 for CDR3 of the light chain.

In some embodiments, the antibody comprises a heavy chain variable region of the amino acid sequence of SEQ ID NO: 9.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 9.

In some embodiments, the antibody comprises a light chain variable region of the amino acid sequence of SEQ ID NO: 49.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 49.

In some embodiments, the antibody comprises a heavy chain variable region of the amino acid sequence of SEQ ID NO: 9 and a light chain variable region of the amino acid sequence of SEQ ID NO: 49.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 9 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 49.

The invention further provides an anti-MERS-S antibody comprising complementarity determining regions (CDRs) with:

i. a sequence that is at least 90% identical to SEQ ID NO: 115 for CDR1 of the heavy chain;

ii. a sequence that is at least 90% identical to SEQ ID NO: 116 for CDR2 of the heavy chain;

iii. a sequence that is at least 90% identical to SEQ ID NO: 117 for CDR3 of the heavy chain;

iv. a sequence that is at least 90% identical to SEQ ID NO: 118 for CDR1 of the light chain;

v. a sequence that is at least 90% identical to SEQ ID NO: 119 for CDR2 of the light chain; and vi. a sequence that is at least 90% identical to SEQ ID NO: 120 for CDR3 of the light chain, wherein the antibody competes for binding to MERS-S with an antibody comprising a heavy chain variable region of the amino acid sequence of SEQ ID NO: 9 and a light chain variable region of the amino acid sequence of SEQ ID NO: 49.

The invention further provides an anti-MERS-S antibody comprising complementarity determining regions (CDRs) with:

i. a sequence that is at least 95% identical to SEQ ID NO: 115 for CDR1 of the heavy chain;

ii. a sequence that is at least 95% identical to SEQ ID NO: 116 for CDR2 of the heavy chain;

iii. a sequence that is at least 95% identical to SEQ ID NO: 117 for CDR3 of the heavy chain;

iv. a sequence that is at least 95% identical to SEQ ID NO: 118 for CDR1 of the light chain;

v. a sequence that is at least 95% identical to SEQ ID NO: 119 for CDR2 of the light chain; and vi. a sequence that is at least 95% identical to SEQ ID NO: 120 for CDR3 of the light chain, wherein the antibody competes for binding to MERS-S with an antibody comprising a heavy chain variable region of the amino acid sequence of SEQ ID NO: 9 and a light chain variable region of the amino acid sequence of SEQ ID NO: 49.

The invention provides an anti-MERS-S antibody that binds to the same epitope as an antibody comprising a heavy chain variable region of the amino acid sequence of SEQ ID NO: 20 and a light chain variable region of the amino acid sequence of SEQ ID NO: 40.

The invention further provides an anti-MERS-S antibody that binds to the same epitope as a heavy chain-only antibody comprising a heavy chain variable region of the amino acid sequence of SEQ ID NO: 20.

The invention further provides an anti-MERS-S antibody that competes for binding to MERS-S with an antibody comprising a heavy chain variable region of the amino acid sequence of SEQ ID NO: 20 and a light chain variable region of the amino acid sequence of SEQ ID NO: 40. The invention further provides an anti-MERS-S antibody that competes for binding to MERS-S with a heavy chain-only antibody comprising a heavy chain variable region of the amino acid sequence of SEQ ID NO: 20.

The invention further provides an anti-MERS-S antibody comprising complementarity determining regions (CDRs) with the sequences of:

i. SEQ ID NO: 121 for CDR1 of the heavy chain;

ii. SEQ ID NO: 122 for CDR2 of the heavy chain;

iii. SEQ ID NO: 123 for CDR3 of the heavy chain;

iv. SEQ ID NO: 124 for CDR1 of the light chain;

v. SEQ ID NO: 125 for CDR2 of the light chain; and vi. SEQ ID NO: 126 for CDR3 of the light chain.

In some embodiments, the antibody comprises a heavy chain variable region of the amino acid sequence of SEQ ID NO: 20.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 20.

In some embodiments, the antibody comprises a light chain variable region of the amino acid sequence of SEQ ID NO: 40.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 40.

In some embodiments, the antibody comprises a heavy chain variable region of the amino acid sequence of SEQ ID NO: 20 and a light chain variable region of the amino acid sequence of SEQ ID NO: 40.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 20 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 40.

The invention further provides an anti-MERS-S antibody comprising complementarity determining regions (CDRs) with:

i. a sequence that is at least 90% identical to SEQ ID NO: 121 for CDR1 of the heavy chain;

ii. a sequence that is at least 90% identical to SEQ ID NO: 122 for CDR2 of the heavy chain;

iii. a sequence that is at least 90% identical to SEQ ID NO: 123 for CDR3 of the heavy chain;

iv. a sequence that is at least 90% identical to SEQ ID NO: 124 for CDR1 of the light chain;

v. a sequence that is at least 90% identical to SEQ ID NO: 125 for CDR2 of the light chain; and vi. a sequence that is at least 90% identical to SEQ ID NO: 126 for CDR3 of the light chain, wherein the antibody competes for binding to MERS-S with an antibody comprising a heavy chain variable region of the amino acid sequence of SEQ ID NO: 20 and a light chain variable region of the amino acid sequence of SEQ ID NO: 40.

The invention further provides an anti-MERS-S antibody comprising complementarity determining regions (CDRs) with:

i. a sequence that is at least 95% identical to SEQ ID NO: 121 for CDR1 of the ii. a sequence that is at least 95% identical to SEQ ID NO: 122 for CDR2 of the heavy chain;

iii. a sequence that is at least 95% identical to SEQ ID NO: 123 for CDR3 of the heavy chain;

iv. a sequence that is at least 95% identical to SEQ ID NO: 124 for CDR1 of the light chain;

v. a sequence that is at least 95% identical to SEQ ID NO: 125 for CDR2 of the light chain; and vi. a sequence that is at least 95% identical to SEQ ID NO: 126 for CDR3 of the light chain, wherein the antibody competes for binding to MERS-S with an antibody comprising a heavy chain variable region of the amino acid sequence of SEQ ID NO: 20 and a light chain variable region of the amino acid sequence of SEQ ID NO: 40.

The invention provides an anti-MERS-S antibody that binds to the same epitope as an antibody comprising a heavy chain variable region of the amino acid sequence of SEQ ID NO: 22 and a light chain variable region of the amino acid sequence of SEQ ID NO: 59.

The invention further provides an anti-MERS-S antibody that binds to the same epitope as a heavy chain-only antibody comprising a heavy chain variable region of the amino acid sequence of SEQ ID NO: 22.

The invention further provides an anti-MERS-S antibody that competes for binding to MERS-S with an antibody comprising a heavy chain variable region of the amino acid sequence of SEQ ID NO: 22 and a light chain variable region of the amino acid sequence of SEQ ID NO: 59.

The invention further provides an anti-MERS-S antibody that competes for binding to MERS-S with a heavy chain-only antibody comprising a heavy chain variable region of the amino acid sequence of SEQ ID NO: 22.

The invention further provides an anti-MERS-S antibody comprising complementarity determining regions (CDRs) with the sequences of:

i. SEQ ID NO: 127 for CDR1 of the heavy chain;
ii. SEQ ID NO: 128 for CDR2 of the heavy chain;
iii. SEQ ID NO: 129 for CDR3 of the heavy chain;
iv. SEQ ID NO: 130 for CDR1 of the light chain;
v. SEQ ID NO: 131 for CDR2 of the light chain; and
vi. SEQ ID NO: 132 for CDR3 of the light chain.

In some embodiments, the antibody comprises a heavy chain variable region of the amino acid sequence of SEQ ID NO: 22.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 22.

In some embodiments, the antibody comprises a light chain variable region of the amino acid sequence of SEQ ID NO: 59.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 59.

In some embodiments, the antibody comprises a heavy chain variable region of the amino acid sequence of SEQ ID NO: 22 and a light chain variable region of the amino acid sequence of SEQ ID NO: 59.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 22 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 59.

The invention further provides an anti-MERS-S antibody comprising complementarity determining regions (CDRs) with:

i. a sequence that is at least 90% identical to SEQ ID NO: 127 for CDR1 of the heavy chain;
ii. a sequence that is at least 90% identical to SEQ ID NO: 128 for CDR2 of the heavy chain;
iii. a sequence that is at least 90% identical to SEQ ID NO: 129 for CDR3 of the heavy chain;
iv. a sequence that is at least 90% identical to SEQ ID NO: 130 for CDR1 of the light chain;
v. a sequence that is at least 90% identical to SEQ ID NO: 131 for CDR2 of the light chain; and
vi. a sequence that is at least 90% identical to SEQ ID NO: 132 for CDR3 of the light chain, wherein the antibody competes for binding to MERS-S with an antibody comprising a heavy chain variable region of the amino acid sequence of SEQ ID NO: 22 and a light chain variable region of the amino acid sequence of SEQ ID NO: 59.

The invention further provides an anti-MERS-S antibody comprising complementarity determining regions (CDRs) with:

i. a sequence that is at least 95% identical to SEQ ID NO: 127 for CDR1 of the heavy chain;
ii. a sequence that is at least 95% identical to SEQ ID NO: 128 for CDR2 of the heavy chain;
iii. a sequence that is at least 95% identical to SEQ ID NO: 129 for CDR3 of the heavy chain;
iv. a sequence that is at least 95% identical to SEQ ID NO: 130 for CDR1 of the light
v. a sequence that is at least 95% identical to SEQ ID NO: 131 for CDR2 of the light chain; and
vi. a sequence that is at least 95% identical to SEQ ID NO: 132 for CDR3 of the light chain, wherein the antibody competes for binding to MERS-S with an antibody comprising a heavy chain variable region of the amino acid sequence of SEQ ID NO: 22 and a light chain variable region of the amino acid sequence of SEQ ID NO: 59.

Figure 2D:
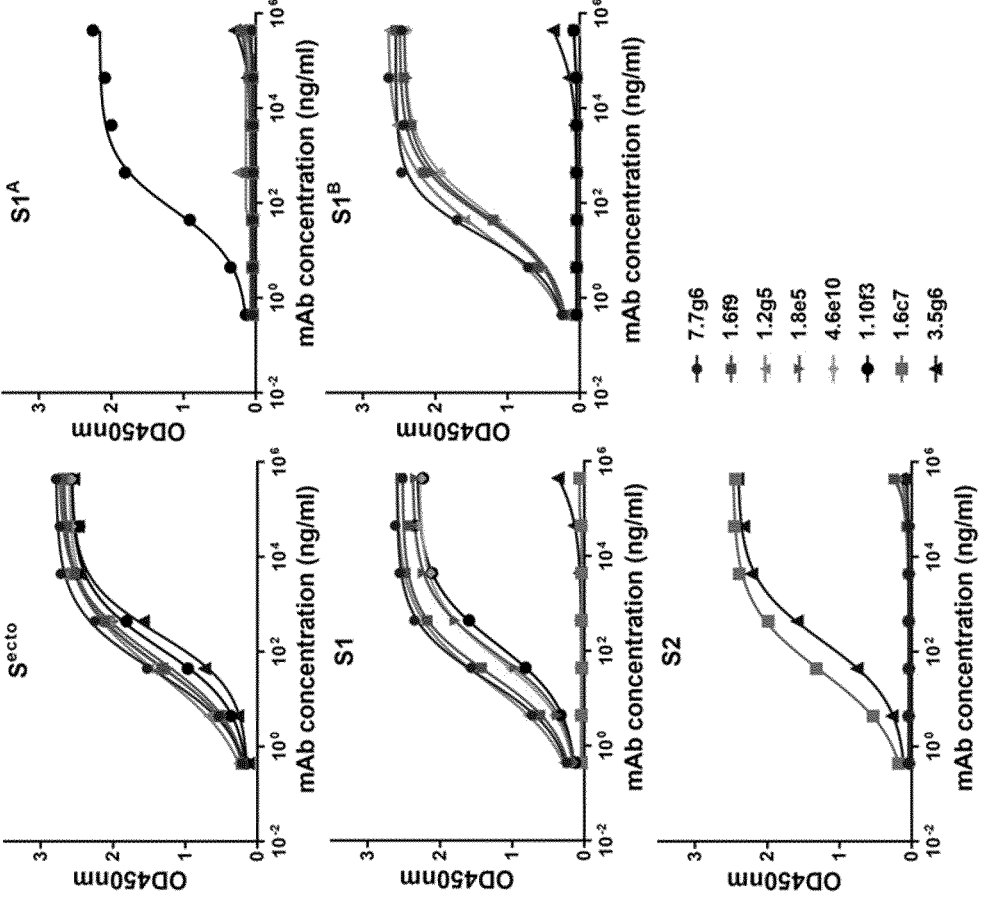

The 1.8e5 and 4.6e10 antibodies bind to the $S1_B$ domain (see FIGS. 5A, 16 and 19). The examples show that each of the 1.8e5 and 4.6e10 antibodies binds to MERS-S 1 with a strong binding affinity (FIGS. 2F and 3A shows affinity values of approximately $3.2 \times 10^{-10}$ and $3.6 \times 10^{-10}$, respectively). Each of the 1.8e5 and 4.6e10 antibodies is also shown to be capable of neutralizing MERS-S VSV pseudoparticles infection (see FIGS. 16 and 19). The 1.8e5 and 4.6e10 antibodies are advantageously capable of neutralizing MERS-S pseudovirus infectivity with an IC50 of approximately 0.09026 and 0.03131 g/ml, respectively (see FIG. 16). In addition, the 1.8e5 and 4.6e10 antibodies are advantageously capable of neutralizing MERS-CoV infectivity with an IC50 of approximately 1.25 and 0.32 µg/ml, respectively (see FIG. 16). The examples also show that a human IgG1 comprising the heavy and light chain variable sequences of one of the 1.8e5 and 4.6e10 antibodies is advantageously capable of neutralizing MERS-S pseudovirus infectivity with an $IC_{50}$ of approximately 2.59 and 0.07 pg/ml, respectively (see FIG. 16). The 1.8e5 and 4.6e10 antibodies are also shown to be capable of inhibiting MERS-S-DPP4 receptor binding (see FIG. 20). The examples also show that each of the 1.8e5 and 4.6e10 antibodies is protective in vivo in that 80% of treated mice survived after 12 days post-infection with MERS-CoV (see FIG. 24). The epitope recognized by the 4.6e10 antibody is shown to comprise residues 507 and 509 of the MERS-S protein (see FIG. 5A).

Similar functional properties can be expected to be associated with the antibodies defined below which share structural and binding characteristics with the 1.8e5 and/or 4.6e10 antibodies.

The invention provides an anti-MERS-S antibody that binds to the same epitope as an antibody comprising a heavy chain variable region of the amino acid sequence of SEQ ID NO: 32 and a light chain variable region of the amino acid sequence of SEQ ID NO: 56.

The invention further provides an anti-MERS-S antibody that binds to the same epitope as a heavy chain-only antibody comprising a heavy chain variable region of the amino acid sequence of SEQ ID NO: 32.

The invention further provides an anti-MERS-S antibody that competes for binding to MERS-S with an antibody comprising a heavy chain variable region of the amino acid sequence of SEQ ID NO: 32 and a light chain variable region of the amino acid sequence of SEQ ID NO: 56.

The invention further provides an anti-MERS-S antibody that competes for binding to MERS-S with a heavy chain-only antibody comprising a heavy chain variable region of the amino acid sequence of SEQ ID NO: 32.

The invention further provides an anti-MERS-S antibody comprising complementarity determining regions (CDRs) with the sequences of:
    i. SEQ ID NO: 133 for CDR1 of the heavy chain;
    ii. SEQ ID NO: 134 for CDR2 of the heavy chain;
    iii. SEQ ID NO: 135 for CDR3 of the heavy chain;
    iv. SEQ ID NO: 136 for CDR1 of the light chain;
    v. SEQ ID NO: 137 for CDR2 of the light chain; and
    vi. SEQ ID NO: 138 for CDR3 of the light chain.

In some embodiments, the antibody comprises a heavy chain variable region of the amino acid sequence of SEQ ID NO: 32.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 32.

In some embodiments, the antibody comprises a light chain variable region of the amino acid sequence of SEQ ID NO: 56.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 56.

In some embodiments, the antibody comprises a heavy chain variable region of the amino acid sequence of SEQ ID NO: 32 and a light chain variable region of the amino acid sequence of SEQ ID NO: 56.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 32 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 56.

The invention further provides an anti-MERS-S antibody comprising complementarity determining regions (CDRs) with:
    i. a sequence that is at least 90% identical to SEQ ID NO: 133 for CDR1 of the heavy chain;
    ii. a sequence that is at least 90% identical to SEQ ID NO: 134 for CDR2 of the heavy chain;
    iii. a sequence that is at least 90% identical to SEQ ID NO: 135 for CDR3 of the heavy chain;
    iv. a sequence that is at least 90% identical to SEQ ID NO: 136 for CDR1 of the light chain;
    v. a sequence that is at least 90% identical to SEQ ID NO: 137 for CDR2 of the light
    vi. a sequence that is at least 90% identical to SEQ ID NO: 138 for CDR3 of the light chain,
wherein the antibody competes for binding to MERS-S with an antibody comprising a heavy chain variable region of the amino acid sequence of SEQ ID NO: 32 and a light chain variable region of the amino acid sequence of SEQ ID NO: 56.

The invention further provides an anti-MERS-S antibody comprising complementarity determining regions (CDRs) with:
    i. a sequence that is at least 95% identical to SEQ ID NO: 133 for CDR1 of the heavy chain;
    ii. a sequence that is at least 95% identical to SEQ ID NO: 134 for CDR2 of the heavy chain;
    iii. a sequence that is at least 95% identical to SEQ ID NO: 135 for CDR3 of the heavy chain;
    iv. a sequence that is at least 95% identical to SEQ ID NO: 136 for CDR1 of the light chain;
    v. a sequence that is at least 95% identical to SEQ ID NO: 137 for CDR2 of the light chain; and
    vi. a sequence that is at least 95% identical to SEQ ID NO: 138 for CDR3 of the light chain,
wherein the antibody competes for binding to MERS-S with an antibody comprising a heavy chain variable region of the amino acid sequence of SEQ ID NO: 32 and a light chain variable region of the amino acid sequence of SEQ ID NO: 56.

The invention provides an anti-MERS-S antibody that binds to the same epitope as an antibody comprising a heavy chain variable region of the amino acid sequence of SEQ ID NO: 17 and a light chain variable region of the amino acid sequence of SEQ ID NO: 67. Accordingly, in some embodiments, the anti-MERS-S antibody binds to an epitope that comprises residues 507 and 509 of the MERS-S protein (SEQ ID NO: 81).

The invention further provides an anti-MERS-S antibody that binds to the same epitope as a heavy chain-only antibody comprising a heavy chain variable region of the amino acid sequence of SEQ ID NO: 17.

The invention further provides an anti-MERS-S antibody that competes for binding to MERS-S with an antibody comprising a heavy chain variable region of the amino acid sequence of SEQ ID NO: 17 and a light chain variable region of the amino acid sequence of SEQ ID NO: 67.

The invention further provides an anti-MERS-S antibody that competes for binding to MERS-S with a heavy chain-only antibody comprising a heavy chain variable region of the amino acid sequence of SEQ ID NO: 17.

The invention further provides an anti-MERS-S antibody comprising complementarity determining regions (CDRs) with the sequences of:
    i. SEQ ID NO: 139 for CDR1 of the heavy chain;
    ii. SEQ ID NO: 140 for CDR2 of the heavy chain;
    iii. SEQ ID NO: 141 for CDR3 of the heavy chain;
    iv. SEQ ID NO: 142 for CDR1 of the light chain;
    v. SEQ ID NO: 143 for CDR2 of the light chain; and
    vi. SEQ ID NO: 144 for CDR3 of the light chain.

In some embodiments, the antibody comprises a heavy chain variable region of the amino acid sequence of SEQ ID NO: 17.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 17.

In some embodiments, the antibody comprises a light chain variable region of the amino acid sequence of SEQ ID NO: 67.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 67.

In some embodiments, the antibody comprises a heavy chain variable region of the amino acid sequence of SEQ ID NO: 17 and a light chain variable region of the amino acid sequence of SEQ ID NO: 67.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 17 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 67.

The invention further provides an anti-MERS-S antibody comprising complementarity determining regions (CDRs) with:

i. a sequence that is at least 90% identical to SEQ ID NO: 139 for CDR1 of the heavy chain;
ii. a sequence that is at least 90% identical to SEQ ID NO: 140 for CDR2 of the heavy chain;
iii. a sequence that is at least 90% identical to SEQ ID NO: 141 for CDR3 of the heavy chain;
iv. a sequence that is at least 90% identical to SEQ ID NO: 142 for CDR1 of the light chain;
v. a sequence that is at least 90% identical to SEQ ID NO: 143 for CDR2 of the light chain; and
vi. a sequence that is at least 90% identical to SEQ ID NO: 144 for CDR3 of the light chain,
wherein the antibody competes for binding to MERS-S with an antibody comprising a heavy chain variable region of the amino acid sequence of SEQ ID NO: 17 and a light chain variable region of the amino acid sequence of SEQ ID NO: 67.

The invention further provides an anti-MERS-S antibody comprising complementarity determining regions (CDRs) with:

i. a sequence that is at least 95% identical to SEQ ID NO: 139 for CDR1 of the heavy chain;
ii. a sequence that is at least 95% identical to SEQ ID NO: 140 for CDR2 of the heavy chain;
iii. a sequence that is at least 95% identical to SEQ ID NO: 141 for CDR3 of the heavy chain;
iv. a sequence that is at least 95% identical to SEQ ID NO: 142 for CDR1 of the light chain;
v. a sequence that is at least 95% identical to SEQ ID NO: 143 for CDR2 of the light chain; and
vi. a sequence that is at least 95% identical to SEQ ID NO: 144 for CDR3 of the light chain,
wherein the antibody competes for binding to MERS-S with an antibody comprising a heavy chain variable region of the amino acid sequence of SEQ ID NO: 17 and a light chain variable region of the amino acid sequence of SEQ ID NO: 67.

The 1.10f3 antibody targets the sialic acid binding MERS S1$_A$ domain (see FIG. 5A) and inhibits Sia-binding activity (e.g. as determined by a haemagglutination inhibition assay in FIG. 22). The examples show that the 1.10f3 antibody binds to MERS-S1 with a strong binding affinity (FIG. 3A shows an affinity value of approximately 4.8×10$^{-9}$ M). The examples also show that the 1.10f3 antibody is protective in vivo in that 40% of treated mice survived after 12 days post-infection with MERS-CoV (see FIG. 24).

Similar functional properties can be expected to be associated with the antibodies defined below which share structural and binding characteristics with the 1.10f3 antibody.

The invention provides an anti-MERS-S antibody that binds to the same epitope as an antibody comprising a heavy chain variable region of the amino acid sequence of SEQ ID NO: 18 and a light chain variable region of the amino acid sequence of SEQ ID NO: 58.

The invention further provides an anti-MERS-S antibody that binds to the same epitope as a heavy chain-only antibody comprising a heavy chain variable region of the amino acid sequence of SEQ ID NO: 18.

The invention further provides an anti-MERS-S antibody that competes for binding to MERS-S with an antibody comprising a heavy chain variable region of the amino acid sequence of SEQ ID NO: 18 and a light chain variable region of the amino acid sequence of SEQ ID NO: 58.

The invention further provides an anti-MERS-S antibody that competes for binding to MERS-S with a heavy chain-only antibody comprising a heavy chain variable region of the amino acid sequence of SEQ ID NO: 18.

The invention further provides an anti-MERS-S antibody comprising complementarity determining regions (CDRs) with the sequences of:

i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

In some embodiments, the antibody comprises a heavy chain variable region of the amino acid sequence of SEQ ID NO: 18.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 18.

In some embodiments, the antibody comprises a light chain variable region of the amino acid sequence of SEQ ID NO: 58.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 58.

In some embodiments, the antibody comprises a heavy chain variable region of the amino acid sequence of SEQ ID NO: 18 and a light chain variable region of the amino acid sequence of SEQ ID NO: 58.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 18 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 58.

The invention further provides an anti-MERS-S antibody comprising complementarity determining regions (CDRs) with:

i. a sequence that is at least 90% identical to SEQ ID NO: 145 for CDR1 of the heavy chain;

ii. a sequence that is at least 90% identical to SEQ ID NO: 146 for CDR2 of the heavy chain;

iii. a sequence that is at least 90% identical to SEQ ID NO: 147 for CDR3 of the heavy chain;

iv. a sequence that is at least 90% identical to SEQ ID NO: 148 for CDR1 of the light chain;

v. a sequence that is at least 90% identical to SEQ ID NO: 149 for CDR2 of the light chain; and vi. a sequence that is at least 90% identical to SEQ ID NO: 150 for CDR3 of the light chain, wherein the antibody competes for binding to MERS-S with an antibody comprising a heavy chain variable region of the amino acid sequence of SEQ ID NO: 18 and a light chain variable region of the amino acid sequence of SEQ ID NO: 58.

The invention further provides an anti-MERS-S antibody comprising complementarity determining regions (CDRs) with:

i. a sequence that is at least 95% identical to SEQ ID NO: 145 for CDR1 of the heavy chain;

ii. a sequence that is at least 95% identical to SEQ ID NO: 146 for CDR2 of the heavy chain;

iii. a sequence that is at least 95% identical to SEQ ID NO: 147 for CDR3 of the heavy chain;

iv. a sequence that is at least 95% identical to SEQ ID NO: 148 for CDR1 of the light chain;

v. a sequence that is at least 95% identical to SEQ ID NO: 149 for CDR2 of the light chain; and vi. a sequence that is at least 95% identical to SEQ ID NO: 150 for CDR3 of the light chain, wherein the antibody competes for binding to MERS-S with an antibody comprising a heavy chain variable region of the amino acid sequence of SEQ ID NO: 18 and a light chain variable region of the amino acid sequence of SEQ ID NO: 58.

Figure 29A:
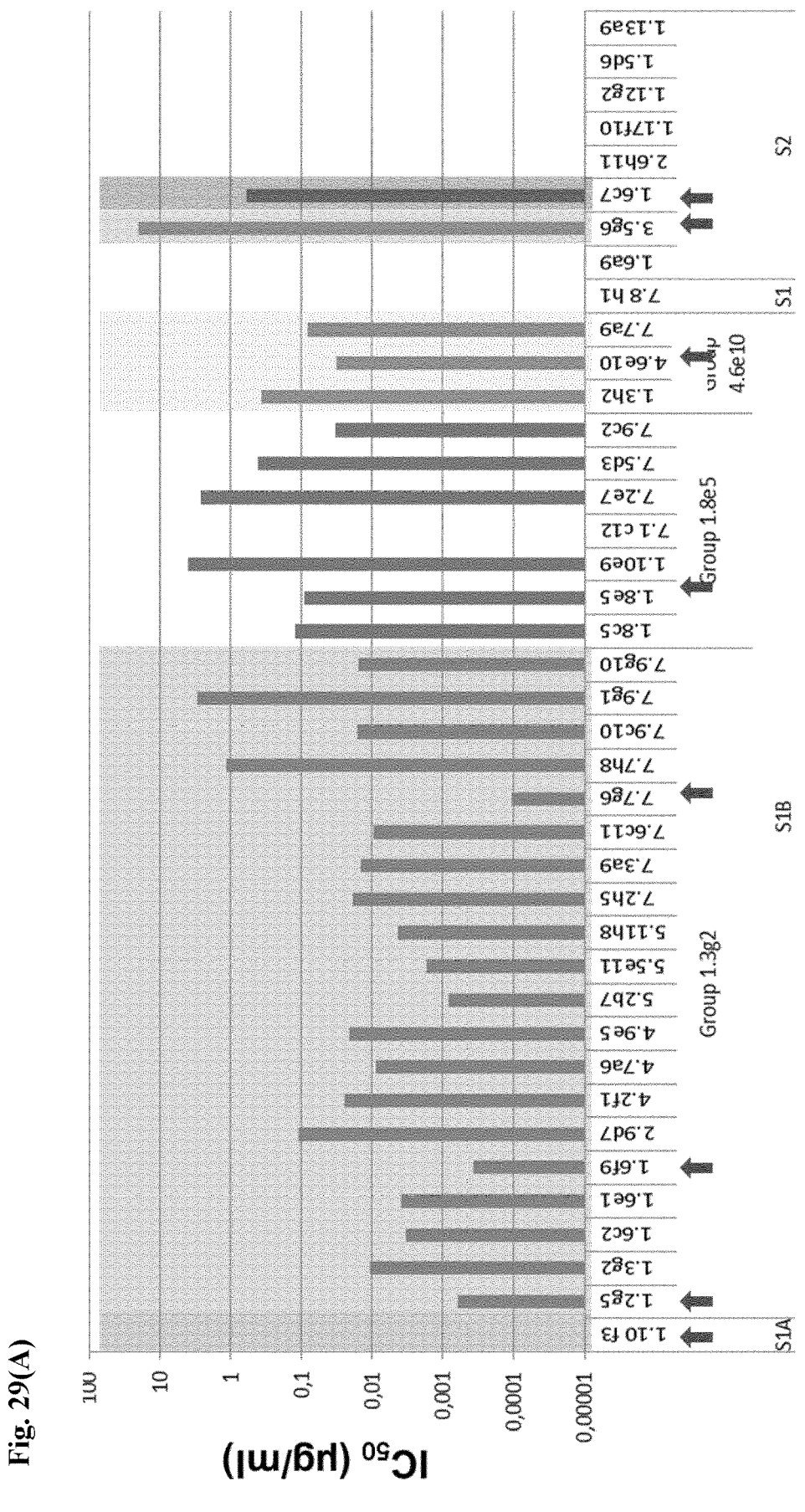

The 1.8c5 and 7.1c12 antibodies bind to the $S1_B$ domain (see FIGS. 5A and 29(A)). Each of these antibodies belongs to the 1.8e5 group. The 1.8c5 antibody exhibits neutralising activity (see FIG. 29(A)). Similar functional properties can be expected to be associated with the antibodies defined below which share structural and binding characteristics with the 1.8c5 and/or 7.1c12 antibodies.

The invention provides an anti-MERS-S antibody that binds to the same epitope as an antibody comprising a heavy chain variable region of the amino acid sequence of SEQ ID NO: 299 and a light chain variable region of the amino acid sequence of SEQ ID NO: 300.

The invention further provides an anti-MERS-S antibody that binds to the same epitope as a heavy chain-only antibody comprising a heavy chain variable region of the amino acid sequence of SEQ ID NO: 299.

The invention further provides an anti-MERS-S antibody that competes for binding to MERS-S with an antibody comprising a heavy chain variable region of the amino acid sequence of SEQ ID NO: 299 and a light chain variable region of the amino acid sequence of SEQ ID NO: 300.

The invention further provides an anti-MERS-S antibody that competes for binding to MERS-S with a heavy chain-only antibody comprising a heavy chain variable region of the amino acid sequence of SEQ ID NO: 299.

The invention further provides an anti-MERS-S antibody comprising complementarity determining regions (CDRs) with the sequences of:

i. SEQ ID NO: 301 for CDR1 of the heavy chain;

ii. SEQ ID NO: 302 for CDR2 of the heavy chain;

iii. SEQ ID NO: 303 for CDR3 of the heavy chain;

iv. SEQ ID NO: 304 for CDR1 of the light chain;

v. SEQ ID NO: 305 for CDR2 of the light chain; and vi. SEQ ID NO: 306 for CDR3 of the light chain.

In some embodiments, the antibody comprises a heavy chain variable region of the amino acid sequence of SEQ ID NO: 299.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 2993.

In some embodiments, the antibody comprises a light chain variable region of the amino acid sequence of SEQ ID NO: 300.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 300.

In some embodiments, the antibody comprises a heavy chain variable region of the amino acid sequence of SEQ ID NO: 299 and a light chain variable region of the amino acid sequence of SEQ ID NO: 300.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 299 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 300.

The invention further provides an anti-MERS-S antibody comprising complementarity determining regions (CDRs) with:

i. a sequence that is at least 90% identical to SEQ ID NO: 301 for CDR1 of the heavy chain;

ii. a sequence that is at least 90% identical to SEQ ID NO: 302 for CDR2 of the heavy chain;

iii. a sequence that is at least 90% identical to SEQ ID NO: 303 for CDR3 of the heavy chain;

iv. a sequence that is at least 90% identical to SEQ ID NO: 304 for CDR1 of the light chain;

v. a sequence that is at least 90% identical to SEQ ID NO: 305 for CDR2 of the light chain; and vi. a sequence that is at least 90% identical to SEQ ID NO: 306 for CDR3 of the light chain, wherein the antibody competes for binding to MERS-S with an antibody comprising a heavy chain variable region of the amino acid sequence of SEQ ID NO: 299 and a light chain variable region of the amino acid sequence of SEQ ID NO: 300.

The invention further provides an anti-MERS-S antibody comprising complementarity determining regions (CDRs) with:

i. a sequence that is at least 95% identical to SEQ ID NO: 301 for CDR1 of the heavy chain;

ii. a sequence that is at least 95% identical to SEQ ID NO: 302 for CDR2 of the heavy chain;

iii. a sequence that is at least 95% identical to SEQ ID NO: 303 for CDR3 of the heavy chain;

iv. a sequence that is at least 95% identical to SEQ ID NO: 304 for CDR1 of the light chain;

v. a sequence that is at least 95% identical to SEQ ID NO: 305 for CDR2 of the light chain; and vi. a sequence that is at least 95% identical to SEQ ID NO: 306 for CDR3 of the light chain, wherein the antibody competes for binding to MERS-S with an antibody comprising a heavy chain variable region of the amino acid sequence of SEQ ID NO: 299 and a light chain variable region of the amino acid sequence of SEQ ID NO: 300.

The invention provides an anti-MERS-S antibody that binds to the same epitope as an antibody comprising a heavy chain variable region of the amino acid sequence of SEQ ID NO: 307 and a light chain variable region of the amino acid sequence of SEQ ID NO: 308.

The invention further provides an anti-MERS-S antibody that binds to the same epitope as a heavy chain-only antibody comprising a heavy chain variable region of the amino acid sequence of SEQ ID NO: 307.

The invention further provides an anti-MERS-S antibody that competes for binding to MERS-S with an antibody comprising a heavy chain variable region of the amino acid sequence of SEQ ID NO: 307 and a light chain variable region of the amino acid sequence of SEQ ID NO: 308.

The invention further provides an anti-MERS-S antibody that competes for binding to MERS-S with a heavy chain-only antibody comprising a heavy chain variable region of the amino acid sequence of SEQ ID NO: 307.

The invention further provides an anti-MERS-S antibody comprising complementarity determining regions (CDRs) with the sequences of:

i. SEQ ID NO: 309 for CDR1 of the heavy chain;
ii. SEQ ID NO: 310 for CDR2 of the heavy chain;
iii. SEQ ID NO: 311 for CDR3 of the heavy chain;
iv. SEQ ID NO: 312 for CDR1 of the light chain;
v. SEQ ID NO: 313 for CDR2 of the light chain; and
vi. SEQ ID NO: 314 for CDR3 of the light chain.

In some embodiments, the antibody comprises a heavy chain variable region of the amino acid sequence of SEQ ID NO: 307.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 307.

In some embodiments, the antibody comprises a light chain variable region of the amino acid sequence of SEQ ID NO: 308.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 308.

In some embodiments, the antibody comprises a heavy chain variable region of the amino acid sequence of SEQ ID NO: 307 and a light chain variable region of the amino acid sequence of SEQ ID NO: 308.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 307 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 308.

The invention further provides an anti-MERS-S antibody comprising complementarity determining regions (CDRs) with:

i. a sequence that is at least 90% identical to SEQ ID NO: 309 for CDR1 of the heavy chain;
ii. a sequence that is at least 90% identical to SEQ ID NO: 310 for CDR2 of the heavy chain;
iii. a sequence that is at least 90% identical to SEQ ID NO: 311 for CDR3 of the heavy chain;
iv. a sequence that is at least 90% identical to SEQ ID NO: 312 for CDR1 of the light chain;
v. a sequence that is at least 90% identical to SEQ ID NO: 313 for CDR2 of the light chain; and
vi. a sequence that is at least 90% identical to SEQ ID NO: 314 for CDR3 of the light chain, wherein the antibody competes for binding to MERS-S with an antibody comprising a heavy chain variable region of the amino acid sequence of SEQ ID NO: 307 and a light chain variable region of the amino acid sequence of SEQ ID NO: 308.

The invention further provides an anti-MERS-S antibody comprising complementarity determining regions (CDRs) with:

i. a sequence that is at least 95% identical to SEQ ID NO: 309 for CDR1 of the heavy chain;
ii. a sequence that is at least 95% identical to SEQ ID NO: 310 for CDR2 of the heavy chain;
iii. a sequence that is at least 95% identical to SEQ ID NO: 311 for CDR3 of the
iv. a sequence that is at least 95% identical to SEQ ID NO: 312 for CDR1 of the light chain;
v. a sequence that is at least 95% identical to SEQ ID NO: 313 for CDR2 of the light chain; and
vi. a sequence that is at least 95% identical to SEQ ID NO: 314 for CDR3 of the light chain, wherein the antibody competes for binding to MERS-S with an antibody comprising a heavy chain variable region of the amino acid sequence of SEQ ID NO: 307 and a light chain variable region of the amino acid sequence of SEQ ID NO: 308.

The 7.7a9 antibody binds to the SIB domain and exhibits neutralising activity (see FIGS. 5(A) and 29(A)). This antibody belongs to the 4.6e10 group. Similar functional properties can be expected to be associated with the antibodies defined below which share structural and binding characteristics with the 7.7a9 antibody.

The invention provides an anti-MERS-S antibody that binds to the same epitope as an antibody comprising a heavy chain variable region of the amino acid sequence of SEQ ID NO: 315 and a light chain variable region of the amino acid sequence of SEQ ID NO: 316.

The invention further provides an anti-MERS-S antibody that binds to the same epitope as a heavy chain-only antibody comprising a heavy chain variable region of the amino acid sequence of SEQ ID NO: 315.

The invention further provides an anti-MERS-S antibody that competes for binding to MERS-S with an antibody comprising a heavy chain variable region of the amino acid sequence of SEQ ID NO: 315 and a light chain variable region of the amino acid sequence of SEQ ID NO: 316.

The invention further provides an anti-MERS-S antibody that competes for binding to MERS-S with a heavy chain-only antibody comprising a heavy chain variable region of the amino acid sequence of SEQ ID NO: 315.

The invention further provides an anti-MERS-S antibody comprising complementarity determining regions (CDRs) with the sequences of:

i. SEQ ID NO: 317 for CDR1 of the heavy chain;

ii. SEQ ID NO: 318 for CDR2 of the heavy chain;

iii. SEQ ID NO: 319 for CDR3 of the heavy chain;

iv. SEQ ID NO: 320 for CDR1 of the light chain;

v. SEQ ID NO: 321 for CDR2 of the light chain; and vi. SEQ ID NO: 322 for CDR3 of the light chain.

In some embodiments, the antibody comprises a heavy chain variable region of the amino acid sequence of SEQ ID NO: 315.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 315.

In some embodiments, the antibody comprises a light chain variable region of the amino acid sequence of SEQ ID NO: 316.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 316.

In some embodiments, the antibody comprises a heavy chain variable region of the amino acid sequence of SEQ ID NO: 315 and a light chain variable region of the amino acid sequence of SEQ ID NO: 316.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 315 and (ii) an amino acid sequence that is at least 80%, 81%, 82%, 83%, 84%, 85%, 86%, 87%, 88% 89%, 90%, 91%, 92%, 93%, 94%, 95%, 96%, 97%, 98%, or 99% identical to a light chain variable region of the amino acid sequence of SEQ ID NO: 316.

The invention further provides an anti-MERS-S antibody comprising complementarity determining regions (CDRs) with:

i. a sequence that is at least 90% identical to SEQ ID NO: 317 for CDR1 of the heavy chain;

ii. a sequence that is at least 90% identical to SEQ ID NO: 318 for CDR2 of the heavy chain;

iii. a sequence that is at least 90% identical to SEQ ID NO: 319 for CDR3 of the heavy chain;

iv. a sequence that is at least 90% identical to SEQ ID NO: 320 for CDR1 of the light chain;

v. a sequence that is at least 90% identical to SEQ ID NO: 321 for CDR2 of the light chain; and vi. a sequence that is at least 90% identical to SEQ ID NO: 322 for CDR3 of the light chain, wherein the antibody competes for binding to MERS-S with an antibody comprising a heavy chain variable region of the amino acid sequence of SEQ ID NO: 315 and a light chain variable region of the amino acid sequence of SEQ ID NO: 316.

The invention further provides an anti-MERS-S antibody comprising complementarity determining regions (CDRs) with:

i. a sequence that is at least 95% identical to SEQ ID NO: 317 for CDR1 of the heavy chain;

ii. a sequence that is at least 95% identical to SEQ ID NO: 318 for CDR2 of the heavy chain;

iii. a sequence that is at least 95% identical to SEQ ID NO: 319 for CDR3 of the heavy chain;

iv. a sequence that is at least 95% identical to SEQ ID NO: 320 for CDR1 of the light v. a sequence that is at least 95% identical to SEQ ID NO: 321 for CDR2 of the light chain; and vi. a sequence that is at least 95% identical to SEQ ID NO: 322 for CDR3 of the light chain, wherein the antibody competes for binding to MERS-S with an antibody comprising a heavy chain variable region of the amino acid sequence of SEQ ID NO: 315 and a light chain variable region of the amino acid sequence of SEQ ID NO: 316.

The 7.7f3, 4.2c3, 4.9f12, 4.7a6, 7.7 h8, 7.3a9, 7.6c11, 7.9c10, 7.9 g1, 2.9d7, 7.9c2, 7.2e7, 1.3 h2, 7.5d3, 7.9 g10, 7.2 h5, 1.6e1, 1.6c2, 5.11 h8 and 1.10e9 antibodies bind to MERS-S1 with a strong binding affinity (FIG. 3A shows affinity values of approximately $1.2\times10^{-10}$, $1.2\times10^{-10}$, $1.3\times10^{-10}$, $1.3\times10^{-10}$, $5.4\times10^{-10}$, $4.3\times10^{-10}$, $4.0\times10^{-10}$, $1.1\times10^{-1\,0}$, $2.1\times10^{-10}$, $3.5\times10^{-10}$, $1.2\times10^{-8}$, $2.6\times10^{-9}$, $1.9\times10^{-9}$, $6.0\times10^{-9}$, $2.0\times10^{10}$, $3.6\times10^{-10}$, $1.1\times10^{-10}$, $8.6\times10^{-10}$, $6.8\times10^{-11}$ and $4.4\times10^{-10}$, respectively). The 1.3 h2 antibody is shown to specifically bind to the S1$^B$ domain (see FIG. 5A).

Similar functional properties can be expected to be associated with the antibodies defined below which share structural and binding characteristics with one or more of the 7.7f3, 4.2c3, 4.9f12, 4.7a6, 7.7 h8, 7.3a9, 7.6c11, 7.9c10, 7.9 g1, 2.9d7, 7.9c2, 7.2e7, 1.3 h2, 7.5d3, 7.9 g10, 7.2 h5, 1.6e1, 1.6c2, 5.11 h8 and 1.10e9 antibodies.

The invention provides an anti-MERS-S antibody that binds to the same epitope as an antibody comprising a heavy chain variable region of the amino acid sequence of SEQ ID NO: 2 and a light chain variable region of the amino acid sequence of SEQ ID NO: 42.

The invention further provides an anti-MERS-S antibody that binds to the same epitope as a heavy chain-only antibody comprising a heavy chain variable region of the amino acid sequence of SEQ ID NO: 2.

The invention further provides an anti-MERS-S antibody that competes for binding to MERS-S with an antibody comprising a heavy chain variable region of the amino acid sequence of SEQ ID NO: 2 and a light chain variable region of the amino acid sequence of SEQ ID NO: 42.

The invention further provides an anti-MERS-S antibody that competes for binding to MERS-S with a heavy chain-only antibody comprising a heavy chain variable region of the amino acid sequence of SEQ ID NO: 2.

The invention further provides an anti-MERS-S antibody comprising complementarity determining regions (CDRs) with the sequences of:

i. SEQ ID NO: 151 for CDR1 of the heavy chain;

ii. SEQ ID NO: 152 for CDR2 of the heavy chain;

iii. SEQ ID NO: 153 for CDR3 of the heavy chain;

iv. SEQ ID NO: 154 for CDR1 of the light chain;

v. SEQ ID NO: 155 for CDR2 of the light chain; and vi. SEQ ID NO: 156 for CDR3 of the light chain.

In some embodiments, the antibody comprises a heavy chain variable region of the amino acid sequence of SEQ ID NO: 2.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 2.

In some embodiments, the antibody comprises a light chain variable region of the amino acid sequence of SEQ ID NO: 42.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 42.

In some embodiments, the antibody comprises a heavy chain variable region of the amino acid sequence of SEQ ID NO: 2 and a light chain variable region of the amino acid sequence of SEQ ID NO: 42.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 2 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 42.

The invention further provides an anti-MERS-S antibody comprising complementarity determining regions (CDRs) with:

i. a sequence that is at least 90% identical to SEQ ID NO: 151 for CDR1 of the heavy chain;

ii. a sequence that is at least 90% identical to SEQ ID NO: 152 for CDR2 of the heavy chain;

iii. a sequence that is at least 90% identical to SEQ ID NO: 153 for CDR3 of the heavy chain;

iv. a sequence that is at least 90% identical to SEQ ID NO: 154 for CDR1 of the light chain;

v. a sequence that is at least 90% identical to SEQ ID NO: 155 for CDR2 of the light chain; and vi. a sequence that is at least 90% identical to SEQ ID NO: 156 for CDR3 of the light chain, wherein the antibody competes for binding to MERS-S with an antibody comprising a heavy chain variable region of the amino acid sequence of SEQ ID NO: 2 and a light chain variable region of the amino acid sequence of SEQ ID NO: 42.

The invention further provides an anti-MERS-S antibody comprising complementarity determining regions (CDRs) with:

i. a sequence that is at least 95% identical to SEQ ID NO: 151 for CDR1 of the ii. a sequence that is at least 95% identical to SEQ ID NO: 152 for CDR2 of the heavy chain;

iii. a sequence that is at least 95% identical to SEQ ID NO: 153 for CDR3 of the heavy chain;

iv. a sequence that is at least 95% identical to SEQ ID NO: 154 for CDR1 of the light chain;

v. a sequence that is at least 95% identical to SEQ ID NO: 155 for CDR2 of the light chain; and vi. a sequence that is at least 95% identical to SEQ ID NO: 156 for CDR3 of the light chain, wherein the antibody competes for binding to MERS-S with an antibody comprising a heavy chain variable region of the amino acid sequence of SEQ ID NO: 2 and a light chain variable region of the amino acid sequence of SEQ ID NO: 42.

The invention provides an anti-MERS-S antibody that binds to the same epitope as an antibody comprising a heavy chain variable region of the amino acid sequence of SEQ ID NO: 3 and a light chain variable region of the amino acid sequence of SEQ ID NO: 43.

The invention further provides an anti-MERS-S antibody that binds to the same epitope as a heavy chain-only antibody comprising a heavy chain variable region of the amino acid sequence of SEQ ID NO: 3.

The invention further provides an anti-MERS-S antibody that competes for binding to MERS-S with an antibody comprising a heavy chain variable region of the amino acid sequence of SEQ ID NO: 3 and a light chain variable region of the amino acid sequence of SEQ ID NO: 43.

The invention further provides an anti-MERS-S antibody that competes for binding to MERS-S with a heavy chain-only antibody comprising a heavy chain variable region of the amino acid sequence of SEQ ID NO: 3.

The invention further provides an anti-MERS-S antibody comprising complementarity determining regions (CDRs) with the sequences of:

i. SEQ ID NO: 157 for CDR1 of the heavy chain;

ii. SEQ ID NO: 158 for CDR2 of the heavy chain;

iii. SEQ ID NO: 159 for CDR3 of the heavy chain;

iv. SEQ ID NO: 160 for CDR1 of the light chain;

v. SEQ ID NO: 161 for CDR2 of the light chain; and vi. SEQ ID NO: 162 for CDR3 of the light chain.

In some embodiments, the antibody comprises a heavy chain variable region of the amino acid sequence of SEQ ID NO: 3.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 3.

In some embodiments, the antibody comprises a light chain variable region of the amino acid sequence of SEQ ID NO: 43.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 43.

In some embodiments, the antibody comprises a heavy chain variable region of the amino acid sequence of SEQ ID NO: 3 and a light chain variable region of the amino acid sequence of SEQ ID NO: 43.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 3 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 43.

The invention further provides an anti-MERS-S antibody comprising complementarity determining regions (CDRs) with:

i. a sequence that is at least 90% identical to SEQ ID NO: 157 for CDR1 of the heavy chain;

ii. a sequence that is at least 90% identical to SEQ ID NO: 158 for CDR2 of the heavy chain;

iii. a sequence that is at least 90% identical to SEQ ID NO: 159 for CDR3 of the heavy chain;

iv. a sequence that is at least 90% identical to SEQ ID NO: 160 for CDR1 of the light chain;

v. a sequence that is at least 90% identical to SEQ ID NO: 161 for CDR2 of the light chain; and vi. a sequence that is at least 90% identical to SEQ ID NO: 162 for CDR3 of the light chain, wherein the antibody competes for binding to MERS-S with an antibody comprising a heavy chain variable region of the amino acid sequence of SEQ ID NO: 3 and a light chain variable region of the amino acid sequence of SEQ ID NO: 43.

The invention further provides an anti-MERS-S antibody comprising complementarity determining regions (CDRs) with:

i. a sequence that is at least 95% identical to SEQ ID NO: 157 for CDR1 of the heavy chain;

ii. a sequence that is at least 95% identical to SEQ ID NO: 158 for CDR2 of the heavy chain;

iii. a sequence that is at least 95% identical to SEQ ID NO: 159 for CDR3 of the heavy chain;

iv. a sequence that is at least 95% identical to SEQ ID NO: 160 for CDR1 of the light v. a sequence that is at least 95% identical to SEQ ID NO: 161 for CDR2 of the light chain; and vi. a sequence that is at least 95% identical to SEQ ID NO: 162 for CDR3 of the light chain, wherein the antibody competes for binding to MERS-S with an antibody comprising a heavy chain variable region of the amino acid sequence of SEQ ID NO: 3 and a light chain variable region of the amino acid sequence of SEQ ID NO: 43.

The invention provides an anti-MERS-S antibody that binds to the same epitope as an antibody comprising a heavy chain variable region of the amino acid sequence of SEQ ID NO: 4 and a light chain variable region of the amino acid sequence of SEQ ID NO: 44.

The invention further provides an anti-MERS-S antibody that binds to the same epitope as a heavy chain-only antibody comprising a heavy chain variable region of the amino acid sequence of SEQ ID NO: 4.

The invention further provides an anti-MERS-S antibody that competes for binding to MERS-S with an antibody comprising a heavy chain variable region of the amino acid sequence of SEQ ID NO: 4 and a light chain variable region of the amino acid sequence of SEQ ID NO: 44.

The invention further provides an anti-MERS-S antibody that competes for binding to MERS-S with a heavy chain-only antibody comprising a heavy chain variable region of the amino acid sequence of SEQ ID NO: 4.

The invention further provides an anti-MERS-S antibody comprising complementarity determining regions (CDRs) with the sequences of:

i. SEQ ID NO: 163 for CDR1 of the heavy chain;

ii. SEQ ID NO: 164 for CDR2 of the heavy chain;

iii. SEQ ID NO: 165 for CDR3 of the heavy chain;

iv. SEQ ID NO: 166 for CDR1 of the light chain;

v. SEQ ID NO: 167 for CDR2 of the light chain; and vi. SEQ ID NO: 168 for CDR3 of the light chain.

In some embodiments, the antibody comprises a heavy chain variable region of the amino acid sequence of SEQ ID NO: 4.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 4.

In some embodiments, the antibody comprises a light chain variable region of the amino acid sequence of SEQ ID NO: 44.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 44.

In some embodiments, the antibody comprises a heavy chain variable region of the amino acid sequence of SEQ ID NO: 4 and a light chain variable region of the amino acid sequence of SEQ ID NO: 44.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 4 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 44.

The invention further provides an anti-MERS-S antibody comprising complementarity determining regions (CDRs) with:

i. a sequence that is at least 90% identical to SEQ ID NO: 163 for CDR1 of the heavy chain;

ii. a sequence that is at least 90% identical to SEQ ID NO: 164 for CDR2 of the iii. a sequence that is at least 90% identical to SEQ ID NO: 165 for CDR3 of the heavy chain;

iv. a sequence that is at least 90% identical to SEQ ID NO: 166 for CDR1 of the light chain;

v. a sequence that is at least 90% identical to SEQ ID NO: 167 for CDR2 of the light chain; and vi. a sequence that is at least 90% identical to SEQ ID NO: 168 for CDR3 of the light chain, wherein the antibody competes for binding to MERS-S with an antibody comprising a heavy chain variable region of the amino acid sequence of SEQ ID NO: 4 and a light chain variable region of the amino acid sequence of SEQ ID NO: 44.

The invention further provides an anti-MERS-S antibody comprising complementarity determining regions (CDRs) with:

i. a sequence that is at least 95% identical to SEQ ID NO: 163 for CDR1 of the heavy chain;

ii. a sequence that is at least 95% identical to SEQ ID NO: 164 for CDR2 of the heavy chain;

iii. a sequence that is at least 95% identical to SEQ ID NO: 165 for CDR3 of the heavy chain;

iv. a sequence that is at least 95% identical to SEQ ID NO: 166 for CDR1 of the light chain;

v. a sequence that is at least 95% identical to SEQ ID NO: 167 for CDR2 of the light chain; and vi. a sequence that is at least 95% identical to SEQ ID NO: 168 for CDR3 of the light chain, wherein the antibody competes for binding to MERS-S with an antibody comprising a heavy chain variable region of the amino acid sequence of SEQ ID NO: 4 and a light chain variable region of the amino acid sequence of SEQ ID NO: 44.

The invention provides an anti-MERS-S antibody that binds to the same epitope as an antibody comprising a heavy chain variable region of the amino acid sequence of SEQ ID NO: 5 and a light chain variable region of the amino acid sequence of SEQ ID NO: 45.

The invention further provides an anti-MERS-S antibody that binds to the same epitope as a heavy chain-only antibody comprising a heavy chain variable region of the amino acid sequence of SEQ ID NO: 5.

The invention further provides an anti-MERS-S antibody that competes for binding to MERS-S with an antibody comprising a heavy chain variable region of the amino acid sequence of SEQ ID NO: 5 and a light chain variable region of the amino acid sequence of SEQ ID NO: 45.

The invention further provides an anti-MERS-S antibody that competes for binding to MERS-S with a heavy chain-only antibody comprising a heavy chain variable region of the amino acid sequence of SEQ ID NO: 5.

The invention further provides an anti-MERS-S antibody comprising complementarity determining regions (CDRs) with the sequences of:

i. SEQ ID NO: 169 for CDR1 of the heavy chain;
    ii. SEQ ID NO: 170 for CDR2 of the heavy chain;
    iii. SEQ ID NO: 171 for CDR3 of the heavy chain;
    iv. SEQ ID NO: 172 for CDR1 of the light chain;
    v. SEQ ID NO: 173 for CDR2 of the light chain; and
    vi. SEQ ID NO: 174 for CDR3 of the light chain.

In some embodiments, the antibody comprises a heavy chain variable region of the amino acid sequence of SEQ ID NO: 5.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 5.

In some embodiments, the antibody comprises a light chain variable region of the amino acid sequence of SEQ ID NO: 45.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 45.

In some embodiments, the antibody comprises a heavy chain variable region of the amino acid sequence of SEQ ID NO: 5 and a light chain variable region of the amino acid sequence of SEQ ID NO: 45.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 5 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 45.

The invention further provides an anti-MERS-S antibody comprising complementarity determining regions (CDRs) with:

i. a sequence that is at least 90% identical to SEQ ID NO: 169 for CDR1 of the heavy chain;
    ii. a sequence that is at least 90% identical to SEQ ID NO: 170 for CDR2 of the heavy chain;
    iii. a sequence that is at least 90% identical to SEQ ID NO: 171 for CDR3 of the heavy chain;
    iv. a sequence that is at least 90% identical to SEQ ID NO: 172 for CDR1 of the light
    v. a sequence that is at least 90% identical to SEQ ID NO: 173 for CDR2 of the light chain; and
    vi. a sequence that is at least 90% identical to SEQ ID NO: 174 for CDR3 of the light chain, wherein the antibody competes for binding to MERS-S with an antibody comprising a heavy chain variable region of the amino acid sequence of SEQ ID NO: 5 and a light chain variable region of the amino acid sequence of SEQ ID NO: 45.

The invention further provides an anti-MERS-S antibody comprising complementarity determining regions (CDRs) with:

i. a sequence that is at least 95% identical to SEQ ID NO: 169 for CDR1 of the heavy chain;
    ii. a sequence that is at least 95% identical to SEQ ID NO: 170 for CDR2 of the heavy chain;
    iii. a sequence that is at least 95% identical to SEQ ID NO: 171 for CDR3 of the heavy chain;
    iv. a sequence that is at least 95% identical to SEQ ID NO: 172 for CDR1 of the light chain;
    v. a sequence that is at least 95% identical to SEQ ID NO: 173 for CDR2 of the light chain; and
    vi. a sequence that is at least 95% identical to SEQ ID NO: 174 for CDR3 of the light chain, wherein the antibody competes for binding to MERS-S with an antibody comprising a heavy chain variable region of the amino acid sequence of SEQ ID NO: 5 and a light chain variable region of the amino acid sequence of SEQ ID NO: 45.

The invention provides an anti-MERS-S antibody that binds to the same epitope as an antibody comprising a heavy chain variable region of the amino acid sequence of SEQ ID NO: 6 and a light chain variable region of the amino acid sequence of SEQ ID NO: 46.

The invention further provides an anti-MERS-S antibody that binds to the same epitope as a heavy chain-only antibody comprising a heavy chain variable region of the amino acid sequence of SEQ ID NO: 6.

The invention further provides an anti-MERS-S antibody that competes for binding to MERS-S with an antibody comprising a heavy chain variable region of the amino acid sequence of SEQ ID NO: 6 and a light chain variable region of the amino acid sequence of SEQ ID NO: 46.

The invention further provides an anti-MERS-S antibody that competes for binding to MERS-S with a heavy chain-only antibody comprising a heavy chain variable region of the amino acid sequence of SEQ ID NO: 6.

The invention further provides an anti-MERS-S antibody comprising complementarity determining regions (CDRs) with the sequences of:

i. SEQ ID NO: 175 for CDR1 of the heavy chain;
    ii. SEQ ID NO: 176 for CDR2 of the heavy chain;
    iii. SEQ ID NO: 177 for CDR3 of the heavy chain;
    iv. SEQ ID NO: 178 for CDR1 of the light chain;
    v. SEQ ID NO: 179 for CDR2 of the light chain; and
    vi. SEQ ID NO: 180 for CDR3 of the light chain.

In some embodiments, the antibody comprises a heavy chain variable region of the amino acid sequence of SEQ ID NO: 6.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 6.

In some embodiments, the antibody comprises a light chain variable region of the amino acid sequence of SEQ ID NO: 46.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 46.

In some embodiments, the antibody comprises a heavy chain variable region of the amino acid sequence of SEQ ID NO: 6 and a light chain variable region of the amino acid sequence of SEQ ID NO: 46.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 6 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 46.

The invention further provides an anti-MERS-S antibody comprising complementarity determining regions (CDRs) with:

i. a sequence that is at least 90% identical to SEQ ID NO: 175 for CDR1 of the heavy chain;

ii. a sequence that is at least 90% identical to SEQ ID NO: 176 for CDR2 of the heavy chain;

iii. a sequence that is at least 90% identical to SEQ ID NO: 177 for CDR3 of the heavy chain;

iv. a sequence that is at least 90% identical to SEQ ID NO: 178 for CDR1 of the light chain;

v. a sequence that is at least 90% identical to SEQ ID NO: 179 for CDR2 of the light chain; and vi. a sequence that is at least 90% identical to SEQ ID NO: 180 for CDR3 of the light chain, wherein the antibody competes for binding to MERS-S with an antibody comprising a heavy chain variable region of the amino acid sequence of SEQ ID NO: 6 and a light chain variable region of the amino acid sequence of SEQ ID NO: 46.

The invention further provides an anti-MERS-S antibody comprising complementarity determining regions (CDRs) with:

i. a sequence that is at least 95% identical to SEQ ID NO: 175 for CDR1 of the heavy chain;

ii. a sequence that is at least 95% identical to SEQ ID NO: 176 for CDR2 of the heavy chain;

iii. a sequence that is at least 95% identical to SEQ ID NO: 177 for CDR3 of the heavy chain;

iv. a sequence that is at least 95% identical to SEQ ID NO: 178 for CDR1 of the light chain;

v. a sequence that is at least 95% identical to SEQ ID NO: 179 for CDR2 of the light chain; and vi. a sequence that is at least 95% identical to SEQ ID NO: 180 for CDR3 of the light chain, wherein the antibody competes for binding to MERS-S with an antibody comprising a heavy chain variable region of the amino acid sequence of SEQ ID NO: 6 and a light chain variable region of the amino acid sequence of SEQ ID NO: 46.

The invention provides an anti-MERS-S antibody that binds to the same epitope as an antibody comprising a heavy chain variable region of the amino acid sequence of SEQ ID NO: 7 and a light chain variable region of the amino acid sequence of SEQ ID NO: 47.

The invention further provides an anti-MERS-S antibody that binds to the same epitope as a heavy chain-only antibody comprising a heavy chain variable region of the amino acid sequence of SEQ ID NO: 7.

The invention further provides an anti-MERS-S antibody that competes for binding to MERS-S with an antibody comprising a heavy chain variable region of the amino acid sequence of SEQ ID NO: 7 and a light chain variable region of the amino acid sequence of SEQ ID NO: 47.

The invention further provides an anti-MERS-S antibody that competes for binding to MERS-S with a heavy chain-only antibody comprising a heavy chain variable region of the amino acid sequence of SEQ ID NO: 7.

The invention further provides an anti-MERS-S antibody comprising complementarity determining regions (CDRs) with the sequences of:

i. SEQ ID NO: 181 for CDR1 of the heavy chain;

ii. SEQ ID NO: 182 for CDR2 of the heavy chain;

iii. SEQ ID NO: 183 for CDR3 of the heavy chain;

iv. SEQ ID NO: 184 for CDR1 of the light chain;

v. SEQ ID NO: 185 for CDR2 of the light chain; and vi. SEQ ID NO: 186 for CDR3 of the light chain.

In some embodiments, the antibody comprises a heavy chain variable region of the amino acid sequence of SEQ ID NO: 7.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 7.

In some embodiments, the antibody comprises a light chain variable region of the amino acid sequence of SEQ ID NO: 47.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 47.

In some embodiments, the antibody comprises a heavy chain variable region of the amino acid sequence of SEQ ID NO: 7 and a light chain variable region of the amino acid sequence of SEQ ID NO: 47.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 7 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 47.

The invention further provides an anti-MERS-S antibody comprising complementarity determining regions (CDRs) with:

i. a sequence that is at least 90% identical to SEQ ID NO: 181 for CDR1 of the heavy chain;

ii. a sequence that is at least 90% identical to SEQ ID NO: 182 for CDR2 of the heavy chain;

iii. a sequence that is at least 90% identical to SEQ ID NO: 183 for CDR3 of the heavy chain;

iv. a sequence that is at least 90% identical to SEQ ID NO: 184 for CDR1 of the light chain;

v. a sequence that is at least 90% identical to SEQ ID NO: 185 for CDR2 of the light chain; and vi. a sequence that is at least 90% identical to SEQ ID NO: 186 for CDR3 of the light chain, wherein the antibody competes for binding to MERS-S with an antibody comprising a heavy chain variable region of the amino acid sequence of SEQ ID NO: 7 and a light chain variable region of the amino acid sequence of SEQ ID NO: 47.

The invention further provides an anti-MERS-S antibody comprising complementarity determining regions (CDRs) with:

i. a sequence that is at least 95% identical to SEQ ID NO: 181 for CDR1 of the ii. a sequence that is at least 95% identical to SEQ ID NO: 182 for CDR2 of the heavy chain;

iii. a sequence that is at least 95% identical to SEQ ID NO: 183 for CDR3 of the heavy chain;

iv. a sequence that is at least 95% identical to SEQ ID NO: 184 for CDR1 of the light chain;

v. a sequence that is at least 95% identical to SEQ ID NO: 185 for CDR2 of the light chain; and vi. a sequence that is at least 95% identical to SEQ ID NO: 186 for CDR3 of the light chain, wherein the antibody competes for binding to MERS-S with an antibody comprising a heavy chain variable region of the amino acid sequence of SEQ ID NO: 7 and a light chain variable region of the amino acid sequence of SEQ ID NO: 47.

The invention provides an anti-MERS-S antibody that binds to the same epitope as an antibody comprising a heavy chain variable region of the amino acid sequence of SEQ ID NO: 8 and a light chain variable region of the amino acid sequence of SEQ ID NO: 48.

The invention further provides an anti-MERS-S antibody that binds to the same epitope as a heavy chain-only antibody comprising a heavy chain variable region of the amino acid sequence of SEQ ID NO: 8.

The invention further provides an anti-MERS-S antibody that competes for binding to MERS-S with an antibody comprising a heavy chain variable region of the amino acid sequence of SEQ ID NO: 8 and a light chain variable region of the amino acid sequence of SEQ ID NO: 48.

The invention further provides an anti-MERS-S antibody that competes for binding to MERS-S with a heavy chain-only antibody comprising a heavy chain variable region of the amino acid sequence of SEQ ID NO: 8.

The invention further provides an anti-MERS-S antibody comprising complementarity determining regions (CDRs) with the sequences of:

i. SEQ ID NO: 187 for CDR1 of the heavy chain;

ii. SEQ ID NO: 188 for CDR2 of the heavy chain;

iii. SEQ ID NO: 189 for CDR3 of the heavy chain;

iv. SEQ ID NO: 190 for CDR1 of the light chain;

v. SEQ ID NO: 191 for CDR2 of the light chain; and vi. SEQ ID NO: 192 for CDR3 of the light chain.

In some embodiments, the antibody comprises a heavy chain variable region of the amino acid sequence of SEQ ID NO: 8.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 8.

In some embodiments, the antibody comprises a light chain variable region of the amino acid sequence of SEQ ID NO: 48.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 48.

In some embodiments, the antibody comprises a heavy chain variable region of the amino acid sequence of SEQ ID NO: 8 and a light chain variable region of the amino acid sequence of SEQ ID NO: 48.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 8 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 48.

The invention further provides an anti-MERS-S antibody comprising complementarity determining regions (CDRs) with:

i. a sequence that is at least 90% identical to SEQ ID NO: 187 for CDR1 of the heavy chain;

ii. a sequence that is at least 90% identical to SEQ ID NO: 188 for CDR2 of the heavy chain;

iii. a sequence that is at least 90% identical to SEQ ID NO: 189 for CDR3 of the heavy chain;

iv. a sequence that is at least 90% identical to SEQ ID NO: 190 for CDR1 of the light chain;

v. a sequence that is at least 90% identical to SEQ ID NO: 191 for CDR2 of the light chain; and vi. a sequence that is at least 90% identical to SEQ ID NO: 192 for CDR3 of the light chain, wherein the antibody competes for binding to MERS-S with an antibody comprising a heavy chain variable region of the amino acid sequence of SEQ ID NO: 8 and a light chain variable region of the amino acid sequence of SEQ ID NO: 48.

The invention further provides an anti-MERS-S antibody comprising complementarity determining regions (CDRs) with:

i. a sequence that is at least 95% identical to SEQ ID NO: 187 for CDR1 of the heavy chain;

ii. a sequence that is at least 95% identical to SEQ ID NO: 188 for CDR2 of the heavy chain;

iii. a sequence that is at least 95% identical to SEQ ID NO: 189 for CDR3 of the heavy chain;

iv. a sequence that is at least 95% identical to SEQ ID NO: 190 for CDR1 of the light v. a sequence that is at least 95% identical to SEQ ID NO: 191 for CDR2 of the light chain; and vi. a sequence that is at least 95% identical to SEQ ID NO: 192 for CDR3 of the light chain, wherein the antibody competes for binding to MERS-S with an antibody comprising a heavy chain variable region of the amino acid sequence of SEQ ID NO: 8 and a light chain variable region of the amino acid sequence of SEQ ID NO: 48.

The invention provides an anti-MERS-S antibody that binds to the same epitope as an antibody comprising a heavy chain variable region of the amino acid sequence of SEQ ID NO: 10 and a light chain variable region of the amino acid sequence of SEQ ID NO: 50.

The invention further provides an anti-MERS-S antibody that binds to the same epitope as a heavy chain-only antibody comprising a heavy chain variable region of the amino acid sequence of SEQ ID NO: 10.

The invention further provides an anti-MERS-S antibody that competes for binding to MERS-S with an antibody comprising a heavy chain variable region of the amino acid sequence of SEQ ID NO: 10 and a light chain variable region of the amino acid sequence of SEQ ID NO: 50.

The invention further provides an anti-MERS-S antibody that competes for binding to MERS-S with a heavy chain-only antibody comprising a heavy chain variable region of the amino acid sequence of SEQ ID NO: 10.

The invention further provides an anti-MERS-S antibody comprising complementarity determining regions (CDRs) with the sequences of:

i. SEQ ID NO: 193 for CDR1 of the heavy chain;
ii. SEQ ID NO: 194 for CDR2 of the heavy chain;
iii. SEQ ID NO: 195 for CDR3 of the heavy chain;
iv. SEQ ID NO: 196 for CDR1 of the light chain;
v. SEQ ID NO: 197 for CDR2 of the light chain; and
vi. SEQ ID NO: 198 for CDR3 of the light chain.

In some embodiments, the antibody comprises a heavy chain variable region of the amino acid sequence of SEQ ID NO: 10.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 10.

In some embodiments, the antibody comprises a light chain variable region of the amino acid sequence of SEQ ID NO: 50.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 50.

In some embodiments, the antibody comprises a heavy chain variable region of the amino acid sequence of SEQ ID NO: 10 and a light chain variable region of the amino acid sequence of SEQ ID NO: 50.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 10 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 50.

The invention further provides an anti-MERS-S antibody comprising complementarity determining regions (CDRs) with:

i. a sequence that is at least 90% identical to SEQ ID NO: 193 for CDR1 of the heavy chain;
ii. a sequence that is at least 90% identical to SEQ ID NO: 194 for CDR2 of the
iii. a sequence that is at least 90% identical to SEQ ID NO: 195 for CDR3 of the heavy chain;
iv. a sequence that is at least 90% identical to SEQ ID NO: 196 for CDR1 of the light chain;
v. a sequence that is at least 90% identical to SEQ ID NO: 197 for CDR2 of the light chain; and
vi. a sequence that is at least 90% identical to SEQ ID NO: 198 for CDR3 of the light chain,
wherein the antibody competes for binding to MERS-S with an antibody comprising a heavy chain variable region of the amino acid sequence of SEQ ID NO: 10 and a light chain variable region of the amino acid sequence of SEQ ID NO: 50.

The invention further provides an anti-MERS-S antibody comprising complementarity determining regions (CDRs) with:

i. a sequence that is at least 95% identical to SEQ ID NO: 193 for CDR1 of the heavy chain;
ii. a sequence that is at least 95% identical to SEQ ID NO: 194 for CDR2 of the heavy chain;
iii. a sequence that is at least 95% identical to SEQ ID NO: 195 for CDR3 of the heavy chain;
iv. a sequence that is at least 95% identical to SEQ ID NO: 196 for CDR1 of the light chain;
v. a sequence that is at least 95% identical to SEQ ID NO: 197 for CDR2 of the light chain; and
vi. a sequence that is at least 95% identical to SEQ ID NO: 198 for CDR3 of the light chain,
wherein the antibody competes for binding to MERS-S with an antibody comprising a heavy chain variable region of the amino acid sequence of SEQ ID NO: 10 and a light chain variable region of the amino acid sequence of SEQ ID NO: 50.

The invention provides an anti-MERS-S antibody that binds to the same epitope as an antibody comprising a heavy chain variable region of the amino acid sequence of SEQ ID NO: 11 and a light chain variable region of the amino acid sequence of SEQ ID NO: 51.

The invention further provides an anti-MERS-S antibody that binds to the same epitope as a heavy chain-only antibody comprising a heavy chain variable region of the amino acid sequence of SEQ ID NO: 11.

The invention further provides an anti-MERS-S antibody that competes for binding to MERS-S with an antibody comprising a heavy chain variable region of the amino acid sequence of SEQ ID NO: 11 and a light chain variable region of the amino acid sequence of SEQ ID NO: 51.

The invention further provides an anti-MERS-S antibody that competes for binding to MERS-S with a heavy chain-only antibody comprising a heavy chain variable region of the amino acid sequence of SEQ ID NO: 11.

The invention further provides an anti-MERS-S antibody comprising complementarity determining regions (CDRs) with the sequences of:

i. SEQ ID NO: 199 for CDR1 of the heavy chain;
ii. SEQ ID NO: 200 for CDR2 of the heavy chain;
iii. SEQ ID NO: 201 for CDR3 of the heavy chain;
iv. SEQ ID NO: 202 for CDR1 of the light chain;
v. SEQ ID NO: 203 for CDR2 of the light chain; and
vi. SEQ ID NO: 204 for CDR3 of the light chain.

In some embodiments, the antibody comprises a heavy chain variable region of the amino acid sequence of SEQ ID NO: 11.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 11.

In some embodiments, the antibody comprises a light chain variable region of the amino acid sequence of SEQ ID NO: 51.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 51.

In some embodiments, the antibody comprises a heavy chain variable region of the amino acid sequence of SEQ ID NO: 11 and a light chain variable region of the amino acid sequence of SEQ ID NO: 51.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 11 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 51.

The invention further provides an anti-MERS-S antibody comprising complementarity determining regions (CDRs) with:

i. a sequence that is at least 90% identical to SEQ ID NO: 199 for CDR1 of the heavy chain;
ii. a sequence that is at least 90% identical to SEQ ID NO: 200 for CDR2 of the heavy chain;
iii. a sequence that is at least 90% identical to SEQ ID NO: 201 for CDR3 of the heavy chain;
iv. a sequence that is at least 90% identical to SEQ ID NO: 202 for CDR1 of the light
v. a sequence that is at least 90% identical to SEQ ID NO: 203 for CDR2 of the light chain; and
vi. a sequence that is at least 90% identical to SEQ ID NO: 204 for CDR3 of the light chain, wherein the antibody competes for binding to MERS-S with an antibody comprising a heavy chain variable region of the amino acid sequence of SEQ ID NO: 11 and a light chain variable region of the amino acid sequence of SEQ ID NO: 51.

The invention further provides an anti-MERS-S antibody comprising complementarity determining regions (CDRs) with:

i. a sequence that is at least 95% identical to SEQ ID NO: 199 for CDR1 of the heavy chain;
ii. a sequence that is at least 95% identical to SEQ ID NO: 200 for CDR2 of the heavy chain;
iii. a sequence that is at least 95% identical to SEQ ID NO: 201 for CDR3 of the heavy chain;
iv. a sequence that is at least 95% identical to SEQ ID NO: 202 for CDR1 of the light chain;
v. a sequence that is at least 95% identical to SEQ ID NO: 203 for CDR2 of the light chain; and
vi. a sequence that is at least 95% identical to SEQ ID NO: 204 for CDR3 of the light chain, wherein the antibody competes for binding to MERS-S with an antibody comprising a heavy chain variable region of the amino acid sequence of SEQ ID NO: 11 and a light chain variable region of the amino acid sequence of SEQ ID NO: 51.

The invention provides an anti-MERS-S antibody that binds to the same epitope as an antibody comprising a heavy chain variable region of the amino acid sequence of SEQ ID NO: 12 and a light chain variable region of the amino acid sequence of SEQ ID NO: 52.

The invention further provides an anti-MERS-S antibody that binds to the same epitope as a heavy chain-only antibody comprising a heavy chain variable region of the amino acid sequence of SEQ ID NO: 12.

The invention further provides an anti-MERS-S antibody that competes for binding to MERS-S with an antibody comprising a heavy chain variable region of the amino acid sequence of SEQ ID NO: 12 and a light chain variable region of the amino acid sequence of SEQ ID NO: 52.

The invention further provides an anti-MERS-S antibody that competes for binding to MERS-S with a heavy chain-only antibody comprising a heavy chain variable region of the amino acid sequence of SEQ ID NO: 12.

The invention further provides an anti-MERS-S antibody comprising complementarity determining regions (CDRs) with the sequences of:

i. SEQ ID NO: 205 for CDR1 of the heavy chain;
ii. SEQ ID NO: 206 for CDR2 of the heavy chain;
iii. SEQ ID NO: 207 for CDR3 of the heavy chain;
iv. SEQ ID NO: 208 for CDR1 of the light chain;
v. SEQ ID NO: 209 for CDR2 of the light chain; and
vi. SEQ ID NO: 210 for CDR3 of the light chain.

In some embodiments, the antibody comprises a heavy chain variable region of the amino acid sequence of SEQ ID NO: 12.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 12.

In some embodiments, the antibody comprises a light chain variable region of the amino acid sequence of SEQ ID NO: 52.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 52.

In some embodiments, the antibody comprises a heavy chain variable region of the amino acid sequence of SEQ ID NO: 12 and a light chain variable region of the amino acid sequence of SEQ ID NO: 52.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 12 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 52.

The invention further provides an anti-MERS-S antibody comprising complementarity determining regions (CDRs) with:

i. a sequence that is at least 90% identical to SEQ ID NO: 205 for CDR1 of the heavy chain;
ii. a sequence that is at least 90% identical to SEQ ID NO: 206 for CDR2 of the heavy chain;
iii. a sequence that is at least 90% identical to SEQ ID NO: 207 for CDR3 of the heavy chain;
iv. a sequence that is at least 90% identical to SEQ ID NO: 208 for CDR1 of the light chain;
v. a sequence that is at least 90% identical to SEQ ID NO: 209 for CDR2 of the light chain; and
vi. a sequence that is at least 90% identical to SEQ ID NO: 210 for CDR3 of the light chain, wherein the antibody competes for binding to MERS-S with an antibody comprising a heavy chain variable region of the amino acid sequence of SEQ ID NO: 12 and a light chain variable region of the amino acid sequence of SEQ ID NO: 52.

The invention further provides an anti-MERS-S antibody comprising complementarity determining regions (CDRs) with:

i. a sequence that is at least 95% identical to SEQ ID NO: 205 for CDR1 of the heavy chain;

ii. a sequence that is at least 95% identical to SEQ ID NO: 206 for CDR2 of the heavy chain;

iii. a sequence that is at least 95% identical to SEQ ID NO: 207 for CDR3 of the heavy chain;

iv. a sequence that is at least 95% identical to SEQ ID NO: 208 for CDR1 of the light chain;

v. a sequence that is at least 95% identical to SEQ ID NO: 209 for CDR2 of the light chain; and vi. a sequence that is at least 95% identical to SEQ ID NO: 210 for CDR3 of the light chain, wherein the antibody competes for binding to MERS-S with an antibody comprising a heavy chain variable region of the amino acid sequence of SEQ ID NO: 12 and a light chain variable region of the amino acid sequence of SEQ ID NO: 52.

The invention provides an anti-MERS-S antibody that binds to the same epitope as an antibody comprising a heavy chain variable region of the amino acid sequence of SEQ ID NO: 13 and a light chain variable region of the amino acid sequence of SEQ ID NO: 34.

The invention further provides an anti-MERS-S antibody that binds to the same epitope as a heavy chain-only antibody comprising a heavy chain variable region of the amino acid sequence of SEQ ID NO: 13.

The invention further provides an anti-MERS-S antibody that competes for binding to MERS-S with an antibody comprising a heavy chain variable region of the amino acid sequence of SEQ ID NO: 13 and a light chain variable region of the amino acid sequence of SEQ ID NO: 34.

The invention further provides an anti-MERS-S antibody that competes for binding to MERS-S with a heavy chain-only antibody comprising a heavy chain variable region of the amino acid sequence of SEQ ID NO: 13.

The invention further provides an anti-MERS-S antibody comprising complementarity determining regions (CDRs) with the sequences of:

i. SEQ ID NO: 211 for CDR1 of the heavy chain;

ii. SEQ ID NO: 212 for CDR2 of the heavy chain;

iii. SEQ ID NO: 213 for CDR3 of the heavy chain;

iv. SEQ ID NO: 214 for CDR1 of the light chain;

v. SEQ ID NO: 215 for CDR2 of the light chain; and vi. SEQ ID NO: 216 for CDR3 of the light chain.

In some embodiments, the antibody comprises a heavy chain variable region of the amino acid sequence of SEQ ID NO: 13.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 13.

In some embodiments, the antibody comprises a light chain variable region of the amino acid sequence of SEQ ID NO: 34.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 34.

In some embodiments, the antibody comprises a heavy chain variable region of the amino acid sequence of SEQ ID NO: 13 and a light chain variable region of the amino acid sequence of SEQ ID NO: 34.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 13 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 34.

The invention further provides an anti-MERS-S antibody comprising complementarity determining regions (CDRs) with:

i. a sequence that is at least 90% identical to SEQ ID NO: 211 for CDR1 of the heavy chain;

ii. a sequence that is at least 90% identical to SEQ ID NO: 212 for CDR2 of the heavy chain;

iii. a sequence that is at least 90% identical to SEQ ID NO: 213 for CDR3 of the heavy chain;

iv. a sequence that is at least 90% identical to SEQ ID NO: 214 for CDR1 of the light chain;

v. a sequence that is at least 90% identical to SEQ ID NO: 215 for CDR2 of the light chain; and vi. a sequence that is at least 90% identical to SEQ ID NO: 216 for CDR3 of the light chain, wherein the antibody competes for binding to MERS-S with an antibody comprising a heavy chain variable region of the amino acid sequence of SEQ ID NO: 13 and a light chain variable region of the amino acid sequence of SEQ ID NO: 34.

The invention further provides an anti-MERS-S antibody comprising complementarity determining regions (CDRs) with:

i. a sequence that is at least 95% identical to SEQ ID NO: 211 for CDR1 of the ii. a sequence that is at least 95% identical to SEQ ID NO: 212 for CDR2 of the heavy chain;

iii. a sequence that is at least 95% identical to SEQ ID NO: 213 for CDR3 of the heavy chain;

iv. a sequence that is at least 95% identical to SEQ ID NO: 214 for CDR1 of the light chain;

v. a sequence that is at least 95% identical to SEQ ID NO: 215 for CDR2 of the light chain; and vi. a sequence that is at least 95% identical to SEQ ID NO: 216 for CDR3 of the light chain, wherein the antibody competes for binding to MERS-S with an antibody comprising a heavy chain variable region of the amino acid sequence of SEQ ID NO: 13 and a light chain variable region of the amino acid sequence of SEQ ID NO: 34.

The invention provides an anti-MERS-S antibody that binds to the same epitope as an antibody comprising a heavy chain variable region of the amino acid sequence of SEQ ID NO: 14 and a light chain variable region of the amino acid sequence of SEQ ID NO: 35.

The invention further provides an anti-MERS-S antibody that binds to the same epitope as a heavy chain-only antibody comprising a heavy chain variable region of the amino acid sequence of SEQ ID NO: 14.

The invention further provides an anti-MERS-S antibody that competes for binding to MERS-S with an antibody comprising a heavy chain variable region of the amino acid sequence of SEQ ID NO: 14 and a light chain variable region of the amino acid sequence of SEQ ID NO: 35.

The invention further provides an anti-MERS-S antibody that competes for binding to MERS-S with a heavy chain-only antibody comprising a heavy chain variable region of the amino acid sequence of SEQ ID NO: 14.

The invention further provides an anti-MERS-S antibody comprising complementarity determining regions (CDRs) with the sequences of:

i. SEQ ID NO: 217 for CDR1 of the heavy chain;
ii. SEQ ID NO: 218 for CDR2 of the heavy chain;
iii. SEQ ID NO: 219 for CDR3 of the heavy chain;
iv. SEQ ID NO: 220 for CDR1 of the light chain;
v. SEQ ID NO: 221 for CDR2 of the light chain; and
vi. SEQ ID NO: 222 for CDR3 of the light chain.

In some embodiments, the antibody comprises a heavy chain variable region of the amino acid sequence of SEQ ID NO: 14.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 14.

In some embodiments, the antibody comprises a light chain variable region of the amino acid sequence of SEQ ID NO: 35.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 35.

In some embodiments, the antibody comprises a heavy chain variable region of the amino acid sequence of SEQ ID NO: 14 and a light chain variable region of the amino acid sequence of SEQ ID NO: 35.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 14 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 35.

The invention further provides an anti-MERS-S antibody comprising complementarity determining regions (CDRs) with:

i. a sequence that is at least 90% identical to SEQ ID NO: 217 for CDR1 of the heavy chain;
ii. a sequence that is at least 90% identical to SEQ ID NO: 218 for CDR2 of the heavy chain;
iii. a sequence that is at least 90% identical to SEQ ID NO: 219 for CDR3 of the heavy chain;
iv. a sequence that is at least 90% identical to SEQ ID NO: 220 for CDR1 of the light chain;
v. a sequence that is at least 90% identical to SEQ ID NO: 221 for CDR2 of the light chain; and
vi. a sequence that is at least 90% identical to SEQ ID NO: 222 for CDR3 of the light chain, wherein the antibody competes for binding to MERS-S with an antibody comprising a heavy chain variable region of the amino acid sequence of SEQ ID NO: 14 and a light chain variable region of the amino acid sequence of SEQ ID NO: 35.

The invention further provides an anti-MERS-S antibody comprising complementarity determining regions (CDRs) with:

i. a sequence that is at least 95% identical to SEQ ID NO: 217 for CDR1 of the heavy chain;
ii. a sequence that is at least 95% identical to SEQ ID NO: 218 for CDR2 of the heavy chain;
iii. a sequence that is at least 95% identical to SEQ ID NO: 219 for CDR3 of the heavy chain;
iv. a sequence that is at least 95% identical to SEQ ID NO: 220 for CDR1 of the light
v. a sequence that is at least 95% identical to SEQ ID NO: 221 for CDR2 of the light chain; and
vi. a sequence that is at least 95% identical to SEQ ID NO: 222 for CDR3 of the light chain, wherein the antibody competes for binding to MERS-S with an antibody comprising a heavy chain variable region of the amino acid sequence of SEQ ID NO: 14 and a light chain variable region of the amino acid sequence of SEQ ID NO: 35.

The invention provides an anti-MERS-S antibody that binds to the same epitope as an antibody comprising a heavy chain variable region of the amino acid sequence of SEQ ID NO: 15 and a light chain variable region of the amino acid sequence of SEQ ID NO: 53.

The invention further provides an anti-MERS-S antibody that binds to the same epitope as a heavy chain-only antibody comprising a heavy chain variable region of the amino acid sequence of SEQ ID NO: 15.

The invention further provides an anti-MERS-S antibody that competes for binding to MERS-S with an antibody comprising a heavy chain variable region of the amino acid sequence of SEQ ID NO: 15 and a light chain variable region of the amino acid sequence of SEQ ID NO: 53.

The invention further provides an anti-MERS-S antibody that competes for binding to MERS-S with a heavy chain-only antibody comprising a heavy chain variable region of the amino acid sequence of SEQ ID NO: 15.

The invention further provides an anti-MERS-S antibody comprising complementarity determining regions (CDRs) with the sequences of:

i. SEQ ID NO: 223 for CDR1 of the heavy chain;
ii. SEQ ID NO: 224 for CDR2 of the heavy chain;
iii. SEQ ID NO: 225 for CDR3 of the heavy chain;
iv. SEQ ID NO: 226 for CDR1 of the light chain;
v. SEQ ID NO: 227 for CDR2 of the light chain; and
vi. SEQ ID NO: 228 for CDR3 of the light chain.

In some embodiments, the antibody comprises a heavy chain variable region of the amino acid sequence of SEQ ID NO: 15.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 15.

In some embodiments, the antibody comprises a light chain variable region of the amino acid sequence of SEQ ID NO: 53.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 53.

In some embodiments, the antibody comprises a heavy chain variable region of the amino acid sequence of SEQ ID NO: 15 and a light chain variable region of the amino acid sequence of SEQ ID NO: 53.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 15 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 53.

The invention further provides an anti-MERS-S antibody comprising complementarity determining regions (CDRs) with:
   i. a sequence that is at least 90% identical to SEQ ID NO: 223 for CDR1 of the heavy chain;
   ii. a sequence that is at least 90% identical to SEQ ID NO: 224 for CDR2 of the
   iii. a sequence that is at least 90% identical to SEQ ID NO: 225 for CDR3 of the heavy chain;
   iv. a sequence that is at least 90% identical to SEQ ID NO: 226 for CDR1 of the light chain;
   v. a sequence that is at least 90% identical to SEQ ID NO: 227 for CDR2 of the light chain; and
   vi. a sequence that is at least 90% identical to SEQ ID NO: 228 for CDR3 of the light chain,
wherein the antibody competes for binding to MERS-S with an antibody comprising a heavy chain variable region of the amino acid sequence of SEQ ID NO: 15 and a light chain variable region of the amino acid sequence of SEQ ID NO: 53.

The invention further provides an anti-MERS-S antibody comprising complementarity determining regions (CDRs) with:
   i. a sequence that is at least 95% identical to SEQ ID NO: 223 for CDR1 of the heavy chain;
   ii. a sequence that is at least 95% identical to SEQ ID NO: 224 for CDR2 of the heavy chain;
   iii. a sequence that is at least 95% identical to SEQ ID NO: 225 for CDR3 of the heavy chain;
   iv. a sequence that is at least 95% identical to SEQ ID NO: 226 for CDR1 of the light chain;
   v. a sequence that is at least 95% identical to SEQ ID NO: 227 for CDR2 of the light chain; and
   vi. a sequence that is at least 95% identical to SEQ ID NO: 228 for CDR3 of the light chain,
wherein the antibody competes for binding to MERS-S with an antibody comprising a heavy chain variable region of the amino acid sequence of SEQ ID NO: 15 and a light chain variable region of the amino acid sequence of SEQ ID NO: 53.

The invention provides an anti-MERS-S antibody that binds to the same epitope as an antibody comprising a heavy chain variable region of the amino acid sequence of SEQ ID NO: 16 and a light chain variable region of the amino acid sequence of SEQ ID NO: 61.

The invention further provides an anti-MERS-S antibody that binds to the same epitope as a heavy chain-only antibody comprising a heavy chain variable region of the amino acid sequence of SEQ ID NO: 16.

The invention further provides an anti-MERS-S antibody that competes for binding to MERS-S with an antibody comprising a heavy chain variable region of the amino acid sequence of SEQ ID NO: 16 and a light chain variable region of the amino acid sequence of SEQ ID NO: 61.

The invention further provides an anti-MERS-S antibody that competes for binding to MERS-S with a heavy chain-only antibody comprising a heavy chain variable region of the amino acid sequence of SEQ ID NO: 16.

The invention further provides an anti-MERS-S antibody comprising complementarity determining regions (CDRs) with the sequences of:
   i. SEQ ID NO: 229 for CDR1 of the heavy chain;
   ii. SEQ ID NO: 230 for CDR2 of the heavy chain;
   iii. SEQ ID NO: 231 for CDR3 of the heavy chain;
   iv. SEQ ID NO: 232 for CDR1 of the light chain;
   v. SEQ ID NO: 233 for CDR2 of the light chain; and
   vi. SEQ ID NO: 234 for CDR3 of the light chain.

In some embodiments, the antibody comprises a heavy chain variable region of the amino acid sequence of SEQ ID NO: 16.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 16.

In some embodiments, the antibody comprises a light chain variable region of the amino acid sequence of SEQ ID NO: 61.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 61.

In some embodiments, the antibody comprises a heavy chain variable region of the amino acid sequence of SEQ ID NO: 16 and a light chain variable region of the amino acid sequence of SEQ ID NO: 61.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 16 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 61.

The invention further provides an anti-MERS-S antibody comprising complementarity determining regions (CDRs) with:
   i. a sequence that is at least 90% identical to SEQ ID NO: 229 for CDR1 of the heavy chain;
   ii. a sequence that is at least 90% identical to SEQ ID NO: 230 for CDR2 of the heavy chain;
   iii. a sequence that is at least 90% identical to SEQ ID NO: 231 for CDR3 of the heavy chain;
   iv. a sequence that is at least 90% identical to SEQ ID NO: 232 for CDR1 of the light
   v. a sequence that is at least 90% identical to SEQ ID NO: 233 for CDR2 of the light chain; and
   vi. a sequence that is at least 90% identical to SEQ ID NO: 234 for CDR3 of the light chain,
wherein the antibody competes for binding to MERS-S with an antibody comprising a heavy chain variable region of the amino acid sequence of SEQ ID NO: 16 and a light chain variable region of the amino acid sequence of SEQ ID NO: 61.

The invention further provides an anti-MERS-S antibody comprising complementarity determining regions (CDRs) with:

i. a sequence that is at least 95% identical to SEQ ID NO: 229 for CDR1 of the heavy chain;

ii. a sequence that is at least 95% identical to SEQ ID NO: 230 for CDR2 of the heavy chain;

iii. a sequence that is at least 95% identical to SEQ ID NO: 231 for CDR3 of the heavy chain;

iv. a sequence that is at least 95% identical to SEQ ID NO: 232 for CDR1 of the light chain;

v. a sequence that is at least 95% identical to SEQ ID NO: 233 for CDR2 of the light chain; and vi. a sequence that is at least 95% identical to SEQ ID NO: 234 for CDR3 of the light chain, wherein the antibody competes for binding to MERS-S with an antibody comprising a heavy chain variable region of the amino acid sequence of SEQ ID NO: 16 and a light chain variable region of the amino acid sequence of SEQ ID NO: 61.

The invention provides an anti-MERS-S antibody that binds to the same epitope as an antibody comprising a heavy chain variable region of the amino acid sequence of SEQ ID NO: 21 and a light chain variable region of the amino acid sequence of SEQ ID NO: 36.

The invention further provides an anti-MERS-S antibody that binds to the same epitope as a heavy chain-only antibody comprising a heavy chain variable region of the amino acid sequence of SEQ ID NO: 21.

The invention further provides an anti-MERS-S antibody that competes for binding to MERS-S with an antibody comprising a heavy chain variable region of the amino acid sequence of SEQ ID NO: 21 and a light chain variable region of the amino acid sequence of SEQ ID NO: 36.

The invention further provides an anti-MERS-S antibody that competes for binding to MERS-S with a heavy chain-only antibody comprising a heavy chain variable region of the amino acid sequence of SEQ ID NO: 21.

The invention further provides an anti-MERS-S antibody comprising complementarity determining regions (CDRs) with the sequences of:

i. SEQ ID NO: 235 for CDR1 of the heavy chain;

ii. SEQ ID NO: 236 for CDR2 of the heavy chain;

iii. SEQ ID NO: 237 for CDR3 of the heavy chain;

iv. SEQ ID NO: 238 for CDR1 of the light chain;

v. SEQ ID NO: 239 for CDR2 of the light chain; and vi. SEQ ID NO: 240 for CDR3 of the light chain.

In some embodiments, the antibody comprises a heavy chain variable region of the amino acid sequence of SEQ ID NO: 21.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 21.

In some embodiments, the antibody comprises a light chain variable region of the amino acid sequence of SEQ ID NO: 36.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 36.

In some embodiments, the antibody comprises a heavy chain variable region of the amino acid sequence of SEQ ID NO: 21 and a light chain variable region of the amino acid sequence of SEQ ID NO: 36.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 21 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 36.

The invention further provides an anti-MERS-S antibody comprising complementarity determining regions (CDRs) with:

i. a sequence that is at least 90% identical to SEQ ID NO: 235 for CDR1 of the heavy chain;

ii. a sequence that is at least 90% identical to SEQ ID NO: 236 for CDR2 of the heavy chain;

iii. a sequence that is at least 90% identical to SEQ ID NO: 237 for CDR3 of the heavy chain;

iv. a sequence that is at least 90% identical to SEQ ID NO: 238 for CDR1 of the light chain;

v. a sequence that is at least 90% identical to SEQ ID NO: 239 for CDR2 of the light chain; and vi. a sequence that is at least 90% identical to SEQ ID NO: 240 for CDR3 of the light chain, wherein the antibody competes for binding to MERS-S with an antibody comprising a heavy chain variable region of the amino acid sequence of SEQ ID NO: 21 and a light chain variable region of the amino acid sequence of SEQ ID NO: 36.

The invention further provides an anti-MERS-S antibody comprising complementarity determining regions (CDRs) with:

i. a sequence that is at least 95% identical to SEQ ID NO: 235 for CDR1 of the heavy chain;

ii. a sequence that is at least 95% identical to SEQ ID NO: 236 for CDR2 of the heavy chain;

iii. a sequence that is at least 95% identical to SEQ ID NO: 237 for CDR3 of the heavy chain;

iv. a sequence that is at least 95% identical to SEQ ID NO: 238 for CDR1 of the light chain;

v. a sequence that is at least 95% identical to SEQ ID NO: 239 for CDR2 of the light chain; and vi. a sequence that is at least 95% identical to SEQ ID NO: 240 for CDR3 of the light chain, wherein the antibody competes for binding to MERS-S with an antibody comprising a heavy chain variable region of the amino acid sequence of SEQ ID NO: 21 and a light chain variable region of the amino acid sequence of SEQ ID NO: 36.

The invention provides an anti-MERS-S antibody that binds to the same epitope as an antibody comprising a heavy chain variable region of the amino acid sequence of SEQ ID NO: 23 and a light chain variable region of the amino acid sequence of SEQ ID NO: 54.

The invention further provides an anti-MERS-S antibody that binds to the same epitope as a heavy chain-only antibody comprising a heavy chain variable region of the amino acid sequence of SEQ ID NO: 23.

The invention further provides an anti-MERS-S antibody that competes for binding to MERS-S with an antibody comprising a heavy chain variable region of the amino acid sequence of SEQ ID NO: 23 and a light chain variable region of the amino acid sequence of SEQ ID NO: 54.

The invention further provides an anti-MERS-S antibody that competes for binding to MERS-S with a heavy chain-only antibody comprising a heavy chain variable region of the amino acid sequence of SEQ ID NO: 23.

The invention further provides an anti-MERS-S antibody comprising complementarity determining regions (CDRs) with the sequences of:

i. SEQ ID NO: 241 for CDR1 of the heavy chain;
    ii. SEQ ID NO: 242 for CDR2 of the heavy chain;
    iii. SEQ ID NO: 243 for CDR3 of the heavy chain;
    iv. SEQ ID NO: 244 for CDR1 of the light chain;
    v. SEQ ID NO: 245 for CDR2 of the light chain; and
    vi. SEQ ID NO: 246 for CDR3 of the light chain.

In some embodiments, the antibody comprises a heavy chain variable region of the amino acid sequence of SEQ ID NO: 23.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 23.

In some embodiments, the antibody comprises a light chain variable region of the amino acid sequence of SEQ ID NO: 54.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 54.

In some embodiments, the antibody comprises a heavy chain variable region of the amino acid sequence of SEQ ID NO: 23 and a light chain variable region of the amino acid sequence of SEQ ID NO: 54.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 23 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 54.

The invention further provides an anti-MERS-S antibody comprising complementarity determining regions (CDRs) with:

i. a sequence that is at least 90% identical to SEQ ID NO: 241 for CDR1 of the heavy chain;
    ii. a sequence that is at least 90% identical to SEQ ID NO: 242 for CDR2 of the heavy chain;
    iii. a sequence that is at least 90% identical to SEQ ID NO: 243 for CDR3 of the heavy chain;
    iv. a sequence that is at least 90% identical to SEQ ID NO: 244 for CDR1 of the light chain;
    v. a sequence that is at least 90% identical to SEQ ID NO: 245 for CDR2 of the light chain; and
    vi. a sequence that is at least 90% identical to SEQ ID NO: 246 for CDR3 of the light chain, wherein the antibody competes for binding to MERS-S with an antibody comprising a heavy chain variable region of the amino acid sequence of SEQ ID NO: 23 and a light chain variable region of the amino acid sequence of SEQ ID NO: 54.

The invention further provides an anti-MERS-S antibody comprising complementarity determining regions (CDRs) with:

i. a sequence that is at least 95% identical to SEQ ID NO: 241 for CDR1 of the
    ii. a sequence that is at least 95% identical to SEQ ID NO: 242 for CDR2 of the heavy chain;
    iii. a sequence that is at least 95% identical to SEQ ID NO: 243 for CDR3 of the heavy chain;
    iv. a sequence that is at least 95% identical to SEQ ID NO: 244 for CDR1 of the light chain;
    v. a sequence that is at least 95% identical to SEQ ID NO: 245 for CDR2 of the light chain; and
    vi. a sequence that is at least 95% identical to SEQ ID NO: 246 for CDR3 of the light chain, wherein the antibody competes for binding to MERS-S with an antibody comprising a heavy chain variable region of the amino acid sequence of SEQ ID NO: 23 and a light chain variable region of the amino acid sequence of SEQ ID NO: 54.

The invention provides an anti-MERS-S antibody that binds to the same epitope as an antibody comprising a heavy chain variable region of the amino acid sequence of SEQ ID NO: 24 and a light chain variable region of the amino acid sequence of SEQ ID NO: 37.

The invention further provides an anti-MERS-S antibody that binds to the same epitope as a heavy chain-only antibody comprising a heavy chain variable region of the amino acid sequence of SEQ ID NO: 24.

The invention further provides an anti-MERS-S antibody that competes for binding to MERS-S with an antibody comprising a heavy chain variable region of the amino acid sequence of SEQ ID NO: 24 and a light chain variable region of the amino acid sequence of SEQ ID NO: 37.

The invention further provides an anti-MERS-S antibody that competes for binding to MERS-S with a heavy chain-only antibody comprising a heavy chain variable region of the amino acid sequence of SEQ ID NO: 24.

The invention further provides an anti-MERS-S antibody comprising complementarity determining regions (CDRs) with the sequences of:

i. SEQ ID NO: 247 for CDR1 of the heavy chain;
    ii. SEQ ID NO: 248 for CDR2 of the heavy chain;
    iii. SEQ ID NO: 249 for CDR3 of the heavy chain;
    iv. SEQ ID NO: 250 for CDR1 of the light chain;
    v. SEQ ID NO: 251 for CDR2 of the light chain; and
    vi. SEQ ID NO: 252 for CDR3 of the light chain.

In some embodiments, the antibody comprises a heavy chain variable region of the amino acid sequence of SEQ ID NO: 24.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 24.

In some embodiments, the antibody comprises a light chain variable region of the amino acid sequence of SEQ ID NO: 37.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 37.

In some embodiments, the antibody comprises a heavy chain variable region of the amino acid sequence of SEQ ID NO: 24 and a light chain variable region of the amino acid sequence of SEQ ID NO: 37.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 24 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 37.

The invention further provides an anti-MERS-S antibody comprising complementarity determining regions (CDRs) with:

i. a sequence that is at least 90% identical to SEQ ID NO: 247 for CDR1 of the heavy chain;

ii. a sequence that is at least 90% identical to SEQ ID NO: 248 for CDR2 of the heavy chain;

iii. a sequence that is at least 90% identical to SEQ ID NO: 249 for CDR3 of the heavy chain;

iv. a sequence that is at least 90% identical to SEQ ID NO: 250 for CDR1 of the light chain;

v. a sequence that is at least 90% identical to SEQ ID NO: 251 for CDR2 of the light chain; and vi. a sequence that is at least 90% identical to SEQ ID NO: 252 for CDR3 of the light chain, wherein the antibody competes for binding to MERS-S with an antibody comprising a heavy chain variable region of the amino acid sequence of SEQ ID NO: 24 and a light chain variable region of the amino acid sequence of SEQ ID NO: 37.

The invention further provides an anti-MERS-S antibody comprising complementarity determining regions (CDRs) with:

i. a sequence that is at least 95% identical to SEQ ID NO: 247 for CDR1 of the heavy chain;

ii. a sequence that is at least 95% identical to SEQ ID NO: 248 for CDR2 of the heavy chain;

iii. a sequence that is at least 95% identical to SEQ ID NO: 249 for CDR3 of the heavy chain;

iv. a sequence that is at least 95% identical to SEQ ID NO: 250 for CDR1 of the light v. a sequence that is at least 95% identical to SEQ ID NO: 251 for CDR2 of the light chain; and vi. a sequence that is at least 95% identical to SEQ ID NO: 252 for CDR3 of the light chain, wherein the antibody competes for binding to MERS-S with an antibody comprising a heavy chain variable region of the amino acid sequence of SEQ ID NO: 24 and a light chain variable region of the amino acid sequence of SEQ ID NO: 37.

The invention provides an anti-MERS-S antibody that binds to the same epitope as an antibody comprising a heavy chain variable region of the amino acid sequence of SEQ ID NO: 25 and a light chain variable region of the amino acid sequence of SEQ ID NO: 64.

The invention further provides an anti-MERS-S antibody that binds to the same epitope as a heavy chain-only antibody comprising a heavy chain variable region of the amino acid sequence of SEQ ID NO: 25.

The invention further provides an anti-MERS-S antibody that competes for binding to MERS-S with an antibody comprising a heavy chain variable region of the amino acid sequence of SEQ ID NO: 25 and a light chain variable region of the amino acid sequence of SEQ ID NO: 64.

The invention further provides an anti-MERS-S antibody that competes for binding to MERS-S with a heavy chain-only antibody comprising a heavy chain variable region of the amino acid sequence of SEQ ID NO: 25.

The invention further provides an anti-MERS-S antibody comprising complementarity determining regions (CDRs) with the sequences of:

i. SEQ ID NO: 253 for CDR1 of the heavy chain;

ii. SEQ ID NO: 254 for CDR2 of the heavy chain;

iii. SEQ ID NO: 255 for CDR3 of the heavy chain;

iv. SEQ ID NO: 256 for CDR1 of the light chain;

v. SEQ ID NO: 257 for CDR2 of the light chain; and vi. SEQ ID NO: 258 for CDR3 of the light chain.

In some embodiments, the antibody comprises a heavy chain variable region of the amino acid sequence of SEQ ID NO: 25.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 25.

In some embodiments, the antibody comprises a light chain variable region of the amino acid sequence of SEQ ID NO: 64.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 64.

In some embodiments, the antibody comprises a heavy chain variable region of the amino acid sequence of SEQ ID NO: 25 and a light chain variable region of the amino acid sequence of SEQ ID NO: 64.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 25 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 64.

The invention further provides an anti-MERS-S antibody comprising complementarity determining regions (CDRs) with:

i. a sequence that is at least 90% identical to SEQ ID NO: 253 for CDR1 of the heavy chain;

ii. a sequence that is at least 90% identical to SEQ ID NO: 254 for CDR2 of the iii. a sequence that is at least 90% identical to SEQ ID NO: 255 for CDR3 of the heavy chain;

iv. a sequence that is at least 90% identical to SEQ ID NO: 256 for CDR1 of the light chain;

v. a sequence that is at least 90% identical to SEQ ID NO: 257 for CDR2 of the light chain; and vi. a sequence that is at least 90% identical to SEQ ID NO: 258 for CDR3 of the light chain, wherein the antibody competes for binding to MERS-S with an antibody comprising a heavy chain variable region of the amino acid sequence of SEQ ID NO: 25 and a light chain variable region of the amino acid sequence of SEQ ID NO: 64.

The invention further provides an anti-MERS-S antibody comprising complementarity determining regions (CDRs) with:

i. a sequence that is at least 95% identical to SEQ ID NO: 253 for CDR1 of the heavy chain;

ii. a sequence that is at least 95% identical to SEQ ID NO: 254 for CDR2 of the heavy chain;

iii. a sequence that is at least 95% identical to SEQ ID NO: 255 for CDR3 of the heavy chain;

iv. a sequence that is at least 95% identical to SEQ ID NO: 256 for CDR1 of the light chain;

v. a sequence that is at least 95% identical to SEQ ID NO: 257 for CDR2 of the light chain; and vi. a sequence that is at least 95% identical to SEQ ID NO: 258 for CDR3 of the light chain, wherein the antibody competes for binding to MERS-S with an antibody comprising a heavy chain variable region of the amino acid sequence of SEQ ID NO: 25 and a light chain variable region of the amino acid sequence of SEQ ID NO: 64.

The invention provides an anti-MERS-S antibody that binds to the same epitope as an antibody comprising a heavy chain variable region of the amino acid sequence of SEQ ID NO: 27 and a light chain variable region of the amino acid sequence of SEQ ID NO: 38.

The invention further provides an anti-MERS-S antibody that binds to the same epitope as a heavy chain-only antibody comprising a heavy chain variable region of the amino acid sequence of SEQ ID NO: 27.

The invention further provides an anti-MERS-S antibody that competes for binding to MERS-S with an antibody comprising a heavy chain variable region of the amino acid sequence of SEQ ID NO: 27 and a light chain variable region of the amino acid sequence of SEQ ID NO: 38.

The invention further provides an anti-MERS-S antibody that competes for binding to MERS-S with a heavy chain-only antibody comprising a heavy chain variable region of the amino acid sequence of SEQ ID NO: 27.

The invention further provides an anti-MERS-S antibody comprising complementarity determining regions (CDRs) with the sequences of:

i. SEQ ID NO: 259 for CDR1 of the heavy chain;

ii. SEQ ID NO: 260 for CDR2 of the heavy chain;

iii. SEQ ID NO: 261 for CDR3 of the heavy chain;

iv. SEQ ID NO: 262 for CDR1 of the light chain;

v. SEQ ID NO: 263 for CDR2 of the light chain; and vi. SEQ ID NO: 264 for CDR3 of the light chain.

In some embodiments, the antibody comprises a heavy chain variable region of the amino acid sequence of SEQ ID NO: 27.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 27.

In some embodiments, the antibody comprises a light chain variable region of the amino acid sequence of SEQ ID NO: 38.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 38.

In some embodiments, the antibody comprises a heavy chain variable region of the amino acid sequence of SEQ ID NO: 27 and a light chain variable region of the amino acid sequence of SEQ ID NO: 38.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 27 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 38.

The invention further provides an anti-MERS-S antibody comprising complementarity determining regions (CDRs) with:

i. a sequence that is at least 90% identical to SEQ ID NO: 259 for CDR1 of the heavy chain;

ii. a sequence that is at least 90% identical to SEQ ID NO: 260 for CDR2 of the heavy chain;

iii. a sequence that is at least 90% identical to SEQ ID NO: 261 for CDR3 of the heavy chain;

iv. a sequence that is at least 90% identical to SEQ ID NO: 262 for CDR1 of the light v. a sequence that is at least 90% identical to SEQ ID NO: 263 for CDR2 of the light chain; and vi. a sequence that is at least 90% identical to SEQ ID NO: 264 for CDR3 of the light chain, wherein the antibody competes for binding to MERS-S with an antibody comprising a heavy chain variable region of the amino acid sequence of SEQ ID NO: 27 and a light chain variable region of the amino acid sequence of SEQ ID NO: 38.

The invention further provides an anti-MERS-S antibody comprising complementarity determining regions (CDRs) with:

i. a sequence that is at least 95% identical to SEQ ID NO: 259 for CDR1 of the heavy chain;

ii. a sequence that is at least 95% identical to SEQ ID NO: 260 for CDR2 of the heavy chain;

iii. a sequence that is at least 95% identical to SEQ ID NO: 261 for CDR3 of the heavy chain;

iv. a sequence that is at least 95% identical to SEQ ID NO: 262 for CDR1 of the light chain;

v. a sequence that is at least 95% identical to SEQ ID NO: 263 for CDR2 of the light chain; and vi. a sequence that is at least 95% identical to SEQ ID NO: 264 for CDR3 of the light chain, wherein the antibody competes for binding to MERS-S with an antibody comprising a heavy chain variable region of the amino acid sequence of SEQ ID NO: 27 and a light chain variable region of the amino acid sequence of SEQ ID NO: 38.

The invention provides an anti-MERS-S antibody that binds to the same epitope as an antibody comprising a heavy chain variable region of the amino acid sequence of SEQ ID NO: 30 and a light chain variable region of the amino acid sequence of SEQ ID NO: 55.

The invention further provides an anti-MERS-S antibody that binds to the same epitope as a heavy chain-only antibody comprising a heavy chain variable region of the amino acid sequence of SEQ ID NO: 30.

The invention further provides an anti-MERS-S antibody that competes for binding to MERS-S with an antibody comprising a heavy chain variable region of the amino acid sequence of SEQ ID NO: 30 and a light chain variable region of the amino acid sequence of SEQ ID NO: 55.

The invention further provides an anti-MERS-S antibody that competes for binding to MERS-S with a heavy chain-only antibody comprising a heavy chain variable region of the amino acid sequence of SEQ ID NO: 30.

The invention further provides an anti-MERS-S antibody comprising complementarity determining regions (CDRs) with the sequences of:

i. SEQ ID NO: 265 for CDR1 of the heavy chain;
ii. SEQ ID NO: 266 for CDR2 of the heavy chain;
iii. SEQ ID NO: 267 for CDR3 of the heavy chain;
iv. SEQ ID NO: 268 for CDR1 of the light chain;
v. SEQ ID NO: 269 for CDR2 of the light chain; and
vi. SEQ ID NO: 270 for CDR3 of the light chain.

In some embodiments, the antibody comprises a heavy chain variable region of the amino acid sequence of SEQ ID NO: 30.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 30.

In some embodiments, the antibody comprises a light chain variable region of the amino acid sequence of SEQ ID NO: 55.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 55.

In some embodiments, the antibody comprises a heavy chain variable region of the amino acid sequence of SEQ ID NO: 30 and a light chain variable region of the amino acid sequence of SEQ ID NO: 55.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 30 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 55.

The invention further provides an anti-MERS-S antibody comprising complementarity determining regions (CDRs) with:

i. a sequence that is at least 90% identical to SEQ ID NO: 265 for CDR1 of the heavy chain;
ii. a sequence that is at least 90% identical to SEQ ID NO: 266 for CDR2 of the heavy chain;
iii. a sequence that is at least 90% identical to SEQ ID NO: 267 for CDR3 of the heavy chain;
iv. a sequence that is at least 90% identical to SEQ ID NO: 268 for CDR1 of the light chain;
v. a sequence that is at least 90% identical to SEQ ID NO: 269 for CDR2 of the light chain; and
vi. a sequence that is at least 90% identical to SEQ ID NO: 270 for CDR3 of the light chain, wherein the antibody competes for binding to MERS-S with an antibody comprising a heavy chain variable region of the amino acid sequence of SEQ ID NO: 30 and a light chain variable region of the amino acid sequence of SEQ ID NO: 55.

The invention further provides an anti-MERS-S antibody comprising complementarity determining regions (CDRs) with:

i. a sequence that is at least 95% identical to SEQ ID NO: 265 for CDR1 of the heavy chain;
ii. a sequence that is at least 95% identical to SEQ ID NO: 266 for CDR2 of the heavy chain;
iii. a sequence that is at least 95% identical to SEQ ID NO: 267 for CDR3 of the heavy chain;
iv. a sequence that is at least 95% identical to SEQ ID NO: 268 for CDR1 of the light chain;
v. a sequence that is at least 95% identical to SEQ ID NO: 269 for CDR2 of the light chain; and
vi. a sequence that is at least 95% identical to SEQ ID NO: 270 for CDR3 of the light chain, wherein the antibody competes for binding to MERS-S with an antibody comprising a heavy chain variable region of the amino acid sequence of SEQ ID NO: 30 and a light chain variable region of the amino acid sequence of SEQ ID NO: 55.

The 4.2f1 and 4.9e5 antibodies bind to the S1$^B$ domain and exhibit neutralising activity (see FIG. 29(A)). Each of these antibodies belongs to group 1.3 g2. Similar functional properties can be expected to be associated with the antibodies defined below which share structural and binding characteristics with the 4.2f1 and/or 4.9e5 antibodies.

The invention provides an anti-MERS-S antibody that binds to the same epitope as an antibody comprising a heavy chain variable region of the amino acid sequence of SEQ ID NO: 283 and a light chain variable region of the amino acid sequence of SEQ ID NO: 284.

The invention further provides an anti-MERS-S antibody that binds to the same epitope as a heavy chain-only antibody comprising a heavy chain variable region of the amino acid sequence of SEQ ID NO: 283.

The invention further provides an anti-MERS-S antibody that competes for binding to MERS-S with an antibody comprising a heavy chain variable region of the amino acid sequence of SEQ ID NO: 283 and a light chain variable region of the amino acid sequence of SEQ ID NO: 284.

The invention further provides an anti-MERS-S antibody that competes for binding to MERS-S with a heavy chain-only antibody comprising a heavy chain variable region of the amino acid sequence of SEQ ID NO: 283.

The invention further provides an anti-MERS-S antibody comprising complementarity determining regions (CDRs) with the sequences of:

i. SEQ ID NO: 285 for CDR1 of the heavy chain;
ii. SEQ ID NO: 286 for CDR2 of the heavy chain;
iii. SEQ ID NO: 287 for CDR3 of the heavy chain;
iv. SEQ ID NO: 288 for CDR1 of the light chain;
v. SEQ ID NO: 289 for CDR2 of the light chain; and
vi. SEQ ID NO: 290 for CDR3 of the light chain.

In some embodiments, the antibody comprises a heavy chain variable region of the amino acid sequence of SEQ ID NO: 283.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 283.

In some embodiments, the antibody comprises a light chain variable region of the amino acid sequence of SEQ ID NO: 284.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 284.

In some embodiments, the antibody comprises a heavy chain variable region of the amino acid sequence of SEQ ID NO: 283 and a light chain variable region of the amino acid sequence of SEQ ID NO: 284.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 283 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 284.

The invention further provides an anti-MERS-S antibody comprising complementarity determining regions (CDRs) with:

i. a sequence that is at least 90% identical to SEQ ID NO: 285 for CDR1 of the heavy chain;

ii. a sequence that is at least 90% identical to SEQ ID NO: 286 for CDR2 of the heavy chain;

iii. a sequence that is at least 90% identical to SEQ ID NO: 287 for CDR3 of the heavy chain;

iv. a sequence that is at least 90% identical to SEQ ID NO: 288 for CDR1 of the light chain;

v. a sequence that is at least 90% identical to SEQ ID NO: 289 for CDR2 of the light chain; and vi. a sequence that is at least 90% identical to SEQ ID NO: 290 for CDR3 of the light chain, wherein the antibody competes for binding to MERS-S with an antibody comprising a heavy chain variable region of the amino acid sequence of SEQ ID NO: 283 and a light chain variable region of the amino acid sequence of SEQ ID NO: 284.

The invention further provides an anti-MERS-S antibody comprising complementarity determining regions (CDRs) with:

i. a sequence that is at least 95% identical to SEQ ID NO: 285 for CDR1 of the heavy chain;

ii. a sequence that is at least 95% identical to SEQ ID NO: 286 for CDR2 of the heavy chain;

iii. a sequence that is at least 95% identical to SEQ ID NO: 287 for CDR3 of the heavy chain;

iv. a sequence that is at least 95% identical to SEQ ID NO: 288 for CDR1 of the light chain;

v. a sequence that is at least 95% identical to SEQ ID NO: 289 for CDR2 of the light chain; and vi. a sequence that is at least 95% identical to SEQ ID NO: 290 for CDR3 of the light chain, wherein the antibody competes for binding to MERS-S with an antibody comprising a heavy chain variable region of the amino acid sequence of SEQ ID NO: 283 and a light chain variable region of the amino acid sequence of SEQ ID NO: 284.

The invention provides an anti-MERS-S antibody that binds to the same epitope as an antibody comprising a heavy chain variable region of the amino acid sequence of SEQ ID NO: 291 and a light chain variable region of the amino acid sequence of SEQ ID NO: 292.

The invention further provides an anti-MERS-S antibody that binds to the same epitope as a heavy chain-only antibody comprising a heavy chain variable region of the amino acid sequence of SEQ ID NO: 291.

The invention further provides an anti-MERS-S antibody that competes for binding to MERS-S with an antibody comprising a heavy chain variable region of the amino acid sequence of SEQ ID NO: 291 and a light chain variable region of the amino acid sequence of SEQ ID NO: 292.

The invention further provides an anti-MERS-S antibody that competes for binding to MERS-S with a heavy chain-only antibody comprising a heavy chain variable region of the amino acid sequence of SEQ ID NO: 291.

The invention further provides an anti-MERS-S antibody comprising complementarity determining regions (CDRs) with the sequences of:

i. SEQ ID NO: 293 for CDR1 of the heavy chain;

ii. SEQ ID NO: 294 for CDR2 of the heavy chain;

iii. SEQ ID NO: 295 for CDR3 of the heavy chain;

iv. SEQ ID NO: 296 for CDR1 of the light chain;

v. SEQ ID NO: 297 for CDR2 of the light chain; and vi. SEQ ID NO: 298 for CDR3 of the light chain.

In some embodiments, the antibody comprises a heavy chain variable region of the amino acid sequence of SEQ ID NO: 291.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 291.

In some embodiments, the antibody comprises a light chain variable region of the amino acid sequence of SEQ ID NO: 292.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 292.

In some embodiments, the antibody comprises a heavy chain variable region of the amino acid sequence of SEQ ID NO: 291 and a light chain variable region of the amino acid sequence of SEQ ID NO: 292.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 291 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 292.

The invention further provides an anti-MERS-S antibody comprising complementarity determining regions (CDRs) with:

i. a sequence that is at least 90% identical to SEQ ID NO: 293 for CDR1 of the heavy chain;

ii. a sequence that is at least 90% identical to SEQ ID NO: 294 for CDR2 of the heavy chain;

iii. a sequence that is at least 90% identical to SEQ ID NO: 295 for CDR3 of the heavy chain;

iv. a sequence that is at least 90% identical to SEQ ID NO: 296 for CDR1 of the light chain;

v. a sequence that is at least 90% identical to SEQ ID NO: 297 for CDR2 of the light chain; and vi. a sequence that is at least 90% identical to SEQ ID NO: 298 for CDR3 of the light chain, wherein the antibody competes for binding to MERS-S with an antibody comprising a heavy chain variable region of the amino acid sequence of SEQ ID NO: 291 and a light chain variable region of the amino acid sequence of SEQ ID NO: 292.

The invention further provides an anti-MERS-S antibody comprising complementarity determining regions (CDRs) with:

i. a sequence that is at least 95% identical to SEQ ID NO: 293 for CDR1 of the heavy chain;

ii. a sequence that is at least 95% identical to SEQ ID NO: 294 for CDR2 of the heavy chain;

iii. a sequence that is at least 95% identical to SEQ ID NO: 295 for CDR3 of the iv. a sequence that is at least 95% identical to SEQ ID NO: 296 for CDR1 of the light chain;

v. a sequence that is at least 95% identical to SEQ ID NO: 297 for CDR2 of the light chain; and vi. a sequence that is at least 95% identical to SEQ ID NO: 298 for CDR3 of the light chain, wherein the antibody competes for binding to MERS-S with an antibody comprising a heavy chain variable region of the amino acid sequence of SEQ ID NO: 291 and a light chain variable region of the amino acid sequence of SEQ ID NO: 292.

The 7.4f3 antibody binds to the S1$_B$ domain (see FIG. 5A). Similar functional properties can be expected to be associated with the antibodies defined below which share structural and binding characteristics with the 7.4f3 antibody.

The invention provides an anti-MERS-S antibody that binds to the same epitope as an antibody comprising a heavy chain variable region of the amino acid sequence of SEQ ID NO: 323 and a light chain variable region of the amino acid sequence of SEQ ID NO: 324.

The invention further provides an anti-MERS-S antibody that binds to the same epitope as a heavy chain-only antibody comprising a heavy chain variable region of the amino acid sequence of SEQ ID NO: 323.

The invention further provides an anti-MERS-S antibody that competes for binding to MERS-S with an antibody comprising a heavy chain variable region of the amino acid sequence of SEQ ID NO: 323 and a light chain variable region of the amino acid sequence of SEQ ID NO: 324.

The invention further provides an anti-MERS-S antibody that competes for binding to MERS-S with a heavy chain-only antibody comprising a heavy chain variable region of the amino acid sequence of SEQ ID NO: 323.

The invention further provides an anti-MERS-S antibody comprising complementarity determining regions (CDRs) with the sequences of:

i. SEQ ID NO: 325 for CDR1 of the heavy chain;

ii. SEQ ID NO: 326 for CDR2 of the heavy chain;

iii. SEQ ID NO: 327 for CDR3 of the heavy chain;

iv. SEQ ID NO: 328 for CDR1 of the light chain;

v. SEQ ID NO: 329 for CDR2 of the light chain; and vi. SEQ ID NO: 330 for CDR3 of the light chain.

In some embodiments, the antibody comprises a heavy chain variable region of the amino acid sequence of SEQ ID NO: 323.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 323.

In some embodiments, the antibody comprises a light chain variable region of the amino acid sequence of SEQ ID NO: 324.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 324.

In some embodiments, the antibody comprises a heavy chain variable region of the amino acid sequence of SEQ ID NO: 323 and a light chain variable region of the amino acid sequence of SEQ ID NO: 324.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 323 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 324.

The invention further provides an anti-MERS-S antibody comprising complementarity determining regions (CDRs) with:

i. a sequence that is at least 90% identical to SEQ ID NO: 325 for CDR1 of the heavy chain;

ii. a sequence that is at least 90% identical to SEQ ID NO: 326 for CDR2 of the heavy chain;

iii. a sequence that is at least 90% identical to SEQ ID NO: 327 for CDR3 of the heavy chain;

iv. a sequence that is at least 90% identical to SEQ ID NO: 328 for CDR1 of the light chain;

v. a sequence that is at least 90% identical to SEQ ID NO: 329 for CDR2 of the light chain; and vi. a sequence that is at least 90% identical to SEQ ID NO: 330 for CDR3 of the light chain, wherein the antibody competes for binding to MERS-S with an antibody comprising a heavy chain variable region of the amino acid sequence of SEQ ID NO: 323 and a light chain variable region of the amino acid sequence of SEQ ID NO: 324.

The invention further provides an anti-MERS-S antibody comprising complementarity determining regions (CDRs) with:

i. a sequence that is at least 95% identical to SEQ ID NO: 325 for CDR1 of the heavy chain;

ii. a sequence that is at least 95% identical to SEQ ID NO: 326 for CDR2 of the heavy chain;

iii. a sequence that is at least 95% identical to SEQ ID NO: 327 for CDR3 of the heavy chain;

iv. a sequence that is at least 95% identical to SEQ ID NO: 328 for CDR1 of the light v. a sequence that is at least 95% identical to SEQ ID NO: 329 for CDR2 of the light chain; and vi. a sequence that is at least 95% identical to SEQ ID NO: 330 for CDR3 of the light chain, wherein the antibody competes for binding to MERS-S with an antibody comprising a heavy chain variable region of the amino acid sequence of SEQ ID NO: 323 and a light chain variable region of the amino acid sequence of SEQ ID NO: 324.

The 7.8hl antibody binds to the S1 domain (see FIG. 29A). Similar functional properties can be expected to be associated with the antibodies defined below which share structural and binding characteristics with the 7.8hl antibody.

The invention provides an anti-MERS-S antibody that binds to the same epitope as an antibody comprising a heavy chain variable region of the amino acid sequence of SEQ ID NO: 331 and a light chain variable region of the amino acid sequence of SEQ ID NO: 332.

The invention further provides an anti-MERS-S antibody that binds to the same epitope as a heavy chain-only antibody comprising a heavy chain variable region of the amino acid sequence of SEQ ID NO: 331.

The invention further provides an anti-MERS-S antibody that competes for binding to MERS-S with an antibody comprising a heavy chain variable region of the amino acid sequence of SEQ ID NO: 331 and a light chain variable region of the amino acid sequence of SEQ ID NO: 332.

The invention further provides an anti-MERS-S antibody that competes for binding to MERS-S with a heavy chain-only antibody comprising a heavy chain variable region of the amino acid sequence of SEQ ID NO: 331.

The invention further provides an anti-MERS-S antibody comprising complementarity determining regions (CDRs) with the sequences of:

i. SEQ ID NO: 333 for CDR1 of the heavy chain;
ii. SEQ ID NO: 334 for CDR2 of the heavy chain;
iii. SEQ ID NO: 335 for CDR3 of the heavy chain;
iv. SEQ ID NO: 336 for CDR1 of the light chain;
v. SEQ ID NO: 337 for CDR2 of the light chain; and
vi. SEQ ID NO: 338 for CDR3 of the light chain.

In some embodiments, the antibody comprises a heavy chain variable region of the amino acid sequence of SEQ ID NO: 331.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 331.

In some embodiments, the antibody comprises a light chain variable region of the amino acid sequence of SEQ ID NO: 332.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 332.

In some embodiments, the antibody comprises a heavy chain variable region of the amino acid sequence of SEQ ID NO: 331 and a light chain variable region of the amino acid sequence of SEQ ID NO: 332.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 331 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 332.

The invention further provides an anti-MERS-S antibody comprising complementarity determining regions (CDRs) with:

i. a sequence that is at least 90% identical to SEQ ID NO: 333 for CDR1 of the
ii. a sequence that is at least 90% identical to SEQ ID NO: 334 for CDR2 of the heavy chain;
iii. a sequence that is at least 90% identical to SEQ ID NO: 335 for CDR3 of the heavy chain;
iv. a sequence that is at least 90% identical to SEQ ID NO: 336 for CDR1 of the light chain;
v. a sequence that is at least 90% identical to SEQ ID NO: 337 for CDR2 of the light chain; and
vi. a sequence that is at least 90% identical to SEQ ID NO: 338 for CDR3 of the light chain, wherein the antibody competes for binding to MERS-S with an antibody comprising a heavy chain variable region of the amino acid sequence of SEQ ID NO: 331 and a light chain variable region of the amino acid sequence of SEQ ID NO: 332.

The invention further provides an anti-MERS-S antibody comprising complementarity determining regions (CDRs) with:

i. a sequence that is at least 95% identical to SEQ ID NO: 333 for CDR1 of the heavy chain;
ii. a sequence that is at least 95% identical to SEQ ID NO: 334 for CDR2 of the heavy chain;
iii. a sequence that is at least 95% identical to SEQ ID NO: 335 for CDR3 of the heavy chain;
iv. a sequence that is at least 95% identical to SEQ ID NO: 336 for CDR1 of the light chain;
v. a sequence that is at least 95% identical to SEQ ID NO: 337 for CDR2 of the light chain; and
vi. a sequence that is at least 95% identical to SEQ ID NO: 338 for CDR3 of the light chain, wherein the antibody competes for binding to MERS-S with an antibody comprising a heavy chain variable region of the amino acid sequence of SEQ ID NO: 331 and a light chain variable region of the amino acid sequence of SEQ ID NO: 332.

The 1.6a9, 2.6 h11, 1.17f10, 1.12 g2, 1.5d6 and 1.13a9 antibodies bind to the S2 domain (see FIG. 29A). These antibodies do not exhibit neutralising activity in the assays tested (see FIGS. 8 and 29A). Similar functional properties can be expected to be associated with the antibodies defined below which share structural and binding characteristics with one or more of the 1.6a9, 2.6 h11, 1.17f10, 1.12 g2, 1.5d6 and 1.13a9 antibodies.

The invention provides an anti-MERS-S antibody that binds to the same epitope as an antibody comprising a heavy chain variable region of the amino acid sequence of SEQ ID NO: 339 and a light chain variable region of the amino acid sequence of SEQ ID NO: 340.

The invention further provides an anti-MERS-S antibody that binds to the same epitope as a heavy chain-only antibody comprising a heavy chain variable region of the amino acid sequence of SEQ ID NO: 339.

The invention further provides an anti-MERS-S antibody that competes for binding to MERS-S with an antibody comprising a heavy chain variable region of the amino acid sequence of SEQ ID NO: 339 and a light chain variable region of the amino acid sequence of SEQ ID NO: 340.

The invention further provides an anti-MERS-S antibody that competes for binding to MERS-S with a heavy chain-only antibody comprising a heavy chain variable region of the amino acid sequence of SEQ ID NO: 339.

The invention further provides an anti-MERS-S antibody comprising complementarity determining regions (CDRs) with the sequences of:

i. SEQ ID NO: 341 for CDR1 of the heavy chain;

ii. SEQ ID NO: 342 for CDR2 of the heavy chain;

i SEQ ID NO: 343 for CDR3 of the heavy chain;

iv. SEQ ID NO: 344 for CDR1 of the light chain;

v. SEQ ID NO: 345 for CDR2 of the light chain; and vi. SEQ ID NO: 346 for CDR3 of the light chain.

In some embodiments, the antibody comprises a heavy chain variable region of the amino acid sequence of SEQ ID NO: 339.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 339.

In some embodiments, the antibody comprises a light chain variable region of the amino acid sequence of SEQ ID NO: 340.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 340.

In some embodiments, the antibody comprises a heavy chain variable region of the amino acid sequence of SEQ ID NO: 339 and a light chain variable region of the amino acid sequence of SEQ ID NO: 340.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 339 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 340.

The invention further provides an anti-MERS-S antibody comprising complementarity determining regions (CDRs) with:

i. a sequence that is at least 90% identical to SEQ ID NO: 341 for CDR1 of the heavy chain;

ii. a sequence that is at least 90% identical to SEQ ID NO: 342 for CDR2 of the iii. a sequence that is at least 90% identical to SEQ ID NO: 343 for CDR3 of the heavy chain;

iv. a sequence that is at least 90% identical to SEQ ID NO: 344 for CDR1 of the light chain;

v. a sequence that is at least 90% identical to SEQ ID NO: 345 for CDR2 of the light chain; and vi. a sequence that is at least 90% identical to SEQ ID NO: 346 for CDR3 of the light chain, wherein the antibody competes for binding to MERS-S with an antibody comprising a heavy chain variable region of the amino acid sequence of SEQ ID NO: 339 and a light chain variable region of the amino acid sequence of SEQ ID NO: 340.

The invention further provides an anti-MERS-S antibody comprising complementarity determining regions (CDRs) with:

i. a sequence that is at least 95% identical to SEQ ID NO: 341 for CDR1 of the heavy chain;

ii. a sequence that is at least 95% identical to SEQ ID NO: 342 for CDR2 of the heavy chain;

iii. a sequence that is at least 95% identical to SEQ ID NO: 343 for CDR3 of the heavy chain;

iv. a sequence that is at least 95% identical to SEQ ID NO: 344 for CDR1 of the light chain;

v. a sequence that is at least 95% identical to SEQ ID NO: 345 for CDR2 of the light chain; and vi. a sequence that is at least 95% identical to SEQ ID NO: 346 for CDR3 of the light chain, wherein the antibody competes for binding to MERS-S with an antibody comprising a heavy chain variable region of the amino acid sequence of SEQ ID NO: 339 and a light chain variable region of the amino acid sequence of SEQ ID NO: 340.

The invention provides an anti-MERS-S antibody that binds to the same epitope as an antibody comprising a heavy chain variable region of the amino acid sequence of SEQ ID NO: 347 and a light chain variable region of the amino acid sequence of SEQ ID NO: 348.

The invention further provides an anti-MERS-S antibody that binds to the same epitope as a heavy chain-only antibody comprising a heavy chain variable region of the amino acid sequence of SEQ ID NO: 347.

The invention further provides an anti-MERS-S antibody that competes for binding to MERS-S with an antibody comprising a heavy chain variable region of the amino acid sequence of SEQ ID NO: 347 and a light chain variable region of the amino acid sequence of SEQ ID NO: 348.

The invention further provides an anti-MERS-S antibody that competes for binding to MERS-S with a heavy chain-only antibody comprising a heavy chain variable region of the amino acid sequence of SEQ ID NO: 347.

The invention further provides an anti-MERS-S antibody comprising complementarity determining regions (CDRs) with the sequences of:

i. SEQ ID NO: 349 for CDR1 of the heavy chain;

ii. SEQ ID NO: 350 for CDR2 of the heavy chain;

iii. SEQ ID NO: 351 for CDR3 of the heavy chain;

iv. SEQ ID NO: 352 for CDR1 of the light chain;

v. SEQ ID NO: 353 for CDR2 of the light chain; and vi. SEQ ID NO: 354 for CDR3 of the light chain.

In some embodiments, the antibody comprises a heavy chain variable region of the amino acid sequence of SEQ ID NO: 347.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 347.

In some embodiments, the antibody comprises a light chain variable region of the amino acid sequence of SEQ ID NO: 348.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 348.

In some embodiments, the antibody comprises a heavy chain variable region of the amino acid sequence of SEQ ID NO: 347 and a light chain variable region of the amino acid sequence of SEQ ID NO: 348.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 347 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 348.

The invention further provides an anti-MERS-S antibody comprising complementarity determining regions (CDRs) with:

i. a sequence that is at least 90% identical to SEQ ID NO: 349 for CDR1 of the heavy chain;

ii. a sequence that is at least 90% identical to SEQ ID NO: 350 for CDR2 of the heavy chain;

iii. a sequence that is at least 90% identical to SEQ ID NO: 351 for CDR3 of the heavy chain;

iv. a sequence that is at least 90% identical to SEQ ID NO: 352 for CDR1 of the light v. a sequence that is at least 90% identical to SEQ ID NO: 353 for CDR2 of the light chain; and vi. a sequence that is at least 90% identical to SEQ ID NO: 354 for CDR3 of the light chain, wherein the antibody competes for binding to MERS-S with an antibody comprising a heavy chain variable region of the amino acid sequence of SEQ ID NO: 347 and a light chain variable region of the amino acid sequence of SEQ ID NO: 348.

The invention further provides an anti-MERS-S antibody comprising complementarity determining regions (CDRs) with:

i. a sequence that is at least 95% identical to SEQ ID NO: 349 for CDR1 of the heavy chain;

ii. a sequence that is at least 95% identical to SEQ ID NO: 350 for CDR2 of the heavy chain;

iii. a sequence that is at least 95% identical to SEQ ID NO: 351 for CDR3 of the heavy chain;

iv. a sequence that is at least 95% identical to SEQ ID NO: 352 for CDR1 of the light chain;

v. a sequence that is at least 95% identical to SEQ ID NO: 353 for CDR2 of the light chain; and vi. a sequence that is at least 95% identical to SEQ ID NO: 354 for CDR3 of the light chain, wherein the antibody competes for binding to MERS-S with an antibody comprising a heavy chain variable region of the amino acid sequence of SEQ ID NO: 347 and a light chain variable region of the amino acid sequence of SEQ ID NO: 348.

The invention provides an anti-MERS-S antibody that binds to the same epitope as an antibody comprising a heavy chain variable region of the amino acid sequence of SEQ ID NO: 355 and a light chain variable region of the amino acid sequence of SEQ ID NO: 356.

The invention further provides an anti-MERS-S antibody that binds to the same epitope as a heavy chain-only antibody comprising a heavy chain variable region of the amino acid sequence of SEQ ID NO: 355.

The invention further provides an anti-MERS-S antibody that competes for binding to MERS-S with an antibody comprising a heavy chain variable region of the amino acid sequence of SEQ ID NO: 355 and a light chain variable region of the amino acid sequence of SEQ ID NO: 356.

The invention further provides an anti-MERS-S antibody that competes for binding to MERS-S with a heavy chain-only antibody comprising a heavy chain variable region of the amino acid sequence of SEQ ID NO: 355.

The invention further provides an anti-MERS-S antibody comprising complementarity determining regions (CDRs) with the sequences of:

i. SEQ ID NO: 357 for CDR1 of the heavy chain;

ii. SEQ ID NO: 358 for CDR2 of the heavy chain;

iii. SEQ ID NO: 359 for CDR3 of the heavy chain;

iv. SEQ ID NO: 360 for CDR1 of the light chain;

v. SEQ ID NO: 361 for CDR2 of the light chain; and vi. SEQ ID NO: 362 for CDR3 of the light chain.

In some embodiments, the antibody comprises a heavy chain variable region of the amino acid sequence of SEQ ID NO: 355.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 355.

In some embodiments, the antibody comprises a light chain variable region of the amino acid sequence of SEQ ID NO: 356.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 356.

In some embodiments, the antibody comprises a heavy chain variable region of the amino acid sequence of SEQ ID NO: 355 and a light chain variable region of the amino acid sequence of SEQ ID NO: 356.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 355 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 356.

The invention further provides an anti-MERS-S antibody comprising complementarity determining regions (CDRs) with:

i. a sequence that is at least 90% identical to SEQ ID NO: 357 for CDR1 of the heavy chain;

ii. a sequence that is at least 90% identical to SEQ ID NO: 358 for CDR2 of the heavy chain;

iii. a sequence that is at least 90% identical to SEQ ID NO: 359 for CDR3 of the heavy chain;

iv. a sequence that is at least 90% identical to SEQ ID NO: 360 for CDR1 of the light chain;

v. a sequence that is at least 90% identical to SEQ ID NO: 361 for CDR2 of the light chain; and vi. a sequence that is at least 90% identical to SEQ ID NO: 362 for CDR3 of the light chain, wherein the antibody competes for binding to MERS-S with an antibody comprising a heavy chain variable region of the amino acid sequence of SEQ ID NO: 355 and a light chain variable region of the amino acid sequence of SEQ ID NO: 356.

The invention further provides an anti-MERS-S antibody comprising complementarity determining regions (CDRs) with:

i. a sequence that is at least 95% identical to SEQ ID NO: 357 for CDR1 of the heavy chain;

ii. a sequence that is at least 95% identical to SEQ ID NO: 358 for CDR2 of the heavy chain;

iii. a sequence that is at least 95% identical to SEQ ID NO: 359 for CDR3 of the heavy chain;

iv. a sequence that is at least 95% identical to SEQ ID NO: 360 for CDR1 of the light chain;

v. a sequence that is at least 95% identical to SEQ ID NO: 361 for CDR2 of the light chain; and vi. a sequence that is at least 95% identical to SEQ ID NO: 362 for CDR3 of the light chain, wherein the antibody competes for binding to MERS-S with an antibody comprising a heavy chain variable region of the amino acid sequence of SEQ ID NO: 355 and a light chain variable region of the amino acid sequence of SEQ ID NO: 356.

The invention provides an anti-MERS-S antibody that binds to the same epitope as an antibody comprising a heavy chain variable region of the amino acid sequence of SEQ ID NO: 363 and a light chain variable region of the amino acid sequence of SEQ ID NO: 364.

The invention further provides an anti-MERS-S antibody that binds to the same epitope as a heavy chain-only antibody comprising a heavy chain variable region of the amino acid sequence of SEQ ID NO: 363.

The invention further provides an anti-MERS-S antibody that competes for binding to MERS-S with an antibody comprising a heavy chain variable region of the amino acid sequence of SEQ ID NO: 363 and a light chain variable region of the amino acid sequence of SEQ ID NO: 364.

The invention further provides an anti-MERS-S antibody that competes for binding to MERS-S with a heavy chain-only antibody comprising a heavy chain variable region of the amino acid sequence of SEQ ID NO: 363.

The invention further provides an anti-MERS-S antibody comprising complementarity determining regions (CDRs) with the sequences of:

i. SEQ ID NO: 365 for CDR1 of the heavy chain;

ii. SEQ ID NO: 366 for CDR2 of the heavy chain;

iii. SEQ ID NO: 367 for CDR3 of the heavy chain;

iv. SEQ ID NO: 368 for CDR1 of the light chain;

v. SEQ ID NO: 369 for CDR2 of the light chain; and vi. SEQ ID NO: 370 for CDR3 of the light chain.

In some embodiments, the antibody comprises a heavy chain variable region of the amino acid sequence of SEQ ID NO: 363.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 363.

In some embodiments, the antibody comprises a light chain variable region of the amino acid sequence of SEQ ID NO: 364.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 364.

In some embodiments, the antibody comprises a heavy chain variable region of the amino acid sequence of SEQ ID NO: 363 and a light chain variable region of the amino acid sequence of SEQ ID NO: 364.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 363 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 364.

The invention further provides an anti-MERS-S antibody comprising complementarity determining regions (CDRs) with:

i. a sequence that is at least 90% identical to SEQ ID NO: 365 for CDR1 of the heavy chain;

ii. a sequence that is at least 90% identical to SEQ ID NO: 366 for CDR2 of the heavy chain;

iii. a sequence that is at least 90% identical to SEQ ID NO: 367 for CDR3 of the heavy chain;

iv. a sequence that is at least 90% identical to SEQ ID NO: 368 for CDR1 of the light chain;

v. a sequence that is at least 90% identical to SEQ ID NO: 369 for CDR2 of the light chain; and vi. a sequence that is at least 90% identical to SEQ ID NO: 370 for CDR3 of the light chain, wherein the antibody competes for binding to MERS-S with an antibody comprising a heavy chain variable region of the amino acid sequence of SEQ ID NO: 363 and a light chain variable region of the amino acid sequence of SEQ ID NO: 364.

The invention further provides an anti-MERS-S antibody comprising complementarity determining regions (CDRs) with:

i. a sequence that is at least 95% identical to SEQ ID NO: 365 for CDR1 of the ii. a sequence that is at least 95% identical to SEQ ID NO: 366 for CDR2 of the heavy chain;

iii. a sequence that is at least 95% identical to SEQ ID NO: 367 for CDR3 of the heavy chain;

iv. a sequence that is at least 95% identical to SEQ ID NO: 368 for CDR1 of the light chain;

v. a sequence that is at least 95% identical to SEQ ID NO: 369 for CDR2 of the light chain; and vi. a sequence that is at least 95% identical to SEQ ID NO: 370 for CDR3 of the light chain, wherein the antibody competes for binding to MERS-S with an antibody comprising a heavy chain variable region of the amino acid sequence of SEQ ID NO: 363 and a light chain variable region of the amino acid sequence of SEQ ID NO: 364.

The invention provides an anti-MERS-S antibody that binds to the same epitope as an antibody comprising a heavy chain variable region of the amino acid sequence of SEQ ID NO: 371 and a light chain variable region of the amino acid sequence of SEQ ID NO: 372.

The invention further provides an anti-MERS-S antibody that binds to the same epitope as a heavy chain-only antibody comprising a heavy chain variable region of the amino acid sequence of SEQ ID NO: 371.

The invention further provides an anti-MERS-S antibody that competes for binding to MERS-S with an antibody comprising a heavy chain variable region of the amino acid sequence of SEQ ID NO: 371 and a light chain variable region of the amino acid sequence of SEQ ID NO: 372.

The invention further provides an anti-MERS-S antibody that competes for binding to MERS-S with a heavy chain-only antibody comprising a heavy chain variable region of the amino acid sequence of SEQ ID NO: 371.

The invention further provides an anti-MERS-S antibody comprising complementarity determining regions (CDRs) with the sequences of:

vii. SEQ ID NO: 373 for CDR1 of the heavy chain;
viii. SEQ ID NO: 374 for CDR2 of the heavy chain;
ix. SEQ ID NO: 375 for CDR3 of the heavy chain;
x. SEQ ID NO: 376 for CDR1 of the light chain;
xi. SEQ ID NO: 377 for CDR2 of the light chain; and
xii. SEQ ID NO: 378 for CDR3 of the light chain.

In some embodiments, the antibody comprises a heavy chain variable region of the amino acid sequence of SEQ ID NO: 371.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 371.

In some embodiments, the antibody comprises a light chain variable region of the amino acid sequence of SEQ ID NO: 372.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 372.

In some embodiments, the antibody comprises a heavy chain variable region of the amino acid sequence of SEQ ID NO: 371 and a light chain variable region of the amino acid sequence of SEQ ID NO: 372.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 371 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 372.

The invention further provides an anti-MERS-S antibody comprising complementarity determining regions (CDRs) with:

i. a sequence that is at least 90% identical to SEQ ID NO: 373 for CDR1 of the heavy chain;
ii. a sequence that is at least 90% identical to SEQ ID NO: 374 for CDR2 of the heavy chain;
iii. a sequence that is at least 90% identical to SEQ ID NO: 375 for CDR3 of the heavy chain;
iv. a sequence that is at least 90% identical to SEQ ID NO: 376 for CDR1 of the light chain;
v. a sequence that is at least 90% identical to SEQ ID NO: 377 for CDR2 of the light chain; and
vi. a sequence that is at least 90% identical to SEQ ID NO: 378 for CDR3 of the light chain, wherein the antibody competes for binding to MERS-S with an antibody comprising a heavy chain variable region of the amino acid sequence of SEQ ID NO: 371 and a light chain variable region of the amino acid sequence of SEQ ID NO: 372.

The invention further provides an anti-MERS-S antibody comprising complementarity determining regions (CDRs) with:

i. a sequence that is at least 95% identical to SEQ ID NO: 373 for CDR1 of the heavy chain;

ii. a sequence that is at least 95% identical to SEQ ID NO: 374 for CDR2 of the heavy chain;
iii. a sequence that is at least 95% identical to SEQ ID NO: 375 for CDR3 of the heavy chain;
iv. a sequence that is at least 95% identical to SEQ ID NO: 376 for CDR1 of the light
v. a sequence that is at least 95% identical to SEQ ID NO: 377 for CDR2 of the light chain; and
vi. a sequence that is at least 95% identical to SEQ ID NO: 378 for CDR3 of the light chain, wherein the antibody competes for binding to MERS-S with an antibody comprising a heavy chain variable region of the amino acid sequence of SEQ ID NO: 371 and a light chain variable region of the amino acid sequence of SEQ ID NO: 372.

The invention provides an anti-MERS-S antibody that binds to the same epitope as an antibody comprising a heavy chain variable region of the amino acid sequence of SEQ ID NO: 379 and a light chain variable region of the amino acid sequence of SEQ ID NO: 380.

The invention further provides an anti-MERS-S antibody that binds to the same epitope as a heavy chain-only antibody comprising a heavy chain variable region of the amino acid sequence of SEQ ID NO: 379.

The invention further provides an anti-MERS-S antibody that competes for binding to MERS-S with an antibody comprising a heavy chain variable region of the amino acid sequence of SEQ ID NO: 379 and a light chain variable region of the amino acid sequence of SEQ ID NO: 380.

The invention further provides an anti-MERS-S antibody that competes for binding to MERS-S with a heavy chain-only antibody comprising a heavy chain variable region of the amino acid sequence of SEQ ID NO: 379.

The invention further provides an anti-MERS-S antibody comprising complementarity determining regions (CDRs) with the sequences of:

i. SEQ ID NO: 381 for CDR1 of the heavy chain;
ii. SEQ ID NO: 382 for CDR2 of the heavy chain;
iii. SEQ ID NO: 383 for CDR3 of the heavy chain;
iv. SEQ ID NO: 384 for CDR1 of the light chain;
v. SEQ ID NO: 385 for CDR2 of the light chain; and
vi. SEQ ID NO: 386 for CDR3 of the light chain.

In some embodiments, the antibody comprises a heavy chain variable region of the amino acid sequence of SEQ ID NO: 379.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 379.

In some embodiments, the antibody comprises a light chain variable region of the amino acid sequence of SEQ ID NO: 380.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 380.

In some embodiments, the antibody comprises a heavy chain variable region of the amino acid sequence of SEQ ID NO: 379 and a light chain variable region of the amino acid sequence of SEQ ID NO: 380.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 379 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 380.

The invention further provides an anti-MERS-S antibody comprising complementarity determining regions (CDRs) with:

i. a sequence that is at least 90% identical to SEQ ID NO: 381 for CDR1 of the heavy chain;

ii. a sequence that is at least 90% identical to SEQ ID NO: 382 for CDR2 of the iii. a sequence that is at least 90% identical to SEQ ID NO: 383 for CDR3 of the heavy chain;

iv. a sequence that is at least 90% identical to SEQ ID NO: 384 for CDR1 of the light chain;

v. a sequence that is at least 90% identical to SEQ ID NO: 385 for CDR2 of the light chain; and vi. a sequence that is at least 90% identical to SEQ ID NO: 386 for CDR3 of the light chain, wherein the antibody competes for binding to MERS-S with an antibody comprising a heavy chain variable region of the amino acid sequence of SEQ ID NO: 379 and a light chain variable region of the amino acid sequence of SEQ ID NO: 380.

The invention further provides an anti-MERS-S antibody comprising complementarity determining regions (CDRs) with:

i. a sequence that is at least 95% identical to SEQ ID NO: 381 for CDR1 of the heavy chain;

ii. a sequence that is at least 95% identical to SEQ ID NO: 382 for CDR2 of the heavy chain;

iii. a sequence that is at least 95% identical to SEQ ID NO: 383 for CDR3 of the heavy chain;

iv. a sequence that is at least 95% identical to SEQ ID NO: 384 for CDR1 of the light chain;

v. a sequence that is at least 95% identical to SEQ ID NO: 385 for CDR2 of the light chain; and vi. a sequence that is at least 95% identical to SEQ ID NO: 386 for CDR3 of the light chain, wherein the antibody competes for binding to MERS-S with an antibody comprising a heavy chain variable region of the amino acid sequence of SEQ ID NO: 379 and a light chain variable region of the amino acid sequence of SEQ ID NO: 380.

The section below specifies features that are combinable with each of the previous embodiments, as appropriate.

In some embodiments, the antibody binds to MERS-S with a $K_D$ of $10^{-7}$ M or less, $10^{-8}$ M or less, $10^{-9}$ M or less, or $10^{-10}$ M or less. In some embodiments, antibody binding affinity is determined using an Octet® RED96 system (ForteBio, Inc.). For example, a Flag-tagged S1 domain or a Flag-tagged S2 domain may be immobilized to an anti-Flag biosensor and incubated with varying concentrations of the antibody in solution, binding data are then collected. In some embodiments, antibody binding affinity is determined by surface plasmon resonance.

In some embodiments, the antibody is capable of inhibiting the interaction between MERS-S and the DPP4 receptor by at least 20%, at least 30%, at least 40%, at least 50%, at least 60%, at least 70%, at least 80%, at least 90%, at least 95%, at least 99% or 100%. In some embodiments, the capability for inhibiting the interaction between MERS-S and the DPP4 receptor is measured in a blocking ELISA assay.

In some embodiments, the antibody is capable of neutralizing MERS-CoV infectivity of human host cells by more than 50%, by more than 60%, by more than 70%, by more than 80%, by more than 90%, by more than 95%, by more than 99% or by 100%. In some embodiments, the 50% inhibitory concentration ($IC_{50}$) value of the antibody for neutralizing MERS-CoV infectivity is less than 100 µg/ml, less than 50 µg/ml, less than 40 g/ml, less than 30 µg/ml, less than 20 µg/ml, less than 15 µg/ml, less than 10 g/ml, less than 5 µg/ml, less than 1 µg/ml, less than 0.1 µg/ml, less than 0.01 g/ml, less than 0.001 pg/ml or less than 0.0001 pg/ml. In some embodiments, the neutralizing capability of anti-MERS-S antibodies is measured in a virus-like particle (VLP) neutralization assay (Tang et al. (2012) *PNAS* 111 (19):E2018-E2026).

In some embodiments, the antibody is capable of interfering with the attachment of MERS-CoV S protein to sialic acid. The $S1^A$ domain is thought to be responsible for binding of the S protein to sialic acid. Accordingly, antibodies that bind to the $S1^A$ domain may be capable of interfering with the attachment of MERS-CoV S protein to sialic acid. In some embodiments, this interference is assessed by determining the level of sialic-acid dependent hemagglutination by the MERS-$S1^A$ domain (e.g. as described in Li, Hulswit et al. 2017). Inhibition of $S1^A$ domain-mediated hemaglutination in this assay indicates that the test antibody is capable of interfering with the attachment of MERS-CoV S protein to sialic acid.

In some embodiments, the antibody is capable of interfering with interfering with MERS-CoV S protein-mediated membrane fusion. The S2 domain is thought to be responsible for mediating membrane fusion. Accordingly, antibodies that bind to the S2 domain may be capable of interfering with interfering with MERS-CoV S protein-mediated membrane fusion. To test this property, a MERS-CoV-S driven cell-cell fusion assay may be used (e.g. an assay which uses a GFP-tagged MERS-CoV spike protein that has a mutated the furin cleavage site at the S1/S2 junction). Inhibition of the formation of syncytia in this assay indicates that the test antibody is capable of interfering with MERS-CoV S protein-mediated membrane fusion.

In some embodiments, whether a test antibody competes with a reference antibody for binding to MERS-S is determined using an in vitro binding competition assay. For example, a Flag-tagged S1 domain or a Flag-tagged S2 domain may be immobilized to an anti-Flag biosensor, the association of the reference antibody to the immobilized Flag-tagged S1 or S2 domain is then measured (e.g. using the Octet® RED96 system, ForteBio, Inc.) and then the degree of additional binding is assessed by exposing the immobilized Flag-tagged S1 or S2 domain to the test antibody in the presence of the reference antibody.

In some embodiments, the anti-MERS antibody recognizes MERS-CoV and one or more additional beta coronaviruses. For example, in some embodiments the anti-MERS antibody recognizes: (i) MERS-CoV and mouse hepatitis virus (MHV), (ii) MERS-CoV and severe acute respiratory syndrome coronavirus (SARS-CoV), or (iii) MERS-CoV, MHV and SARS-CoV.

In some embodiments, the anti-MERS antibody is a heavy chain-only antibody.

Anti-MERS-S Heavy Chain-Only Antibodies

The examples show that the 1G3 heavy chain-only antibody binds to the S1 domain with a strong binding affinity of approximately $2.17 \times 10^{-8}$. The 1G3 antibody is advantageously capable of neutralizing MERS-S pseudovirus infectivity (e.g. see FIG. 31). Similar functional properties can be expected to be associated with the heavy chain-only antibodies defined below which share structural and functional characteristics with the 1G3 heavy chain-only antibody.

The invention further provides an anti-MERS-S heavy chain-only antibody that binds to the same epitope as a heavy chain-only antibody comprising a heavy chain variable region of the amino acid sequence of SEQ ID NO: 75.

The invention further provides an anti-MERS-S heavy chain-only antibody that competes for binding to MERS-S with a heavy chain-only antibody comprising a heavy chain variable region of the amino acid sequence of SEQ ID NO: 75.

The invention further provides an anti-MERS-S heavy chain-only antibody comprising complementarity determining regions (CDRs) with the sequences of:
    i. SEQ ID NO: 271 for CDR1 of the heavy chain;
    ii. SEQ ID NO: 272 for CDR2 of the heavy chain; and
    iii. SEQ ID NO: 273 for CDR3 of the heavy chain.

In some embodiments, the heavy chain-only antibody comprises a heavy chain variable region of the amino acid sequence of SEQ ID NO: 75.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 75.

The invention further provides an anti-MERS-S heavy chain-only antibody comprising complementarity determining regions (CDRs) with the sequences of:
    i. a sequence that is at least 90% identical to SEQ ID NO: 271 for CDR1 of the heavy chain;
    ii. a sequence that is at least 90% identical to SEQ ID NO: 272 for CDR2 of the heavy chain; and
    iii. a sequence that is at least 90% identical to SEQ ID NO: 273 for CDR3 of the heavy chain,
wherein the antibody competes for binding to MERS-S with an antibody comprising a heavy chain variable region of the amino acid sequence of SEQ ID NO: 75.

The invention further provides an anti-MERS-S heavy chain-only antibody comprising complementarity determining regions (CDRs) with the sequences of:
    i. a sequence that is at least 95% identical to SEQ ID NO: 271 for CDR1 of the heavy chain;
    ii. a sequence that is at least 95% identical to SEQ ID NO: 272 for CDR2 of the heavy chain; and
    iii. a sequence that is at least 95% identical to SEQ ID NO: 273 for CDR3 of the heavy chain,
wherein the antibody competes for binding to MERS-S with an antibody comprising a heavy chain variable region of the amino acid sequence of SEQ ID NO: 75.

The examples show that the 1H5 heavy chain-only antibody binds to the S1 domain with a strong binding affinity of approximately $1.09 \times 10^{-8}$. The 1H5 antibody is advantageously capable of neutralizing MERS-S pseudovirus infectivity (e.g. see FIG. 31). Similar functional properties can be expected to be associated with the heavy chain-only antibodies defined below which share structural and functional characteristics with the 1H5 heavy chain-only antibody.

The invention further provides an anti-MERS-S heavy chain-only antibody that binds to the same epitope as a heavy chain-only antibody comprising a heavy chain variable region of the amino acid sequence of SEQ ID NO: 78.

The invention further provides an anti-MERS-S heavy chain-only antibody that competes for binding to MERS-S with a heavy chain-only antibody comprising a heavy chain variable region of the amino acid sequence of SEQ ID NO: 78.

The invention further provides an anti-MERS-S heavy chain-only antibody comprising complementarity determining regions (CDRs) with the sequences of:
    i. SEQ ID NO: 274 for CDR1 of the heavy chain;
    ii. SEQ ID NO: 275 for CDR2 of the heavy chain; and
    iii. SEQ ID NO: 276 for CDR3 of the heavy chain.

In some embodiments, the heavy chain-only antibody comprises a heavy chain variable region of the amino acid sequence of SEQ ID NO: 78.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 78.

The invention further provides an anti-MERS-S heavy chain-only antibody comprising complementarity determining regions (CDRs) with the sequences of:
    i. a sequence that is at least 90% identical to SEQ ID NO: 274 for CDR1 of the heavy chain;
    ii. a sequence that is at least 90% identical to SEQ ID NO: 275 for CDR2 of the heavy chain; and
    iii. a sequence that is at least 90% identical to SEQ ID NO: 276 for CDR3 of the heavy chain,
wherein the antibody competes for binding to MERS-S with an antibody comprising a heavy chain variable region of the amino acid sequence of SEQ ID NO: 78.

The invention further provides an anti-MERS-S heavy chain-only antibody comprising complementarity determining regions (CDRs) with the sequences of:
    i. a sequence that is at least 95% identical to SEQ ID NO: 274 for CDR1 of the heavy chain;
    ii. a sequence that is at least 95% identical to SEQ ID NO: 275 for CDR2 of the heavy chain; and
    iii. a sequence that is at least 95% identical to SEQ ID NO: 276 for CDR3 of the heavy chain,
wherein the antibody competes for binding to MERS-S with an antibody comprising a heavy chain variable region of the amino acid sequence of SEQ ID NO: 78.

The examples show that the 1E10 heavy chain-only antibody binds to the S1 domain with a strong binding affinity of approximately $1 \times 10^9$. The 1E10 antibody is advantageously capable of neutralizing MERS-S pseudovirus infectivity (e.g. see FIG. 31). Similar functional properties can be expected to be associated with the heavy chain-only antibodies defined below which share structural and functional characteristics with the 1E10 heavy chain-only antibody.

The invention further provides an anti-MERS-S heavy chain-only antibody that binds to the same epitope as a heavy chain-only antibody comprising a heavy chain variable region of the amino acid sequence of SEQ ID NO: 80.

The invention further provides an anti-MERS-S heavy chain-only antibody that competes for binding to MERS-S with a heavy chain-only antibody comprising a heavy chain variable region of the amino acid sequence of SEQ ID NO: 80.

The invention further provides an anti-MERS-S heavy chain-only antibody comprising complementarity determining regions (CDRs) with the sequences of:
    i. SEQ ID NO: 277 for CDR1 of the heavy chain;
    ii. SEQ ID NO: 278 for CDR2 of the heavy chain; and
    iii. SEQ ID NO: 279 for CDR3 of the heavy chain.

In some embodiments, the heavy chain-only antibody comprises a heavy chain variable region of the amino acid sequence of SEQ ID NO: 80.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 80.

The invention further provides an anti-MERS-S heavy chain-only antibody comprising complementarity determining regions (CDRs) with the sequences of:

i. a sequence that is at least 90% identical to SEQ ID NO: 277 for CDR1 of the ii. a sequence that is at least 90% identical to SEQ ID NO: 278 for CDR2 of the heavy chain; and iii. a sequence that is at least 90% identical to SEQ ID NO: 279 for CDR3 of the heavy chain, wherein the antibody competes for binding to MERS-S with an antibody comprising a heavy chain variable region of the amino acid sequence of SEQ ID NO: 80.

The invention further provides an anti-MERS-S heavy chain-only antibody comprising complementarity determining regions (CDRs) with the sequences of:

i. a sequence that is at least 95% identical to SEQ ID NO: 277 for CDR1 of the heavy chain;

ii. a sequence that is at least 95% identical to SEQ ID NO: 278 for CDR2 of the heavy chain; and iii. a sequence that is at least 95% identical to SEQ ID NO: 279 for CDR3 of the heavy chain, wherein the antibody competes for binding to MERS-S with an antibody comprising a heavy chain variable region of the amino acid sequence of SEQ ID NO: 80.

The examples show that the 5F1 heavy chain-only antibody binds to the S1 domain and has MERS-CoV neutralising activity (see FIG. 31). Similar functional properties can be expected to be associated with the heavy chain-only antibodies defined below which share structural and functional characteristics with the 5F1 heavy chain-only antibody.

The invention further provides an anti-MERS-S heavy chain-only antibody that binds to the same epitope as a heavy chain-only antibody comprising a heavy chain variable region of the amino acid sequence of SEQ ID NO: 77.

The invention further provides an anti-MERS-S heavy chain-only antibody that competes for binding to MERS-S with a heavy chain-only antibody comprising a heavy chain variable region of the amino acid sequence of SEQ ID NO: 77.

The invention further provides an anti-MERS-S heavy chain-only antibody comprising complementarity determining regions (CDRs) with the sequences of:

i. SEQ ID NO: 280 for CDR1 of the heavy chain;

ii. SEQ ID NO: 281 for CDR2 of the heavy chain; and iii. SEQ ID NO: 282 for CDR3 of the heavy chain.

In some embodiments, the heavy chain-only antibody comprises a heavy chain variable region of the amino acid sequence of SEQ ID NO: 77.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 77.

The invention further provides an anti-MERS-S heavy chain-only antibody comprising complementarity determining regions (CDRs) with the sequences of:

i. a sequence that is at least 90% identical to SEQ ID NO: 280 for CDR1 of the heavy chain;

ii. a sequence that is at least 90% identical to SEQ ID NO: 281 for CDR2 of the heavy chain; and iii. a sequence that is at least 90% identical to SEQ ID NO: 282 for CDR3 of the heavy chain, wherein the antibody competes for binding to MERS-S with an antibody comprising a heavy chain variable region of the amino acid sequence of SEQ ID NO: 77.

The invention further provides an anti-MERS-S heavy chain-only antibody comprising complementarity determining regions (CDRs) with the sequences of:

i. a sequence that is at least 95% identical to SEQ ID NO: 280 for CDR1 of the heavy chain;

ii. a sequence that is at least 95% identical to SEQ ID NO: 281 for CDR2 of the heavy chain; and iii. a sequence that is at least 95% identical to SEQ ID NO: 282 for CDR3 of the heavy chain, wherein the antibody competes for binding to MERS-S with an antibody comprising a heavy chain variable region of the amino acid sequence of SEQ ID NO: 77.

The invention further provides an anti-MERS-S heavy chain-only antibody that binds to the same epitope as a heavy chain-only antibody comprising a heavy chain variable region of the amino acid sequence of any one of SEQ ID NOs: 410-420, 422-429 and 431-434. The invention further provides an anti-MERS-S heavy chain-only antibody that competes for binding to MERS-S with a heavy chain-only antibody comprising a heavy chain variable region of the amino acid sequence of any one of SEQ ID NOs: 410-420, 422-429 and 431-434.

The invention further provides a heavy chain-only antibody comprising a heavy chain variable region of the amino acid sequence of any one of SEQ ID NOs: 410-420, 422-429 and 431-434.

The invention further provides a heavy antibody comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of any one of SEQ ID NOs: 410-420, 422-429 and 431-434.

The invention further provides an anti-MERS-S heavy chain-only antibody comprising complementarity determining regions (CDRs) of heavy chain variable region of the amino acid sequence of any one of SEQ ID NOs: 410-420, 422-429 and 431-434.

The section below specifies features that are combinable with each of the previous embodiments, as appropriate.

In some embodiments, the heavy chain-only antibody binds to MERS-S with a $K_D$ of $10^{-7}$ M or less, $10^{-8}$ M or less, $10^{-9}$ M or less, or $10^{-1}$ M or less. In some embodiments, antibody binding affinity is determined using an Octet® RED96 system (ForteBio, Inc.). For example, a Flag-tagged S1 domain or a Flag-tagged S2 domain may be immobilized to an anti-Flag biosensor and incubated with varying concentrations of the antibody in solution, binding data are then collected. In some embodiments, antibody binding affinity is determined by surface plasmon resonance.

In some embodiments, the heavy chain-only antibody is capable of inhibiting the interaction between MERS-S and the DPP4 receptor by at least 20%, at least 30%, at least 40%, at least 50%, at least 60%, at least 70%, at least 80%, at least 90%, at least 95%, at least 99% or 100%. In some embodiments, the capability for inhibiting the interaction between MERS-S and the DPP4 receptor is measured in a blocking ELISA assay.

In some embodiments, the heavy chain-only antibody is capable of neutralizing MERS-CoV infectivity of human host cells by more than 50%, by more than 60%, by more than 70%, by more than 80%, by more than 90%, by more than 95%, by more than 99% or by 100%. In some embodiments, the 50% inhibitory concentration ($IC_{50}$) value of the antibody for neutralizing MERS-CoV infectivity is less than 100 µg/ml, less than 50 µg/ml, less than 40 µg/ml, less than µg/ml, less than 20 µg/ml, less than 15 µg/ml, less than 10 µg/ml, less than 5 µg/ml, less than 1 µg/ml, less than 0.1 pg/ml, less than 0.01 µg/ml, less than 0.001 µg/ml or less than 0.0001 µg/ml. In some embodiments, the neutralizing capability of anti-MERS-S antibodies is measured in a virus-like particle (VLP) neutralization assay (Tang et al. (2012) *PNAS* 111(19):E2018-E2026).

In some embodiments, whether a test antibody competes with a reference antibody for binding to MERS-S is determined using an in vitro binding competition assay. For example, a Flag-tagged S1 domain or a Flag-tagged S2 domain may be immobilized to an anti-Flag biosensor, the association of the reference antibody to the immobilized Flag-tagged S1 or S2 domain is then measured (e.g. using the Octet® RED96 system, ForteBio, Inc.) and then the degree of additional binding is assessed by exposing the immobilized Flag-tagged S1 or S2 domain to the test antibody in the presence of the reference antibody.

In some embodiments, the anti-MERS heavy chain-only antibody recognizes MERS-CoV and one or more additional beta coronaviruses. For example, in some embodiments the anti-MERS antibody recognizes: (i) MERS-CoV and mouse hepatitis virus (MHV), (ii) MERS-CoV and severe acute respiratory syndrome coronavirus (SARS-CoV), or (iii) MERS-CoV, MHV and SARS-CoV.

Combinations of Anti-MERS Antibodies

It is envisaged that a combination of anti-MERS antibodies targeting different domains and functions of the viral glycoprotein may be more protective against virus infection than single epitope mAb therapy. The presence of protective antibody epitopes in multiple spike domains, suggests that multi-domain approaches of spike-based vaccines may provide a broader repertoire of immune responses compared to RBD-focused vaccine antigen and reduce the risk of viral antigenic escape. In some cases, a combination of antibodies provides synergistic protective activity against MERS-CoV.

Accordingly, the invention provides a composition comprising two, three, four, five, six, seven, eight, nine or ten of the anti-MERS antibodies disclosed herein.

In some embodiments, the invention provides a combination of anti-MERS-S1 antibody and an anti-MERS-S2 antibody.

Figure 2E:
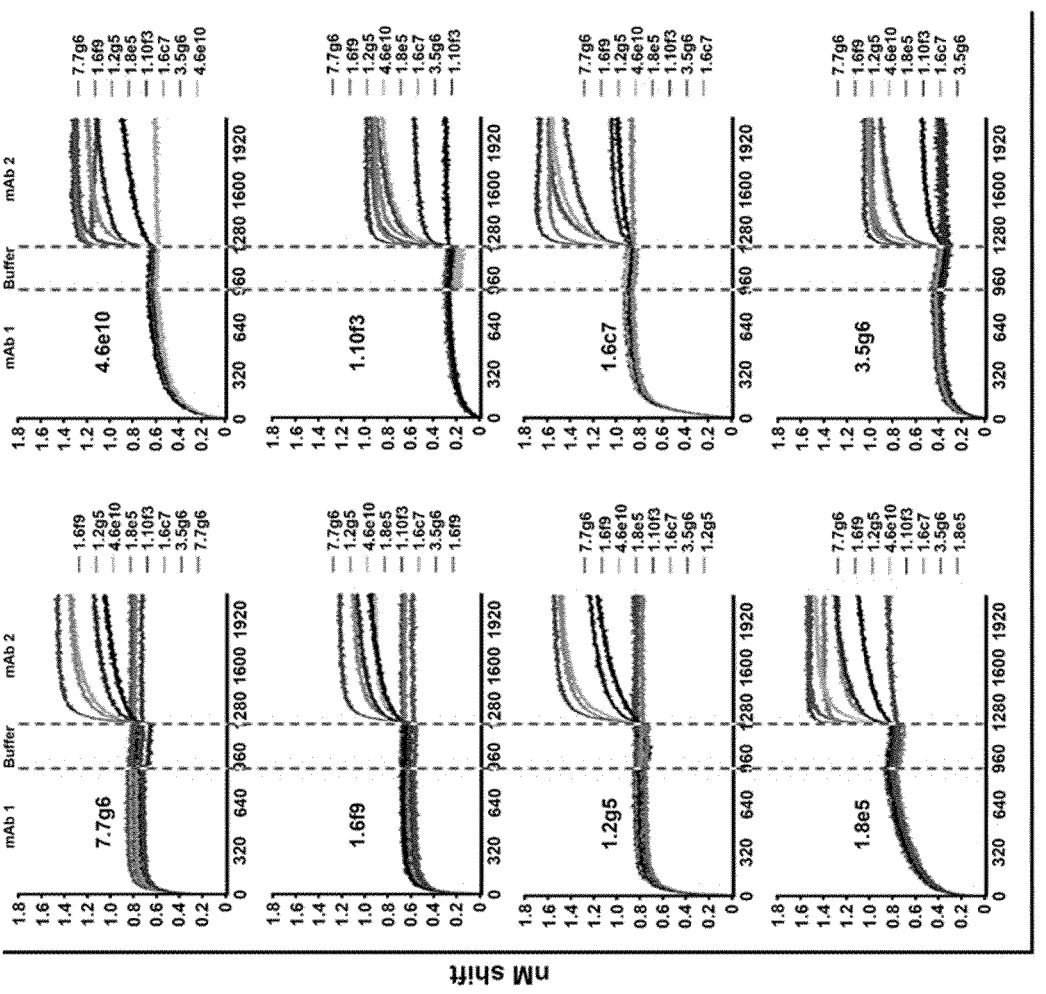
Figure 2F:
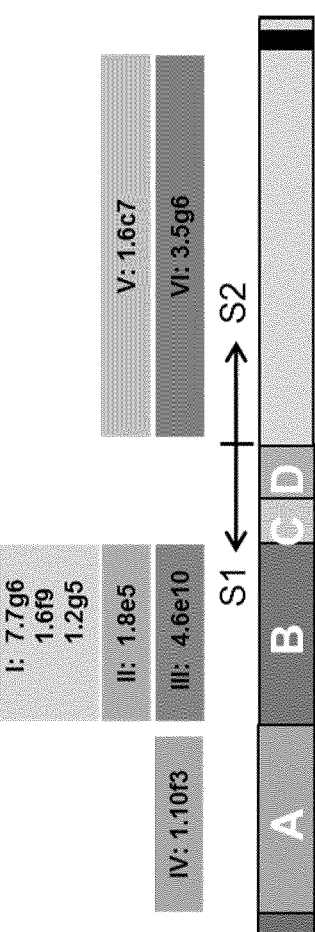
Figure 2G:
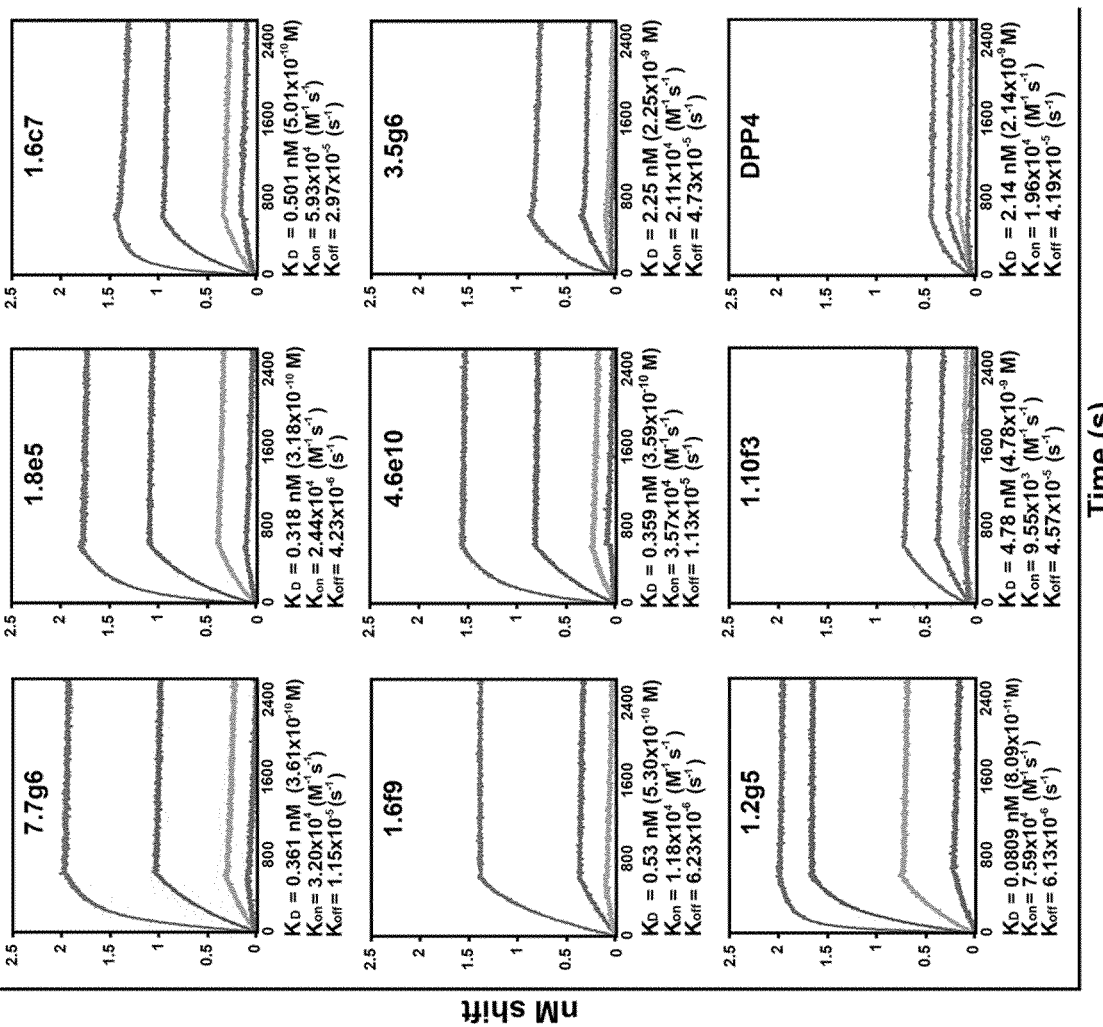

The 7.7 g6 and 1.6c7 antibodies bind to the S1 and S2 domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 95 for CDR1 of the heavy chain;
ii. SEQ ID NO: 96 for CDR2 of the heavy chain;
iii. SEQ ID NO: 97 for CDR3 of the heavy chain;
iv. SEQ ID NO: 98 for CDR1 of the light chain;
v. SEQ ID NO: 99 for CDR2 of the light chain; and
vi. SEQ ID NO: 100 for CDR3 of the light chain, and
(b) an anti-MERS-S antibody comprising complementarity determining regions (CDRs) with the sequences of:
i. SEQ ID NO: 83 for CDR1 of the heavy chain;
ii. SEQ ID NO: 84 for CDR2 of the heavy chain;
iii. SEQ ID NO: 85 for CDR3 of the heavy chain;

iv. SEQ ID NO: 86 for CDR1 of the light chain;
v. SEQ ID NO: 87 for CDR2 of the light chain; and
vi. SEQ ID NO: 88 for CDR3 of the light chain.
Accordingly, in some embodiments, the invention provides a combination comprising:
(a) an anti-MERS-S antibody comprising a heavy chain variable region of the amino acid sequence of SEQ ID NO: 28 and a light chain variable region of the amino acid sequence of SEQ ID NO: 63.
(b) an anti-MERS-S antibody comprising a heavy chain variable region of the amino acid sequence of SEQ ID NO: 70 and a light chain variable region of the amino acid sequence of SEQ ID NO: 74.
The 1.6f9 and 1.607 antibodies bind to the S1 and S2 domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 101 for CDR1 of the heavy chain;
ii. SEQ ID NO: 102 for CDR2 of the heavy chain;
iii. SEQ ID NO: 103 for CDR3 of the heavy chain;
iv. SEQ ID NO: 104 for CDR1 of the light chain;
v. SEQ ID NO: 105 for CDR2 of the light chain; and
vi. SEQ ID NO: 106 for CDR3 of the light chain, and
(b) an anti-MERS-S antibody comprising complementarity determining regions (CDRs) with the sequences of:
i. SEQ ID NO: 83 for CDR1 of the heavy chain;
ii. SEQ ID NO: 84 for CDR2 of the heavy chain;
iii. SEQ ID NO: 85 for CDR3 of the heavy chain;
iv. SEQ ID NO: 86 for CDR1 of the light chain;
v. SEQ ID NO: 87 for CDR2 of the light chain; and
vi. SEQ ID NO: 88 for CDR3 of the light chain.
Accordingly, in some embodiments, the invention provides a combination comprising:
(a) an anti-MERS-S antibody comprising a heavy chain variable region of the amino acid sequence of SEQ ID NO: 26 and a light chain variable region of the amino acid sequence of SEQ ID NO: 65.
(b) an anti-MERS-S antibody comprising a heavy chain variable region of the amino acid sequence of SEQ ID NO: 70 and a light chain variable region of the amino acid sequence of SEQ ID NO: 74.
The 1.2 g5 and 1.6c7 antibodies bind to the S1 and S2 domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 109 for CDR1 of the heavy chain;
ii. SEQ ID NO: 110 for CDR2 of the heavy chain;
iii. SEQ ID NO: 111 for CDR3 of the heavy chain;
iv. SEQ ID NO: 112 for CDR1 of the light chain;
v. SEQ ID NO: 113 for CDR2 of the light chain; and
vi. SEQ ID NO: 114 for CDR3 of the light chain, and
(b) an anti-MERS-S antibody comprising complementarity determining regions (CDRs) with the sequences of:
i. SEQ ID NO: 83 for CDR1 of the heavy chain;
ii. SEQ ID NO: 84 for CDR2 of the heavy chain;
iii. SEQ ID NO: 85 for CDR3 of the heavy chain;
iv. SEQ ID NO: 86 for CDR1 of the light chain;
v. SEQ ID NO: 87 for CDR2 of the light chain; and
vi. SEQ ID NO: 88 for CDR3 of the light chain.
Accordingly, in some embodiments, the invention provides a combination comprising:
(a) an anti-MERS-S antibody comprising a heavy chain variable region of the amino acid sequence of SEQ ID NO: 107 and a light chain variable region of the amino
acid sequence of SEQ ID NO: 108.

(b) an anti-MERS-S antibody comprising a heavy chain
variable region of the amino acid sequence of SEQ ID
NO: 70 and a light chain variable region of the amino
acid sequence of SEQ ID NO: 74.

The 1.8e5 and 1.6o7 antibodies bind to the S1 and S2
domains of MERS-S, respectively (see FIG. 2E). Accord-
ingly, in some embodiments, the invention provides a com-
bination comprising:

(a) an anti-MERS-S antibody comprising complementar-
ity determining regions (CDRs) with the sequences of:
i. SEQ ID NO: 133 for CDR1 of the heavy chain;
ii. SEQ ID NO: 134 for CDR2 of the heavy chain;
iii. SEQ ID NO: 135 for CDR3 of the heavy chain;
iv. SEQ ID NO: 136 for CDR1 of the light chain;
v. SEQ ID NO: 137 for CDR2 of the light chain; and
vi. SEQ ID NO: 138 for CDR3 of the light chain, and (b) an anti-MERS-S antibody comprising complementar-
ity determining regions (CDRs) with the sequences of:
i. SEQ ID NO: 83 for CDR1 of the heavy chain;
ii. SEQ ID NO: 84 for CDR2 of the heavy chain;
iii. SEQ ID NO: 85 for CDR3 of the heavy chain;
iv. SEQ ID NO: 86 for CDR1 of the light chain;
v. SEQ ID NO: 87 for CDR2 of the light chain; and
vi. SEQ ID NO: 88 for CDR3 of the light chain.

Accordingly, in some embodiments, the invention pro-
vides a combination comprising:

(a) an anti-MERS-S antibody comprising a heavy chain
variable region of the amino acid sequence of SEQ ID
NO: 32 and a light chain variable region of the amino
acid sequence of SEQ ID NO: 56.

(b) an anti-MERS-S antibody comprising a heavy chain
variable region of the amino acid sequence of SEQ ID
NO: 70 and a light chain variable region of the amino
acid sequence of SEQ ID NO: 74.

The 4.6e10 and 1.6c7 antibodies bind to the S1 and S2
domains of MERS-S, respectively (see FIG. 2E). Accord-
ingly, in some embodiments, the invention provides a com-
bination comprising:

(a) an anti-MERS-S antibody comprising complementar-
ity determining regions (CDRs) with the sequences of:
i. SEQ ID NO: 139 for CDR1 of the heavy chain;
ii. SEQ ID NO: 140 for CDR2 of the heavy chain;
iii. SEQ ID NO: 141 for CDR3 of the heavy chain;
iv. SEQ ID NO: 142 for CDR1 of the light chain;
v. SEQ ID NO: 143 for CDR2 of the light chain; and
vi. SEQ ID NO: 144 for CDR3 of the light chain, and (b) an anti-MERS-S antibody comprising complementar-
ity determining regions (CDRs) with the sequences of:
i. SEQ ID NO: 83 for CDR1 of the heavy chain;
ii. SEQ ID NO: 84 for CDR2 of the heavy chain;
iii. SEQ ID NO: 85 for CDR3 of the heavy chain;
iv. SEQ ID NO: 86 for CDR1 of the light chain;
v. SEQ ID NO: 87 for CDR2 of the light chain; and
vi. SEQ ID NO: 88 for CDR3 of the light chain.

Accordingly, in some embodiments, the invention pro-
vides a combination comprising:

(a) an anti-MERS-S antibody comprising a heavy chain
variable region of the amino acid sequence of SEQ ID
NO: 17 and a light chain variable region of the amino
acid sequence of SEQ ID NO: 67.

(b) an anti-MERS-S antibody comprising a heavy chain
variable region of the amino acid sequence of SEQ ID
NO: 70 and a light chain variable region of the amino
acid sequence of SEQ ID NO: 74.

The 1.10f3 and 1.6c7 antibodies bind to the S1 and S2
domains of MERS-S, respectively (see FIG. 2E). Accord-
ingly, in some embodiments, the invention provides a com-
bination comprising:

(a) an anti-MERS-S antibody comprising complementar-
ity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain, and (b) an anti-MERS-S antibody comprising complementar-
ity determining regions (CDRs) with the sequences of:
i. SEQ ID NO: 83 for CDR1 of the heavy chain;
ii. SEQ ID NO: 84 for CDR2 of the heavy chain;
iii. SEQ ID NO: 85 for CDR3 of the heavy chain;
iv. SEQ ID NO: 86 for CDR1 of the light chain;
v. SEQ ID NO: 87 for CDR2 of the light chain; and
vi. SEQ ID NO: 88 for CDR3 of the light chain.

Accordingly, in some embodiments, the invention pro-
vides a combination comprising:

(a) an anti-MERS-S antibody comprising a heavy chain
variable region of the amino acid sequence of SEQ ID
NO: 18 and a light chain variable region of the amino
acid sequence of SEQ ID NO: 58.

(b) an anti-MERS-S antibody comprising a heavy chain
variable region of the amino acid sequence of SEQ ID
NO: 70 and a light chain variable region of the amino
acid sequence of SEQ ID NO: 74.

The 7.7 g6 and 3.5 g6 antibodies bind to the S1 and S2
domains of MERS-S, respectively (see FIG. 2E). Accord-
ingly, in some embodiments, the invention provides a com-
bination comprising:

(a) an anti-MERS-S antibody comprising complementar-
ity determining regions (CDRs) with the sequences of:
i. SEQ ID NO: 95 for CDR1 of the heavy chain;
ii. SEQ ID NO: 96 for CDR2 of the heavy chain;
iii. SEQ ID NO: 97 for CDR3 of the heavy chain;
iv. SEQ ID NO: 98 for CDR1 of the light chain;
v. SEQ ID NO: 99 for CDR2 of the light chain; and
vi. SEQ ID NO: 100 for CDR3 of the light chain, and (b) an anti-MERS-S antibody comprising complementar-
ity determining regions (CDRs) with the sequences of:
i. SEQ ID NO: 89 for CDR1 of the heavy chain;
ii. SEQ ID NO: 90 for CDR2 of the heavy chain;
iii. SEQ ID NO: 91 for CDR3 of the heavy chain;
iv. SEQ ID NO: 92 for CDR1 of the light chain;
v. SEQ ID NO: 93 for CDR2 of the light chain; and
vi. SEQ ID NO: 94 for CDR3 of the light chain.

Accordingly, in some embodiments, the invention pro-
vides a combination comprising:

(a) an anti-MERS-S antibody comprising a heavy chain
variable region of the amino acid sequence of SEQ ID
NO: 28 and a light chain variable region of the amino
acid sequence of SEQ ID NO: 63.

(b) an anti-MERS-S antibody comprising a heavy chain
variable region of the amino acid sequence of SEQ ID
NO: 69 and a light chain variable region of the amino
acid sequence of SEQ ID NO: 72.

The 1.6f9 and 3.5 g6 antibodies bind to the S1 and S2
domains of MERS-S, respectively (see FIG. 2E). Accord-
ingly, in some embodiments, the invention provides a com-
bination comprising:

(a) an anti-MERS-S antibody comprising complementarity determining regions (CDRs) with the sequences of:
i. SEQ ID NO: 101 for CDR1 of the heavy chain;
ii. SEQ ID NO: 102 for CDR2 of the heavy chain;
iii. SEQ ID NO: 103 for CDR3 of the heavy chain;
iv. SEQ ID NO: 104 for CDR1 of the light chain;
v. SEQ ID NO: 105 for CDR2 of the light chain; and
vi. SEQ ID NO: 106 for CDR3 of the light chain, and
(b) an anti-MERS-S antibody comprising complementarity determining regions (CDRs) with the sequences of:
i. SEQ ID NO: 89 for CDR1 of the heavy chain;
ii. SEQ ID NO: 90 for CDR2 of the heavy chain;
iii. SEQ ID NO: 91 for CDR3 of the heavy chain;
iv. SEQ ID NO: 92 for CDR1 of the light chain;
v. SEQ ID NO: 93 for CDR2 of the light chain; and
vi. SEQ ID NO: 94 for CDR3 of the light chain.

Accordingly, in some embodiments, the invention provides a combination comprising:
(a) an anti-MERS-S antibody comprising a heavy chain variable region of the amino acid sequence of SEQ ID NO: 26 and a light chain variable region of the amino acid sequence of SEQ ID NO: 65.
(b) an anti-MERS-S antibody comprising a heavy chain variable region of the amino acid sequence of SEQ ID NO: 69 and a light chain variable region of the amino acid sequence of SEQ ID NO: 72.

The 1.2 g5 and 3.5 g6 antibodies bind to the S1 and S2 domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 109 for CDR1 of the heavy chain;
ii. SEQ ID NO: 110 for CDR2 of the heavy chain;
iii. SEQ ID NO: 111 for CDR3 of the heavy chain;
iv. SEQ ID NO: 112 for CDR1 of the light chain;
v. SEQ ID NO: 113 for CDR2 of the light chain; and
vi. SEQ ID NO: 114 for CDR3 of the light chain, and
(b) an anti-MERS-S antibody comprising complementarity determining regions (CDRs) with the sequences of:
i. SEQ ID NO: 89 for CDR1 of the heavy chain;
ii. SEQ ID NO: 90 for CDR2 of the heavy chain;
iii. SEQ ID NO: 91 for CDR3 of the heavy chain;
iv. SEQ ID NO: 92 for CDR1 of the light chain;
v. SEQ ID NO: 93 for CDR2 of the light chain; and
vi. SEQ ID NO: 94 for CDR3 of the light chain.

Accordingly, in some embodiments, the invention provides a combination comprising:
(a) an anti-MERS-S antibody comprising a heavy chain variable region of the amino acid sequence of SEQ ID NO: 107 and a light chain variable region of the amino acid sequence of SEQ ID NO: 108.
(b) an anti-MERS-S antibody comprising a heavy chain variable region of the amino acid sequence of SEQ ID NO: 69 and a light chain variable region of the amino acid sequence of SEQ ID NO: 72.

The 1.8e5 and 3.5 g6 antibodies bind to the S1 and S2 domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 133 for CDR1 of the heavy chain;
ii. SEQ ID NO: 134 for CDR2 of the heavy chain;
iii. SEQ ID NO: 135 for CDR3 of the heavy chain;
iv. SEQ ID NO: 136 for CDR1 of the light chain;

v. SEQ ID NO: 137 for CDR2 of the light chain; and
vi. SEQ ID NO: 138 for CDR3 of the light chain, and
(b) an anti-MERS-S antibody comprising complementarity determining regions (CDRs) with the sequences of:
i. SEQ ID NO: 89 for CDR1 of the heavy chain;
ii. SEQ ID NO: 90 for CDR2 of the heavy chain;
iii. SEQ ID NO: 91 for CDR3 of the heavy chain;
iv. SEQ ID NO: 92 for CDR1 of the light chain;
v. SEQ ID NO: 93 for CDR2 of the light chain; and
vi. SEQ ID NO: 94 for CDR3 of the light chain.

Accordingly, in some embodiments, the invention provides a combination comprising:
(a) an anti-MERS-S antibody comprising a heavy chain variable region of the amino acid sequence of SEQ ID NO: 32 and a light chain variable region of the amino acid sequence of SEQ ID NO: 56.
(b) an anti-MERS-S antibody comprising a heavy chain variable region of the amino acid sequence of SEQ ID NO: 69 and a light chain variable region of the amino acid sequence of SEQ ID NO: 72.

The 4.6e10 and 3.5 g6 antibodies bind to the S1 and S2 domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 139 for CDR1 of the heavy chain;
ii. SEQ ID NO: 140 for CDR2 of the heavy chain;
iii. SEQ ID NO: 141 for CDR3 of the heavy chain;
iv. SEQ ID NO: 142 for CDR1 of the light chain;
v. SEQ ID NO: 143 for CDR2 of the light chain; and
vi. SEQ ID NO: 144 for CDR3 of the light chain, and
(b) an anti-MERS-S antibody comprising complementarity determining regions (CDRs) with the sequences of:
i. SEQ ID NO: 89 for CDR1 of the heavy chain;
ii. SEQ ID NO: 90 for CDR2 of the heavy chain;
iii. SEQ ID NO: 91 for CDR3 of the heavy chain;
iv. SEQ ID NO: 92 for CDR1 of the light chain;
v. SEQ ID NO: 93 for CDR2 of the light chain; and
vi. SEQ ID NO: 94 for CDR3 of the light chain.

Accordingly, in some embodiments, the invention provides a combination comprising:
(a) an anti-MERS-S antibody comprising a heavy chain variable region of the amino acid sequence of SEQ ID NO: 17 and a light chain variable region of the amino acid sequence of SEQ ID NO: 67.
(b) an anti-MERS-S antibody comprising a heavy chain variable region of the amino acid sequence of SEQ ID NO: 69 and a light chain variable region of the amino acid sequence of SEQ ID NO: 72.

The 1.10f3 and 3.5 g6 antibodies bind to the S1 and S2 domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain, and
(b) an anti-MERS-S antibody comprising complementarity determining regions (CDRs) with the sequences of:
i. SEQ ID NO: 89 for CDR1 of the heavy chain;
ii. SEQ ID NO: 90 for CDR2 of the heavy chain;
iii. SEQ ID NO: 91 for CDR3 of the heavy chain;
iv. SEQ ID NO: 92 for CDR1 of the light chain;

v. SEQ ID NO: 93 for CDR2 of the light chain; and vi. SEQ ID NO: 94 for CDR3 of the light chain.

Accordingly, in some embodiments, the invention provides a combination comprising:

(a) an anti-MERS-S antibody comprising a heavy chain variable region of the amino acid sequence of SEQ ID NO: 18 and a light chain variable region of the amino acid sequence of SEQ ID NO: 58.

(b) an anti-MERS-S antibody comprising a heavy chain variable region of the amino acid sequence of SEQ ID NO: 69 and a light chain variable region of the amino acid sequence of SEQ ID NO: 72.

The 1E10 heavy chain-only antibody and the 1.6c7 H2L2 antibody bind to the S1 and S2 domains, respectively. Accordingly, in some embodiments, the invention provides a combination comprising:

(a) an anti-MERS-S heavy chain-only antibody comprising complementarity determining regions (CDRs) with the sequences of:

i. SEQ ID NO: 277 for CDR1 of the heavy chain;

ii. SEQ ID NO: 278 for CDR2 of the heavy chain; and iii. SEQ ID NO: 279 for CDR3 of the heavy chain, and (b) an anti-MERS-S antibody comprising complementarity determining regions (CDRs) with the sequences of:

i. SEQ ID NO: 83 for CDR1 of the heavy chain;

ii. SEQ ID NO: 84 for CDR2 of the heavy chain;

iii. SEQ ID NO: 85 for CDR3 of the heavy chain;

iv. SEQ ID NO: 86 for CDR1 of the light chain;

v. SEQ ID NO: 87 for CDR2 of the light chain; and vi. SEQ ID NO: 88 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 80, and (b) an anti-MERS-S antibody comprising a heavy chain variable region of the amino acid sequence of SEQ ID NO: 70 and a light chain variable region of the amino acid sequence of SEQ ID NO: 74.

The 1E10 heavy chain-only antibody and the 3.5 g6 H2L2 antibody bind to the S1 and S2 domains, respectively. Accordingly, in some embodiments, the invention provides a combination comprising:

(a) an anti-MERS-S heavy chain-only antibody comprising complementarity determining regions (CDRs) with the sequences of:

i. SEQ ID NO: 277 for CDR1 of the heavy chain;

ii. SEQ ID NO: 278 for CDR2 of the heavy chain; and iii. SEQ ID NO: 279 for CDR3 of the heavy chain, and (b) an anti-MERS-S antibody comprising complementarity determining regions (CDRs) with the sequences of:

i. SEQ ID NO: 89 for CDR1 of the heavy chain;

ii. SEQ ID NO: 90 for CDR2 of the heavy chain;

iii. SEQ ID NO: 91 for CDR3 of the heavy chain;

iv. SEQ ID NO: 92 for CDR1 of the light chain;

v. SEQ ID NO: 93 for CDR2 of the light chain; and vi. SEQ ID NO: 94 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 80, and (b) an anti-MERS-S antibody comprising a heavy chain variable region of the amino acid sequence of SEQ ID NO: 69 and a light chain variable region of the amino acid sequence of SEQ ID NO: 72.

The 1G3 heavy chain-only antibody and the 1.6c7 H2L2 antibody bind to the S1 and S2 domains, respectively. Accordingly, in some embodiments, the invention provides a combination comprising:

(a) an anti-MERS-S heavy chain-only antibody comprising complementarity determining regions (CDRs) with the sequences of:

i. SEQ ID NO: 271 for CDR1 of the heavy chain;

ii. SEQ ID NO: 272 for CDR2 of the heavy chain; and iii. SEQ ID NO: 273 for CDR3 of the heavy chain, and (b) an anti-MERS-S antibody comprising complementarity determining regions (CDRs) with the sequences of:

i. SEQ ID NO: 83 for CDR1 of the heavy chain;

ii. SEQ ID NO: 84 for CDR2 of the heavy chain;

iii. SEQ ID NO: 85 for CDR3 of the heavy chain;

iv. SEQ ID NO: 86 for CDR1 of the light chain;

v. SEQ ID NO: 87 for CDR2 of the light chain; and vi. SEQ ID NO: 88 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 75, and (b) an anti-MERS-S antibody comprising a heavy chain variable region of the amino acid sequence of SEQ ID NO: 70 and a light chain variable region of the amino acid sequence of SEQ ID NO: 74.

The 1G3 heavy chain-only antibody and the 3.5 g6 H2L2 antibody bind to the S1 and S2 domains, respectively. Accordingly, in some embodiments, the invention provides a combination comprising:

(a) an anti-MERS-S heavy chain-only antibody comprising complementarity determining regions (CDRs) with the sequences of:

i. SEQ ID NO: 271 for CDR1 of the heavy chain;

ii. SEQ ID NO: 272 for CDR2 of the heavy chain; and iii. SEQ ID NO: 273 for CDR3 of the heavy chain, and (b) an anti-MERS-S antibody comprising complementarity determining regions (CDRs) with the sequences of:

i. SEQ ID NO: 89 for CDR1 of the heavy chain;

ii. SEQ ID NO: 90 for CDR2 of the heavy chain;

iii. SEQ ID NO: 91 for CDR3 of the heavy chain;

iv. SEQ ID NO: 92 for CDR1 of the light chain;

v. SEQ ID NO: 93 for CDR2 of the light chain; and vi. SEQ ID NO: 94 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 75, and (b) an anti-MERS-S antibody comprising a heavy chain variable region of the amino acid sequence of SEQ ID NO: 69 and a light chain variable region of the amino acid sequence of SEQ ID NO: 72.

The 1H5 heavy chain-only antibody and the 1.6c7 H2L2 antibody bind to the S1 and S2 domains, respectively. Accordingly, in some embodiments, the invention provides a combination comprising:

(a) an anti-MERS-S heavy chain-only antibody comprising complementarity determining regions (CDRs) with the sequences of:

i. SEQ ID NO: 274 for CDR1 of the heavy chain;

ii. SEQ ID NO: 275 for CDR2 of the heavy chain; and iii. SEQ ID NO: 276 for CDR3 of the heavy chain, and (b) an anti-MERS-S antibody comprising complementarity determining regions (CDRs) with the sequences of:

i. SEQ ID NO: 83 for CDR1 of the heavy chain;

ii. SEQ ID NO: 84 for CDR2 of the heavy chain;

iii. SEQ ID NO: 85 for CDR3 of the heavy chain;

iv. SEQ ID NO: 86 for CDR1 of the light chain;

v. SEQ ID NO: 87 for CDR2 of the light chain; and vi. SEQ ID NO: 88 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 78, and (b) an anti-MERS-S antibody comprising a heavy chain variable region of the amino acid sequence of SEQ ID NO: 70 and a light chain variable region of the amino acid sequence of SEQ ID NO: 74.

The 1H5 heavy chain-only antibody and the 3.5 g6 H2L2 antibody bind to the S1 and S2 domains, respectively. Accordingly, in some embodiments, the invention provides a combination comprising:

(a) an anti-MERS-S heavy chain-only antibody comprising complementarity determining regions (CDRs) with the sequences of:

i. SEQ ID NO: 274 for CDR1 of the heavy chain;

ii. SEQ ID NO: 275 for CDR2 of the heavy chain; and iii. SEQ ID NO: 276 for CDR3 of the heavy chain, and (b) an anti-MERS-S antibody comprising complementarity determining regions (CDRs) with the sequences of:

i. SEQ ID NO: 89 for CDR1 of the heavy chain;

ii. SEQ ID NO: 90 for CDR2 of the heavy chain;

iii. SEQ ID NO: 91 for CDR3 of the heavy chain;

iv. SEQ ID NO: 92 for CDR1 of the light chain;

v. SEQ ID NO: 93 for CDR2 of the light chain; and vi. SEQ ID NO: 94 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 78, and (b) an anti-MERS-S antibody comprising a heavy chain variable region of the amino acid sequence of SEQ ID NO: 69 and a light chain variable region of the amino acid sequence of SEQ ID NO: 72.

The 5F1 heavy chain-only antibody and the 1.6c7 H2L2 antibody bind to the S1 and S2 domains, respectively. Accordingly, in some embodiments, the invention provides a combination comprising:

(a) an anti-MERS-S heavy chain-only antibody comprising complementarity determining regions (CDRs) with the sequences of:

i. SEQ ID NO: 280 for CDR1 of the heavy chain;

ii. SEQ ID NO: 281 for CDR2 of the heavy chain; and iii. SEQ ID NO: 282 for CDR3 of the heavy chain, and (b) an anti-MERS-S antibody comprising complementarity determining regions (CDRs) with the sequences of:

i. SEQ ID NO: 83 for CDR1 of the heavy chain;

ii. SEQ ID NO: 84 for CDR2 of the heavy chain;

iii. SEQ ID NO: 85 for CDR3 of the heavy chain;

iv. SEQ ID NO: 86 for CDR1 of the light chain;

v. SEQ ID NO: 87 for CDR2 of the light chain; and vi. SEQ ID NO: 88 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 77, and (b) an anti-MERS-S antibody comprising a heavy chain variable region of the amino acid sequence of SEQ ID NO: 70 and a light chain variable region of the amino acid sequence of SEQ ID NO: 74.

The 5F1 heavy chain-only antibody and the 3.5 g6 H2L2 antibody bind to the S1 and S2 domains, respectively. Accordingly, in some embodiments, the invention provides a combination comprising:

(a) an anti-MERS-S heavy chain-only antibody comprising complementarity determining regions (CDRs) with the sequences of:

i. SEQ ID NO: 280 for CDR1 of the heavy chain;

ii. SEQ ID NO: 281 for CDR2 of the heavy chain; and iii. SEQ ID NO: 282 for CDR3 of the heavy chain, and (b) an anti-MERS-S antibody comprising complementarity determining regions (CDRs) with the sequences of:

i. SEQ ID NO: 89 for CDR1 of the heavy chain;

ii. SEQ ID NO: 90 for CDR2 of the heavy chain;

iii. SEQ ID NO: 91 for CDR3 of the heavy chain;

iv. SEQ ID NO: 92 for CDR1 of the light chain;

v. SEQ ID NO: 93 for CDR2 of the light chain; and vi. SEQ ID NO: 94 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 77, and (b) an anti-MERS-S antibody comprising a heavy chain variable region of the amino acid sequence of SEQ ID NO: 69 and a light chain variable region of the amino acid sequence of SEQ ID NO: 72.

The 7.7 g6 and 1.10f3 antibodies bind to the S1$^B$ and S1$^A$ domains of MERS-S, respectively (see FIG. 2E). Accordingly, in some embodiments, the invention provides a combination comprising:

(a) an anti-MERS-S antibody comprising complementarity determining regions (CDRs) with the sequences of:

i. SEQ ID NO: 95 for CDR1 of the heavy chain;

ii. SEQ ID NO: 96 for CDR2 of the heavy chain;

iii. SEQ ID NO: 97 for CDR3 of the heavy chain;

iv. SEQ ID NO: 98 for CDR1 of the light chain;

v. SEQ ID NO: 99 for CDR2 of the light chain; and vi. SEQ ID NO: 100 for CDR3 of the light chain, and (b) an anti-MERS-S antibody comprising complementarity determining regions (CDRs) with the sequences of:

i. SEQ ID NO: 145 for CDR1 of the heavy chain;

ii. SEQ ID NO: 146 for CDR2 of the heavy chain;

iii. SEQ ID NO: 147 for CDR3 of the heavy chain;

iv. SEQ ID NO: 148 for CDR1 of the light chain;

v. SEQ ID NO: 149 for CDR2 of the light chain; and vi. SEQ ID NO: 150 for CDR3 of the light chain.

Accordingly, in some embodiments, the invention provides a combination comprising:

(a) an anti-MERS-S antibody comprising a heavy chain variable region of the amino acid sequence of SEQ ID NO: 28 and a light chain variable region of the amino acid sequence of SEQ ID NO: 63.

(b) an anti-MERS-S antibody comprising a heavy chain variable region of the amino acid sequence of SEQ ID NO: 18 and a light chain variable region of the amino acid sequence of SEQ ID NO: 58.

The 1.6f9 and 1.10f3 antibodies bind to the S1$^B$ and S1$^A$ domains of MERS-S, respectively (see FIG. 2E). Accordingly, in some embodiments, the invention provides a combination comprising:

(a) an anti-MERS-S antibody comprising complementarity determining regions (CDRs) with the sequences of:

i. SEQ ID NO: 101 for CDR1 of the heavy chain;

ii. SEQ ID NO: 102 for CDR2 of the heavy chain;

iii. SEQ ID NO: 103 for CDR3 of the heavy chain;
iv. SEQ ID NO: 104 for CDR1 of the light chain;
v. SEQ ID NO: 105 for CDR2 of the light chain; and
vi. SEQ ID NO: 106 for CDR3 of the light chain, and
(b) an anti-MERS-S antibody comprising complementarity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

Accordingly, in some embodiments, the invention provides a combination comprising:
(a) an anti-MERS-S antibody comprising a heavy chain variable region of the amino acid sequence of SEQ ID NO: 26 and a light chain variable region of the amino acid sequence of SEQ ID NO: 65.
(b) an anti-MERS-S antibody comprising a heavy chain variable region of the amino acid sequence of SEQ ID NO: 18 and a light chain variable region of the amino acid sequence of SEQ ID NO: 58.

The 1.2 g5 and 1.10f3 antibodies bind to the S1$^B$ and S1$^A$ domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 109 for CDR1 of the heavy chain;
ii. SEQ ID NO: 110 for CDR2 of the heavy chain;
iii. SEQ ID NO: 111 for CDR3 of the heavy chain;
iv. SEQ ID NO: 112 for CDR1 of the light chain;
v. SEQ ID NO: 113 for CDR2 of the light chain; and
vi. SEQ ID NO: 114 for CDR3 of the light chain, and
(b) an anti-MERS-S antibody comprising complementarity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

Accordingly, in some embodiments, the invention provides a combination comprising:
(a) an anti-MERS-S antibody comprising a heavy chain variable region of the amino acid sequence of SEQ ID NO: 107 and a light chain variable region of the amino acid sequence of SEQ ID NO: 108.
(b) an anti-MERS-S antibody comprising a heavy chain variable region of the amino acid sequence of SEQ ID NO: 18 and a light chain variable region of the amino acid sequence of SEQ ID NO: 58.

The 1.8e5 and 1.10f3 antibodies bind to the S1$^B$ and S1$^A$ domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 133 for CDR1 of the heavy chain;
ii. SEQ ID NO: 134 for CDR2 of the heavy chain;
iii. SEQ ID NO: 135 for CDR3 of the heavy chain;
iv. SEQ ID NO: 136 for CDR1 of the light chain;
v. SEQ ID NO: 137 for CDR2 of the light chain; and
vi. SEQ ID NO: 138 for CDR3 of the light chain, and
(b) an anti-MERS-S antibody comprising complementarity determining regions (CDRs) with the sequences of:

i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

Accordingly, in some embodiments, the invention provides a combination comprising:
(a) an anti-MERS-S antibody comprising a heavy chain variable region of the amino acid sequence of SEQ ID NO: 32 and a light chain variable region of the amino acid sequence of SEQ ID NO: 56.
(b) an anti-MERS-S antibody comprising a heavy chain variable region of the amino acid sequence of SEQ ID NO: 18 and a light chain variable region of the amino acid sequence of SEQ ID NO: 58.

The 4.6e10 and 1.10f3 antibodies bind to the S1$^B$ and S1$^A$ domains of MERS-S, respectively (see FIG. 2E). Accordingly, in some embodiments, the invention provides a combination comprising:
(a) an anti-MERS-S antibody comprising complementarity determining regions (CDRs) with the sequences of:
i. SEQ ID NO: 139 for CDR1 of the heavy chain;
ii. SEQ ID NO: 140 for CDR2 of the heavy chain;
iii. SEQ ID NO: 141 for CDR3 of the heavy chain;
iv. SEQ ID NO: 142 for CDR1 of the light chain;
v. SEQ ID NO: 143 for CDR2 of the light chain; and
vi. SEQ ID NO: 144 for CDR3 of the light chain, and
(b) an anti-MERS-S antibody comprising complementarity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

Accordingly, in some embodiments, the invention provides a combination comprising:
(a) an anti-MERS-S antibody comprising a heavy chain variable region of the amino acid sequence of SEQ ID NO: 17 and a light chain variable region of the amino acid sequence of SEQ ID NO: 67.
(b) an anti-MERS-S antibody comprising a heavy chain variable region of the amino acid sequence of SEQ ID NO: 18 and a light chain variable region of the amino acid sequence of SEQ ID NO: 58.

The 1E10 heavy chain-only antibody exhibits neutralising activity (see FIG. 31) and the 1.10f3 H2L2 antibody targets the sialic acid binding MERS S1$_A$ domain (see FIG. 5A) and inhibits Sia-binding activity. Accordingly, in some embodiments, the invention provides a combination comprising:
(a) an anti-MERS-S heavy chain-only antibody comprising complementarity determining regions (CDRs) with the sequences of:
i. SEQ ID NO: 277 for CDR1 of the heavy chain;
ii. SEQ ID NO: 278 for CDR2 of the heavy chain; and
iii. SEQ ID NO: 279 for CDR3 of the heavy chain, and
(b) an anti-MERS-S antibody comprising complementarity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 80, and (b) an anti-MERS-S antibody comprising a heavy chain variable region of the amino acid sequence of SEQ ID NO: 18 and a light chain variable region of the amino acid sequence of SEQ ID NO: 58.

The 1G3 heavy chain-only antibody exhibits neutralising activity (see FIG. 31) and the 1.10f3 H2L2 antibody targets the sialic acid binding MERS $S1_A$ domain (see FIG. 5A) and inhibits Sia-binding activity. Accordingly, in some embodiments, the invention provides a combination comprising:

(a) an anti-MERS-S heavy chain-only antibody comprising complementarity determining regions (CDRs) with the sequences of:
i. SEQ ID NO: 271 for CDR1 of the heavy chain;
ii. SEQ ID NO: 272 for CDR2 of the heavy chain; and
iii. SEQ ID NO: 273 for CDR3 of the heavy chain, and (b) an anti-MERS-S antibody comprising complementarity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 75, and (b) an anti-MERS-S antibody comprising a heavy chain variable region of the amino acid sequence of SEQ ID NO: 18 and a light chain variable region of the amino acid sequence of SEQ ID NO: 58.

The 1H5 heavy chain-only antibody exhibits neutralising activity (see FIG. 31) and the 1.10f3 H2L2 antibody targets the sialic acid binding MERS $S1^A$ domain (see FIG. 5A) and inhibits Sia-binding activity. Accordingly, in some embodiments, the invention provides a combination comprising:

(a) an anti-MERS-S heavy chain-only antibody comprising complementarity determining regions (CDRs) with the sequences of:
i. SEQ ID NO: 274 for CDR1 of the heavy chain;
ii. SEQ ID NO: 275 for CDR2 of the heavy chain; and
iii. SEQ ID NO: 276 for CDR3 of the heavy chain, and (b) an anti-MERS-S antibody comprising complementarity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 78, and (b) an anti-MERS-S antibody comprising a heavy chain variable region of the amino acid sequence of SEQ ID NO: 18 and a light chain variable region of the amino acid sequence of SEQ ID NO: 58.

The 5F1 heavy chain-only antibody exhibits neutralising activity (see FIG. 31) and the 1.10f3 H2L2 antibody targets the sialic acid binding MERS $S1^A$ domain (see FIG. 5A) and inhibits Sia-binding activity. Accordingly, in some embodiments, the invention provides a combination comprising:

(a) an anti-MERS-S heavy chain-only antibody comprising complementarity determining regions (CDRs) with the sequences of:
i. SEQ ID NO: 280 for CDR1 of the heavy chain;
ii. SEQ ID NO: 281 for CDR2 of the heavy chain; and
iii. SEQ ID NO: 282 for CDR3 of the heavy chain, and (b) an anti-MERS-S antibody comprising complementarity determining regions (CDRs) with the sequences of:
i. SEQ ID NO: 145 for CDR1 of the heavy chain;
ii. SEQ ID NO: 146 for CDR2 of the heavy chain;
iii. SEQ ID NO: 147 for CDR3 of the heavy chain;
iv. SEQ ID NO: 148 for CDR1 of the light chain;
v. SEQ ID NO: 149 for CDR2 of the light chain; and
vi. SEQ ID NO: 150 for CDR3 of the light chain.

Accordingly, in some embodiments, the invention provides a combination comprising:

(a) an anti-MERS-S heavy chain-only antibody comprising a heavy chain variable region of the amino acid sequence of SEQ ID NO: 77, and (b) an anti-MERS-S antibody comprising a heavy chain variable region of the amino acid sequence of SEQ ID NO: 18 and a light chain variable region of the amino acid sequence of SEQ ID NO: 58.

Antibodies that Recognize Spike Proteins from Different Coronaviruses

Figure 2H:
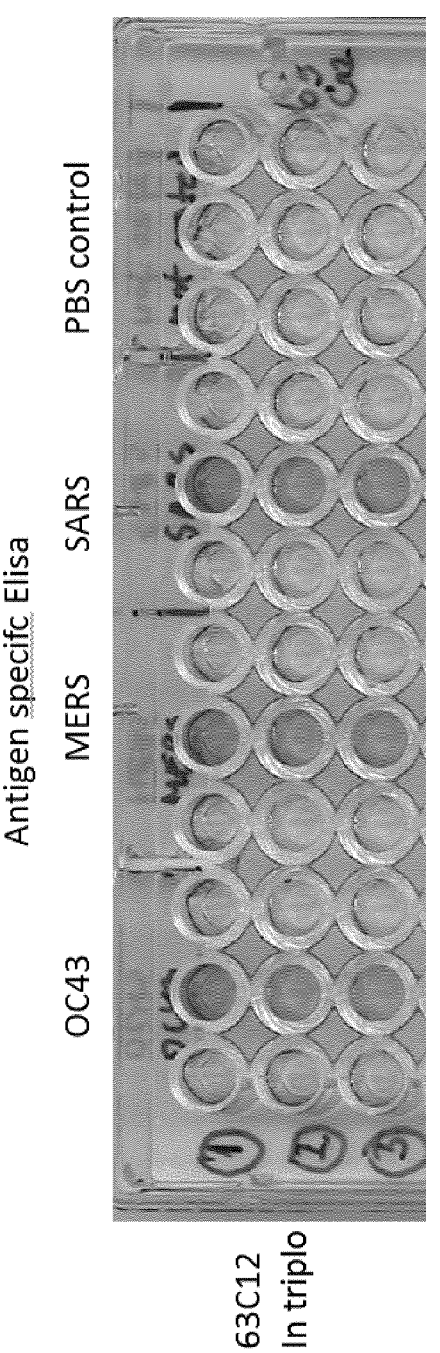

FIG. 2H shows that the 63c12 antibody recognizes spike proteins from OC43, MERS and SARS viruses.

Similar functional properties can be expected to be associated with the antibodies defined below which share structural and binding characteristics with the 63c12 antibody.

The invention provides an anti-MERS-S antibody that binds to the same epitope as an antibody comprising a heavy chain variable region of the amino acid sequence of SEQ ID NO: 480 and a light chain variable region of the amino acid sequence of SEQ ID NO: 458.

The invention further provides an anti-MERS-S antibody that binds to the same epitope as a heavy chain-only antibody comprising a heavy chain variable region of the amino acid sequence of SEQ ID NO: 480.

The invention further provides an anti-MERS-S antibody that competes for binding to MERS-S with an antibody comprising a heavy chain variable region of the amino acid sequence of SEQ ID NO: 480 and a light chain variable region of the amino acid sequence of SEQ ID NO: 458.

The invention further provides an anti-MERS-S antibody that competes for binding to MERS-S with a heavy chain-only antibody comprising a heavy chain variable region of the amino acid sequence of SEQ ID NO: 480.

The invention further provides an anti-MERS-S antibody comprising complementarity determining regions (CDRs) with the sequences of:
i. SEQ ID NO: 617 for CDR1 of the heavy chain;
ii. SEQ ID NO: 618 for CDR2 of the heavy chain;
iii. SEQ ID NO: 619 for CDR3 of the heavy chain;
iv. SEQ ID NO: 614 for CDR1 of the light chain;
v. SEQ ID NO: 615 for CDR2 of the light chain; and
vi. SEQ ID NO: 616 for CDR3 of the light chain.

In some embodiments, the antibody comprises a heavy chain variable region of the amino acid sequence of SEQ ID NO: 480.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 480.

In some embodiments, the antibody comprises a light chain variable region of the amino acid sequence of SEQ ID NO: 458.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 458.

In some embodiments, the antibody comprises a heavy chain variable region of the amino acid sequence of SEQ ID NO: 480 and a light chain variable region of the amino acid sequence of SEQ ID NO: 458.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 480 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 458.

The invention further provides an anti-MERS-S antibody comprising complementarity determining regions (CDRs) with:

i. a sequence that is at least 90% identical to SEQ ID NO: 617 for CDR1 of the heavy chain;

ii. a sequence that is at least 90% identical to SEQ ID NO: 618 for CDR2 of the heavy chain;

iii. a sequence that is at least 90% identical to SEQ ID NO: 619 for CDR3 of the heavy chain;

iv. a sequence that is at least 90% identical to SEQ ID NO: 614 for CDR1 of the light v. a sequence that is at least 90% identical to SEQ ID NO: 615 for CDR2 of the light chain; and vi. a sequence that is at least 90% identical to SEQ ID NO: 616 for CDR3 of the light chain, wherein the antibody competes for binding to MERS-S with an antibody comprising a heavy chain variable region of the amino acid sequence of SEQ ID NO: 480 and a light chain variable region of the amino acid sequence of SEQ ID NO: 458.

The invention further provides an anti-MERS-S antibody comprising complementarity determining regions (CDRs) with:

i. a sequence that is at least 95% identical to SEQ ID NO: 617 for CDR1 of the heavy chain;

ii. a sequence that is at least 95% identical to SEQ ID NO: 618 for CDR2 of the heavy chain;

iii. a sequence that is at least 95% identical to SEQ ID NO: 619 for CDR3 of the heavy chain;

iv. a sequence that is at least 95% identical to SEQ ID NO: 614 for CDR1 of the light chain;

v. a sequence that is at least 95% identical to SEQ ID NO: 615 for CDR2 of the light chain; and vi. a sequence that is at least 95% identical to SEQ ID NO: 616 for CDR3 of the light chain, wherein the antibody competes for binding to MERS-S with an antibody comprising a heavy chain variable region of the amino acid sequence of SEQ ID NO: 480 and a light chain variable region of the amino acid sequence of SEQ ID NO: 458.

Like the 63c12 antibody, the other antibodies in FIG. 2C also recognize spike proteins from different Coronaviruses. Similar functional properties can be expected to be associated with the antibodies defined below which share structural and binding characteristics with the antibodies in FIG. 2C.

The invention provides an antibody that binds to a Coronavirus spike protein (e.g. MERS-S), wherein the antibody binds to the same epitope as an antibody comprising a heavy chain variable region of the amino acid sequence of SEQ ID NO: 488 and a light chain variable region of the amino acid sequence of SEQ ID NO: 436.

The invention provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 488.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 488 and a light chain variable region of the amino acid sequence of SEQ ID NO: 436.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 488.

The invention further provides an antibody that binds to a Coronavirus spike protein (e.g. MERS-S), wherein the antibody comprises complementarity determining regions (CDRs) with the sequences of:

i. SEQ ID NO: 503 for CDR1 of the heavy chain;

ii. SEQ ID NO: 504 for CDR2 of the heavy chain;

iii. SEQ ID NO: 505 for CDR3 of the heavy chain;

iv. SEQ ID NO: 500 for CDR1 of the light chain;

v. SEQ ID NO: 501 for CDR2 of the light chain; and vi. SEQ ID NO: 502 for CDR3 of the light chain.

In some embodiments, the antibody comprises a heavy chain variable region of the amino acid sequence of SEQ ID NO: 488.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 488.

In some embodiments, the antibody comprises a light chain variable region of the amino acid sequence of SEQ ID NO: 436.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 436.

In some embodiments, the antibody comprises a heavy chain variable region of the amino acid sequence of SEQ ID NO: 488 and a light chain variable region of the amino acid sequence of SEQ ID NO: 436.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 488 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 436.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 503 for CDR1 of the heavy chain;

ii. a sequence that is at least 90% identical to SEQ ID NO: 504 for CDR2 of the iii. a sequence that is at least 90% identical to SEQ ID NO: 505 for CDR3 of the heavy chain;

iv. a sequence that is at least 90% identical to SEQ ID NO: 500 for CDR1 of the light chain;

v. a sequence that is at least 90% identical to SEQ ID NO: 501 for CDR2 of the light chain; and vi. a sequence that is at least 90% identical to SEQ ID NO: 502 for CDR3 of the light chain, and wherein the antibody competes for binding to a Coronavirus spike protein (e.g. MERS-S) with an antibody comprising a heavy chain variable region of the amino acid sequence of SEQ ID NO: 488 and a light chain variable region of the amino acid sequence of SEQ ID NO: 436.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 503 for CDR1 of the heavy chain;

ii. a sequence that is at least 95% identical to SEQ ID NO: 504 for CDR2 of the heavy chain;

iii. a sequence that is at least 95% identical to SEQ ID NO: 505 for CDR3 of the heavy chain;

iv. a sequence that is at least 95% identical to SEQ ID NO: 500 for CDR1 of the light chain;

v. a sequence that is at least 95% identical to SEQ ID NO: 501 for CDR2 of the light chain; and vi. a sequence that is at least 95% identical to SEQ ID NO: 502 for CDR3 of the light chain, and wherein the antibody competes for binding to a Coronavirus spike protein (e.g. MERS-S) with an antibody comprising a heavy chain variable region of the amino acid sequence of SEQ ID NO: 488 and a light chain variable region of the amino acid sequence of SEQ ID NO: 436.

The invention provides an antibody that binds to a Coronavirus spike protein (e.g. MERS-S), wherein the antibody binds to the same epitope as an antibody comprising a heavy chain variable region of the amino acid sequence of SEQ ID NO: 486 and a light chain variable region of the amino acid sequence of SEQ ID NO: 437.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 486.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 486 and a light chain variable region of the amino acid sequence of SEQ ID NO: 437.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 486.

The invention further provides an antibody that binds to a Coronavirus spike protein (e.g. MERS-S), wherein the antibody comprises complementarity determining regions (CDRs) with the sequences of:

i. SEQ ID NO: 509 for CDR1 of the heavy chain;

ii. SEQ ID NO: 510 for CDR2 of the heavy chain;

iii. SEQ ID NO: 511 for CDR3 of the heavy chain;

iv. SEQ ID NO: 506 for CDR1 of the light chain;

v. SEQ ID NO: 507 for CDR2 of the light chain; and vi. SEQ ID NO: 508 for CDR3 of the light chain.

In some embodiments, the antibody comprises a heavy chain variable region of the amino acid sequence of SEQ ID NO: 486.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 486.

In some embodiments, the antibody comprises a light chain variable region of the amino acid sequence of SEQ ID NO: 437.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 437.

In some embodiments, the antibody comprises a heavy chain variable region of the amino acid sequence of SEQ ID NO: 488 and a light chain variable region of the amino acid sequence of SEQ ID NO: 437.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 486 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 437.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 509 for CDR1 of the ii. a sequence that is at least 90% identical to SEQ ID NO: 510 for CDR2 of the heavy chain;

iii. a sequence that is at least 90% identical to SEQ ID NO: 511 for CDR3 of the heavy chain;

iv. a sequence that is at least 90% identical to SEQ ID NO: 506 for CDR1 of the light chain;

v. a sequence that is at least 90% identical to SEQ ID NO: 507 for CDR2 of the light chain; and vi. a sequence that is at least 90% identical to SEQ ID NO: 508 for CDR3 of the light chain, and wherein the antibody competes for binding to a Coronavirus spike protein (e.g. MERS-S) with an antibody comprising a heavy chain variable region of the amino acid sequence of SEQ ID NO: 486 and a light chain variable region of the amino acid sequence of SEQ ID NO: 437.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 509 for CDR1 of the heavy chain;

ii. a sequence that is at least 95% identical to SEQ ID NO: 510 for CDR2 of the heavy chain;

iii. a sequence that is at least 95% identical to SEQ ID NO: 511 for CDR3 of the heavy chain;

iv. a sequence that is at least 95% identical to SEQ ID NO: 506 for CDR1 of the light chain;

v. a sequence that is at least 95% identical to SEQ ID NO: 507 for CDR2 of the light vi. a sequence that is at least 95% identical to SEQ ID NO: 508 for CDR3 of the light chain, and wherein the antibody competes for binding to a Coronavirus spike protein (e.g. MERS-S) with an antibody comprising a heavy chain variable region of the amino acid sequence of SEQ ID NO: 486 and a light chain variable region of the amino acid sequence of SEQ ID NO: 437.

The invention provides an antibody that binds to a Coronavirus spike protein (e.g. MERS-S), wherein the antibody binds to the same epitope as an antibody comprising a heavy chain variable region of the amino acid sequence of SEQ ID NO: 499 and a light chain variable region of the amino acid sequence of SEQ ID NO: 438.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 499.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 499 and a light chain variable region of the amino acid sequence of SEQ ID NO: 438.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 499.

The invention further provides an antibody that binds to a Coronavirus spike protein (e.g. MERS-S), wherein the antibody comprises complementarity determining regions (CDRs) with the sequences of:

i. SEQ ID NO: 515 for CDR1 of the heavy chain;

ii. SEQ ID NO: 516 for CDR2 of the heavy chain;

iii. SEQ ID NO: 517 for CDR3 of the heavy chain;

iv. SEQ ID NO: 512 for CDR1 of the light chain;

v. SEQ ID NO: 513 for CDR2 of the light chain; and vi. SEQ ID NO: 514 for CDR3 of the light chain.

In some embodiments, the antibody comprises a heavy chain variable region of the amino acid sequence of SEQ ID NO: 499.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 499.

In some embodiments, the antibody comprises a light chain variable region of the amino acid sequence of SEQ ID NO: 438.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 438.

In some embodiments, the antibody comprises a heavy chain variable region of the amino acid sequence of SEQ ID NO: 499 and a light chain variable region of the amino acid sequence of SEQ ID NO: 438.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 499 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 438.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 515 for CDR1 of the ii. a sequence that is at least 90% identical to SEQ ID NO: 516 for CDR2 of the heavy chain;

iii. a sequence that is at least 90% identical to SEQ ID NO: 517 for CDR3 of the heavy chain;

iv. a sequence that is at least 90% identical to SEQ ID NO: 512 for CDR1 of the light chain;

v. a sequence that is at least 90% identical to SEQ ID NO: 513 for CDR2 of the light chain; and vi. a sequence that is at least 90% identical to SEQ ID NO: 514 for CDR3 of the light chain, and wherein the antibody competes for binding to a Coronavirus spike protein (e.g. MERS-S) with an antibody comprising a heavy chain variable region of the amino acid sequence of SEQ ID NO: 499 and a light chain variable region of the amino acid sequence of SEQ ID NO: 438.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 515 for CDR1 of the heavy chain;

ii. a sequence that is at least 95% identical to SEQ ID NO: 516 for CDR2 of the heavy chain;

iii. a sequence that is at least 95% identical to SEQ ID NO: 517 for CDR3 of the heavy chain;

iv. a sequence that is at least 95% identical to SEQ ID NO: 512 for CDR1 of the light chain;

v. a sequence that is at least 95% identical to SEQ ID NO: 513 for CDR2 of the light vi. a sequence that is at least 95% identical to SEQ ID NO: 514 for CDR3 of the light chain, and wherein the antibody competes for binding to a Coronavirus spike protein (e.g. MERS-S) with an antibody comprising a heavy chain variable region of the amino acid sequence of SEQ ID NO: 499 and a light chain variable region of the amino acid sequence of SEQ ID NO: 438.

The invention provides an antibody that binds to a Coronavirus spike protein (e.g. MERS-S), wherein the antibody binds to the same epitope as an antibody comprising a heavy chain variable region of the amino acid sequence of SEQ ID NO: 497 and a light chain variable region of the amino acid sequence of SEQ ID NO: 439.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 497.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 497 and a light chain variable region of the amino acid sequence of SEQ ID NO: 439.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 497.

The invention further provides an antibody that binds to a Coronavirus spike protein (e.g. MERS-S), wherein the antibody comprises complementarity determining regions (CDRs) with the sequences of:
    i. SEQ ID NO: 521 for CDR1 of the heavy chain;
    ii. SEQ ID NO: 522 for CDR2 of the heavy chain;
    iii. SEQ ID NO: 523 for CDR3 of the heavy chain;
    iv. SEQ ID NO: 518 for CDR1 of the light chain;
    v. SEQ ID NO: 519 for CDR2 of the light chain; and
    vi. SEQ ID NO: 520 for CDR3 of the light chain.

In some embodiments, the antibody comprises a heavy chain variable region of the amino acid sequence of SEQ ID NO: 497.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 497.

In some embodiments, the antibody comprises a light chain variable region of the amino acid sequence of SEQ ID NO: 439.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 439.

In some embodiments, the antibody comprises a heavy chain variable region of the amino acid sequence of SEQ ID NO: 497 and a light chain variable region of the amino acid sequence of SEQ ID NO: 439.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 497 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 439.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 521 for CDR1 of the
    ii. a sequence that is at least 90% identical to SEQ ID NO: 522 for CDR2 of the heavy chain;
    iii. a sequence that is at least 90% identical to SEQ ID NO: 523 for CDR3 of the heavy chain;
    iv. a sequence that is at least 90% identical to SEQ ID NO: 518 for CDR1 of the light chain;
    v. a sequence that is at least 90% identical to SEQ ID NO: 519 for CDR2 of the light chain; and
    vi. a sequence that is at least 90% identical to SEQ ID NO: 520 for CDR3 of the light chain,
and wherein the antibody competes for binding to a Coronavirus spike protein (e.g. MERS-S) with an antibody comprising a heavy chain variable region of the amino acid sequence of SEQ ID NO: 497 and a light chain variable region of the amino acid sequence of SEQ ID NO: 439.

The invention further provides an antibody that binds to a Coronavirus spike protein (e.g. MERS-S), wherein the antibody comprises complementarity determining regions (CDRs) with:
    i. a sequence that is at least 95% identical to SEQ ID NO: 521 for CDR1 of the heavy chain;
    ii. a sequence that is at least 95% identical to SEQ ID NO: 522 for CDR2 of the heavy chain;
    iii. a sequence that is at least 95% identical to SEQ ID NO: 523 for CDR3 of the heavy chain;
    iv. a sequence that is at least 95% identical to SEQ ID NO: 518 for CDR1 of the light chain;
    v. a sequence that is at least 95% identical to SEQ ID NO: 519 for CDR2 of the light
    vi. a sequence that is at least 95% identical to SEQ ID NO: 520 for CDR3 of the light chain,
and wherein the antibody competes for binding to a Coronavirus spike protein (e.g. MERS-S) with an antibody comprising a heavy chain variable region of the amino acid sequence of SEQ ID NO: 497 and a light chain variable region of the amino acid sequence of SEQ ID NO: 439.

The invention provides an antibody that binds to a Coronavirus spike protein (e.g. MERS-S), wherein the antibody binds to the same epitope as an antibody comprising a heavy chain variable region of the amino acid sequence of SEQ ID NO: 482 and a light chain variable region of the amino acid sequence of SEQ ID NO: 440.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 482.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 482 and a light chain variable region of the amino acid sequence of SEQ ID NO: 440.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 482.

The invention further provides an antibody that binds to a Coronavirus spike protein (e.g. MERS-S), wherein the antibody comprises complementarity determining regions (CDRs) with the sequences of:

i. SEQ ID NO: 527 for CDR1 of the heavy chain;

ii. SEQ ID NO: 528 for CDR2 of the heavy chain;

iii. SEQ ID NO: 529 for CDR3 of the heavy chain;

iv. SEQ ID NO: 524 for CDR1 of the light chain;

v. SEQ ID NO: 525 for CDR2 of the light chain; and vi. SEQ ID NO: 526 for CDR3 of the light chain.

In some embodiments, the antibody comprises a heavy chain variable region of the amino acid sequence of SEQ ID NO: 482.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 482.

In some embodiments, the antibody comprises a light chain variable region of the amino acid sequence of SEQ ID NO: 440.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 440.

In some embodiments, the antibody comprises a heavy chain variable region of the amino acid sequence of SEQ ID NO: 482 and a light chain variable region of the amino acid sequence of SEQ ID NO: 440.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 482 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 440.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 527 for CDR1 of the ii. a sequence that is at least 90% identical to SEQ ID NO: 528 for CDR2 of the heavy chain;

iii. a sequence that is at least 90% identical to SEQ ID NO: 529 for CDR3 of the heavy chain;

iv. a sequence that is at least 90% identical to SEQ ID NO: 524 for CDR1 of the light chain;

v. a sequence that is at least 90% identical to SEQ ID NO: 525 for CDR2 of the light chain; and vi. a sequence that is at least 90% identical to SEQ ID NO: 526 for CDR3 of the light chain, and wherein the antibody competes for binding to a Coronavirus spike protein (e.g. MERS-S) with an antibody comprising a heavy chain variable region of the amino acid sequence of SEQ ID NO: 482 and a light chain variable region of the amino acid sequence of SEQ ID NO: 440.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 527 for CDR1 of the heavy chain;

ii. a sequence that is at least 95% identical to SEQ ID NO: 528 for CDR2 of the heavy chain;

iii. a sequence that is at least 95% identical to SEQ ID NO: 529 for CDR3 of the heavy chain;

iv. a sequence that is at least 95% identical to SEQ ID NO: 524 for CDR1 of the light chain;

v. a sequence that is at least 95% identical to SEQ ID NO: 525 for CDR2 of the light vi. a sequence that is at least 95% identical to SEQ ID NO: 526 for CDR3 of the light chain, and wherein the antibody competes for binding to a Coronavirus spike protein (e.g. MERS-S) with an antibody comprising a heavy chain variable region of the amino acid sequence of SEQ ID NO: 482 and a light chain variable region of the amino acid sequence of SEQ ID NO: 440.

The invention provides an antibody that binds to a Coronavirus spike protein (e.g. MERS-S), wherein the antibody binds to the same epitope as an antibody comprising a heavy chain variable region of the amino acid sequence of SEQ ID NO: 471 and a light chain variable region of the amino acid sequence of SEQ ID NO: 441.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 471.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 471 and a light chain variable region of the amino acid sequence of SEQ ID NO: 441.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 471.

The invention further provides an antibody that binds to a Coronavirus spike protein (e.g. MERS-S), wherein the antibody comprises complementarity determining regions (CDRs) with the sequences of:

i. SEQ ID NO: 533 for CDR1 of the heavy chain;

ii. SEQ ID NO: 534 for CDR2 of the heavy chain;

iii. SEQ ID NO: 535 for CDR3 of the heavy chain;

iv. SEQ ID NO: 530 for CDR1 of the light chain;

v. SEQ ID NO: 531 for CDR2 of the light chain; and vi. SEQ ID NO: 532 for CDR3 of the light chain.

In some embodiments, the antibody comprises a heavy chain variable region of the amino acid sequence of SEQ ID NO: 471.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 471.

In some embodiments, the antibody comprises a light chain variable region of the amino acid sequence of SEQ ID NO: 441.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 441.

In some embodiments, the antibody comprises a heavy chain variable region of the amino acid sequence of SEQ ID NO: 471 and a light chain variable region of the amino acid sequence of SEQ ID NO: 441.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 471 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 441.

The invention further provides an antibody that binds to a Coronavirus spike protein (e.g. MERS-S), wherein the antibody comprises complementarity determining regions (CDRs) with:
    i. a sequence that is at least 90% identical to SEQ ID NO: 533 for CDR1 of the
    ii. a sequence that is at least 90% identical to SEQ ID NO: 534 for CDR2 of the heavy chain;
    iii. a sequence that is at least 90% identical to SEQ ID NO: 535 for CDR3 of the heavy chain;
    iv. a sequence that is at least 90% identical to SEQ ID NO: 530 for CDR1 of the light chain;
    v. a sequence that is at least 90% identical to SEQ ID NO: 531 for CDR2 of the light chain; and
    vi. a sequence that is at least 90% identical to SEQ ID NO: 532 for CDR3 of the light chain,
and wherein the antibody competes for binding to a Coronavirus spike protein (e.g. MERS-S) with an antibody comprising a heavy chain variable region of the amino acid sequence of SEQ ID NO: 471 and a light chain variable region of the amino acid sequence of SEQ ID NO: 441.

The invention further provides an antibody that binds to a Coronavirus spike protein (e.g. MERS-S), wherein the antibody comprises complementarity determining regions (CDRs) with:
    i. a sequence that is at least 95% identical to SEQ ID NO: 533 for CDR1 of the heavy chain;
    ii. a sequence that is at least 95% identical to SEQ ID NO: 534 for CDR2 of the heavy chain;
    iii. a sequence that is at least 95% identical to SEQ ID NO: 535 for CDR3 of the heavy chain;
    iv. a sequence that is at least 95% identical to SEQ ID NO: 530 for CDR1 of the light chain;
    v. a sequence that is at least 95% identical to SEQ ID NO: 531 for CDR2 of the light
    vi. a sequence that is at least 95% identical to SEQ ID NO: 532 for CDR3 of the light chain,
and wherein the antibody competes for binding to a Coronavirus spike protein (e.g. MERS-S) with an antibody comprising a heavy chain variable region of the amino acid sequence of SEQ ID NO: 471 and a light chain variable region of the amino acid sequence of SEQ ID NO: 441.

The invention provides an antibody that binds to a Coronavirus spike protein (e.g. MERS-S), wherein the antibody binds to the same epitope as an antibody comprising a heavy chain variable region of the amino acid sequence of SEQ ID NO: 483 and a light chain variable region of the amino acid sequence of SEQ ID NO: 442.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 483.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 483 and a light chain variable region of the amino acid sequence of SEQ ID NO: 442.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 483.

The invention further provides an antibody that binds to a Coronavirus spike protein (e.g. MERS-S), wherein the antibody comprises complementarity determining regions (CDRs) with the sequences of:
    i. SEQ ID NO: 539 for CDR1 of the heavy chain;
    ii. SEQ ID NO: 540 for CDR2 of the heavy chain;
    iii. SEQ ID NO: 541 for CDR3 of the heavy chain;
    iv. SEQ ID NO: 536 for CDR1 of the light chain;
    v. SEQ ID NO: 537 for CDR2 of the light chain; and
    vi. SEQ ID NO: 538 for CDR3 of the light chain.

In some embodiments, the antibody comprises a heavy chain variable region of the amino acid sequence of SEQ ID NO: 483.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 483.

In some embodiments, the antibody comprises a light chain variable region of the amino acid sequence of SEQ ID NO: 442.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 442.

In some embodiments, the antibody comprises a heavy chain variable region of the amino acid sequence of SEQ ID NO: 483 and a light chain variable region of the amino acid sequence of SEQ ID NO: 442.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 483 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 442.

The invention further provides an antibody that binds to a Coronavirus spike protein (e.g. MERS-S), wherein the antibody comprises complementarity determining regions (CDRs) with:
    i. a sequence that is at least 90% identical to SEQ ID NO: 539 for CDR1 of the
    ii. a sequence that is at least 90% identical to SEQ ID NO: 540 for CDR2 of the heavy chain;
    iii. a sequence that is at least 90% identical to SEQ ID NO: 541 for CDR3 of the heavy chain;
    iv. a sequence that is at least 90% identical to SEQ ID NO: 536 for CDR1 of the light chain;
    v. a sequence that is at least 90% identical to SEQ ID NO: 537 for CDR2 of the light chain; and vi. a sequence that is at least 90% identical to SEQ ID NO: 538 for CDR3 of the light chain, and wherein the antibody competes for binding to a Coronavirus spike protein (e.g. MERS-S) with an antibody comprising a heavy chain variable region of the amino acid sequence of SEQ ID NO: 483 and a light chain variable region of the amino acid sequence of SEQ ID NO: 442.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 539 for CDR1 of the heavy chain;

ii. a sequence that is at least 95% identical to SEQ ID NO: 540 for CDR2 of the heavy chain;

iii. a sequence that is at least 95% identical to SEQ ID NO: 541 for CDR3 of the heavy chain;

iv. a sequence that is at least 95% identical to SEQ ID NO: 536 for CDR1 of the light chain;

v. a sequence that is at least 95% identical to SEQ ID NO: 537 for CDR2 of the light vi. a sequence that is at least 95% identical to SEQ ID NO: 538 for CDR3 of the light chain, and wherein the antibody competes for binding to a Coronavirus spike protein (e.g. MERS-S) with an antibody comprising a heavy chain variable region of the amino acid sequence of SEQ ID NO: 483 and a light chain variable region of the amino acid sequence of SEQ ID NO: 442.

The invention provides an antibody that binds to a Coronavirus spike protein (e.g. MERS-S), wherein the antibody binds to the same epitope as an antibody comprising a heavy chain variable region of the amino acid sequence of SEQ ID NO: 489 and a light chain variable region of the amino acid sequence of SEQ ID NO: 443.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 489.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 489 and a light chain variable region of the amino acid sequence of SEQ ID NO: 443.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 489.

The invention further provides an antibody that binds to a Coronavirus spike protein (e.g. MERS-S), wherein the antibody comprises complementarity determining regions (CDRs) with the sequences of:

i. SEQ ID NO: 545 for CDR1 of the heavy chain;

ii. SEQ ID NO: 546 for CDR2 of the heavy chain;

iii. SEQ ID NO: 547 for CDR3 of the heavy chain;

iv. SEQ ID NO: 542 for CDR1 of the light chain;

v. SEQ ID NO: 543 for CDR2 of the light chain; and vi. SEQ ID NO: 544 for CDR3 of the light chain.

In some embodiments, the antibody comprises a heavy chain variable region of the amino acid sequence of SEQ ID NO: 489.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 489.

In some embodiments, the antibody comprises a light chain variable region of the amino acid sequence of SEQ ID NO: 443.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 443.

In some embodiments, the antibody comprises a heavy chain variable region of the amino acid sequence of SEQ ID NO: 489 and a light chain variable region of the amino acid sequence of SEQ ID NO: 443.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 489 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 443.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 545 for CDR1 of the ii. a sequence that is at least 90% identical to SEQ ID NO: 546 for CDR2 of the heavy chain;

iii. a sequence that is at least 90% identical to SEQ ID NO: 547 for CDR3 of the heavy chain;

iv. a sequence that is at least 90% identical to SEQ ID NO: 542 for CDR1 of the light chain;

v. a sequence that is at least 90% identical to SEQ ID NO: 543 for CDR2 of the light chain; and vi. a sequence that is at least 90% identical to SEQ ID NO: 544 for CDR3 of the light chain, and wherein the antibody competes for binding to a Coronavirus spike protein (e.g. MERS-S) with an antibody comprising a heavy chain variable region of the amino acid sequence of SEQ ID NO: 489 and a light chain variable region of the amino acid sequence of SEQ ID NO: 443.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 545 for CDR1 of the heavy chain;

ii. a sequence that is at least 95% identical to SEQ ID NO: 546 for CDR2 of the heavy chain;

iii. a sequence that is at least 95% identical to SEQ ID NO: 547 for CDR3 of the heavy chain;

iv. a sequence that is at least 95% identical to SEQ ID NO: 542 for CDR1 of the light chain;

v. a sequence that is at least 95% identical to SEQ ID NO: 543 for CDR2 of the light vi. a sequence that is at least 95% identical to SEQ ID NO: 544 for CDR3 of the light chain, and wherein the antibody competes for binding to a Coronavirus spike protein (e.g. MERS-S) with an antibody comprising a heavy chain variable region of the amino acid sequence of SEQ ID NO: 489 and a light chain variable region of the amino acid sequence of SEQ ID NO: 443.

The invention provides an antibody that binds to a Coronavirus spike protein (e.g. MERS-S), wherein the antibody binds to the same epitope as an antibody comprising a heavy chain variable region of the amino acid sequence of SEQ ID NO: 479 and a light chain variable region of the amino acid sequence of SEQ ID NO: 444.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 479.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 479 and a light chain variable region of the amino acid sequence of SEQ ID NO: 444.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 479.

The invention further provides an antibody that binds to a Coronavirus spike protein (e.g. MERS-S), wherein the antibody comprises complementarity determining regions (CDRs) with the sequences of:

i. SEQ ID NO: 551 for CDR1 of the heavy chain;
  ii. SEQ ID NO: 552 for CDR2 of the heavy chain;
  iii. SEQ ID NO: 553 for CDR3 of the heavy chain;
  iv. SEQ ID NO: 548 for CDR1 of the light chain;
  v. SEQ ID NO: 549 for CDR2 of the light chain; and
  vi. SEQ ID NO: 550 for CDR3 of the light chain.

In some embodiments, the antibody comprises a heavy chain variable region of the amino acid sequence of SEQ ID NO: 479.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 479.

In some embodiments, the antibody comprises a light chain variable region of the amino acid sequence of SEQ ID NO: 444.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 444.

In some embodiments, the antibody comprises a heavy chain variable region of the amino acid sequence of SEQ ID NO: 479 and a light chain variable region of the amino acid sequence of SEQ ID NO: 444.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 479 and (ii) an amino acid sequence that is at least 80%, 81%, 82%, 83%, 84%, 85%, 86%, 87%, 88%, 89%, 90%, 91%, 92%, 93%, 94%, 95%, 96%, 97%; 98%, or 99% identical to a light chain variable region of the amino acid sequence of SEQ ID NO: 444.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 551 for CDR1 of the
  ii. a sequence that is at least 90% identical to SEQ ID NO: 552 for CDR2 of the heavy chain;
  iii. a sequence that is at least 90% identical to SEQ ID NO: 553 for CDR3 of the heavy chain;
  iv. a sequence that is at least 90% identical to SEQ ID NO: 548 for CDR1 of the light chain;
  v. a sequence that is at least 90% identical to SEQ ID NO: 549 for CDR2 of the light chain; and
  vi. a sequence that is at least 90% identical to SEQ ID NO: 550 for CDR3 of the light chain, and wherein the antibody competes for binding to a Coronavirus spike protein (e.g. MERS-S) with an antibody comprising a heavy chain variable region of the amino acid sequence of SEQ ID NO: 479 and a light chain variable region of the amino acid sequence of SEQ ID NO: 444.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 551 for CDR1 of the heavy chain;
  ii. a sequence that is at least 95% identical to SEQ ID NO: 552 for CDR2 of the heavy chain;
  iii. a sequence that is at least 95% identical to SEQ ID NO: 553 for CDR3 of the heavy chain;
  iv. a sequence that is at least 95% identical to SEQ ID NO: 548 for CDR1 of the light chain;
  v. a sequence that is at least 95% identical to SEQ ID NO: 549 for CDR2 of the light
  vi. a sequence that is at least 95% identical to SEQ ID NO: 550 for CDR3 of the light chain, and wherein the antibody competes for binding to a Coronavirus spike protein (e.g. MERS-S) with an antibody comprising a heavy chain variable region of the amino acid sequence of SEQ ID NO: 479 and a light chain variable region of the amino acid sequence of SEQ ID NO: 444.

The invention provides an antibody that binds to a Coronavirus spike protein (e.g. MERS-S), wherein the antibody binds to the same epitope as an antibody comprising a heavy chain variable region of the amino acid sequence of SEQ ID NO: 474 and a light chain variable region of the amino acid sequence of SEQ ID NO: 445.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 474.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 474 and a light chain variable region of the amino acid sequence of SEQ ID NO: 445.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 474.

The invention further provides an antibody that binds to a Coronavirus spike protein (e.g. MERS-S), wherein the antibody comprises complementarity determining regions (CDRs) with the sequences of:

i. SEQ ID NO: 557 for CDR1 of the heavy chain;
    ii. SEQ ID NO: 558 for CDR2 of the heavy chain;
    iii. SEQ ID NO: 559 for CDR3 of the heavy chain;
    iv. SEQ ID NO: 554 for CDR1 of the light chain;
    v. SEQ ID NO: 555 for CDR2 of the light chain; and
    vi. SEQ ID NO: 556 for CDR3 of the light chain.

In some embodiments, the antibody comprises a heavy chain variable region of the amino acid sequence of SEQ ID NO: 474.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 474.

In some embodiments, the antibody comprises a light chain variable region of the amino acid sequence of SEQ ID NO: 445.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 445.

In some embodiments, the antibody comprises a heavy chain variable region of the amino acid sequence of SEQ ID NO: 474 and a light chain variable region of the amino acid sequence of SEQ ID NO: 445.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 474 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 445.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 557 for CDR1 of the
    ii. a sequence that is at least 90% identical to SEQ ID NO: 558 for CDR2 of the heavy chain;
    iii. a sequence that is at least 90% identical to SEQ ID NO: 559 for CDR3 of the heavy chain;
    iv. a sequence that is at least 90% identical to SEQ ID NO: 554 for CDR1 of the light chain;
    v. a sequence that is at least 90% identical to SEQ ID NO: 555 for CDR2 of the light chain; and
    vi. a sequence that is at least 90% identical to SEQ ID NO: 556 for CDR3 of the light chain, and wherein the antibody competes for binding to a Coronavirus spike protein (e.g. MERS-S) with an antibody comprising a heavy chain variable region of the amino acid sequence of SEQ ID NO: 474 and a light chain variable region of the amino acid sequence of SEQ ID NO: 445.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 557 for CDR1 of the heavy chain;
    ii. a sequence that is at least 95% identical to SEQ ID NO: 558 for CDR2 of the heavy chain;
    iii. a sequence that is at least 95% identical to SEQ ID NO: 559 for CDR3 of the heavy chain;
    iv. a sequence that is at least 95% identical to SEQ ID NO: 554 for CDR1 of the light chain;
    v. a sequence that is at least 95% identical to SEQ ID NO: 555 for CDR2 of the light
    vi. a sequence that is at least 95% identical to SEQ ID NO: 556 for CDR3 of the light chain, and wherein the antibody competes for binding to a Coronavirus spike protein (e.g. MERS-S) with an antibody comprising a heavy chain variable region of the amino acid sequence of SEQ ID NO: 474 and a light chain variable region of the amino acid sequence of SEQ ID NO: 445.

The invention provides an antibody that binds to a Coronavirus spike protein (e.g. MERS-S), wherein the antibody binds to the same epitope as an antibody comprising a heavy chain variable region of the amino acid sequence of SEQ ID NO: 487 and a light chain variable region of the amino acid sequence of SEQ ID NO: 446.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 487.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 487 and a light chain variable region of the amino acid sequence of SEQ ID NO: 446.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 487.

The invention further provides an antibody that binds to a Coronavirus spike protein (e.g. MERS-S), wherein the antibody comprises complementarity determining regions (CDRs) with the sequences of:

i. SEQ ID NO: 563 for CDR1 of the heavy chain;
    ii. SEQ ID NO: 564 for CDR2 of the heavy chain;
    iii. SEQ ID NO: 565 for CDR3 of the heavy chain;
    iv. SEQ ID NO: 560 for CDR1 of the light chain;
    v. SEQ ID NO: 561 for CDR2 of the light chain; and
    vi. SEQ ID NO: 562 for CDR3 of the light chain.

In some embodiments, the antibody comprises a heavy chain variable region of the amino acid sequence of SEQ ID NO: 487.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 487.

In some embodiments, the antibody comprises a light chain variable region of the amino acid sequence of SEQ ID NO: 446.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 446.

In some embodiments, the antibody comprises a heavy chain variable region of the amino acid sequence of SEQ ID NO: 487 and a light chain variable region of the amino acid sequence of SEQ ID NO: 446.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 487 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 446.

The invention further provides an antibody that binds to a Coronavirus spike protein (e.g. MERS-S), wherein the antibody comprises complementarity determining regions (CDRs) with:
- i. a sequence that is at least 90% identical to SEQ ID NO: 563 for CDR1 of the
- ii. a sequence that is at least 90% identical to SEQ ID NO: 564 for CDR2 of the heavy chain;
- iii. a sequence that is at least 90% identical to SEQ ID NO: 565 for CDR3 of the heavy chain;
- iv. a sequence that is at least 90% identical to SEQ ID NO: 560 for CDR1 of the light chain;
- v. a sequence that is at least 90% identical to SEQ ID NO: 561 for CDR2 of the light chain; and
- vi. a sequence that is at least 90% identical to SEQ ID NO: 562 for CDR3 of the light chain, and wherein the antibody competes for binding to a Coronavirus spike protein (e.g. MERS-S) with an antibody comprising a heavy chain variable region of the amino acid sequence of SEQ ID NO: 487 and a light chain variable region of the amino acid sequence of SEQ ID NO: 446.

The invention further provides an antibody that binds to a Coronavirus spike protein (e.g. MERS-S), wherein the antibody comprises complementarity determining regions (CDRs) with:
- i. a sequence that is at least 95% identical to SEQ ID NO: 563 for CDR1 of the heavy chain;
- ii. a sequence that is at least 95% identical to SEQ ID NO: 564 for CDR2 of the heavy chain;
- iii. a sequence that is at least 95% identical to SEQ ID NO: 565 for CDR3 of the heavy chain;
- iv. a sequence that is at least 95% identical to SEQ ID NO: 560 for CDR1 of the light chain;
- v. a sequence that is at least 95% identical to SEQ ID NO: 561 for CDR2 of the light
- vi. a sequence that is at least 95% identical to SEQ ID NO: 562 for CDR3 of the light chain, and wherein the antibody competes for binding to a Coronavirus spike protein (e.g. MERS-S) with an antibody comprising a heavy chain variable region of the amino acid sequence of SEQ ID NO: 487 and a light chain variable region of the amino acid sequence of SEQ ID NO: 446.

The invention provides an antibody that binds to a Coronavirus spike protein (e.g. MERS-S), wherein the antibody binds to the same epitope as an antibody comprising a heavy chain variable region of the amino acid sequence of SEQ ID NO: 472 and a light chain variable region of the amino acid sequence of SEQ ID NO: 447.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 472.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 472 and a light chain variable region of the amino acid sequence of SEQ ID NO: 447.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 472.

The invention further provides an antibody that binds to a Coronavirus spike protein (e.g. MERS-S), wherein the antibody comprises complementarity determining regions (CDRs) with the sequences of:
- i. SEQ ID NO: 569 for CDR1 of the heavy chain;
- ii. SEQ ID NO: 570 for CDR2 of the heavy chain;
- iii. SEQ ID NO: 571 for CDR3 of the heavy chain;
- iv. SEQ ID NO: 566 for CDR1 of the light chain;
- v. SEQ ID NO: 567 for CDR2 of the light chain; and
- vi. SEQ ID NO: 568 for CDR3 of the light chain.

In some embodiments, the antibody comprises a heavy chain variable region of the amino acid sequence of SEQ ID NO: 472.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 472.

In some embodiments, the antibody comprises a light chain variable region of the amino acid sequence of SEQ ID NO: 447.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 447.

In some embodiments, the antibody comprises a heavy chain variable region of the amino acid sequence of SEQ ID NO: 472 and a light chain variable region of the amino acid sequence of SEQ ID NO: 447.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 472 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 447.

The invention further provides an antibody that binds to a Coronavirus spike protein (e.g. MERS-S), wherein the antibody comprises complementarity determining regions (CDRs) with:

i. a sequence that is at least 90% identical to SEQ ID NO:
569 for CDR1 of the
ii. a sequence that is at least 90% identical to SEQ ID NO:
570 for CDR2 of the heavy chain;
iii. a sequence that is at least 90% identical to SEQ ID
NO: 571 for CDR3 of the heavy chain;
iv. a sequence that is at least 90% identical to SEQ ID NO:
566 for CDR1 of the light chain;
v. a sequence that is at least 90% identical to SEQ ID NO:
567 for CDR2 of the light chain; and
vi. a sequence that is at least 90% identical to SEQ ID NO:
568 for CDR3 of the light chain,
and wherein the antibody competes for binding to a Coronavirus spike protein (e.g. MERS-S) with an antibody comprising a heavy chain variable region of the amino acid sequence of SEQ ID NO: 472 and a light chain variable region of the amino acid sequence of SEQ ID NO: 447.

The invention further provides an antibody that binds to a Coronavirus spike protein (e.g. MERS-S), wherein the antibody comprises complementarity determining regions (CDRs) with:
i. a sequence that is at least 95% identical to SEQ ID NO:
569 for CDR1 of the heavy chain;
ii. a sequence that is at least 95% identical to SEQ ID NO:
570 for CDR2 of the heavy chain;
iii. a sequence that is at least 95% identical to SEQ ID
NO: 571 for CDR3 of the heavy chain;
iv. a sequence that is at least 95% identical to SEQ ID NO:
566 for CDR1 of the light chain;
v. a sequence that is at least 95% identical to SEQ ID NO:
567 for CDR2 of the light
vi. a sequence that is at least 95% identical to SEQ ID NO:
568 for CDR3 of the light chain,
and wherein the antibody competes for binding to a Coronavirus spike protein (e.g. MERS-S) with an antibody comprising a heavy chain variable region of the amino acid sequence of SEQ ID NO: 472 and a light chain variable region of the amino acid sequence of SEQ ID NO: 447.

The invention provides an antibody that binds to a Coronavirus spike protein (e.g. MERS-S), wherein the antibody binds to the same epitope as an antibody comprising a heavy chain variable region of the amino acid sequence of SEQ ID NO: 477 and a light chain variable region of the amino acid sequence of SEQ ID NO: 449.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 477.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 477 and a light chain variable region of the amino acid sequence of SEQ ID NO: 449.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 477.

The invention further provides an antibody that binds to a Coronavirus spike protein (e.g. MERS-S), wherein the antibody comprises complementarity determining regions (CDRs) with the sequences of:

i. SEQ ID NO: 575 for CDR1 of the heavy chain;
ii. SEQ ID NO: 576 for CDR2 of the heavy chain;
iii. SEQ ID NO: 577 for CDR3 of the heavy chain;
iv. SEQ ID NO: 572 for CDR1 of the light chain;
v. SEQ ID NO: 573 for CDR2 of the light chain; and
vi. SEQ ID NO: 574 for CDR3 of the light chain.

In some embodiments, the antibody comprises a heavy chain variable region of the amino acid sequence of SEQ ID NO: 477.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 477.

In some embodiments, the antibody comprises a light chain variable region of the amino acid sequence of SEQ ID NO: 449.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 449.

In some embodiments, the antibody comprises a heavy chain variable region of the amino acid sequence of SEQ ID NO: 477 and a light chain variable region of the amino acid sequence of SEQ ID NO: 449.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 477 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 449.

The invention further provides an antibody that binds to a Coronavirus spike protein (e.g. MERS-S), wherein the antibody comprises complementarity determining regions (CDRs) with:
i. a sequence that is at least 90% identical to SEQ ID NO:
575 for CDR1 of the
ii. a sequence that is at least 90% identical to SEQ ID NO:
576 for CDR2 of the heavy chain;
iii. a sequence that is at least 90% identical to SEQ ID
NO: 577 for CDR3 of the heavy chain;
iv. a sequence that is at least 90% identical to SEQ ID NO:
572 for CDR1 of the light chain;
v. a sequence that is at least 90% identical to SEQ ID NO:
573 for CDR2 of the light chain; and
vi. a sequence that is at least 90% identical to SEQ ID NO:
574 for CDR3 of the light chain,
and wherein the antibody competes for binding to a Coronavirus spike protein (e.g. MERS-S) with an antibody comprising a heavy chain variable region of the amino acid sequence of SEQ ID NO: 477 and a light chain variable region of the amino acid sequence of SEQ ID NO: 449.

The invention further provides an antibody that binds to a Coronavirus spike protein (e.g. MERS-S), wherein the antibody comprises complementarity determining regions (CDRs) with:
i. a sequence that is at least 95% identical to SEQ ID NO:
575 for CDR1 of the heavy chain;
ii. a sequence that is at least 95% identical to SEQ ID NO:
576 for CDR2 of the heavy chain;

iii. a sequence that is at least 95% identical to SEQ ID NO: 577 for CDR3 of the heavy chain;

iv. a sequence that is at least 95% identical to SEQ ID NO: 572 for CDR1 of the light chain;

v. a sequence that is at least 95% identical to SEQ ID NO: 573 for CDR2 of the light vi. a sequence that is at least 95% identical to SEQ ID NO: 574 for CDR3 of the light chain, and wherein the antibody competes for binding to a Coronavirus spike protein (e.g. MERS-S) with an antibody comprising a heavy chain variable region of the amino acid sequence of SEQ ID NO: 477 and a light chain variable region of the amino acid sequence of SEQ ID NO: 449.

The invention provides an antibody that binds to a Coronavirus spike protein (e.g. MERS-S), wherein the antibody binds to the same epitope as an antibody comprising a heavy chain variable region of the amino acid sequence of SEQ ID NO: 473 and a light chain variable region of the amino acid sequence of SEQ ID NO: 451.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 473.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 473 and a light chain variable region of the amino acid sequence of SEQ ID NO: 451.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 473.

The invention further provides an antibody that binds to a Coronavirus spike protein (e.g. MERS-S), wherein the antibody comprises complementarity determining regions (CDRs) with the sequences of:

i. SEQ ID NO: 581 for CDR1 of the heavy chain;

ii. SEQ ID NO: 582 for CDR2 of the heavy chain;

iii. SEQ ID NO: 583 for CDR3 of the heavy chain;

iv. SEQ ID NO: 578 for CDR1 of the light chain;

v. SEQ ID NO: 579 for CDR2 of the light chain; and vi. SEQ ID NO: 580 for CDR3 of the light chain.

In some embodiments, the antibody comprises a heavy chain variable region of the amino acid sequence of SEQ ID NO: 473.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 473.

In some embodiments, the antibody comprises a light chain variable region of the amino acid sequence of SEQ ID NO: 451.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 451.

In some embodiments, the antibody comprises a heavy chain variable region of the amino acid sequence of SEQ ID NO: 473 and a light chain variable region of the amino acid sequence of SEQ ID NO: 451.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 473 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 451.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 581 for CDR1 of the ii. a sequence that is at least 90% identical to SEQ ID NO: 582 for CDR2 of the heavy chain;

iii. a sequence that is at least 90% identical to SEQ ID NO: 583 for CDR3 of the heavy chain;

iv. a sequence that is at least 90% identical to SEQ ID NO: 578 for CDR1 of the light chain;

v. a sequence that is at least 90% identical to SEQ ID NO: 579 for CDR2 of the light chain; and vi. a sequence that is at least 90% identical to SEQ ID NO: 580 for CDR3 of the light chain, and wherein the antibody competes for binding to a Coronavirus spike protein (e.g. MERS-S) with an antibody comprising a heavy chain variable region of the amino acid sequence of SEQ ID NO: 473 and a light chain variable region of the amino acid sequence of SEQ ID NO: 451.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 581 for CDR1 of the heavy chain;

ii. a sequence that is at least 95% identical to SEQ ID NO: 582 for CDR2 of the heavy chain;

iii. a sequence that is at least 95% identical to SEQ ID NO: 583 for CDR3 of the heavy chain;

iv. a sequence that is at least 95% identical to SEQ ID NO: 578 for CDR1 of the light chain;

v. a sequence that is at least 95% identical to SEQ ID NO: 579 for CDR2 of the light vi. a sequence that is at least 95% identical to SEQ ID NO: 580 for CDR3 of the light chain, and wherein the antibody competes for binding to a Coronavirus spike protein (e.g. MERS-S) with an antibody comprising a heavy chain variable region of the amino acid sequence of SEQ ID NO: 473 and a light chain variable region of the amino acid sequence of SEQ ID NO: 451.

The invention provides an antibody that binds to a Coronavirus spike protein (e.g. MERS-S), wherein the antibody binds to the same epitope as an antibody comprising a heavy chain variable region of the amino acid sequence of SEQ ID NO: 476 and a light chain variable region of the amino acid sequence of SEQ ID NO: 453.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 476.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 476 and a light chain variable region of the amino acid sequence of SEQ ID NO: 453.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 476.

The invention further provides an antibody that binds to a Coronavirus spike protein (e.g. MERS-S), wherein the antibody comprises complementarity determining regions (CDRs) with the sequences of:

i. SEQ ID NO: 593 for CDR1 of the heavy chain;

ii. SEQ ID NO: 594 for CDR2 of the heavy chain;

iii. SEQ ID NO: 595 for CDR3 of the heavy chain;

iv. SEQ ID NO: 590 for CDR1 of the light chain;

v. SEQ ID NO: 591 for CDR2 of the light chain; and vi. SEQ ID NO: 592 for CDR3 of the light chain.

In some embodiments, the antibody comprises a heavy chain variable region of the amino acid sequence of SEQ ID NO: 476.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 476.

In some embodiments, the antibody comprises a light chain variable region of the amino acid sequence of SEQ ID NO: 453.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 453.

In some embodiments, the antibody comprises a heavy chain variable region of the amino acid sequence of SEQ ID NO: 476 and a light chain variable region of the amino acid sequence of SEQ ID NO: 453.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 476 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 453.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 593 for CDR1 of the ii. a sequence that is at least 90% identical to SEQ ID NO: 594 for CDR2 of the heavy chain;

iii. a sequence that is at least 90% identical to SEQ ID NO: 595 for CDR3 of the heavy chain;

iv. a sequence that is at least 90% identical to SEQ ID NO: 590 for CDR1 of the light chain;

v. a sequence that is at least 90% identical to SEQ ID NO: 591 for CDR2 of the light chain; and vi. a sequence that is at least 90% identical to SEQ ID NO: 592 for CDR3 of the light chain, and wherein the antibody competes for binding to a Coronavirus spike protein (e.g. MERS-S) with an antibody comprising a heavy chain variable region of the amino acid sequence of SEQ ID NO: 476 and a light chain variable region of the amino acid sequence of SEQ ID NO: 453.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 593 for CDR1 of the heavy chain;

ii. a sequence that is at least 95% identical to SEQ ID NO: 594 for CDR2 of the heavy chain;

iii. a sequence that is at least 95% identical to SEQ ID NO: 595 for CDR3 of the heavy chain;

iv. a sequence that is at least 95% identical to SEQ ID NO: 590 for CDR1 of the light chain;

v. a sequence that is at least 95% identical to SEQ ID NO: 591 for CDR2 of the light vi. a sequence that is at least 95% identical to SEQ ID NO: 592 for CDR3 of the light chain, and wherein the antibody competes for binding to a Coronavirus spike protein (e.g. MERS-S) with an antibody comprising a heavy chain variable region of the amino acid sequence of SEQ ID NO: 476 and a light chain variable region of the amino acid sequence of SEQ ID NO: 453.

The invention provides an antibody that binds to a Coronavirus spike protein (e.g. MERS-S), wherein the antibody binds to the same epitope as an antibody comprising a heavy chain variable region of the amino acid sequence of SEQ ID NO: 490 and a light chain variable region of the amino acid sequence of SEQ ID NO: 455.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 490.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 490 and a light chain variable region of the amino acid sequence of SEQ ID NO: 455.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 490.

The invention further provides an antibody that binds to a Coronavirus spike protein (e.g. MERS-S), wherein the antibody comprises complementarity determining regions (CDRs) with the sequences of:

i. SEQ ID NO: 599 for CDR1 of the heavy chain;

ii. SEQ ID NO: 600 for CDR2 of the heavy chain;

iii. SEQ ID NO: 601 for CDR3 of the heavy chain;

iv. SEQ ID NO: 596 for CDR1 of the light chain;

v. SEQ ID NO: 597 for CDR2 of the light chain; and vi. SEQ ID NO: 598 for CDR3 of the light chain.

In some embodiments, the antibody comprises a heavy chain variable region of the amino acid sequence of SEQ ID NO: 490.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 490.

In some embodiments, the antibody comprises a light chain variable region of the amino acid sequence of SEQ ID NO: 455.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 455.

In some embodiments, the antibody comprises a heavy chain variable region of the amino acid sequence of SEQ ID NO: 490 and a light chain variable region of the amino acid sequence of SEQ ID NO: 455.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 490 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 455.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 599 for CDR1 of the
ii. a sequence that is at least 90% identical to SEQ ID NO: 600 for CDR2 of the heavy chain;
iii. a sequence that is at least 90% identical to SEQ ID NO: 601 for CDR3 of the heavy chain;
iv. a sequence that is at least 90% identical to SEQ ID NO: 596 for CDR1 of the light chain;
v. a sequence that is at least 90% identical to SEQ ID NO: 597 for CDR2 of the light chain; and
vi. a sequence that is at least 90% identical to SEQ ID NO: 598 for CDR3 of the light chain, and wherein the antibody competes for binding to a Coronavirus spike protein (e.g. MERS-S) with an antibody comprising a heavy chain variable region of the amino acid sequence of SEQ ID NO: 490 and a light chain variable region of the amino acid sequence of SEQ ID NO: 455.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 599 for CDR1 of the heavy chain;
ii. a sequence that is at least 95% identical to SEQ ID NO: 600 for CDR2 of the heavy chain;
iii. a sequence that is at least 95% identical to SEQ ID NO: 601 for CDR3 of the heavy chain;
iv. a sequence that is at least 95% identical to SEQ ID NO: 596 for CDR1 of the light chain;
v. a sequence that is at least 95% identical to SEQ ID NO: 597 for CDR2 of the light
vi. a sequence that is at least 95% identical to SEQ ID NO: 598 for CDR3 of the light chain, and wherein the antibody competes for binding to a Coronavirus spike protein (e.g. MERS-S) with an antibody comprising a heavy chain variable region of the amino acid sequence of SEQ ID NO: 490 and a light chain variable region of the amino acid sequence of SEQ ID NO: 455.

The invention provides an antibody that binds to a Coronavirus spike protein (e.g. MERS-S), wherein the antibody binds to the same epitope as an antibody comprising a heavy chain variable region of the amino acid sequence of SEQ ID NO: 478 and a light chain variable region of the amino acid sequence of SEQ ID NO: 456.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 478.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 478 and a light chain variable region of the amino acid sequence of SEQ ID NO: 456.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 478.

The invention further provides an antibody that binds to a Coronavirus spike protein (e.g. MERS-S), wherein the antibody comprises complementarity determining regions (CDRs) with the sequences of:

i. SEQ ID NO: 605 for CDR1 of the heavy chain;
ii. SEQ ID NO: 606 for CDR2 of the heavy chain;
iii. SEQ ID NO: 607 for CDR3 of the heavy chain;
iv. SEQ ID NO: 602 for CDR1 of the light chain;
v. SEQ ID NO: 603 for CDR2 of the light chain; and
vi. SEQ ID NO: 604 for CDR3 of the light chain.

In some embodiments, the antibody comprises a heavy chain variable region of the amino acid sequence of SEQ ID NO: 478.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 478.

In some embodiments, the antibody comprises a light chain variable region of the amino acid sequence of SEQ ID NO: 456.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 456.

In some embodiments, the antibody comprises a heavy chain variable region of the amino acid sequence of SEQ ID NO: 478 and a light chain variable region of the amino acid sequence of SEQ ID NO: 456.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 478 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 456.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 605 for CDR1 of the ii. a sequence that is at least 90% identical to SEQ ID NO: 606 for CDR2 of the heavy chain;

iii. a sequence that is at least 90% identical to SEQ ID NO: 607 for CDR3 of the heavy chain;

iv. a sequence that is at least 90% identical to SEQ ID NO: 602 for CDR1 of the light chain;

v. a sequence that is at least 90% identical to SEQ ID NO: 603 for CDR2 of the light chain; and vi. a sequence that is at least 90% identical to SEQ ID NO: 604 for CDR3 of the light chain, and wherein the antibody competes for binding to a Coronavirus spike protein (e.g. MERS-S) with an antibody comprising a heavy chain variable region of the amino acid sequence of SEQ ID NO: 478 and a light chain variable region of the amino acid sequence of SEQ ID NO: 456.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 605 for CDR1 of the heavy chain;

ii. a sequence that is at least 95% identical to SEQ ID NO: 606 for CDR2 of the heavy chain;

iii. a sequence that is at least 95% identical to SEQ ID NO: 607 for CDR3 of the heavy chain;

iv. a sequence that is at least 95% identical to SEQ ID NO: 602 for CDR1 of the light chain;

v. a sequence that is at least 95% identical to SEQ ID NO: 603 for CDR2 of the light vi. a sequence that is at least 95% identical to SEQ ID NO: 604 for CDR3 of the light chain, and wherein the antibody competes for binding to a Coronavirus spike protein (e.g. MERS-S) with an antibody comprising a heavy chain variable region of the amino acid sequence of SEQ ID NO: 478 and a light chain variable region of the amino acid sequence of SEQ ID NO: 456.

The invention provides an antibody that binds to a Coronavirus spike protein (e.g. MERS-S), wherein the antibody binds to the same epitope as an antibody comprising a heavy chain variable region of the amino acid sequence of SEQ ID NO: 481 and a light chain variable region of the amino acid sequence of SEQ ID NO: 457.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 481.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 481 and a light chain variable region of the amino acid sequence of SEQ ID NO: 457.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 481.

The invention further provides an antibody that binds to a Coronavirus spike protein (e.g. MERS-S), wherein the antibody comprises complementarity determining regions (CDRs) with the sequences of:

i. SEQ ID NO: 611 for CDR1 of the heavy chain;

ii. SEQ ID NO: 612 for CDR2 of the heavy chain;

iii. SEQ ID NO: 613 for CDR3 of the heavy chain;

iv. SEQ ID NO: 608 for CDR1 of the light chain;

v. SEQ ID NO: 609 for CDR2 of the light chain; and vi. SEQ ID NO: 610 for CDR3 of the light chain.

In some embodiments, the antibody comprises a heavy chain variable region of the amino acid sequence of SEQ ID NO: 481.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 481.

In some embodiments, the antibody comprises a light chain variable region of the amino acid sequence of SEQ ID NO: 457.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 457.

In some embodiments, the antibody comprises a heavy chain variable region of the amino acid sequence of SEQ ID NO: 481 and a light chain variable region of the amino acid sequence of SEQ ID NO: 457.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 481 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 457.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 611 for CDR1 of the ii. a sequence that is at least 90% identical to SEQ ID NO: 612 for CDR2 of the heavy chain;

iii. a sequence that is at least 90% identical to SEQ ID NO: 613 for CDR3 of the heavy chain;

iv. a sequence that is at least 90% identical to SEQ ID NO: 608 for CDR1 of the light chain;

v. a sequence that is at least 90% identical to SEQ ID NO: 609 for CDR2 of the light chain; and vi. a sequence that is at least 90% identical to SEQ ID NO: 610 for CDR3 of the light chain, and wherein the antibody competes for binding to a Coronavirus spike protein (e.g. MERS-S) with an antibody comprising a heavy chain variable region of the amino acid sequence of SEQ ID NO: 481 and a light chain variable region of the amino acid sequence of SEQ ID NO: 457.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 611 for CDR1 of the heavy chain;

ii. a sequence that is at least 95% identical to SEQ ID NO: 612 for CDR2 of the heavy chain;

iii. a sequence that is at least 95% identical to SEQ ID NO: 613 for CDR3 of the heavy chain;

iv. a sequence that is at least 95% identical to SEQ ID NO: 608 for CDR1 of the light chain;

v. a sequence that is at least 95% identical to SEQ ID NO: 609 for CDR2 of the light vi. a sequence that is at least 95% identical to SEQ ID NO: 610 for CDR3 of the light chain, and wherein the antibody competes for binding to a Coronavirus spike protein (e.g. MERS-S) with an antibody comprising a heavy chain variable region of the amino acid sequence of SEQ ID NO: 481 and a light chain variable region of the amino acid sequence of SEQ ID NO: 457.

The invention provides an antibody that binds to a Coronavirus spike protein (e.g. MERS-S), wherein the antibody binds to the same epitope as an antibody comprising a heavy chain variable region of the amino acid sequence of SEQ ID NO: 485 and a light chain variable region of the amino acid sequence of SEQ ID NO: 460.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 485.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 485 and a light chain variable region of the amino acid sequence of SEQ ID NO: 460.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 485.

The invention further provides an antibody that binds to a Coronavirus spike protein (e.g. MERS-S), wherein the antibody comprises complementarity determining regions (CDRs) with the sequences of:

i. SEQ ID NO: 623 for CDR1 of the heavy chain;

ii. SEQ ID NO: 624 for CDR2 of the heavy chain;

iii. SEQ ID NO: 625 for CDR3 of the heavy chain;

iv. SEQ ID NO: 620 for CDR1 of the light chain;

v. SEQ ID NO: 621 for CDR2 of the light chain; and vi. SEQ ID NO: 622 for CDR3 of the light chain.

In some embodiments, the antibody comprises a heavy chain variable region of the amino acid sequence of SEQ ID NO: 485.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 485.

In some embodiments, the antibody comprises a light chain variable region of the amino acid sequence of SEQ ID NO: 460.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 460.

In some embodiments, the antibody comprises a heavy chain variable region of the amino acid sequence of SEQ ID NO: 485 and a light chain variable region of the amino acid sequence of SEQ ID NO: 460.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 485 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 460.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 623 for CDR1 of the ii. a sequence that is at least 90% identical to SEQ ID NO: 624 for CDR2 of the heavy chain;

iii. a sequence that is at least 90% identical to SEQ ID NO: 625 for CDR3 of the heavy chain;

iv. a sequence that is at least 90% identical to SEQ ID NO: 620 for CDR1 of the light chain;

v. a sequence that is at least 90% identical to SEQ ID NO: 621 for CDR2 of the light chain; and vi. a sequence that is at least 90% identical to SEQ ID NO: 622 for CDR3 of the light chain, and wherein the antibody competes for binding to a Coronavirus spike protein (e.g. MERS-S) with an antibody comprising a heavy chain variable region of the amino acid sequence of SEQ ID NO: 485 and a light chain variable region of the amino acid sequence of SEQ ID NO: 460.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 623 for CDR1 of the heavy chain;

ii. a sequence that is at least 95% identical to SEQ ID NO: 624 for CDR2 of the heavy chain;

iii. a sequence that is at least 95% identical to SEQ ID NO: 625 for CDR3 of the heavy chain;

iv. a sequence that is at least 95% identical to SEQ ID NO: 620 for CDR1 of the light chain;

v. a sequence that is at least 95% identical to SEQ ID NO: 621 for CDR2 of the light vi. a sequence that is at least 95% identical to SEQ ID NO: 622 for CDR3 of the light chain, and wherein the antibody competes for binding to a Coronavirus spike protein (e.g. MERS-S) with an antibody comprising a heavy chain variable region of the amino acid sequence of SEQ ID NO: 485 and a light chain variable region of the amino acid sequence of SEQ ID NO: 460.

The invention provides an antibody that binds to a Coronavirus spike protein (e.g. MERS-S), wherein the antibody binds to the same epitope as an antibody comprising a heavy chain variable region of the amino acid sequence of SEQ ID NO: 470 and a light chain variable region of the amino acid sequence of SEQ ID NO: 462.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 470.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 470 and a light chain variable region of the amino acid sequence of SEQ ID NO: 462.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 470.

The invention further provides an antibody that binds to a Coronavirus spike protein (e.g. MERS-S), wherein the antibody comprises complementarity determining regions (CDRs) with the sequences of:

i. SEQ ID NO: 629 for CDR1 of the heavy chain;
    ii. SEQ ID NO: 630 for CDR2 of the heavy chain;
    iii. SEQ ID NO: 631 for CDR3 of the heavy chain;
    iv. SEQ ID NO: 626 for CDR1 of the light chain;
    v. SEQ ID NO: 627 for CDR2 of the light chain; and
    vi. SEQ ID NO: 628 for CDR3 of the light chain.

In some embodiments, the antibody comprises a heavy chain variable region of the amino acid sequence of SEQ ID NO: 470.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 470.

In some embodiments, the antibody comprises a light chain variable region of the amino acid sequence of SEQ ID NO: 462.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 462.

In some embodiments, the antibody comprises a heavy chain variable region of the amino acid sequence of SEQ ID NO: 470 and a light chain variable region of the amino acid sequence of SEQ ID NO: 462.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 470 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 462.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 629 for CDR1 of the
    ii. a sequence that is at least 90% identical to SEQ ID NO: 630 for CDR2 of the heavy chain;
    iii. a sequence that is at least 90% identical to SEQ ID NO: 631 for CDR3 of the heavy chain;
    iv. a sequence that is at least 90% identical to SEQ ID NO: 626 for CDR1 of the light chain;
    v. a sequence that is at least 90% identical to SEQ ID NO: 627 for CDR2 of the light chain; and
    vi. a sequence that is at least 90% identical to SEQ ID NO: 628 for CDR3 of the light chain, and wherein the antibody competes for binding to a Coronavirus spike protein (e.g. MERS-S) with an antibody comprising a heavy chain variable region of the amino acid sequence of SEQ ID NO: 470 and a light chain variable region of the amino acid sequence of SEQ ID NO: 462.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 629 for CDR1 of the heavy chain;
    ii. a sequence that is at least 95% identical to SEQ ID NO: 630 for CDR2 of the heavy chain;
    iii. a sequence that is at least 95% identical to SEQ ID NO: 631 for CDR3 of the heavy chain;
    iv. a sequence that is at least 95% identical to SEQ ID NO: 626 for CDR1 of the light chain;
    v. a sequence that is at least 95% identical to SEQ ID NO: 627 for CDR2 of the light
    vi. a sequence that is at least 95% identical to SEQ ID NO: 628 for CDR3 of the light chain, and wherein the antibody competes for binding to a Coronavirus spike protein (e.g. MERS-S) with an antibody comprising a heavy chain variable region of the amino acid sequence of SEQ ID NO: 470 and a light chain variable region of the amino acid sequence of SEQ ID NO: 462.

The invention provides an antibody that binds to a Coronavirus spike protein (e.g. MERS-S), wherein the antibody binds to the same epitope as an antibody comprising a heavy chain variable region of the amino acid sequence of SEQ ID NO: 495 and a light chain variable region of the amino acid sequence of SEQ ID NO: 464.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 495.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 495 and a light chain variable region of the amino acid sequence of SEQ ID NO: 464.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 495.

The invention further provides an antibody that binds to a Coronavirus spike protein (e.g. MERS-S), wherein the antibody comprises complementarity determining regions (CDRs) with the sequences of:

i. SEQ ID NO: 635 for CDR1 of the heavy chain;
ii. SEQ ID NO: 636 for CDR2 of the heavy chain;
iii. SEQ ID NO: 637 for CDR3 of the heavy chain;
iv. SEQ ID NO: 632 for CDR1 of the light chain;
v. SEQ ID NO: 633 for CDR2 of the light chain; and
vi. SEQ ID NO: 634 for CDR3 of the light chain.

In some embodiments, the antibody comprises a heavy chain variable region of the amino acid sequence of SEQ ID NO: 495.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 495.

In some embodiments, the antibody comprises a light chain variable region of the amino acid sequence of SEQ ID NO: 464.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 464.

In some embodiments, the antibody comprises a heavy chain variable region of the amino acid sequence of SEQ ID NO: 495 and a light chain variable region of the amino acid sequence of SEQ ID NO: 464.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 495 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 464.

The invention further provides an antibody that binds to a Coronavirus spike protein (e.g. MERS-S), wherein the antibody comprises complementarity determining regions (CDRs) with:
i. a sequence that is at least 90% identical to SEQ ID NO: 635 for CDR1 of the
ii. a sequence that is at least 90% identical to SEQ ID NO: 636 for CDR2 of the heavy chain;
iii. a sequence that is at least 90% identical to SEQ ID NO: 637 for CDR3 of the heavy chain;
iv. a sequence that is at least 90% identical to SEQ ID NO: 632 for CDR1 of the light chain;
v. a sequence that is at least 90% identical to SEQ ID NO: 633 for CDR2 of the light chain; and
vi. a sequence that is at least 90% identical to SEQ ID NO: 634 for CDR3 of the light chain,
and wherein the antibody competes for binding to a Coronavirus spike protein (e.g. MERS-S) with an antibody comprising a heavy chain variable region of the amino acid sequence of SEQ ID NO: 495 and a light chain variable region of the amino acid sequence of SEQ ID NO: 464.

The invention further provides an antibody that binds to a Coronavirus spike protein (e.g. MERS-S), wherein the antibody comprises complementarity determining regions (CDRs) with:
i. a sequence that is at least 95% identical to SEQ ID NO: 635 for CDR1 of the heavy chain;
ii. a sequence that is at least 95% identical to SEQ ID NO: 636 for CDR2 of the heavy chain;

iii. a sequence that is at least 95% identical to SEQ ID NO: 637 for CDR3 of the heavy chain;
iv. a sequence that is at least 95% identical to SEQ ID NO: 632 for CDR1 of the light chain;
v. a sequence that is at least 95% identical to SEQ ID NO: 633 for CDR2 of the light
vi. a sequence that is at least 95% identical to SEQ ID NO: 634 for CDR3 of the light chain,
and wherein the antibody competes for binding to a Coronavirus spike protein (e.g. MERS-S) with an antibody comprising a heavy chain variable region of the amino acid sequence of SEQ ID NO: 495 and a light chain variable region of the amino acid sequence of SEQ ID NO: 464.

The invention provides an antibody that binds to a Coronavirus spike protein (e.g. MERS-S), wherein the antibody binds to the same epitope as an antibody comprising a heavy chain variable region of the amino acid sequence of SEQ ID NO: 475 and a light chain variable region of the amino acid sequence of SEQ ID NO: 465.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 475.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 475 and a light chain variable region of the amino acid sequence of SEQ ID NO: 465.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 475.

The invention further provides an antibody that binds to a Coronavirus spike protein (e.g. MERS-S), wherein the antibody comprises complementarity determining regions (CDRs) with the sequences of:
i. SEQ ID NO: 641 for CDR1 of the heavy chain;
ii. SEQ ID NO: 642 for CDR2 of the heavy chain;
iii. SEQ ID NO: 643 for CDR3 of the heavy chain;
iv. SEQ ID NO: 638 for CDR1 of the light chain;
v. SEQ ID NO: 639 for CDR2 of the light chain; and
vi. SEQ ID NO: 640 for CDR3 of the light chain.

In some embodiments, the antibody comprises a heavy chain variable region of the amino acid sequence of SEQ ID NO: 475.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 475.

In some embodiments, the antibody comprises a light chain variable region of the amino acid sequence of SEQ ID NO: 465.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 465.

In some embodiments, the antibody comprises a heavy chain variable region of the amino acid sequence of SEQ ID NO: 475 and a light chain variable region of the amino acid sequence of SEQ ID NO: 465.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 475 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 465.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 641 for CDR1 of the ii. a sequence that is at least 90% identical to SEQ ID NO: 642 for CDR2 of the heavy chain;

iii. a sequence that is at least 90% identical to SEQ ID NO: 643 for CDR3 of the heavy chain;

iv. a sequence that is at least 90% identical to SEQ ID NO: 638 for CDR1 of the light chain;

v. a sequence that is at least 90% identical to SEQ ID NO: 639 for CDR2 of the light chain; and vi. a sequence that is at least 90% identical to SEQ ID NO: 640 for CDR3 of the light chain, and wherein the antibody competes for binding to a Coronavirus spike protein (e.g. MERS-S) with an antibody comprising a heavy chain variable region of the amino acid sequence of SEQ ID NO: 475 and a light chain variable region of the amino acid sequence of SEQ ID NO: 465.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 641 for CDR1 of the heavy chain;

ii. a sequence that is at least 95% identical to SEQ ID NO: 642 for CDR2 of the heavy chain;

iii. a sequence that is at least 95% identical to SEQ ID NO: 643 for CDR3 of the heavy chain;

iv. a sequence that is at least 95% identical to SEQ ID NO: 638 for CDR1 of the light chain;

v. a sequence that is at least 95% identical to SEQ ID NO: 639 for CDR2 of the light vi. a sequence that is at least 95% identical to SEQ ID NO: 640 for CDR3 of the light chain, and wherein the antibody competes for binding to a Coronavirus spike protein (e.g. MERS-S) with an antibody comprising a heavy chain variable region of the amino acid sequence of SEQ ID NO: 475 and a light chain variable region of the amino acid sequence of SEQ ID NO: 465.

The invention provides an antibody that binds to a Coronavirus spike protein (e.g. MERS-S), wherein the antibody binds to the same epitope as an antibody comprising a heavy chain variable region of the amino acid sequence of SEQ ID NO: 493 and a light chain variable region of the amino acid sequence of SEQ ID NO: 466.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 493.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 493 and a light chain variable region of the amino acid sequence of SEQ ID NO: 466.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 493.

The invention further provides an antibody that binds to a Coronavirus spike protein (e.g. MERS-S), wherein the antibody comprises complementarity determining regions (CDRs) with the sequences of:

i. SEQ ID NO: 647 for CDR1 of the heavy chain;

ii. SEQ ID NO: 648 for CDR2 of the heavy chain;

iii. SEQ ID NO: 649 for CDR3 of the heavy chain;

iv. SEQ ID NO: 644 for CDR1 of the light chain;

v. SEQ ID NO: 645 for CDR2 of the light chain; and vi. SEQ ID NO: 646 for CDR3 of the light chain.

In some embodiments, the antibody comprises a heavy chain variable region of the amino acid sequence of SEQ ID NO: 493.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 493.

In some embodiments, the antibody comprises a light chain variable region of the amino acid sequence of SEQ ID NO: 466.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 466.

In some embodiments, the antibody comprises a heavy chain variable region of the amino acid sequence of SEQ ID NO: 493 and a light chain variable region of the amino acid sequence of SEQ ID NO: 466.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 493 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 466.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 647 for CDR1 of the ii. a sequence that is at least 90% identical to SEQ ID NO: 648 for CDR2 of the heavy chain;

iii. a sequence that is at least 90% identical to SEQ ID NO: 649 for CDR3 of the heavy chain;

iv. a sequence that is at least 90% identical to SEQ ID NO: 644 for CDR1 of the light chain;

v. a sequence that is at least 90% identical to SEQ ID NO: 645 for CDR2 of the light chain; and vi. a sequence that is at least 90% identical to SEQ ID NO: 646 for CDR3 of the light chain, and wherein the antibody competes for binding to a Coronavirus spike protein (e.g. MERS-S) with an antibody comprising a heavy chain variable region of the amino acid sequence of SEQ ID NO: 493 and a light chain variable region of the amino acid sequence of SEQ ID NO: 466.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 647 for CDR1 of the heavy chain;

ii. a sequence that is at least 95% identical to SEQ ID NO: 648 for CDR2 of the heavy chain;

iii. a sequence that is at least 95% identical to SEQ ID NO: 649 for CDR3 of the heavy chain;

iv. a sequence that is at least 95% identical to SEQ ID NO: 644 for CDR1 of the light chain;

v. a sequence that is at least 95% identical to SEQ ID NO: 645 for CDR2 of the light vi. a sequence that is at least 95% identical to SEQ ID NO: 646 for CDR3 of the light chain, and wherein the antibody competes for binding to a Coronavirus spike protein (e.g. MERS-S) with an antibody comprising a heavy chain variable region of the amino acid sequence of SEQ ID NO: 493 and a light chain variable region of the amino acid sequence of SEQ ID NO: 466.

The invention provides an antibody that binds to a Coronavirus spike protein (e.g. MERS-S), wherein the antibody binds to the same epitope as an antibody comprising a heavy chain variable region of the amino acid sequence of SEQ ID NO: 491 and a light chain variable region of the amino acid sequence of SEQ ID NO: 468.

The invention further provides an antibody that binds to a Coronavirus spike protein (e.g. MERS-S), wherein the antibody binds to the same epitope as a heavy chain-only antibody comprising a heavy chain variable region of the amino acid sequence of SEQ ID NO: 491.

The invention further provides an antibody that binds to a Coronavirus spike protein (e.g. MERS-S), wherein the antibody competes for binding to a Coronavirus spike protein (e.g. MERS-S) with an antibody comprising a heavy chain variable region of the amino acid sequence of SEQ ID NO: 491 and a light chain variable region of the amino acid sequence of SEQ ID NO: 468.

The invention further provides an antibody that binds to a Coronavirus spike protein (e.g. MERS-S), wherein the antibody competes for binding to a Coronavirus spike protein (e.g. MERS-S) with a heavy chain-only antibody comprising a heavy chain variable region of the amino acid sequence of SEQ ID NO: 491.

The invention further provides an antibody that binds to a Coronavirus spike protein (e.g. MERS-S), wherein the antibody comprises complementarity determining regions (CDRs) with the sequences of:

i. SEQ ID NO: 653 for CDR1 of the heavy chain;

ii. SEQ ID NO: 654 for CDR2 of the heavy chain;

iii. SEQ ID NO: 655 for CDR3 of the heavy chain;

iv. SEQ ID NO: 650 for CDR1 of the light chain;

v. SEQ ID NO: 651 for CDR2 of the light chain; and vi. SEQ ID NO: 652 for CDR3 of the light chain.

In some embodiments, the antibody comprises a heavy chain variable region of the amino acid sequence of SEQ ID NO: 491.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 491.

In some embodiments, the antibody comprises a light chain variable region of the amino acid sequence of SEQ ID NO: 468.

In some embodiments, the antibody comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 468.

In some embodiments, the antibody comprises a heavy chain variable region of the amino acid sequence of SEQ ID NO: 491 and a light chain variable region of the amino acid sequence of SEQ ID NO: 468.

In some embodiments, the antibody comprises: (i) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a heavy chain variable region of the amino acid sequence of SEQ ID NO: 491 and (ii) an amino acid sequence that is at least 80%, 81%, 82%, 83%, 84%, 85%, 86%, 87%, 88%, 89%, 90%, 91%, 92%, 93%, 94%, 95%, 96%, 97%, 98%, or 99% identical to a light chain variable region of the amino acid sequence of SEQ ID NO: 468.

The invention further provides an antibody that binds to a Coronavirus spike protein (e.g. MERS-S), wherein the antibody comprises complementarity determining regions (CDRs) with:

i. a sequence that is at least 90% identical to SEQ ID NO: 653 for CDR1 of the ii. a sequence that is at least 90% identical to SEQ ID NO: 654 for CDR2 of the heavy chain;

iii. a sequence that is at least 90% identical to SEQ ID NO: 655 for CDR3 of the heavy chain;

iv. a sequence that is at least 90% identical to SEQ ID NO: 650 for CDR1 of the light chain;

v. a sequence that is at least 90% identical to SEQ ID NO: 651 for CDR2 of the light chain; and vi. a sequence that is at least 90% identical to SEQ ID NO: 652 for CDR3 of the light chain, and wherein the antibody competes for binding to a Coronavirus spike protein (e.g. MERS-S) with an antibody comprising a heavy chain variable region of the amino acid sequence of SEQ ID NO: 491 and a light chain variable region of the amino acid sequence of SEQ ID NO: 468.

The invention further provides an antibody that binds to a Coronavirus spike protein (e.g. MERS-S), wherein the antibody comprises complementarity determining regions (CDRs) with:

i. a sequence that is at least 95% identical to SEQ ID NO: 653 for CDR1 of the heavy chain;

ii. a sequence that is at least 95% identical to SEQ ID NO: 654 for CDR2 of the heavy chain;

iii. a sequence that is at least 95% identical to SEQ ID NO: 655 for CDR3 of the heavy chain;

iv. a sequence that is at least 95% identical to SEQ ID NO: 650 for CDR1 of the light chain;

v. a sequence that is at least 95% identical to SEQ ID NO: 651 for CDR2 of the light vi. a sequence that is at least 95% identical to SEQ ID NO: 652 for CDR3 of the light chain, and wherein the antibody competes for binding to a Coronavirus spike protein (e.g. MERS-S) with an antibody comprising a heavy chain variable region of the amino acid sequence of SEQ ID NO: 491 and a light chain variable region of the amino acid sequence of SEQ ID NO: 468.

Antibodies

In some embodiments, the antibody of the invention is a polyclonal, monoclonal, multispecific, mouse, human, humanized, primatized or chimeric antibody or a single-chain antibody. The term "antibody" encompasses entire tetrameric antibodies and antigen-binding fragments thereof. In some embodiments, the antigen-binding fragment thereof is selected from a VH domain, Fab, Fab', F(ab')2, Fd, Fv, a single-chain Fv (scFv) and a disulfide-linked Fv (sdFv).

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a VH domain associated with a VL domain, the VH and $V_L$ domains may be situated relative to one another in any suitable arrangement. For example, the variable region may be dimeric and contain VH—VH, VH—VL or VL—VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) VH-$C_H$1; (ii) VH-$C_H$2; (iii) VH-$C_H$3; (iv) VH-$C_H$1-$C_H$2; (V) VH-$C_H$1-$C_H$2-$C_H$3; (vi) VH-$C_H$2-$C_H$3; (vii) VH-$C_L$; (viii) VL-$C_H$1; (ix) VL-$C_H$2; (x) VL-$C_H$3; (xi) VL-$C_H$1-$C_H$2; (xii) VL-$C_H$1-$C_H$2-$C_H$3; (xiii) VL-$C_H$2-$C_H$3; and (Xiv) VL-$C_L$.

In any configuration of variable and constant domains, including any of the exemplary configurations listed above, the variable and constant domains may be either directly linked to one another or may be linked by a full or partial hinge or linker region. A hinge or linker region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be mono-specific or multi-specific (e.g., bi-specific). A multi-specific antigen-binding fragment of an antibody will typically comprise at least two different variable domains, wherein each variable domain is capable of specifically binding to a separate antigen or to a different epitope on the same antigen. Any multi-specific antibody format, including the exemplary bi-specific antibody formats disclosed herein, may be adapted for use in the context of an antigen-binding fragment of an antibody of the present invention using routine techniques available in the art.

In some embodiments, the antibody contains an Fc domain or a portion thereof that binds to the FcRn receptor. As a non-limiting example, a suitable Fc domain may be derived from an immunoglobulin subclass such as IgA, IgE, IgG or IgM. In some embodiments, a suitable Fc domain is derived from IgG1, IgG2, IgG3, or IgG4. Particularly suitable Fc domains include those derived from human antibodies.

In some embodiments, the antibody is a human antibody.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J. Mol. Biol. 273:927-948 (1997); and Martin et al., Proc. Natl. Acad. Sci. USA 86:9268-9272 (1989). Public databases are also available for identifying CDR sequences within an antibody.

In certain embodiments, the antibodies or antigen-binding fragments of the present invention are bispecific comprising a first binding specificity to a first epitope in the MERS-CoV spike protein and a second binding specificity to a second epitope in the MERS-CoV spike protein wherein the first and second epitopes are distinct and non-overlapping.

In certain embodiments, the antibodies or antigen-binding fragments of the present invention are tri-specific comprising a first binding specificity to a first epitope in the MERS-CoV spike protein, a second binding specificity to a second epitope in the receptor binding domain of MERS-CoV spike protein and a third binding specificity to a third epitope in the MERS-CoV spike protein, wherein the first, second and third epitopes are distinct and non-overlapping.

In certain embodiments, the antibodies or antigen-binding fragments of the present invention are quadri-specific comprising a first binding specificity to a first epitope in the MERS-CoV spike protein, a second binding specificity to a second epitope in the MERS-CoV spike protein, a third binding specificity to a third epitope in the MERS-CoV spike protein, wherein the first, second, third and fourth epitopes are distinct and non-overlapping.

In certain embodiments, the antibodies or antigen-binding fragments of the present invention are multispecific comprising multiple binding specificities for epitopes in the MERS-CoV spike protein that are distinct and non-overlapping.

In certain embodiments, the antibodies or antigen-binding fragments of the present invention are bispecific comprising a first binding specificity to a first epitope in the receptor binding domain of MERS-CoV spike protein and a second binding specificity to a second epitope in the receptor binding domain of MERS-CoV spike protein wherein the first and second epitopes are distinct and non-overlapping.

In certain embodiments, the antibodies or antigen-binding fragments of the present invention are tri-specific comprising a first binding specificity to a first epitope in the receptor binding domain of MERS-CoV spike protein, a second binding specificity to a second epitope in the receptor binding domain of MERS-CoV spike protein and a third binding specificity to a third epitope in the receptor binding domain of MERS-CoV spike protein, wherein the first, second and third epitopes are distinct and non-overlapping.

In certain embodiments, the antibodies or antigen-binding fragments of the present invention are quadri-specific comprising a first binding specificity to a first epitope in the receptor binding domain of MERS-CoV spike protein, a second binding specificity to a second epitope in the receptor binding domain of MERS-CoV spike protein, a third binding specificity to a third epitope in the receptor binding domain of MERS-CoV spike protein, a fourth binding specificity to a fourth epitope in the receptor binding domain of MERS-CoV spike protein, wherein the first, second, third and fourth epitopes are distinct and non-overlapping.

In certain embodiments, the antibodies or antigen-binding fragments of the present invention are multispecific comprising multiple binding specificities for epitopes in the receptor binding domain of MERS-CoV spike protein that are distinct and non-overlapping.

In certain embodiments, the antibodies or antigen-binding fragments of the present invention are multispecific comprising a binding specificity for an epitope in the MERS-CoV spike protein and one or more binding specificities for epitopes in spike proteins from other Coronaviruses (e.g. SARS, OC43, HKU1 or NL63). In some embodiments, the epitopes are distinct and non-overlapping.

In certain embodiments, the antibodies or antigen-binding fragments of the present invention are bispecific comprising a first binding specificity to a first epitope in the MERS-CoV spike protein and a second binding specificity to a second epitope in the spike protein of another Coronavirus (e.g. SARS, OC43, HKU1 or NL63), wherein the first and second epitopes are distinct and non-overlapping. In some embodiments, the first epitope is in the receptor binding domain of MERS-CoV spike protein.

In certain embodiments, the antibodies or antigen-binding fragments of the present invention are tri-specific comprising a first binding specificity to a first epitope in the MERS-CoV spike protein, a second binding specificity to a second epitope in the spike protein of another Coronavirus (e.g. SARS, OC43, HKU1 or NL63), and a third binding specificity to a third epitope in the spike protein of another Coronavirus (e.g. SARS, OC43, HKU1 or NL63), wherein the first, second and third epitopes are distinct and non-overlapping. In some embodiments, the first epitope is in the receptor binding domain of MERS-CoV spike protein.

In certain embodiments, the antibodies or antigen-binding fragments of the present invention are quadri-specific comprising a first binding specificity to a first epitope in the receptor binding domain of MERS-CoV spike protein, a second binding specificity to a second epitope in the spike protein of another Coronavirus (e.g. SARS, OC43, HKU1 or NL63), and a third binding specificity to a third epitope in the spike protein of another Coronavirus (e.g. SARS, OC43, HKU1 or NL63), a fourth binding specificity to a fourth epitope in the spike protein of another Coronavirus (e.g. SARS, OC43, HKU1 or NL63), wherein the first, second, third and fourth epitopes are distinct and non-overlapping.

The invention encompasses a human anti-MERS-CoV-S monoclonal antibody conjugated to a therapeutic moiety ("immunoconjugate"), such as a toxoid or an anti-viral drug to treat MERS infection. As used herein, the term "immunoconjugate" refers to an antibody which is chemically or biologically linked to a radioactive agent, a cytokine, an interferon, a target or reporter moiety, an enzyme, a peptide or protein or a therapeutic agent. The antibody may be linked to the radioactive agent, cytokine, interferon, target or reporter moiety, enzyme, peptide or therapeutic agent at any location along the molecule so long as it is able to bind its target.

Examples of immunoconjugates include antibody drug conjugates and antibody-toxin fusion proteins. In one embodiment, the agent may be a second different antibody to MERS-CoV spike protein. In certain embodiments, the antibody may be conjugated to an agent specific for a virally infected cell. The type of therapeutic moiety that may be conjugated to the anti-MERS-CoV-S antibody and will take into account the condition to be treated and the desired therapeutic effect to be achieved. Examples of suitable agents for forming immunoconjugates are known in the art; see for example, WO 05/103081.

Nucleic Acids

The term "polynucleotide" or "nucleic acid" includes both single-stranded and double-stranded nucleotide polymers. The nucleotides comprising the nucleic acid can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate.

The invention provides nucleic acids encoding anti-MERS-S antibodies or portions thereof.

For example, the invention provides nucleic acid molecules encoding any one of the following heavy chain variable region sequences: SEQ ID NOs: 2-18, 20-28, 30, 32, 69, 70, 75, 77, 78, 80, 107, 283, 291, 299, 307, 315, 323, 331, 339, 347, 355, 363, 371, 379, 410-420, 422-429 and 431-434. The invention also provides nucleic acid molecules that are at least 90%, at least 95%, at least 98% or at least 99% identical to nucleic acids encoding any one of the following heavy chain variable region sequences: SEQ ID NOs: 2-18, 20-28, 30, 32, 69, 70, 75, 77, 78, 80, 107, 283, 291, 299, 307, 315, 323, 331, 339, 347, 355, 363, 371, 379, 410-420, 422-429 and 431-434.

For example, the invention provides nucleic acid molecules encoding any one of the following light chain variable region sequences: SEQ ID NOs: 34-38, 40, 42-56, 58, 59, 61, 63-65, 67, 72, 74, 108, 284, 292, 300, 308, 316, 324, 332, 340, 348, 356, 364, 372 and 380. The invention also provides nucleic acid molecules that are at least 90%, at least 95%, at least 98% or at least 99% identical to nucleic acids encoding any one of the following light chain variable region sequences: SEQ ID NOs: 34-38, 40, 42-56, 58, 59, 61, 63-65, 67, 72, 74, 108, 284, 292, 300, 308, 316, 324, 332, 340, 348, 356, 364, 372 and 380.

For example, the invention provides nucleic acid molecules encoding: (i) any one of the following heavy chain variable region sequences: SEQ ID NOs: 2-18, 20-28, 30, 32, 69, 70, 75, 77, 78, 80, 107, 283, 291, 299, 307, 315, 323, 331, 339, 347, 355, 363, 371, 379, 410-420, 422-429 and 431-434 and (ii) any one of the following light chain variable region sequences: SEQ ID NOs: 34-38, 40, 42-56, 58, 59, 61, 63-65, 67, 72, 74, 108, 284, 292, 300, 308, 316, 324, 332, 340, 348, 356, 364, 372 and 380. The invention also provides nucleic acid molecules that are at least 90%, at least 95%, at least 98% or at least 99% identical to nucleic acids encoding: (i) any one of the following heavy chain variable region sequences: SEQ ID NOs: 2-18, 20-28, 30, 32, 69, 70, 75, 77, 78, 80, 107, 283, 291, 299, 307, 315, 323, 331, 339, 347, 355, 363, 371, 379, 410-420, 422-429 and 431-434 and (ii) any one of the following light chain variable region sequences: SEQ ID NOs: 34-38, 40, 42-56, 58, 59, 61, 63-65, 67, 72, 74, 108, 284, 292, 300, 308, 316, 324, 332, 340, 348, 356, 364, 372 and 380.

For example, the invention provides nucleic acid molecules encoding a heavy chain variable region sequence that comprises the CDR sequences of any one of the following heavy chain variable region sequences: SEQ ID NOs: 2-18, 20-28, 30, 32, 69, 70, 75, 77, 78, 80, 107, 283, 291, 299, 307, 315, 323, 331, 339, 347, 355, 363, 371, 379, 410-420, 422-429 and 431-434. In some embodiments, the invention provides nucleic acid molecules encoding a heavy chain variable region sequence that comprises any one of the following groups of three CDR sequences: 83-85, 89-91, 95-97, 101-103, 109-111, 115-117, 121-123, 127-129, 133-135, 139-141, 145-147, 151-153, 157-159, 163-165, 169-171, 175-177, 181-183, 187-189, 193-195, 199-201, 205-207, 211-213, 217-219, 223-225, 229-231, 235-237, 241-243, 247-249, 253-255, 259-261, 265-267, 271-273, 274-276, 277-279, 280-282, 285-287, 293-295, 301-303, 309-311, 317-319, 325-327, 333-335, 341-343, 349-351, 357-359, 365-367, 373-375 and 381-383.

The invention also provides nucleic acid molecules that encode a heavy chain variable region sequence that comprises CDR sequences that are at least 90%, at least 95%, at least 98% or at least 99% identical to the CDR sequences of any one of the following heavy chain variable region sequences: SEQ ID NOs: 2-18, 20-28, 30, 32, 69, 70, 75, 77, 78, 80, 107, 283, 291, 299, 307, 315, 323, 331, 339, 347, 355, 363, 371, 379, 410-420, 422-429 and 431-434. In some embodiments, the invention provides nucleic acid molecules that encode a heavy chain variable region sequence that comprises CDR1, CDR2 and CDR3 sequences that are at least 90%, at least 95%, at least 98% or at least 99% identical to the CDR1, CDR2 and CDR3, respectively, of any one of the following groups of three CDR sequences: 83-85, 89-91, 95-97, 101-103, 109-111, 115-117, 121-123, 127-129, 133-135, 139-141, 145-147, 151-153, 157-159, 163-165, 169-171, 175-177, 181-183, 187-189, 193-195, 199-201,205-207,211-213,217-219,223-225,229-231, 235-237, 241-243, 247-249, 253-255, 259-261, 265-267, 271-273, 274-276, 277-279, 280-282, 285-287, 293-295, 301-303, 309-311, 317-319, 325-327, 333-335, 341-343, 349-351, 357-359, 365-367, 373-375 and 381-383.

For example, the invention provides nucleic acid molecules encoding a light chain variable region sequence that comprises the CDR sequences of any one of the following light chain variable region sequences: SEQ ID NOs: 34-38, 40, 42-56, 58, 59, 61, 63-65, 67, 72, 74, 108, 284, 292, 300, 308, 316, 324, 332, 340, 348, 356, 364, 372 and 380. In some embodiments, the invention provides nucleic acid molecules encoding a light chain variable region sequence that comprises any one of the following groups of three CDR sequences: 86-88, 92-94, 98-100, 104-106,112-114, 118-120, 124-126, 130-132, 136-138, 142-144, 148-150, 154-156, 160-162, 166-168, 172-174, 178-180, 184-186, 190-192, 196-198, 202-204, 208-210, 214-216, 220-222, 226-228, 232-234, 238-240, 244-246, 250-252, 256-258, 262-264, 268-270, 288-290, 296-298, 304-306, 312-314, 320-322, 328-330, 336-338, 344-346, 352-354, 360-362, 368-370, 376-378 and 384-386. The invention also provides nucleic acid molecules that encode a light chain variable region sequence that comprises CDR sequences that are at least 90%, at least 95%, at least 98% or at least 99% identical to the CDR sequences of any one of the following light chain variable region sequences: SEQ ID NOs: 34-38, 40, 42-56, 58, 59, 61, 63-65, 67, 72, 74, 108, 284, 292, 300, 308, 316, 324, 332, 340, 348, 356, 364, 372 and 380. In some embodiments, the invention provides nucleic acid molecules that encode a light chain variable region sequence that comprises CDR1, CDR2 and CDR3 sequences that are at least 90%, at least 95%, at least 98% or at least 99% identical to the CDR1, CDR2 and CDR3, respectively, of any one of the following groups of three CDR sequences: 86-88, 92-94, 98-100, 104-106, 112-114, 118-120, 124-126, 130-132, 136-138, 142-144, 148-150, 154-156, 160-162, 166-168, 172-174, 178-180, 184-186, 190-192, 196-198, 202-204, 208-210, 214-216, 220-222, 226-228, 232-234, 238-240, 244-246, 250-252, 256-258, 262-264, 268-270, 288-290, 296-298, 304-306, 312-314, 320-322, 328-330, 336-338, 344-346, 352-354, 360-362, 368-370, 376-378 and 384-386.

For example, the invention provides nucleic acid molecules encoding: (i) a heavy chain variable region sequence that comprises the CDR sequences of any one of the following heavy chain variable region sequences: SEQ ID NOs: 2-18, 20-28, 30, 32, 69, 70, 75, 77, 78, 80, 107, 283, 291, 299, 307, 315, 323, 331, 339, 347, 355, 363, 371, 379, 410-420, 422-429 and 431-434 and (ii) a light chain variable region sequence that comprises the CDR sequences of any one of the following light chain variable region sequences: SEQ ID NOs: 34-38, 40, 42-56, 58, 59, 61, 63-65, 67, 72, 74, 108, 284, 292, 300, 308, 316, 324, 332, 340, 348, 356, 364, 372 and 380. In some embodiments, the invention provides nucleic acid molecules encoding (i) a heavy chain variable region sequence that comprises any one of the following groups of three CDR sequences: 83-85, 89-91, 95-97, 101-103, 109-111, 115-117, 121-123, 127-129, 133-135, 139-141, 145-147, 151-153, 157-159, 163-165, 169-171, 175-177, 181-183, 187-189, 193-195, 199-201, 205-207, 211-213, 217-219, 223-225, 229-231, 235-237, 241-243, 247-249, 253-255, 259-261, 265-267, 271-273, 274-276, 277-279, 280-282, 285-287, 293-295, 301-303, 309-311, 317-319, 325-327, 333-335, 341-343, 349-351, 357-359, 365-367, 373-375 and 381-383 and (ii) a light chain variable region sequence that comprises any one of the following groups of three CDR sequences: 86-88, 92-94, 98-100, 104-106, 112-114, 118-120, 124-126, 130-132, 136-138, 142-144, 148-150, 154-156, 160-162, 166-168, 172-174, 178-180, 184-186, 190-192, 196-198, 202-204, 208-210, 214-216, 220-222, 226-228, 232-234, 238-240, 244-246, 250-252, 256-258, 262-264, 268-270, 288-290, 296-298, 304-306, 312-314, 320-322, 328-330, 336-338, 344-346, 352-354, 360-362, 368-370, 376-378 and 384-386. The invention also provides nucleic acid molecules that encode: (i) a heavy chain variable region sequence that comprises CDR sequences that are at least 90%, at least 95%, at least 98% or at least 99% identical to the CDR sequences of any one of the following heavy chain variable region sequences: SEQ ID NOs: 2-18, 20-28, 30, 32, 69, 70, 75, 77, 78, 80, 107, 283, 291, 299, 307, 315, 323, 331, 339, 347, 355, 363, 371, 379, 410-420, 422-429 and 431-434 and (ii) a light chain variable region sequence that comprises CDR sequences that are at least 90%, at least 95%, at least 98% or at least 99% identical to the CDR sequences of any one of the following light chain variable region sequences: SEQ ID NOs: 34-38, 40, 42-56, 58, 59, 61, 63-65, 67, 72, 74, 108, 284, 292, 300, 308, 316, 324, 332, 340, 348, 356, 364, 372 and 380. In some embodiments, the invention provides nucleic acid molecules that encode (i) a heavy chain variable region sequence that comprises CDR1, CDR2 and CDR3 sequences that are at least 90%, at least 95%, at least 98% or at least 99% identical to the CDR1, CDR2 and CDR3, respectively, of any one of the following groups of three CDR sequences: 83-85, 89-91, 95-97, 101-103, 109-111, 115-117, 121-123, 127-129, 133-135, 139-141, 145-147, 151-153, 157-159, 163-165, 169-171, 175-177, 181-183, 187-189, 193-195, 199-201, 205-207, 211-213, 217-219, 223-225, 229-231, 235-237, 241-243, 247-249, 253-255, 259-261, 265-267, 271-273, 274-276, 277-279, 280-282, 285-287, 293-295, 301-303, 309-311, 317-319, 325-327, 333-335, 341-343, 349-351, 357-359, 365-367, 373-375 and 381-383 and (ii) a light chain variable region sequence that comprises CDR1, CDR2 and CDR3 sequences that are at least 90%, at least 95%, at least 98% or at least 99% identical to the CDR1, CDR2 and CDR3, respectively, of any one of the following groups of three CDR sequences: 86-88, 92-94, 98-100, 104-106, 112-114, 118-120, 124-126, 130-132, 136-138, 142-144, 148-150, 154-156, 160-162, 166-168, 172-174,178-180, 184-186, 190-192, 196-198, 202-204, 208-210, 214-216, 220-222, 226-228, 232-234, 238-240, 244-246, 250-252, 256-258, 262-264, 268-270, 288-290, 296-298, 304-306, 312-314, 320-322, 328-330, 336-338, 344-346, 352-354, 360-362, 368-370, 376-378 and 384-386.

The invention further provides recombinant expression vectors capable of expressing a polypeptide comprising a heavy or light chain variable region of an anti-MERS-S antibody. For example, the invention provides recombinant expression vectors comprising any of the nucleic acid molecules mentioned above.

The invention further provides host cells into which any of the vectors mentioned above have been introduced. The invention further provides methods of producing the antibodies and antibody fragments of the invention by culturing the host cells under conditions permitting production of the antibodies or antibody fragments, and recovering the antibodies and antibody fragments so produced.

Pharmaceutical Compositions

The invention provides pharmaceutical composition comprising an antibody of the invention. In some embodiments, the pharmaceutical composition further comprises a pharmaceutically acceptable carrier. The term "pharmaceutically acceptable carrier" includes any and all solvents, buffers, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion). For example, in some embodiments, a composition for intravenous administration typically is a solution in sterile isotonic aqueous buffer.

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention provides therapeutic compositions comprising the anti-MERS-CoV-S antibodies or antigen-binding fragments thereof of the present invention. Therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFEC-TIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a subject to be administered, target disease, conditions, route of administration, and the like. When an antibody of the present invention is used for treating a disease or disorder in an adult patient, or for preventing such a disease, it is advantageous to administer the antibody of the present invention normally at a single dose of about 0.1 to about 60 mg/kg body weight, more preferably about 5 to about 60, about 10 to about 50, or about 20 to about 50 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Methods of Production

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103) Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, Monoclonal Antibodies: Principles and Practice, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, humanized antibodies can be produced in transgenic plants, as an inexpensive production alternative to existing mammalian systems. For example, the transgenic plant may be a tobacco plant, i.e., Nicotiania benthamiana, and Nicotiana tabaccum. The antibodies are purified from the plant leaves. Stable transformation of the plants can be achieved through the use of Agrobacterium tumefaciens or particle bombardment. For example, nucleic acid expression vectors containing at least the heavy and light chain sequences are expressed in bacterial cultures, i.e., A. tumefaciens strain BLA4404, via transformation. Infiltration of the plants can be accomplished via injection. Soluble leaf extracts can be prepared by grinding leaf tissue in a mortar and by centrifugation. Isolation and purification of the antibodies can be readily be performed by many of the methods known to the skilled artisan in the art. Other methods for antibody production in plants are described in, for example, Fischer et al., Vaccine, 2003, 21:820-5; and Ko et al, Current Topics in Microbiology and Immunology, Vol. 332, 2009, pp. 55-78. As such, the present invention further provides any cell or plant comprising a vector that encodes the antibody of the present invention, or produces the antibody of the present invention.

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in WO 2006/008548, WO 2007/096779, WO 2010/109165, WO 2010/070263, WO 2014/141189 and WO 2014/141192.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include Moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cell's cytoplasm. Avipox virus vectors result in only a short-term expression of the nucleic acid. Adenovirus vectors, adeno-associated virus vectors and herpes simplex virus (HSV) vectors are preferred for introducing the nucleic acid into neural cells. The adenovirus vector results in a shorter-term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, CaPO4 precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of MERS-CoV in a sample. The antibody can also be used to try to bind to and disrupt MERS-CoV.

In a preferred embodiment, the antibodies of the present invention are full-length antibodies, containing an Fc region similar to wild-type Fc regions that bind to Fc receptors.

Heteroconjugate antibodies are also within the scope of the present invention. Heteroconjugate antibodies are composed of two covalently joined antibodies. It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in neutralizing or preventing viral infection. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)). In a preferred embodiment, the antibody of the present invention has modifications of the Fc region, such that the Fc region does not bind to the Fc receptors. Preferably, the Fc receptor is Fcγ receptor. Particularly preferred are antibodies with modification of the Fc region such that the Fc region does not bind to Fcγ but still binds to neonatal Fc receptor.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include 212Bi, 131I 131In, 90Y, and 186Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene tri-aminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun 133:1335-2549 (1984); Jansen et al, Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-male-imidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-de-rivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Methods for the screening of antibodies that possess the desired specificity include, but are not limited to, enzyme linked immunosorbent assay (ELISA) and other immunologically mediated techniques known within the art.

Methods of Producing Cross-Reactive Antibodies

The invention provides a method for producing antibodies that binding to two or more Coronaviruses, wherein the method comprises immunizing an animal sequentially with spike proteins from the two or more Coronaviruses. Sequential immunization of spike proteins from different Coronaviruses advantageously boosts antibodies against epitopes that are conserved between the different spike proteins. An immunization schedule for an exemplary method of the invention is shown in FIG. 1F.

In some embodiments, the interval between sequential immunizations is one week, two weeks, three weeks or four weeks. In some embodiments, the interval between sequential immunizations is two weeks.

In some embodiments, the method comprises two rounds of sequential immunizations with the spike proteins from the two or more Coronaviruses. In some embodiments, the method comprises three rounds of sequential immunizations with the spike proteins from the two or more Coronaviruses. In some embodiments, the method comprises four rounds of sequential immunizations with the spike proteins from the two or more Coronaviruses.

In some embodiments, the interval between sequential immunizations is two weeks and the method comprises two rounds of sequential immunizations.

In some embodiments, the spike proteins are selected from OC43, MERS and SARS spike proteins. In some embodiments, the animal is immunized sequentially with spike proteins from OC43, MERS and SARS.

In some embodiments, the interval between sequential immunizations is two weeks, the method comprises two rounds of sequential immunizations and the animal is immunized sequentially with spike proteins from OC43, MERS and SARS.

In some embodiments, the method comprises a booster immunization in which each of the spike proteins from the two or more Coronaviruses is administered to the animal.

In some embodiments, the interval between sequential immunizations is two weeks, the method comprises two rounds of sequential immunizations, the animal is immunized sequentially with spike proteins from OC43, MERS and SARS and the method further comprises a booster immunization in which each of the spike proteins from OC43, MERS and SARS is administered to the animal.

In some embodiments the animal is a rodent (e.g. a mouse or a rat) or a chicken. In some embodiments, the animal is a mouse.

In some embodiments, the interval between sequential immunizations is two weeks, the method comprises two rounds of sequential immunizations, the animal is immunized sequentially with spike proteins from OC43, MERS and SARS, the method further comprises a booster immunization in which each of the spike proteins from OC43, MERS and SARS is administered to the animal, and the animal is a mouse.

In some embodiments, the B-cells are harvested from spleen and/or lymph nodes one, two, three, four, five, six, seven, eight, nine or ten days after the last immunization. In some embodiments, the B-cells are harvested from spleen and/or lymph nodes four days after the last immunization.

In some embodiments, the interval between sequential immunizations is two weeks, the method comprises two rounds of sequential immunizations, the animal is immunized sequentially with spike proteins from OC43, MERS and SARS, the method further comprises a booster immunization in which each of the spike proteins from OC43, MERS and SARS is administered to the animal, the B-cells are harvested from spleen and lymph nodes four days after the last immunization and the animal is a mouse.

Uses of Antibodies that Recognize Coronaviruses

Antibodies directed against a Coronavirus (CoV) as the spike protein may be used in methods known within the art relating to the localization and/or quantitation of CoV (e.g., for use in measuring levels of the CoV protein within appropriate physiological samples, for use in diagnostic methods, for use in imaging the protein, and the like). In a given embodiment, antibodies specific to a CoV, or derivative, fragment, analog or homolog thereof, that contain the antibody derived antigen binding domain, are utilized as pharmacologically active compounds (referred to hereinafter as "Therapeutics").

An antibody specific for a CoV can be used to isolate a CoV polypeptide by standard techniques, such as immunoaffinity, chromatography or immunoprecipitation. Antibodies directed against a CoV protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Accordingly, the anti-CoV spike protein (CoV-S) antibodies of the present invention may be used to detect and/or measure CoV in a sample, e.g., for diagnostic purposes. Some embodiments contemplate the use of one or more antibodies of the present invention in assays to detect a disease or disorder such as viral infection. Exemplary diagnostic assays for CoV may comprise, e.g., contacting a sample, obtained from a patient, with an anti-CoV-S antibody of the invention, wherein the anti-CoV-S antibody is labelled with a detectable label or reporter molecule or used as a capture ligand to selectively isolate MERS-CoV from patient samples. Alternatively, an unlabelled anti-CoV-S antibody can be used in diagnostic applications in combination with a secondary antibody which is itself detectably labelled. The detectable label or reporter molecule can be a radioisotope, such as $^{3}$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure CoV in a sample include enzyme-linked immunosorbent assay (ELISA), radioimmunoassay (RIA), and fluorescence-activated cell sorting (FACS).

Samples that can be used in CoV diagnostic assays according to the present invention include any tissue or fluid sample obtainable from a patient, which contains detectable quantities of either CoV spike protein, or fragments thereof, under normal or pathological conditions. Generally, levels of CoV spike protein in a particular sample obtained from a healthy patient (e.g., a patient not afflicted with a disease associated with CoV) will be measured to initially establish a baseline, or standard, level of CoV. This baseline level of CoV can then be compared against the levels of CoV measured in samples obtained from individuals suspected of having a CoV-associated condition, or symptoms associated with such condition.

The antibodies specific for CoV spike protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface Antibodies of the invention, including polyclonal, monoclonal, humanized and fully human antibodies, may be used as therapeutic agents. Such agents will generally be employed to treat or prevent a CoV-related disease or pathology in a subject. An antibody preparation, preferably one having high specificity and high affinity for its target antigen, is administered to the subject and will generally have an effect due to its binding with the target. Administration of the antibody may abrogate or inhibit or interfere with the internalization of the virus into a cell. For example, the antibody may bind to the target and prevents MERS-CoV binding the DPP4 receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a CoV protein or a fragment thereof of the invention, as well as other molecules identified by the screening assays disclosed herein, can be administered for the treatment of a CoV-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Formulations can contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a CoV (or a protein or a protein fragment thereof) in a sample. Preferably, the antibody contains a detectable label. Antibodies can be polyclonal, or more preferably, monoclonal. An intact antibody is preferred. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999)). Passive immunization using neutralizing human monoclonal antibodies could provide an immediate treatment strategy for emergency prophylaxis and treatment of CoV infection and related diseases and disorders while the alternative and more time-consuming development of vaccines and new drugs in underway.

The invention provides for both prophylactic and therapeutic methods of treating a subject at risk of (or susceptible to) a CoV-related disease or disorder.

In one aspect, the invention provides methods for preventing a CoV-related disease or disorder in a subject by administering to the subject an antibody of the invention. Optionally, two or more anti-CoV antibodies are co-administered.

Subjects at risk for a CoV-related diseases or disorders include patients who have been exposed to the CoV. For example, the subjects have travelled to regions or countries of the world in which other CoV infections have been reported and confirmed. Administration of a prophylactic agent can occur prior to the manifestation of symptoms characteristic of the CoV-related disease or disorder, such that a disease or disorder is prevented or, alternatively, delayed in its progression.

In some embodiments, the antibody of the present invention can be administered with other antibodies or antibody fragments known to neutralize CoV. Administration of said antibodies can be sequential, concurrent, or alternating.

Another aspect of the invention pertains to methods of treating a CoV-related disease or disorder in a patient. In one embodiment, the method involves administering an agent (e.g., an agent identified by a screening assay described herein and/or monoclonal antibody identified according to the methods of the invention), or combination of agents that neutralize the CoV to a patient suffering from the disease or disorder.

Uses of Anti-MERS-S Antibodies

Antibodies directed against a MERS-CoV as the spike protein may be used in methods known within the art relating to the localization and/or quantitation of MERS-CoV (e.g., for use in measuring levels of the MERS-CoV protein within appropriate physiological samples, for use in diagnostic methods, for use in imaging the protein, and the like). In a given embodiment, antibodies specific to an MERS-CoV, or derivative, fragment, analog or homolog thereof, that contain the antibody derived antigen binding domain, are utilized as pharmacologically active compounds (referred to hereinafter as "Therapeutics").

An antibody specific for a MERS-CoV can be used to isolate a MERS-CoV polypeptide by standard techniques, such as immunoaffinity, chromatography or immunoprecipitation. Antibodies directed against an MERS-CoV protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Accordingly, the anti-MERS-CoV-S antibodies of the present invention may be used to detect and/or measure MERS-CoV in a sample, e.g., for diagnostic purposes. Some embodiments contemplate the use of one or more antibodies of the present invention in assays to detect a disease or disorder such as viral infection. Exemplary diagnostic assays for MERS-CoV may comprise, e.g., contacting a sample, obtained from a patient, with an anti-MERS-CoV-S antibody of the invention, wherein the anti-MERS-CoV-S antibody is labelled with a detectable label or reporter molecule or used as a capture ligand to selectively isolate MERS-CoV from patient samples. Alternatively, an unlabelled anti-MERS-CoV-S antibody can be used in diagnostic applications in combination with a secondary antibody which is itself detectably labelled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure MERS-CoV in a sample include enzyme-linked immunosorbent assay (ELISA), radioimmunoassay (RIA), and fluorescence-activated cell sorting (FACS).

Samples that can be used in MERS-CoV diagnostic assays according to the present invention include any tissue or fluid sample obtainable from a patient, which contains detectable quantities of either MERS-CoV spike protein, or fragments thereof, under normal or pathological conditions. Generally, levels of MERS-CoV spike protein in a particular sample obtained from a healthy patient (e.g., a patient not afflicted with a disease associated with MERS-CoV) will be measured to initially establish a baseline, or standard, level of MERS-CoV. This baseline level of MERS-CoV can then be compared against the levels of MERS-CoV measured in samples obtained from individuals suspected of having a MERS-CoV-associated condition, or symptoms associated with such condition.

The antibodies specific for MERS-CoV spike protein may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface Antibodies of the invention, including polyclonal, monoclonal, humanized and fully human antibodies, may be used as therapeutic agents. Such agents will generally be employed to treat or prevent a MERS-CoV-related disease or pathology in a subject. An antibody preparation, preferably one having high specificity and high affinity for its target antigen, is administered to the subject and will generally have an effect due to its binding with the target. Administration of the antibody may abrogate or inhibit or interfere with the internalization of the virus into a cell. In this case, the antibody binds to the target and prevents MERS-CoV binding the DPP4 receptor.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a MERS-CoV protein or a fragment thereof of the invention, as well as other molecules identified by the screening assays disclosed herein, can be administered for the treatment of a MERS-CoV-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Formulations can contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a MERS-CoV (or a protein or a protein fragment thereof) in a sample. Preferably, the antibody contains a detectable label. Antibodies can be polyclonal, or more preferably, monoclonal. An intact antibody is preferred. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999)). Passive immunization using neutralizing human monoclonal antibodies could provide an immediate treatment strategy for emergency prophylaxis and treatment of MERS-CoV infection and related diseases and disorders while the alternative and more time-consuming development of vaccines and new drugs in underway.

The invention provides for both prophylactic and therapeutic methods of treating a subject at risk of (or susceptible to) a MERS-CoV-related disease or disorder.

In one aspect, the invention provides methods for preventing a MERS-CoV-related disease or disorder in a subject by administering to the subject an antibody of the invention. Optionally, two or more anti-MERS-CoV antibodies are co-administered.

Subjects at risk for a MERS-CoV-related diseases or disorders include patients who have been exposed to the MERS-CoV. For example, the subjects have travelled to regions or countries of the world in which other MERS-CoV infections have been reported and confirmed.

Administration of a prophylactic agent can occur prior to the manifestation of symptoms characteristic of the MERS-CoV-related disease or disorder, such that a disease or disorder is prevented or, alternatively, delayed in its progression.

In some embodiments, the antibody of the present invention can be administered with other antibodies or antibody fragments known to neutralize MERS-CoV. Administration of said antibodies can be sequential, concurrent, or alternating.

Another aspect of the invention pertains to methods of treating a MERS-CoV-related disease or disorder in a patient. In one embodiment, the method involves administering an agent (e.g., an agent identified by a screening assay described herein and/or monoclonal antibody identified according to the methods of the invention), or combination of agents that neutralize the MERS-CoV to a patient suffering from the disease or disorder.

Cross-reactive anti-MERS-S antibodies of the invention, which bind to MERS-CoV and to one or more other beta-coronaviruses (e.g. SARS-CoV, MHV), may be used in the diagnosis and treatment of infections by the one or more other betacoronaviruses (e.g. SARS-CoV, MHV).

Accordingly, each of the above statements relating to the uses of anti-MERS-S antibodies in the context of MERS-CoV diagnosis and treatment are also applicable to the context of the diagnosis and treatment of the one or more other betacoronaviruses (e.g. SARS-CoV, MHV) recognized by the cross-reactive anti-MERS-S antibodies of the invention.

Coronaviruses

Coronaviruses enter cells through a large spike protein on their envelopes. The coronavirus spike protein is a membrane anchored trimer and contains two subunits, receptor binding subunit S1 and membrane fusion subunit S2. The S2 subunits from group I and group II coronaviruses share both sequence and structural homology; they contain homologous heptad repeat segments that fold into a conserved trimers of hairpin structure, which is essential for membrane fusion. Surprisingly, the S1 subunits from group I and group II coronaviruses have no obvious sequence homology. Nevertheless, they can be divided approximately into N terminal region, central region, and C terminal region. Coronaviruses are believed to have common ancestors because they share similar replication mechanisms, genomic structures, and overall gene sequences.

Among all of the coronavirus genes, the one encoding the spike protein is the most variable.

Between the spike protein subunits, S1 is more variable than S2. The current structural divergences of the S1 subunits reveal the tremendous evolutionary pressure that coronaviruses face to adapt to different host receptors, and they also reflect on the evolutionary history of coronaviruses and their receptor selections.

In general, coronaviruses are well known and most of those who are diagnosed with it recover completely with no complications after receiving the needed supportive therapy. However, in some of the patients who are infected, serious complications can develop affecting the respiratory system and the kidneys and can cause death, especially among the elderly and in patients with chronic respiratory and cardiac conditions and among immune compromised patients.

Coronaviruses (CoVs), a genus of the Coronaviridae family, are positive strand RNA viruses with the largest viral genome of all RNA viruses (27-32 Kb). The genomic RNA is capped, polyadenylated and covered with nucleocapsid proteins. The virus is enveloped and carries large spike glycoproteins. All CoVs employ a common genome organization where the replicase gene encompasses the 5' two thirds of the genome and is comprised of two overlapping open reading frames (ORFs), ORF1a and ORF1b.

The structural gene region, which covers the 3' third of the genome, encodes the canonical set of structural protein genes in the order 5' spike (S) envelope (E) membrane (M) and nucleocapsid (N)-3'. Some beta CoVs carry an additional structural protein encoding a hemagglutinin esterase (HE). The gene is located between the ORF1b and S gene. Expression of the nonstructural replicase proteins is mediated by translation of the genomic RNA that gives rise to the biosynthesis of two large polyproteins, ppla (encoded by ORF1a) and pplab (encoded by ORF1a and ORF1b) facilitated by a ribosomal frame shift at the ORF1a/1b junction.

In contrast, the structural proteins are translated from sub genomic (sg) mRNAs. These sg mRNAs are the result of discontinuous transcription, a hallmark of CoV gene expression. The structural gene region also harbours several ORFs that are interspersed along the structural protein coding genes. The number and location of these accessory ORFs varies between the CoV species.

Although coronaviruses were first identified nearly 60 years ago, they only received notoriety in 2003 when one of their members was identified as the aetiological agent of severe acute respiratory syndrome (SARS). Previously these viruses were known to be important agents of respiratory and enteric infections of domestic and companion animals and to cause approximately 15% of all cases of the common cold. Coronaviruses (CoVs), a genus of the Coronaviridae family, are positive strand RNA viruses with the largest viral genome of all RNA viruses (27-32 Kb). The genomic RNA is capped, polyadenylated and covered with nucleocapsid proteins. The virus is enveloped and carries large spike glycoproteins. All CoVs employ a common genome organization where the replicase gene encompasses the 5'-two thirds of the genome and is comprised of two overlapping open reading frames (ORFs), ORF1a and ORF1b. The structural gene region, which covers the 3'-third of the genome, encodes the canonical set of structural protein genes in the order 5'-spike (S)—envelope (E)—membrane (M) and nucleocapsid (N)—3'. Some beta-CoVs carry an additional structural protein encoding a heamagglutinin-esterase (HE). The gene is located between the ORF1b and S gene. Expression of the nonstructural replicase proteins is mediated by translation of the genomic RNA that gives rise to the biosynthesis of two large polyproteins, ppla (encoded by ORF1a) and pplab (encoded by ORF1a and ORF1b) facilitated by a ribosomal frame shift at the ORF1a/1b junction. In contrast, the structural proteins are translated from sub genomic (sg) mRNAs. These sg mRNAs are the result of discontinuous transcription, a hallmark of CoV gene expression. The structural gene region also harbors several ORFs that are interspersed along the structural protein coding genes. The number and location of these accessory ORFs varies between the CoV species.

In animals CoV infections can lead to a variety of syndromes, e.g. bronchitis, gastroenteritis, progressive demyelinating encephalitis, diarrhea, peritonitis and respiratory tract disease. The first reports on human CoVs (HCoV) appeared in the mid-1960s. The human viruses were isolated from persons with common cold, and two species were detected: HCoV-229E and HCoV-OC43. Almost 40 years later, SARS-CoV was identified as the causative agent of the Severe Acute Respiratory Syndrome (SARS). A highly effective global public health response prevented further spread of this virus, and as a result SARS-CoV was eradicated from the human population. Soon thereafter it became clear that there are more HCoVs. HCoV-NL63 was identified in 2004 and HCoV-HKU1 in 2005. Infections by these viruses are as common and wide spread as HCoV-229E and HCoV-OC43 infections. The SARS outbreak intensified the research on the unknown animal CoVs. As many as 16 new animal CoV species were identified by 2008. There are currently around 29 complete reference genome sequences available in Genbank of the various viruses. Recently, the Coronavirus Study Group of the International Committee for Taxonomy of Viruses has proposed renaming the traditional group 1, 2, and 3 coronaviruses into the genus Alphacoronavirus, Betacoronavirus, and Gammacoronavirus, respectively (talk ictvonline_Org/media/p/1230_aspx). Each genus is subdivided into different species on the basis of sequence identity in the replicase domains of the polyprotein pplab.

The classification of the family Coronaviridae and the organization of the established subfamily Coronavirinae is based upon rooted phylogeny and pair-wise comparisons using Coronaviridae-wide conserved domains in replicase polyprotein pplab as well as the structural proteins S, E, M and N. In rooted trees, the proposed genera Alpha-, Beta- and Gammacoronavirus consistently form three distinct monophyletic groups and in pair-wise comparisons, they form three robust non-overlapping clusters. The inter-group pair-wise scores for coronaviruses are comparable to those calculated for structural and non-structural proteins of different genera in other RNA virus families (e.g. Potyviridae, Picornaviridae). Based on this de facto criterion phylogroups 1 through 3 are named into genera designated Alpha-, Beta and Gammacoronavirus, respectively. The 90% aa sequence identity threshold now proposed as a species demarcation criterion within each genus has been determined from the analysis of pair-wise aa distances in seven conserved replicase domains (nsp3 ADRP, nsp5 (3CLpro), nspl2 (RdRp), nspl3 (Hell), nspl4 (ExoN), nspl5 (NendoU) and nspl6 (O-MT)) of 156 viruses in the Coronaviridae. In this analysis, 20 distinct groups (17 coronaviruses, 2 toroviruses, 1 bafinivirus) are unambiguously recognized as non-overlapping clusters (with the largest intra-cluster distance being smaller than the smallest inter-cluster distance). Of these clusters, at least 7 fall into the genus Betacoronavirus, each of which represents a distinct betacoronavirus species (Beta-coronavirus 1, Murine coronavirus, Human coronavirus HKU1, Rousettus bat coronavirus HKU9, *Tylonycteris* bat coronavirus HKU4, *Pipistrellus* bat coronavirus HKU5, Severe acute respiratory syndrome-related coronavirus (SARS-CoV) and Middle East respiratory syndrome coronavirus (MERS-CoV)). The Betacoronavirus genus is additionally considered to contain 4 lineages (A, B, C and D). Human coronaviruses HCoV-HKU1 and HCoV-OC43 belong to lineage A while human coronavirus SARS-CoV belongs to lineage B. MERS-CoV belongs to lineage C. Other human coronaviruses, such as HCoV-NL63 and HCoV-229E, are even more distinct since these two human pathogens belong to a different genus, the Alphacoronavirus genus.

MERS-CoV

"MERS-CoV", also called as "MERS coronavirus", refers to the newly-emerged Middle East Respiratory Syndrome—Corona Virus which was first isolated in the Arabian peninsula in 2012 (Zaki et al 2012, NEJM 367: 1814-1820) and identified as the cause for the outbreak of severe acute respiratory disease. It was initially called human coronavirus-EMC (Erasmus Medical Centre; hCoV-EMC). It belongs to the betacoronavirus lineage 2c and causes severe respiratory disease, similar to the Severe Acute Respiratory Syndrome coronavirus (SARS-CoV) that emerged in China in 2002. The MERS coronavirus has been found to be closely related to coronaviruses found in bats and camels. It binds via the viral spike protein to human host cell receptor dipeptidyl peptidase 4 (DPP4). MERS-CoV spike protein has been found to bind to DPP4 of other species, especially bats and camels (Raj et al 2013, Nature 495: 251-254).

The spike protein of the MERS coronavirus is referred to as "MERS-CoV-S" or "MERS-S", also called "S protein". The MERS-CoV spike protein is a 1353 amino acid type I membrane glycoprotein which assembles into trimers that constitute the spikes or peplomers on the surface of the enveloped MERS coronavirus particle. The protein has two essential functions, host receptor binding and membrane fusion, which are attributed to the N-terminal (S1, amino acid residues 1-751) and C-terminal (S2, amino acid residues 752-1353) halves of the S protein. MERS-CoV-S binds to its cognate receptor, dipeptidyl peptidase 4 (DPP4) via about 230-amino acid long receptor binding domain (RBD) present in the S1 subunit. Mou et al (2013) have shown in J. Virology (vol 87, pages 9379-9383) that the MERS-CoV RBD is located within the residues 358-588 of the spike protein. The amino acid sequence of full-length MERS-CoV spike protein is exemplified by the amino acid sequence of spike protein of MERS-CoV isolate EMC/2012 provided in GenBank as accession number AFS88936.1 (SEQ ID NO: 81). The term "MERS-CoV-S" also includes protein variants of MERS-CoV spike protein isolated from different MERS-CoV isolates, e.g., Jordan-N3/2012, England-Qatar/2012, Al-Hasa_1_2013, Al-Hasa_2_2013, Al-Hasa_3_2013, Al-Hasa_4_2013, Al-Hasa 12, Al-Hasa_15, Al-Hasa 16, Al-Hasa 17, Al-Hasa_18, Al-Hasa 19, Al-Hasa_21, Al-Hasa 25, Bisha_1, BuraidahJ, England 1, Hafr-AI-BatinJ, Hafr-AI-Batin 2, Hafr-AI-Batin_6, Jeddah_1, KFU-HKU 1, KFU-HKU 13, Munich, Qatar3, Qatar4, RiyadhJ, Riyadh_2, Riyadh_3, Riyadh_3, Riyadh_4, Riyadh_5, Riyadh_9, Riyadh_14, Taif_1, UAE, and Wadi-Ad-Dawasir. The term "MERS-CoV-S" includes recombinant MERS-CoV spike protein or a fragment thereof. The term also encompasses MERS-CoV spike protein, or a fragment thereof coupled to, for example, histidine tag, mouse or human Fc, or a signal sequence such as ROR1. For example, the term includes sequences comprising a mouse Fc (mIgG2a) or human Fc (hIgG1) at the C-terminal, coupled to amino acid residues 367-606 of full-length MERS-CoV spike protein. The term also includes protein variants that comprise a histidine tag at the C-terminal, coupled to amino acid residues 367-606 of full-length MERS-CoV spike protein.

DPP4 (dipeptidyl peptidase 4) is a receptor for MERS-CoV and is a 766-amino acid type II transmembrane glycoprotein present in a dimeric form on the cell surface. It is an exopeptidase that cleaves dipeptides from hormones and chemokines after a proline amino acid residue, thereby regulating their bioactivity. In humans, DPP4 is primarily expressed on the epithelial cells in kidney, small intestine, liver and prostate, on ciliated and non-ciliated cells in the upper and lower respiratory tract, and on immune cells (i.e., CD4+, CD8+, dendritic cells and macrophages). Unless specified as being from a non-human species, the term "DPP4", as used herein, means human DPP4.

MERS infection (or "MERS-CoV infection" or Middle East Respiratory Syndrome) refers to the severe acute respiratory illness caused by MERS coronavirus and first reported in Saudi Arabia in 2012. The term includes respiratory tract infection, often in the lower respiratory tract. The symptoms include high fever, cough, shortness of breath pneumonia, gastro-intestinal symptoms such as diarrhoea, organ failure (kidney failure and renal dysfunction), septic shock and death in severe cases.

Definitions

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3.

However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term "recombinant", as used herein, refers to antibodies or antigen-binding fragments thereof of the invention created, expressed, isolated or obtained by technologies or methods known in the art as recombinant DNA technology which include, e.g., DNA splicing and transgenic expression. The term refers to antibodies expressed in a non-human mammal (including transgenic non-human mammals, e.g., transgenic mice), or a cell (e.g., CHO cells) expression system or isolated from a recombinant combinatorial human antibody library.

An "isolated antibody", as used herein, is intended to refer to an antibody that is substantially free of other antibodies (Abs) having different antigenic specificities (e.g., an isolated antibody that specifically binds MERS-S, or a fragment thereof, is substantially free of Abs that specifically bind antigens other than MERS-S.

A "blocking antibody" or a "neutralizing antibody", as used herein (or an "antibody that neutralizes MERS-S activity" or "antagonist antibody"), is intended to refer to an antibody whose binding to MERS-S results in inhibition of at least one biological activity of MERS-CoV. For example, an antibody of the invention may prevent or block MERS-CoV binding to DPP4.

The term "surface plasmon resonance", as used herein, refers to an optical phenomenon that allows for the analysis of real-time biomolecular interactions by detection of alterations in protein concentrations within a biosensor matrix, for example using a ForteBio Octet instrument or the BIA-CORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of nonlinear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "competes", as used herein, means an antibody or antigen-binding fragment thereof binds to an antigen and inhibits or blocks the binding of another antibody or antigen-binding fragment thereof. The term also includes competition between two antibodies in both orientations, i.e., a first antibody that binds and blocks binding of second antibody and vice-versa. In certain embodiments, the first antibody and second antibody may bind to the same epitope. Alternatively, the first and second antibodies may bind to different, but overlapping epitopes such that binding of one inhibits or blocks the binding of the second antibody, e.g., via steric hindrance. Cross-competition between antibodies may be measured by methods known in the art, for example, by a real-time, label-free bio-layer interferometry assay. Cross-competition between two antibodies may be expressed as the binding of the second antibody that is less than the background signal due to self-self binding (wherein first and second antibodies is the same antibody). Cross-competition between 2 antibodies may be expressed, for example, as % binding of the second antibody that is less than the baseline self-self background binding (wherein first and second antibodies is the same antibody).

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403-410 and (1997) Nucleic Acids Res. 25:3389-3402.

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

As used herein, the term "subject" refers to an animal, preferably a mammal, more preferably a human, in need of amelioration, prevention and/or treatment of a disease or disorder such as viral infection. The term includes human subjects who have or are at risk of having MERS infection.

As used herein, the terms "treat", "treating", or "treatment" refer to the reduction or amelioration of the severity of at least one symptom or indication of MERS infection due to the administration of a therapeutic agent such as an antibody of the present invention to a subject in need thereof. The terms include inhibition of progression of disease or of worsening of infection. The terms also include positive prognosis of disease, i.e., the subject may be free of infection or may have reduced or no viral titers upon administration of a therapeutic agent such as an antibody of the present invention. The therapeutic agent may be administered at a therapeutic dose to the subject.

The terms "prevent", "preventing" or "prevention" refer to inhibition of manifestation of viral infection (e.g. beta-coronavirus infection, such as MERS infection) or any symptoms or indications of viral infection (e.g. betacoronavirus infection, such as MERS infection) upon administration of an antibody of the present invention. The term includes prevention of spread of infection in a subject exposed to the virus or at risk of having a viral infection (e.g. betacoronavirus infection, such as MERS infection).

As used herein, the term "anti-viral drug" refers to any anti-infective drug or therapy used to treat, prevent, or ameliorate a viral infection in a subject. The term "anti-viral drug" includes, but is not limited to ribavirin, oseltamivir, zanamivir, interferon-alpha2b, analgesics and corticosteroids. In the context of the present invention, the viral infections include infection caused by human coronaviruses, including but not limited to, MERS-CoV, HCoV_229E, HCoV_NL63, HCoV-OC43, HCoV_HKU1, and SARS-CoV.

General

The term "comprising" encompasses "including" as well as "consisting" e.g. a composition "comprising" X may consist exclusively of X or may include something additional e.g. X+Y.

The term "about" in relation to a numerical value x is optional and means, for example, $x\pm10\%$.

Various aspects and embodiments of the invention are described below in more detail by way of example. It will be appreciated that modification of detail may be made without departing from the scope of the invention.

EXAMPLES

Example 1—Anti-MERS S Protein H2L2 Antibodies

H2L2 mice are transgenic mice that produce hybrid human/rat antibodies. The VH and VK binding regions are completely human whereas the constant part has a rat origin. These antibodies are generated from two transgenic loci coding for the heavy chain and the kappa light chain of the antibody. Production of endogenous murine antibodies is prevented through inactivation of the endogenous heavy and light chain gene loci (see, e.g., WO 2014/141189).

Figures 1C, 1D, 1E:
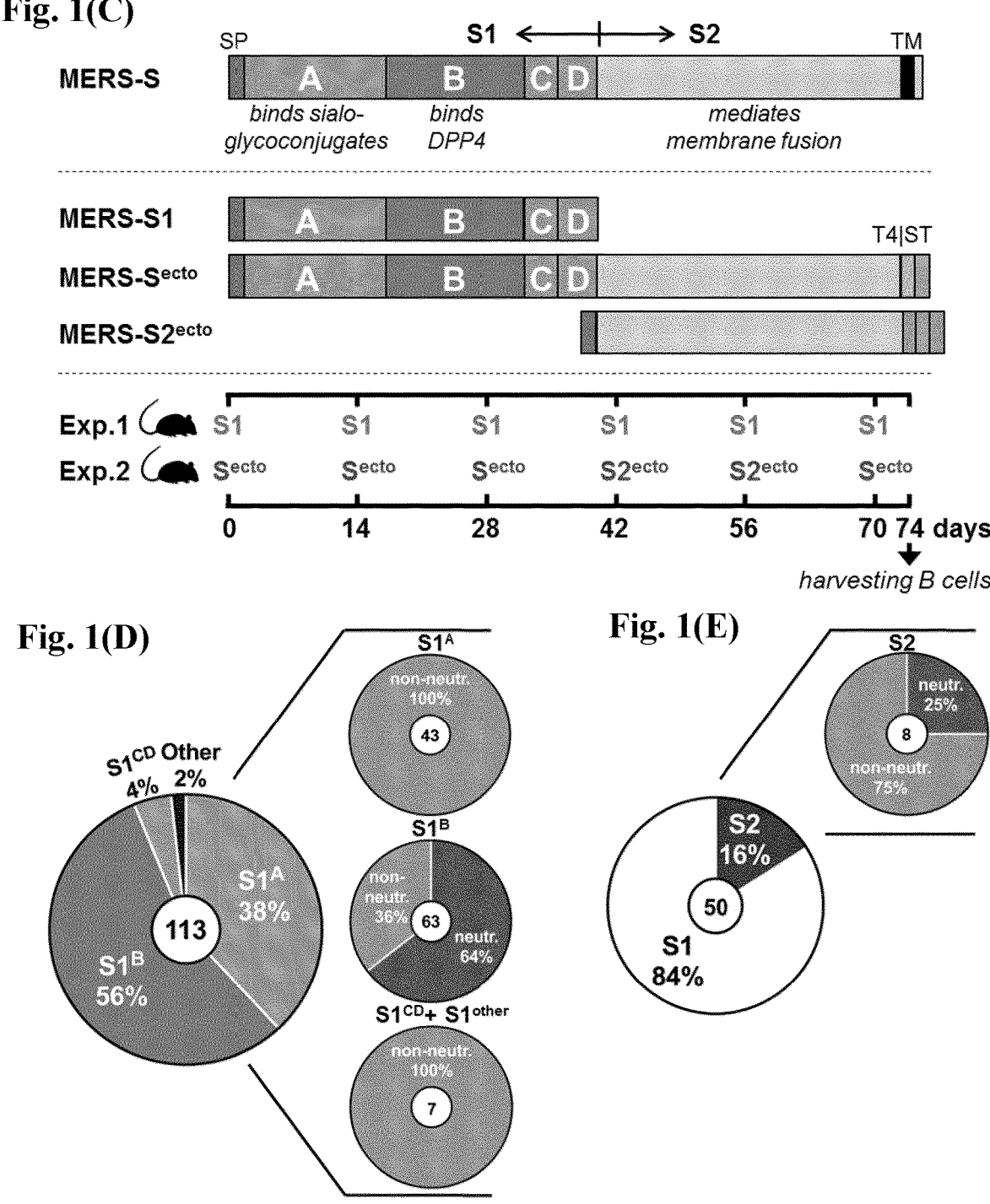
Figure 1F:
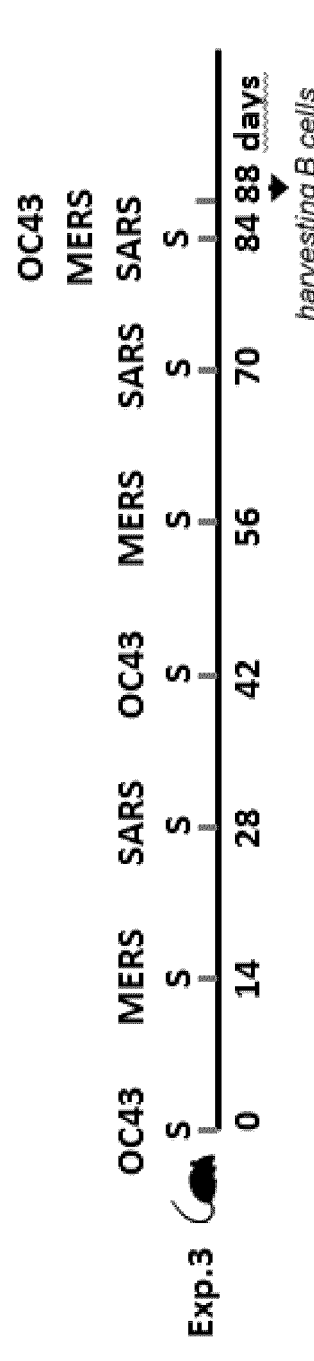

Six H2L2 mice were immunized with the recombinant S1 protein dimer consisting of MERS CoV S1 (1-747aa) fused to human Fc (see FIG. 1). After 5 immunisations and a final boost the B cells from each mouse were harvested. Splenic and lymph node B cells were fused with SP 2/0 myeloma cell line, ATCC #CRL-1581, to generate hybridomas producing antibodies against MERS CoV S1 protein.

Supernatants of 4553 hybridomas were screened for MERS-S1 antibody-containing reactivity by ELISA. 113 hybridomas were positive for MERS-S1, of which 56% bound to the $S1_A$ domain and 38% bound to the S1B domain. 4% of the MERS-S1-reactive antibodies bound to either the Sic or $S1_D$ domains and 2% of the MERS-S1-reactive antibodies did not bind to any of the S1 domains, indicative of binding to interdomain epitopes.

Six H2L2 mice were also immunized with a combination of trimeric MERS-CoV ectodomain and S2 protein (3× immunization with MERS S ectodomain-T4Fd-ST followed by 2× immunization with MERS S2-3×ST and final boost with MERS S ectodomain-T4Fd-ST using standard immunization protocols). Hybridoma cell lines were generated from splenic and lymph node B cells.

Supernatants of 1158 hybridomas were screened for MERS-S antibody-containing reactivity by ELISA. 50 hybridomas were positive for binding in a MERS-S ectodmain ELISA.

The neutralization capacities and epitopes of prioritized MERS-CoV S1 and S2 mAbs were established using luciferase-encoding MERS-S pseudotyped recombinant vesicular stomatitis virus (rVSV-MERS-S) (FIG. 6). ~40 antibodies were observed to neutralize MERS CoV infection (VN titer=0.1-1000 ng/ml). Each of these antibodies bind to the receptor binding domain (SiB) of MERS-S and block the interaction between MERS-S 1 and the DPP4 receptor. The majority of the antibodies recognize conformational epitopes. Epitope binning studies showed that the anti-MERS-$S1_B$ antibodies fall into three epitope groups. The human VH and $V_L$ antibody sequences were cloned into appropriate human constant region vectors. MAb 7.7 g6 and 1.6f9 are the most potent in terms of neutralization. The cDNA of the heavy and light chains of each of the antibodies were sequenced and the preliminary affinities measured using ForteBio (FIGS. 2-4). KD values of $6.8×10^{-1}$ to $1.2×10^{-8}$ were observed.

The anti-MERS-S1 antibodies obtained are more potent than antibodies reported in previously published work. The most potent antibody obtained in these experiments, 7.7 g6, has an approximately ten-fold higher neutralizing activity compared to the most potent antibody that has been described in previously published work.

Two out of the eight identified MERS-S2-specific antibodies were found to neutralize MERS-S pseudovirus. One of the S2 specific mAbs (1.6c7) is neutralizing and cross-reactive towards other betacoronaviruses (FIG. 5). The antibodies that were prioritized for further development and evaluation are listed in FIG. 6. The antibodies have been produced in HEK-293T cells after transient co-transfection of HC and LC-encoding plasmids. Purified human antibodies show similar viral neutralization capacity in comparison to the (chimeric human VH/rat constant region) H2L2 antibodies.

Screening of neutralizing antibodies for antigen binding competition identified seven epitope groups, which was used for selection of lead antibodies (FIG. 28).

Example 2—Binding of Lead Anti-MERS S Protein H2L2 Antibodies to the MERS-CoV Spike Protein From the set of MERS-CoV-S specific H2L2 antibodies, a panel of eight monoclonal antibodies (mAbs 1.10f3, 7.7 g6, 1.6f9, 1.2 g5, 1.8e5, 4.6e10, 1.6c7 and 3.5 g6) were selected with epitopes distributed throughout different domains of the MERS-CoV spike protein for further detailed biophysical and functional characterization. Selection of H2L2 mAbs was based on their unique VH and VL region sequences and on their capacity to neutralize MERS-CoV relative to other mAbs within an epitope group (FIG. 29). Neutralizing antibodies targeting the $S1^A$ sialic acid binding domain could not be detected, but nevertheless one non-neutralizing mAb (1.10f3) that recognizes this domain was selected. Fully human mAbs were generated by cloning the genes of the variable region of light and heavy chain into human IgG1 expression vectors. Likewise, IgG1 expression vectors were generated for expression of a previously reported potent MERS-CoV-neutralizing antibody (anti-MERS control) (Pascal et al. (2015) PNAS USA 112(28): 8738-8743). as a benchmark antibody. In addition, an irrelevant antibody recognizing the Strep-tag affinity tag (isotype control) was used. All reformatted antibodies were expressed in human HEK-293T cells and purified using Protein A affinity purification (FIG. 18).

Epitope mapping of the purified human mAbs to the different domains on MERS-CoV S was done by ELISA using soluble MERS-CoV $S^{ecto}$, S1, $S1^A$ $S1^B$ or $S2^{ecto}$ as antigens (FIG. 26B). Domain-level epitope mapping confirmed that mAb 1.10f3 bound to the sialic acid binding domain $S1^A$; 7.7 g6, 1.6f9, 1.2 g5, 1.8e5 and 4.6e10 targeted the receptor binding domain $S1^B$ whereas mAbs 1.6c7 and 3.5 g6 bound the ectodomain of the membrane fusion subunit S2 (FIG. 2C).

Next competition for binding of lead antibodies to the MERS-S ectodomain was tested using bio-layer interferometry (FIG. 2D). The binding competition data indicated the existence of six epitope groups suggesting the presence of six distinct epitopes targeted by the eight lead mAbs on the MERS-CoV S protein: group I (7.7 g6, 1.6f9 and 1.2 g5), group II (1.8e5) and group III (4.6e10) on the $S1^B$ domain, group IV (1.10f3) on the $S1^A$ domain, and groups V (1.6c7) and VI (3.5 g6) on the S2 ectodomain. Antibodies of different groups competed minimally with each other, indicating that their epitopes were largely distinct (FIGS. 2D and E).

The binding kinetics of the eight human monoclonal antibodies were determined by bio-layer interferometry. Strep-tagged MERS-S ectodomain was captured on the protein-A sensor via an anti-Streptag antibody and kinetic binding parameters of antibodies were determined at 25° C.

and pH 7.4. All antibodies displayed high affinity binding for the MERS-S ectodomain with equilibrium dissociation constants (KD) in the nano- to picomolar range (0.081 nM to 4.78 nM) (FIG. 2F). The binding affinity of the MERS-CoV receptor DPP4 to MERS-S was measured in the same set up, and was lower compared to the binding affinity of the mAbs that target the receptor binding domain $S1^B$(FIG. 2F).

Example 3—Anti-MERS-S H2L2 mAbs Bind Cell Surface-Displayed MERS-CoV Spike Protein To assess whether the lead mAbs can bind full-length MERS-CoV S expressed on the cell surface, Huh-7 cells were transfected with plasmid encoding MERS-CoV S. The spike gene was C-terminally extended with GFP to monitor MERS-S expression, and mutated at the furin cleavage site to stabilize the spike protein in its native prefusion state and to prevent MERS-S-mediated cell-cell fusion. Binding of lead mAbs to cell-surface expressed MERS-S was analyzed by flow cytometry and immunofluorescence. All anti-MERS-S mAbs bound to non-permeabilized, MERS-S transfected (GFP-positive) Huh-7 cells in both assays, indicative for binding to cell surface displayed MERS-CoV S (FIG. 3B and FIG. 30).

Binding of mAbs to cell-surface exposed MERS-CoV S quantified by the median fluorescent intensities correlated with the binding affinities for recombinant MERS-S ectodomain as measured by bio-layer interferometry (FIG. 2F and FIG. 3B).

Example 4—Neutralization Activity of Anti-MERS-S H2L2 mAbs

Figure 19A:
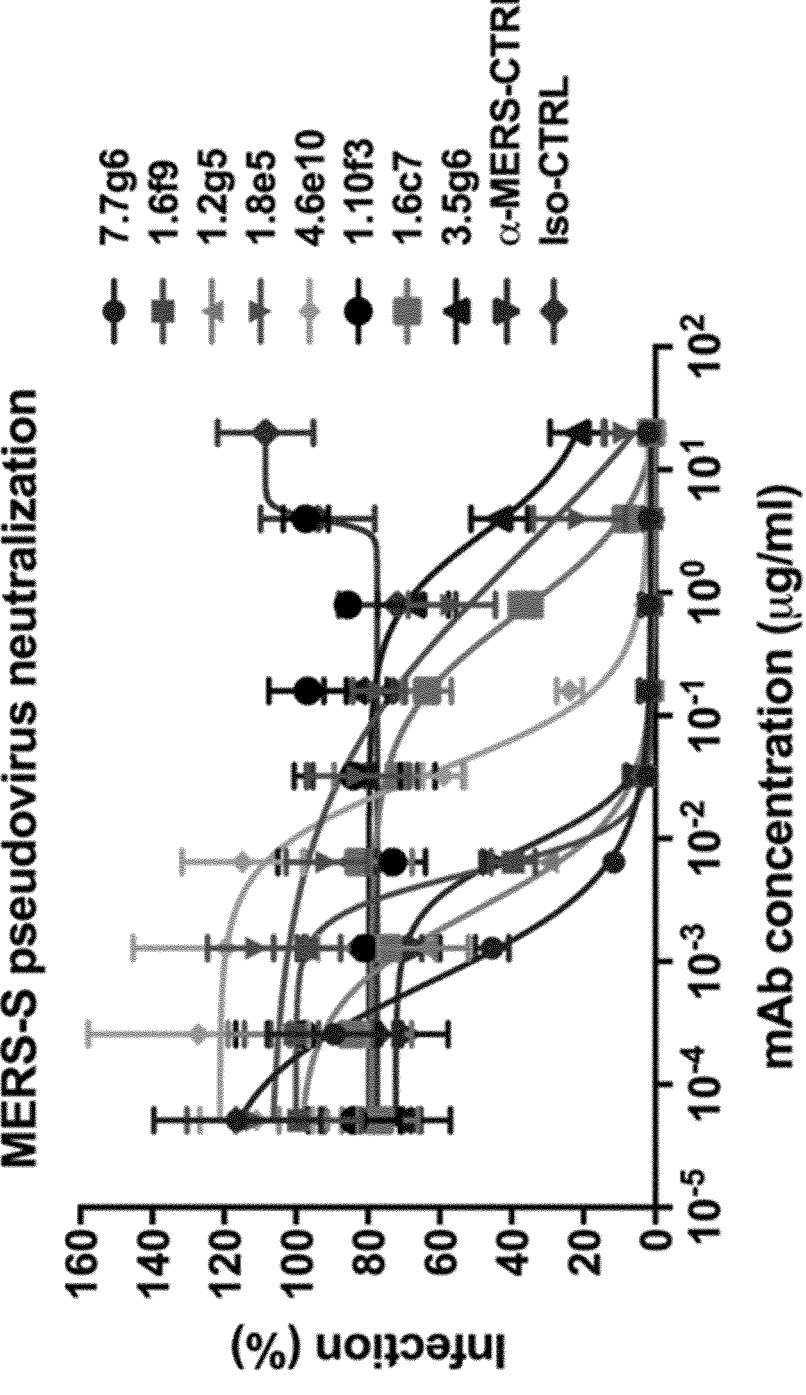

The ability of human lead mAbs to neutralize MERS-CoV infection in vitro was tested on Vero cells with luciferase-encoding MERS-S pseudotyped virus and with authentic MERS-CoV on Huh-7 cells in a plaque reduction neutralization test (PRNT) (FIGS. 19A and B). Levels of virus neutralization varied among the individual antibodies as summarized in FIG. 19B. The 7.7 g6, 1.6f9 and 1.2 g5 mAbs all targeting epitope group I on MERS-S1$^B$ showed the most potent neutralizing activity, and displayed picomolar half-maximal inhibitory concentrations against MERS-S pesudotyped virus ($IC_{50}$=7-30 pM) and authentic MERS-CoV ($PRNT_{50}$=53-200 pM), which was equivalent to or lower than our benchmark MERS-S neutralizing monoclonal antibody that targets the same domain.

MERS-S1$^B$ mAbs from epitope group II (mAb 1.8e5) and III (mAb 4.6e10) neutralized MERS-S pseudovirus infection at nanomolar concentrations ($IC_{50}$=10 and 0.32 nM, respectively), and exhibited no detectable or moderate neutralizing activity against authentic MERS-CoV ($PRNT_{50}$=>6.67 and 6.67 nM, respectively). The MERS-S1$^A$-specific mAb 1.10f3 lacked MERS-CoV neutralization activity in both virus neutralization assays. The anti-MERS-S2 mAbs 1.6c7 and 3.5 g6 were able to neutralize MERS-S pseudovirus ($IC_{50}$=2.45 and 16.6 nM, respectively), albeit at higher concentrations than the most potent neutralizing MERS-S1$^B$ mAbs (about 100-fold higher). The isotype control did not show any neutralization in both assays. Collectively, our data demonstrate that antibodies targeting the receptor binding domain S1$^B$ of the MERS-CoV spike protein display the highest potential for neutralization of MERS-CoV infection in vitro.

Example 5—Anti-MERS-S1$^B$ mAbs Neutralize MERS-CoV by Blocking Receptor Binding To understand the mechanism of action of lead mAbs, antibody interference with the diverse functions of the MERS-CoV S domains was assessed. To assess whether antibodies can compete with virus binding to the host receptor DPP4, an ELISA-based receptor binding inhibition assay was developed, in which binding of MERS-S ectodomain to DPP4-coated ELISA plates is quantified and interference with receptor binding by antibodies is measured as a reduction in binding signal. In absence of antibodies, the MERS-S ectodomain showed stable binding to DPP4 (FIG. 20A). Whereas anti-MERS-S1$^B$ mAb 1.8e5 showed weak interference with binding of MERS-S ectodomain to DPP4, all other MERS-S1$^B$-specific mAbs (mAbs 7.7 g6, 1.6f9, 1.2 g5, 4.6e10 and anti-MERS-CTRL) potently inhibited binding of MERS-S ectodomain to DPP4 in a concentration dependent manner (FIG. 20A). The data indicate that these antibodies partly overlap with or bind sufficiently close to the receptor-binding site on S1$^B$ to compete with receptor binding. None of the antibodies that bind outside the RBD domain (MERS-S1$^A$ and -S2) could block receptor binding. The potency of the S1$^B$-specific mAbs to inhibit receptor binding corresponds with the ability of these antibodies to neutralize virus infection (FIG. 19B), indicating that the inhibition of virus-receptor interaction by these antibodies is their main mechanism of neutralization in vitro.

Example 6—Anti-MERS-S1$^A$ mAb 1.10f3 Blocks Binding of MERS-S1$^A$ to Sialoglycoconjugates Recently it was demonstrated that the MERS-S1$^A$ domain facilitates virus binding to cell-surface sialoglycoconjugates, which can serve as a cell attachment factor for MERS-CoV (Li, Hulswit et al. 2017 PNAS USA 114(40): E8508-E8517). It was therefore assessed whether the MERS-S1$^A$-targeting mAb 1.10f3 can interfere with binding of MERS-S1$^A$ to sialoglycoconjugates on the surface of erythrocytes using the hemaglutination inhibition assay. To this end lumazine synthase (LS) nanoparticles multivalently displaying MERS-S1$^A$ (S1$^A$-LS) were used, which were earlier employed to demonstrate the sialic-acid dependent hemagglutination by the MERS-S1$^A$ domain (Li, Hulswit et al. 2017).

Hemagglutination was observed when S1$^A$-LS was mixed with erythrocytes (FIG. 21A). S1$^A$-LS mediated hemagluti-nation was abrogated upon addition of the MERS-S1$^A$ mAb 1.103 but not upon addition of the isotype control. Next, it was assessed whether interference of 1.10f3 with binding to sialylated receptors could inhibit Sia-dependent MERS-CoV infection. Binding to sialoglycans may aid MERS-CoV entry into DPP4-positive cells, depending on the cell type. Infection of Vero cells does not depend on cell surface sialic acids, concurrent with a low abundancy of the MERS-CoV S1$^A$ µlycotopes on those cells (Li, Hulswit et al. 2017). Correspondingly, infection of Vero cells with MERS-S pseudovirus could not be inhibited by 1.10f3 (FIG. 19). By contrast, infection of human lung Calu-3 cells was shown to rely on cell surface sialic acids which correlated with the abundance of MERS-CoV S1$^A$ receptors (Li, Hulswit et al. 2017). Contrary to Vero cells, infection of Calu-3 cells could be inhibited by 1.10f3 (FIG. 21B) suggesting that antibody binding to MERS-S1$^A$ can neutralize MERS-CoV infection via inhibition of virus binding to cell surface sialoglycans.

Example 7—Anti-MERS-S2 H2L2 mAbs Interfere with MERS-S Mediated Membrane Fusion The coronavirus S2 subunit encompasses the machinery for fusion of viral and host cell membranes, a process that is driven by extensive refolding of the metastable prefusion S2 into a stable postfusion state (Walls et al. 2017 PNAS USA 114(42):11157-11162). It was therefore hypothesized that antibodies targeting the MERS-S2 subunit might neutralize MERS-CoV infection by inhibiting this fusion process. To test this, a MERS-CoV-S driven cell-cell fusion assay was developed using a modified MERS-CoV spike protein. To monitor expression of MERS-CoV S in cells, the viral fusion protein was extended C-terminally with GFP. In addition, the furin cleavage site was mutated at the S1/S2 junction to increase the dependency of MERS-CoV S fusion activation on exogenous addition of trypsin. Expression of this MERS-S variant upon transfection of DPP4-expressing Huh-7 cells could be readily observed by the GFP signal (FIG. 21C). Upon addition of trypsin, large GFP-fluorescent syncytia were detected indicating MERS-S-mediated cell-cell fusion (FIG. 21C). As expected, addition of anti-MERS-S 1$^B$ (7.7 g6) blocked formation of syncytia since cell-cell fusion is dependent on receptor interaction. No effect on syncytium formation was seen for the MERS-S1$^A$ mAb 1.10f3. In contrast, the MERS-S2-specific mAbs 1.6c7 and 3.5 g6 both blocked syncytium formation. Since both neutralizing antibodies did not interfere with receptor binding (FIG. 20A), it was surmised that binding of these S2-specific antibodies inhibit infection by preventing conformational changes in the S2 subunit of the MERS-CoV spike protein that are required for fusion.

Example 8—Protective Activity of H2L2 mAbs from Lethal MERS-CoV Challenge

To assess the prophylactic efficacy of our lead mAbs against MERS-CoV infection in vivo, transgenic K18-hDPP4 mice expressing human DPP4 were used (Li, Wohlford-Lenane et al. 2016 The Journal of Infectious Diseases 213(5):712-722). Six hours prior to MERS-CoV infection, mice (5 mice/group) were injected intraperitoneally with a 50 microgram dose of each mAb (equivalent to 1.8 mg mAb per kg body weight). The percentage of survival and weight change following challenge was monitored for 12 days. MERS-CoV infection was consistently lethal as all mice that received the monoclonal isotype control showed significant weight loss and had succumbed to the infection between 7 and 8 days post challenge (FIG. 24). Contrarily, all MERS-S1$^B$ binding mAbs showed high levels of protection against lethal MERS-CoV challenge (80-100%, FIG. 25). Anti-MERS-S1$^B$ mAbs 7.7 g6, 1.2 g5 and the benchmark anti-MERS control mAb uniformly protected animals from death, whereas the MERS-S1$^B$ mAbs 1.6f9, 1.8e5 and 4.6e10 protected 4 out of 5 animals (80%) in this model. The MERS-S1$^A$ binding mAb 1.10f3 afforded partial protection from mortality (40%). Notably, the anti-MERS-S2 mAbs 1.6c7 and 3.5 g6 protected all five animals from lethal infection. Relative to the isotype control treated mice, mice treated with MERS-S specific antibodies showed reduced weight loss (FIG. 24). These results highlight that antibodies targeting non-RBD domains (i.e. S1$^A$ and S2) of the MERS-CoV spike protein can contribute to humoral immunity against MERS-CoV. infection.

Example 9—Anti-MERS S Protein HCAb Antibodies

HCAb mice are transgenic mice that also have the endogenous loci inactivated but which carry a hybrid human/mouse transgenic locus that codes for the production of heavy chain only antibodies (WO2014141189 Al).

Six HCAb mice were immunized with purified MERS S1 antigen. Of these mice, two reacted sufficiently as evidenced by ELISA. Lymph nodes were subsequently harvested to isolate RNA and to make VH-specific cDNA (see, e.g., e.g. WO 2010/109165). Amplified VHs were cloned into the pCAG hygro-mG1 expression vector. After bacterial transformation and isolation of plasmid DNA of ~-1200 colonies, HEK 293T transformants were obtained in a 96 well format.

Supernatants were subsequently screened four days after transfection with a MERS-S 1 specific ELISA. The VH sequences of ELISA-positive clones (>60) were sequenced resulting in the identification of 23 unique sequences (two of which are shown in FIG. 7). After larger scale production of unique clones, nine HCAbs were confirmed to target the MERS-S 1 antigen. Four out of these nine HCAbs subsequently showed virus neutralization activity. Epitope binning subsequently showed that they recognize at least two different epitopes. Interestingly, the HCAbs appear to target similar epitopes as some H2L2 antibodies. Affinity measurements showed that their affinities are lower than those of most H2L2 antibodies (1G3 $K_D$ 2.17×10$^{-8}$; 1H5 $K_D$ 1.09× 10$^{-8}$; 1E10 $K_D$ 1×10$^{-9}$).

Example 10—Cross-Reactive Anti-CoV Antibodies

A group of six H2L2 mice were sequentially immunized in two weeks intervals of purified ectodomains of HCoV-OC43, MERS-CoV and SARS-CoV, as outlined in FIG. 1F. Sequential immunization of the three different antigens (OC43-S, MERS-S and SARS-S) was performed with the aim of boosting antibodies against conserved epitopes among all three different antigens.

Antigens were injected at 25 pg/mouse using Stimune Adjuvant (Prionics) freshly prepared according to the manufacturer instruction for first injection, while boosting was done using Ribi (Sigma) adjuvant. Injections were done subcutaneously into the left and right groin each (50 μl) and 100 μl intraperitoneally. Four days after the last injection, spleen and lymph nodes are harvested, and hybridomas made by standard method using SP 2/0 myeloma cell line (ATCC #CRL-1581) as a fusion partner. Hybridomas were screened in antigen-specific ELISA and those selected for further development, subcloned and produced on a small scale (100 ml of medium). For this purpose, hybridomas are cultured in serum- and protein-free medium for hybridoma culturing (PFHM-II (1λ) Gibco) with addition of non-essential amino acids 100× NEAA, Biowhittaker Lonza Cat BE13-114E). Antibodies were purified from the cell supernatant using Protein-G affinity chromatography. Purified antibodies were stored at 4° C. until use.

Light and heavy variable region sequences of human antibodies that recognize more than one Coronavirus S protein, which were obtained according to this method, are shown in FIG. 2C.

FIG. 2H shows ELISA assay results confirming that the 63c12 antibody, which is one of the antibodies in FIG. 2C, recognizes S proteins of OC43, MERS and SARS viruses.

Example 11—Materials and Methods

Production of recombinant MERS-Co VSproteins. A gene encoding the MERS-CoV spike glycoprotein (EMC isolate; GenBank acc.no: YP_009047204.1) was synthesized by GenScript USA Inc. and the sequence was codon-optimized to maximize expression in the baculovirus expression system. To produce soluble MERS-S ectodomain, the gene fragment encoding the MERS-CoV S ectodomain (amino acid 19-1262) was cloned in-frame between honeybee melittin (HBM) secretion signal peptide and T4 fibritin (foldon) trimerization domain followed by Strep-tag purification tag in the pFastbac transfer vector (Invitrogen, Carlsbad, CA, USA). The furin cleavage site $R^{747}SVR^{751}$ at the S1/S2 junction was mutated to KSVR, to prevent cleavage by furin at this position. The genes encoding MERS-S1 subunit (amino acid 19-748), MERS-S2 ectodomain (amino acid 752-1262), MERS-S1$^A$ (amino acid 19-357), and MERS-S1$^B$ (358-588) were cloned in-frame between the HBM secretion signal peptide and a triple StrepTag purification tag in the pFastbac transfer vector. Generation of bacmid DNA and recombinant baculovirus was performed according to protocols from Bac-to-Bac system (Invitrogen, Carlsbad, CA, USA) and expression of MERS-CoV S variants was performed by infection of recombinant baculovirus of Sf-9 cells. Recombinant proteins were harvested from cell culture supernatants 3 days post infection and purified using Strep-Tactin sepharose affinity chromatography (IBA, Germany). The soluble MERS-S ectodomain used for immunization was produced in the *Drosophila* expression system as described before (Walls et al. 2006 Nature 531:114-117), by cloning the gene insert from the pFastbac transfer vector into the pMT expression vector (Invitrogen, Thermo Fisher Scientific, the Netherlands). Production of recombinant MERS-S1 (amino acid 1-747) used for immunization and of soluble DPP4 was described previously (Mou et al. 2013 Journal of Virology 87(16):9379-9383). In brief, the MERS-S1 (amino acid 1-747) encoding sequence was C-terminally fused to a gene fragment encoding the Fc region of human IgG and cloned into the pCAGGS mammalian expression vector, expressed by plasmid transfection in HEK-293T cells, and affinity purified from the culture supernatant using Protein A affinity chromatography. The Fc part of S1-Fc fusion protein was proteolytically removed by thrombin following Protein A affinity purification using the thrombin cleavage site present at the S1-Fc junction. The sequence encoding the human DPP4 ectodomain (amino acid 39—766)N-terminally fused to the Streptag purification tag was cloned into the pCAGGS vector, expressed by plasmid transfection of HEK-293T cells and purified from the cell culture supernatant using StrepTactin sepharose affinity chromatography. Production of lumazine synthase (LS) nanoparticles displaying the MERS-CoV spike domain S1$^A$ (S1$^A$-LS) has been described previously (Li, Hulswit et al. 2017). In brief, the MERS-S1$^A$ encoding sequence (residues 19-357) was N-terminally fused to a CD5 signal peptide sequence, followed by a Streptag purification tag sequence (IBA) and C-terminally fused to the lumazine synthase-encoding sequence from Aquifex aeolicus (GenBank WP_010880027.1) via a Gly-Ser linker, and subsequent cloned into the pCAGGS vector, expressed in HEK-293T cells and purified from the cell culture supernatant using StrepTactin affinity chromatography.

Production of recombinant H2L2 monoclonal antibodies. For recombinant mAb production, cDNA's encoding the variable heavy (VH) and light (VL) chain regions of anti-MERS-S H2L2 mAbs were cloned into expression plasmids containing the human IgG1 heavy chain and Ig kappa light chain constant regions, respectively (Invitrogen). Both plasmids contain the interleukin-2 signal sequence to enable efficient secretion of recombinant antibodies. Synthetic VH and VL gene fragments of the benchmark antibody (MERS-CTRL) were synthezised based on previously described sequences for the MERS-S monoclonal antibody 'H1H15211P' (Kyratsous, 20 May 2015, WO 2015/179535 A1). Recombinant human anti-MERS-S antibodies were produced in HEK-293T cells following transfection with pairs of the IgG1 heavy and light chain expression plasmids according to protocols from Invivogen. Antibodies were purified from supernatants using Protein-A affinity chromatography. Purified antibodies were stored at 4° C. until use.

Generation of Anti-MERS-CoV-S H2L2

Two groups of six H2L2 mice were immunized in two weeks intervals six times with purified MERS-S1 (group I) and MERS-S ectodomain followed by MERS-S2 antigen (group II). Antigens were injected at 20 µg/mouse using Stimune Adjuvant (Prionics) freshly prepared according to the manufacturer instruction for first injection, while boosting was done using Ribi (Sigma) adjuvant. Injections were done subcutaneously into the left and right groin each (50 µl) and 100 µl intraperitoneally. Four days after the last injection, spleen and lymph nodes are harvested, and hybridomas made by standard method using SP 2/0 myeloma cell line, (ATCC #CRL-1581) as a fusion partner. Hybridomas were screened in antigen-specific ELISA and those selected for further development, subcloned and produced on a small scale (100 ml of medium). For this purpose, hybrydomas are cultured in serum-free and protein free medium for hybridoma culturing (PFHM-II (1X) Gibco) with addition of non-essential amino acids 100× NEAA, Biowhittaker Lonza Cat BE13-114E). Antibodies were purified from the cell supernatant using Protein-G affinity chromatography. Purified antibodies were stored at 4° C. until use.

MERS-Spseudotyped virus neutralization assay. Production of VSV pseudotyped with MERS-S was performed according to Whitt 2010 with some adaptations. Briefly, HEK-293T cells were transfected with a pCAGGS expression vector encoding MERS-S carrying a 16-a.a. cytoplasmic tail truncation. One day post transfection, cells were infected with the VSV-G pseudotyped VSVAG bearing the firefly (Photinus pyralis) luciferase reporter gene (Kaname et al. 2010 J. Virol. 84:3210-3219). 24 hours later, MERS-S-VSVAG pseudotypes were harvested and titrated on African green monkey kidney Vero cells. In the virus neutralization assay, MERS-S mAbs were serially diluted at two times the desired final concentration in DMEM supplemented with 1% fetal calf serum (Bodinco B.V), 100 U/ml Penicillin and 100 µg/ml Streptomycin. Diluted mAbs were incubated with an equal volume of MERS-S-VSVAG pseudotypes for 1 hour at room temperature, inoculated on confluent Vero monolayers in 96-well plated, and further incubated at 37° C. for 24 hours. Luciferase activity was measured on a Berthold Centro LB 960 plate luminometer using D-luciferin as a substrate (Promega). The percentage of infectivity was calculated as ratio of luciferase readout in the presence of mAbs normalized to luciferase readout in the absence of mAb. The half maximal inhibitory concentrations (IC$_{50}$) were determined using 4-parameter logistic regression (GraphPad Prism version 7.0).

MERS-CoV neutralization assay. Neutralization of authentic MERS-CoV was performed using a plaque reduction neutralization test (PRNT) as described earlier (Stalin Raj et al. Sci Adv. 4: eaas9667). In brief, mAbs were two-fold serially diluted and mixed with MERS-CoV for 1 hour. The mixture was then added to Huh-7 cells and incubated for 1 hr, after which the cells were washed and further incubated in medium for 8 hrs. Subsequently, the cells were washed, fixed, permeabilized and the infection was detected using immunofluorescent staining. The PRNT titer was determined as the highest mAb dilution resulting in a >50% reduction in the number of infected cells (PRNT$_{50}$).

ELISA Analysis of MERS-CoV S Binding by Antibodies.

NUNC Maxisorp plates (Thermo Scientific) were coated with the indicated MERS-CoV antigen at 100 ng/well at 4° C. overnight. Plates were washed three times with Phosphate Saline Buffer (PBS) containing 0.05% Tween-20 and blocked with 3% Bovine Serum Albumin (BSA) in PBS containing 0.1% Tween-20 at room temperature for 2 hours. Four-folds serial dilutions of mAbs starting at 10 g/ml (diluted in blocking buffer) were added and plates were incubated for 1 hour at room temperature. Plates were washed three times and incubated with HRP-conjugated goat anti-human secondary antibody (ITK Southern Biotech) diluted 1:2000 in blocking buffer for one hour at room temperature. HRP activity was measured at 450 nm using tetramethylbenzidine substrate (BioFX) and an ELISA plate reader (EL-808, Biotek).

ELISA analysis of receptor binding inhibition by antibodies. Recombinant soluble DPP4 was coated on NUNC Maxisorp plates (Thermo Scientific) at 4° C. overnight. Plates were washed three times with PBS containing 0.05% Tween-20 and blocked with 3% BSA in PBS containing 0.1% Tween-20 at room temperature for 2 hours. Recombinant MERS-CoV S ectodomain and serially diluted anti-MERS mAbs were mixed for 1 h at RT, added to the plate for 1 hour at room temperature, after which plates were washed three times. Binding of MERS-CoV S ectodomain to DPP4 was detected using HRP-conjugated anti-StrepMAb (IBA, Germany) that recognizes the Streptag affinity tag on the MERS-CoV S ectodomain. Detection of HRP activity was performed as described above.

Antibody competition assay. Competition among mAbs for binding to the same epitope on MERS-CoV S was determined using Bio-Layer Interferometry (BLI) on Octet QK (Pall ForteBio) at 25° C. All reagents were diluted in PBS. The assay was performed following these steps: 1). anti-Strep mAb (50 g/ml) was coated on Protein A biosensor (Pall ForteBio) for 30 mins, 2) blocking of sensor with rabbit IgG (50 g/ml) for 30 mins, 3). Recombinant Strep-tagged MERS-CoV S ectodomain (50 g/ml) was immobilized to the sensor for 15 mins 4). Addition of mAb #1 (50 g/ml) for 15 min to allow saturation of binding to the immobilized antigen, 5) Addition of a mAb #2 (50 g/ml) for 15 mins. The first antibody (mAb #1) was taken along to verify saturation of binding. A 5-minutes washing step in PBS was included in between steps.

Binding kinetics and affinity measurements. Binding kinetics and affinity of mAbs to the MERS-S ectodomain was measured by BLI using the Octet QK at 25° C. The optimal loading concentration of anti-MERS-S mAbs onto anti-human Fc biosensors (Pall ForteBio) was predetermined to avoid saturation of the sensor. Kinetic binding assay was performed by loading anti-MERS mAb at optimal concentration (42 nM) on anti-human Fc biosensor for 10 mins. Antigen association step was performed by incubating the sensor with a range of concentrations of the recombinant MERS-S ectodomain (200-67-22-7.4 nM) for 10 min, followed by a dissociation step in PBS for 60 min. The kinetics constants were calculated using 1:1 Langmuir binding model on Fortebio Data Analysis 7.0 software.

Immunofluorescence microscopy. Huh-7 cells were seeded with density of $10^5$ cells per ml. After reaching 70-80% confluency, cells were transfected with expression plasmid encoding full length MERS-S that was C-terminally fused to the green fluorescence protein (GFP) and mutated in its furin cleavage site ($R^{751}S$) to prevent furin cleavage at the S1/S2 junction. Two days post transfection, cells were fixed by incubation with 4% paraformaldehyde in PBS for 20 min at room temperature. After extensive washing in PBS containing 0.05% Tween-20, cells were blocked using 10% Fetal Calf Serum (Bodinco B.V) diluted in PBS with 0.05% Tween-20 for 20 min at room temperature. MERS-S cell surface staining was performed by incubation of MERS-S transfected cells with anti-MERS-S mAbs at concentration of 1.25 pg/ml for 1 h at room temperature, followed by incubation with AlexaFluor 568 conjugated goat anti-human IgG (H+L) cross-adsorbed secondary antibody (Invitrogen, Thermo Fisher Scientific, the Netherlands) for 1 h at room temperature. Isotype control was included to check for background signal. Staining of nuclei was performed using 4,6-diamidino-2-phenylindole (DAPI). Fluorescence images were recorded using EVOS FL fluorescence microscope (Thermo Fisher Scientific, the Netherlands).

FACS

Huh-7 cells were seeded with density of $2.5 \times 10^5$ cells per ml in a T75 flask. After reaching 70-80% confluency, cells were transfected with expression plasmid encoding full length MERS-S—C-terminally fused to the green fluorescence protein (GFP)—using jetPRIME® (Polyplus transfection, New York, USA). The furin recognition site in the MERS-S was mutated to inhibit the cleavage of protein. Two days post transfection, cells were dissociated by cell dissociation solution (Sigma-aldrich, Merck KGaA, Darmstadt, Germany; cat no. C5914). Single cell suspensions in FACS buffer were centrifuged at 400×g for 10 min. Cells were then fixed by incubation with 4% paraformaldehyde in PBS for 15 min at room temperature. After centrifugation at 600×g for 10 min, paraformaldehyde was removed. Followed by a washing step in Phosphate Saline Buffer (PBS), cells were blocked using 10% Normal Goat Serum (Gibco, Thermo Fisher Scientific, the Netherlands) diluted in PBS for 45 min at room temperature. Surface staining of MERS-S was performed by incubation of cells with anti MERS-CoV mAbs at concentration of 5 g/ml for 1 h at room temperature, followed by incubation with goat anti-human IgG (H+L) cross-adsorbed secondary antibody, Alexa Fluor 649 (Invitrogen, Thermo Fisher Scientific, the Netherlands) for 45 min at room temperature. Cells were subjected to flow cytometric analysis with a FACS-Calibur flow cytometer (BD Biosciences), cells were gated for GFP expression. The results were analysed by FlowJo (version 10), and mean fluorescence intensities were calculated.

Hemagglutination inhibition assay. Potency of mAbs to inhibit hemagglutination by MERS-S1$^4$-displaying lumazine synthase nanoparticles (S1$^4$-LS) was performed according to Li et al. with slight modification (Li, Hulswit et al. 2017). Two-fold serial dilutions of S1$^4$-LS in PBS containing 0.1% bovine serum albumin (BSA) were mixed with 0.5% human erythrocyte in V-bottom 96-well plate (Greiner Bio-One), and incubated at 4° C. for 2 hrs. The hemagglutination titer was scored, and concentration of S1$^4$-LS that resulted in 8 hemagglutination units was determined. Subsequently, two-fold serial dilutions of anti-MERS-CoV mAbs in PBS containing 0.1% BSA were mixed with S1$^4$-LS (8 hemagglutination units) in a V-bottom 96-well plate. After 30 mins incubation at room temperature, human erythrocytes were added to a final concentration of 0.5% (v/v). The mixture was incubated at 4° C. for 2 hours and the hemagglutination inhibition activity by anti-MERS-S mAbs was scored.

Fusion inhibition assay. Huh-7 cells were seeded with density of $10^5$ cells per ml. After reaching 70-80% confluency, cells were transfected with expression plasmid encoding full length MERS-CoV S fused to Green Fluorescence Protein (GFP) using jetPRIME® (Polyplus transfection, New York, USA; cat no. 114-07). The furin recognition site in the MERS-CoV S was mutated to inhibit the cleavage of protein. Two days post transfection, cells were treated with 10 g/ml trypsin (to activate MERS-CoV spike fusion function) in the presence or absence of 10 μg/ml anti-MERS-CoV S mAbs. After incubation at 37° C. for 2 hrs, the cells were fixed by incubation with 4% paraformaldehyde in PBS for 20 min at room temperature and stained for nuclei with 4,6-diamidino-2-phenylindole (DAPI). Cells expressing MERS-CoV S were detected by fluorescence microscopy using the C-terminally appended GFP and MERS-CoV S-mediated cell-cell fusion was observed by the formation of (fluorescent) multi-nucleated syncytia. The fluorescence images were recorded using the EVOS FL fluorescence microscope (Thermo Fisher Scientific, the Netherlands).

Antibody-Mediated Protection of Mice Challenged with MERS-CoV.

In vivo efficacy of mAbs specific for the S protein of MERS-CoV, and of an isotype matched negative control mAbs was evaluated in the protection of the transgenic mouse model K18 TghDpp4 expressing the receptor for the human MERS-CoV susceptible to virulent virus (Li, Wohlford-Lenane et al. 2016). To test the prophylactic efficacy of mAbs in vivo groups of 5 mice, 20-30 weeks old, were given 10 mg of the antibody per kg mouse by intraperitoneal injection, 6 hours before intranasal infection with a lethal dose of MERS-CoV (EMC isolate; $5 \times 10^3$, pfu/mouse). Mice that received the best virus neutralizing antibodies were fully protected, whereas all the mice administered the negative control antibody died.

Antigen-Specific ELISA for Cross-Reactive Anti-CoV Antibodies

The following method was used to generate the ELISA assay results shown for the 63c12 antibody in FIG. 2H.

ELISA plate was coated with 5 microgram/ml of OC43-S, MERS-S and SARS-S (50 microliters) or PBS over night at 4° C. After washing (3× PBS/Tween 20 0.05%, 3×PBS) and blocking for 40 min at RT with 100 microliter/well with 1% milk/1 % BSA, plates were incubated with production medium from hybridoma (63c12). 25 microliter of production medium (out of 25 ml from 15 cm dish) was mixed with 25 microliters of 2% milk/2% BSA and added to each elisa plate well. Experiment was done in triplicates. After incubation for 2 h at RT, plates were washed as previously and incubated for 1 h at RT with 50 microliters of monoclonal mouse anti-rat isotype specific antibodies-HRP conjugated (IgG1, IgG2b and IgG2c) 1:2000 dilution (Absea). After repeated washing step, 50 microliter of peroxidase substrate (1×TMB, Invitrogen) was added, the reaction stopped by adding 0.16M sulphuric acid $H_2SO_4$ and ELISA plate analysed on BioTek microplate reader 800 TS at 450 nm.

The invention claimed is:

1. An antibody that binds to Middle East Respiratory Syndrome coronavirus (MERS-CoV) spike protein (MERS-S), wherein the antibody comprises a heavy chain that comprises a heavy chain variable region (VH) and a light chain that comprises a light chain variable region (VL):

wherein:

(a) the VH comprises a heavy chain complementarity determining region (CDR) 1 with a sequence of SEQ ID NO: 83, a heavy chain CDR2 with a sequence of SEQ ID NO: 84, and a heavy chain CDR3 with a sequence of SEQ ID NO: 85; and the VL comprises a light chain CDR1 with a sequence of SEQ ID NO: 86; a light chain CDR2 with a sequence of SEQ ID NO: 87, and a light chain CDR3 with a sequence of SEQ ID NO: 88, (b) the VH comprises a heavy chain CDR1 with a sequence of SEQ ID NO: 89, a heavy chain CDR2 with a sequence of SEQ ID NO: 90, and a heavy chain CDR3 with a sequence of SEQ ID NO: 91; and the VL comprises a light chain CDR1 with a sequence of SEQ ID NO: 92, a light chain CDR2 with a sequence of SEQ ID NO: 93, and a light chain CDR3 with a sequence of SEQ ID NO: 94, (c) the VH comprises a heavy chain CDR1 with a sequence of SEQ ID NO: 139, a heavy chain CDR2 with a sequence of SEQ ID NO: 140, and a heavy chain CDR3 with a sequence of SEQ ID NO: 141; and the VL comprises a light chain CDR1 with a sequence of SEQ ID NO: 142, a light chain CDR2 with a sequence of SEQ ID NO: 143, and a light chain CDR3 with a sequence of SEQ ID NO: 144, (d) the VH comprises a heavy chain CDR1 with a sequence of SEQ ID NO: 133, a heavy chain CDR2 with a sequence of SEQ ID NO: 134, and a heavy chain CDR3 with a sequence of SEQ ID NO: 135; and the VL comprises a light chain CDR1 with a sequence of SEQ ID NO: 136, a light chain CDR2 with a sequence of SEQ ID NO: 137, and a light chain CDR3 with a sequence of SEQ ID NO: 138, (e) the VH comprises a heavy chain CDR1 with a sequence of SEQ ID NO: 127, a heavy chain CDR2 with a sequence of SEQ ID NO: 128, and a heavy chain CDR3 with a sequence of SEQ ID NO: 129; and the VL comprises a light chain CDR1 with a sequence of SEQ ID NO: 130, a light chain CDR2 with a sequence of SEQ ID NO: 131, and a light chain CDR3 with a sequence of SEQ ID NO: 132, (f) the VH comprises a heavy chain CDR1 with a sequence of SEQ ID NO: 95, a heavy chain CDR2 with a sequence of SEQ ID NO: 96, and a heavy chain CDR3 with a sequence of SEQ ID NO: 97; and the VL comprises a light chain CDR1 with a sequence of SEQ ID NO: 98, a light chain CDR2 with a sequence of SEQ ID NO: 99, and a light chain CDR3 with a sequence of SEQ ID NO: 100, (g) the VH comprises a heavy chain CDR1 with a sequence of SEQ ID NO: 101, a heavy chain CDR2 with a sequence of SEQ ID NO: 102, and a heavy chain CDR3 with a sequence of SEQ ID NO: 103; and the VL comprises a light chain CDR1 with a sequence of SEQ ID NO: 104, a light chain CDR2 with a sequence of SEQ ID NO: 105, and a light chain CDR3 with a sequence of SEQ ID NO: 106, (h) the VH comprises a heavy chain CDR1 with a sequence of SEQ ID NO: 109, a heavy chain CDR2 with a sequence of SEQ ID NO: 110, and a heavy chain CDR3 with a sequence of SEQ ID NO: 111; and the VL comprises a light chain CDR1 with a sequence of SEQ ID NO: 112, a light chain CDR2 with a sequence of SEQ ID NO: 113, and a light chain CDR3 with a sequence of SEQ ID NO: 114, (i) the VH comprises a heavy chain CDR1 with a sequence of SEQ ID NO: 145, a heavy chain CDR2 with a sequence of SEQ ID NO: 146, and a heavy chain CDR3 with a sequence of SEQ ID NO: 147; and the VL comprises a light chain CDR1 with a sequence of SEQ ID NO: 148, a light chain CDR2 with a sequence of SEQ ID NO: 149, and a light chain CDR3 with a sequence of SEQ ID NO: 150, or (j) the VH comprises a heavy chain CDR1 with a sequence of SEQ ID NO: 617, a heavy chain CDR2 with a sequence of SEQ ID NO: 618, and a heavy chain CDR3 with a sequence of SEQ ID NO: 619; and the VL comprises a light chain CDR1 with a sequence of SEQ ID NO: 614, a light chain CDR2 with a sequence of SEQ ID NO: 615, and a light chain CDR3 with a sequence of SEQ ID NO: 616.

2. The antibody of claim 1, wherein the antibody comprises the VH, which comprises the amino acid sequence of SEQ ID NO: 70 and the VL, which comprises the amino acid sequence of SEQ ID NO: 74; or wherein the antibody comprises the VH, which comprises the amino acid sequence of SEQ ID NO: 69 and the VL, which comprises the amino acid sequence of SEQ ID NO: 72.

3. The antibody of claim 1, wherein the antibody comprises the VH, which comprises the amino acid sequence of SEQ ID NO: 17 and the VL, which comprises the amino acid sequence of SEQ ID NO: 67;

the antibody comprises the VH, which comprises the amino acid sequence of SEQ ID NO: 32 and the VL, which comprises the amino acid sequence of SEQ ID NO: 56;

the antibody comprises the VH, which comprises the amino acid sequence of SEQ ID NO: 22 and the VL, which comprises the amino acid sequence of SEQ ID NO: 59;

the antibody comprises the VH, which comprises the amino acid sequence of SEQ ID NO: 28 and the VL, which comprises the amino acid sequence of SEQ ID NO: 63;

the antibody comprises the VH, which comprises the amino acid sequence of SEQ ID NO: 26 and the VL, which comprises the amino acid sequence of SEQ ID NO: 65; or the antibody comprises the VH, which comprises the amino acid sequence of SEQ ID NO: 107 and the VL, which comprises the amino acid sequence of SEQ ID NO: 108.

4. The antibody of claim 1, wherein the antibody comprises the VH, which comprises the amino acid sequence of SEQ ID NO: 18 and the VL, which comprises the amino acid sequence of SEQ ID NO: 58.

5. The antibody of claim 1, wherein the antibody comprises the VH, which comprises the amino acid sequence of SEQ ID NO: 480 and the VL, which comprises the amino acid sequence of SEQ ID NO: 458.

6. The antibody of claim 1, wherein the antibody is an Fab, Fab', F(ab')2, Fv, a single-chain Fv (scFv) or a disulfide-linked Fv (sdFv).

7. An isolated nucleic acid encoding the antibody of claim 1.

8. A pharmaceutical composition comprising the antibody of claim 1, and a pharmaceutically acceptable carrier.

9. A method for treating or ameliorating MERS-CoV infection in a subject in need thereof, wherein the method comprises administrating an effective amount of the antibody of claim 1 to the subject.

10. An antibody that binds to Middle East Respiratory Syndrome coronavirus (MERS-CoV) spike protein (MERS-S), wherein the antibody comprises a heavy chain that comprises a heavy chain variable region (VH), which comprises the amino acid sequence of SEQ ID NO: 28 and a light chain that comprises a light chain variable region (VL), which comprises the amino acid sequence of SEQ ID NO: 63.

11. A method for treating or ameliorating MERS-CoV infection in a subject in need thereof, wherein the method comprises administrating an effective amount of the antibody of claim 10 to the subject.

* * * * *